United States Patent

Nagase et al.

[11] Patent Number: 5,972,953
[45] Date of Patent: *Oct. 26, 1999

[54] BRAIN CELL PROTECTIVE AGENT

[75] Inventors: Hiroshi Nagase; Yoshifumi Imamura, both of Kamakura; Takashi Endo, Chigasaki; Susumu Matsuda; Yasushi Miyauchi, both of Kamakura, all of Japan

[73] Assignee: Toray Industries, Ltd., Tokyo, Japan

[*] Notice: This patent issued on a continued prosecution application filed under 37 CFR 1.53(d), and is subject to the twenty year patent term provisions of 35 U.S.C. 154(a)(2).

[21] Appl. No.: 08/745,041

[22] Filed: Nov. 7, 1996

Related U.S. Application Data

[62] Division of application No. 08/403,759, filed as application No. PCT/JP94/01186, Jul. 19, 1994, abandoned.

[30] Foreign Application Priority Data

Jul. 19, 1993 [JP] Japan .................................. 5-177963

[51] Int. Cl.⁶ .................................................. A61K 31/485
[52] U.S. Cl. ................................ 514/282; 546/44; 546/45
[58] Field of Search ............................................. 514/282

[56] References Cited

U.S. PATENT DOCUMENTS

| | | |
|---|---|---|
| 3,819,635 | 6/1974 | Pachter . |
| 4,241,067 | 12/1980 | Kobyecki et al. ................. 514/282 |
| 4,267,182 | 5/1981 | Holaday et al. ................. 514/282 |
| 4,362,870 | 12/1982 | Portoghese ................. 514/282 |
| 4,401,672 | 8/1983 | Portoghese ................. 514/282 |
| 4,401,692 | 8/1983 | Portoghese ................. 514/282 |
| 4,767,718 | 8/1988 | Meyers . |
| 4,806,556 | 2/1989 | Portoghese ................. 546/44 |
| 4,816,586 | 3/1989 | Portoghese ................. 544/340 |
| 4,906,637 | 3/1990 | Faden ................. 514/282 |
| 4,925,848 | 5/1990 | Lewis ................. 514/282 |
| 5,219,861 | 6/1993 | Kanematsu ................. 514/282 |
| 5,556,838 | 9/1996 | Mayer et al. ................. 514/282 |
| 5,739,145 | 4/1998 | Nagase et al. ................. 514/282 |
| 5,834,478 | 11/1998 | Ito ................. 514/282 |
| 5,852,030 | 12/1998 | Nagase et al. ................. 514/279 |

FOREIGN PATENT DOCUMENTS

| | | |
|---|---|---|
| 0577847 | 1/1994 | European Pat. Off. . |
| 4118826 | 10/1941 | Japan . |
| 61-271275 | 12/1986 | Japan . |
| 62-277324 | 12/1987 | Japan . |
| 9315081 | 8/1993 | WIPO . |
| WO 9501178 | 1/1995 | WIPO . |
| 9503307 | 2/1995 | WIPO . |
| 9503308 | 2/1995 | WIPO . |
| WO 9503308 | 2/1995 | WIPO . |

OTHER PUBLICATIONS

Lyeth et al Chemical Abstr. vol. 123 entry 133374, 1995.
Nagase et al Chem. Abstr. vol. 123 entry 9747 abstracting WO 95–03308 1995.
Lyett et al Neuropeptides vol. 29, pp. 11–19, 1995.
Choi, Neuron, vol. 1, pp. 633–634 (1988).
Schoenecker, et al., "Opioid Agonist and . . . ", *J. Med. Chem.*, vol. 30, No. 5, 1987, pp. 933–935.

*Primary Examiner*—Donald G. Daus
*Attorney, Agent, or Firm*—Birch, Stewart, Kolasch & Birch, LLP

[57] ABSTRACT

The present invention relates to a novel brain cell protective agent having for its active ingredient a morphinan derivative represented with Compound 1

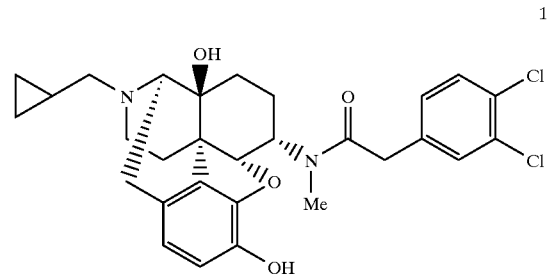

or pharmacologically acceptable acid addition salt thereof. The compounds used in the present invention were found to have excellent defensive effects against brain nerve cell necrosis in both in vitro and in vivo pharmacological evaluations, and can be used as useful preventive and therapeutic agents of ischemic brain disorders, brain nerve cell disorders and dementia.

11 Claims, No Drawings

BRAIN CELL PROTECTIVE AGENT

This application is a divisional of application Ser. No. 08/403,759, filed on Mar. 17, 1995, abandoned, which is a national stage entry of PCT/JP94/01 filed Jul. 19, 1994, the entire contents of which are hereby incorporated by reference.

TECHNICAL FIELD

The present invention relates to a novel brain cell protective agent that is effective in the prevention and treatment of ischemic brain disorders, cerebral nerve cell disorders and dementia.

BACKGROUND ART

In recent years, there has been an increase in the number of ischemic diseases affecting the brain and cardiovascular system accompanying aging. Cerebrovascular disorders caused by intracerebral hemorrhage and intracerebral thrombus, such as cerebral infarction, cerebral hemorrhage, cerebral arteriosclerosis and cerebral phlebothrombosis, and brain disorders such as functional brain damage caused by head injury and so forth bring about a shortage of glucose and oxygen used as energy sources for nerve cell activity. Due to the resulting necrosis of nerve cells at the ischemic site, various symptoms are manifest as sequelae of this necrosis, including cerebrovascular dementia and other disorders. In addition, accompanying the increasing proportion of elderly persons in society resulting from prolongation of the average life span, the problem of such diseases as senile dementia of Alzheimer type is becoming a serious problem both medically and socially. In the past, drugs that were developed against these ischemic cerebrovascular disorders and psychoneurotic symptoms accompanying senile dementia consisted primarily of those that mainly increased blood flow to the brain to promote the supply of glucose, oxygen and so forth to the ischemic site. Although these drugs are referred to with obscure expressions such as cerebral circulatory ameliorants, cerebral metabolic activators and cerebral function ameliorants in terms of their action and mechanism, despite being considered to be effective in improving peripheral symptoms such as hynobulia, emotional disorders and behavioral abnormalities, their effects are not clear with respect to improvement of the core symptoms of dementia such as memory disorders. Thus, at present, since there is no drug which is able to effectively treat these diseases, the development of a therapeutic drug is desired that demonstrates more reliable action and effects while also being safe and easy to use.

In response to the present circumstances, the present invention attempts to provide a novel brain cell protective agent that is effective in the prevention and treatment of ischemic brain disorders, cerebral nerve cell disorders and dementia.

DISCLOSURE OF THE INVENTION

As a result of earnest studies to solve the above-mentioned problems, the inventors of the present invention found that the morphinan derivative indicated in the above-mentioned general formula (I) is a compound that has excellent brain cell protective action, thus leading to completion of the present invention.

Namely, the present invention relates to a brain cell protective agent having for its active ingredient a morphinan derivative represented with general formula (I) or pharmacologically acceptable acid addition salt thereof:

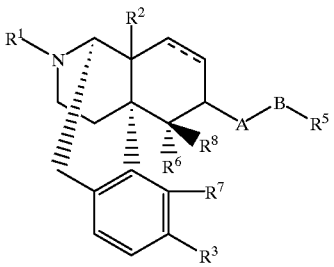

(I)

[wherein, ----- represents a single or double bond; $R^1$ represents an alkyl group having 1–5 carbon atoms, a cycloalkylalkyl group having 4–7 carbon atoms, a cycloalkenylalkyl group having 5–7 carbon atoms, an aryl group having 6–12 carbon atoms, an aralkyl group having 7–13 carbon atoms, an alkenyl group having 4–7 carbon atoms, an allyl group, a furan-2-ylalkyl group having 1–5 carbon atoms or a thiophen-2-ylalkyl group having 1–5 carbon atoms; $R^2$ represents a hydrogen atom, a hydroxy group, a nitro group, an alkanoyloxy group having 1–5 carbon atoms, an alkoxy group having 1–5 carbon atoms, an alkyl group having 1–5 carbon atoms or —$NR^9R^{10}$ (wherein, $R^9$ represents a hydrogen atom or alkyl group having 1–5 carbon atoms, and $R^{10}$ represents a hydrogen atom, alkyl group having 1–5 carbon atoms or —$C(=O)R^{11}$ (wherein, $R^{11}$ represents a hydrogen atom, phenyl group or alkyl group having 1–5 carbon atoms)); $R^3$ represents a hydrogen atom, a hydroxy group, an alkanoyloxy group having 1–5 carbon atoms or an alkoxy group having 1–5 carbon atoms; A represents —XC(=Y)—, —XC(=Y)Z—, —X—, —$XSO_2$— or —$OC(OR^4)R^4$— (where, X, Y and Z respectively and independently represent $NR^4$, S or O, $R^4$ represents a hydrogen atom, a straight chain or branched chain alkyl group having 1–14 carbon atoms (which may be substituted with at least one type of substituent group selected from the group consisting of an alkoxy group having 1–5 carbon atoms, an alkanoyloxy group having 1–5 carbon atoms, fluorine, chlorine, bromine, iodine, a nitro group and a cyano group), a cycloalkyl alkyl group having 4 to 15 carbon atoms (which may be substituted with at least one type of substituent group selected from the group consisting of an alkyl group having 1–5 carbon atoms, an aryl group having 6–12 carbon atoms, an alkoxy group having 1–5 carbon atoms, an alkanoyloxy group having 1–5 carbon atoms, fluorine, chlorine, bromine, iodine, a nitro group, a cyano group and a trifluoromethyl group), an aralkyl group having 7–15 carbon atoms (which may be substituted with at least one type of substituent group selected from the group consisting an alkyl group having 1–5 carbon atoms, an aryl group having 6–12 carbon atoms, an alkoxy group having 1–5 carbon atoms, an alkanoyloxy group having 1–5 carbon atoms, fluorine, chlorine, bromine, iodine, a nitro group, a cyano group and a trifluoromethyl group), or an aryl group having 6–12 carbon atoms (which may be substituted with at least one substituent group selected from the group consisting of an alkyl group having 1–5 carbon atoms, an aryl group having 6–12 carbon atoms, an alkoxy group having 1–5 carbon atoms, an alkanoyloxy group having 1–5 carbon atoms, fluorine, chlorine, bromine, iodine, a nitro group, a cyano group and a trifluoromethyl group), and wherein $R^4$ may be identical or different); B represents a valence bond, a straight chain or branched chain alkylene group having 1–14 carbon atoms (which may be substituted with at least one type of substituent group selected from the group consisting of an alkoxy group having 1–5 carbon atoms, an alkanoyloxy group having 1–5 carbon atoms, a hydroxy group, fluorine, chlorine, bromine, iodine, an amino group, a nitro group, a cyano group, a trifluoromethyl group and a phenoxy group, and wherein from 1 to 3 methylene groups may be replaced with carbonyl groups), a straight chain or branched chain, acyclic, unsaturated hydrocarbon having 2–14 carbon atoms and containing from 1 to 3 double and/or triple bonds (which may be substituted with at least one type of substituent group selected from the group consisting of an alkoxy group having 1–5 carbon atoms, an alkanoyloxy group having 1–5 carbon atoms, a hydroxy group, fluorine, chlorine, bromine, iodine, an amino group, a nitro group, a cyano group, a trifluoromethyl group and a phenoxy group, and wherein from 1 to 3 methylene groups may be replaced with carbonyl groups), or a straight chain or branched chain, saturated or unsaturated hydrocarbon having 1–14 carbon atoms and containing from 1 to 5 thioether, ether and/or amino bonds (wherein hetero atoms are not bonded directly to A, and from 1 to 3 methylene groups may be replaced with carbonyl groups); $R^5$ represents a hydrogen atom or an organic group having the basic skeleton shown below:

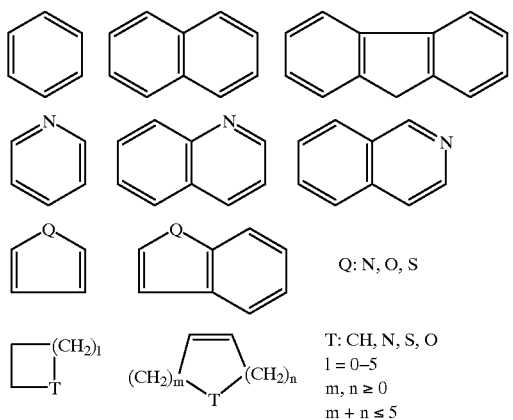

Organic group represented by $R^5$ (which may be substituted with at least one type of substituent group selected from the group consisting of an alkyl group having 1–5 carbon atoms, an alkoxy group having 1–5 carbon atoms, an alkanoyloxy group having 1–5 carbon atoms, a hydroxy group, fluorine, chlorine, bromine, iodine, an amino group, a nitro group, a cyano group, an isothiocyanato group, a trifluoromethyl group, a trifluoromethoxy group and a methylenedioxy group); $R^6$ represents a hydrogen atom; $R^7$ represents a hydrogen atom, hydroxy group, alkoxy group having 1–5 carbon atoms or alkanoyloxy group having 1–5 carbon atoms, or $R^6$ and $R^7$ collectively represent —O—, —CH$_2$— or —S—; $R^8$ represents a hydrogen atom, an alkyl group having 1–5 carbon atoms or an alkanoyl group having 1–5 carbon atoms; and, general formula (I) includes the (+) form, (−) form and (±) form].

BEST MODE FOR CARRYING OUT THE INVENTION

Preferable examples of $R^1$ in general formula (I) include an alkyl group having 1–5 carbon atoms, a cycloalkylmethyl group having 4–7 carbon atoms, a cycloalkenylmethyl group having 5–7 carbon atoms, a phenylalkyl group having 7–13 carbon atoms, an alkenyl group having 4–7 carbon atoms, an allyl group, a furan-2-yl-alkyl group having 1–5 carbon atoms, and a thiophen-2-yl-alkyl group having 1–5 carbon atoms, while particularly preferable examples include methyl, ethyl, propyl, butyl, cyclopropylmethyl, cyclobutylmethyl, cyclopentylmethyl, cyclopentenylmethyl, cyclohexenylmethyl, benzyl, phenethyl, trans-2-butenyl, 2-methyl-2-butenyl, allyl, furan-2-yl-methyl and thiophen-2-yl-methyl groups.

Preferable examples of $R^2$ include a hydrogen atom, hydroxy, nitro, acetoxy, methoxy, methyl, ethyl, propyl, amino, dimethylamino, acetylamino and benzoylamino groups, while particularly preferable examples include a hydrogen atom, hydroxy, nitro, acetoxy, methyl and dimethylamino groups.

Preferable examples of $R^3$ include a hydrogen atom, hydroxy, acetoxy and methoxy groups.

Preferable examples of A include —NR$^4$C(=O)—, —OC(=O)—, —OC(=S)—, —NR$^4$C(=O)O—, —NR$^4$C(=O)NR$^4$—, —NR$^4$C((=S)NR$^4$—, —NR$^4$— and —NR$^4$SO$_2$— (wherein $R^4$ is the same as previously defined), particularly preferable examples include —NR$^4$C(=O)—, —NR$^4$C(=O)O—, —NR$^4$C(=O)NR$^4$—, —NR$^4$C(=S)NR$^4$— and —NR$^4$— (wherein $R^4$ is the same as previously defined), while still more preferable examples include —NR$^4$C(=O)— and —NR$^4$— (wherein $R^4$ is the same as previously defined).

Preferable examples of $R^4$ include a hydrogen atom, a straight chain or branched chain alkyl group having 1–14 carbon atoms, a cycloalkylalkyl group having 4–15 carbon atoms, an aralkyl group having 7–15 carbon atoms and a phenyl group, while there are also cases in which it is better for these groups to be substituted with a substituent group such as a methyl group, an ethyl group, a propyl group, a butyl group, a pentyl group, a phenyl group, a methoxy group, an ethoxy group, an acetoxy group, fluorine, chlorine, bromine, iodine, a nitro group, a cyano group or a trifluoromethyl group. Particularly preferable examples of these include a methyl group, an ethyl group, a propyl group, an isopropyl group, a butyl group, an isobutyl group, a pentyl group, a benzyl group, a phenethyl group, a phenylpropyl group, a phenylbutyl group, a diphenylethyl group and a cyclohexylmethyl group.

Preferable examples of B include —(CH$_2$)n— (n=0–14), —(CH$_2$)n—C(=O)— (n=1–14), —CH=CH—(CH$_2$)n— (n=0–10), —C≡C— (CH$_2$)n— (n=0–10), —CH$_2$—O—, —CH$_2$—S—, —CH$_2$—O—(CH$_2$)$_2$—O—(CH$_2$)$_2$—, —CH$_2$—O—CH$_2$—NH—CH$_2$—O—CH$_2$—, and —CH$_2$—O—CH$_2$—S—CH$_2$—O—CH$_2$—, while particularly preferable examples include —(CH$_2$)n— (n=0–14), —CH=CH—(CH$_2$)n— (n0–10), —C≡C—(CH$_2$)n— (n=0–10), —CH$_2$—O— and —CH$_2$—S—.

Preferable examples of R5 include a hydrogen atom or an organic group having the basic skeleton shown below:

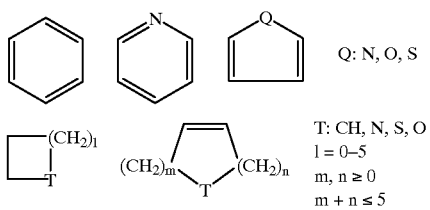

(which may be substituted with at least one type of substituent group selected from the group consisting of an alkyl group having 1–5 carbon atoms, an alkoxy group having 1–5 carbon atoms, an alkanoyloxy group having 1–5 carbon atoms, a hydroxy group, fluorine, chlorine, bromine, an amino group, a nitro group, a cyano group, an isothiocyanato group, a trifluoromethyl group and a trifluoromethoxy group), while particularly preferable examples include a hydrogen atom, phenyl, 3,4-dichlorophenyl, 4-chlorophenyl, 3-chlorophenyl, 2-chlorophenyl, 3,4-difluorophenyl, 4-fluorophenyl, 3-fluorophenyl, 2-fluorophenyl, 4-bromophenyl, 3-bromophenyl, 2-bromophenyl, 4-nitrophenyl, 3-nitrophenyl, 2-nitrophenyl, 4-trifluoromethylphenyl, 3-trifluoromethylphenyl, 2-trifluoromethylphenyl, 4-methylphenyl, 3-methylphenyl, 2-methylphenyl, 4-methoxyphenyl, 3-methoxyphenyl, 2-methoxyphenyl, 3-furanyl, 2-furanyl, 3-thienyl, 2-thienyl, cyclopentyl and cyclohexyl groups, although naturally not limited to these groups.

Preferable examples of pharmacologically preferable acid addition salts include, but are naturally not limited to, inorganic acid salts such as hydrochloride, sulfate, nitrate, hydrobromide, hydroiodide and phosphate; organic carboxylates such as acetate, lactate, citrate, oxalate, glutarate, malate, tartrate, fumarate, mandelate, maleate, benzoate and phthalate; and, organic sulfonates such as methanesulfonate, ethanesulfonate, benzenesulfonate, p-toluenesulfonate and camphorsulfonate, while particularly preferable examples include hydrochloride, hydrobromide, phosphate, tartrate and methanesulfonate.

Among the compounds of the general formula (I) of the present invention, compound 1

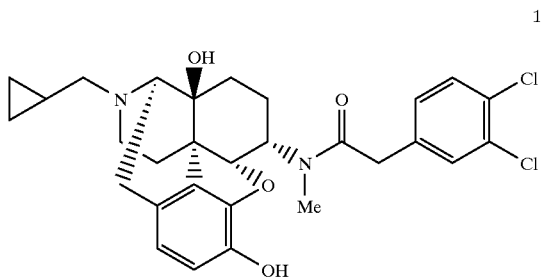

wherein ⋯⋯ is a single bond, $R^1$ is a cyclopropylmethyl group, $R^2$ and $R^3$ are hydroxy groups, A is α—$NR^4C$ (=O)—, $R^4$ is a methyl group, B is —$CH_2$—, $R^5$ is 3,4-dichlorophenyl, $R^6$ and $R^7$ are together —O— and $R^8$ is a hydrogen atom is named 17-cyclopropylmethyl-4,5α-epoxy-3,14β-dihydroxy-6α-(N-methyl-3,4-dichlorophenylacetamido)morphinan.

In accordance with the above nomenclature system, concrete examples of the compound of the present invention are as follows:

17-cyclopropylmethyl-4,5α-epoxy-3,14β-dihydroxy-6α-(N-methylcinnamamido) morphinan, 17-cyclopropylmethyl-4,5α-epoxy-3,14β-dihydroxy-6α-(N-methylbenzyloxycarbamido)morphinan, 17-cyclopropylmethyl-4,5α-epoxy-3,14β-dihydroxy-6α-(N-methylphenylmethanesulfonamido)morphinan, 17-allyl-4,5α-epoxy-3,14β-dihydroxy-6α-(N-methyl-3,4-dichlorophenylacetamido) morphinan, 17-allyl-4,5α-epoxy-3,14β-dihydroxy-6α-(N-methylcinnamamido)morphinan, 17-allyl-4,5α-epoxy-3,14β-dihydroxy-6α-(N-methylbenzyloxycarbamido)morphinan,
17-allyl-4,5α-epoxy-3,14β-dihydroxy-6α-(N-methylphenylmethanesulfonamido) morphinan, 17-methyl-4,5α-epoxy-3,14β-dihydroxy-6α-(N-methyl-3,4-dichlorophenylacetamido)morphinan, 17-methyl-4,5α-epoxy-3,14β-dihydroxy-6α-(N-methylcinnamamido) morphinan, 17-methyl-4,5α-epoxy-3,14β-dihydroxy-6α-(N-methylbenzyloxycarbamido) morphinan, 17-methyl-4,5α-epoxy-3,14β-dihydroxy-6α-(N-methylphenylmethanesulfonamido) morphinan, 17-phenethyl-4,5α-epoxy-3,14β-dihydroxy-6α-(N-methyl-3,4-dichlorophenylacetamido)morphinan, 17-phenethyl-4,5α-epoxy-3,14β-dihydroxy-6α-(N-methylcinnamamido) morphinan, 17-phenethyl-4,5α-epoxy-3,14β-dihydroxy-6α-(N-methylbenzyloxycarbamido) morphinan, 17-phenethyl-4,5α-epoxy-3,14β-dihydroxy-6α-(N-methylphenylmethanesulfonamido)morphinan, 17-cyclopropylmethyl-4,5α-epoxy-3-hydroxy-14β-acetoxy-6α-(N-methyl-3,4-dichlorophenylacetamido) morphinan, 17-cyclopropylmethyl-4,5α-epoxy-3-hydroxy-14β-acetoxy-6α-(N-methylcinnamamido)morphinan, 17-cyclopropylmethyl-4,5α-epoxy-3-hydroxy-14β-acetoxy-6α-(N-methylbenzyloxycarbamido)morphinan, 17-cyclopropylmethyl-4,5α-epoxy-3-hydroxy-14β-acetoxy-6α- (N-methylphenylmethanesulfonamido) morphinan, 17-allyl-4,5α-epoxy-3-hydroxy-14β-acetoxy-6α-(N-methyl-3,4-dichlorophenylacetamido)morphinan, 17-allyl-4,5α-epoxy-3-hydroxy-14β-acetoxy-6α-(N-methylcinnamamido)morphinan, 17-allyl-4,5α-epoxy-3-hydroxy-14β-acetoxy-6α-(N-methylbenzyloxycarbamido) morphinan, 17-allyl-4,5α-epoxy-3-hydroxy-14β-acetoxy-6α-(N-methylphenylmethanesulfonamido)morphinan,
17-methyl-4,5α-epoxy-3-hydroxy-14β-acetoxy-6α-(N-methyl-3,4-dichlorophenylacetamido)morphinan, 17-methyl-4,5α-epoxy-3-hydroxy-14β-acetoxy-6α-(N-methylcinnamamido)morphinan, 17-methyl-4,5α-epoxy-3-hydroxy-14β-acetoxy-6α-(N-methylbenzyloxycarbamido) morphinan, 17-methyl-4,5α-epoxy-3-hydroxy-14β-acetoxy-6α-(N-methylphenylmethanesulfonamido) morphinan, 17-phenethyl-4,5α-epoxy-3-hydroxy-14β-acetoxy-6α-(N-methyl-3,4-dichlorophenylacetamido) morphinan, 17-phenethyl-4,5α-epoxy-3-hydroxy-14β-acetoxy-6α-(N-methylcinnamamido)morphinan, 17-phenethyl-4,5α-epoxy-3-hydroxy-14β-acetoxy-6α-(N-methylbenzyloxycarbamido)morphinan, 17-phenethyl-4,5α-epoxy-3-hydroxy-14β-acetoxy-6α-(N-methylphenylmethanesulfonamido)morphinan, 17-cyclopropylmethyl-4,5α-epoxy-14β-hydroxy-6α-(N-methyl-3,4-dichlorophenylacetamido)morphinan, 17-cyclopropylmethyl-4,5α-epoxy-14β-hydroxy-6α-(N-methylcinnamamido)morphinan, 17-cyclopropylmethyl-4,5α-epoxy-14β-hydroxy-6α-(N-methylbenzyloxycarbamido)morphinan, 17-cyclopropylmethyl-4,5α-epoxy-14β-hydroxy-6α-(N-methylphenylmethanesulfonamido)morphinan, 17-allyl-4,5α-epoxy-14β-hydroxy-6α-(N-methyl-3,4-dichlorophenylacetamido)morphinan, 17-allyl-4,5α-epoxy-14β-hydroxy-6α-(N-methylcinnamamido)morphinan, 17-allyl-4,5α-epoxy-14β-hydroxy-6α-(N-methylbenzyloxycarbamido)morphinan, 17-allyl-4,5α-epoxy-14β-hydroxy-6α-(N-methylphenylmethanesulfonamido)morphinan, 17-methyl-4,5α-epoxy-14β-hydroxy-6α-(N-methyl-3,4-dichlorophenylacetamido)morphinan,
17-methyl-4,5α-epoxy-14β-hydroxy-6α-(N-methylcinnamamido)morphinan, 17-methyl-4,5α-epoxy-14β-hydroxy-6α-(N-methylbenzyloxycarbamido) morphinan, 17-methyl-4,5α-epoxy-14β-hydroxy-6α-(N-methylphenylmethanesulfonamido)morphinan, 17-phenethyl-4,5α-epoxy-14β-hydroxy-6α-(N-methyl-3,4-dichlorophenylacetamido)morphinan, 17-phenethyl-4,5α- epoxy-14β-hydroxy-6α-(N-methylcinnamamido) morphinan, 17-phenethyl-4,5α-epoxy-14β-hydroxy-6α-(N-methylbenzyloxycarbamido)morphinan, 17-phenethyl-4,5α-epoxy-14β-hydroxy-6α-(N-methylphenylmethanesulfonamido)morphinan, 17-cyclopropylmethyl-4,5α-epoxy-14β-acetoxy-6α-(N-methyl-3,4-dichlorophenylacetamido)morphinan, 17-cyclopropylmethyl-4,5α-epoxy-14β-acetoxy-6α-(N-methylcinnamamido)morphinan, 17-cyclopropylmethyl-4,5α-epoxy-14β-acetoxy-6α-(N-methylbenzyloxycarbamido)morphinan, 17-cyclopropylmethyl-4,5α-epoxy-14β-acetoxy-6α-(N-methylphenylmethanesulfonamido)morphinan, 17-allyl-4,5α-epoxy-14β-actoxy-6α-(N-methyl-3,4-dichlorophenylacetamido)morphinan, 17-allyl-4,5α-epoxy-14β-acetoxy-6α-(N-methylcinnamamido)morphinan, 17-allyl-4,5α-epoxy-14β-acetoxy-6α-(N-methylbenzyloxycarbamido)morphinan, 17-allyl-4,5α-epoxy-14β-acetoxy-6α-(N-methylphenylmethanesulfonamido)morphinan, 17-methyl-4,5α-epoxy-14β-acetoxy-6α-(N-methyl-3,4-dichlorophenylacetamido)morphinan, 17-methyl-4,5α-epoxy-14β-acetoxy-6α-(N-methylcinnamamido)morphinan, 17-methyl-4,5α-epoxy-14β-acetoxy-6α-(N-methylbenzyloxycarbamido)morphinan, 17-methyl-4,5α-epoxy-14β-acetoxy-6α-(N-methylphenylmethanesulfonamido)morphinan, 17-phenethyl-4,5α-epoxy-14β-acetoxy-6α-(N-methyl-3,4-dichlorophenylacetamido)morphinan, 17-phenethyl-4,5α-epoxy-14β-acetoxy-6α-(N-methylcinnamamido)morphinan, 17-phenethyl-4,5α-epoxy-14β-acetoxy-6α-(N-methylbenzyloxycarbamido)morphinan, 17-phenethyl-4,5α-epoxy-14β-acetoxy-6α-(N-methylphenylmethanesulfonamido)morphinan, 17-cyclopropylmethyl-4,5α-epoxy-3-methoxy-14β-hydroxy-6α-N-methyl-3,4-dichlorophenylacetamido)morphinan, 17-cyclopropylmethyl-4,5α-epoxy-3-methoxy-14β-hydroxy-6α-(N-methylcinnamamido)morphinan, 17-cyclopropylmethyl-4,5α-epoxy-3-methoxy-14β-hydroxy-6α-(N-methylbenzyloxycarbamido)morphinan, 17-cyclopropylmethyl-4,5α-epoxy-3-methoxy-14β-hydroxy-6α-(N-methylphenylmethanesulfonamido)morphinan, 17-allyl-4,5α-epoxy-3-methoxy-14β-hydroxy-6α-(N-methyl-3,4-dichlorophenylacetamido)morphinan, 17-allyl-4,5α-epoxy-3-methoxy-14β-hydroxy-6α-(N-methylcinamamido)morphinan, 17-allyl-4,5α-epoxy-3-methoxy-14β-hydroxy-6α-(N-methylbenzyloxycarbamido)morphinan, 17-allyl-4,5α-epoxy-3-methoxy-14β-hydroxy-6α-(N-methylphenylmethanesulfonamido)morphinan, 17-methyl-4,5α-epoxy-3-methoxy-14β-hydroxy-6α-(N-methyl-3,4-dichlorophenylacetamido)morphinan, 17-methyl-4,5α-epoxy-3-methoxy-14β-hydroxy-6α-(N-methylcinnamamido)morphinan, 17-methyl-4,5α-epoxy-3-methoxy-14β-hydroxy-6α-(N-methylbenzyloxycarbamido)morphinan, 17-methyl-4,5α-epoxy-3-methoxy-14β-hydroxy-6α-(N-methylphenylmethanesulfonamido)morphinan, 17-phenethyl-4,5α-epoxy-3-methoxy-14β-hydroxy-6α-(N-methyl-3,4-dichlorophenylacetamido)morphinan, 17-phenethyl-4,5α-epoxy-3-methoxy-14β-hydroxy-6α-(N-methylcinnamamido)morphinan, 17-phenethyl-4,5α-epoxy-3-methoxy-14β-hydroxy-6α-(N-methylbenzyloxycarbamido)morphinan, 17-phenethyl-4,5α-epoxy-3-methoxy-14β-hydroxy-6α-(N-methylphenylmethanesulfonamido)morphinan, 17-cyclopropylmetyl-4,5α-epoxy-3-methoxy-14β-acetoxy-6α-(N-methyl-3,4-dichlorophenylacetamido)morphinan, 17-cyclopropylmethyl-4,5α-epoxy-3-methoxy-14β-acetoxy-6α-(N-methylcinnamamido)morphinan, 17-cyclopropylmethyl-4,5α-epoxy-3-methoxy-14β-acetoxy-6α-(N-methylbenzyloxycarbamido)morphinan, 17-cyclopropylmethyl-4,5α-epoxy-3-methoxy-14β-acetoxy-6α-(N-methylphenylmethanesulfonamido)morphinan, 17-allyl-4,5α-epoxy-3-methoxy-14β-acetoxy-6α-(N-methyl-3,4-dichlorophenylacetamido)morphinan, 17-allyl-4,5α-epoxy-3-methoxy-14β-acetoxy-6α-(N-methylcinnamamido)morphinan, 17-allyl-4,5α-epoxy-3-methoxy-14β-acetoxy-6α-(N-methylbenzyloxycarbamido)morphinan, 17-allyl-4,5α-epoxy-3-methoxy-14β-acetoxy-6α-(N-methylphenylmethanesulfonamido)morphinan, 17-methyl-4,5α-epoxy-3-methoxy-14β-acetoxy-6α-(N-methyl-3,4-dichlorophenylacetamido)morphinan, 17-methyl-4,5α-epoxy-3-methoxy-14β-acetoxy-6α-(N-methylcinnamamido)morphinan, 17-methyl-4,5α-epoxy-3-methoxy-14β-acetoxy-6α-(N-methylbenzyloxycarbamido)morphinan, 17-methyl-4,5α-epoxy-3-methoxy-14β-acetoxy-6α-(N-methylphenylmethanesulfonamido)morphinan, 17-phenethyl-4,5α-epoxy-3-methoxy-14β-acetoxy-6α-(N-methyl-3,4-dichlorophenylacetamido)morphinan, 17-phenethyl-4,5α-epoxy-3-methoxy-14β-acetoxy-6α-(N-methylcinnamamido)morphinan, 17-phenethyl-4,5(1-epoxy-3-methoxy-14β-acetoxy-6α-(N-methylbenzyloxycarbamido)morphinan, 17-phenethyl-4,5α-epoxy-3-methoxy-14β-acetoxy-6α-(N-methylphenylmethanesulfonamido)morphinan, 17-cyclopropylmethyl-4,5α-epoxy-3-acetoxy-14β-hydroxy-6α-(N-methyl-3,4-dichlorophenylacetamido)morphinan, 17-cyclopropylmethyl-4,5α-epoxy-3-acetoxy-14β-hydroxy-6-α-(N-methylcinnamamido)morphinan, 17-cyclopropylmethyl-4,5α-epoxy-3-acetoxy-14β-hydroxy-6α-(N-methylbenzyloxycarbamido)morphinan, 17-cyclopropylmethyl-4,5α-epoxy-3-acetoxy-14β-hydroxy-6α-(N-methylphenylmethanesulfonamido)morphinan, 17-allyl-4,5α-epoxy-3-acetoxy-14β-hydroxy-6α-(N-methyl-3,4-dichlorophenylacetamido)morphinan, 17-allyl-4,5α-epoxy-3-acetoxy-14β-hydroxy-6α-(N-methylcinnamamido)morphinan, 17-allyl-4,5α-epoxy-3-acetoxy-14β-hydroxy-6α-(N-methylbenzyloxycarbamido)morphinan, 17-allyl-4,5α-epoxy-3-acetoxy-14β-hydroxy-6α-(N-methylphenylmethanesulfonamido)morphinan, 17-methyl-4,5α-epoxy-3-acetoxy-14β-hydroxy-6α-(N-methyl-3,4-dichlorophenylacetamido)morphinan, 17-methyl-4,5α-epoxy-3-acetoxy-14β-hydroxy-6α-(N-methylcinnamamido)morphinan, 17-methyl-4,5α-epoxy-3-acetoxy-14β-hydroxy-6α-(N-methylbenzyloxycarbamido)morphinan, 17-methyl-4,5α-epoxy-3-acetoxy-14β-hydroxy-6α-(N-methylphenylmethanesulfonamido)morphinan, 17-phenethyl-4,5α-epoxy-3-acetoxy-14β-hydroxy-6α-(N-methyl-3,4-dichlorophenylacetamido)morphinan, 17-phenethyl-4,5α-epoxy-3-acetoxy-14β-hydroxy-6α-(N-methylcinnamamido)morphinan, 17-phenethyl-4,5α-epoxy-3-acetoxy-14β-hydroxy-6α-(N-methylbenzyloxycarbamido)morphinan, 17-phenethyl-4,5α-epoxy-3-acetoxy-14β-hydroxy-6α-(N-methylphenylmethanesulfonamido)morphinan, 17-cyclopropylmethyl-4,5α-epoxy-3,14β-diacetoxy-6α-(N-methyl-3,4-dichlorophenylacetamido)morphinan, 17-cyclopropylmethyl-4,5α-epoxy-3,14β-diacetoxy-6α-(N-methylcinnamamido)morphinan, 17-cyclopropylmethyl-4,5α-epoxy-3,14β-diacetoxy-6α-(N-methylbenzyloxycarbamido)morphinan, 17-cyclopropylmethyl-4,5α-epoxy-3,14β-diacetoxy-6α-(N-methylphenylmethanesulfonamido)morphinan, 17-allyl-4,5α-epoxy-3,14β-diacetoxy-6α-(N-methyl-3,4-dichlorophenylacetamido)morphinan, 17-allyl-4,5α-epoxy- 3,14β-diacetoxy-6α-(N-methylcinnamamido)morphinan, 17-allyl-4,5α-epoxy-3,14(3-diacetoxy-6α-(N-methylbenzyloxycarbamido)morphinan, 17-allyl-4,5α-epoxy-3,14β-diacetoxy-6α-(N-methylphenylmethanesulfonamido)morphinan, 17-methyl-4,5α-epoxy-3,14β-diacetoxy-6α-(N-methyl-3,4-dichlorophenylacetamido)morphinan, 17-methyl-4,5α-epoxy-3,14β-diacetoxy-6α-(N-methylcinnamamido)morphinan, 17-methyl-4,5α-epoxy-3,14β-diacetoxy-6α-(N-methylbenzyloxycarbamido)morphinan, 17-methyl-4,5α-epoxy-3,14β-diacetoxy-6α-(N-methylphenylmethanesulfonamido)morphinan, 17-phenethyl-4,5α-epoxy-3,14β-diacetoxy-6α-(N-methyl-3,4-dichlorophenylacetamido)morphinan, 17-phenethyl-4,5α-epoxy-3,14β-diacetoxy-6α-(N-methylcinnamamido)morphinan, 17-phenethyl-4,5α-epoxy-3,14β-diacetoxy-6α-(N-methylbenzyloxycarbamido)morphinan, 17-phenethyl-4,5α-epoxy-3,14β-diacetoxy-6α-(N-methylphenylmethanesulfonamido)morphinan, 17-cyclopropylmethyl-4,5α-epoxy-3,14β-dihydroxy-6α-(N-isobutyl-3,4-dichlorophenylacetamido)morphinan, 17-cyclopropylmethyl-4,5α-epoxy-3,14β-dihydroxy-6α-(N-isobutylcinnamamido)morphinan, 17-cyclopropylmethyl-4,5α-epoxy-3,14β-dihydroxy-6α-(N-isobutylbenzyloxycarbamido)morphinan, 17-cyclopropylmethyl-4,5α-epoxy-3,14β-dihydroxy-6α-(N-isobutylphenylmethanesulfonamamido)morphinan, 17-allyl-4,5α-epoxy-3,14β-dihydroxy-6α-(N-isobutyl-3,4-dichlorophenylacetamido)morphinan, 17-allyl-4,5α-epoxy-3,14β-dihydroxy-6α-(N-isobutylcinnamamido)morphinan, 17-allyl-4,5α-epoxy-3,14β-dihydroxy-6α-(N-isobutylbenzyloxycarbamido)morphinan, 17-allyl-4,5α-epoxy-3,14β-dihydroxy-6α-(N-isobutylphenylmethanesulfonamido)morphinan, 17-metyl-4,5α-epoxy-3,14β-dihydroxy-6α-(N-isobutyl-3,4-dichlorophenylacetamido)morphinan, 17-methyl-4,5α-epoxy-3,14β-dihydroxy-6α-(N-isobutylcinnamamido)morphinan, 17-methyl-4,5α-epoxy-3,14β-dihydroxy-6α-(N-isobutylbenzyloxycarbamido)morphinan, 17-methyl-4,5α-epoxy-3,14β-dihydroxy-6α-(N-isobutylphenylmethanesulfonamido)morphinan, 17-phenethyl-4,5(1-epoxy-3,14β-dihydroxy-6α-(N-isobutyl-3,4-dichlorophenylacetamido)morphinan, 17-phenethyl-4,5α-epoxy-3,14β-dihydroxy-6α-(N-isobutylcinnamamido)morphinan, 17-phenethyl-4,5α-epoxy-3,14β-dihydroxy-6α-(N-isobutylbenzyloxycarbamido)morphinan, 17-phenethyl-4,5α-epoxy-3,14β-dihydroxy-6α-(N-isobutylphenylmethanesulfonamido)morphinan, 17-cyclopropylmethyl-4,5α-epoxy-3-hydroxy-14β-acetoxy-6α-(N-isobutyl-3,4-dichlorophenylacetamido)morphinan, 17-cyclopropylmethyl-4,5α-epoxy-3-hydroxy-14β-acetoxy-6α-(N-isobutylcinnamamido)morphinan, 17-cyclopropylmethyl-4,5α-epoxy-3-hydroxy-14β-acetoxy-6α-(N-isobutylbenzyloxycarbamido)morphinan, 17-cyclopropylmethyl-4,5α-epoxy-3-hydroxy-14β-acetoxy-6α-(N-isobutylphenylmethanesulfonamido)morphinan, 17-allyl-4,5α-epoxy-3-hydroxy-14β-acetoxy-6α-(N-isobutyl-3,4-dichlorophenylacetamido)morphinan, 17-allyl-4,5α-epoxy-3-hydroxy- 14β-acetoxy-6α-(N-isobutylcinnamamido)morphinan, 17-allyl-4,5β-epoxy-3-hydroxy-14β-acetoxy-6α-(N-isobutylbenzyloxycarbamido)morphinan, 17-allyl-4,5α-epoxy-3-hydroxy-14β-acetoxy-6α-(N-isobutylphenylmethanesulfonamido)morphinan, 17-methyl-4,5α-epoxy-3-hydroxy-14β-acetoxy-6α-(N-isobutyl-3,4-dichlorophenylacetamido)morphinan, 17-methyl-4,5α-epoxy-3-hydroxy-14β-acetoxy-6α-(N-isobutylcinnamamido)morphinan, 17-methyl-4,5α-epoxy-3-hydroxy-14β-acetoxy-6α-(N-isobutylbenzyloxycarbamido)morphinan, 17-methyl-4,5α-epoxy-3-hydroxy-14β-acetoxy-6α-(N-isobutylphenylmethanesulfonamido)morphinan, 17-phenethyl-4,5α-epoxy-3-hydroxy-14β-acetoxy-6α-(N-isobutyl-3,4-dichlorophenylacetamido)morphinan, 17-phenethyl-4,5α-epoxy-3-hydroxy-14β-acetoxy-6α-(N-isobutylcinnamamido)morphinan, 17-phenethyl-4,5α-epoxy-3-hydroxy-14β-acetoxy-6α-(N-isobutylbenzyloxycarbamido)morphinan, 17-phenethyl-4,5α-epoxy-3-hydroxy-14β-acetoxy-6α-(N-isobutylphenylmethanesulfonamido)morphinan, 17-cyclopropylmethyl-4,5α-epoxy-14β-hydroxy-6α-(N-isobutyl-3,4-dichlorophenylacetamido)morphinan, 17-cyclopropylmethyl-4,5α-epoxy-14β-hydroxy-6α-(N-isobutylcinnamamido)morphinan, 17-cyclopropylmethyl-4,5α-epoxy-14β-hydroxy-6α-(N-isobutylbenzyloxycarbamido)morphinan, 17-cyclopropylmethyl-4,5α-epoxy-14β-hydroxy-6α-(N-isobutylphenylmethanesulfonamido)morphinan, 17-allyl-4,5α-epoxy-14β-hydroxy-6α-(N-isobutyl-3,4-dichlorophenylacetamido)morphinan, 17-allyl-4,5α-epoxy-14β-hydroxy-6α-(N-isobutylcinnamamido)morphinan, 17-allyl-4,5α-epoxy-14β-hydroxy-6α-(N-isobutylbenzyloxycarbamido)morphinan, 17-allyl-4,5α-epoxy-14β-hydroxy-6α-(N-isobutylphenylmethanesulfonamido)morphinan, 17-methyl-4,5α-epoxy-14β-hydroxy-6α-(N-isobutyl-3,4-dichlorophenylacetamido)morphinan, 17-methyl-4,5α-epoxy-14β-hydroxy-6α-(N-isobutylcinnamamido)morphinan, 17-methyl-4,5α-epoxy-14β-hydroxy-6α-(N-isobutylbenzyloxycarbamido)morphinan, 17-methyl-4,5α-epoxy-14β-hydroxy-6α-(N-isobutylphenylmethanesulfonamido)morphinan, 17-phenethyl-4,5α-epoxy-14β-hydroxy-6α-(N-isobutyl-3,4-dichlorophenylacetamido)morphinan, 17-phenethyl-4,5α-epoxy-14β-hydroxy-6α-(N-isobutylcinnamamido)morphinan, 17-phenethyl-4,5α-epoxy-14β-hydroxy-6α-(N-isobutylbenzyloxycarbamido)morphinan, 17-phenethyl-4,5α-epoxy-14β-hydroxy-6α-(N-isobutylphenylmethanesulfonamido)morphinan, 17-cyclopropylmethyl-4,5α-epoxy-14β-acetoxy-6α-(N-isobutyl-3,4-dichlorophenylacetamido)morphinan, 17-cyclopropylmethyl-4,5α-epoxy-14β-acetoxy-6α-(N-isobutylcinnamamido)morphinan, 17-cyclopropylmethyl-4,5α-epoxy-14β-acetoxy-6α-(N-isobutylbenzyloxycarbamido)morphinan, 17-cyclopropylmethyl-4,5α-epoxy-14β-acetoxy-6α-(N-isobutylphenylmethanesulfonamido)morphinan, 17-allyl-4,5α-epoxy-14β-acetoxy-6α-(N-isobutyl-3,4-dichlorophenylacetamido)morphinan, 17-allyl-4,5α-epoxy-14β-acetoxy-6α-(N-isobutylcinnamamido)morphinan, 17-allyl-4,5α-epoxy-14β-acetoxy-6α-(N-isobutylbenzyloxycarbamido)morphinan, 17-allyl-4,5α-epoxy-14β-acetoxy-6α-(N-isobutylphenylmethanesulfonamido)morphinan, 17-methyl-4,5α-epoxy-14β-acetoxy-6α-(N-isobutyl-3,4-dichlorophenylacetamido)morphinan, 17-methyl-4,5α-epoxy-14β-acetoxy-6α-(N-isobutylcinnamamido)morphinan, 17-methyl-4,5α-epoxy-14β-acetoxy-6α-(N-isobutylbenzyloxycarbamido)morphinan, 17-methyl-4,5α-epoxy-14β-acetoxy-6α-(N-isobutylphenylmethanesulfonamido)morphinan, 17-phenethyl-4,5α-epoxy-14β-acetoxy-6α-(N-isobutyl-3,4-dichlorophenylacetamido)morphinan, 17-phenethyl-4,5α- epoxy-14β-acetoxy-6α-(N-isobutylcinnamamido) morphinan, 17-phenethyl-4,5α-epoxy-14β-acetoxy-60α-(N-isobutylbenzyloxycarbamido)morphinan, 17-phenethyl-4,5α-epoxy-14β-acetoxy- 6α-(N-isobutylphenylmethanesulfonamido)morphinan, 17-cyclopropylmethyl-4,5α-epoxy-3-methoxy-14β-hydroxy-6α-(N-isobutyl-3,4-dichlorophenylacetamido) morphinan, 17-cyclopropylmethyl-4,5α-epoxy-3-methoxy-14β-hydroxy-6α-(N-isobutylcinnamamido)morphinan, 17-cyclopropylmethyl-4,5α-epoxy-3-methoxy-14β-hydroxy-6α-(N-isobutylbenzyloxycarbamido)morphinan, 17-cyclopropylmethyl-4,5α-epoxy-3-methoxy-14β-hydroxy-6α-(N-isobutylphenylmethanesulfonamido) morphinan, 17-allyl-4,5α-epoxy-3-methoxy-14β-hydroxy-6α-(N-isobutyl-3,4-dichlorophenylacetamido)morphinan, 17-allyl-4,5α-epoxy-3-methoxy-14β-hydroxy-6α-(N-isobutylcinnamamido)morphinan, 17-allyl-4,5α-epoxy-3-methoxy-14β-hydroxy-6α-(N-isobutylbenzyloxycarbamido)morphinan, 17-allyl-4,5α-epoxy-3-methoxy-14β-hydroxy-6α-(N-isobutylphenylmethanesulfonamido)morphinan, 17-methyl-4,5α-epoxy-3-methoxy-14β-hydroxy-6α-(N-isobutyl-3,4-dichlorophenylacetamido)morphinan, 17-methyl-4,5α-epoxy-3-methoxy-14β-hydroxy-6α-(N-isobutylcinnamamido)morphinan, 17-methyl-4,5α-epoxy-3-methoxy-14β-hydroxy-6α-(N-isobutylbenzyloxycarbamido)morphinan, 17-methyl-4,5α-epoxy-3-methoxy-14β-hydroxy-6α-(N-isobutylphenylmethanesulfonamido)morphinan, 17-phenethyl-4,5α-epoxy-3-methoxy-14β-hydroxy-6α-(N-isobutyl-3,4-dichlorophenylacetamido)morphinan, 17-phenethyl-4,5α-epoxy-3-methoxy-14β-hydroxy-6α-(N-isobutylcinnamamido)morphinan, 17-phenethyl-4,5α-epoxy-3-methoxy-14β-hydroxy-6α-(N-isobutylbenzyloxycarbamido)morphinan, 17-phenethyl-4,5α-epoxy-3-methoxy-14β-hydroxy-6α-(N-isobutylphenylmethanesulfonamido)morphinan, 17-cyclopropylmethyl-4,5α-epoxy-3-methoxy-14β-acetoxy-6α-(N-isobutyl-3,4-dichlorophenylacetamido) morphinan, 17-cyclopropylmethyl-4,5α-epoxy-3-methoxy-14β-acetoxy-6α-(N-isobutylcinnamamido)morphinan, 17-cyclopropylmethyl-4,5α-epoxy-3-methoxy-14β-acetoxy-6α-(N-isobutylbenzyloxycarbamido)morphinan, 17-cyclopropylmethyl-4,5α-epoxy-3-methoxy-14β-acetoxy-6α-(N-isobutylphenylmethanesulfonamido) morphinan, 17-allyl-4,5α-epoxy-3-methoxy-14β-acetoxy-6α-(N-isobutyl-3,4-dichlorophenylacetamido)morphinan, 17-allyl-4,5α-epoxy-3-methoxy-14β-acetoxy-6α-(N-isobutylcinnamamido)morphinan, 17-allyl-4,5α-epoxy-3-methoxy-14β-acetoxy-6α-(N-isobutylbenzyloxycarbamido) morphinan, 17-allyl-4,5α-epoxy-3-methoxy-14β-acetoxy-6α-(N-isobutylphenylmethanesulfonamido)morphinan, 17-methyl-4,5α-epoxy-3-methoxy-14β-acetoxy-6α-(N-isobutyl-3,4-dichlorophenylacetamido)morphinan, 17-methyl-4,5α-epoxy-3-methoxy-14β-acetoxy-6α-(N-isobutylcinnamamido)morphinan, 17-methyl-4,5α-epoxy-3-methoxy-14β-acetoxy-6α-(N-isobutylbenzyloxycarbamido)morphinan, 17-methyl-4,5α-epoxy-3-methoxy-14β-acetoxy-6α-(N-isobutylphenylmethanesulfonamido)morphinan, 17-phenethyl-4,5α-epoxy-3-methoxy-14β-acetoxy-6α-(N-isobutyl-3,4-dichlorophenylacetamido)morphinan, 17-phenethyl-4,5α-epoxy-3-methoxy-14β-acetoxy-6α-(N-isobutylcinnamamido)morphinan, 17-phenethyl-4,5α-epoxy-3-methoxy-14β-acetoxy-6α-(N-isobutylbenzyloxycarbamido)morphinan, 17-phenethyl-4,5α-epoxy-3-methoxy-14β-acetoxy-6α-(N-isobutylphenylmethanesulfonamido)morphinan, 17-cyclopropylmethyl-4,5α-epoxy-3-acetoxy-14β-hydroxy-6α-(N-isobutyl-3,4-dichlorophenylacetamido) morphinan, 17-cyclopropylmethyl-4,5α-epoxy-3-acetoxy-14β-hydroxy-6α-(N-isobutylcinnamamido)morphinan, 17-cyclopropylmethyl-4,5α-epoxy-3-acetoxy-14β-hydroxy-6α-(N-isobutylbenzyloxycarbamido)morphinan, 17-cyclopropylmethyl-4,5α-epoxy-3-acetoxy-14β-hydroxy-6α-(N-isobutylphenylmethanesulfonamido) morphinan, 17-allyl-4,5α-epoxy-3-acetoxy-14β-hydroxy-6α- (N- isobutyl-3,4-dichlorophenylacetamido)morphinan, 17-allyl-4,5(1-epoxy-3-acetoxy-14β-hydroxy-6α-(N-isobutylcinnamamido)morphinan, 17-allyl-4,5α-epoxy-3-acetoxy-14β-hydroxy-6α-(N-isobutylbenzyloxycarbamido) morphinan, 17-allyl-4,5α-epoxy-3-acetoxy-14β-hydroxy-6α-(N-isobutylphenylmethanesulfonamido)morphinan, 17-methyl-4,5α-epoxy-3-acetoxy-14β-hydroxy-6α-(N-isobutyl-3,4-dichlorophenylacetamido)morphinan, 17-methyl- 4,5α-epoxy-3-acetoxy-14β-hydroxy-6α-(N-isobutylcinnamamido)morphinan, 17-methyl-4,5α-epoxy-3-acetoxy-14β-hydroxy-6α-(N-isobutylbenzyloxycarbamido)morphinan, 17-methyl-4,5α-epoxy-3-acetoxy-14β-hydroxy-6α-(N-isobutylphenylmethanesulfonamido)morphinan, 17-phenethyl-4,5α-epoxy-3-acetoxy-14β-hydroxy-6α-(N-isobutyl-3,4-dichlorophenylacetamido)morphinan, 17-phenethyl-4,5α-epoxy-3-acetoxy-14β-hydroxy-6α-(N-isobutylcinnamamido)morphinan, 17-phenethyl-4,5α-epoxy-3-acetoxy-14β-hydroxy-6α-(N-isobutylbenzyloxycarbamido)morphinan, 17-phenethyl-4,5α-epoxy-3-acetoxy-14β-hydroxy-6α-(N-isobutylphenylmethanesulfonamido)morphinan, 17-cyclopropylmethyl-4,5α-epoxy-3,14β-diacetoxy-6α-(N-isobutyl-3,4-dichlorophenylacetamido)morphinan, 17-cyclopropylmethyl-4,5α-epoxy-3,14β-diacetoxy-6α-(N-isobutylcinnamamido)morphinan, 17-cyclopropylmethyl-4,5α-epoxy-3,14β-diacetoxy-6α-(N-isobutylbenzyloxycarbamido)morphinan, 17-cyclopropylmethyl-4,5α-epoxy-3,14β-diacetoxy-6α-(N-isobutylphenylmethanesulfonamido)morphinan, 17-allyl-4,5α-epoxy-3,14β-diacetoxy-6α-(N-isobutyl-3,4-dichlorophenylacetamido)morphinan, 17-allyl-4,5α-epoxy-3,14β-diacetoxy-6α-(N-isobutylcinnamamido)morphinan, 17-allyl-4,5α-epoxy-3,14β-diacetoxy-6α-(N-isobutylbenzyloxycarbamido)morphinan, 17-allyl-4,5α-epoxy-3,14β-diacetoxy-6α-(N-isobutylphenylmethanesulfonamido)morphinan, 17-methyl-4,5α-epoxy-3,14β-diacetoxy-6α-(N-isobutyl-3,4-dichlorophenylacetamido)morphinan, 17-methyl-4,5α-epoxy-3,14β-diacetoxy-6α-(N-isobutylcinnamamido) morphinan, 17-methyl-4,5α-epoxy-3,14β-diacetoxy-6α-(N-isobutylbenzyloxycarbamido)morphinan, 17-methyl-4,5α-epoxy-3,14β-diacetoxy-6α-(N-isobutylphenylmethanesulfonamido)morphinan, 17-phenethyl-4,5α-epoxy-3,14β-diacetoxy-6α-(N-isobutyl-3,4-dichlorophenylacetamido)morphinan, 17-phenethyl-4,5α-epoxy-3,14β-diacetoxy-6α-(N-isobutylcinnamamido) morphinan, 17-phenethyl- 4,5(1-epoxy-3,14β-diacetoxy-6α-(N-isobutylbenzyloxycarbamido)morphinan, 17-phenethyl-4,5α-epoxy-3,14-diacetoxy-6α-(N-isobutylphenylmethanesulfonamido)morphinan, 17-cyclopropylmethyl-4,5α-epoxy-14β-hydroxy-6α-(N-isobutyl-3,4-dichlorophenylacetamido)morphinan, 17-cyclopropylmethyl-4,5α-epoxy-14β-hydroxy-6α-(N-isobutylcinnamamido)morphinan, 17-cyclopropylmethyl-4, 5α-epoxy-14β-hydroxy-6β-(N-isobutylbenzyloxycarbamido)morphinan, 17-cyclopropylmethyl-4,5α-epoxy-14β-hydroxy-6α-(N-isobutylphenylmethanesulfonamido)morphinan, 17-allyl-4,5α-epoxy-14β-hydroxy-6α-(N-isobutyl-3,4-dichlorophenylacetamido)morphinan, 17-allyl-4,5α-epoxy-14β-hydroxy-6α-(N-isobutylcinnamamido)morphinan, 17-allyl-4,5α-epoxy-14β-hydroxy-6α-(N-isobutylbenzyloxycarbamido)morphinan, 17-allyl-4,5α-epoxy-14β-hydroxy-6α-(N-isobutylphenylmethanesulfonamido)morphinan, 17-methyl-4,5α-epoxy-14β-hydroxy-6α-(N-isobutyl-3,4-dichlorophenylacetamido)morphinan, 17-methyl-4,5α-epoxy-14β-hydroxy-6α-(N-isobutylcinnamamido)morphinan, 17-methyl-4,5α-epoxy-14β-hydroxy-6α-(N-isobutylbenzyloxycarbamido)morphinan, 17-methyl-4,5α-epoxy-14β-hydroxy-6α-(N-isobutylphenylmethanesulfonamido)morphinan, 17-phenethyl-4,5α-epoxy-14β-hydroxy-6α-(N-isobutyl-3,4-dichlorophenylacetamido)morphinan, 17-phenethyl-4,5α-epoxy-14β-hydroxy-6α-(N-isobutylcinnamamido)morphinan, 17-phenethyl-4,5α-epoxy-14β-hydroxy-6α-(N-isobutylbenzyloxycarbamido)morphinan, 17-phenethyl-4,5α-epoxy-14β-hydroxy-6α-(N-isobutylphenylmethanesulfonamido)morphinan, 17-cyclopropylmethyl-4,5α-epoxy-14β-acetoxy-6α-(N-isobutyl-3,4-dichlorophenylacetamido)morphinan, 17-cyclopropylmethyl-4,5α-epoxy-14β-acetoxy-6α-(N-isobutylcinnamamido)morphinan, 17-cyclopropylmethyl-4,5α-epoxy-14β-acetoxy-6α-(N-isobutylbenzyloxycarbamido) morphinan, 17-cyclopropylmethyl-4,5α-epoxy-14β-acetoxy-6α-(N-isobutylphenylmethanesulfonamido)morphinan, 17-allyl-4,5α-epoxy-14β-acetoxy-6α-(N-isobutyl-3,4-dichlorophenylacetamido)morphinan, 17-allyl-4,5α-epoxy-14β-acetoxy-6α-(N-isobutylcinnamamido)morphinan, 17-allyl-4,5α-epoxy-14β-acetoxy-6α-(N-isobutylbenzyloxycarbamido)morphinan, 17-allyl-4,5α-epoxy-14β-acetoxy-6α-(N-isobutylphenylmethanesulfonamido)morphinan, 17-methyl-4,5α-epoxy-14β-acetoxy-6α-(N-isobutyl-3,4-dichlorophenylacetamido)morphinan, 17-methyl-4,5α-epoxy-14β-acetoxy-6α-(N-isobutylcinnamamido)morphinan, 17-methyl-4,5α-epoxy-14β-acetoxy-6α-(N-isobutylbenzyloxycarbamido)morphinan, 17-methyl-4,5α-epoxy-14β-acetoxy-6α-(N-isobutylphenylmethanesulfonamido)morphinan, 17-phenethyl-4,5α-epoxy-14β-acetoxy-6α-(N-isobutyl-3,4-dichlorophenylacetamido)morphinan, 17-phenethyl-4,5α-epoxy-14β-acetoxy-6α-(N-isobutylcinnamamido)morphinan, 17-phenethyl-4,5α-epoxy-14β-acetoxy-6α-(N-isobutylbenzyloxycarbamido)morphinan, 17-phenethyl-4,5α-epoxy-14β-acetoxy-6α-(N-isobutylphenylmethanesulfonamido)morphinan, 17-cyclopropylmethyl-4,5α-epoxy-3-methoxy-14β-hydroxy-6α-(N-isobutyl-3,4-dichlorophenylacetamido)morphinan, 17-cyclopropylmethyl-4,5α-epoxy-3-methoxy-14β-hydroxy-6α-(N-isobutylcinnamamido)morphinan, 17-cyclopropylmethyl-4,5α-epoxy-3-methoxy-14β-hydroxy-6α-(N-isobutylbenzyloxycarbamido)morphinan, 17-cyclopropylmethyl-4,5α-epoxy-3-methoxy-14β-hydroxy-6α-(N-isobutylphenylmethanesulfonamido)morphinan, 17-allyl-4,5α-epoxy-3-methoxy-14β-hydroxy-6α-(N-isobutyl-3,4-dichlorophenylacetamido)morphinan, 17-allyl-4,5α-epoxy-3-methoxy-14β-hydroxy-6α-(N-isobutylcinnamamido)morphinan, 17-allyl-4,5α-epoxy-3-methoxy-14β-hydroxy-6α-(N-methylbenzyloxycarbamido)morphinan, 17-allyl-4,5α-epoxy-3-methoxy-14β-hydroxy-6α-(N-isobutylphenylmethanesulfonamido)morphinan, 17-methyl-4,5α-epoxy-3-methoxy-14β-hydroxy-6α-(N-isobutyl-3,4-dichlorophenylacetamido)morphinan, 17-methyl-4,5α-epoxy-3-methoxy-14β-hydroxy-6α-(N-isobutylcinnamamido)morphinan, 17-methyl-4,5α-epoxy-3-methoxy-14β-hydroxy-6α-(N-isoutylbenzyloxycarbamido)morphinan, 17-methyl-4,5α-epoxy-3-methoxy-14β-hydroxy-6α-(N-isobutylphenylmethanesulfonamido)morphinan, 17-phenethyl-4,5α-epoxy-3-methoxy-14β-hydroxy-6α-(N-isobutyl-3,4-dichlorophenylacetamido)morphinan, 17-phenethyl-4,5α-epoxy-3-methoxy-14β-hydroxy-6α-(N-isobutylcinnamamido)morphinan, 17-phenethyl-4,5α-epoxy-3-methoxy-14β-hydroxy-6α-(N-isobutylbenzyloxycarbamido)morphinan, 17-phenethyl-4,5α-epoxy-3-methoxy-14β-hydroxy-6α-(N-isobutylmethanesulfonamido)morphinan, 17-cyclopropylmethyl-4,5α-epoxy-3-methoxy-14β-acetoxy-6α-(N-isobutyl-3,4-dichlorophenylacetamido)morphinan, 17-cyclopropylmethyl-4,5α-epoxy-3-methoxy-14β-acetoxy-6α-(N-isobutylcinnamamido)morphinan, 17-cyclopropylmethyl-4,5α-epoxy-3-methoxy-14β-acetoxy-6α-(N-methylbenzyloxycarbamido)morphinan, 17-cyclopropylmethyl-4,5α-epoxy-3-methoxy-14β-acetoxy-6α-(N-isobutylphenylmethanesulfonamido)morphinan, 17-allyl-4,5α-epoxy-3-methoxy-14β-acetoxy-6α-(N-iobutyl-3,4-dichlorophenylacetamido)morphinan, 17-allyl-4,5α-epoxy-3-methoxy-14β-acetoxy-6α-(N-isobutylcinnamamido)morphinan, 17-allyl-4,5α-epoxy-3-methoxy-14β-acetoxy-6α-(N-isobutylbenzyloxycarbamido)morphinan, 17-allyl-4,5α-epoxy-3-methoxy-14β-acetoxy-6α-(N-isobutylphenylmethanesulfonamido)morphinan, 17-methyl-4,5α-epoxy-3-methoxy-14β-acetoxy-6α-(N-isobutyl-3,4-dichlorophenylacetamido)morphinan, 17-methyl-4,5α-epoxy-3-methoxy-14β-acetoxy-6α-(N-isobutylcinnamamido)morphinan, 17-methyl-4,5α-epoxy-3-methoxy-14β-acetoxy-6α-(N-isobutylbenzyloxycarbamido)morphinan, 17-methyl-4,5α-epoxy-3-methoxy-14β-acetoxy-6α-(N-isobutylphenylmethanesulfonamido)morphinan, 17-phenethyl-4,5α-epoxy-3-methoxy-14β-acetoxy-6α-(N-isobutyl-3,4-dichlorophenylacetamido)morphinan, 17-phenethyl-4,α-epoxy-3-methoxy-14β-acetoxy-6α-(N-isobutylcinnamamido)morphinan, 17-phenethyl-4,5α-epoxy-3-methoxy-14β-acetoxy- 6α-(N-isobutylbenzyloxycarbamido)morphinan, 17-phenethyl-4,5α-epoxy-3-methoxy-14β-acetoxy-6α-(N-isobutylphenylmethanesulfonamido)morphinan, 17-cyclopropylmethyl-4,5α-epoxy-3-acetoxy-14β-hydroxy-6α-(N-isobutyl-3,4-dichlorophenylacetamido)morphinan, 17-cyclopropylmethyl-4,5α-epoxy-3-acetoxy-14β-hydroxy-6α-(N-isobutylcinnamamido)morphinan, 17-cyclopropylmethyl-4,5α-epoxy-3-acetoxy- 14β-hydroxy-6α-(N-isobutylbenzyloxycarbamido)morphinan, 17-cyclopropylmethyl-4,5α-epoxy-3-acetoxy-14β-hydroxy-6α-(N-isobutylphenylmethanesulfonamido)morphinan, 17-allyl-4,5α-epoxy-3-acetoxy-14β-hydroxy-6α-(N-isobutyl-3,4-dichlorophenylacetamido)morphinan, 17-allyl-4,5α-epoxy-3-acetoxy-14β-hydroxy-6α-(N-isobutylcinnamamido)morphinan, 17-allyl-4,5α-epoxy-3-acetoxy-14β-hydroxy-6α-(N-isobutylbenzyloxycarbamido)morphinan, 17-allyl-4,5α-epoxy-3-acetoxy-14β-hydroxy-6α-(N-isobutylphenylmethanesulfonamido)morphinan, 17-methyl-4,5α-epoxy-3-acetoxy-14β-hydroxy-6α-(N-isobutyl-3,4-dichlorophenylacetamido)morphinan, 17-methyl-4,5α-epoxy-3-acetoxy-14β-hydroxy-6α-(N-isobutylcinnamamido)morphinan, 17-methyl-4,5α-epoxy- 3-acetoxy-14β-hydroxy-6α-(N-isobutylbenzyloxycarbamido)morphinan, 17-methyl-4,5α-epoxy-3-acetoxy-14β-hydroxy-6α-(N-isobutylphenylmethanesulfonamido)morphinan, 17-phenethyl-4,5α-epoxy-3-acetoxy-14β-hydroxy-6α-(N-isobutyl-3,4-dichlorophenylacetamido)morphinan, 17-phenethyl-4,5α-epoxy-3-acetoxy-14β-hydroxy-6α-(N-isobutylcinnamamido)morphinan, 17-phenethyl-4,5α-epoxy-3-acetoxy-14β-hydroxy-6α-(N-isobutylbenzyloxycarbamido)morphinan, 17-phenethyl-4,5α-epoxy-3-acetoxy-14β-hydroxy-6α-(N-isobutylphenylmethanesulfonamido)morphinan, 17-cyclopropylmethyl-4,5α-epoxy-3,14β-diacetoxy-6α-(N-isobutyl-3,4-dichlorophenylacetamido)morphinan, 17-cyclopropylmethyl-4,5α-epoxy-3,14β-diacetoxy-6α-(N-isobutylcinnamamido)morphinan, 17-cyclopropylmethyl-4,5α-epoxy-3,14β-diacetoxy-6α-(N-isobutylbenzyloxycarbamido)morphinan, 17-cyclopropylmethyl-4,5α-epoxy-3,14β-diacetoxy-6α-(N-isobutylphenylmethanesulfonamido)morphinan, 17-allyl-4,5α-epoxy-3,14β-diacetoxy-6α-(N-isobutyl-3,4-dichlorophenylacetamido)morphinan, 17-allyl-4,5α-epoxy-3,14β-diacetoxy-6α-(N-isobutylcinnamamido)morphinan, 17-allyl-4,5α-epoxy-3,14β-diacetoxy-6α-(N-isobutylbenzyloxycarbamido)morphinan, 17-allyl-4,5α-epoxy-3,14β-diacetoxy-6α-(N-isobutylphenylmethanesulfonamido)morphinan, 17-methyl-4,5α-epoxy-3,14β-diacetoxy-6α-(N-isobutyl-3,4-dichlorophenylacetamido)morphinan, 17-methyl-4,5α-epoxy-3-methoxy-14β-acetoxy-6α-(N-methylcinnamamido)morphinan, 17-methyl-4,5α-epoxy-3,14β-diacetoxy-6α-(N-isobutylbenzyloxycarbamido)morphinan, 17-methyl-4,5α-epoxy-3,14β-diacetoxy-6α-(N-isobutylphenylmethanesulfonamido)morphinan, 17-phenethyl-4,5α-epoxy-3,14β-diacetoxy-6α-(N-isobutyl-3,4-dichlorophenylacetamido)morphinan, 17-phenethyl-4,5α-epoxy-3,14,-diacetoxy-6α-(N-isobutylcinnamamido)morphinan, 17-phenethyl-4,5α-epoxy-3,14(3-diacetoxy-6α-(N-isobutylbenzyloxycarbamido)morphinan, 17-phenethyl-4,5α-epoxy-3,14β-diacetoxy-6α-(N-isobutylphenylmethanesulfonamido)morphinan, 17-cyclopropylmethyl-4,5α-epoxy-3,14β-dihydroxy-6α-(N-methyl-3,4-dichlorophenylacetamido)morphinan, 17-cyclopropylmethyl-4,5α-epoxy-3,14β-dihydroxy-6β-(N-methylcinnamamido)morphinan, 17-cyclopropylmethyl-4,5α-epoxy-3,14β-dihydroxy-6β-(N-methylbenzyloxycarbamido)morphinan, 17-cyclopropylmethyl-4,5α-epoxy-3,14β-dihydroxy-6α-(N-metylphenylmethanesulfonamido)morphinan, 17-allyl-4,5α-epoxy-3,14β-dihydroxy-6β-(N-methyl-3,4-dichlorophenylacetamido)morphinan, 17-allyl-4,5α-epoxy-3,14β-dihydroxy-6α-(N-methylcinnamamido)morphinan, 17-allyl-4,5α-epoxy-3,14β-dihydroxy-6α-(N-methylbenzyloxycarbamido)morphinan, 17-allyl-4,5α-epoxy-3,14β-dihydroxy-6β-(N-methylphenylmethanesulfonamido)morphinan, 17-methyl-4,5α-epoxy-3,14β-dihydroxy-6β-(N-methyl-3,4-dichlorophenylacetamido)morphinan, 17-methyl-4,5α-epoxy-3,14β-dihydroxy-6β-(N-methylcinnamamido)morphinan, 17-methyl-4,5α-epoxy-3,14β-dihydroxy-6β-(N-methylbenzyloxycarbamido)morphinan, 17-methyl-4,5α-epoxy-3,14β-dihydroxy-6β-(N-methylphenylmethanesulfonamido)morphinan, 17-phenethyl-4,5α-epoxy-3,14β-dihydroxy-6β-(N-methyl-3,4-dichlorophenylacetamido) morphinan, 17-phenethyl-4,5α-epoxy-3,14β-dihydroxy-6β-(N-methylcinnamamido) morphinan, 17-phenethyl-4,5α-epoxy-3,14β-dihydroxy-6β-(N-methylbenzyloxycarbamido)morphinan, 17-phenethyl-4,5α-epoxy-3,14β-dihydroxy-6β-(N-methylphenylmethanesulfonamido)morphinan, 17-cyclopropylmethyl-4,5α-epoxy-3-hydroxy-14β-acetoxy-6β-(N-methyl-3,4-dichlorophenylacetamido) morphinan, 17-cyclopropylmethyl-4,5α-epoxy-3-hydroxy-14β-acetoxy-6β-(N-methylcinnamamido)morphinan, 17-cyclopropylmethyl-4,5α-epoxy-3-hydroxy-14β-acetoxy-6β-(N-methylbenzyloxycarbamido)morphinan, 17-cyclopropylmethyl-4,5α-epoxy-3-hydroxy-14β-acetoxy-6β-(N-methylphenylmethanesulfonamido) morphinan, 17-allyl-4,5α-epoxy-3-hydroxy-14β-acetoxy-6β-(N-methyl-3,4-dichlorophenylacetamido)morphinan, 17-allyl-4,5α-epoxy-3-hydroxy-14β-acetoxy-6β-(N-methylcinnamamido)morphinan, 17-allyl-4,5α-epoxy-3-hydroxy-14β-acetoxy-6β-(N-methylbenzyloxycarbamido) morphinan, 17-allyl-4,5α-epoxy-3-hydroxy-14β-acetoxy-6β-(N-methylphenylmethanesulfonamido)morphinan, 17-methyl-4,5α-epoxy-3-hydroxy-14β-acetoxy-6β-(N-methyl-3,4-dichlorophenylacetamido)morphinan, 17-methyl-4,5α-epoxy-3-hydroxy-14β-acetoxy-6β-(N-methylcinnamamido) morphinan, 17-methyl-4,5α-epoxy-3-hydroxy-14β-acetoxy-6β-(N-methylbenzyloxycarbamido)morphinan, 17-methyl-4,5α-epoxy-3-hydroxy-14β-acetoxy-6β-(N-methylphenylmethanesulfonamido)morphinan, 17-phenethyl-4,5α-epoxy-3-hydroxy-14β-acetoxy-6β-(N-methyl-3,4-dichlorophenylacetamido)morphinan, 17-phenethyl-4,5α-epoxy-3-hydroxy-14β-acetoxy-6β-(N-methylcinnamamido)morphinan, 17-phenethyl-4,5α-epoxy-3-hydroxy-14β-acetoxy-6β-(N-methylbenzyloxycarbamido)morphinan, 17-phenethyl-4,5α-epoxy-3-hydroxy-14β-acetoxy-6β-(N-methylphenylmethanesulfonamido)morphinan, 17-cyclopropylmethyl-4,5α-epoxy-14β-hydroxy-6β-(N-methyl-3,4-dichlorophenylacetamido)morphinan, 17-cyclopropylmethyl-4,5α-epoxy-14β-hydroxy-6β-(N-methylcinnamamido)morphinan, 17-cyclopropylmethyl-4,5α-epoxy-14β-hydroxy-6β-(N-methylbenzyloxycarbamido)morphinan, 17-cyclopropylmethyl-4,5α-epoxy-14β-hydroxy-6β-(N-methylphenylmethanesulfonamido)morphinan, 17-allyl-4,5α-epoxy-14β-hydroxy-6β-(N-methyl-3,4-dichlorophenylacetamido)morphinan, 17-allyl-4,5α-epoxy-14β-hydroxy-6β-(N-methylcinnamamido)morphinan, 17-allyl-4,5α-epoxy-14β-hydroxy-6β-(N-methylbenzyloxycarbamido)morphinan, 17-allyl-4,5α-epoxy-14β-hydroxy-6β-(N-methylphenylmethanesulfonamido)morphinan, 17-methyl-4,5α-epoxy-14β-hydroxy-6β-(N-methyl-3,4-dichlorophenylacetamido)morphinan, 17-methyl-4,5α-epoxy-14β-hydroxy-6β-(N-methylcinnamamido) morphinan, 17-methyl-4,5α-epoxy-14β-hydroxy-6β-(N-methylbenzyloxycarbamido)morphinan, 17-methyl-4,5α-epoxy-14β-hydroxy-6β-(N-methylphenylmethanesulfonamido)morphinan, 17-phenethyl-4,5α-epoxy-14β-hydroxy-6β-(N-methyl-3,4-dichlorophenylacetamido)morphinan, 17-phenethyl-4,5α-epoxy-14β-hydroxy-6β-(N-methylcinnamamido) morphinan, 17-phenethyl-4,5α-epoxy-14β-hydroxy-6β-(N-methylbenzyloxycarbamido)morphinan, 17-phenethyl-4,5α-epoxy-14β-hydroxy-6β-(N-methylphenylmethanesulfonamido)morphinan, 17-cyclopropylmethyl-4,5α-epoxy-14β-acetoxy-6β-(N-methyl-3,4-dichlorophenylacetamido)morphinan, 17-cyclopropylmethyl-4,5α-epoxy-14β-acetoxy-6β-(N-methylcinnamamido)morphinan, 17-cyclopropylmethyl-4, 5α-epoxy-14β-acetoxy-6β(N-methylbenzyloxycarbamido) morphinan, 17-cyclopropylmethyl-4,5α-epoxy-14β-acetoxy-6β-(N-methylphenylmethanesulfonamido) morphinan, 17-allyl-4,5α-epoxy-14β-acetoxy-6α-(N-methyl-3,4-dichlorophenylacetamido)morphinan, 17-allyl-4,5α-epoxy-14β-acetoxy-6β-(N-methylcinnamamido) morphinan, 17-allyl-4,5α-epoxy-14β-acetoxy-6β-(N-methylbenzyloxycarbamido)morphinan, 17-allyl-4,5α-epoxy-14β-acetoxy-6β-(N-methylphenylmethanesulfonamido)morphinan, 17-methyl-4,5α-epoxy-14β-acetoxy-6β-(N-methyl-3,4-dichlorophenylacetamido)morphinan, 17-methyl-4,5α-epoxy-14β-acetoxy-6β-(N-methylcinnamamido)morphinan, 17-methyl-4,5α-epoxy-14β-acetoxy-6β-(N-methylbenzyloxycarbamido) morphinan, 17-methyl-4,5α-epoxy-14β-acetoxy-6β-(N-methylphenylmethanesulfonamido)morphinan, 17-phenethyl-4,5α-epoxy-14β-acetoxy-6β-(N-methyl-3,4-dichlorophenylacetamido)morphinan, 17-phenethyl-4,5α-epoxy-14β-acetoxy-6β-(N-methylcinnamamido) morphinan, 17-phenethyl-4,5α-epoxy-14β-acetoxy-6β-(N-methylbenzyloxycarbamido)morphinan, 17-phenethyl-4,5α-epoxy-14β-acetoxy-6β-(N-methylphenylmethanesulfonamido)morphinan, 17-cyclopropylmethyl-4,5α-epoxy-3-methoxy-14β-hydroxy-6β-(N-methyl-3,4-dichlorophenylacetamido) morphinan, 17-cyclopropylmethyl-4,5α-epoxy-3-methoxy-14β-hydroxy-6β-(N-methylcinnamamido)morphinan, 17-cyclopropylmethyl-4,5α-epoxy-3-methoxy-14β-hydroxy-6β-(N-methylbenzyloxycarbamido)morphinan, 17-cyclopropylmethyl-4,5α-epoxy-3-methoxy-14β-hydroxy-6β-(N-methylphenylmethanesulfonamido) morphinan, 17-allyl-4,5α-epoxy-3-methoxy-14β-hydroxy-6β-(N-methyl-3,4-dichlorophenylacetamido)morphinan, 17-allyl-4,5α-epoxy-3-methoxy-14β-hydroxy-6β-(N-methylcinnamamido)morphinan, 17-allyl-4,5α-epoxy-3-methoxy-14β-hydroxy-6β-(N-methylbenzyloxycarbamido) morphinan, 17-allyl-4,5α-epoxy-3-methoxy-14β-hydroxy-6β-(N-methylphenylmethanesulfonamido)morphinan, 17-methyl-4,5α-epoxy-3-methoxy-14β-hydroxy-6β-(N-methyl-3,4-dichlorophenylacetamido)morphinan, 17-methyl-4,5α-epoxy-3-methoxy-14β-hydroxy-6p-(N-methylcinnamamido)morphinan, 17-methyl-4,5α-epoxy-3-methoxy- 14β-hydroxy-6β-(N-methylbenzyloxycarbamido) morphinan, 17-methyl-4,5α-epoxy-3-methoxy-14β-hydroxy-6β-(N-methylphenylmethanesulfonamido) morphinan, 17-phenethyl-4,5α-epoxy-3-methoxy-14β-hydroxy-6β-(N-methyl-3,4-dichlorophenylacetamido) morphinan, 17-phenethyl-4,5α-epoxy-3-methoxy-14β-hydroxy-6β-(N-methylcinnamamido)morphinan, 17-phenethyl-4,5α-epoxy-3-methoxy-14β-hydroxy-6β-(N-methylbenzyloxycarbamido)morphinan, 17-phenethyl-4,5-epoxy-3-methoxy-14β-hydroxy-6β-(N-methylphenylmethanesulfonamido)morphinan, 17-cyclopropylmethyl-4,5α-epoxy-3-methoxy-14β-acetoxy-6β-(N-methyl-3,4-dichlorophenylacetamido) morphinan, 17-cyclopropylmethyl-4,5α-epoxy-3-methoxy-14β-acetoxy-6β-(N-methylcinnamamido)morphinan, 17-cyclopropylmethyl-4,5α-epoxy-3-methoxy-14β-acetoxy-6β-(N-methylbenzyloxycarbamido)morphinan, 17-cyclopropylmethyl-4,5α-epoxy-3-methoxy-14β-acetoxy-6β-(N-methylphenylmethanesulfonamido) morphinan, 17-allyl-4,5α-epoxy-3-methoxy-14β-acetoxy-6β-(N-methyl-3,4-dichlorophenylacetamido)morphinan, 17-allyl-4,5α-epoxy-3-methoxy-14β-acetoxy-6β-(N-methylcinnamamido)morphinan, 17-allyl-4,5α-epoxy-3-methoxy-14β-acetoxy-6β-(N-methylbenzyloxycarbamido)morphinan, 17-allyl-4,5α-epoxy-3-methoxy-14β-acetoxy-6β-(N-methylphenylmethanesulfonamido)morphinan, 17-methyl-4,5α-epoxy-3-methoxy-14β-acetoxy-6β-(N-methyl-3,4-dichlorophenylacetamido)morphinan, 17-methyl-4,5α-epoxy-3-methoxy-14β-acetoxy-6β-(N-methylcinnamamido)morphinan, 17-methyl-4,5α-epoxy-3-methoxy-14β-acetoxy-6β- (N-methylbenzyloxycarbamido) morphinan, 17-methyl-4,5α-epoxy-3-methoxy-14β-acetoxy-6β(N-methylphenylmethanesulfonamido) morphinan, 17-phenethyl-4,5α-epoxy-3-methoxy-14β-acetoxy-6β, (N-methyl-3,4-dichlorophenylacetamido) morphinan, 17-phenethyl-4,5α-epoxy-3-methoxy-14β-acetoxy-6β(N-methylcinnamamido)morphinan, 17-phenethyl-4,5α-epoxy-3-methoxy-14β-acetoxy-6β(N-methylbenzyloxycarbamido)morphinan, 17-phenethyl-4,5α-epoxy-3-methoxy-14β-acetoxy- 6β-(N-methylphenylmethanesulfonamido)morphinan, 17-cyclopropylmethyl-4,5α-epoxy-3-acetoxy-14β-hydroxy-6β-(N-methyl-3,4-dichlorophenylacetamido) morphinan, 17-cyclopropylmethyl-4,5α-epoxy-3-acetoxy-14β-hydroxy-6β-(N-methylcinnamamido)morphinan, 17-cyclopropylmethyl-4,5α-epoxy-3-acetoxy-14β-hydroxy-6β-(N-methylbenzyloxycarbamido)morphinan, 17-cyclopropylmethyl-4,5α-epoxy-3-acetoxy-14β-hydroxy-6β-(N-methylphenylmethanesulfonamido) morphinan, 17-allyl-4,5α-epoxy-3-acetoxy-14β-hydroxy-6β-(N-methyl-3,4-dichlorophenylacetamido)morphinan, 17-allyl-4,5α-epoxy-3-acetoxy-14β-hydroxy-6β-(N-methylcinnamamido)morphinan, 17-allyl-4,5α-epoxy-3-acetoxy-14β-hydroxy-6β-(N-methylbenzyloxycarbamido) morphinan, 17-allyl-4,5α-epoxy-3-acetoxy-14β-hydroxy-6β-(N-methylphenylmethanesulfonamido)morphinan, 17-methyl-4,5α-epoxy-3-acetoxy-14β-hydroxy-6β-(N-methyl-3,4-dichlorophenylacetamido)morphinan, 17-methyl-4,5α-epoxy-3-acetoxy-14β-hydroxy-6β-(N-methylcinnamamido)morphinan, 17-methyl-4,5α-epoxy-3-acetoxy-14β-hydroxy-6β-(N-methylbenzyloxycarbamido)morphinan, 17-methyl-4,5α-epoxy-3-acetoxy-14β-hydroxy-6β-(N-methylphenylmethanesulfonamido)morphinan, 17-phenethyl-4,5α-epoxy-3-acetoxy-14β-hydroxy-6β-(N-methyl-3,4-dichlorophenylacetamido)morphinan, 17-phenethyl-4,5α-epoxy-3-acetoxy-14β-hydroxy-6β-(N-methylcinnamamido)morphinan, 17-phenethyl-4,5α-epoxy-3-acetoxy-14β-hydroxy--6β-(N-methylbenzyloxycarbamido)morphinan, 17-phenethyl-4,5α-epoxy-3-acetoxy-14β-hydroxy-6β-(N-methylphenylmethanesulfonamido)morphinan, 17-cyclopropylmethyl-4,5α-epoxy-3,14β-diacetoxy-6β-(N-methyl-3,4-dichlorophenylacetamido)morphinan, 17-cyclopropylmethyl-4,5α-epoxy-3,14β-diacetoxy-6β-(N-methylcinnamamido)morphinan, 17-cyclopropylmethyl-4,5α-epoxy-3,14β-diacetoxy-6β-(N-methylbenzyloxycarbamido)morphinan, 17-cyclopropylmethyl-4,5α-epoxy-3,14β-diacetoxy-6β-(N-methylphenylmethanesulfonamido)morphinan, 17-allyl-4,5α-epoxy-3,14β-diacetoxy-6β-(N-methyl-3,4-dichlorophenylacetamido)morphinan, 17-allyl-4,5α-epoxy-3,14β-diacetoxy-6β-(N-methylcinnamamido)morphinan, 17-allyl-4,5α-epoxy-3,14β-diacetoxy-6β-(N-methylbenzyloxycarbamido)morphinan, 17 -allyl-4,5α-epoxy-3,14β-diacetoxy-6β-(N-methylphenylmethanesulfonamido)morphinan, 17-methyl-4,5α-epoxy-3,14β-diacetoxy-6β-(N-methyl-3,4-dichlorophenylacetamido)morphinan, 17-methyl-4,5α-epoxy-3,14β-diacetoxy-6β-(N-methylcinnamamido) morphinan, 17-methyl-4,5α-epoxy-3,14β-diacetoxy-6β-(N- methylbenzyloxycarbamido)morphinan, 17-methyl-4,5α-epoxy-3,14β-diacetoxy-6β-(N-methylphenylmethanesulfonamido)morphinan, 17-phenethyl-4,5α-epoxy-3,14β-diacetoxy-6β-(N-methyl-3,4-dichlorophenylacetamido)morphinan, 17-phenethyl-4,5α-epoxy-3 14β-diacetoxy-6β-(N-methylcinnamamido)morphinan, 17-phenethyl-4,5α-epoxy-3,14β-diacetoxy-6β-(N-methylbenzyloxycarbamido)morphinan, 17-phenethyl-4,5α-epoxy-3,14β-diacetoxy-6β-(N-methylphenylmethanesulfonamido)morphinan, 17-cyclopropylmethyl-4,5α-epoxy-3,14β-dihydroxy-6β-(N-isobutyl-3,4-dichlorophenylacetamido) morphinan, 17-cyclopropylmethyl-4,5α-epoxy-3,14β-dihydroxy-6β-(N-isobutylcinnamamido)morphinan, 17-cyclopropylmethyl-4,5α-epoxy-3,14β-dihydroxy-6β-(N-isobutylbenzyloxycarbamido)morphinan, 17-cyclopropylmethyl-4,5α-epoxy-3,14β-dihydroxy-6β-(N-isobutylphenylmethanesulfonamido)morphinan, 17-allyl-4,5α-epoxy-3,14β-dihydroxy-6β-(N-isobutyl-3,4-dichlorophenylacetamido)morphinan, 17-allyl-4,5α-epoxy-3,14β-dihydroxy-6β-(N-isobutylcinnamamido)morphinan, 17-allyl-4,5α-epoxy-3,14-dihydroxy-6β-(N-isobutylbenzyloxycarbamido)morphinan, 17-allyl-4,5α-epoxy-3,14β-dihydroxy-6β(N-isobutylphenylmethanesulfonamido)morphinan, 17-methyl-4,5α-epoxy-3,14β-dihydroxy-6β-(N-isobutyl-3,4-dichlorophenylacetamido)morphinan, 17-methyl-4,5α-epoxy-3,14β-dihydroxy-6β-(N-isobutylcinnamamido)morphinan, 17-methyl-4,5α-epoxy-3,14β-dihydroxy-6β-(N-isobutylbenzyloxycarbamido)morphinan, 17-methyl-4,5α-epoxy-3,14β-dihydroxy-6β-(N-isobutylphenylmethanesulfonamido)morphinan, 17-phenethyl-4,5α-epoxy-3,14β-dihydroxy-6β-(N-isobutyl-3,4-dichlorophenylacetamido)morphinan, 17-phenethyl-4,5α-epoxy-3,14β-dihydroxy-6β-(N-isobutylcinnamamido)morphinan, 17-phenethyl-4,5α-epoxy-3,14β-dihydroxy-6β-(N-isobutylbenzyloxycarbamido)morphinan, 17-phenethyl-4,5α-epoxy-3,14β-dihydroxy-6β-(N-isobutylphenylmethanesulfonamido)morphinan, 17-cyclopropylmethyl-4,5α-epoxy-3-hydroxy-14β-acetoxy-6β-(N-isobutyl-3,4-dichlorophenylacetamido)morphinan, 17-cyclopropylmethyl-4,5α-epoxy-3-hydroxy-14β-acetoxy-6β-(N-isobutylcinnamamido)morphinan, 17-cyclopropylmethyl-4,5α-epoxy-3-hydroxy-14β-acetoxy-6β-(N-isobutylbenzyloxycarbamido)morphinan, 17-cyclopropylmethyl-4,5α-epoxy-3-hydroxy-14β-acetoxy-6β-(N-isobutylphenylmethanesulfonamido)morphinan, 17-allyl-4,5α-epoxy-3-hydroxy-14β-acetoxy-6β-(N-isobutyl-3,4-dichlorophenylacetamido)morphinan, 17-allyl-4,5α-epoxy-3-hydroxy-14β-acetoxy-6β-(N-isobutylcinnamamido)morphinan, 17-allyl-4,5α-epoxy-3-hydroxy-14β-acetoxy-6β-(N-isobutylbenzyloxycarbamido)morphinan, 17-allyl-4,5α-epoxy-3-hydroxy-14βacetoxy-6β-(N-isobutylphenylmethanesulfonamido)morphinan, 17-methyl-4,5α-epoxy-3-hydroxy-14β-acetoxy-6β-(N-isobutyl-3,4-dichlorophenylacetamido)morphinan, 17-methyl-4,5α-epoxy-3-hydroxy-14βacetoxy-6β-(N-isobutylcinnamamido)morphinan, 17-methyl-4,5α-epoxy-3-hydroxy-14β-acetoxy-6β-(N-isobutylbenzyloxycarbamido)morphinan, 17-methyl-4,5α-epoxy-3-hydroxy-14β-acetoxy-6β-(N-isobutylphenylmethanesulfonamido)morphinan, 17-phenethyl-4,5α-epoxy-3-hydroxy-14β-acetoxy-6β-(N-isobutyl-3,4-dichlorophenylacetamido)morphinan, 17-phenethyl-4,5α-epoxy-3-hydroxy-14β-acetoxy-6β-(N-isobutylcinnamamido)morphinan, 17-phenethyl-4,5α-epoxy-3-hydroxy-14β-acetoxy-6β-(N-isobutylbenzyloxycarbamido)morphinan, 17-phenethyl-4,5α-epoxy-3-hydroxy-14β-acetoxy-6β-(N-isobutylphenylmethanesulfonamido)morphinan, 17-cyclopropylmethyl-4,5α-epoxy-14β-hydroxy-6β-(N-isobutyl-3,4-dichlorophenylacetamido)morphinan, 17-cyclopropylmethyl-4,5α-epoxy-14β-hydroxy-6β-(N-isobutylcinnamamido)morphinan, 17-cyclopropylmethyl-4,5α-epoxy-14β-hydroxy-6β-(N-isobutylbenzyloxycarbamido)morphinan, 17-cyclopropylmethyl-4,5α-epoxy-14β-hydroxy-6β-(N-isobutylphenylmethanesulfonamido)morphinan, 17-allyl-4,5α-epoxy-14β-hydroxy-6β-(N-isobutyl-3,4-dichlorophenylacetamido)morphinan, 17-allyl-4,5α-epoxy-14β-hydroxy-6β(N-isobutylcinnamamido)morphinan, 17-allyl-4,5α-epoxy-14β-hydroxy-6β-(N-isobutylbenzyloxycarbamido)morphinan, 17-allyl-4,5α-epoxy-14β-hydroxy-6β-(N-isobutylphenylmethanesulfonamido)morphinan, 17-methyl-4,5α-epoxy-14β-hydroxy-6β-(N-isobutyl-3,4-dichlorophenylacetamido)morphinan, 17-methyl-4,5α-epoxy-14β-hydroxy-6β-(N-isobutylcinnamamido)morphinan, 17-methyl-4,5α-epoxy-14β-hydroxy-6β-(N-isobutylbenzyloxycarbamido)morphinan, 17-methyl-4,5α-epoxy-14β-hydroxy-6β-(N-isobutylphenylmethanesulfonamido)morphinan, 17-phenethyl-4,5α-epoxy-14β-hydroxy-6β-(N-isobutyl-3,4-dichlorophenylacetamido)morphinan, 17-phenethyl-4,5α-epoxy-14β-hydroxy-6β-(N-isobutylcinnamamido)morphinan, 17-phenethyl-4,5α-epoxy-14β-hydroxy-6β-(N-isobutylbenzyloxycarbamido)morphinan, 17-phenethyl-4,5α-epoxy-14β-hydroxy-6β-(N-isobutylphenylmethanesulfonamido)morphinan, 17-cyclopropylmethyl-4,5α-epoxy-14β-acetoxy-6β-(N-isobutyl-3,4-dichlorophenylacetamido)morphinan, 17-cyclopropylmethyl-4,5α-epoxy-14β-acetoxy-6β-(N-isobutylcinnamamido)morphinan, 17-cyclopropylmethyl-4,5α-epoxy-14β-acetoxy-6β-(N-isobutylbenzyloxycarbamido)morphinan, 17-cyclopropylmethyl-4,5α-epoxy-14β-acetoxy-6β-(N-isobutylphenylmethanesulfonamido)morphinan, 17-allyl-4,5α-epoxy-14β-acetoxy-6β-(N-isobutyl-3,4-dichlorophenylacetamido)morphinan, 17-allyl-4,5α-epoxy-14β-acetoxy-6β-(N-isobutylcinnamamido)morphinan, 17-allyl-4,5α-epoxy-14β-acetoxy-6β-(N-isobutylbenzyloxycarbamido)morphinan, 17-allyl-4,5α-epoxy-14β-acetoxy-6β-(N-isobutylphenylmethanesulfonamido)morphinan, 17-methyl-4,5α-epoxy-14β-acetoxy-6β-(N-isobutyl-3,4-dichlorophenylacetamido)morphinan, 17-methyl-4,5α-epoxy-14β-acetoxy-6β-(N-isobutylcinnamamido)morphinan, 17-methyl-4,5α-epoxy-14β-acetoxy-6β-(N-isobutylbenzyloxycarbamido)morphinan, 17-methyl-4,5α-epoxy-14β-acetoxy-6β-(N-isobutylphenylmethanesulfonamido)morphinan, 17-phenethyl-4,5α-epoxy-14β-acetoxy-6β-(N-isobutyl-3,4-dichlorophenylacetamido)morphinan, 17-phenethyl-4,5α-epoxy-14β-acetoxy-6β-(N-isobutylcinnamamido)morphinan, 17-phenethyl-4,5α-epoxy-14β-acetoxy-6β-(N-isobutylbenzyloxycarbamido)morphinan, 17-phenethyl-4,5α-epoxy-14β-acetoxy-6β-(N-isobutylphenylmethanesulfonamido)morphinan, 17-cyclopropylmethyl-4,5α-epoxy-3-methoxy-14β-hydroxy-6β-(N-isobutyl-3,4-dichlorophenylacetamido) morphinan, 17-cyclopropylmethyl-4,5α-epoxy-3-methoxy-14β-hydroxy-6β-(N-isobutylcinnamamido)morphinan, 17-cyclopropylmethyl-4,5α-epoxy-3-methoxy-14β- hydroxy-6β-(N-isobutylbenzyloxycarbamido)morphinan, 17-cyclopropylmethyl-4,5α-epoxy-3-methoxy-14β-hydroxy-6β-(N-isobutylphenylmethanesulfonamido) morphinan, 17-allyl-4,5α-epoxy-3-methoxy-14β-hydroxy-6β-(N-isobutyl-3,4-dichlorophenylacetamido)morphinan, 17-allyl-4,5α-epoxy-3-methoxy-14β-hydroxy-6β-(N-isobutylcinnamamido)morphinan, 17-allyl-4,5α-epoxy-3-methoxy-14β-hydroxy-6β-(N-isobutylbenzyloxycarbamido)morphinan, 17-allyl-4,5α-epoxy-3-methoxy-14β-hydroxy-6β-(N-isobutylphenylmethanesulfonamido)morphinan, 17-methyl-4,5α-epoxy-3-methoxy-14β-hydroxy-6β-(N-isobutyl-3,4-dichlorophenylacetamido)morphinan, 17-methyl-4,5α-epoxy-3-methoxy-14β-hydroxy-6β-(N-isobutylcinnamamido)morphinan, 17-methyl-4,5α-epoxy-3-methoxy-14β-hydroxy-6β-(N-isobutylbenzyloxycarbamido)morphinan, 17-methyl-4,5α-epoxy-3-methoxy-14β-hydroxy-6β-(N-isobutylphenylmethanesulfonamido)morphinan, 17-phenethyl-4,5α-epoxy-3-methoxy-14β-hydroxy-6β-(N-isobutyl-3,4-dichlorophenylacetamido)morphinan, 17-phenethyl-4,5α-epoxy-3-methoxy-14β-hydroxy-6β-(N-isobutylcinnamamido)morphinan, 17-phenethyl-4,5(1-epoxy-3-methoxy-14β-hydroxy-6β-(N-isobutylbenzyloxycarbamido)morphinan, 17-phenethyl-4,5α-epoxy-3-methoxy-14β-hydroxy-6β-(N-isobutylphenylmethanesulfonamido)morphinan, 17-cyclopropylmethyl-4,5α-epoxy-3-methoxy-14β-acetoxy-6β-(N-isobutyl-3,4-dichlorophenylacetamido) morphinan, 17-cyclopropylmethyl-4,5α-epoxy-3-methoxy-14β-acetoxy-6β-(N-isobutylcinnamamido)morphinan, 17-cyclopropylmethyl-4,5α-epoxy-3-methoxy-14β-acetoxy-6β-(N-isobutylbenzyloxycarbamido)morphinan, 17-cyclopropylmethyl-4,5α-epoxy-3-methoxy-14β-acetoxy-6β-(N-isobutylphenylmethanesulfonamido) morphinan, 17-allyl-4,5α-epoxy-3-methoxy-14β-acetoxy-6β-(N-isobutyl-3,4-dichlorophenylacetamido)morphinan, 17-allyl-4,5α-epoxy-3-methoxy-14β-acetoxy-6β-(N-isobutylcinnamamido)morphinan, 17-allyl-4,5α-epoxy-3-methoxy-14β-acetoxy-6β-(N-isobutylbenzyloxycarbamido) morphinan, 17-allyl-4,5α-epoxy-3-methoxy-14β-acetoxy-6β-(N-isobutylphenylmethanesulfonamido)morphinan, 17-methyl-4,5α-epoxy-3-methoxy-14β-acetoxy-6β-(N-isobutyl-3,4-dichlorophenylacetamido)morphinan, 17-methyl-4,5α-epoxy-3-methoxy-14β-acetoxy-6β-(N-isobutylcinnamamido)morphinan, 17-methyl-4,5(-epoxy-3-methoxy-14β-acetoxy-6β-(N-isobutylbenzyloxycarbamido) morphinan, 17-methyl-4,5α-epoxy-3-methoxy-14β-acetoxy-6β-(N-isobutylphenylmethanesulfonamido) morphinan, 17-phenethyl-4,51α-epoxy-3-methoxy-14β-acetoxy-6β-(N-isobutyl-3,4 -dichlorophenylacetamido) morphinan, 17-phenethyl-4,5α-epoxy-3-methoxy-14β-acetoxy-6β-(N-isobutylcinnamamido)morphinan, 17-phenethyl-4,5α-epoxy-3-methoxy-14β-acetoxy-6β-(N-isobutylbenzyloxycarbamido)morphinan, 17-phenethyl-4,5α-epoxy-3-methoxy-14β-acetoxy-6β-(N-isobutylphenylmethanesulfonamido)morphinan, 17-cyclopropylmethyl-4,5α-epoxy-3-acetoxy-14β-hydroxy-6β-(N-isobutyl-3,4-dichlorophenylacetamido) morphinan, 17-cyclopropylmethyl-4,5α-epoxy-3-acetoxy-14β-hydroxy-6β-(N-isobutylcinnamamido)morphinan, 17-cyclopropylmethyl-4,5α-epoxy-3-acetoxy-14β-hydroxy-6β-(N-isobutylbenzyloxycarbamido)morphinan, 17-cyclopropylmethyl-4,5α-epoxy-3-acetoxy-14β-hydroxy-6β-(N-isobutylphenylmethanesulfonamido) morphinan, 17-allyl-4,5α-epoxy-3-acetoxy-14β-hydroxy-6β-(N-isobutyl-3,4-dichlorophenylacetamido)morphinan, 17-allyl-4,5α-epoxy-3-acetoxy-14β-hydroxy-6β-(N-isobutylcinnamamido)morphinan, 17-allyl-4,5α-epoxy-3-acetoxy-14β-hydroxy-6β-(N-isobutylbenzyloxycarbamido) morphinan, 17-allyl-4,5α-epoxy-3-acetoxy-14β-hydroxy-6β-(N-isobutylphenylmethanesulfonamido)morphinan, 17-methyl-4,5α-epoxy-3-acetoxy-14β-hydroxy-6β-(N-isobutyl-3,4-dichlorophenylacetamido)morphinan, 17-methyl-4,5α-epoxy-3-acetoxy-14β-hydroxy-6β-(N-isobutylcinnamamido)morphinan, 17-methyl-4,5α-epoxy-3-acetoxy-14β-hydroxy-6β-(N-isobutylbenzyloxycarbamido)morphinan, 17-methyl-4,5α-epoxy-3-acetoxy-14β-hydroxy-6β-(N-isobutylphenylmethanesulfonamido)morphinan, 17-phenethyl-4,5α-epoxy-3-acetoxy-14β-hydroxy-6β-(N-isobutyl-3,4-dichlorophenylacetamido)morphinan, 17-phenethyl-4,5α-epoxy-3-acetoxy-14β-hydroxy-6β-(N-isobutylcinnamamido)morphinan, 17-phenethyl-4,5α-epoxy-3-acetoxy-14β-hydroxy-6β-(N-isobutylbenzyloxycarbamido)morphinan, 17-phenethyl-4,5α-epoxy-3-acetoxy-14β-hydroxy-6β-(N-isobutylphenylmethanesulfonamido)morphinan, 17-cyclopropylmethyl-4,5α-epoxy-3,14β-diacetoxy-6β-(N-isobutyl-3,4-dichlorophenylacetamido)morphinan, 17-cyclopropylmethyl-4,5α-epoxy-3,14β-diacetoxy-6β-(N-isobutylcinnamamido)morphinan, 17-cyclopropylmethyl-4,5α-epoxy-3,14β-diacetoxy-6β-(N-isobutylbenzyloxycarbamido)morphinan, 17-cyclopropylmethyl-4,5α-epoxy-3,14β-diacetoxy-6β-(N-isobutylphenylmethanesulfonamido)morphinan, 17-allyl-4,5α-epoxy-3,14β-diacetoxy-6β-(N-isobutyl-3,4-dichlorophenylacetamido)morphinan, 17-allyl-4,5α-epoxy-3,14β-diacetoxy-6β-(N-isobutylcinnamamido)morphinan, 17-allyl-4,5α-epoxy-3,14β-diacetoxy-6β-(N-isobutylbenzyloxycarbamido)morphinan, 17-allyl-4,5α-epoxy-3,14β-diacetoxy-6β-(N-isobutylphenylmethanesulfonamido)morphinan, 17-methyl-4,5α-epoxy-3,14β-diacetoxy-6β-(N-isobutyl-3,4-dichlorophenylacetamido) morphinan, 17-methyl-4,5α-epoxy-3,14-diacetoxy-6β-(N-isobutylcinnamamido) morphinan, 17-methyl-4,5α-epoxy-3,14β-diacetoxy-6β-(N-isobutylbenzyloxycarbamido)morphinan, 17-methyl-4,5α-epoxy-3,14β-diacetoxy-6β-(N-isobutylphenylmethanesulfonamido)morphinan, 17-phenethyl-4,5α-epoxy-3,14-diacetoxy-6β-(N-isobutyl-3, 4-dichlorophenylacetamido) morphinan, 17-phenethyl-4,5α-epoxy-3,14β-diacetoxy-6β-(N-isobutylcinnamamido) morphinan, 17-phenethyl-4,5α-epoxy-3,14β-diacetoxy-6β-(N-isobutylbenzyloxycarbamido)morphinan, 17-phenethyl-4,5α-epoxy-3,14β-diacetoxy-6β-(N-isobutylphenylmethanesulfonamido)morphinan, 17-cyclopropylmethyl-4,5α-epoxy-3,14β-dihydroxy-6α-(N-methyl-3,4-dichlorobenzamido)morphinan, 17-allyl-4,5α-epoxy-3,14β-dihydroxy-6α-(N-methyl-3,4-dichlorobenzamido)morphinan, 17-cyclopropylmethyl-4,5α-epoxy-3,14β-dihydroxy-6β-(N-methyl-3,4-dichlorobenzamido)morphinan, 17-allyl-4,5α-epoxy-3,14β-dihydroxy-6β-(N-methyl-3,4-dichlorobenzamido) morphinan, 17-cyclopropylmethyl-4,5α-epoxy-3,14β-dihydroxy-6α-(N-ethyl-3,4-dichlorophenylacetamido) morphinan, 17-allyl-4,5α-epoxy-3,14β-dihydroxy-6α-(N-ethyl-3,4-dichlorophenylacetamido)morphinan, 17-cyclopropylmethyl-4,5α-epoxy-3,14β-dihydroxy-6α-(N-ethyl-3,4-dichlorophenylacetamido)morphinan, 17-allyl-4,5α-epoxy-3,14β-dihydroxy-6β-(N-ethyl-3,4-dichlorophenylacetamido)morphinan, 17-cyclopropylmethyl-4,5α-epoxy-3,14β-dihydroxy-6α-(N-methyl-3-phenylpropionamido)morphinan, 17-allyl-4, 5α-epoxy-3,14β-dihydroxy-6α-(N-methyl-3-phenylpropionamido)morphinan, 17-cyclopropylmethyl-4,5α-epoxy-3,14β-dihydroxy-6β-(N-methyl-3-phenylpropionamido)morphinan, 17-allyl-4,5α-epoxy-3,14β-dihydroxy-6β-(N-methyl-3-phenylpropionamido)morphinan, 17-cyclopropylmethyl-4,5α-epoxy-3,14β-dihydroxy-6α-(N-methyl-3-(5-chlorobenzo[b]thienyl)acetamido)morphinan, 17-allyl-4,5α-epoxy-3,14β-dihydroxy-6α-[N-methyl-3-(5-chlorobenzo[b]thienyl)bacetamido]morphinan, 17-cyclopropylmethyl-4,5α-epoxy-3,14β-dihydroxy-6β-[N-methyl-3-(5-chlorobenzo[b]thienyl)acetamido]morphinan, 17-allyl-4,5α-epoxy-3,14β-dihydroxy-6β-[N-methyl-3-(5-chlorobenzo[b]thienyl)acetamido]morphinan, 17-cyclopropylmethyl-4,5α-epoxy-3,14β-dihydroxy-6α-(N-methylphenylacetamido)morphinan, 17-allyl-4,5α-epoxy-3,14β-dihydroxy-6α-(N-methylphenylacetamido)morphinan, 17-cyclopropylmethyl-4,5α-epoxy-3,14β-dihydroxy-6β-(N-methylphenylacetamido)morphinan, 17-allyl-4,5α-epoxy-3,14β-dihydroxy-6β-(N-methylphenylacetamido)morphinan, 17-cyclopropylmethyl-4,5α-epoxy-3,14β-dihydroxy-6α-(N-methylcyclohexylacetamido)morphinan, 17-allyl-4,5α-epoxy-3,14β-dihydroxy-6α-(N-methylcyclohexylacetamido)morphinan, 17-cyclopropylmethyl-4,5α-epoxy-3,14β-dihydroxy-6β-(N-methylcyclohexylacetamido)morphinan, 17-allyl-4,5α-epoxy-3,14-dihydroxy-6β-(N-methylcyclohexylacetamido)morphinan, 17-cyclopropylmethyl-4,5α-epoxy-3,14β-dihydroxy-6β-(N-methyl-3-bromophenylacetamido)morphinan, 17-allyl-4,5α-epoxy-3,14β-dihydroxy-6β-(N-methyl-3-bromophenylacetamido)morphinan, 17-cyclopropylmethyl-4,5α-epoxy-3,14β-dihydroxy-6α-(N-methyl-3-bromophenylacetamido)morphinan, 17-allyl-4,5α-epoxy-3,14β-dihydroxy-6α-(N-methyl-3-bromophenylacetamido)morphinan, 17-cyclopropylmethyl-4,5α-epoxy-3,14β-dihydroxy-6β-(N-methyl-4-benzo[b]thienylacetamido)morphinan, 17-allyl-4,5α-epoxy-3,14β-dihydroxy-6α-(N-methyl-4-benzo[b]thienylacetamido)morphinan, 17-cyclopropylmethyl-4,5α-epoxy-3,14β-dihydroxy-6β-(N-methyl-4-benzo[b]thienylacetamido)morphinan, 17-allyl- 4,5α-epoxy-3,14β-dihydroxy-6β-(N-methyl-4-benzo [b]thienylacetamido)morphinan, 17-cyclopropylmethyl-4,5α-epoxy-3,14β-dihydroxy-6α-(N-methyl-3,4-dichlorocinnamamido)morphinan, 17-allyl-4,5α-epoxy-3,14β-dihydroxy-6α-(N-methyl-3,4-dichlorocinnamamido)morphinan, 17-cyclopropylmethyl-4,5α-epoxy-3,14β-dihydroxy-6β-(N-methyl-3,4-dichlorocinnamamido)morphinan, 17-allyl-4,5α-epoxy-3,14β-dihydroxy-6β-(N-methyl-3,4-dichlorocinnamamido)morphinan, 17-cyclopropylmethyl-4,5α-epoxy-3,14β-dihydroxy-6α-(N-methyl-4-bromophenylacetamido)morphinan, 17-allyl-4,5α-epoxy-3,14β-dihydroxy-6α-(N-methyl-4-bromophenylacetamido)morphinan, 17-cyclopropylmethyl-4,5α-epoxy-3,14β-dihydroxy-6β(N-methyl-4-bromophenylacetamido)morphinan, 17-allyl-4,5α-epoxy-3,14β-dihydroxy-6β-(N-methyl-4-bromophenylacetamido)morphinan, 17-cyclopropylmethyl-4,5α-epoxy-3,14β-dihydroxy-6α-[(R)-N-methyl-2-phenylpropionamido]morphinan, 17-allyl-4,5α-epoxy-3,14β-dihydroxy-6α-[(R)-N-methyl-2-phenylpropionamido]morphinan, 17-cyclopropylmethyl-4,5α-epoxy-3,14β-dihydroxy-6β-[(R)-N-methyl-2-phenylpropionamido]morphinan, 17-allyl-4,5α-epoxy-3,14β-dihydroxy-6β-[(R)-N-methyl-2-phenylpropionamido]morphinan, 17-cyclopropylmethyl-4,5α-epoxy-3,14β-dihydroxy-6α-[(R)-N-methylmethoxyphenylacetamido]morphinan, 17-allyl-4,5α-epoxy-3,14β-dihydroxy-6α-[(R)-N-methylmethoxyphenylacetamido]morphinan, 17-cyclopropylmethyl-4,5α-epoxy-3,14β-dihydroxy-6β-[(R)-N-methylmethoxyphenylacetamido]morphinan, 17-allyl-4,5α-epoxy-3,14β-dihydroxy-6β[(R)-N-methylmethoxyphenylacetamido]morphinan, 17-cyclopropylmethyl-4,5α-epoxy-3,14β-dihydroxy-6α-[(S)-N-methylmethoxyphenylacetamido]morphinan, 17-allyl-4,5α-epoxy-3,14β-dihydroxy-6α- [(S)-N-methylmethoxyphenylacetamido]morphinan, 17-cyclopropylmethyl-4,5α-epoxy-3,14β-dihydroxy-6β-(S)-N-methylmethoxyphenylacetamido)morphinan, 17-allyl-4,5α-epoxy- 3,14β-dihydroxy-6β-[(S)-N-methylmethoxyphenylacetamido]morphinan, 17-cyclopropylmethyl-4,5α-epoxy-3,14β-dihydroxy-6α-(3,4-dichlorophenylacetamido)morphinan, 17-allyl-4,5α-epoxy-3,14β-dihydroxy-6α- (3,4-dichlorophenylacetamido)morphinan, 17-cyclopropylmethyl-4,5α-epoxy-3,14β-dihydroxy-6β-(3,4-dichlorophenylacetamido)morphinan, 17-allyl-4,5α-epoxy-3,14β-dihydroxy-6β-(3,4-dichlorophenylacetamido)morphinan, 17-cyclopropylmethyl-4,5α-epoxy-3,14β-dihydroxy-6α-(N-methyl-3,4-difluorophenylacetamido)morphinan, 17-allyl-4,5α-epoxy-3,14β-dihydroxy-6β- (N-methyl-3,4-difluorophenylacetamido)morphinan, 17-cyclopropylmethyl-4,5α-epoxy-3,14β-dihydroxy-6β-(N-methyl-3,4-difluorophenylacetamido)morphinan, 17-allyl-4,5α-epoxy-3,14β-dihydroxy- 6β-(N-methyl-3,4-difluorophenylacetamido)morphinan, 17-cyclopropylmethyl-4,5α-epoxy-3,14β-dihydroxy-6α-(N-methyl-3-trifluoromethylphenylacetamido)morphinan, 17-allyl-4,5α-epoxy-3,14β-dihydroxy-6α-(N-methyl-3-trifluoromethylphenylacetamido)morphinan, 17-cyclopropylmethyl-4,5α-epoxy-3,14β-dihydroxy-6β-(N-methyl-3-trifluoromethylphenylacetamido)morphinan, 17-allyl-4,5α-epoxy-3,14β-dihydroxy-6β-(N-methyl-3-trifluoromethylphenylacetamido)morphinan, 17-cyclopropylmethyl-4,5α-epoxy-3,14β-dihydroxy-6α-[(S)-N-methyl-2-phenylpropionamido]morphinan, 17-allyl-4,5α-epoxy-3,14β-dihydroxy-6α-[(S)-N-methyl-2-phenylpropionamido]morphinan, 17-cyclopropylmethyl-4,5α-epoxy-3,14β-dihydroxy-6β-[(S)-N-methyl-2-phenylpropionamido]morphinan, 17-allyl-4,5α-epoxy-3,14β-dihydroxy-6β-[(S)-N-methyl-2-phenylpropionamido]morphinan, 17-cyclopropylmethyl-4,5α-epoxy-3,14β-dihydroxy-6α-[N-methyl-N-2-(3,4-dichlorophenyl)ethylamino]morphinan, 17-allyl-4,5α-epoxy-3,14β-dihydroxy-6α-[N-methyl-N-2-(3,4-dichlorophenyl)ethylamino]morphinan, 17-cyclopropylmethyl- 4,5α-epoxy-3,14β-dihydroxy-6β-[N-methyl-N-2-(3,4-dichlorophenyl)ethylamino]morphinan, 17-allyl-4,5α-epoxy-3,14β-dihydroxy-6β-[N-methyl-N-2-(3,4-dichlorophenyl)ethylamino]morphinan, 17-cyclopropylmethyl-4,5α-epoxy-3,14β-dihydroxy-6α-(N-methyl-4-nitrophenylacetamido)morphinan, 17-allyl-4,5α-epoxy-3,14β-dihydroxy-6α-(N-methyl-4-nitrophenylacetamido)morphinan, 17-cyclopropylmethyl-4,5α-epoxy-3,14β-dihydroxy-6β-(N-methyl-4-nitrophenylacetamido)morphinan, 17-allyl-4,5α-epoxy-3,14β-dihydroxy-6β-(N-methyl-4-nitrophenylacetamido)morphinan, 17-cyclopropylmethyl-4,5α-epoxy-3,14β-dihydroxy-6α-(N-methyl-4-aminophenylacetamido)morphinan, 17-allyl-4,5α-epoxy-3,14β-dihydroxy-6α-(N-methyl-4-aminophenylacetamido)morphinan, 17-cyclopropylmethyl-4,5α-epoxy-3,14β-dihydroxy-6α-(N-methyl-4-aminophenylacetamido)morphinan, 17-allyl,-

4,5α-epoxy-3,14β-dihydroxy-6β-(N-methyl-4-aminophenylacetamido)morphinan, 17-cyclopropylmethyl-4,5α-epoxy-3,14β-dihydroxy-6α-(N-methylcyclohexylcarboxyamido)morphinan, 17-allyl-4,5α-epoxy-3,14β-dihydroxy-6α-(N-methylcyclohexylcarboxyamido)morphinan, 17-cyclopropylmethyl-4,5α-epoxy-3,14β-dihydroxy-6β-(N-methylcyclohexylcarboxyamido)morphinan, 17-allyl-4,5α-epoxy-3,14β-dihydroxy-6β-(N-methylcyclohexylcarboxyamido)morphinan, 17-cyclopropylmethyl-4,5α-epoxy-3,14β-dihydroxy-6α-(N-methylbenzamido)morphinan, 17-allyl-4,5α-epoxy-3,14β-dihydroxy-6α-(N-methylbenzamido)morphinan, 17-cyclopropylmethyl-4,5α-epoxy-3,14β-dihydroxy-6β-(N-methylbenzamido)morphinan, 17-allyl-4,5α-epoxy-3,14β-dihydroxy-6β-(N-methylbenzamido)morphinan, 17-cyclopropylmethyl-4,5α-epoxy-3,14β-dihydroxy-6α-(N-methyl-4-phenylbutyroamido)morphinan, 17-allyl-4,5α-epoxy-3,14β-dihydroxy-6α-(N-methyl-4-phenylbutyroamido)morphinan, 17-cyclopropylmethyl-4,5α-epoxy-3,14β-dihydroxy-6β-(N-methyl-4-phenylbutyroamido)morphinan, 17-allyl-4,5α-epoxy-3,14β-dihydroxy-6β-(N-methyl-4-phenylbutyroamido)morphinan, 17-cyclopropylmethyl-4,5α-epoxy-3,14β-dihydroxy-6α-(N-methyl-2-bromophenylacetamido)morphinan, 17-allyl-4,5α-epoxy-3,14β-dihydroxy-6α-(N-methyl-2-bromophenylacetamido)morphinan, 17-cyclopropylmethyl-4,5α-epoxy-3,14β-dihydroxy-6β-(N-methyl-2-bromophenylacetamido)morphinan, 17-allyl-4,5α-epoxy-3,14β-dihydroxy-6β-(N-methyl-2-bromophenylacetamido)morphinan, 17-cyclopropylmethyl-4,5α-epoxy-3,14β-dihydroxy-6α-(N-methyl-6-phenylhexanoamido)morphinan, 17-allyl-4,5α-epoxy-3,14β-dihydroxy-6α-(N-methyl-6-phenylhexanoamido)morphinan, 17-cyclopropylmethyl-4,5α-epoxy-3,14β-dihydroxy-6β-(N-methyl-6-phenylhexanoamido)morphinan, 17-allyl-4,5α-epoxy-3,14β-dihydroxy-6β-(N-methyl-6-phenylhexanoamido)morphinan, 17-cyclopropylmethyl-4,5α-epoxy-3,14β-dihydroxy-6α-(N-methyl-3-fluorophenylacetamido)morphinan, 17-allyl-4,5α-epoxy-3,14β-dihydroxy-6α-(N-methyl-3-fluorophenylacetamido)morphinan, 17-cyclopropylmethyl-4,5α-epoxy-3,14β-dihydroxy-6β-(N-methyl-3-fluorophenylacetamido)morphinan, 17-allyl-4,5α-epoxy-3,14β-dihydroxy-6β-(N-methyl-3-fluorophenylacetamido)morphinan, 17-cyclopropylmethyl-4,5α-epoxy-3,14β-dihydroxy-6α-[N-methyl-N'-(3,4-dichlorophenyl)ureido]morphinan, 17-allyl-4,5α-epoxy-3,14β-dihydroxy-6β-[N-methyl-N'-(3,4-dichlorophenyl)ureido]morphinan, 17-cyclopropylmethyl-4,5α-epoxy-3,14β-dihydroxy-6β-[N-methyl-N'-(3,4-dichlorophenyl)ureido]morphinan, 17-allyl-4,5α-epoxy-3,14β-dihydroxy-6β-[N-methyl-N'-(3,4-dichlorophenyl)ureido]morphinan, 17-cyclopropylmethyl-4,5α-epoxy-3,14β-dihydroxy-6α-(N-methyl-N'-benzylureido)morphinan, 17-allyl-4,5α-epoxy-3,14β-dihydroxy-6α-(N-methyl-N'-benzylureido)morphinan, 17-cyclopropylmethyl-4,5α-epoxy-3,14β-dihydroxy-6β-(N-methyl-N'-benzylureido)morphinan, 17-allyl-4,5α-epoxy-3,14β-dihydroxy-6β-(N-methyl-N'-benzylureido)morphinan, 17-cyclopropylmethyl-4,5α-epoxy-3,14β-dihydroxy-6α-(N-methyl-3-nitrophenylacetamido)morphinan, 17-allyl-4,5α-epoxy-3,14β-dihydroxy-6α-(N-methyl-3-nitrophenylacetamido)morphinan, 17-cyclopropylmethyl-4,5α-epoxy-3,14β-dihydroxy-6β-(N-methyl-3-nitrophenylacetamido)morphinan, 17-allyl-4,5α-epoxy-3,14β-dihydroxy-6β-(N-methyl-3-nitrophenylacetamido)morphinan, 17-cyclopropylmethyl-4,5α-epoxy-3,14β-dihydroxy-6α-(N-methyl-4-pyridylacetamido)morphinan, 17-allyl-4,5α-epoxy-3,14β-dihydroxy-6α-(N-methyl-4-pyridylacetamido)morphinan, 17-cyclopropylmethyl-4,5α-epoxy-3,14β-dihydroxy-6α-(N-methyl-4-pyridylacetamido)morphinan, 17-allyl-4,5α-epoxy-3,14β-dihydroxy-6β-(N-methyl-4-pyridylacetamido)morphinan, 17-cyclopropylmethyl-4,5α-epoxy-3,14β-dihydroxy-6α-[N-methyl-trans-3-(3-thienyl)acrylamido]morphinan, 17-allyl-4,5α-epoxy-3,14β-dihydroxy-6α-[N-methyl-trans-3-(3-thienyl)acrylamido]morphinan, 17-cyclopropylmethyl-4,5α-epoxy-3,14β-dihydroxy-6β-[N-methyl-trans-3-(3-thienyl)acrylamido]morphinan, 17-allyl-4,5α-epoxy-3,14β-dihydroxy-6β-[N-methyl-trans-3-(3-thienyl)acrylamido]morphinan, 17-cyclopropylmethyl-4,5α-epoxy-3,14β-dihydroxy-6α-(N-methylthiophenoxyacetamido)morphinan, 17-allyl-4,5α-epoxy-3,14β-dihydroxy-6α-(N-methylthiophenoxyacetamido)morphinan, 17-cyclopropylmethyl-4,5α-epoxy-3,14β-dihydroxy-6β-(N-methylthiophenoxyacetamido)morphinan, 17-allyl-4,5α-epoxy-3,14β-dihydroxy-6β-(N-methylthiophenoxyacetamido)morphinan, 17-cyclopropylmethyl-4,5α-epoxy-3,14β-dihydroxy-6α-(N-methylphenoxyacetamido)morphinan, 17-allyl-4,5α-epoxy-3,14β-dihydroxy-6α-(N-methylphenoxyacetamido)morphinan, 17-cyclopropylmethyl-4,5α-epoxy-3,14β-dihydroxy-6β-(N-methylphenoxyacetamido)morphinan, 17-allyl-4,5α-epoxy-3,14β-dihydroxy-6β-(N-methylphenoxyacetamido)morphinan, 17-cyclopropylmethyl-4,5α-epoxy-3,14β-dihydroxy-6α-(N-methyl-4-nitrobenzyloxycarbamido)morphinan, 17-allyl-4,5α-epoxy-3,14β-dihydroxy-6α-(N-methyl-4-nitrobenzyloxycarbamido)morphinan, 17-cyclopropylmethyl-4,5α-epoxy-3,14β-dihydroxy-6β-(N-methyl-4-nitrobenzyloxycarbamido)morphinan, 17-allyl-4,5α-epoxy-3,14β-dihydroxy-6β-(N-methyl-4-nitrobenzyloxycarbamido)morphinan, 17-cyclopropylmethyl-4,5α-epoxy-3,14β-dihydroxy-6α-(N-methyl-3-pyridylmethoxycarbamido)morphinan, 17-allyl-4,5α-epoxy-3,14β-dihydroxy-6α-(N-methyl-3-pyridylmethoxycarbamido)morphinan, 17-cyclopropylmethyl-4,5α-epoxy-3,14β-dihydroxy-6β-(N-methyl-3-pyridylmethoxycarbamido)morphinan, 17-allyl-4,5α-epoxy-3,14β-dihydroxy-6β-(N-methyl-3-pyridylmethoxycarbamido)morphinan, 17-cyclopropylmethyl-4,5α-epoxy-3,14β-dihydroxy-6α-(N-methyl-3,4-dichlorophenylmethanesulfonamido)morphinan, 17-allyl-4,5α-epoxy-3,14β-dihydroxy-6α-(N-methyl-3,4-dichlorophenylmethane-sulfonamido)morphinan, 17-cyclopropylmethyl-4,5α-epoxy-3,14β-dihydroxy-6β-(N-methyl-3,4-dichlorophenylmethanesulfonamido)morphinan, 17-allyl-4,5α-epoxy-3,14β-dihydroxy-6β-(N-methyl-3,4-dichlorophenylmethanesulfonamido)morphinan, 17-cyclopropylmethyl-4,5α-epoxy-3,14β-dihydroxy-6α-(N-methyl-N'-benzylthioureido)morphinan, 17-ally-4,5α-epoxy-3,14β-dihydroxy-6α-(N-methyl-N'-benzylthioureido)morphinan, 17-cyclopropylmethyl-4,5α-epoxy-3,14β-dihydroxy-6β-(N-methyl-N'-benzylthioureido)morphinan, 17-allyl-4,5α-epoxy-3,14β-dihydroxy-6β-N-methyl-N'-benzylthioureido)morphinan, 17-cyclopropylmethyl-4,5α-epoxy-3,14β-dihydroxy-6α-(N-methylhexanoamido)morphinan, 17-allyl-4,5α-epoxy-3, 14β-dihydroxy-6α-(N-methylhexanoamido)morphinan, 17-cyclopropylmethyl-4,5α-epoxy-3,14β-dihydroxy-6β-(N-methylhexanoamido)morphinan, 17-allyl-4,5α-epoxy-3,14β-dihydroxy-6β-(N-methylhexanoamido)morphinan, 17-cyclopropylmethyl-4,5α-epoxy-3,14β-dihydroxy-6α-(N-methylheptanoamido)morphinan, 17-allyl-4,5α-epoxy-3,14β-dihydroxy-6α-(N-methylheptanoamido)morphinan, 17-cyclopropylmethyl-4,5α-epoxy-3,14β-dihydroxy-6β-(N-methylheptanoamido)morphinan, 17-allyl-4,5α-epoxy-3,14β-dihydroxy-6β-(N-methylheptanoamido)morphinan, 17-cyclopropylmethyl-4,5α-epoxy-3,14β-dihydroxy-6α-(N-methyl-3-aminophenylacetamido)morphinan, 17-allyl-4,5α-epoxy-3,14β-dihydroxy-6α-(N-methyl-3-aminophenylacetamido)morphinan, 17-cyclopropylmethyl-4,5α-epoxy-3,14β-dihydroxy-6β-(N-methyl-3-aminophenylacetamido)morphinan, 17-allyl-4,5α-epoxy-3,14β-dihydroxy-6β-(N-methyl-3-aminophenylacetamido)morphinan, 17-cyclopropylmethyl-4,5α-epoxy-3,14β-dihydroxy-6α-(N-methyl-2-pyridylacetamido)morphinan, 17-allyl-4,5α-epoxy-3,14β-dihydroxy-6α-(N-methyl-2-pyridylacetamido)morphinan, 17-cyclopropylmethyl-4,5α-epoxy-3,14β-dihydroxy-6β-(N-methyl-2-pyridylacetamido)morphinan, 17-allyl-4,5α-epoxy-3,14β-dihydroxy-6β-(N-methyl-2-pyridylacetamido)morphinan, 17-cyclopropylmethyl-4,5α-epoxy-3,14β-dihydroxy-6α-[N-methyl-3-(3-pyridyl)propionamido]morphinan, 17-allyl-4,5α-epoxy-3,14β-dihydroxy-6α-[N-methyl-3-(3-pyridyl)propionamido]morphinan, 17-cyclopropylmethyl-4,5α-epoxy-3,14β-dihydroxy-6β-[N-methyl-3-(3-pyridyl)propionamido]morphinan, 17-allyl-4,5α-epoxy-3,14β-dihydroxy-6β-[N-methyl-3-(3-pyridyl)propionamido]morphinan, 17-cyclopropylmethyl-4,5α-epoxy-3,14β-dihydroxy-6α-(3-phenylpropioyloxy)morphinan, 17-allyl-4,5α-epoxy-3,14β-dihydroxy-6α-(3-phenylpropioyloxy)morphinan, 17-cyclopropylmethyl-4,5α-epoxy-3,14β-dihydroxy-6β-(3-phenylpropioyloxy)morphinan, 17-allyl-4,5α-epoxy-3,14β-dihydroxy-6β-(3-phenylpropioyloxy)morphinan, 17-cyclopropylmethyl-4,5α-epoxy-3,14β-dihydroxy-6α-[2-(3-furyl)ethenylsulfonyloxy]morphinan, 17-allyl-4,5α-epoxy-3,14β-dihydroxy-6α-[2-(3-furyl)ethenylsulfonyloxy]morphinan, 17-cyclopropylmethyl-4,5α-epoxy-3,14β-dihydroxy-6β-[2-(3-furyl)ethenylsulfonyloxy]morphinan, 17-allyl-4,5α-epoxy-3,14β-dihydroxy-6β-[2-(3-furyl) ethenylsulfonyloxy]morphinan, 17-cyclopropylmethyl-4,5α-epoxy-3,14β-dihydroxy-6α-(N-methyl-3-trifluoromethylcinnamamido)morphinan, 17-cyclopropylmethyl-4,5α-epoxy-3,14β-dihydroxy-6α-[N-methyl-trans-3-(3-furyl)acrylamido]morphinan, 17-cyclopropylmethyl-4,5α-epoxy-3,14β-dihydroxy-6α-(N-methyl-4-trifluoromethylcinnamamido)morphinan, 17-cyclopropylmethyl-4,5α-epoxy-3,14β-dihydroxy-6α-(N-methyl-3-phenylpropiolamido)morphinan, 17-allyl-4,5α-epoxy-3,14β-dihydroxy-6α-(N-methyl-3-trifluoromethylcinnamamido)morphinan, 17-allyl-4,5α-epoxy-3,14β-dihydroxy-6α-[N-methyl-trans-3-(3-furyl)acrylamido]morphinan, 17-allyl-4,5α-epoxy-3,14β-dihydroxy-6α-(N-methyl-4-trifluoromethylcinnamamido)morphinan, 17-allyl-4,5α-epoxy-3,14β-dihydroxy-6α-(N-methyl-3-phenylpropiolamido)morphinan, 17-methyl-4,5α-epoxy-3,14β-dihydroxy-6α-(N-methyl-3-trifluoromethylcinnamamido)morphinan, 17-methyl-4,5α-epoxy-3,14β-dihydroxy-6α-[N-methyl-trans-3-(3-furyl)acrylamido]morphinan, 17-methyl-4,5α-epoxy-3,14β-dihydroxy-6α-(N-methyl-4-trifluoromethylcinnamamido) morphinan, 17-methyl-4,5α-epoxy-3,14β-dihydroxy-6α-(N-methyl-3-phenylpropiolamido)morphinan, 17-phenethyl-4,5α-epoxy-3,14β-dihydroxy-6α-(N-methyl-3-trifluoromethylcinnamamido)morphinan, 17-phenethyl-4,5α-epoxy-3,14β-dihydroxy-6α-[N-methyl-trans-3-(3-furyl)acrylamido]morphinan, 17-phenethyl-4,5α-epoxy- 3,14β-dihydroxy-6α-(N-methyl-4-trifluoromethylcinnamamido) morphinan, 17-phenethyl-4,5α-epoxy-3,14β-dihydroxy-6α-(N-methyl-3-phenylpropiolamido)morphinan, 17-cyclopropylmethyl-4,5α-epoxy-3-hydroxy-14β-acetoxy-6α-(N-methyl-3-trifluoromethylcinnamamido))morphinan, 17-cyclopropylmethyl-4,5α-epoxy-3-hydroxy-14β-acetoxy-6α-[N-methyl-trans-3-(3-furyl)acrylamido]morphinan, 17-cyclopropylmethyl-4,5α-epoxy-3-hydroxy-14β-acetoxy-6α-(N-methyl-4-trifluoromethylcinnamamido)morphinan, 17-cyclopropylmethyl-4,5α-epoxy-3-hydroxy-14β-acetoxy-6α-(N-methyl-3-phenylpropiolamido)morphinan, 17-allyl-4,5α-epoxy-3-hydroxy-14β-acetoxy-6α-(N-methyl-3-trifluoromethylcinnamamido)morphinan, 17-allyl-4,5α-epoxy-3-hydroxy-14β-acetoxy-6α-[N-methyl-trans-3-(3-furyl)acrylamido]morphinan, 17-allyl-4,5α-epoxy-3-hydroxy-14β-acetoxy-6α-(N-methyl-4-trifluoromethylcinnamamido)morphinan, 17-allyl-4,5α-epoxy-3-hydroxy-14β-acetoxy-6α-(N-methyl-3-phenylpropiolamido)morphinan, 17-methyl-4,5α-epoxy-3-hydroxy-14β-acetoxy-6α-(N-methyl-3-trifluoromethylcinnamamido)morphinan, 17-methyl-4,5α-epoxy-3-hydroxy-14β-acetoxy-6α-methyl-trans-3-(3-furyl)acrylamido]morphinan, 17-methyl-4,5α-epoxy-3-hydroxy-14β-acetoxy-6α-(N-methyl-4-trifluoromethylcinnamamido)morphinan, 17-methyl-4,5α-epoxy-3-hydroxy-14β-acetoxy-6α-(N-methyl-3-phenylpropiolamido)morphinan, 17-phenethyl-4,5α-epoxy-3-hydroxy-14β-acetoxy-6α-(N-methyl-3-trifluoromethylcinnamamido)morphinan, 17-phenethyl-4,5α-epoxy-3-hydroxy-14β-acetoxy-6α-(N-methyl-trans-3-(3-furyl)acrylamido)morphinan, 17-phenethyl-4,5α-epoxy-3-hydroxy-14β-acetoxy-6α-(N-methyl-4-trifluoromethylcinnamamido)morphinan, 17-phenethyl-4,5α-epoxy-3-hydroxy-14β-acetoxy-6α-(N-methyl-3-phenylpropiolamido)morphinan, 17-cyclopropylmethyl-4,5α-epoxy-14β-hydroxy-6α-(N-methyl-3-trifluoromethylcinnamamido)morphinan, 17-cyclopropylmethyl-4,5α-epoxy-14β-hydroxy-6α-[N-methyl-trans-3-(3-furyl)acrylamido]morphinan, 17-cyclopropylmethyl-4,5α-epoxy-14β-hydroxy-6α-(N-methyl-4-trifluoromethylcinnamamido)morphinan, 17-cyclopropylmethyl-4,5α-epoxy-14β-hydroxy-6β-(N-methyl-3-phenylpropiolamido)morphinan, 17-allyl-4,5α-epoxy-14β-hydroxy-6α-(N-methyl-3-trifluoromethylcinnamamido)morphinan, 17-allyl-4,5α-epoxy-14β-hydroxy-6α-[N-methyl-trans-3-(3-furyl)acrylamido]morphinan, 17-allyl-4,5α-epoxy-14β-hydroxy-6α-(N-methyl-4-trifluoromethylcinnamamido)morphinan, 17-allyl-4,5α-epoxy-14β-hydroxy-6α-(N-methyl-3-phenylpropiolamido)morphinan, 17-methyl-4,5α-epoxy-14β-hydroxy-6α-(N-methyl-3-trifluoromethylcinnamamido)morphinan, 17-methyl-4,5α-epoxy-14β-hydroxy-6α-[N-methyl-trans-3-(3-furyl)acrylamido]morphinan, 17-methyl-4,5α-epoxy-14β-hydroxy-6α-(N-methyl-4-trifluoromethylcinnamamido)morphinan, 17-methyl-4,5α-epoxy-14β-hydroxy-6α-(N-methyl-3-phenylpropiolamido)morphinan, 17-phenethyl-4,5α-epoxy-14β-hydroxy-6α-(N-methyl-3-trifluoromethylcinnamamido)morphinan, 17-phenethyl-4,5α-epoxy-14β-hydroxy-6α-[N-methyl-trans-3-(3-furyl)acrylamido]morphinan, 17-phenethyl-4,5α-epoxy-14β-hydroxy-6α-(N-methyl-4-trifluoromethylcinnamamido)

morphinan, 17-phenethyl-4,5α-epoxy-14β-hydroxy-6α-(N-methyl-3-phenylpropiolamido)morphinan, 17-cyclopropylmethyl-4,5α-(epoxy-14β-acetoxy-6α-(N-methyl-3-trifluoromethylcinnamamido)morphinan, 17-cyclopropylmethyl-4,5α-epoxy-14β-acetoxy-6α-[N-methyl-trans-3-(3-furyl)acrylamido]morphinan, 17-cyclopropylmethyl-4,5α-epoxy-14β-acetoxy-6α-(N-methyl-4-trifluoromethylcinnamamido)morphinan, 17-cyclopropylmethyl-4,5α-epoxy-14β-acetoxy-6α-(N-methyl-3-phenylpropiolamido)morphinan, 17-allyl-4,5α-epoxy-14β-acetoxy-6α-(N-methyl-3-trifluoromethylcinnamamido) morphinan, 17-allyl-4,5α-epoxy-14β-acetoxy-6α-[N-methyl-trans-3-(3-furyl)acrylamido]morphinan, 17-allyl-4,5α-epoxy-14β-acetoxy-6α-(N-methyl-4-trifluoromethylcinnamamido)morphinan, 17-allyl-4,5α-epoxy-14β-acetoxy-6α-(N-methyl-3-phenylpropiolamido)morphinan, 17-methyl-4,5α-epoxy-14β-acetoxy-6α-(N-methyl-3-trifluoromethylcinnamamido)morphinan, 17-methyl-4,5α-epoxy-14β-acetoxy-6α-[N-methyl-trans-3-(3-furyl)acrylamido]morphinan, 17-methyl-4,5α-epoxy-14β-acetoxy-6α-(N-methyl-4-trifluoromethylcinnamamido)morphinan, 17-methyl-4,5α-epoxy-14β-acetoxy-6α-(N-methyl-3-phenylpropiolamido)morphinan, 17-phenethyl-4,5α-epoxy-14β-acetoxy-6α-(N-methyl-3-trifluoromethylcinnamamido)morphinan, 17-phenethyl-4,5α-epoxy-14β-acetoxy-6α-[N-methyl-trans-3-(3-furyl)acrylamido]morphinan, 17-phenethyl-4,5α-epoxy-14β-acetoxy-6α-(N-methyl-4-trifluoromethylcinnamamido)morphinan, 17-phenethyl-4,5α-epoxy-14β-acetoxy-6α-(N-methyl-3-phenylpropiolamido)morphinan, 17-cyclopropylmethyl-4,5α-epoxy-3-methoxy-14β-hydroxy-6α-(N-methyl-3-trifluoromethylcinnamamido)morphinan, 17-cyclopropylmethyl-4,5α-epoxy-3-methoxy-14β-hydroxy-6α-[N-methyl-trans-3-(3-furyl)acrylamido]morphinan, 17-cyclopropylmethyl-4,5α-epoxy-3-methoxy-14β-hydroxy-6α-(N-methyl-4-trifluoromethylcinnamamido)morphinan, 17-cyclopropylmethyl-4,5α-epoxy-3-methoxy-14β-hydroxy-6α-(N-methyl-3-phenylpropiolamido)morphinan, 17-allyl-4,5α-epoxy-3-methoxy-14β-hydroxy-6α-(N-methyl-3-trifluoromethylcinnamamido)morphinan, 17-allyl-4,5α-epoxy-3-methoxy-14β-hydroxy-6α-[N-methyl-trans-3-(3-furyl)acrylamido]morphinan, 17-allyl-4,5α-epoxy-3-methoxy-14β-hydroxy-6α-(N-methyl-4-trifluoromethylcinnamamido)morphinan, 17-allyl-4,5α-epoxy-3-methoxy-14β-hydroxy-6α-(N-methyl-3-phenylpropiolamido)morphinan, 17-methyl-4,5α-epoxy-3-methoxy-14β-hydroxy-6α-(N-methyl-3-trifluoromethylcinnamamido)morphinan, 17-methyl-4,5α-epoxy-3-methoxy-14β-hydroxy-6α-[N-methyl-trans-3-(3-furyl)acrylamido]morphinan, 17-methyl-4,5α-epoxy-3-methoxy-14β-hydroxy-6α-(N-methyl-4-trifluoromethylcinnamamido)morphinan, 17-methyl-4,5α-epoxy-3-methoxy-14β-hydroxy-6α-(N-methyl-3-phenylpropiolamido)morphinan, 17-phenethyl-4,5α-epoxy-3-methoxy-14β-hydroxy-6α-(N-methyl-3-trifluoromethylcinnamamido)morphinan, 17-phenethyl-4,5α-epoxy-3-methoxy-14β-hydroxy-6α-[N-methyl-trans-3-(3-furyl)acrylamido]morphinan, 17-phenethyl-4,5α-epoxy-3-methoxy-14β-hydroxy-6α-(N-methyl-4-trifluoromethylcinnamamido)morphinan, 17-phenethyl-4,5α-epoxy-3-methoxy-14β-hydroxy-6α-(N-methyl-3-phenylpropiolamido)morphinan, 17-cyclopropylmethyl-4,5α-epoxy-3-methoxy-14β-acetoxy-6α-(N-methyl-3-trifluoromethylcinnamamido)morphinan, 17-cyclopropylmethyl-4,5α-epoxy-3-methoxy-14β-acetoxy-6α-[N-methyl-trans-3-(3-furyl)acrylamido]morphinan, 17-cyclopropylmethyl-4,5α-epoxy-3-methoxy-14β-acetoxy-6α-(N-methyl-4-trifluoromethylcinnamamido)morphinan, 17-cyclopropylmethyl-4,5α-epoxy-3-methoxy-14β-acetoxy-6α-(N-methyl-3-phenylpropionamido)morphinan, 17-allyl-4,5α-epoxy-3-methoxy-14β-acetoxy-6α-(N-methyl-3-trifluoromethylcinnamamido)morphinan, 17-allyl-4,5α-epoxy-3-methoxy-14β-acetoxy-6α-[N-methyl-trans-3-(3-furyl)acrylamido]morphinan, 17-allyl-4,5α-epoxy-3-methoxy-14β-acetoxy-6α-(N-methyl-4-trifluoromethylcinnamamido)morphinan, 17-allyl-4,5α-epoxy-3-methoxy-14β-acetoxy-6α-(N-methyl-3-phenylpropiolamido)morphinan, 17-methyl-4,5α-epoxy-3-methoxy-14β-acetoxy-6α-(N-methyl-3-trifluoromethylcinnamamido)morphinan, 17-methyl-4,5α-epoxy-3-methoxy-14β-acetoxy-6α-[N-methyl-trans-3-(3-furyl)acrylamido]morphinan, 17-methyl-4,5α-epoxy-3-methoxy-14β-acetoxy-6α-(N-methyl-4-trifluoromethylcinnamamido)morphinan, 17-methyl-4,5α-epoxy-3-methoxy-14β-acetoxy-6α-(N-methyl-3-phenylpropiolamido) morphinan, 17-phenethyl-4,5α-epoxy-3-methoxy-14β-acetoxy-6α-(N-methyl-3-trifluoromethylcinnamamido)morphinan, 17-phenethyl-4,5α-epoxy-3-methoxy-14β-acetoxy-6α-[N-methyl-trans-3-(3-furyl)acrylamido]morphinan, 17-phenethyl-4,5α-epoxy-3-methoxy-14β-acetoxy-6α-(N-methyl-4-trifluoromethylcinnamamido)morphinan, 17-phenethyl-4,5α-epoxy-3-methoxy-14β-acetoxy-6α-(N-methyl-3-phenylpropiolamido)morphinan, 17-cyclopropylmethyl-4,5α-epoxy-3-acetoxy-14β-hydroxy-6α-(N-methyl-3-trifluoromethylcinnamamido)morphinan, 17-cyclopropylmethyl-4,5α-epoxy-3-acetoxy-14β-hydroxy-6α-[N-methyl-trans-3-(3-furyl)acrylamido]morphinan, 17-cyclopropylmethyl-4,5α-epoxy-3-acetoxy-14β-hydroxy-6α-(N-methyl-4-trifluoromethylcinnamamido)morphinan, 17-cyclopropylmethyl-4,5α-epoxy-3-acetoxy-14β-hydroxy-6α-(N-methyl-3-phenylpropiolamido)morphinan, 17-allyl-4,5α-epoxy-3-acetoxy-14β-hydroxy-6α-(N-methyl-3-trifluoromethylcinnamamido)morphinan, 17-allyl-4,5α-epoxy-3-acetoxy-14β-hydroxy-6α-[N-methyl-trans-3-(3-furyl)acrylamido]morphinan, 17-allyl-4,5α-epoxy-3-acetoxy-14β-hydroxy-6α-(N-methyl-4-trifluoromethylcinnamamido)morphinan, 17-allyl-4,5α-epoxy-3-acetoxy-14β-hydroxy-6α-(N-methyl-3-phenylpropiolamido)morphinan, 17-methyl-4,5α-epoxy-3-acetoxy-14β-hydroxy-6α-(N-methyl-3-trifluoromethylcinnamamido)morphinan, 17-methyl-4,5α-epoxy-3-acetoxy-14β-hydroxy-6α-[N-methyl-trans-3-(3-furyl)acrylamido]morphinan, 17-methyl-4,5α-epoxy-3-acetoxy-14β-hydroxy-6α-(N-methyl-4-trifluoromethylcinnamamido)morphinan, 17-methyl-4,5α-epoxy-3-acetoxy-14β-hydroxy-6α-(N-methyl-3-phenylpropiolamido)morphinan, 17-phenethyl-4,5α-epoxy-3-acetoxy-14β-hydroxy-6α-(N-methyl-3-trifluoromethylcinnamamido)morphinan, 17-phenethyl-4,5α-epoxy-3-acetoxy-14β-hydroxy-6α-[N-methyl-trans-3-(3-furyl)acrylamido]morphinan, 17-phenethyl-4,5α-epoxy-3-acetoxy-14β-hydroxy-6α-(N-methyl-4-trifluoromethylcinnamamido)morphinan, 17-phenethyl-4,5α-epoxy-3-acetoxy-14β-hydroxy-6α-(N-methyl-3-phenylpropiolamido)morphinan, 17-cyclopropylmethyl-4,5α-epoxy-3,14β-diacetoxy-6α-(N-methyl-3-trifluoromethylcinnamamido)morphinan, 17-cyclopropylmethyl-4,5α-epoxy-3,14β-diacetoxy-6α-[N-methyl-trans-3-(3-furyl)acrylamido]morphinan, 17-cyclopropylmethyl-4,5α-epoxy-3,14β-diacetoxy-6α-(N-methyl-4-trifluoromethylcinnamamido)morphinan, 17-cyclopropylmethyl-4,5α-epoxy-3,14β-diacetoxy-6α-(N-methyl-3-phenylpropiolamido)morphinan, 17-allyl-4,5α-epoxy-3,14β-diacetoxy-6α-(N-methyl-3-trifluoromethylcinnamamido)morphinan, 17-allyl-4,5α-epoxy-3,14β-diacetoxy-6α-[N-methyl-trans-3-(3-furyl)acrylamido]morphinan, 17-allyl-4,5α-epoxy-3,14β-diacetoxy-6α-(N-methyl-4-trifluoromethylcinnamamido)morphinan, 17-allyl-4,5α-epoxy-3,14β-diacetoxy-6α-(N-methyl-3-phenylpropiolamido)morphinan, 17-methyl-4,5α-epoxy-3,14β-diacetoxy-6α-(N-methyl-3-trifluoromethylcinnamamido)morphinan, 17-methyl-4,5α-epoxy-3,14β-diacetoxy-6α-[N-methyl-trans-3-(3-furyl)acrylamido]morphinan, 17-methyl-4,5α-epoxy-3,14β-diacetoxy-6α-(N-methyl-4-trifluoromethylcinnamamido)morphinan, 17-methyl-4,5α-epoxy-3,14β-diacetoxy-6α-(N-methyl-3-phenylpropiolamido)morphinan, 17-phenethyl-4,5α-epoxy-3,14β-diacetoxy-6α-(N-methyl-3-trifluoromethylcinnamamido)morphinan, 17-phenethyl-4,5α-epoxy-3,14β-diacetoxy-6α-[N-methyl-trans-3-(3-furyl)acrylamido)morphinan, 17-phenethyl-4,5α-epoxy-3,14β-diacetoxy-6α-(N-methyl-4-trifluoromethylcinnamamido)morphinan, 17-phenethyl-4,5α-epoxy-3,14β-diacetoxy-6α-(N-methyl-3-phenylpropiolamido)morphinan, 17-cyclopropylmethyl-4,5α-epoxy-3,14β-dihydroxy- 6α-(N-isobutyl-3-trifluoromethylcinnamamido)morphinan, 17-cyclopropylmethyl-4,5α-epoxy-3,14β-dihydroxy-6α-N-isobutyl-trans-3-(3-furyl)acrylamido]morphinan, 17-cyclopropylmethyl-4,5α-epoxy-3,14β-dihydroxy-6α-(N-isobutyl-4-trifluoromethylcinnamamido)morphinan, 17-cyclopropylmethyl-4,5α-epoxy-3,14β-dihydroxy-6α-(N-isobutyl-3-phenylpropiolamido)morphinan, 17-allyl-4,5α-epoxy-3,14β-dihydroxy-6α-(N-isobutyl-3-trifluoromethylcinnamamido)morphinan, 17-allyl-4,5α-epoxy-3,14β-dihydroxy-6α-[N-isobutyl-trans-3-(3-furyl)acrylamido]morphinan, 17-allyl-4,5α-epoxy-3,14β-dihydroxy-6α-(N-isobutyl-4-trifluoromethylcinnamamido)morphinan, 17-allyl-4,5α-epoxy-3,14β-dihydroxy-6α-(N-isobutyl-3-phenylpropiolamido)morphinan, 17-methyl-4,5α-epoxy-3,14β-dihydroxy-6α-(N-isobutyl-3-trifluoromethylcinnamamido)morphinan, 17-methyl-4,5α-epoxy-3,14β-dihydroxy-6α-[N-isobutyl-trans-3-(3-furyl)acrylamido]morphinan, 17-methyl-4,5α-epoxy-3,14β-dihydroxy-6α-(N-isobutyl-4-trifluoromethylcinnamamido)morphinan, 17-methyl-4,5α-epoxy-3,14β-dihydroxy-6α-(N-isobutyl-3-phenylpropiolamido)morphinan, 17-phenethyl-4,5α-epoxy-3,14β-dihydroxy-6α-(N-isobutyl-3-trifluoromethylcinnamamido)morphinan, 17-phenethyl-4,5α-epoxy-3,14β-dihydroxy-6α-[N-isobutyl-trans-3-(3-furyl)acrylamido]morphinan, 17-phenethyl-4,5α-epoxy-3,14β-dihydroxy-6α-(N-isobutyl-4-trifluoromethylcinnamamido)morphinan, 17-phenethyl-4,5α-epoxy-3,14β-dihydroxy-6α-(N-isobutyl-3-phenylpropiolamido)morphinan, 17-cyclopropylmethyl-4,5α-epoxy-3-hydroxy-14β-acetoxy-6α-(N-isobutyl-3-trifluoromethylcinnamamido)morphinan, 17-cyclopropylmethyl-4,5α-epoxy-3-hydroxy-14β-acetoxy-6α-[N-isobutyl-trans-3-(3-furyl)acrylamido]morphinan, 17-cyclopropylmethyl-4,5α-epoxy- 3-hydroxy-14β-acetoxy-6α-(N-isobutyl-4-trifluoromethylcinnamamido)morphinan, 17-cyclopropylmethyl-4,5α-epoxy-3-hydroxy-14β-acetoxy-6α-(N-isobutyl-3-phenylpropiolamido)morphinan, 17-allyl-4,5α-epoxy-3-hydroxy-14β-acetoxy-6α-(N-isobutyl-3-trifluoromethylcinnamamido)morphinan, 17-allyl-4,5α-epoxy-3-hydroxy-14β-acetoxy-6α-[N-isobutyl-trans-3-(3-furyl)acrylamido]morphinan, 17-allyl-4,5α-epoxy-3-hydroxy-14β-acetoxy-6α-(N-isobutyl-4-trifluoromethylcinnamamido)morphinan, 17-allyl-4,5α-epoxy-3-hydroxy-14β-acetoxy-6α-(N-isobutyl-3-phenylpropiolamido)morphinan, 17-methyl-4,5α-epoxy-3-hydroxy-14β-acetoxy-6α-(N-isobutyl-3-trifluoromethylcinnamamido)morphinan, 17-methyl-4,5α-epoxy-3-hydroxy-14β-acetoxy-6α-[N-isobutyl-trans-3-(3-furyl)acrylamido]morphinan, 17-methyl-4,5α-epoxy-3-hydroxy-14β-acetoxy-6α-(N-isobutyl-4-trifluoromethylcinnamamido)morphinan, 17-methyl-4,5α-epoxy-3-hydroxy-14β-acetoxy-6α-(N-isobutyl-3-phenylpropiolamido)morphinan, 17-phenethyl-4,5α-epoxy-3-hydroxy-14β-acetoxy-6α-(N- isobutyl-3-trifluoromethylcinnamamido)morphinan, 17-phenethyl-4,5α-epoxy-3-hydroxy-14β-acetoxy-6α-[N-isobutyl-trans-3-(3-furyl)acrylamido]morphinan, 17-phenethyl-4,5α-epoxy-3-hydroxy-14β-acetoxy-6α-(N-isobutyl-4-trifluoromethylcinnamamido)morphinan, 17-phenethyl-4,5α-epoxy-3-hydroxy-14β-acetoxy-6α-(N-isobutyl-3-phenylpropiolamido)morphinan, 17-cyclopropylmethyl-4,5α-epoxy-14β-hydroxy-6α-(N-isobutyl-3-trifluoromethylcinnamamido)morphinan, 17-cyclopropylmethyl-4,5α-epoxy-14β-hydroxy-6α-[N-isobutyl-trans-3-(3-furyl)acrylamido]morphinan, 17-cyclopropylmethyl-4,5α-epoxy-14β-hydroxy-6α-(N-isobutyl-4-trifluoromethylcinnamamido)morphinan, 17-cyclopropylmethyl-4,5α-epoxy-14β-hydroxy-6α-(N-isobutyl-3-phenylpropiolamido)morphinan, 17-allyl-4,5α-epoxy-14β-hydroxy-6α-(N-isobutyl-3-trifluoromethylcinnamamido)morphinan, 17-allyl-4,5α-epoxy-14β-hydroxy-6α-[N-isobutyl-trans-3-(3-furyl)acrylamido]morphinan, 17-allyl-4,5α-epoxy-14β-hydroxy-6α-(N-isobutyl-4-trifluoromethylcinnamamido)morphinan, 17-allyl-4,5α-epoxy-14β-hydroxy-6α-(N-isobutyl-3-phenylpropiolamido)morphinan, 17-methyl-4,5α-epoxy-14β-hydroxy-6α-(N-isobutyl-3-trifluoromethylcinnamamido)morphinan, 17-methyl-4,5α-epoxy-14β-hydroxy-6α-[N-isobutyl-trans-3-(3-furyl)acrylamido]morphinan, 17-methyl-4,5α-epoxy-14β-hydroxy-6α-(N-isobutyl-4-trifluoromethylcinnamamido)morphinan, 17-methyl-4,5α-epoxy-14β-hydroxy-6α-(N-isobutyl-3-phenylpropiolamido)morphinan, 17-phenethyl-4,5α-epoxy-14β-hydroxy-6α-(N-isobutyl-3-trifluoromethylcinnamamido)morphinan, 17-phenethyl-4,5α-epoxy-14β-hydroxy-6α-[N-isobutyl-trans-3-(3-furyl)acrylamido]morphinan, 17-phenethyl-4,5α-epoxy-14β-hydroxy-6α-(N-isobutyl-4-trifluoromethylcinnamamido)morphinan, 17-phenethyl-4,5α-epoxy-14β-hydroxy-6α-(N-isobutyl-3-phenylpropiolamido)morphinan, 17-cyclopropylmethyl-4,5α-epoxy-14β-acetoxy-6α-(N-isobutyl-3-trifluoromethylcinnamamido)morphinan, 17-cyclopropylmethyl-4,5α-epoxy-14β-acetoxy-6α-[N-isobutyl-trans-3-(3-furyl)acrylamido]morphinan, 17-cyclopropylmethyl-4,5α-epoxy-14β-acetoxy-6α-(N-isobutyl-4-trifluoromethylcinnamamido)morphinan, 17-cyclopropylmethyl-4,5α-epoxy-14β-acetoxy-6α-(N-isobutyl-3-phenylpropiolamido)morphinan, 17-allyl-4,5α-epoxy-14β-acetoxy-6α-(N-isobutyl-3-trifluoromethylcinnamamido)morphinan, 17-allyl-4,5α-epoxy-14β-acetoxy-6α-[N-isobutyl-trans-3-(3-furyl)acrylamido]morphinan, 17-allyl-4,5α-epoxy-14β-acetoxy-6α-(N-isobutyl-4-trifluoromethylcinnamamido)morphinan, 17-allyl-4,5α- epoxy-14β-acetoxy-6α-(N-isobutyl-3-phenylpropiolamido) morphinan, 17-methyl-4,5α-epoxy-14β-acetoxy-6α-(N-isobutyl-3-trifluoromethylcinnamamido)morphinan, 17-methyl-4,5α-epoxy-14β-acetoxy-6α-[N-isobutyl-trans-3-(3-furyl)acrylamido]morphinan, 17-methyl-4,5α-epoxy-14β-acetoxy-6α-(N-isobutyl-4-trifluoromethylcinnamamido)morphinan, 17-methyl-4,5α-epoxy-14β-acetoxy-6α-(N-isobutyl-3-phenylpropiolamido) morphinan, 17-phenethyl-4,5α-epoxy-14β-acetoxy-6α-(N-isobutyl-3-trifluoromethylcinnamamido)morphinan, 17-phenethyl-4,5α-epoxy-14β-acetoxy-6α-[N-isobutyl-trans-3-(3-furyl)acrylamido]morphinan, 17-phenethyl-4,5α-epoxy-14β-acetoxy-6α-(N-isobutyl-4-trifluoromethylcinnamamido)morphinan, 17-phenethyl-4,5α-epoxy-14β-acetoxy-6α-(N-isobutyl-3-phenylpropiolamido)morphinan, 17-cyclopropylmethyl-4,5α-epoxy-3-methoxy-14β-hydroxy-6α-(N-isobutyl-3-trifluoromethylcinnamamido)morphinan, 17-cyclopropylmethyl-4,5α-epoxy-3-methoxy-14β-hydroxy-6α-[N-isobutyl-trans-3-(3-furyl)acrylamido] morphinan, 17-cyclopropylmethyl-4,5α-epoxy-3-methoxy-14β-hydroxy-6α-(N-isobutyl-4-trifluoromethylcinnamamido)morphinan, 17-cyclopropylmethyl-4,5α-epoxy-3-methoxy-14β-hydroxy-6α-(N-isobutyl-3-phenylpropiolamido)morphinan, 17-allyl-4,5α-epoxy-3-methoxy-14β-hydroxy-6α-(N-isobutyl-3-trifluoromethylcinnamamido)morphinan, 17-allyl-4,5α-epoxy-3-methoxy-14β-hydroxy-6α-[N-isobutyl-trans-3-(3-furyl)acrylamido]morphinan, 17-allyl-4,5α-epoxy-3-methoxy-14β-hydroxy-6α-(N-isobutyl-4-trifluoromethylcinnamamido)morphinan, 17-allyl-4,5α-epoxy-3-methoxy-14β-hydroxy-6α-(N-isobutyl-3-phenylpropiolamido)morphinan, 17-methyl-4,5α-epoxy-3-methoxy-14β-hydroxy-6α-(N-isobutyl-3-trifluoromethylcinnamamido)morphinan, 17-methyl-4,5α-epoxy-3-methoxy-14β-hydroxy-6α-[N-isobutyl-trans-3-(3-furyl)acrylamido]morphinan, 17-methyl-4,5α-epoxy-3-methoxy-14β-hydroxy-6α-(N-isobutyl-4-trifluoromethylcinnamamido)morphinan, 17-methyl-4,5α-epoxy-3-methoxy-14β-hydroxy-6α-(N-isobutyl-3-phenylpropiolamido)morphinan, 17-phenethyl-4,5α-epoxy-3-methoxy-14β-hydroxy-6α-(N-isobutyl-3-trifluoromethylcinnamamido)morphinan, 17-phenethyl-4,5α-epoxy-3-methoxy-14β-hydroxy-6α-[N-isobutyl-trans-3-(3-furyl)acrylamido]morphinan, 17-phenethyl-4,5α-epoxy-3-methoxy-14β-hydroxy-6α-(N-isobutyl-4-trifluoromethylcinnamamido)morphinan, 17-phenethyl-4,5α-epoxy-3-methoxy-14β-hydroxy-6α-(N-isobutyl-3-phenylpropiolamido)morphinan, 17-cyclopropylmethyl-4,5α-epoxy-3-methoxy-14β-acetoxy-6α-(N-isobutyl-3-trifluoromethylcinnamamido) morphinan, 17-cyclopropylmethyl-4,5α-epoxy-3-methoxy-14β-acetoxy-6α-[N-isobutyl-trans-3-(3-furyl)acrylamido] morphinan, 17-cyclopropylmethyl-4,5α-epoxy-3-methoxy-14β-acetoxy-6α-(N-isobutyl-4-trifluoromethylcinnamamido)morphinan, 17-cyclopropylmethyl-4,5α-epoxy-3-methoxy-14β-acetoxy-6α-(N-isobutyl-3-phenylpropiolamido)morphinan, 17-allyl-4,5α-epoxy-3-methoxy-14β-acetoxy-6α-(N-isobutyl-3-trifluoromethylcinnamamido)morphinan, 17-allyl-4,5α-epoxy-3-methoxy-14β-acetoxy-6α-[N-isobutyl-trans-3-(3-furyl)acrylamido]morphinan, 17-allyl-4,5α-epoxy-3-methoxy-14β-acetoxy-6α-(N-isobutyl-4-trifluoromethylcinnamamido)morphinan, 17-allyl-4,5α-epoxy-3-methoxy-14β-acetoxy-6α-(N-isobutyl-3-phenylpropiolamido)morphinan, 17-methyl-4,5α-epoxy-3-methoxy-14β-acetoxy-6α-(N-isobutyl-3-trifluoromethylcinnamamido)morphinan, 17-methyl-4,5α-epoxy-3-methoxy-14β-acetoxy-6α-[N-isobutyl-trans-3-(3-furyl)acrylamido]morphinan, 17-methyl-4,5α-epoxy-3-methoxy-14β-acetoxy-6α-(N-isobutyl-4-trifluoromethylcinnamamido)morphinan, 17-methyl-4,5α-epoxy-3-methoxy-14β-acetoxy-6α-(N-isobutyl-3-phenylpropiolamido)morphinan, 17-phenethyl-4,5α-epoxy-3-methoxy-14β-acetoxy-6α-(N-isobutyl-3-trifluoromethylcinnamamido)morphinan, 17-phenethyl-4,5α-epoxy-3-methoxy-14β-acetoxy-6α-[N-isobutyl-trans-3-(3-furyl)acrylamido]morphinan, 17-phenethyl-4,5α-epoxy-3-methoxy-14β-acetoxy-6α-(N-isobutyl-4-trifluoromethylcinnamamido)morphinan, 17-phenethyl-4,5α-epoxy-3-methoxy-14β-acetoxy-6α-(N-isobutyl-3-phenylpropiolamido)morphinan, 17-cyclopropylmethyl-4,5α-epoxy-3-acetoxy-14β-hydroxy-6α-(N-isobutyl-3-trifluoromethylcinnamamido)morphinan, 17-cyclopropylmethyl-4,5α-epoxy-3-acetoxy-14β-hydroxy-6α-N-isobutyl-trans-3-(3-furyl)acrylamido morphinan, 17-cyclopropylmethyl-4,5α-epoxy-3-acetoxy-14β-hydroxy-6α-(N-isobutyl-4-trifluoromethylcinnamamido)morphinan, 17-cyclopropylmethyl-4,5α-epoxy-3-acetoxy-14β-hydroxy-6α-(N-isobutyl-3-phenylpropiolamido)morphinan, 17-allyl-4,5α-epoxy-3-acetoxy-14β-hydroxy-6α-(N-isobutyl-3-trifluoromethylcinnamamido)morphinan, 17-allyl-4,5α-epoxy-3-acetoxy-14β-hydroxy-6α-[N-isobutyl-trans-3-(3-furyl)acrylamido]morphinan, 17-allyl-4,5α-epoxy-3-acetoxy-14β-hydroxy-6α-(N-isobutyl-4-trifluoromethylcinnamamido)morphinan, 17-allyl-4,5α-epoxy-3-acetoxy-14β-hydroxy-6α-(N-isobutyl-3-phenylpropiolamido)morphinan, 17-methyl-4,5α-epoxy-3-acetoxy-14β-hydroxy-6α-(N-isobutyl-3-trifluoromethylcinnamamido)morphinan, 17-methyl-4,5α-epoxy-3-acetoxy-14β-hydroxy-6α-[N-isobutyl-trans-3-(3-furyl)acrylamido]morphinan, 17-methyl-4,5α-epoxy-3-acetoxy-14β-hydroxy-6α-(N-isobutyl-4-trifluoromethylcinnamamido)morphinan, 17-methyl-4,5α-epoxy-3-acetoxy-14β-hydroxy-6α-(N-isobutyl-3-phenylpropiolamido)morphinan, 17-phenethyl-4,5α-epoxy-3-acetoxy-14β-hydroxy-6α-(N-isobutyl-3-trifluoromethylcinnamamido)morphinan, 17-phenethyl-4,5α-epoxy-3-acetoxy-14β-hydroxy-6α-[N-isobutyl-trans-3-(3-furyl)acrylamido]morphinan, 17-phenethyl-4,5α-epoxy-3-acetoxy-14β-hydroxy-6α-(N-isobutyl-4-trifluoromethylcinnamamido)morphinan, 17-phenethyl-4,5α-epoxy-3-acetoxy-14β-hydroxy-6α-(N-isobutyl-3-phenylpropiolamido)morphinan, 17-cyclopropylmethyl-4,5α-epoxy-3,14β-diacetoxy-6α-(N-isobutyl-3-trifluoromethylcinnamamido)morphinan, 17-cyclopropylmethyl-4,5α-epoxy-3,14β-diacetoxy-6α-[N-isobutyl-trans-3-(3-furyl) acrylamido]morphinan, 17-cyclopropylmethyl-4,5α-epoxy-3,14β-diacetoxy-6α-(N-isobutyl-4-trifluoromethylcinnamamido)morphinan, 17-cyclopropylmethyl-4,5α-epoxy-3,14β-diacetoxy-6α-(N-isobutyl-3-phenylpropiolamido)morphinan, 17-allyl-4,5α-epoxy-3,14β-diacetoxy-6α-(N-isobutyl-3-trifluoromethylcinnamamido)morphinan, 17-allyl-4,5α-epoxy-3,14β-diacetoxy-6α-[N-isobutyl-trans-3-(3-furyl) acrylamido]morphinan, 17-allyl-4,5α-epoxy-3,14β-diacetoxy-6α-(N-isobutyl-4-trifluoromethylcinnamamido)morphinan, 17-allyl-4,5α-epoxy-3,14β-diacetoxy-6α-(N-isobutyl-3-phenylpropiolamido)morphinan, 17-methyl-4,5α-epoxy-3,14β-diacetoxy-6α-(N-isobutyl-3-trifluoromethylcinnamamido)morphinan, 17-methyl-4,5α-epoxy-3,14β-diacetoxy-6α-[N-isobutyl-trans-3-(3-furyl)

acrylamido]morphinan, 17-methyl-4,5α-epoxy-3,14β-diacetoxy-6α-(N-isobutyl-4-trifluoromethylcinnamamido)morphinan, 17-methyl-4,5α-epoxy-3,14β-diacetoxy-6α-(N-isobutyl-3-phenylpropiolamido)morphinan, 17-phenethyl-4,5α-epoxy-3,14β-diacetoxy-6α-(N-isobutyl-3-trifluoromethylcinnamamido)morphinan, 17-phenethyl-4,5α-epoxy-3,14β-diacetoxy-6α-[N-isobutyl-trans-3-(3-furyl) acrylamido]morphinan, 17-phenethyl-4,5α-epoxy-3,14β-diacetoxy-6α-(N-isobutyl-4-trifluoromethylcinnamamido)morphinan, 17-phenethyl-4,5α-epoxy-3,14β-diacetoxy-6α-(N-isobutyl-3-phenylpropiolamido)morphinan, 17-cyclopropylmethyl-4,5α-epoxy-3,14β-dihydroxy-6β-(N-methyl-3-trifluoromethylcinnamamido)morphinan, 17-cyclopropylmethyl-4,5α-epoxy-3,14β-dihydroxy-6α-[N-methyl-trans-3-(3-furyl)acrylamido]morphinan, 17-cyclopropylmethyl-4,5α-epoxy-3,14β-dihydroxy-6α-(N-methyl-4-trifluoromethylcinnamamido)morphinan, 17-cyclopropylmethyl-4,5α-epoxy-3,14β-dihydroxy-6β-(N-methyl-3-phenylpropiolamido)morphinan, 17-allyl-4,5α-epoxy-3,14β-dihydroxy-6β-(N-methyl-3-trifluoromethylcinnamamido)morphinan, 17-allyl-4,5α-epoxy-3,14-dihydroxy-6β-[N-methyl-trans-3-(3-furyl)acrylamido]morphinan, 17-allyl-4,5α-epoxy-3,14β-dihydroxy-6β-(N-methyl-4-trifluoromethylcinnamamido)morphinan, 17-allyl-4,5α-epoxy-3,14β-dihydroxy-6β-(N-methyl-3-phenylpropiolamido)morphinan, 17-methyl-4,5α-epoxy-3,14β-dihydroxy-6β-(N-methyl-3-trifluoromethylcinnamamido)morphinan, 17-methyl-4,5α-epoxy-3,14β-dihydroxy-6β-[N-methyl-trans-3-(3-furyl)acrylamido]morphinan, 17-methyl-4,5α-epoxy-3,14β-dihydroxy-6α-(N-methyl-4-trifluoromethylcinnamamido)morphinan, 17-methyl-4,5α-epoxy-3,14β-dihydroxy-6β-(N-methyl-3-phenylpropiolamido)morphinan, 17-phenethyl-4,5α-epoxy-3,14β-dihydroxy-6β-(N-methyl-3-trifluoromethylcinnamamido)morphinan, 17-phenethyl-4,5α-epoxy-3,14β-dihydroxy-6β-[N-methyl-trans-3-(3-furyl)acrylamido]morphinan, 17-phenethyl-4,5α-epoxy-3,14β-dihydroxy-6β-(N-methyl-4-trifluoromethylcinnamamido)morphinan, 17-phenethyl-4,5α-epoxy-3,14β-dihydroxy-6β-(N-methyl-3-phenylpropiolamido)morphinan, 17-cyclopropylmethyl-4,5α-epoxy-3-hydroxy-14β-acetoxy-6β-(N-methyl-3-trifluoromethylcinnamamido)morphinan, 17-cyclopropylmethyl-4,5α-epoxy-3-hydroxy-14β-acetoxy-6β-[N-methyl-trans-3-(3-furyl)acrylamido]morphinan, 17-cyclopropylmethyl-4,5α-epoxy-3-hydroxy14β-acetoxy-6β-(N-methyl-4-trifluoromethylcinnamamido)morphinan, 17-cyclopropylmethyl-4,5α-epoxy-3-hydroxy-14β-acetoxy-6α-(N-methyl-3-phenylpropiolamido)morphinan, 17-allyl- 4,5α-epoxy-3-hydroxy-14β-acetoxy-6β-(N-methyl-3-trifluoromethylcinnamamido)morphinan, 17-allyl-4,5α-epoxy-3-hydroxy-14β-acetoxy-6α-[N-methyl-trans-3-(3-furyl)acrylamido]morphinan, 17-allyl-4,5α-epoxy-3-hydroxy-14β-acetoxy-6β-(N-methyl-4-trifluoromethylcinnamamido)morphinan, 17-allyl-4,5α-epoxy-3-hydroxy-14β-acetoxy-6β-(N-methyl-3-phenylpropiolamido)morphinan, 17-methyl-4,5α-epoxy-3-hydroxy-14β-acetoxy-6β-(N-methyl-3-trifluoromethylcinnamamido)morphinan, 17-methyl-4,5α-epoxy-3-hydroxy-14β-acetoxy-6β-[N-methyl-trans-3-(3-furyl)acrylamido]morphinan, 17-methyl-4,5α-epoxy-3-hydroxy-14β-acetoxy-6β-(N-methyl-4-trifluoromethylcinnamamido)morphinan, 17-methyl-4,5α-epoxy-3-hydroxy-14β-acetoxy-6β-(N-methyl-3-phenylpropiolamido)morphinan, 17-phenethyl-4,5α-epoxy-3-hydroxy-14β-acetoxy-6β-(N-methyl-3-trifluoromethylcinnamamido)morphinan, 17-phenethyl-4,5α-epoxy-3-hydroxy-14β-acetoxy-6β-[N-methyl-trans-3-(3-furyl)acrylamido]morphinan, 17-phenethyl-4,5α-epoxy-3-hydroxy-14β-acetoxy-6β-(N-methyl-4-trifluoromethylcinnamamido)morphinan, 17-phenethyl-4,5α-epoxy-3-hydroxy-14β-acetoxy-6β-(N-methyl-3-phenylpropiolamido)morphinan, 17-cyclopropylmethyl-4,5α-epoxy-14β-hydroxy-6β-(N-methyl-3-trifluoromethylcinnamamido)morphinan, 17-cyclopropylmethyl-4,5α-epoxy-14β-hydroxy-6β[N-methyl-trans-3-(3-furyl)acrylamido]morphinan, 17-cyclopropylmethyl-4,5α-epoxy-14β-hydroxy-6β-(N-methyl-4-trifluoromethylcinnamamido)morphinan, 17-cyclopropylmethyl-4,5α-epoxy-14β-hydroxy-6β-(N-methyl-3-phenylpropiolamido)morphinan, 17-allyl-4,5α-epoxy-14β-hydroxy-6β-(N-methyl-3-trifluoromethylcinnamamido)morphinan, 17-allyl-4,5α-epoxy-14β-hydroxy-6β-[N-methyl-trans-3-(3-furyl)acrylamido]morphinan, 17-allyl-4,5α-epoxy-14β-hydroxy-6β-(N-methyl-4-trifluoromethylcinnamamido)morphinan, 17-allyl-4,5α-epoxy-14β-hydroxy-6β-(N-methyl-3-phenylpropiolamido)morphinan, 17-methyl-4,5α-epoxy-14β-hydroxy-6β-(N-methyl-3-trifluoromethylcinnamamido)morphinan, 17-methyl-4,5α-epoxy-14β-hydroxy-6β-[N-methyl-trans-3-(3-furyl)acrylamido]morphinan, 17-methyl-4,5α-epoxy-14β-hydroxy-6β-(N-methyl-4-trifluoromethylcinnamamido)morphinan, 17-methyl-4,5α-epoxy-14β-hydroxy-6β-(N-methyl-3-phenylpropiolamido)morphinan, 17-phenethyl-4,5α-epoxy-14β-hydroxy-6β-(N-methyl-3-trifluoromethylcinnamamido)morphinan, 17-phenethyl-4,5α-epoxy-14β-hydroxy-6β-[N-methyl-trans-3-(3-furyl)acrylamido]morphinan, 17-phenethyl-4,5α-epoxy-14β-hydroxy-6β-(N-methyl-4-trifluoromethylcinnamamido)morphinan, 17-phenethyl-4,5α-epoxy-14β-hydroxy-6β-(N-methyl-3-phenylpropiolamido)morphinan, 17-cyclopropylmethyl-4,5α-epoxy-14β-acetoxy-6β-(N-methyl-3-trifluoromethylcinnamamido)morphinan, 17-cyclopropylmethyl-4,5α-epoxy-14β-acetoxy-6β-[N-methyl-trans-3-(3-furyl)acrylamido]morphinan, 17-cyclopropylmethyl-4,5α-epoxy-14β-acetoxy-6β-(N-methyl-4-trifluoromethylcinnamamido)morphinan, 17-cyclopropylmethyl-4,5α-epoxy-14β-acetoxy-6β-(N-methyl-3-phenylpropiolamido)morphinan, 17-allyl-4,5α-epoxy-14β-acetoxy-6β-(N-methyl-3-trifluoromethylcinnamamido) morphinan, 17-allyl-4,5α-epoxy-14β-acetoxy-6β-[N-methyl-trans-3-(3-furyl)acrylamido]morphinan, 17-allyl-4,5α-epoxy-14β-acetoxy-6β-(N-methyl-4-trifluoromethylcinnamamido)morphinan, 17-allyl-4,5α-epoxy-14β-acetoxy-6β-(N-methyl-3-phenylpropiolamido)morphinan, 17-methyl-4,5α-epoxy-14β-acetoxy-6β-(N-methyl-3-trifluoromethylcinnamamido)morphinan, 17-methyl-4,5α-epoxy-14β-acetoxy-6β-[N-methyl-trans-3-(3-furyl)acrylamido]morphinan, 17-methyl-4,5α-epoxy-14β-acetoxy-6β-(N-methyl-4-trifluoromethylcinnamamido)morphinan, 17-methyl-4,5α-epoxy-14β-acetoxy-6β-(N-methyl-3-phenylpropiolamido)morphinan, 17-phenethyl-4,5α-epoxy-14β-acetoxy-6β-(N-methyl-3-trifluoromethylcinnamamido)morphinan, 17-phenethyl-4,5α-epoxy-14β-acetoxy-6β-[N-methyl-trans-3-(3-furyl)acrylamido]morphinan, 17-phenethyl-4,5α-epoxy-14β-acetoxy-6β-(N-methyl-4-trifluoromethylcinnamamido)morphinan, 17-phenethyl-4,5α-epoxy-14β-acetoxy-6β-(N-methyl-3-phenylpropiolamido)morphinan, 17-cyclopropylmethyl-4,5α-epoxy-3-methoxy-14β-hydroxy-6β-(N-methyl-3-trifluoromethylcinnamamido)

morphinan, 17-cyclopropylmethyl-4,5α-epoxy-3-methoxy-14β-hydroxy-6β-[N-methyl-trans-3-(3-furyl) acrylamido] morphinan, 17-cyclopropylmethyl-4,5α-epoxy-3-methoxy-14β-hydroxy-6β-(N-methyl-4-trifluoromethylcinnamamido)morphinan, 17-cyclopropylmethyl-4,5α-epoxy-3-methoxy-14β-hydroxy-6β-(N-methyl-3-phenylpropiolamido)morphinan, 17-allyl-4,5α-epoxy-3-methoxy-14β-hydroxy-6β-(N-methyl-3-trifluoromethylcinnamamido)morphinan, 17-allyl-4,5α-epoxy-3-methoxy-14β-hydroxy-6β-[N-methyl-trans-3-(3-furyl)acrylamido]morphinan, 17-allyl-4,5α-epoxy-3-methoxy-14β-hydroxy-6β-(N-methyl-4-trifluoromethylcinnamamido)morphinan, 17-allyl-4,5α-epoxy-3-methoxy-14β-hydroxy-6β-(N-methyl-3-phenylpropiolamido) morphinan, 17-methyl-4,5α-epoxy-3-methoxy-14β-hydroxy-6β-(N-methyl-3-trifluoromethylcinnamamido)morphinan, 17-methyl-4,5α-epoxy-3-methoxy-14β-hydroxy-6β-[N-methyl-trans-3-(3-furyl) acrylamido]morphinan, 17-methyl-4,5α-epoxy-3-methoxy-14β-hydroxy-6β-(N-methyl-4-trifluoromethylcinnamamido)morphinan, 17-methyl-4,5α-epoxy-3-methoxy-14β-hydroxy-6β-(N-methyl-3-phenylpropiolamido)morphinan, 17-phenethyl-4,5α-epoxy-3-methoxy-14β-hydroxy-6β-(N-methyl-3-trifluoromethylcinnamamido)morphinan, 17-phenethyl-4,5α-epoxy-3-methoxy-14β-hydroxy-6β-[N-methyl-trans-3-(3-furyl)acrylamido]morphinan, 17-phenethyl-4,5α-epoxy-3-methoxy-14β-hydroxy-6β-(N-methyl-4-trifluoromethylcinnamamido)morphinan, 17-phenethyl-4,5α-epoxy-3-methoxy-14β-hydroxy-6β-(N-methyl-3-phenylpropiolamido)morphinan, 17-cyclopropylmethyl-4,5α-epoxy-3-methoxy-14β-acetoxy-6β-(N-methyl-3-trifluoromethylcinnamamido)morphinan, 17-cyclopropylmethyl-4,5α-epoxy-3-methoxy-14β-acetoxy-6β-[N-methyl-trans-3-(3-furyl)acrylamido]morphinan, 17-cyclopropylmethyl-4,5α-epoxy-3-methoxy-14β-acetoxy-6β-(N-methyl-4-trifluoromethylcinnamamido)morphinan, 17-cyclopropylmethyl-4,5α-epoxy-3-methoxy-14β-acetoxy-6β-(N-methyl-3-phenylpropiolamido)morphinan, 17-allyl-4,5α-epoxy-3-methoxy-14β-acetoxy-6β-(N-methyl-3-trifluoromethylcinnamamido)morphinan, 17-allyl-4,5α-epoxy-3-methoxy-14β-acetoxy-6β-[N-methyl-trans-3-(3-furyl)acrylamido]morphinan, 17-allyl-4,5α-epoxy-3-methoxy-14β-acetoxy-6β-(N-methyl-4-trifluoromethylcinnamamido)morphinan, 17-allyl-4,5α-epoxy-3-methoxy-14β-acetoxy-6β-(N-methyl-3-phenylpropiolamido)morphinan, 17-methyl-4,5α-epoxy-3-methoxy-14β-acetoxy-6β-(N-methyl-3-trifluoromethylcinnamamido)morphinan, 17-methyl-4,5α-epoxy-3-methoxy-14β-acetoxy-6β-[N-methyl-trans-3-(3-furyl) acrylamido]morphinan, 17-methyl-4,5α-epoxy-3-methoxy-14β-acetoxy-6β-(N-methyl-4-trifluoromethylcinnamamido)morphinan, 17-methyl-4,5α-epoxy-3-methoxy-14β-acetoxy-6β-(N-methyl-3-phenylpropiolamido)morphinan, 17-phenethyl-4,5α-epoxy-3-methoxy-14β-acetoxy-6β-(N-methyl-3-trifluoromethylcinnamamido)morphinan, 17-phenethyl-4,5α-epoxy-3-methoxy-14β-acetoxy-6β-[N-methyl-trans-3-(3-furyl)acrylamido]morphinan, 17-phenethyl-4,5α-epoxy-3-methoxy-14β-acetoxy-6β-(N-methyl-4-trifluoromethylcinnamamido)morphinan, 17-phenethyl-4,5α-epoxy-3-methoxy-14β-acetoxy-6β-(N-methyl-3-phenylpropiolamido)morphinan, 17-cyclopropylmethyl-4,5α-epoxy-3-acetoxy-14β-hydroxy-6β-(N-methyl-3-trifluoromethylcinnamamido) morphinan, 17-cyclopropylmethyl-4,5α-epoxy-3-acetoxy-14β-hydroxy-6β-[N-methyl-trans-3-(3-furyl)acrylamido] morphinan, 17-cyclopropylmethyl-4,5α-epoxy-3-acetoxy-14β-hydroxy-6β-(N-methyl-4-trifluoromethylcinnamamido)morphinan, 17-cyclopropylmethyl- 4,5α-epoxy-3-acetoxy-14β-hydroxy-6β-(N-methyl-3-phenylpropiolamido)morphinan, 17-allyl-4,5α-epoxy-3-acetoxy 14β-hydroxy-6β-(N-methyl-3-trifluoromethylcinnamamido)morphinan, 17-allyl-4,5α-epoxy-3-acetoxy-14β-hydroxy-6β-[N-methyl-trans-3-(3-furyl)acrylamido]morphinan, 17-allyl-4,5α-epoxy-3-acetoxy-14β-hydroxy-6β-(N-methyl-4-trifluoromethylcinnamamido)morphinan, 17-allyl-4,5α-epoxy-3-acetoxy-14β-hydroxy-6β-(N-methyl-3-phenylpropiolamido)morphinan, 17-methyl-4,5α-epoxy-3-acetoxy-14β-hydroxy-6β-(N-methyl-3-trifluoromethylcinnamamido)morphinan, 17-methyl-4,5α-epoxy-3-acetoxy-14β-hydroxy-6β-[N-methyl-trans-3-(3-furyl)acrylamido]morphinan, 17-methyl-4,5α-epoxy-3-acetoxy-14β-hydroxy-6β-(N-methyl-4-trifluoromethylcinnamamido)morphinan, 17-methyl-4,5α-epoxy-3-acetoxy-14β-hydroxy-6β-(N-methyl-3-phenylpropiolamido)morphinan, 17-phenethyl-4,5α-epoxy-3-acetoxy-14β-hydroxy-6β-(N-methyl-3-trifluoromethylcinnamamido)morphinan, 17-phenethyl-4,5α-epoxy-3-acetoxy-14β-hydroxy-6β-[N-methyl-trans-3-(3-furyl)acrylamido]morphinan, 17-phenethyl-4,5α-epoxy-3-acetoxy-14β-hydroxy-6β-(N-methyl-4-trifluoromethylcinnamamido)morphinan, 17-phenethyl-4,5α-epoxy-3-acetoxy-14β-hydroxy-6β-(N-methyl-3-phenylpropiolamido)morphinan, 17-cyclopropylmethyl-4,5α-epoxy-3,14β-diacetoxy-6β-(N-methyl-3-trifluoromethylcinnamamido)morphinan, 17-cyclopropylmethyl-4,5α-epoxy-3,14β-diacetoxy-6β-[N-methyl-trans-3-(3-furyl)acrylamido]morphinan, 17-cyclopropylmethyl-4,5α-epoxy-3,14β-diacetoxy-6β-(N-methyl-4-trifluoromethylcinnamamido)morphinan, 17-cyclopropylmethyl- 4,5α-epoxy-3,14β-diacetoxy-6β-(N-methyl-3-phenylpropiolamido)morphinan, 17-allyl-4,5α-epoxy-3,14β-diacetoxy-6β-(N-methyl-3-trifluoromethylcinnamamido)morphinan, 17-allyl-4,5α-epoxy-3,14β-diacetoxy-6β-[N-methyl-trans-3-(3-furyl) acrylamido]morphinan, 17-allyl-4,5α-epoxy-3,14β-diacetoxy-6β-(N-methyl-4-trifluoromethylcinnamamido) morphinan, 17-allyl-4,5α-epoxy-3,14β-diacetoxy-6β-(N-methyl-3-phenylpropiolamido)morphinan, 17-methyl-4,5α-epoxy-3,14β-diacetoxy-6β-(N-methyl-3-trifluoromethylcinnamamido)morphinan, 17-methyl-4,5α-epoxy-3,14-diacetoxy-6β-[N-methyl-trans-3-(3-furyl) acrylamido]morphinan, 17-methyl-4,5α-epoxy-3,14β-diacetoxy-6β-(N-methyl-4-trifluoromethylcinnamamido) morphinan, 17-methyl-4,5α-epoxy-3,14β-diacetoxy-6β-(N-methyl-3-phenylpropiolamido)morphinan, 17-phenethyl-4,5α-epoxy-3,14β-diacetoxy-6β-(N-methyl-3-trifluoromethylcinnamamido)morphinan, 17-phenethyl-4,5α-epoxy-3,14β-diacetoxy-6β-[N-methyl-trans-3-(3-furyl) acrylamido]morphinan, 17-phenethyl-4,5α-epoxy-3,14β-diacetoxy-6β-(N-methyl-4-trifluoromethylcinnamamido) morphinan, 17-phenethyl-4,5α-epoxy-3,14β-diacetoxy-6β-(N-methyl-3-phenylpropiolamido)morphinan, 17- cyclopropylmethyl- 4,5α-epoxy-3,14β-dihydroxy-6β-(N-isobutyl-3-trifluoromethylcinnamamido)morphinan, 17-cyclopropylmethyl-4,5α-epoxy-3,14-dihydroxy-6β-[N-isobutyl-trans-3-(3-furyl)acrylamido]morphinan, 17-cyclopropylmethyl-4,5α-epoxy-3,14β-dihydroxy-6β-(N-isobutyl-4-trifluoromethylcinnamamido)morphinan, 17-cyclopropylmethyl-4,5α-epoxy-3,14β-dihydroxy-6-(N-isobutyl-3-phenylpropiolamido)morphinan, 17-allyl-4,5α- epoxy-3,14β-dihydroxy-6β-(N-isobutyl-3-trifluoromethylcinnamamido)morphinan, 17-allyl-4,5α-epoxy-3,14β-dihydroxy-6β-[N-isobutyl-trans-3-(3-furyl)acrylamido]morphinan, 17-allyl-4,5α-epoxy-3,14β-dihydroxy-6β-(N-isobutyl-4-trifluoromethylcinnamamido)morphinan, 17-allyl-4,5α-epoxy-3,14β-dihydroxy-6β-(N-isobutyl-3-phenylpropiolamido)morphinan, 17-methyl-4,5α-epoxy-3,14β-dihydroxy-6β-(N-isobutyl-3-trifluoromethylcinnamamido)morphinan, 17-methyl-4,5α-epoxy-3,14β-dihydroxy-6β-[N-isobutyl-trans-3-(3-furyl)acrylamido]morphinan, 17-methyl-4,5α-epoxy-3,14β-dihydroxy-6β-(N-isobutyl-4-trifluoromethylcinnamamido)morphinan, 17-methyl-4,5α-epoxy-3,14β-dihydroxy-6β-(N-isobutyl-3-phenylpropiolamido)morphinan, 17-phenethyl-4,5α-epoxy-3,14β-dihydroxy-6β-(N-isobutyl-3-trifluoromethylcinnamamido)morphinan, 17-phenethyl-4,5α-epoxy-3,14β-dihydroxy-6β-[N-isobutyl-trans-3-(3-furyl)acrylamido]morphinan, 17-phenethyl-4,5α-epoxy-3,14β-dihydroxy-6β-(N-isobutyl-4-trifluoromethylcinnamamido)morphinan, 17-phenethyl-4,5α-epoxy-3,14β-dihydroxy-6β-(N-isobutyl-3-phenylpropiolamido)morphinan, 17-cyclopropylmethyl-4,5α-epoxy-3-hydroxy-14β-acetoxy-6β-(N-isobutyl-3-trifluoromethylcinnamamido)morphinan, 17-cyclopropylmethyl-4,5α-epoxy-3-hydroxy-14β-acetoxy-6β-[N-isobutyl-trans-3-(3-furyl)acrylamido]morphinan, 17-cyclopropylmethyl-4,5α-epoxy-3-hydroxy-14β-acetoxy-6β-(N-isobutyl-4-trifluoromethylcinnamamido)morphinan, 17-cyclopropylmethyl-4,5α-epoxy-3-hydroxy-14-acetoxy-6β-(N-isobutyl-3-phenylpropiolamido)morphinan, 17-allyl-4,5α-epoxy-3-hydroxy-14β-acetoxy-6β-(N-isobutyl-3-trifluoromethylcinnamamido)morphinan, 17-allyl-4,5α-epoxy-3-hydroxy-14β-acetoxy-6β-[N-isobutyl-trans-3-(3-furyl)acrylamido]morphinan, 17-allyl-4,5α-epoxy-3-hydroxy-14β-acetoxy-6β-(N-isobutyl-4-trifluoromethylcinnamamido)morphinan, 17-allyl-4,5α-epoxy-3-hydroxy-14β-acetoxy-6β-(N-isobutyl-3-phenylpropiolamido)morphinan, 17-methyl-4,5α-epoxy-3-hydroxy-14β-acetoxy-6β-(N-isobutyl-3-trifluoromethylcinnamamido)morphinan, 17-methyl-4,5α-epoxy-3-hydroxy-14β-acetoxy-6β-[N-isobutyl-trans-3-(3-furyl)acrylamido]morphinan, 17-methyl-4,5α-epoxy-3-hydroxy-14β-acetoxy-6β-(N-isobutyl-4-trifluoromethylcinnamamido)morphinan, 17-methyl-4,5α-epoxy-3-hydroxy-14β-acetoxy-6β-(N-isobutyl-3-phenylpropiolamido)morphinan, 17-phenethyl-4,5α-epoxy-3-hydroxy-14β-acetoxy-6β-(N-isobutyl-3-trifluoromethylcinnamamido)morphinan, 17-phenethyl-4,5α-epoxy-3-hydroxy-14β-acetoxy-6β-[N-isobutyl-trans-3-(3-furyl)acrylamido]morphinan, 17-phenethyl-4,5α-epoxy-3-hydroxy-14β-acetoxy-6β-(N-isobutyl-4-trifluoromethylcinnamamido)morphinan, 17-phenethyl-4,5α-epoxy-3-hydroxy-14β-acetoxy-6β-(N-isobutyl-3-phenylpropiolamido)morphinan, 17-cyclopropylmethyl-4,5α-epoxy-14β-hydroxy-6β-(N-isobutyl-3-trifluoromethylcinnamamido)morphinan, 17-cyclopropylmethyl-4,5α-epoxy-14β-hydroxy-6β-[N-isobutyl-trans-3-(3-furyl)acrylamido]morphinan, 17-cyclopropylmethyl-4,5α-epoxy-14β-hydroxy-6β-(N-isobutyl-4-trifluoromethylcinnamamido)morphinan, 17-cyclopropylmethyl-4,5α-epoxy-14β-hydroxy-6β-(N-isobutyl-3-phenylpropiolamido)morphinan, 17-allyl-4,5α-epoxy-14β-hydroxy-6β-(N-isobutyl-3-trifluoromethylcinnamamido)morphinan, 17-allyl-4,5α-epoxy-14β-hydroxy-6β-[N-isobutyl-trans-3-(3-furyl)acrylamido]morphinan, 17-allyl-4,5α-epoxy-14β-hydroxy-6β-(N-isobutyl-4-trifluoromethylcinnamamido)morphinan, 17-allyl-4,5α-epoxy-14β-hydroxy-6β-(N-isobutyl-3-phenylpropiolamido)morphinan, 17-methyl-4,5α-epoxy-14-hydroxy-6β-(N-isobutyl-3-trifluoromethylcinnamamido)morphinan, 17-methyl-4,5α-epoxy-14β-hydroxy-6β-[N-isobutyl-trans-3-(3-furyl)acrylamido]morphinan, 17-methyl-4,5α-epoxy-14β-hydroxy-6β-(N-isobutyl-4-trifluoromethylcinnamamido)morphinan, 17-methyl-4,5α-epoxy-14β-hydroxy-6-(N-isobutyl-3-phenylpropiolamido)morphinan, 17-phenethyl-4,5α-epoxy-14β-hydroxy-6β-(N-isobutyl-3-trifluoromethylcinnamamido)morphinan, 17-phenethyl-4,5α-epoxy-14β-hydroxy-6β-[N-isobutyl-trans-3-(3-furyl)acrylamido]morphinan, 17-phenethyl-4,5α-epoxy-14β-hydroxy-6β-(N-isobutyl-4-trifluoromethylcinnamamido)morphinan, 17-phenethyl-4,5α-epoxy-14β-hydroxy-6β-(N-isobutyl-3-phenylpropiolamido)morphinan, 17-cyclopropylmethyl-4,5α-epoxy-14β-acetoxy-6β-(N-isobutyl-3-trifluoromethylcinnamamido)morphinan, 17-cyclopropylmethyl-4,5α-epoxy-14β-acetoxy-6β-[N-isobutyl-trans-3-(3-furyl)acrylamido]morphinan, 17-cyclopropylmethyl-4,5α-epoxy-14β-acetoxy-6β-(N-isobutyl-4-trifluoromethylcinnamamido)morphinan, 17-cyclopropylmethyl-4,5α-epoxy-14β-acetoxy-6β-(N-isobutyl-3-phenylpropiolamido)morphinan, 17-allyl-4,5a-epoxy-14-acetoxy-6β-(N-isobutyl-3-trifluoromethylcinnamamido)morphinan, 17-allyl-4,5α-epoxy-14-acetoxy-6β-[N-isobutyl-trans-3-(3-furyl)acrylamido]morphinan, 17-allyl-4,5α-epoxy-14β-acetoxy-6β-(N-isobutyl-4-trifluoromethylcinnamamido)morphinan, 17-allyl-4,5α-epoxy-14β-acetoxy-6β-(N-isobutyl-3-phenylpropiolamido)morphinan, 17-methyl-4,5α-epoxy-14β-acetoxy-6β-(N-isobutyl-3-trifluoromethylcinnamamido)morphinan, 17-methyl-4,5α-epoxy-14β-acetoxy-6β-[N-isobutyl-trans-3-(3-furyl)acrylamido]morphinan, 17-methyl-4,5α-epoxy-14β-acetoxy-6β-(N-isobutyl-4-trifluoromethylcinnamamido)morphinan, 17-methyl-4,5α-epoxy-14β-acetoxy-6β-(N-isobutyl-3-phenylpropiolamido)morphinan, 17-phenethyl-4,5α-epoxy-14β-acetoxy-6β-(N-isobutyl-3-trifluoromethylcinnamamido)morphinan, 17-phenethyl-4,5α-epoxy-14β-acetoxy-6β-[N-isobutyl-trans-3-(3-furyl)acrylamido]morphinan, 17-phenethyl-4,5α-epoxy-14β-acetoxy-6β-(N-isobutyl-4-trifluoromethylcinnamamido)morphinan, 17-phenethyl-4,5α-epoxy-14β-acetoxy-6β-(N-isobutyl-3-phenylpropiolamido)morphinan, 17-cyclopropylmethyl-4,5α-epoxy-3-methoxy-14β-hydroxy-6β-(N-isobutyl-3-trifluoromethylcinnamamido)morphinan, 17-cyclopropylmethyl-4,5α-epoxy-3-methoxy-14-hydroxy-6β-[N-isobutyl-trans-3-(3-furyl)acrylamido]morphinan, 17-cyclopropylmethyl-4,5α-epoxy-3-methoxy-14-hydroxy-6β-(N-isobutyl-4-trifluoromethylcinnamamido)morphinan, 17-cyclopropylmethyl-4,5α-epoxy-3-methoxy-14β-hydroxy-6β-(N-isobutyl-3-phenylpropiolamido)morphinan, 17-allyl-4,5α-epoxy-3-methoxy-14β-hydroxy-6β-(N-isobutyl-3-trifluoromethylcinnamamido)morphinan, 17-allyl-4,5α-epoxy-3-methoxy-14β-hydroxy-6β-[N-isobutyl-trans-3-(3-furyl)acrylamido]morphinan, 17-allyl-4,5α-epoxy-3-methoxy-14β-hydroxy-6β-(N-isobutyl-4-trifluoromethylcinnamamido)morphinan, 17-allyl-4,5α-epoxy-3-methoxy-14β-hydroxy-6β-(N- isobutyl-3-phenylpropiolamido)morphinan, 17-methyl-4,5α-epoxy-3-methoxy-14β-hydroxy-6β-(N-isobutyl-3-trifluoromethylcinnamamido)morphinan, 17-methyl-4,5α-epoxy-3-methoxy-14β-hydroxy-6β-[N-isobutyl-trans-3-(3-furyl)acrylamido]morphinan, 17-methyl-4,5α-epoxy-3-methoxy-14β-hydroxy-6β-(N-isobutyl-4-trifluoromethylcinnamamido)morphinan, 17-methyl-4,5α-epoxy-3-methoxy-14β-hydroxy-6β-(N-isobutyl-3-phenylpropiolamido)morphinan, 17-phenethyl-4,5α-epoxy-3-methoxy-14β-hydroxy-6β-(N-isobutyl-3-trifluoromethylcinnamamido)morphinan, 17-phenethyl-4,5α-epoxy-3-methoxy-14β-hydroxy-6β-[N-isobutyl-trans-3-(3-furyl)acrylamido]morphinan, 17-phenethyl-4,5α-epoxy-3-methoxy-14β-hydroxy-6β-(N-isobutyl-4-trifluoromethylcinnamamido)morphinan, 17-phenethyl-4,5α-epoxy-3-methoxy-14β-hydroxy-6β-(N-isobutyl-3-phenylpropiolamido)morphinan, 17-cyclopropylmethyl-4,5α-epoxy-3-methoxy-14β-acetoxy- 6β-(N-isobutyl-3-trifluoromethylcinnamamido)morphinan, 17-cyclopropylmethyl-4,5α-epoxy-3-methoxy-14β-acetoxy-6β-[N-isobutyl-trans-3-(3-furyl)acrylamido]morphinan, 17-cyclopropylmethyl-4,5α-epoxy-3-methoxy-14β-acetoxy- 6β-(N-isobutyl-4-trifluoromethylcinnamamido)morphinan, 17-cyclopropylmethyl-4,5α-epoxy-3-methoxy-14β-acetoxy-6β-(N-isobutyl-3-phenylpropiolamido)morphinan, 17-allyl-4,5α-epoxy-3-methoxy-14β-acetoxy-6β-(N-isobutyl-3-trifluoromethylcinnamamido)morphinan, 17-allyl-4,5α-epoxy-3-methoxy-14β-acetoxy-6β-[N-isobutyl-trans-3-(3-furyl)acrylamido]morphinan, 17-allyl-4,5α-epoxy-3-methoxy-14β-acetoxy-6β-(N-isobutyl-4-trifluoromethylcinnamamido)morphinan, 17-allyl-4,5α-epoxy-3-methoxy-14β-acetoxy-6β-(N-isobutyl-3-phenylpropiolamido)morphinan, 17-methyl-4,5α-epoxy-3-methoxy-14β-acetoxy-6β-(N-isobutyl-3-trifluoromethylcinnamamido)morphinan, 17-methyl-4,5α-epoxy-3-methoxy-14β-acetoxy-6β-[N-isobutyl-trans-3-(3-furyl)acrylamido]morphinan, 17-methyl-4,5α-epoxy-3-methoxy-14β-acetoxy-6β-(N-isobutyl-4-trifluoromethylcinnamamido)morphinan, 17-methyl-4,5α-epoxy-3-methoxy-14β-acetoxy-6β-(N-isobutyl-3-phenylpropiolamido)morphinan, 17-phenethyl-4,5α-epoxy-3-methoxy-14-acetoxy-6β-(N-isobutyl-3-trifluoromethylcinnamamido)morphinan, 17-phenethyl-4,5α-epoxy-3-methoxy-14β-acetoxy-6β-[N-isobutyl-trans-3-(3-furyl)acrylamido]morphinan, 17-phenethyl-4,5α-epoxy-3-methoxy-14β-acetoxy-6β-(N-isobutyl-4-trifluoromethylcinnamamido)morphinan, 17-phenethyl-4,5α-epoxy-3-methoxy-14β-acetoxy-6β-(N-isobutyl-3-phenylpropiolamido)morphinan, 17-cyclopropylmethyl-4,5α-epoxy-3-acetoxy-14β-hydroxy-6β-(N-isobutyl-3-trifluoromethylcinnamamido)morphinan, 17-cyclopropylmethyl-4,5α-epoxy-3-acetoxy-14-hydroxy-6β-[N-isobutyl-trans-3-(3-furyl)acrylamido]morphinan, 17-cyclopropylmethyl-4,5α-epoxy- 3-acetoxy-14β-hydroxy-6β-(N-isobutyl-4-trifluoromethylcinnamamido)morphinan, 17-cyclopropylmethyl-4,5α-epoxy-3-acetoxy-14β-hydroxy-6β-(N-isobutyl-3-phenylpropiolamido)morphinan, 17-allyl-4,5α-epoxy-3-acetoxy-14β-hydroxy-6β-(N-isobutyl-3-trifluoromethylcinnamamido)morphinan, 17-allyl-4,5α-epoxy-3-acetoxy-14β-hydroxy-6β-[N-isobutyl-trans-3-(3-furyl)acrylamido]morphinan, 17-allyl-4,5α-epoxy-3-acetoxy-14β-hydroxy-6β-(N-isobutyl-4-trifluoromethylcinnamamido)morphinan, 17-allyl-4,5α-epoxy-3-acetoxy-14β-hydroxy-6β-(N-isobutyl-3-phenylpropiolamido) morphinan, 17-methyl-4,5α-epoxy-3-acetoxy-14β-hydroxy-6β-(N-isobutyl-3-trifluoromethylcinnamamido)morphinan, 17-methyl-4,5α-epoxy-3-acetoxy-14β-hydroxy-6β-[N-isobutyl-trans-3-(3-furyl)acrylamido]morphinan, 17-methyl-4,5α-epoxy-3-acetoxy-14β-hydroxy-6β-(N-isobutyl-4-trifluoromethylcinnamamido)morphinan, 17-methyl-4,5α-epoxy-3-acetoxy-14β-hydroxy-6β-(N-isobutyl-3-phenylpropiolamido)morphinan, 17-phenethyl-4,5α-epoxy-3-acetoxy-14β-hydroxy-6β-(N-isobutyl-3-trifluoromethylcinnamamido)morphinan, 17-phenethyl-4,5α-epoxy-3-acetoxy-14β-hydroxy-6β-[N-isobutyl-trans-3-(3-furyl)acrylamido]morphinan, 17-phenethyl-4,5α-epoxy-3-acetoxy-14β-hydroxy-6β-(N-isobutyl-4-trifluoromethylcinnamamido)morphinan, 17-phenethyl-4,5α-epoxy-3-acetoxy-14β-hydroxy-6β-(N-isobutyl-3-phenylpropiolamido)morphinan, 17-cyclopropylmethyl-4,5α-epoxy-3,14-diacetoxy-6β-(N-isobutyl-3-trifluoromethylcinnamamido)morphinan, 17-cyclopropylmethyl-4,5α-epoxy-3,14β-diacetoxy-6β-[N-isobutyl-trans-3-(3-furyl)acrylamido]morphinan, 17-cyclopropylmethyl-4,5α-epoxy-3,14β-diacetoxy-6β-(N-isobutyl-4-trifluoromethylcinnamamido)morphinan, 17-cyclopropylmethyl-4,5α-epoxy-3,14β-diacetoxy-6β-(N-isobutyl-3-phenylpropiolamido)morphinan, 17-allyl- 4,5(-epoxy-3,14β-diacetoxy-6β-(N-isobutyl-3-trifluoromethylcinnamamido)morphinan, 17-allyl-4,5α-epoxy-3,14β-diacetoxy-6β-[N-isobutyl-trans-3-(3-furyl)acrylamido]morphinan, 17-allyl-4,5α-epoxy-3,14β-diacetoxy-6β-(N-isobutyl-4-trifluoromethylcinnamamido) morphinan, 17-allyl-4,5α-epoxy-3,14β-diacetoxy-6β-(N-isobutyl-3-phenylpropiolamido)morphinan, 17-methyl-4,5α-epoxy-3,14-diacetoxy-6β-(N-isobutyl-3-trifluoromethylcinnamamido)morphinan, 17-methyl-4,5α-epoxy-3,14β-diacetoxy-6β-[N-isobutyl-trans-3-(3-furyl)acrylamido]morphinan, 17-methyl-4,5α-epoxy-3,14β-diacetoxy-6β-(N-isobutyl-4-trifluoromethylcinnamamido)morphinan, 17-methyl-4,5α-epoxy-3,14β-diacetoxy-6β-(N-isobutyl-3-phenylpropiolamido)morphinan, 17-phenethyl-4,5α-epoxy-3,14β-diacetoxy-6β-(N-isobutyl-3-trifluoromethylcinnamamido)morphinan, 17-phenethyl-4,5α-epoxy-3,14β-diacetoxy-6β-[N-isobutyl-trans-3-(3-furyl)acrylamido]morphinan, 17-phenethyl-4,5α-epoxy-3,14β-diacetoxy-6β-(N-isobutyl-4-trifluoromethylcinnamamido)morphinan, 17-phenethyl-4,5α-epoxy-3,14β-diacetoxy-6β-(N-isobutyl-3-phenylpropiolamido)morphinan, 17-cyclopropylmethyl-4,5α-epoxy-3,14β-dihydroxy-6α-(N-methyl-3-cyclohexylpropionamido)morphinan, 17-allyl-4,5α-epoxy-3,14β-dihydroxy-6α-(N-methyl-3-cyclohexylpropionamido)morphinan, 17-cyclopropylmethyl-4,5α-epoxy-3,14β-dihydroxy-6β-(N-methyl-3-cyclohexylpropionamido)morphinan, 17-allyl-4,5β-epoxy-3,14β-dihydroxy-6β-(N-methyl-3-cyclohexylpropionamido)morphinan, 17-cyclopropylmethyl-4,5α-epoxy-3,14β-dihydroxy-6β-(N-methylbutyloxycarbamido)morphinan, 17-allyl-4,5α-epoxy-3,14β-dihydroxy-6α-(N-methylbutyloxycarbamido)morphinan, 17-cyclopropylmethyl-4,5α-epoxy-3,14β-dihydroxy-6β-(N-methylbutyloxycarbamido)morphinan, 17-allyl-4,5α-epoxy-3,14β-dihydroxy-6β-(N-methylbutyloxycarbamido)morphinan, 17-cyclopropylmethyl-4,5α-epoxy-3,14β-dihydroxy-6α-(N-methyl-3-isothiocyanatophenylacetamido)morphinan, 17-allyl-4,5α-epoxy-3,14β-dihydroxy-6α-(N-methyl-3-isothiocyanatophenylacetamido)morphinan, 17-cyclopropylmethyl-4,5α-epoxy-3,14β-dihydroxy-6β-(N-methyl-3-isothiocyanatophenylacetamido)morphinan, 17-allyl-4,5α-epoxy-3,14β-dihydroxy-6β-(N-methyl-3-isothiocyanatophenylacetamido)morphinan, 17-cyclopropylmethyl-4,5α-epoxy-3,14β-dihydroxy-6α-(N-methyl-2-hexenoamido)morphinan, 17-allyl-4,5α-epoxy-3,14β-dihydroxy-6α-(N-methyl-2-hexenoamido)

morphinan, 17-cyclopropylmethyl-4,5α-epoxy-3,14β-dihydroxy-6β-(N-methyl-2-hexenoamido)morphinan, 17-allyl-4,5α-epoxy-3,14-dihydroxy-6β-(N-methyl-2-hexenoamido)morphinan, 17-cyclopropylmethyl-4,5α-epoxy-3,14β-dihydroxy-6α-(N-methyl-3-fluorocinnamamido)morphinan, 17-allyl-4,5α-epoxy-3,14β-dihydroxy-6α-(N-methyl-3-fluorocinnamamido)morphinan, 17-cyclopropylmethyl-4,5α-epoxy-3,14β-dihydroxy-6β-(N-methyl-3-fluorocinnamamido)morphinan, 17-allyl-4,5α-epoxy-3,14-dihydroxy-6β-(N-methyl-3-fluorocinnamamido)morphinan, 17-cyclopropylmethyl-4,5α-epoxy-3,14β-dihydroxy-6α-(N-methyl-3-methoxycinnamamido)morphinan, 17-allyl-4,5α-epoxy-3,14β-dihydroxy-6α-(N-methyl-3-methoxycinnamamido)morphinan, 17-cyclopropylmethyl-4,5α-epoxy-3,14β-dihydroxy-6β-(N-methyl-3-methoxycinnamamido)morphinan, 17-allyl-4,5α-epoxy-3,14β-dihydroxy-6β-(N-methyl-3-methoxycinnamamido)morphinan, 17-cyclopropylmethyl-4,5α-epoxy-3,14β-dihydroxy-6β-(N-methyl-2-cyclopentylpropionamido)morphinan, 17allyl-4,5α-epoxy-3,14-dihydroxy-6α-(N-methyl-2-cyclopentylpropionamido)morphinan, 17-cyclopropylmethyl-4,5α-epoxy-3,14β-dihydroxy-6β-(N-methyl-2-cyclopentylpropionamido)morphinan, 17-allyl-4,5α-epoxy-3,14β-dihydroxy-6β-(N-methyl-2-cyclopentylpropionamido)morphinan, 17-cyclopropylmethyl-4,5α-epoxy-3,14-dihydroxy-6α-(N-methyl-2-naphthamido)morphinan, 17-allyl-4,5α-epoxy-3,14β-dihydroxy-6α-(N-methyl-2-naphthamido)morphinan, 17-cyclopropylmethyl-4,5α-epoxy-3,14β-dihydroxy-6β-(N-methyl-2-naphthamido)morphinan, 17-allyl-4,5α-epoxy-3,14β-dihydroxy-6β-(N-methyl-2-naphthamido)morphinan, 17-cyclopropylmethyl-4,5α-epoxy-3,14β-dihydroxy-6α-(N-methyl-3-nitrocinnamamido)morphinan, 17-allyl-4,5α-epoxy-3,14β-dihydroxy-6α-(N-methyl-3-nitrocinnamamido)morphinan, 17-cyclopropylmethyl-4,5α-epoxy-3,14β-dihydroxy-6β-(N-methyl-3-nitrocinnamamido)morphinan, 17-allyl-4,5α-epoxy-3,14β-dihydroxy-6β-(N-methyl-3-nitrocinnamamido)morphinan, 17-cyclopropylmethyl-4,5α-epoxy-3,14β-dihydroxy-6α-(N-methyl-2-methoxyethoxycarbamido)morphinan, 17-allyl-4,5α-epoxy-3,14β-dihydroxy-6α-(N-methyl-2-methoxyethoxycarbamido)morphinan, 17-cyclopropylmethyl-4,5α-epoxy-3,14β-dihydroxy-6β-(N-methyl-2-methoxyethoxycarbamido)morphinan, 17-allyl-4,5α-epoxy-3,14β-dihydroxy-6β-(N-methyl-2-methoxyethoxycarbamido)morphinan, 17-cyclopropylmethyl-4,5α-epoxy-3,14β-dihydroxy-6α-(N-methyl-trans-3-cyclohexylacrylamido)morphinan, 17-allyl-4,5α-epoxy-3,14β-dihydroxy-6α-(N-methyl-trans-3-cyclohexylacrylamido)morphinan, 17-cyclopropylmethyl-4,5α-epoxy-3,14β-dihydroxy-6-(N-methyl-trans-3-cyclohexylacrylamido)morphinan, 17-allyl-4,5α-epoxy-3,14β-dihydroxy-6β-(N-methyl-trans-3-cyclohexylacrylamido)morphinan, 17-cyclopropylmethyl-4,5α-epoxy-3, 14β-dihydroxy-6α-(N-methylbenzoylacetamido)morphinan, 17-allyl-4,5α-epoxy- 3,14β-dihydroxy-6α-(N-methylbenzoylacetamido)morphinan, 17-cyclopropylmethyl-4,5α-epoxy-3,14β-dihydroxy-6β-(N-methylbenzoylacetamido)morphinan, 17-allyl-4,5α-epoxy-3,14β-dihydroxy-6β-(N-methylbenzoylacetamido)morphinan, 17-cyclopropylmethyl-4,5α-epoxy-3,14-dihydroxy-6α-[N-methyl-trans-3-(2-furyl)acrylamido]morphinan, 17-allyl-4,5α-epoxy-3,14β-dihydroxy-6α-[N-methyl-trans-3-(2-furyl)acrylamido]morphinan, 17-cyclopropylmethyl-4,5α-epoxy-3,14β-dihydroxy-6β-[N-methyl-trans-3-(2-furyl)acrylamido]morphinan, 17-allyl-4,5α-epoxy-3,14β-dihydroxy-6β-[N-methyl-trans-3-(2-furyl)acrylamido]morphinan, 17-cyclopropylmethyl-4,5α-epoxy-3,14β-dihydroxy-6α-(N-methyl-2-trifluoromethylcinnamamido)morphinan, 17-allyl-4,5α-epoxy-3,14β-dihydroxy-6α-(N-methyl-2-trifluoromethylcinnamamido)morphinan, 17-cyclopropylmethyl-4,5α-epoxy-3,14β-dihydroxy-6β-(N-methyl-2-trifluoromethylcinnamamido)morphinan, 17-allyl-4,5α-epoxy-3,14β-dihydroxy-6β-(N-methyl-2-trifluoromethylcinnamamido)morphinan, 17-cyclopropylmethyl-4,5α-epoxy-3,14β-dihydroxy-6α-(N-methyl-3-isothiocyanatocinnamamido)morphinan, 17-allyl-4,5α-epoxy-3,14-dihydroxy-6α-(N-methyl-3-isothiocyanatocinnamamido)morphinan, 17-cyclopropylmethyl-4,5α-epoxy-3,14-dihydroxy-6β-(N-methyl-3-isothiocyanatocinnamamido)morphinan, 17-allyl-4,5α-epoxy-3,14β-dihydroxy-6β-(N-methyl-3-isothiocyanatocinnamamido)morphinan, 17-cyclopropylmethyl-4,5α-epoxy-3,14β-dihydroxy-6α-(N-methyl-3-methylcinnamamido)morphinan, 17-cyclopropylmethyl-4,5α-epoxy-3,14β-dihydroxy-6α-[N-methyl-3-(4-trifluoromethylphenyl)propiolamido]morphinan, 17-allyl-4,5α-epoxy-3,14β-dihydroxy-6α-(N-methyl-3-methylcinnamamido)morphinan, 17-allyl-4,5α-epoxy-3,14β-dihydroxy-6α-[N-methyl-3-(4-trifluoromethylphenyl)propiolamido]morphinan, 17-methyl- 4,5α-epoxy-3,14β-dihydroxy-6α-(N-methyl-3-methylcinnamamido)morphinan, 17-methyl-4,5α-epoxy-3,14β-dihydroxy-6α-[N-methyl-3-(4-trifluoromethylphenyl)propiolamido]morphinan, 17-phenethyl-4,5α-epoxy-3,14β-dihydroxy-6α-(N-methyl-3-methylcinnamamido)morphinan, 17-phenethyl-4,5α-epoxy-3,14β-dihydroxy-6α-[N-methyl-3-(4-trifluoromethylphenyl)propiolamido]morphinan, 17-cyclopropylmethyl-4,5α-epoxy-14β-acetoxy-3-hydroxy-6α-(N-methyl-3-methylcinnamamido)morphinan, 17-cyclopropylmethyl-4,5α-epoxy-14β-acetoxy-3-hydroxy-6α-[N-methyl-3-(4-trifluoromethylphenyl)propiolamido]morphinan, 17-allyl-4,5α-epoxy-14β-acetoxy-3-hydroxy-6α-(N-methyl-3-methylcinnamamido)morphinan, 17-allyl-4,5α-epoxy-14β-acetoxy-3-hydroxy-6α-[N-methyl-3-(4-trifluoromethylphenyl)propiolamido]morphinan, 17-methyl-4,5α-epoxy-14β-acetoxy-3-hydroxy-6α-(N-methyl-3-methylcinnamamido)morphinan, 17-methyl-4,5α-epoxy-14β-acetoxy-3-hydroxy-6α-[N-methyl-3-(4-trifluoromethylphenyl)propiolamido]morphinan, 17-phenethyl-4,5α-epoxy-14β-acetoxy-3-hydroxy-6α-(N-methyl-3-methylcinnamamido)morphinan, 17-phenethyl-4,5α-epoxy-14β-acetoxy-3-hydroxy-6α-[N-methyl-3-(4-trifluoromethylphenyl)propiolamido]morphinan, 17-cyclopropylmethyl-4,5α-epoxy-14-hydroxy-6α-N-methyl-3-methylcinnamamido)morphinan, 17-cyclopropylmethyl-4,5α-epoxy-14β-hydroxy-6α-[N-methyl-3-(4-trifluoromethylphenyl)propiolamido]morphinan, 17-allyl-4,5α-epoxy-14β-hydroxy-6α-(N-methyl-3-methylcinnamamido)morphinan, 17 -allyl-4,5α-epoxy-14β-hydroxy-6α-[N-methyl-3-(4-trifluoromethylphenyl)propiolamido]morphinan, 17-methyl-4,5α-epoxy-14-hydroxy-6α-(N-methyl-3-methylcinnamamido)morphinan, 17-methyl-4,5α-epoxy-14β-hydroxy-6α-[N-methyl-3-(4-trifluoromethylphenyl)propiolamido]morphinan, 17-phenethyl-4,5α-epoxy-14β-hydroxy-6α-(N-methyl-3-methylcinnamamido)morphinan, 17-phenethyl-4,5α-epoxy- 14β-hydroxy-6α-[N-methyl-3-(4-trifluoromethylphenyl)propiolamido]morphinan, 17-cyclopropylmethyl-4,5α-epoxy-14β-acetoxy-6α-(N-methyl-3-methylcinnamamido)morphinan, 17-cyclopropylmethyl-4,5α-epoxy-14β-acetoxy-6α-[N-methyl-3-(4-trifluoromethylphenyl)propiolamido]morphinan, 17-allyl-4,5α-epoxy-14-acetoxy-6α-(N-methyl-3-methylcinnamamido)morphinan, 17-allyl-4,5α-epoxy-14β-acetoxy-6α-[N-methyl-3-(4-trifluoromethylphenyl)propiolamido]morphinan, 17-methyl-4,5α-epoxy-14β-acetoxy-6α-(N-methyl-3-methylcinnamamido)morphinan, 17-methyl-4,5α-epoxy-14β-acetoxy-6α-[N-methyl-3-(4-trifluoromethylphenyl)propiolamido]morphinan, 17-phenethyl-4,5α-epoxy-14β-acetoxy-6α-(N-methyl-3-methylcinnamamido)morphinan, 17-phenethyl-4,5α-epoxy-14β-acetoxy-6α-[N-methyl-3-(4-trifluoromethylphenyl)propiolamido]morphinan, 17-cyclopropylmethyl-4,5α-epoxy-14βhydroxy-3-methoxy-6α-(N-methyl-3-methylcinnamamido)morphinan, 17-cyclopropylmethyl-4,5α-epoxy-14β-hydroxy-3-methoxy-6α-[N-methyl-3-(4-trifluoromethylphenyl)propiolamido]morphinan, 17-allyl-4,5α-epoxy-14β-hydroxy-3-methoxy-6α-(N-methyl-3-methylcinnamamido)morphinan, 17-allyl-4,5α-epoxy-14β-hydroxy-3-methoxy-6α-[N-methyl-3-(4-trifluoromethylphenyl)propiolamido]morphinan, 17-methyl-4,5α-epoxy-14β-hydroxy-3-methoxy-6α-(N-methyl-3-methylcinnamamido)morphinan, 17-methyl-4,5α-epoxy-14β-hydroxy-3-methoxy-6α-[N-methyl-3-(4-trifluoramethylphenyl)propiolamido]morphinan, 17-phenethyl-4,5α-epoxy-14β-hydroxy-3-methoxy-6α-(N-methyl-3-methylcinnamamido)morphinan, 17-phenethyl-4,5α-epoxy-14-hydroxy-3-methoxy-6α-[N-methyl-3-(4-trifluoromethylphenyl)propiolamido)morphinan, 17-cyclopropylmethyl-4,5α-epoxy-14β-acetoxy-3-methoxy-6α-(N-methyl-3-methylcinnamamido]morphinan, 17-cyclopropylmethyl-4,5α-epoxy-14-acetoxy-3-methoxy-6α-[N-methyl-3-(4-trifluoromethylphenyl)propiolamido]morphinan, 17-allyl-4,5α-epoxy-14β-acetoxy-3-methoxy-6α-(N-methyl-3-methylcinnamamido)morphinan, 17-allyl-4,5α-epoxy-14β-acetoxy-3-methoxy-6α-[N-methyl-3-(4-trifluoromethylphenyl)propiolamido]morphinan, 17-methyl-4,5α-epoxy-14β-acetoxy-3-methoxy-6α-(N-methyl-3-methylcinnamamido)morphinan, 17-methyl-4,5α-epoxy-14β-acetoxy-3-methoxy-6α-[N-methyl-3-(4-trifluoromethylphenyl)propiolamido]morphinan, 17-phenethyl-4,5α-epoxy-14β-acetoxy-3-methoxy-6α-(N-methyl-3-methylcinnamamido)morphinan, 17-phenethyl-4,5α-epoxy-14β-acetoxy-3-methoxy-6α-[N-methyl-3-(4-trifluoromethylphenyl)propiolamido]morphinan, 17-cyclopropylmethyl-4,5α-epoxy-14-hydroxy-3-acetoxy-6α-(N-methyl-3-methylcinnamamido)morphinan, 17-cyclopropylmethyl-4,5α-epoxy-14-hydroxy-3-acetoxy-6α-[N-methyl-3-(4-trifluoromethylphenyl)propiolamido]morphinan, 17-allyl-4,5α-epoxy-14β-hydroxy-3-acetoxy-6α-(N-methyl-3-methylcinnamamido)morphinan, 17-allyl-4,5α-epoxy-14β-hydroxy-3-acetoxy-6α-[N-methyl-3-(4-trifluoromethylphenyl)propiolamido]morphinan, 17-methyl-4,5α-epoxy-14β-hydroxy-3-acetoxy-6α-(N-methyl-3-methylcinnamamido)morphinan, 17-methyl-4,5α-epoxy-14-hydroxy-3-acetoxy-6α-[N-methyl-3-(4-trifluoromethyl-phenyl)propiolamido]morphinan, 17-phenethyl-4,5α-epoxy-14-hydroxy-3-acetoxy-6α-(N-methyl-3-methylcinnamamido)morphinan, 17-phenethyl-4,5α-epoxy-14β-hydroxy-3-acetoxy-6α-[N-methyl-3-(4-trifluoromethylphenyl)propiolamido]morphinan, 17-cyclopropylmethyl-4,5α-epoxy-3,14β-diacetoxy-6α-(N-methyl-3-methylcinnamamido)morphinan, 17-cyclopropylmethyl-4,5α-epoxy-3,14-diacetoxy-6β-[N-methyl-3-(4-trifluoromethylphenyl)propiolamido]morphinan, 17-allyl-4,5α-epoxy-3,14β-diacetoxy-6α-(N-methyl-3-methylcinnamamido)morphinan, 17-allyl-4,5α-epoxy-3,14β-diacetoxy-6α-[N-methyl-3-(4-trifluoromethylphenyl)propiolamido]morphinan, 17-methyl-4,5α-epoxy-3,14β-diacetoxy-6α-(N-methyl-3-methylcinnamamido)morphinan, 17-methyl-4,5α-epoxy-3,14β-diacetoxy-6α- [N-methyl-3-(4-trifluoromethylphenyl)propiolamido]morphinan, 17-phenethyl-4,5α-epoxy-3,14β-diacetoxy-6α-(N-methyl-3-methylcinnamamido)morphinan, 17-phenethyl-4,5α-epoxy-3,14β-diacetoxy-6α-[N-methyl-3-(4-trifluoromethylphenyl)propiolamido]morphinan, 17-cyclopropylmethyl-4,5α-epoxy-3,14β-dihydroxy-6α-(N-isobutyl-3-methylcinnamamido)morphinan, 17-cyclopropylmethyl-4,5α-epoxy-3,14α-dihydroxy-6α-[N-isobutyl-3-(4-trifluoromethylphenyl)propiolamido]morphinan, 17-allyl-4,5α-epoxy-3,14β-dihydroxy-6α-(N-isobutyl-3-methylcinnamamido)morphinan, 17-allyl-4,5α-epoxy-3,14β-dihydroxy-6α-[N-isobutyl-3-(4-trifluoromethylphenyl)propiolamido]morphinan, 17-methyl-4,5α-epoxy-3,14β-dihydroxy-6α-(N-isobutyl-3-methylcinnamamido)morphinan, 17-methyl-4,5α-epoxy-3,14β-dihydroxy-6α-[N-isobutyl-3-(4-trifluoromethylphenyl)propiolamido]morphinan, 17-phenethyl-4,5α-epoxy-3,14β-dihydroxy-6α-(N-isobutyl-3-methylcinnamamido)morphinan, 17-phenethyl-4,5α-epoxy-3,14-dihydroxy-6α-[N-isobutyl-3-(4-trifluoromethylphenyl)propiolamido]morphinan, 17-cyclopropylmethyl-4,5α-epoxy-14β-acetoxy-3-hydroxy-6α-(N-isobutyl-3-methylcinnamamido)morphinan, 17-cyclopropylmethyl-4,5α-epoxy-14β-acetoxy-3-hydroxy-6β-[N-isobutyl-3-(4-trifluoromethylphenyl)propiolamido]morphinan, 17-allyl-4,5α-epoxy-14β-acetoxy-3-hydroxy-6β-(N-isobutyl-3-methylcinnamamido)morphinan, 17-allyl-4,5α-epoxy-14β-acetoxy-3-hydroxy-6α-[N-isobutyl-3-(4-trifluoromethylphenyl)propiolamido]morphinan, 17-methyl-4,5α-epoxy-14β-acetoxy-3-hydroxy-6α-(N-isobutyl-3-methylcinnamamido) morphinan, 17-methyl-4,5α-epoxy-14β-acetoxy-3-hydroxy-6α-[N-isobutyl-3-(4-trifluoromethylphenyl)propiolamido]morphinan, 17-trifluoromethyl-4,5α-epoxy-14β-acetoxy-3-hydroxy-6α-(N-isobutyl-3-methylcinnamamido)morphinan, 17-phenethyl-4,5α-epoxy-14β-acetoxy-3-hydroxy-6α-[N-isobutyl-3-(4-trifluoromethylphenyl)propiolamido]morphinan, 17-cyclopropylmethyl-4,5α-epoxy-14β-hydroxy-6α-(N-isobutyl-3-methylcinnamamido)morphinan, 17-cyclopropylmethyl-4,5α-epoxy-14β-hydroxy-6α-[N-isobutyl-3-(4-trifluoromethylphenyl)propiolamido]morphinan, 17-allyl-4,5α-epoxy-14β-hydroxy-6α-(N-isobutyl-3-methylcinnamamido)morphinan, 17-allyl-4,5α-epoxy-14β-hydroxy-6α-[N-isobutyl-3-(4-trifluoromethylphenyl)propiolamido]morphinan, 17-methyl-4,5α-epoxy-14β-hydroxy-6α-(N-isobutyl-3-methylcinnamamido)morphinan, 17-methyl-4,5α-epoxy-14β-hydroxy-6α-[N-isobutyl-3-(4-trifluoramethylphenyl)propiolamido]morphinan, 17-phenethyl-4,5α-epoxy-14β-hydroxy-6α-(N-isobutyl-3-methylcinnamamido)morphinan, 17-phenethyl-4,5α-epoxy-14β-hydroxy-6α-[N-isobutyl-3-(4-trifluoromethylphenyl)propiolamido]morphinan, 17-cyclopropylmethyl-4,5α-epoxy-14β-acetoxy-6α-(N-isobutyl-3-methylcinnamamido)morphinan, 17-cyclopropylmethyl-4,5α-epoxy-14β-acetoxy-6α-[N- isobutyl-3-(4-trifluoromethylphenyl)propiolamido]morphinan, 17-allyl-4,5α-epoxy-14β-acetoxy-6α-(N-isobutyl-3-methylcinnamamido)morphinan, 17-allyl-4,5α-epoxy-14β-acetoxy-6α-[N-isobutyl-3-(4-trifluoromethylphenyl)propiolamido]morphinan, 17-methyl-4,5α-epoxy-14β-acetoxy-6α-(N-isobutyl-3-methylcinnamamido)morphinan, 17-methyl-4,5α-epoxy-14β-acetoxy-6α-[N-isobutyl-3-(4-trifluoromethylphenyl)propiolamido]morphinan, 17-phenethyl-4,5α-epoxy-14β-acetoxy-6α-(N-isobutyl-3-methylcinnamamido)morphinan, 17-phenethyl-4,5α-epoxy-14β-acetoxy-6α-[N-isobutyl-3-(4-trifluoromethylphenyl)propiolamido]morphinan, 17-cyclopropylmethyl-4,5α-epoxy-14β-hydroxy-3-ethoxy-6α-(N-isobutyl-3-methylcinnamamido)morphinan, 17-cyclopropylmethyl-4,5α-epoxy-14β-hydroxy-3-methoxy-6α-[N-isobutyl-3-(4-trifluoromethylphenyl)propiolamido]morphinan, 17-allyl-4,5α-epoxy-14β-hydroxy-3-methoxy-6α-(N-isobutyl-3-methylcinnamamido)morphinan, 17-allyl-4,5α-epoxy-14β-hydroxy-3-methoxy-6α-[N-isobutyl-3-(4-trifluoromethylphenyl)propiolamido]morphinan, 17-methyl-4,5α-epoxy-14β-hydroxy-3-methoxy-6α-(N-isobutyl-3-methylcinnamamido) morphinan, 17-methyl-4,5α-epoxy-14β-hydroxy-3-methoxy-6α-[N-isobutyl-3-(4-trifluoromethylphenyl)propiolamido]morphinan, 17-phenethyl-4,5α-epoxy-14β-hydroxy-3-methoxy-6α-(N-isobutyl-3-methylcinnamamido)morphinan, 17-phenethyl-4,5α-epoxy-14β-hydroxy-3-methoxy-6α-[N-isobutyl-3-(4-trifluoromethylphenyl)propiolamido]morphinan, 17-cyclopropylmethyl-4,5α-epoxy-14β-acetoxy-3-methoxy-6α-(N-isobutyl-3-methylcinnamamido)morphinan, 17-cyclopropylmethyl-4,5α-epoxy-14β-acetoxy-3-methoxy-6α-[N-isobutyl-3-(4-trifluoromethylphenyl)-propiolamido]morphinan, 17-allyl-4,5α-epoxy-14β-acetoxy-3-methoxy-6α-(N-isobutyl-3-methylcinnamamido)morphinan, 17-allyl-4,5α-epoxy-14β-acetoxy-3-methoxy-6α-[N-isobutyl-3-(4-trifluoromethylphenyl)propiolamido]morphinan, 17-methyl-4,5α-epoxy-14β-acetoxy-3-methoxy-6α-(N-isobutyl-3-methylcinnamamido)morphinan, 17-methyl-4,5α-epoxy-14β-acetoxy-3-methoxy-6α-[N-isobutyl-3-(4-trifluoromethylphenyl)propiolamido]morphinan, 17-phenethyl-4,5α-epoxy-14β-acetoxy-3-methoxy-6α-(N-isobutyl-3-methylcinnamrnamido)morphinan, 17-phenethyl-4,5α-epoxy-14β-acetoxy-3-methoxy-6α-[N-isobutyl-3-(4-trifluoromethylphenyl)propiolamido]morphinan, 17-cyclopropylmethyl-4,5β-epoxy-14β-hydroxy-3-acetoxy-6α-(N-isobutyl-3-methylcinnamamido)morphinan, 17-cyclopropylmethyl-4,5α-epoxy-14β-hydroxy-3-acetoxy-6α-[N-isobutyl-3-(4-trifluoromethylphenyl)-propiolamido]morphinan, 17-allyl-4,5α-epoxy-14β-hydroxy-3-acetoxy-6α-(N-isobutyl-3-methylcinnamamido)morphinan, 17-allyl-4,5α-epoxy-14β-hydroxy-3-acetoxy-6α-[N-isobutyl-3-(4-trifluoromethylphenyl)-propiolamido]morphinan, 17-methyl-4,5α-epoxy-14β-hydroxy-3-acetoxy-6α-(N-isobutyl-3-methylcinnamamido)morphinan, 17-methyl-4,5α-epoxy-14β-hydroxy-3-acetoxy-6α-[N-isobutyl-3-(4-trifluoromethylphenyl)propiolamido]morphinan, 17-phenethyl-4,5α-epoxy-14β-hydroxy-3-acetoxy-6α-(N-isobutyl-3-methylcinnamamido)morphinan, 17-phenethyl-4,5α-epoxy-14β-hydroxy-3-acetoxy-6α-[N-isobutyl-3-(4-trifluoromethylphenyl)propiolamido]morphinan, 17-cyclopropylmethyl-4,5α-epoxy-3,14β-diacetoxy-6α-(N-isobutyl-3-methylcinnamamido)morphinan, 17-cyclopropylmethyl-4,5α-epoxy-3,14β-diacetoxy-6α-[N-isobutyl-3-(4-trifluoromethylphenyl)propiolamido]morphinan, 17-allyl-4,5α-epoxy-3,14β-diacetoxy-6α-(N-isobutyl-3-methylcinnamamido)morphinan, 17-allyl-4,5α-epoxy-3,14β-diacetoxy-6α-[N-isobutyl-3-(4-trifluoromethylphenyl)propiolamido]morphinan, 17-methyl-4,5α-epoxy-3,14β-diacetoxy-6α-(N-isobutyl-3-methylcinnamamido)morphinan, 17-methyl-4,5α-epoxy-3,14β-diacetoxy-6α-[N-isobutyl-3-(4-trifluoromethylphenyl)propiolamido]morphinan, 17-phenethyl-4,5α-epoxy-3,14β-diacetoxy-6α-(N-isobutyl-3-methylcinnamamido)morphinan, 17-phenethyl-4,5α-epoxy-3,14β-diacetoxy-6α-[N-isobutyl-3-(4-trifluoromethylphenyl)propiolamido]morphinan, 17-cyclopropylmethyl-4,5α-epoxy-3,14β-dihydroxy-6β-(N-methyl-3-methylcinnamamido)morphinan, 17-cyclopropylmethyl-4,5α-epoxy-3,14β-dihydroxy-6β-[N-methyl-3-(4-trifluoromethylphenyl)propiolamido]morphinan, 17-allyl-4,5α-epoxy-3,14β-dihydroxy-6β-(N-methyl-3-methylcinnamamido)morphinan, 17-allyl-4,5α-epoxy-3,14β-dihydroxy-6β-[N-methyl-3-(4-trifluoromethylphenyl)propiolamido]morphinan, 17-methyl-4,5α-epoxy-3,14β-dihydroxy-6β-(N-methyl-3-methylcinnamamido)morphinan, 17-methyl-4,5α-epoxy-3,14β-dihydroxy-6β-[N-methyl-3-(4-trifluoromethylphenyl)propiolamido]morphinan, 17-phenethyl-4,5α-epoxy-3,14β-dihydroxy-6β-(N-methyl-3-methylcinnamamido)morphinan, 17-phenethyl-4,5α-epoxy-3,14β-dihydroxy-6β-[N-methyl-3-(4-trifluoromethylphenyl)propiolamido]morphinan, 17-cyclopropylmethyl-4,5α-epoxy-14β-acetoxy-3-hydroxy-6β-(N-methyl-3-methylcinnamamido)morphinan, 17-cyclopropylmethyl-4,5α-epoxy-14β-acetoxy-3-hydroxy-6β-[N-methyl-3-(4-trifluoromethylphenyl)propiolamido]-morphinan, 17-allyl-4,5α-epoxy-14β-acetoxy-3-hydroxy-6β-(N-methyl-3-methylcinnamamido)morphinan, 17-allyl-4,5α-epoxy-14β-acetoxy-3-hydroxy-6β-[N-methyl-3-(4-trifluoromethylphenyl)propiolamido]morphinan, 17-methyl-4,5α-epoxy-14β-acetoxy-3-hydroxy-6β-(N-methyl-3-methylcinnamamido)morphinan, 17-methyl-4,5α-epoxy-14β-acetoxy-3-hydroxy-6β-[N-methyl-3-(4-trifluoromethylphenyl)propiolamido]morphinan, 17-phenethyl-4,5α-epoxy-14β-acetoxy-3-hydroxy-6β-(N-methyl-3-methylcinnamamido)morphinan, 17-phenethyl-4,5α-epoxy-14β-acetoxy-3-hydroxy-6β-[N-methyl-3-(4-trifluoromethylphenyl)propiolamido]morphinan, 17-cyclopropylmethyl-4,5α-epoxy-14β-hydroxy-6β-(N-methyl-3-methylcinnamamido)morphinan, 17-cyclopropylmethyl-4,5α-epoxy-14β-hydroxy-6β-[N-methyl-3-(4-trifluoromethylphenyl)propiolamido]morphinan, 17-allyl-4,5α-epoxy-14β-hydroxy-6β-(N-methyl-3-methylcinnamamido)morphinan, 17-allyl-4,5α-epoxy-14β-hydroxy-6β-[N-methyl-3-(4-trifluoromethylphenyl)-propiolamido]morphinan, 17-methyl-4,5α-epoxy-14β-hydroxy-6β-(N-methyl-3-methylcinnamamido)morphinan, 17-methyl-4,5α-epoxy-14β-hydroxy-6β-[N-methyl-3-(4-trifluoromethylphenyl)propiolamido]morphinan, 17-phenethyl-4,5α-epoxy-14β-hydroxy-6β-(N-methyl-3-methylcinnamamido)morphinan, 17-phenethyl-4,5α-epoxy-14β-hydroxy-6β-[N-methyl-3-(4-trifluoromethylphenyl)-propiolamido]morphinan, 17-cyclopropylmethyl-4,5α-epoxy-14β-acetoxy-6β-(N-methyl-3-methylcinnamamido)morphinan, 17-cyclopropylmethyl-4,5α-epoxy-14β-acetoxy-6β-[N-methyl-3-(4-trifluoromethylphenyl)propiolamido]-morphinan, 17-allyl-4,5α-epoxy-14β-acetoxy-6β-(N-methyl-3-methylcinnamamido)morphinan, 17-allyl-4,5α- epoxy-14β-acetoxy-6β-[N-methyl-3-(4-trifluoromethylphenyl)propiolamido]morphinan, 17-methyl-4,5α-epoxy-14β-acetoxy-6β-(N-methyl-3-methylcinnamamido)morphinan, 17-methyl-4,5α-epoxy-14β-acetoxy-6β-[N-methyl-3-(4-trifluoromethylphenyl)-propiolamido]morphinan, 17-phenethyl-4,5α-epoxy-14β-acetoxy-6β-(N-methyl -3-methylcinnamamido)morphinan, 17-phenethyl-4,5α-epoxy-14β-acetoxy-6β-[N-methyl-3-(4-trifluoromethylphenyl)propiolamido]morphinan, 17-cyclopropylmethyl-4,5α-epoxy-14β-hydroxy-3-methoxy-6β-(N-methyl-3-methylcinnamamido)morphinan, 17-cyclopropylmethyl-4,5α-epoxy-14β-hydroxy-3-methoxy-6β-[N-methyl-3-(4-trifluoromethylphenyl)propiolamido]-morphinan, 17-allyl-4,5α-epoxy-14β-hydroxy-3-methoxy-6β-(N-methyl-3-methylcinnamamido)morphinan, 17-allyl-4,5α-epoxy-14β-hydroxy-3-methoxy-6β-[N-methyl-3-(4-trifluoromethylphenyl)propiolamido]morphinan, 17-methyl-4,5α-epoxy-14β-hydroxy-3-methoxy-6β-(N-methyl-3-methylcinnamamido)morphinan, 17-methyl-4,5α-epoxy-14β-hydroxy-3-methoxy-6β-[N-methyl-3-(4-trifluoromethylphenyl)propiolamido]morphinan, 17-phenethyl-4,5α-epoxy-14β-hydroxy-3-methoxy-6β-(N-methyl-3-methylcinnamamido)morphinan, 17-phenethyl-4,5α-epoxy-14β-hydroxy-3-methoxy-6β-[N-methyl-3-(4-trifluoromethylphenyl)propiolamido]morphinan, 17 -cyclopropylmethyl-4,5α-epoxy-14β-acetoxy-3-methoxy-6β-(N-methyl-3-methylcinnamamido)morphinan, 17-cyclopropylmethyl-4,5α-epoxy-14β-acetoxy-3-methoxy-6β-[N-methyl-3-(4-trifluoromethylphenyl)propiolamido]-morphinan, 17-allyl-4,5α-epoxy-14β-acetoxy-3-methoxy-6β-(N-methyl-3-methylcinnamamido)morphinan, 17-allyl-4,5α-epoxy-14β-acetoxy-3-methoxy-6β-[N-methyl-3-(4-trifluoromethylphenyl)propiolamido]morphinan, 17-methyl-4,5α-epoxy-14β-acetoxy-3-methoxy-6β-(N-methyl-3-methylcinnamamido)morphinan, 17-methyl-4,5α-epoxy-14β-acetoxy-3-methoxy-6β-[N-methyl-3-(4-trifluoromethylphenyl)propiolamido]morphinan, 17-phenethyl-4,5α-epoxy-14β-acetoxy-3-methoxy-6β-(N-methyl-3-methylcinnamamido)morphinan, 17-phenethyl-4,5α-epoxy-14β-acetoxy-3-methoxy-6β-[N-methyl-3-(4-trifluoromethylphenyl)propiolamido]morphinan, 17-cyclopropylmethyl-4,5α-epoxy-14β-hydroxy-3-acetoxy-6β-(N-methyl-3-methylcinnamamido)morphinan, 17-cyclopropylmethyl-4,5α-epoxy-14β-hydroxy-3-acetoxy-6β-[N-methyl-3-(4-trifluoromethylphenyl)propiolamido]-morphinan, 17-allyl-4,5α-epoxy-14β-hydroxy-3-acetoxy-6β-(N-methyl-3-methylcinnamamido)morphinan, 17-allyl-4,5α-epoxy-14β-hydroxy-3-acetoxy-6β-[N-methyl-3-(4-trifluoromethylphenyl)propiolamido]morphinan, 17-methyl-4,5α-epoxy-14β-hydroxy-3-acetoxy-6β-(N-methyl-3-methylcinnamamido)morphinan, 17-methyl-4,5α-epoxy-14β-hydroxy-3-acetoxy-6β-[N-methyl-3-(4-trifluoromethylphenyl) propiolamido]morphinan, 17-phenethyl-4,5α-epoxy-14β-hydroxy-3-acetoxy-6β-(N-methyl-3-methylcinnamamido)morphinan, 17-phenethyl-4,5α-epoxy-14β-hydroxy-3-acetoxy-6β-[N-methyl-3-(4-trifluoromethylphenyl)propiolamido]morphinan, 17-cyclopropylmethyl-4,5α-epoxy-3,14β-diacetoxy-6β-(N-methyl-3-methylcinnamamido)morphinan, 17-cyclopropylmethyl -4,5α-epoxy-3,14β-diacetoxy-6β-[N-methyl-3-(4-trifluoromethylphenyl)propiolamido)morphinan, 17 -allyl-4,5α-epoxy-3,14β-diacetoxy-6β-(N-methyl-3-methylcinnamamido)morphinan, 17-allyl-4,5α-epoxy-3,14β-diacetoxy-6β-[N-methyl-3-(4-trifluoromethylphenyl) propiolamido]morphinan, 17-methyl-4,5α-epoxy-3,14β-diacetoxy-6β-(N-methyl-3-methylcinnamamido)morphinan, 17-methyl-4,5α-epoxy-3,14β-diacetoxy-6β-[N-methyl-3-(4-trifluoromethylphenyl) propiolamido]morphinan, 17-phenethyl-4,5α-epoxy-3,14β-diacetoxy-6β-(N-methyl-3-methylcinnamamido) morphinan, 17-phenethyl-4,5α-epoxy-3,14β-diacetoxy-6β-[N-methyl-3-(4-trifluoromethylphenyl)propiolamido] morphinan, 17-cyclopropylmethyl-4,5α-epoxy-3,14β-dihydroxy-6β-(N-isobutyl-3-methylcinnamamido)morphinan, 17-cyclopropylmethyl-4,5α-epoxy-3,14β-dihydroxy-6β-[N-isobutyl-3-(4-trifluoromethylphenyl)propiolamido]-morphinan, 17-allyl-4,5α-epoxy-3,14β-dihydroxy-6β-(N-isobutyl-3-methylcinnamamido)morphinan, 17-allyl-4,5α-epoxy-3,14β-dihydroxy-6β-[N-isobutyl-3-(4-trifluoromethylphenyl)propiolamido]morphinan, 17-methyl-4,5α-epoxy-3,14β-dihydroxy-6β-(N-isobutyl-3-methylcinnamamido)morphinan, 17-methyl-4,5α-epoxy-3,14β-dihydroxy-6β-[N-isobutyl-3-(4-trifluoromethylphenyl) propiolamido)morphinan, 17-phenethyl-4,5α-epoxy-3,14β-dihydroxy-6β-(N-isobutyl-3-methylcinnamamido) morphinan, 17-phenethyl-4,5α-epoxy-3,14β-dihydroxy-6β-[N-isobutyl-3-(4-trifluoromethylphenyl)propiolamido] morphinan, 17-cyclopropylmethyl-4,5α-epoxy-14β-acetoxy-3-hydroxy-6β-(N-isobutyl-3-methylcinnamamido)morphinan, 17-cyclopropylmethyl-4,5α-epoxy-14β-acetoxy-3-hydroxy-6β-[N-isobutyl-3-(4-trifluoromethylphenyl)-propiolamido)morphinan, 17-allyl-4,5α-epoxy-14β-acetoxy-3-hydroxy-6β-(N-isobutyl-3-methylcinnamamido) morphinan, 17-allyl-4,5α-epoxy-14β-acetoxy-3-hydroxy-6β-[N-isobutyl-3-(4-trifluoromethylphenyl)propiolamido] morphinan, 17-methyl-4,5α-epoxy-14β-acetoxy-3-hydroxy-6β-(N-isobutyl-3-methylcinnamamido)morphinan, 17-methyl-4,5α-epoxy-14β-acetoxy-3-hydroxy-6β-[N-isobutyl-3-(4-trifluoromethylphenyl)propiolamido] morphinan, 17 -phenethyl-4,5α-epoxy-14β-acetoxy-3-hydroxy-6β-(N-isobutyl-3-methylcinnamamido)morphinan, 17-phenethyl-4,5α-epoxy-14β-acetoxy-3-hydroxy-6β-[N-isobutyl-3-(4-trifluoromethylphenyl)propiolamido] morphinan, 17-cyclopropylmethyl-4,5α-epoxy-14β-hydroxy-6β-(N-isobutyl-3-methylcinnamamido)morphinan, 17-cyclopropylmethyl-4,5α-epoxy-14β-hydroxy-6β-[N-isobutyl-3-(4-trifluoromethylphenyl)propiolamido]-morphinan, 17-allyl-4,5α-epoxy-14β-hydroxy-6β-(N-isobutyl-3-methylcinnamamido)morphinan, 17-allyl-4,5α-epoxy-14β-hydroxy-6β-[N-isobutyl-3-(4-trifluoromethylphenyl)propiolamido]morphinan, 17-methyl-4,5α-epoxy-14β-hydroxy-6β-(N-isobutyl-3-methylcinnamamido)morphinan, 17-methyl-4,5α-epoxy-14β-hydroxy-6β-[N-isobutyl-3-(4-trifluoromethylphenyl) propiolamido]morphinan, 17-phenethyl-4,5α-epoxy-14β-hydroxy-6β-(N-isobutyl-3-methylcinnamamido)morphinan, 17-phenethyl-4,5α-epoxy-14β-hydroxy-6β-[N-isobutyl-3-(4-trifluoromethylphenyl)propiolamido]morphinan, 17-cyclopropylmethyl-4,5α-epoxy-14β-acetoxy-6β-(N-isobutyl-3-methylcinnamamido)morphinan, 17-cyclopropylmethyl-4,5α-epoxy-14β-acetoxy-6β-[N-isobutyl-3-(4-trifluoromethylphenyl)propiolamido]-morphinan, 17-allyl-4,5α-epoxy-14β-acetoxy-6β-(N-isobutyl-3-methylcinnamamido)morphinan, 17-allyl-4,5α-epoxy-14β-acetoxy-6β-[N-isobutyl-3-(4-trifluoromethylphenyl)propiolamido]morphinan, 17-methyl-4,5α-epoxy-14β-acetoxy-6β-(N-isobutyl-3-methylcinnamamido)morphinan, 17-methyl-4,5α-epoxy- 14β-acetoxy-6β-[N-isobutyl-3-(4-trifluoromethylphenyl) propiolamido]morphinan, 17-phenethyl-4,5α-epoxy-14β-acetoxy-6β-(N-isobutyl-3-methylcinnamamido)morphinan, 17-phenethyl-4,5α-epoxy-14β-acetoxy-6β-[N-isobutyl-3-(4-trifluoromethylphenyl)propiolamido]morphinan, 17-cyclopropylmethyl-4,5α-epoxy-14β-hydroxy-3-methoxy-6β-(N-isobutyl-3-methylcinnamamido)morphinan, 17-cyclopropylmethyl-4,5α-epoxy-14β-hydroxy-3-methoxy-6β-[N-isobutyl-3-(4-trifluoromethylphenyl)-propiolamido]morphinan, 17-allyl-4,5α-epoxy-14β-hydroxy-3-methoxy-6β-(N-isobutyl-3-methylcinnamamido)morphinan, 17-allyl-4,5α-epoxy-14β-hydroxy-3-methoxy-6β-[N-isobutyl-3-(4-trifluoromethylphenyl)propiolamido]morphinan, 17-methyl-4,5α-epoxy-14β-hydroxy-3-methoxy-6β-(N-isobutyl-3-methylcinnamamido)morphinan, 17-methyl-4,5α-epoxy-14β-hydroxy-3-methoxy-6β-[N-isobutyl-3-(4-trifluoromethylphenyl)propiolamido]morphinan, 17-phenethyl-4,5α-epoxy-14β-hydroxy-3-methoxy-6β-(N-isobutyl-3-methylcinnamamido)morphinan, 17-phenethyl-4,5α-epoxy-14β-hydroxy-3-methoxy-6β-[N-isobutyl-3-(4-trifluoromethylphenyl)propiolamido]morphinan, 17-cyclopropylmethyl-4,5α-epoxy-14β-acetoxy-3-methoxy-6β-(N-isobutyl-3-methylcinnamamido)morphinan, 17-cyclopropylmethyl-4,5α-epoxy-14β-acetoxy-3-methoxy-6β-[N-isobutyl-3-(4-trifluoromethylphenyl)-propiolamido]morphinan, 17-allyl-4,5α-epoxy-14β-acetoxy-3-methoxy-6β-(N-isobutyl-3-methylcinnamamido)morphinan, 17-allyl-4,5α-epoxy-14β-acetoxy-3-methoxy-6β-[N-isobutyl-3-(4-trifluoromethylphenyl)propiolamido]morphinan, 17-methyl-4,5α-epoxy-14β-acetoxy-3-methoxy-6β-(N-isobutyl-3-methylcinnamamido)morphinan, 17-methyl-4,5α-epoxy-14β-acetoxy-3-methoxy-6β-[N-isobutyl-3-(4-trifluoromethylphenyl)propiolamido]morphinan, 17-phenethyl-4,5α-epoxy-14β-acetoxy-3-methoxy-6β-(N-isobutyl-3-methylcinnamamido)morphinan, 17-phenethyl-4,5α-epoxy-14β-acetoxy-3-methoxy-6β-(N-isobutyl-3-(4-trifluoromethylphenyl)propiolamido]morphinan, 17-cyclopropylmethyl-4,5α-epoxy-14β-hydroxy-3-acetoxy-6β-(N-isobutyl-3-methylcinnamamido)morphinan, 17-cyclopropylmethyl-4,5α-epoxy-14β-hydroxy-3-acetoxy-6β-[N-isobutyl-3-(4-trifluoromethylphenyl)-propiolamido]morphinan, 17-allyl-4,5α-epoxy-14β-hydroxy-3-acetoxy-6β-(N-isobutyl-3-methylcinnamamido)morphinan, 17-allyl-4,5α-epoxy-14β-hydroxy-3-acetoxy-6β-[N-isobutyl-3-(4-trifluoromethylphenyl)-propiolamido]morphinan, 17-methyl-4,5α-epoxy-14β-hydroxy-3-acetoxy-6β-(N-isobutyl-3-methylcinnamamido)morphinan, 17-methyl-4,5α-epoxy-14β-hydroxy-3-acetoxy-6β-[N-isobutyl-3-(4-trifluoromethylphenyl)propiolamido]morphinan, 17-phenethyl-4,5α-epoxy-14β-hydroxy-3-acetoxy-6β-(N-isobutyl-3-methylcinnamamido)morphinan, 17-phenethyl-4,5α-epoxy-14β-hydroxy-3-acetoxy-6β-[N-isobutyl-3-(4-trifluoromethylphenyl)propiolamido]morphinan, 17-cyclopropylmethyl-4,5α-epoxy-3,14β-diacetoxy-6β-(N-isobutyl-3-methylcinnamamido)morphinan, 17-cyclopropylmethyl-4,5α-epoxy-3,14β-diacetoxy-6β-[N-isobutyl-3-(4-trifluoromethylphenyl)propiolamido]morphinan, 17-allyl-4,5α-epoxy-3,14β-diacetoxy-6β-(N-isobutyl-3-methylcinnamamido)morphinan, 17-allyl-4,5α-epoxy-3,14β-diacetoxy-6β-[N-isobutyl-3-(4-trifluoromethylphenyl)propiolamido]morphinan, 17-methyl-4,5α-epoxy-3,14β-diacetoxy-6β-(N-isobutyl-3-methylcinnamamido)morphinan, 17-methyl-4,5α-epoxy-3,14β-diacetoxy-6β-[N-isobutyl-3-(4-trifluoromethylphenyl)propiolamido]morphinan, 17-phenethyl-4,5α-epoxy-3,14β-diacetoxy-6β-(N-isobutyl-3-methylcinnamamido)morphinan, 17-phenethyl-4,5α-epoxy-3,14β-diacetoxy-6β-[N-isobutyl-3-(4-trifluoromethylphenyl)propiolamido)morphinan, 17-cyclopropylmethyl-4,5α-epoxy-3,14β-dihydroxy-6α-[N-methyl-3-(3-trifluoromethylphenyl)propiolamido]-morphinan, 17-allyl-4,5α-epoxy-3,14β-dihydroxy-6α-[N-methyl-3-(3-trifluoromethylphenyl)propiolamido]-morphinan, 17-cyclopropylmethyl-4,5α-epoxy-3,14β-dihydroxy-6β-[N-methyl-3-(3-trifluoromethylphenyl)-propiolamido]morphinan, 17-allyl-4,5α-epoxy-3,14β-dihydroxy-6β-[N-methyl-3-(3-trifluoromethylphenyl)-propiolamido]morphinan, 17-cyclopropylmethyl-4,5α-epoxy-3,14β-dihydroxy-6α-[N-methyl-trans-3-(2-thienyl)acrylamido]morphinan, 17-allyl-4,5α-epoxy-3,14β-dihydroxy-6α-[N-methyl-trans-3-(2-thienyl)acrylamido]morphinan, 17-cyclopropylmethyl-4,5α-epoxy-3,14β-dihydroxy-6β-[N-methyl-trans-3-(2-thienyl)acrylamido]morphinan, 17-allyl-4,5α-epoxy-3,14β-dihydroxy-6β-[N-methyl-trans-3-(2-thienyl)acrylamido]morphinan, 17-cyclopropylmethyl-4,5α-epoxy-3-hydroxy-6α-(N-methyl-3-trifluoromethylcinnamamido)morphinan, 17-cyclopropylmethyl-4,5α-epoxy-3-hydroxy-6α-[N-methyl-trans-3-(3-furyl)acrylamido]morphinan, 17-cyclopropylmethyl-4,5α-epoxy-3-hydroxy-6α-(N-methyl-3-methylcinnamamido)morphinan, 17-cyclopropylmethyl-4,5α-epoxy-3-hydroxy-6α-[N-methyl-3-(4-trifluoromethylphenyl)propiolamido] morphinan, 17-allyl-4,5α-epoxy-3-hydroxy-6α-(N-methyl-3-trifluoromethylcinnamamido)morphinan, 17-allyl-4,5α-epoxy-3-hydroxy-6α-[N-methyl-trans-3-(3-furyl)acrylamido]morphinan, 17-allyl-4,5α-epoxy-3-hydroxy-6α-(N-methyl-3-methylcinnamamido)morphinan, 17-allyl-4,5α-epoxy-3-hydroxy-6α-[N-methyl-3-(4-trifluoromethylphenyl)propiolamido]morphinan, 17-methyl-4,5α-epoxy-3-hydroxy-6α-(N-methyl-3-trifluoromethylcinnamamido)morphinan, 17-methyl-4,5α-epoxy-3-hydroxy-6α-[N-methyl-trans-3-(3-furyl)-acrylamido]morphinan, 17-methyl-4,5α-epoxy-3-hydroxy-6α-(N-methyl-3-methylcinnamamido)morphinan, 17-methyl-4,5α-epoxy-3-hydroxy-6α-[N-methyl-3-(4-trifluoromethylphenyl)propiolamido]morphinan, 17-phenethyl-4,5α-epoxy-3-hydroxy-6α-(N-methyl-3-trifluoromethylcinnamamido)morphinan, 17-phenethyl-4,5α-epoxy-3-hydroxy-6α-[N-methyl-trans-3-(3-furyl)acrylamido]morphinan, 17-phenethyl-4,5α-epoxy-3-hydroxy-6α-(N-methyl-3-methylcinnamamido)morphinan, 17-phenethyl-4,5α-epoxy-3-hydroxy-6α-[N-methyl-3-(4-trifluoromethylphenyl)propiolamido]morphinan, 17-cyclopropylmethyl-4,5α-epoxy-3-hydroxy-14β-nitro-6α-(N-methyl-3-trifluoromethylcinnamamido)morphinan, 17-cyclopropylmethyl-4,5α-epoxy-3-hydroxy-14β-nitro-6α-[N-methyl-trans-3-(3-furyl)acrylamido]-morphinan, 17-cyclopropylmethyl-4,5α-epoxy-3-hydroxy-14β-nitro-6α-(N-methyl-3-methylcinnamamido)morphinan, 17-cyclopropylmethyl-4,5α-epoxy-3-hydroxy-14β-nitro-6α-[N-methyl-3-(4-trifluoromethylphenyl)propiolamido]-morphinan, 17-allyl-4,5α-epoxy-3-hydroxy-14β-nitro-6α-(N-methyl-3-trifluoromethylcinnamamido)morphinan, 17-allyl-4,5α-epoxy-3-hydroxy-14β-nitro-6α-[N-methyl-trans-3-(3-furyl)acrylamido]morphinan, 17-allyl-4,5α-epoxy-3-hydroxy-14β-nitro-6α-(N-methyl-3-methylcinnamamido)morphinan, 17-allyl-4,5α-epoxy-3-hydroxy-14β-nitro-6α-[N-methyl-3-(4-trifluoromethylphenyl)propiolamido]morphinan, 17-methyl-4,5α-epoxy-3-hydroxy-14β-nitro-6α-(N-methyl-3-trifluoromethylcinnamamido)morphinan, 17-methyl-4,5α-epoxy-3-hydroxy-14β-nitro-6α-[N-methyl-trans-3-(3-furyl)acrylamido]morphinan, 17-methyl-4,5α-epoxy-3-hydroxy-14β-nitro-6α-(N-methyl-3-methylcinnamamido)morphinan, 17-methyl-4,5α-epoxy-3-hydroxy-14β-nitro-6α-[N-methyl-3-(4-trifluoromethylphenyl)propiolamido]-morphinan, 17-phenethyl-4,5α-epoxy-3-hydroxy-14β-nitro-6α-(N-methyl-3-trifluoromethylcinnamamido)morphinan, 17-phenethyl-4,5α-epoxy-3-hydroxy-14β-nitro-6α-[N-methyl-trans-3-(3-furyl)acrylamido]-morphinan, 17-phenethyl-4,5α-epoxy-3-hydroxy-14β-nitro-6α-(N-methyl-3-methylcinnamamido)morphinan, 17-phenethyl-4,5α-epoxy-3-hydroxy-14β-nitro-6α-[N-methyl-3-(4-trifluoromethylphenyl)propiolamido]morphinan, 17-cyclopropylmethyl-4,5α-epoxy-3-hydroxy-14β-dimethylamino-6α-(N-methyl-3-trifluoromethylcinnamamido)morphinan, 17-cyclopropylmethyl-4,5α-epoxy-3-hydroxy-14β-dimethylamino-6α-[N-methyl-trans-3-(3-furyl)acrylamido]morphinan, 17-cyclopropylmethyl-4,5α-epoxy-3-hydroxy-14β-dimethylamino-6α-(N-methyl-3-ethylcinnamamido)morphinan, 17-cyclopropylmethyl-4,5α-epoxy-3-hydroxy-14β-dimethylamino-6α-[N-methyl-3-(4-trifluoromethylphenyl)propiolamido]morphinan, 17-allyl-4,5α-epoxy-3-hydroxy-14β-dimethylamino-6α-(N-methyl-3-trifluoromethylcinnamamido)morphinan, 17-allyl-4,5α-epoxy-3-hydroxy-14β-dimethylamino-6α-[N-methyl-trans-3-(3-furyl)acrylamido]morphinan, 17-allyl-4,5α-epoxy-3-hydroxy-14β-dimethylamino-6α-(N-methyl-3-methylcinnamamido)morphinan, 17-allyl-4,5α-epoxy-3-hydroxy-14β-dimethylamino-6α-[N-methyl-3-(4-trifluoromethylphenyl)propiolamido]morphinan, 17-methyl-4,5α-epoxy-3-hydroxy-14β-dimethylamino-6α-(N-methyl-3-trifluoromethylcinnamamido)morphinan, 17-methyl-4,5α-epoxy-3-hydroxy-14β-dimethylamino-6α-[N-methyl-trans-3-(3-furyl)acrylamido]morphinan, 17-methyl-4,5α-epoxy-3-hydroxy-14β-dimethylamino-6α-(N-methyl-3-methylcinnamamido)morphinan, 17-methyl-4,5α-epoxy-3-hydroxy-14β-dimethylamino-6α-[N-methyl-3-(4-trifluoromethylphenyl)propiolamido]morphinan, 17-phenethyl-4,5α-epoxy-3-hydroxy-14β-dimethylamino-6α-(N-methyl-3-trifluoromethylcinnamamido)morphinan, 17-phenethyl-4,5α-epoxy-3-hydroxy-14β-dimethylamino-6α-[N-methyl-trans-3-(3-furyl)acrylamido]morphinan, 17-phenethyl-4,5α-epoxy-3-hydroxy-14β-dimethylamino-6α-(N-methyl-3-methylcinnamamido)morphinan, 17-phenethyl-4,5α-epoxy-3-hydroxy-14β-dimethylamino-6α-[N-methyl-3-(4-trifluoromethylphenyl)propiolamido]morphinan, 17-cyclopropylmethyl-4,5α-epoxy-3-hydroxy-14β-methyl-6α-(N-methyl-3-trifluoromethylcinnamamido)morphinan, 17-cyclopropylmethyl-4,5α-epoxy-3-hydroxy-14β-methyl-6α-[N-methyl-trans-3-(3-furyl)acrylamido]morphinan, 17-cyclopropylmethyl-4,5α-epoxy-3-hydroxy-14β-methyl-6α-(N-methyl-3-methylcinnamamido)morphinan, 17-cyclopropylmethyl-4,5α-epoxy-3-hydroxy-14β-methyl-6α-[N-methyl-3-(4-trifluoromethylphenyl)propiolamido]morphinan, 17-allyl-4,5α-epoxy-3-hydroxy-14β-methyl-6α-(N-methyl-3-trifluoromethylcinnamamido)morphinan, 17-allyl-4,5α-epoxy-3-hydroxy-14β-methyl-6α-[N-methyl-trans-3-(3-furyl)acrylamido]morphinan, 17-allyl-4,5α-epoxy-3-hydroxy-14β-methyl-6α-(N-methyl-3-methylcinnamamido)morphinan, 17-allyl-4,5α-epoxy-3-hydroxy-14β-methyl-6α-[N-methyl-3-(4-trifluoromethylphenyl)propiolamido]morphinan, 14β,17-dimethyl-4,5α-epoxy-3-hydroxy-6α-(N-methyl-3-trifluoromethylcinnamamido)morphinan, 14β,17-dimethyl-4,5α-epoxy-3-hydroxy-6α-[N-methyl-trans-3-(3-furyl)acrylamido]morphinan, 14β,17-dimethyl-4,5α-epoxy-3-hydroxy-6α-(N-methyl-3-methylcinnamamido)morphinan, 14β,17-dimethyl-4,5α-epoxy-3-hydroxy-6α-[N-methyl-3-(4-trifluoromethylphenyl)propiolamido]-morphinan, 17-phenethyl-4,5α-epoxy-3-hydroxy-14β-methyl-6α-(N-methyl-3-trifluoromethylcinnamamido)morphinan, 17-phenethyl-4,5α-epoxy-3-hydroxy-14β-methyl-6α-[N-methyl-trans-3-(3-furyl)acrylamido]morphinan, 17-phenethyl-4,5α-epoxy-3-hydroxy-14β-methyl-6α-(N-methyl-3-methylcinnamamido)morphinan, 17-phenethyl-4,5α-epoxy-3-hydroxy-14β-methyl-6α-[N-methyl-3-(4-trifluoromethylphenyl)propiolamido]morphinan, 17-cyclopropylmethyl-3,14β-dihydroxy-6α-(N-methyl-3-trifluoromethylcinnamamido)morphinan, 17-cyclopropylmethyl-3,14β-dihydroxy-6α-[N-methyl-trans-3-(3-furyl)acrylamido]morphinan, 17-cyclopropylmethyl-3,14β-dihydroxy-6α-(N-methyl-3-methylcinnamamido)morphinan, 17-cyclopropylmethyl-3,14β-dihydroxy-6α-[N-methyl-3-(4-trifluoromethylphenyl)propiolamido]morphinan, 17-allyl-3,14β-dihydroxy-6α-(N-methyl-3-trifluoromethylcinnamamido)morphinan, 17-allyl-3,14β-dihydroxy-6α-[N-methyl-trans-3-(3-furyl)acrylamido]morphinan, 17-allyl-3,14β-dihydroxy-6α-(N-methyl-3-methylcinnamamido)morphinan, 17-allyl-3,14β-dihydroxy-6α-[N-methyl-3-(4-trifluoromethylphenyl)-propiolamido]morphinan, 17-methyl-3,14β-dihydroxy-6α-(N-methyl-3-trifluoromethylcinnamamido)morphinan, 17-methyl-3,14β-dihydroxy-6α-[N-methyl-trans-3-(3-furyl)acrylamido]morphinan, 17-methyl-3,14β-dihydroxy-6α-(N-methyl-3-methylcinnamamido)morphinan, 17-methyl-3,14β-dihydroxy-6α-[N-methyl-3-(4-trifluoromethylphenyl)propiolamido]morphinan, 17-phenethyl-3,14β-dihydroxy-6α-(N-methyl-3-trifluoromethylcinnamamido)morphinan, 17-phenethyl-3,14β-dihydroxy-6α-[N-methyl-trans-3-(3-furyl)acrylamido]morphinan, 17-phenethyl-3,14β-dihydroxy-6α-(N-methyl-3-methylcinnamamido)morphinan, 17-phenethyl-3,14β-dihydroxy-6α-[N-methyl-3-(4-trifluoromethylphenyl)propiolamido]morphinan, 17-cyclopropylmethyl-3,14β-dihydroxy-4-methoxy-6α-(N-methyl-3-trifluoromethylcinnamamido)morphinan, 17-cyclopropylmethyl-3,14β-dihydroxy-4-methoxy-6α-[N-methyl-trans-3-(3-furyl)acrylamido]morphinan, 17-cyclopropylmethyl-3,14β-dihydroxy-4-methoxy-6α-(N-methyl-3-methylcinnamamido)morphinan, 17-cyclopropylmethyl-3,14β-dihydroxy-4-methoxy-6α-[N-methyl-3-(4-trifluoromethylphenyl)propiolamido]-morphinan, 17-allyl-3,14β-dihydroxy-4-methoxy-6α-(N-methyl-3-trifluoromethylcinnamamido)morphinan, 17-allyl-3,14β-dihydroxy-4-methoxy-6α-[N-methyl-trans-3-(3-furyl)acrylamido]morphinan, 17-allyl-3,14β-dihydroxy-4-methoxy-6α-(N-methyl-3-methylcinnamamido)morphinan, 17-allyl-3,14β-dihydroxy-4-methoxy-6α-[N-methyl-3-(4-trifluoromethylphenyl)propiolamido]morphinan, 17-methyl-3,14β-dihydroxy-4-methoxy-6α-(N-methyl-3-trifluoromethylcinnamamido)morphinan, 17-methyl-3,14β-dihydroxy-4-methoxy-6α-[N-methyl-trans-3-(3-furyl)acrylamido]morphinan, 17-methyl-3,14β-dihydroxy-4-methoxy-6α-(N-methyl-3-methylcinnamamido)morphinan, 17-methyl-3,14β-dihydroxy-4-methoxy-6α-[N-methyl-3-(4-trifluoromethylphenyl)propiolamido]morphinan, 17-phenethyl-3,14β-dihydroxy-4-methoxy-6α-(N-methyl-3-trifluoromethylcinnamamido)morphinan, 17-phenethyl-3,14β-dihydroxy-4-methoxy-6α-[N-methyl-trans-3-(3-furyl)acrylamido]morphinan, 17-phenethyl-3,14β-dihydroxy-4-methoxy-6-(N-methyl-3-methylcinnamamido)morphinan, 17-phenethyl-3,14β-dihydroxy-4-methoxy-6α-[N-methyl-3-(4-trifluoromethylphenyl)propiolamido]morphinan, 17-cyclopropylmethyl-4,5α-epoxy-3,14β-dihydroxy-5β-methyl-6α-(N-methyl-3-trifluoromethylcinnamamido)morphinan, 17-cyclopropylmethyl-4,5α-epoxy-3,14β-dihydroxy-5β-methyl-6α-[N-methyl-trans-3-(3-furyl)acrylamido]morphinan, 17-cyclopropylmethyl-4,5α-epoxy-3,14β-dihydroxy-5β-methyl-6α-(N-methyl-3-methylcinnamamido)morphinan, 17-cyclopropylmethyl-4,5α-epoxy-3,14β-dihydroxy-5β-methyl-6α-[N-methyl-3-(4-trifluoromethylphenyl) propiolamido]morphinan, 17-allyl-4,5α-epoxy-3,14β-dihydroxy-5β-methyl-6α-(N-methyl-3-trifluoromethylcinnamamido)morphinan, 17-allyl-4,5α-epoxy-3,14β-dihydroxy-5β-methyl-6α-[N-methyl-trans-3-(3-furyl)acrylamido]morphinan, 17-allyl-4,5α-epoxy-3,14β-dihydroxy-5β-methyl-6α-(N-methyl-3-methylcinnamamido)morphinan, 17-allyl-4,5α-epoxy-3,14β-dihydroxy-5β-methyl-6α-[N-methyl-3-(4-trifluoromethylphenyl)propiolamido]morphinan, 5β,17-dimethyl-4,5α-epoxy-3,14β-dihydroxy-6α-(N-methyl-3-trifluoromethylcinnamamido)morphinan, 5β,17-dimethyl-4,5α-epoxy-3,14β-dihydroxy-6α-[N-methyl-trans-3-(3-furyl)acrylamido]morphinan, 5β,17-dimethyl-4,5α-epoxy-3,14β-dihydroxy-6α-(N-methyl-3-methylcinnamamido)morphinan, 5β,17-dimethyl-4,5α-epoxy-3,14β-dihydroxy-6α-[N-methyl-3-(4-trifluoromethylphenyl)propiolamido]morphinan, 17-phenethyl-4,5α-epoxy-3,14β-dihydroxy-5β-methyl-6α-(N-methyl-3-trifluoromethylcinnamamido)morphinan, 17-phenethyl-4,5α-epoxy-3,14β-dihydroxy-5β-methyl-6α-[N-methyl-trans-3-(3-furyl)acrylamido]-morphinan, 17-phenethyl-4,5α-epoxy-3,14β-dihydroxy-5β-methyl-6α-(N-methyl-3-methylcinnamamido)morphinan, 17-phenethyl-4,5α-epoxy-3,14β-dihydroxy-5β-methyl-6α-[N-methyl-3-(4-trifluoromethylphenyl)propiolamido]-morphinan, 17-cyclopropylmethyl-7,8-didehydro-4,5α-epoxy-3,14β-dihydroxy-6α-(N-methyl-3-trifluoromethylcinnamamido)morphinan, 17-cyclopropylmethyl-7,8-didehydro-4,5α-epoxy-3,14β-dihydroxy-6α-(N-methyl-trans-3-(3-furyl)acrylamido]morphinan, 17-cyclopropylmethyl-7,8-didehydro-4,5α-epoxy-3,14β-dihydroxy-6α-(N-methyl-3-methylcinnamamido)morphinan, 17-cyclopropylmethyl-7,8-didehydro-4,5α-epoxy-3,14β-dihydroxy-6α-[N-methyl-3-(4-trifluoromethylphenyl)propiolamido]morphinan, 17-allyl-7,8-didehydro-4,5α-epoxy-3,14β-dihydroxy-6α-(N-methyl-3-trifluoromethylcinnamamido)morphinan, 17-allyl-7,8-didehydro-4,5α-epoxy-3,14β-dihydroxy-6α-[N-methyl-trans-3-(3-furyl)acrylamido]morphinan, 17-allyl-7,8-didehydro-4,5α-epoxy-3,14β-dihydroxy-6α-(N-methyl-3-methylcinnamamido)morphinan, 17-allyl-7,8-didehydro-4,5α-epoxy-3,14β-dihydroxy-6α-(N-methyl-3-(4-trifluoromethylphenyl)propiolamido]morphinan, 17-methyl-7,8-didehydro-4,5α-epoxy-3,14β-dihydroxy-6α-(N-methyl-3-trifluoromethylcinnamamido)morphinan, 17-methyl-7,8-didehydro-4,5α-epoxy-3,14β-dihydroxy-6α-[N-methyl-trans-3-(3-furyl)acrylamido]morphinan, 17-methyl-7,8-didehydro-4,5α-epoxy-3,14β-dihydroxy-6α-(N-methyl-3-methylcinnamamido)morphinan, 17-methyl-7,8-didehydro-4,5α-epoxy-3,14β-dihydroxy-6α-[N-methyl-3-(4-trifluoromethylphenyl)propiolamido]-morphinan, 17-phenethyl-7,8-didehydro-4,5α-epoxy-3,14β-dihydroxy-6α-(N-methyl-3-trifluoromethylcinnamamido)morphinan, 17-phenethyl-7,8-didehydro-4,5α-epoxy-3,14β-dihydroxy-6α-[N-methyl-trans-3-(3-furyl)acrylamido]morphinan, 17-phenethyl-7,8-didehydro-4,5α-epoxy-3,14β-dihydroxy-6α-(N-methyl-3-methylcinnamamido)morphinan, 17-phenethyl-7,8-didehydro-4,5α-epoxy-3,14β-dihydroxy-6α-[N-methyl-3-(4-trifluoromethylphenyl)propiolamido]morphinan, 17-cyclopropylmethyl-4,5α-epoxy-3-hydroxy-6β-(N-methyl-3-trifluoromethylcinnamamido)morphinan, 17-cyclopropylmethyl-4,5α-epoxy-3-hydroxy-6β-[N-methyl-trans-3-(3-furyl)acrylamido]morphinan, 17-cyclopropylmethyl-4,5α-epoxy-3-hydroxy-6β-(N-methyl-3-methylcinnamamido)morphinan, 17-cyclopropylmethyl-4,5α-epoxy-3-hydroxy-6β-[N-methyl-3-(4-trifluoromethylphenyl)propiolamido]morphinan, 17-allyl-4,5α-epoxy-3-hydroxy-6β-(N-methyl-3-trifluoromethylcinnamamido)morphinan, 17-allyl-4,5α-epoxy-3-hydroxy-6β-[N-methyl-trans-3-(3-furyl)acrylamido]morphinan, 17-allyl-4,5α-epoxy-3-hydroxy-6β-(N-methyl-3-methylcinnamamido)morphinan, 17-allyl-4,5α-epoxy-3-hydroxy-6β-[N-methyl-3-(4-trifluoromethylphenyl)propiolamido]morphinan, 17-methyl-4,5α-epoxy-3-hydroxy-6α-(N-methyl-3-trifluoromethylcinnamamido)morphinan, 17-methyl-4,5α-epoxy-3-hydroxy-6β-[N-methyl-trans-3-(3-furyl)acrylamido]morphinan, 17-methyl-4,5α-epoxy-3-hydroxy-6β-(N-methyl-3-methylcinnamamido)morphinan, 17-methyl-4,5α-epoxy-3-hydroxy-6β-[N-methyl-3-(4-trifluoromethylphenyl)propiolamido]morphinan, 17-phenethyl-4,5α-epoxy-3-hydroxy-6β-(N-methyl-3-trifluoromethylcinnamamido)morphinan, 17-phenethyl-4,5α-epoxy-3-hydroxy-6β-[N-methyl-trans-3-(3-furyl)acrylamido]morphinan, 17-phenethyl-4,5α-epoxy-3-hydroxy-6β-(N-methyl-3-methylcinnamamido)morphinan, 17-phenethyl-4,5α-epoxy-3-hydroxy-6β-[N-methyl-3-(4-trifluoromethylphenyl)propiolamido)morphinan, 17-cyclopropylmethyl-4,5α-epoxy-3-hydroxy-14β-nitro-6β-(N-methyl-3-trifluoromethylcinnamamido)morphinan, 17-cyclopropylmethyl-4,5α-epoxy-3-hydroxy-14β-nitro-6β-[N-methyl-trans-3-(3-furyl)acrylamido]-morphinan, 17-cyclopropylmethyl-4,5α-epoxy-3-hydroxy-14β-nitro-6β-(N-methyl-3-methylcinnamamido)morphinan, 17-cyclopropylmethyl-4,5α-epoxy-3-hydroxy-14β-nitro-6β-(N-methyl-3-(4-trifluoromethylphenyl)propiolamido]-morphinan, 17-allyl-4,5α-epoxy-3-hydroxy-14β-nitro-6β-(N-methyl-3-trifluoromethylcinnamamido)morphinan, 17-allyl-4,5α-epoxy-3-hydroxy-14β-nitro-6β-[N-methyl-trans-3-(3-furyl)acrylamido]morphinan, 17-allyl-4,5α-epoxy-3-hydroxy-14β-nitro-6β-(N-methyl-3-methylcinnamamido)morphinan, 17-allyl-4,5α-epoxy-3-hydroxy-14β-nitro-6β-[N-methyl-3-(4-trifluoromethylphenyl)propiolamido]morphinan, 17-methyl-4,5α-epoxy-3-hydroxy-14β-nitro-6β-(N-methyl-3-trifluoromethylcinnamamido)morphinan, 17-methyl-4,5α-epoxy-3-hydroxy-14β-nitro-6β-[N-methyl-trans-3-(3-furyl)acrylamido]morphinan, 17-methyl-4,5α-epoxy-3-hydroxy-14β-nitro-6β-(N-methyl-3-methylcinnamamido)morphinan, 17-methyl-4,5α-epoxy-3-hydroxy-14β-nitro-6β-[N-methyl-3-(4-trifluoromethylphenyl)propiolamido]-morphinan, 17-phenethyl-4,5α-epoxy-3-hydroxy-14β-nitro-6β-(N-methyl-3-trifluoromethylcinnamamido)morphinan, 17-phenethyl-4,5α-epoxy-3-hydroxy-14β-nitro-6β-[N-methyl-trans-3-(3-furyl)acrylamido]morphinan, 17-phenethyl-4,5α-epoxy-3-hydroxy-14β-nitro-6β-(N-methyl-3-methylcinnamamido)morphinan, 17-phenethyl-4,5α-epoxy-3-hydroxy-14β-nitro-6β-[N-methyl-3-(4-trifluoromethylphenyl)propiolamido]morphinan, 17-cyclopropylmethyl-4,5α-epoxy-3-hydroxy-14β-dimethylamino-6β-(N-methyl-3- trifluoromethylcinnamamido)morphinan, 17-cyclopropylmethyl-4,5α-epoxy-3-hydroxy-14β-dimethylamino-6β-[N-methyl-trans-3-(3-furyl)acrylamido]morphinan, 17-cyclopropylmethyl-4,5α-epoxy-3-hydroxy-14β-dimethylamino-6β-(N-methyl-3-methylcinnamamido)morphinan, 17-cyclopropylmethyl-4,5α-epoxy-3-hydroxy-14β-dimethylamino-6β-[N-methyl-3-(4-trifluoromethylphenyl)propiolamido]morphinan, 17-allyl-4,5α-epoxy-3-hydroxy-14β-dimethylamino-6β-(N-methyl-3-trifluoromethylcinnamamido)morphinan, 17-allyl-4,5α-epoxy-3-hydroxy-14β-dimethylamino-6β-[N-methyl-trans-3-(3-furyl)acrylamido]morphinan, 17-allyl-4,5α-epoxy-3-hydroxy-14β-dimethylamino-6β-(N-methyl-3-methylcinnamamido)morphinan, 17-allyl-4,5α-epoxy-3-hydroxy-14β-dimethylamino-6β-[N-methyl-3-(4-trifluoromethylphenyl)propiolamido]morphinan, 17-methyl-4,5α-epoxy-3-hydroxy-14β-dimethylamino-6β-(N-methyl-3-trifluoromethylcinnamamido)morphinan, 17-methyl-4,5α-epoxy-3-hydroxy-14β-dimethylamino-6β-[N-methyl-trans-3-(3-furyl)acrylamido]morphinan, 17-methyl-4,5α-epoxy-3-hydroxy-14β-dimethylamino-6β-(N-methyl-3-methylcinnamamido)morphinan, 17-methyl-4,5α-epoxy-3-hydroxy-14β-dimethylamino-6β-[N-methyl-3-(4-trifluoromethylphenyl)propiolamido]morphinan, 17-phenethyl-4,5α-epoxy-3-hydroxy-14β-dimethylamino-6β-(N-methyl-3-trifluoromethylcinnamamido)morphinan, 17-phenethyl-4,5α-epoxy-3-hydroxy-14β-dimethylamino-6β-[N-methyl-trans-3-(3-furyl)acrylamido]morphinan, 17-phenethyl-4,5α-epoxy-3-hydroxy-14β-dimethylamino-6β-(N-methyl-3-methylcinnamamido)morphinan, 17-phenethyl-4,5α-epoxy-3-hydroxy-14β-dimethylamino-6β-[N-methyl-3-(4-trifluoromethylphenyl)propiolamido]morphinan, 17-cyclopropylmethyl-4,5α-epoxy-3-hydroxy-14β-methyl-6β-(N-methyl-3-trifluoromethylcinnamamido)morphinan, 17-cyclopropylmethyl-4,5α-epoxy-3-hydroxy-14β-methyl-6β-[N-methyl-trans-3-(3-furyl)acrylamido]morphinan, 17-cyclopropylmethyl-4,5α-epoxy-3-hydroxy-14β-methyl-6β-(N-methyl-3-methylcinnamamido)morphinan, 17-cyclopropylmethyl-4,5α-epoxy-3-hydroxy-14β-methyl-6β-[N-methyl-3-(4-trifluoromethylphenyl)propiolamido]morphinan, 17-allyl-4,5α-epoxy-3-hydroxy-14β-methyl-6β-(N-methyl-3-trifluoromethylcinnamamido)morphinan, 17-allyl-4,5α-epoxy-3-hydroxy-14β-methyl-6β-[N-methyl-trans-3-(3-furyl)acrylamido]morphinan, 17-allyl-4,5α-epoxy-3-hydroxy-14β-methyl-6β-(N-methyl-3-methylcinnamamido)-morphinan, 17-allyl-4,5α-epoxy-3-hydroxy-14β-methyl-6β-[N-methyl-3-(4-trifluoromethylphenyl)propiolamido]-morphinan, 14β,17-dimethyl-4,5α-epoxy-3-hydroxy-6β-(N-methyl-3-trifluoromethylcinnamamido)morphinan, 14β,17-dimethyl-4,5α-epoxy-3-hydroxy-6β-[N-methyl-trans-3-(3-furyl)acrylamido]morphinan, 14β,17-dimethyl-4,5α-epoxy-3-hydroxy-6β-(N-methyl-3-methylcinnamamido)morphinan, 14β,17-dimethyl-4,5α-epoxy-3-hydroxy-6β-[N-methyl-3-(4-trifluoromethylphenyl)propiolamido]morphinan, 17-phenethyl-4,5α-epoxy-3-hydroxy-14β-methyl-6β-(N-methyl-3-trifluoromethylcinnamamido)morphinan, 17-phenethyl-4,5α-epoxy-3-hydroxy-14β-methyl-6β-[N-methyl-trans-3-(3-furyl)acrylamido]morphinan, 17-phenethyl-4,5α-epoxy-3-hydroxy-14β-methyl-6β-(N-methyl-3-methylcinnamamido)morphinan, 17-phenethyl-4,5α-epoxy-3-hydroxy-14β-methyl-6β-[N-methyl-3-(4-trifluoromethylphenyl)propiolamido]-morphinan, 17-cyclopropylmethyl-3,14β-dihydroxy-6β-(N-methyl-3-trifluoromethylcinnamamido)morphinan, 17-cyclopropylmethyl-3,14β-dihydroxy-6β-[N-methyl-trans-3-(3-furyl)acrylamido]morphinan, 17-cyclopropylmethyl-3,14β-dihydroxy-6β-(N-methyl-3-methylcinnamamido)-morphinan, 17-cyclopropylmethyl-3,14β-dihydroxy-6β-[N-methyl-3-(4-trifluoromethylphenyl)propiolamido]-morphinan, 17-allyl-3,14β-dihydroxy-6β-(N-methyl-3-trifluoromethylcinnamamido)morphinan, 17-allyl-3,14β-dihydroxy-6β-[N-methyl-trans-3-(3-furyl)acrylamido]-morphinan, 17-allyl-3,14β-dihydroxy-6β-(N-methyl-3-methylcinnamamido)morphinan, 17-allyl-3,14β-dihydroxy-6β-[N-methyl-3-(4-trifluoromethylphenyl)-propiolamido]morphinan, 17-methyl-3,14β-dihydroxy-6β-(N-methyl-3-trifluoromethylcinnamamido)morphinan, 17-methyl-3,14β-dihydroxy-6β-[N-methyl-trans-3-(3-furyl)acrylamido]morphinan, 17-methyl-3,14β-dihydroxy-6β-(N-methyl-3-methylcinnamamido)morphinan, 17-methyl-3,14β-dihydroxy-6β-[N-methyl-3-(4-trifluoromethylphenyl)propiolamido]morphinan, 17-phenethyl-3,14β-dihydroxy-6β-(N-methyl-3-trifluoromethylcinnamamido)morphinan, 17-phenethyl-3,14β-dihydroxy-6β-[N-methyl-trans-3-(3-furyl)acrylamido]morphinan, 17-phenethyl-3,14β-dihydroxy-6β-(N-methyl-3-methylcinnamamido)morphinan, 17-phenethyl-3,14β-dihydroxy-6β-[N-methyl-3-(4-trifluoromethylphenyl)propiolamido]morphinan, 17-cyclopropylmethyl-3,14β-dihydroxy-4-methoxy-6β-(N-methyl-3-trifluoromethylcinnamamido)morphinan, 17-cyclopropylmethyl-3,14β-dihydroxy-4-methoxy-6β-[N-methyl-trans-3-(3-furyl)acrylamido]morphinan, 17-cyclopropylmethyl-3,14β-dihydroxy-4-methoxy-6β-(N-methyl-3-methylcinnamamido)morphinan, 17-cyclopropylmethyl-3,14β-dihydroxy-4-methoxy-6β-[N-methyl-3-(4-trifluoromethylphenyl)propiolamido]-morphinan, 17-allyl-3,14β-dihydroxy-4-methoxy-6β-(N-methyl-3-trifluoromethylcinnamamido)morphinan, 17-allyl-3,14β-dihydroxy-4-methoxy-6β-[N-methyl-trans-3-(3-furyl)acrylamido]morphinan, 17-allyl-3,14β-dihydroxy-4-methoxy-6β-(N-methyl-3-methylcinnamamido)morphinan, 17-allyl-3,14β-dihydroxy-4-methoxy-6β-[N-methyl-3-(4-trifluoromethylphenyl)propiolamido]morphinan, 17-methyl-3,14β-dihydroxy-4-methoxy-6β-(N-methyl-3-trifluoromethylcinnamamido)morphinan, 17-methyl-3,14β-dihydroxy-4-methoxy-6β-[N-methyl-trans-3-(3-furyl)acrylamido]morphinan, 17-methyl-3,14β-dihydroxy-4-methoxy-6β-(N-methyl-3-methylcinnamamido)morphinan, 17-methyl-3,14β-dihydroxy-4-methoxy-6β-[N-methyl-3-(4-trifluoromethylphenyl)propiolamido]morphinan, 17-phenethyl-3,14β-dihydroxy-4-methoxy-6β-(N-methyl-3-trifluoromethylcinnamamido)morphinan, 17-phenethyl-3,14β-dihydroxy-4-methoxy-6β-[N-methyl-trans-3-(3-furyl)acrylamido]morphinan, 17-phenethyl-3,14β-dihydroxy-4-methoxy-6β-(N-methyl-3-methylcinnamamido)morphinan, 17-phenethyl-3,14β-dihydroxy-4-methoxy-6β-[N-methyl-3-(4-trifluoromethylphenyl)propiolamido]morphinan, 17-cyclopropylmethyl-4,5α-epoxy-3,14β-dihydroxy-5β-methyl-6β-(N-methyl-3-trifluoromethylcinnamamido)-morphinan, 17-cyclopropylmethyl-4,5α-epoxy-3,14β-dihydroxy-5β-methyl-6β-[N-methyl-trans-3-(3-furyl)acrylamido]morphinan, 17-cyclopropylmethyl-4,5α-epoxy-3,14β-dihydroxy-5β-methyl-6β-(N-methyl-3-methylcinnamamido)morphinan, 17-cyclopropylmethyl-4,5α-epoxy-3,14β-dihydroxy-5β-methyl-6β-[N-methyl-3-(4-trifluoromethylphenyl)propiolamido]morphinan, 17-allyl-4,5α-epoxy-3,14β-dihydroxy-5β-methyl-6β-(N-methyl-3-trifluoromethylcinnamamido)morphinan, 17-allyl-4,5α-epoxy-3,14β-dihydroxy-5β-methyl-6β-[N-methyl-trans-3-(3-furyl)acrylamido]morphinan, 17-allyl-4,5α- epoxy-3,14β-dihydroxy-5β-methyl-6β-(N-methyl-3-methylcinnamamido)morphinan, 17-allyl-4,5α-epoxy-3,14β-dihydroxy-5β-methyl-6β-[N-methyl-3-(4-trifluoromethylphenyl)propiolamido]morphinan, 5β,17-dimethyl-4,5α-epoxy-3,14β-dihydroxy-6β-(N-methyl-3-trifluoromethylcinnamamido)morphinan, 5β,17-dimethyl-4,5α-epoxy-3,14β-dihydroxy-6β-[N-methyl-trans-3-(3-furyl)acrylamido]morphinan, 5β,17-dimethyl-4,5α-epoxy-3,14β-dihydroxy-6β-(N-methyl-3-methylcinnamamido)-morphinan, 5β,17-dimethyl-4,5α-epoxy-3,14β-dihydroxy-6β-[N-methyl-3-(4-trifluoromethylphenyl)propiolamido]-morphinan, 17-phenethyl-4,5α-epoxy-3,14β-dihydroxy-5β-methyl-6β-(N-methyl-3-trifluoromethylcinnamamido)-morphinan, 17-phenethyl-4,5α-epoxy-3,14β-dihydroxy-5-methyl-6β-[N-methyl-trans-3-(3-furyl)acrylamido]-morphinan, 17-phenethyl-4,5α-epoxy-3,14β-dihydroxy-5β-methyl-6β-(N-methyl-3-methylcinnamamido)morphinan, 17-phenethyl-4,5α-epoxy-3,14β-dihydroxy-5β-methyl-6β-[N-methyl-3-(4-trifluoromethylphenyl)propiolamido]-morphinan, 17-cyclopropylmethyl-7,8-didehydro-4,5α-epoxy-3,14β-dihydroxy-6β-(N-methyl-3-trifluoromethylcinnamamido)morphinan, 17-cyclopropylmethyl-7,8-didehydro-4,5α-epoxy-3,14β-dihydroxy-6β-[N-methyl-trans-3-(3-furyl)acrylamido]morphinan, 17-cyclopropylmethyl-7,8-didehydro-4,5α-epoxy-3,14β-dihydroxy-6β-(N-methyl-3-methylcinnamamido)-morphinan, 17-cyclopropylmethyl-7,8-didehydro-4,5α-epoxy-3,14β-dihydroxy-6β-[N-methyl-3-(4-trifluoromethylphenyl) propiolamido]morphinan, 17-allyl-7,8-didehydro-4,5α-epoxy-3,14β-dihydroxy-6β-(N-methyl-3-trifluoromethylcinnamamido)morphinan, 17-allyl-7,8-didehydro-4,5α-epoxy-3,14β-dihydroxy-6β-[N-methyl-trans-3-(3-furyl)acrylamido]morphinan, 17-allyl-7,8-didehydro-4,5α-epoxy-3,14β-dihydroxy-6β-(N-methyl-3-methylcinnamamido)morphinan, 17-allyl-7,8-didehydro-4,5α-epoxy-3,14β-dihydroxy-6β-[N-methyl-3-(4-trifluoromethylphenyl)propiolamido]morphinan, 17-methyl-7,8-didehydro-4,5α-epoxy-3,14β-dihydroxy-6β-(N-methyl-3-trifluoromethylcinnamamido)-morphinan, 17-methyl-7,8-didehydro-4,5α-epoxy-3,14β-dihydroxy-6β-[N-methyl-trans-3-(3-furyl)acrylamido]-morphinan, 17-methyl-7,8-didehydro-4,5α-epoxy-3,14β-dihydroxy-6β-(N-methyl-3-methylcinnamamido)morphinan, 17-methyl-7,8-didehydro-4,5α-epoxy-3,14β-dihydroxy-6β-[N-methyl-3-(4-trifluoromethylphenyl)propiolamido]-morphinan, 17-phenethyl-7,8-didehydro-4,5α-epoxy-3,14β-dihydroxy-6β-(N-methyl-3-trifluoromethylcinnamamido)morphinan, 17-phenethyl-7,8-didehydro-4,5α-epoxy-3,14β-dihydroxy-6β-[N-methyl-trans-3-(3-furyl)acrylamido]morphinan, 17-phenethyl-7,8-didehydro-4,5α-epoxy-3,14β-dihydroxy-6β-(N-methyl-3-methylcinnamamido)morphinan, 17-phenethyl-7,8-didehydro-4,5α-epoxy-3,14β-dihydroxy-6β-[N-methyl-3-(4-trifluoromethylphenyl)propiolamido]morphinan, 17-cyclopropylmethyl-4,5α-epoxy-3,14β-dihydroxy-6α-(N-ethyl-3-trifluoromethylcinnamamido)morphinan, 17-cyclopropylmethyl-4,5α-epoxy-3,14β-dihydroxy-6α-(N-isopropyl-3-trifluoromethylcinnamamido)morphinan, 17-cyclopropylmethyl-4,5α-epoxy-3,14β-dihydroxy-6α-(N-butyl-3-trifluoromethylcinnamamido)morphinan, 17-cyclopropylmethyl-4,5α-epoxy-3,14β-dihydroxy-6α-(N-pentyl-3-trifluoromethylcinnamamido)morphinan, 17-cyclopropylmethyl-4,5α-epoxy-3-methoxy-14β-hydroxy-6α-(N-ethyl-3-trifluoromethylcinnamamido)morphinan, 17-cyclopropylmethyl-4,5α-epoxy-3-methoxy-14β-hydroxy-6α-(N-isopropyl-3-trifluoromethylcinnamamido)morphinan, 17-cyclopropylmethyl-4,5α-epoxy-3-methoxy-14β-hydroxy-6α-(N-butyl-3-trifluoromethylcinnamamido)morphinan, 17-cyclopropylmethyl-4,5α-epoxy-3-methoxy-14β-hydroxy-6α-(N-pentyl-3-trifluoromethylcinnamamido)morphinan, 17-cyclopropylmethyl-4,5α-epoxy-3-acetoxy-14β-hydroxy-6α-(N-ethyl-3-trifluoromethylcinnamamido)morphinan, 17-cyclopropylmethyl-4,5α-epoxy-3-acetoxy-14β-hydroxy-6α-(N-isopropyl-3-trifluoromethylcinnamamido)morphinan, 17-cyclopropylmethyl-4,5α-epoxy-3-acetoxy-14β-hydroxy-6α-(N-butyl-3-trifluoromethylcinnamamido)morphinan, 17-cyclopropylmethyl-4,5α-epoxy-3-acetoxy-14β-hydroxy-6α-(N-pentyl-3-trifluoromethylcinnamamido)morphinan, 17-cyclopropylmethyl-4,5α-epoxy-3,14β-dihydroxy-6α-(N-ethyl-6-phenylhexanoamido)morphinan, 17-cyclopropylmethyl-4,5α-epoxy-3,14β-dihydroxy-6α-(N-isopropyl-6-phenylhexanoamido)morphinan, 17-cyclopropylmethyl-4,5α-epoxy-3,14β-dihydroxy-6α-(N-butyl-6-phenylhexanoamido)morphinan, 17-cyclopropylmethyl-4,5α-epoxy-3,14β-dihydroxy-6α-(N-isobutyl-6-phenylhexanoamido)morphinan, 17-cyclopropylmethyl-4,5α-epoxy-3,14β-dihydroxy-6α-(N-pentyl-6-phenylhexanoamido)morphinan, 17-cyclopropylmethyl-4,5α-epoxy-3-methoxy-14β-hydroxy-6α-(N-ethyl-6-phenylhexanoamido)morphinan, 17-cyclopropylmethyl-4,5α-epoxy-3-methoxy-14β-hydroxy-6α-(N-isopropyl-6-phenylhexanoamido)morphinan, 17-cyclopropylmethyl-4,5α-epoxy-3-methoxy-14β-hydroxy-6α-(N-butyl-6-phenylhexanoamido)-morphinan, 17-cyclopropylmethyl-4,5α-epoxy-3-methoxy-14β-hydroxy-6α-(N-isobutyl-6-phenylhexanoamido)morphinan, 17-cyclopropylmethyl-4,5α-epoxy-3-methoxy-14β-hydroxy-6α-(N-pentyl-6-phenylhexanoamido)morphinan, 17-cyclopropylmethyl-4,5α-epoxy-3-acetoxy-14β-hydroxy-6α-(N-ethyl-6-phenylhexanoamido)morphinan, 17-cyclopropylmethyl-4,5α-epoxy-3-acetoxy-14β-hydroxy-6α-(N-isopropyl-6-phenylhexanoamido)morphinan, 17-cyclopropylmethyl-4,5α-epoxy-3-acetoxy-14β-hydroxy-6α-(N-butyl-6-phenylhexanoamido)morphinan, 17-cyclopropylmethyl-4,5α-epoxy-3-acetoxy-14β-hydroxy-6α-(N-isobutyl-6-phenylhexanoamido)morphinan, 17-cyclopropylmethyl-4,5α-epoxy-3-acetoxy-14β-hydroxy-6α-(N-pentyl-6-phenylhexanoamido)morphinan, 17-cyclopropylmethyl-4,5α-epoxy-3,14β-dihydroxy-6α-(N-methyl-8-phenyloctanoamido)-morphinan, 17-cyclopropylmethyl-4,5α-epoxy-3,14β-dihydroxy-6α-(N-ethyl-8-phenyloctanoamido)morphinan, 17-cyclopropylmethyl-4,5α-epoxy-3,14β-dihydroxy-6α-(N-isopropyl-8-phenyloctanoamido)morphinan, 17-cyclopropylmethyl-4,5α-epoxy-3,14β-dihydroxy-6α-(N-butyl-8-phenyloctanoamido)morphinan, 17-cyclopropylmethyl-4,5α-epoxy-3,14β-dihydroxy-6α-(N-isobutyl-8-phenyloctanoamido)morphinan, 17-cyclopropylmethyl-4,5α-epoxy-3,14β-dihydroxy-6α-(N-pentyl-8-phenyloctanoamido)morphinan, 17-cyclopropylmethyl-4,5α-epoxy-3-methoxy-14β-hydroxy-6α-(N-methyl-8-phenyloctanoamido)morphinan, 17-cyclopropylmethyl-4,5α-epoxy-3-methoxy-14β-hydroxy-6α-(N-ethyl-8-phenyloctanoamido)-morphinan, 17-cyclopropylmethyl-4,5α-epoxy-3-methoxy-14β-hydroxy-6α-(N-isopropyl-8-phenyloctanoamido)morphinan, 17-cyclopropylmethyl-4,5α-epoxy-3-methoxy-14β-hydroxy-6α-(N-butyl-8-phenyloctanoamido)morphinan, 17-cyclopropylmethyl-4,5α-epoxy-3-methoxy-14β-hydroxy-6α-(N-isobutyl-8 -phenyloctanoamido)

morphinan, 17-cyclopropylmethyl-4,5α-epoxy-3-methoxy-14β-hydroxy-6α-(N-pentyl-8-phenyloctanoamido)morphinan, 17-cyclopropylmethyl-4,5α-epoxy-3-acetoxy-14β-hydroxy-6α-(N-methyl-8-phenyloctanoamido)morphinan, 17-cyclopropylmethyl-4,5α-epoxy-3-acetoxy-14β-hydroxy-6α-(N-ethyl-8-phenyloctanoamido)morphinan, 17-cyclopropylmethyl-4,5α-epoxy-3-acetoxy-14β-hydroxy-6α-(N-isopropyl-8-phenyloctanoamido)morphinan, 17-cyclopropylmethyl-4,5α-epoxy-3-acetoxy-14β-hydroxy-6α-(N-butyl-8-phenyloctanoamido)-morphinan, 17-cyclopropylmethyl-4,5α-epoxy-3-acetoxy-14β-hydroxy-6α-(N-isobutyl-8-phenyloctanoamido)morphinan, 17-cyclopropylmethyl-4,5α-epoxy-3-acetoxy-14β-hydroxy-6α-(N-pentyl-8-phenyloctanoamido)morphinan, 17-cyclopropylmethyl-4,5α-epoxy-3,14β-dihydroxy-6α-(N-methyl-11-phenyl-undecanoamido)morphinan, 17-cyclopropylmethyl-4,5α-epoxy-3,14β-dihydroxy-6α-(N-ethyl-11-phenylundecanoamido)-morphinan, 17-cyclopropylmethyl-4,5α-epoxy-3,14β-dihydroxy-6α-(N-isopropyl-11-phenylundecanoamido)-morphinan, 17-cyclopropylmethyl-4,5α-epoxy-3,14β-dihydroxy-6α-(N-butyl-11-phenylundecanoamido)morphinan, 17-cyclopropylmethyl-4,5α-epoxy-3,14β-dihydroxy-6α-(N-isobutyl-11-phenylundecanoamido)morphinan, 17-cyclopropylmethyl-4,5α-epoxy-3,14β-dihydroxy-6α-(N-pentyl-11-phenylundecanoamido)morphinan, 17-cyclopropylmethyl-4,5α-epoxy-3-methoxy-14β-hydroxy-6α-(N-methyl-11-phenyl-undecanoamido)morphinan, 17-cyclopropylmethyl-4,5α-epoxy-3-methoxy-14β-hydroxy-6α-(N-ethyl-11-phenylundecanoamido)morphinan, 17-cyclopropylmethyl-4,5α-epoxy-3-methoxy-14β-hydroxy-6α-(N-isopropyl-11-phenylundecanoamido)morphinan, 17-cyclopropylmethyl-4,5α-epoxy-3-methoxy-14β-hydroxy-6α-(N-butyl-11-phenylundecanoamido)-morphinan, 17-cyclopropylmethyl-4,5α-epoxy-3-methoxy-14β-hydroxy-6α-(N-isobutyl-11-phenylundecanoamido)morphinan, 17-cyclopropylmethyl-4,5α-epoxy-3-methoxy-14β-hydroxy-6α-(N-pentyl-11-phenylundecanoamido)morphinan, 17-cyclopropylmethyl-4,5α-epoxy-3-acetoxy-14β-hydroxy-6α-(N-methyl-11-phenylundecanoamido)morphinan, 17-cyclopropylmethyl-4,5α-epoxy-3-acetoxy-14β-hydroxy-6α-(N-ethyl-11-phenylundecanoamido)morphinan, 17-cyclopropylmethyl-4,5α-epoxy-3-acetoxy-14β-hydroxy-6α-(N-isopropyl-11-phenyl-undecanoamido)morphinan, 17-cyclopropylmethyl-4,5α-epoxy-3-acetoxy-14β-hydroxy-6α-(N-butyl-11-phenylundecanoamido)morphinan, 17-cyclopropylmethyl-4,5α-epoxy-3-acetoxy-14β-hydroxy-6α-(N-isobutyl-11-phenylundecanoamido)morphinan, 17-cyclopropylmethyl-4,5α-epoxy-3-acetoxy-14β-hydroxy-6α-(N-pentyl-11-phenylundecanoamido)-morphinan, 17-cyclopropylmethyl-4,5α-epoxy-3,14β-dihydroxy-6α-(N-methyl-5-cyclohexylpentanoamido)-morphinan, 17-cyclopropylmethyl-4,5α-epoxy-3,14β-dihydroxy-6α-(N-ethyl-5-cyclohexylpentanoamido)morphinan, 17-cyclopropylmethyl-4,5α-epoxy-3,14β-dihydroxy-6α-(N-isopropyl-5-cyclohexylpentanoamido)morphinan, 17-cyclopropylmethyl-4,5α-epoxy-3,14β-dihydroxy-6α-(N-butyl-5-cyclohexylpentanoamido)morphinan, 17-cyclopropylmethyl-4,5α-epoxy-3,14β-dihydroxy-6α-(N-isobutyl-5-cyclohexylpentanoamido)morphinan, 17-cyclopropylmethyl-4,5α-epoxy-3,14β-dihydroxy-6α-(N-pentyl-5-cyclohexylpentanoamido)morphinan, 17-cyclopropylmethyl-4,5α-epoxy-3-methoxy-14β-hydroxy-6α-(N-methyl-5-cyclohexylpentanoamido)morphinan, 17-cyclopropylmethyl-4,5α-epoxy-3-methoxy-14β-hydroxy-6α-(N-ethyl-5-cyclohexylpentanoamido)morphinan, 17-cyclopropylmethyl-4,5α-epoxy-3-methoxy-14β-hydroxy-6α-(N-isopropyl-5-cyclohexylpentanoamido)morphinan, 17-cyclopropylmethyl-4,5α-epoxy-3-methoxy-14β-hydroxy-6α-(N-butyl-5-cyclohexylpentanoamido)morphinan, 17-cyclopropylmethyl-4,5α-epoxy-3-methoxy-14β-hydroxy-6α-(N-isobutyl-5-cyclohexylpentanoamido)morphinan, 17-cyclopropylmethyl-4,5α-epoxy-3-methoxy-14β-hydroxy-6α-(N-pentyl-5-cyclohexylpentanoamido)morphinan, 17-cyclopropylmethyl-4,5α-epoxy-3-acetoxy-14β-hydroxy-6α-(N-methyl-5-cyclohexylpentanoamido)morphinan, 17-cyclopropylmethyl-4,5α-epoxy-3-acetoxy-14β-hydroxy-6α-(N-ethyl-5 -cyclohexylpentanoamido)morphinan, 17-cyclopropylmethyl-4,5α-epoxy-3-acetoxy-14β-hydroxy-6α-(N-isopropyl-5-cyclohexylpentanoamido)morphinan, 17-cyclopropylmethyl-4,5α-epoxy-3-acetoxy-14β-hydroxy-6α-(N-butyl-5-cyclohexylpentanoamido)morphinan, 17-cyclopropylmethyl-4,5α-epoxy-3-acetoxy-14β-hydroxy-6α-(N-isobutyl-5-cyclohexylpentanoamido)morphinan, 17-cyclopropylmethyl-4,5α-epoxy-3-acetoxy-14β-hydroxy-6α-(N-pentyl-5-cyclohexylpentanoamido)morphinan, 17-cyclopropylmethyl-4,5α-epoxy-3,14β-dihydroxy-6α-(N-methyl-5-benzoylpentanoamido)morphinan, 17-cyclopropylmethyl-4,5α-epoxy-3,14β-dihydroxy-6α-(N-ethyl-5-benzoylpentanoamido)morphinan, 17-cyclopropylmethyl-4,5α-epoxy-3,14β-dihydroxy-6α-(N-isopropyl-5-benzoylpentanoamido)morphinan, 17-cyclopropylmethyl-4,5α-epoxy-3,14β-dihydroxy-6α-(N-butyl-5-benzoylpentanoamido)morphinan, 17-cyclopropylmethyl-4,5α-epoxy-3,14β-dihydroxy-6α-(N-isobutyl-5-benzoylpentanoamido)morphinan, 17-cyclopropylmethyl-4,5α-epoxy-3,14β-dihydroxy-6α-(N-pentyl-5-benzoylpentanoamido)morphinan, 17-cyclopropylmethyl-4,5α-epoxy-3-methoxy-14β-hydroxy-6α-(N-methyl-5-benzoylpentanoamido)morphinan, 17-cyclopropylmethyl-4,5α-epoxy-3-methoxy-14β-hydroxy-6α-(N-ethyl-5-benzoylpentanoamido)morphinan, 17-cyclopropylmethyl-4,5α-epoxy-3-methoxy-14β-hydroxy-6α-(N-isopropyl-5-benzoylpentanoamido)morphinan, 17-cyclopropylmethyl-4,5α-epoxy-3-methoxy-14β-hydroxy-6α-(N-butyl-5-benzoylpentanoamido)morphinan, 17-cyclopropylmethyl-4,5α-epoxy-3-methoxy-14β-hydroxy-6α-(N-isobutyl-5-benzoylpentanoamido)morphinan, 17-cyclopropylmethyl-4,5α-epoxy-3-methoxy-14β-hydroxy-6α-(N-pentyl-5-benzoylpentanoamido)-morphinan, 17-cyclopropylmethyl-4,5α-epoxy-3-acetoxy-14β-hydroxy-6α-(N-methyl-5-benzoylpentanoamido)morphinan, 17-cyclopropylmethyl-4,5α-epoxy-3-acetoxy-14β-hydroxy-6α-(N-ethyl-5-benzoylpentanoamido)morphinan, 17-cyclopropylmethyl-4,5α-epoxy-3-acetoxy-14β-hydroxy-6α-(N-isopropyl-5-benzoylpentanoamido)morphinan, 17-cyclopropylmethyl-4,5α-epoxy-3-acetoxy-14β-hydroxy-6α-(N-butyl-5 -benzoylpentanoamido)morphinan, 17-cyclopropylmethyl-4,5α-epoxy-3-acetoxy-14β-hydroxy-6α-(N-isobutyl-5-benzoylpentanoamido)morphinan, 17-cyclopropylmethyl-4,5α-epoxy-3-acetoxy-14β-hydroxy-6α-(N-pentyl-5-benzoylpentanoamido)-morphinan, 17-cyclopropylmethyl-4,5α-epoxy-3,14β-dihydroxy-6α-(N-methyl-6-phenylhexylamino)morphinan, 17-cyclopropylmethyl-4,5α-epoxy-3,14β-dihydroxy-6α-(N-ethyl-6-phenylhexylamino)morphinan, 17-cyclopropylmethyl-4,5α-epoxy-3,14β-dihydroxy-6α-(N-isopropyl-6-phenylhexyl-amino)morphinan, 17-cyclopropylmethyl-4,5α-epoxy-3,14β-dihydroxy-6α-(N-butyl-6-phenylhexylamino)morphinan, 17-cyclopropylmethyl-4,5α-epoxy-3,14β-dihydroxy-6α-(N-isobutyl-6-phenylhexylamino)morphinan, 17-cyclopropylmethyl-4,5α-epoxy-3,14β- dihydroxy-6α-(N-pentyl-6-phenylhexylamino)morphinan, 17-cyclopropylmethyl-4,5α-epoxy-3-methoxy-14β-hydroxy-6α-(N-methyl-6-phenylhexylamino)-morphinan, 17-cyclopropylmethyl-4,5α-epoxy-3-methoxy-14β-hydroxy-6α-(N-ethyl-6-phenylhexylamino)morphinan, 17-cyclopropylmethyl-4,5α-epoxy-3-methoxy-14β-hydroxy-6α-(N-isopropyl-6-phenylhexylamino)morphinan, 17-cyclopropylmethyl-4,5α-epoxy-3-methoxy-14β-hydroxy-6α-(N-butyl-6-phenylhexylamino)morphinan, 17-cyclopropylmethyl-4,5α-epoxy-3-methoxy-14β-hydroxy-6α-(N-isobutyl-6-phenylhexyl-amino)morphinan, 17-cyclopropylmethyl-4,5α-epoxy-3-methoxy-14β-hydroxy-6α-(N-pentyl-6-phenylhexylamino)-morphinan, 17-cyclopropylmethyl-4,5α-epoxy-3-acetoxy-14β-hydroxy-6α-(N-methyl-6-phenylhexylamino)morphinan, 17-cyclopropylmethyl-4,5α-epoxy-3-acetoxy-14β-hydroxy-6α-(N-ethyl-6-phenylhexylamino)morphinan, 17-cyclopropylmethyl-4,5α-epoxy-3-acetoxy-14β-hydroxy-6α-(N-isopropyl-6-phenylhexylamino)morphinan, 17-cyclopropylmethyl-4,5α-epoxy-3-acetoxy-14β-hydroxy-6α-(N-butyl-6-phenylhexyl-amino)morphinan, 17-cyclopropylmethyl-4,5α-epoxy-3-acetoxy-14β-hydroxy-6α-(N-isobutyl-6-phenylhexylamino)-morphinan, 17-cyclopropylmethyl-4,5α-epoxy-3-acetoxy-14β-hydroxy-6α-(N-pentyl-6-phenylhexylamino)morphinan, 17-allyl-4,5α-epoxy-3,14β-dihydroxy-6α-(N-ethyl-3-trifluoromethylcinnamamido)morphinan, 17-allyl-4,5α-epoxy-3,14β-dihydroxy-6α-(N-isopropyl-3-trifluoromethylcinnamamido)morphinan, 17-allyl-4,5α-epoxy-3,14β-dihydroxy-6α-(N-butyl-3-trifluoromethylcinnamamido)-morphinan, 17-allyl-4,5α-epoxy-3,14β-dihydroxy-6α-(N-pentyl-3-trifluoromethylcinnamamido)morphinan, 17-allyl-4,5α-epoxy-3-methoxy-14β-hydroxy-6α-(N-ethyl-3-trifluoromethylcinnamamido)morphinan, 17-allyl-4,5α-epoxy-3-methoxy-14β-hydroxy-6α-(N-isopropyl-3-trifluoromethylcinnamamido)morphinan, 17-allyl-4,5α-epoxy-3-methoxy-14β-hydroxy-6α-(N-butyl-3-trifluoromethylcinnamamido)morphinan, 17-allyl-4,5α-epoxy-3-methoxy-14β-hydroxy-6α-(N-pentyl-3-trifluoromethylcinnamamido)morphinan, 17-allyl-4,5α-epoxy-3-acetoxy-14β-hydroxy-6α-(N-ethyl-3-trifluoromethylcinnamamido)morphinan, 17-allyl-4,5α-epoxy-3-acetoxy-14β-hydroxy-6α-(N-isopropyl-3-trifluoromethylcinnamamido)morphinan, 17-allyl-4,5α-epoxy-3-acetoxy-14β-hydroxy-6α-(N-butyl-3-trifluoromethylcinnamamido)morphinan, 17-allyl-4,5α-epoxy-3-acetoxy-14β-hydroxy-6α-(N-pentyl-3-trifluoromethylcinnamamido)morphinan, 17-allyl-4,5α-epoxy-3,14β-dihydroxy-6α-(N-ethyl-6-phenylhexanoamido)morphinan, 17-allyl-4,5α-epoxy-3,14β-dihydroxy-6α-(N-isopropyl-6-phenylhexanoamido)morphinan, 17-allyl-4,5α-epoxy-3,14β-dihydroxy-6α-(N-butyl-6-phenylhexanoamido)morphinan, 17-allyl-4,5α-epoxy-3,14β-dihydroxy-6α-(N-isobutyl-6-phenylhexanoamido)morphinan, 17-allyl-4,5α-epoxy-3,14β-dihydroxy-6α-(N-pentyl-6-phenylhexanoamido)morphinan, 17-allyl-4,5α-epoxy-3-methoxy-14β-hydroxy-6α-(N-ethyl-6-phenylhexanoamido)morphinan, 17-allyl-4,5α-epoxy-3-methoxy-14β-hydroxy-6α-(N-isopropyl-6-phenylhexanoamido)-morphinan, 17-allyl-4,5α-epoxy-3-methoxy-14β-hydroxy-6α-(N-butyl-6-phenylhexanoamido)morphinan, 17-allyl-4,5α-epoxy-3-methoxy-14β-hydroxy-6α-(N-isobutyl-6-phenylhexanoamido)morphinan, 17-allyl-4,5α-epoxy-3-methoxy-14β-hydroxy-6α-(N-pentyl-6-phenylhexanoamido)morphinan, 17-allyl-4,5α-epoxy-3-acetoxy-14β-hydroxy-6α-(N-ethyl-6-phenylhexanoamido)morphinan, 17-allyl-4,5α-epoxy-3-acetoxy-14β-hydroxy-6α-(N-isopropyl-6-phenylhexanoamido)-morphinan, 17-allyl-4,5α-epoxy-3-acetoxy-14β-hydroxy-6α-(N-butyl-6-phenylhexanoamido)morphinan, 17-allyl-4,5α-epoxy-3-acetoxy-14β-hydroxy-6α-(N-isobutyl-6-phenylhexanoamido)morphinan, 17-allyl-4,5α-epoxy-3-acetoxy-14β-hydroxy-6α-(N-pentyl-6-phenylhexanoamido)morphinan, 17-allyl-4,5α-epoxy-3,14β-dihydroxy-6α-(N-methyl-8-phenyloctanoamido)morphinan, 17-allyl-4,5α-epoxy-3,14β-dihydroxy-6α-(N-ethyl-8-phenyloctanoamido)morphinan, 17-allyl-4,5α-epoxy-3,14β-dihydroxy-6α-(N-isopropyl-8-phenyloctanoamido)morphinan, 17-allyl-4,5α-epoxy-3,14β-dihydroxy-6α-(N-butyl-8-phenyloctanoamido)morphinan, 17-allyl-4,5α-epoxy-3,14β-dihydroxy-6α-(N-isobutyl-8-phenyloctanoamido)morphinan, 17-allyl-4,5α-epoxy-3,14β-dihydroxy-6α-(N-pentyl-8-phenyloctanoamido)morphinan, 17-allyl-4,5α-epoxy-3-methoxy-14β-hydroxy-6α-(N-methyl-8-phenyloctanoamido)morphinan, 17-allyl-4,5α-epoxy-3-methoxy-14β-hydroxy-6α-(N-ethyl-8-phenyloctanoamido)-morphinan, 17-allyl-4,5α-epoxy-3-methoxy-14β-hydroxy-6α-(N-isopropyl-8-phenyloctanoamido)morphinan, 17-allyl-4,5α-epoxy-3-methoxy-14β-hydroxy-6α-(N-butyl-8-phenyloctanoamido)morphinan, 17-allyl-4,5α-epoxy-3-methoxy-14β-hydroxy-6α-(N-isobutyl-8-phenyloctanoamido)morphinan, 17-allyl-4,5α-epoxy-3-methoxy-14β-hydroxy-6α-(N-pentyl-8-phenyloctanoamido)morphinan, 17-allyl-4,5α-epoxy-3-acetoxy-14β-hydroxy-6α-(N-methyl-8-phenyloctanoamido)-morphinan, 17-allyl-4,5α-epoxy-3-acetoxy-14β-hydroxy-6α-(N-ethyl-8-phenyloctanoamido)morphinan, 17-allyl-4,5α-epoxy-3-acetoxy-14β-hydroxy-6α-(N-isopropyl-8-phenyloctanoamido)morphinan, 17-allyl-4,5α-epoxy-3-acetoxy-14β-hydroxy-6α-(N-butyl-8-phenyloctanoamido)morphinan, 17-allyl-4,5α-epoxy-3-acetoxy-14β-hydroxy-6α-(N-isobutyl-8-phenyloctanoamido)morphinan, 17-allyl-4,5α-epoxy-3-acetoxy-14β-hydroxy-6α-(N-pentyl-8-phenyloctanoamido)morphinan, 17-allyl-4,5α-epoxy-3,14β-dihydroxy-6α-(N-methyl-11-phenylundecanoamido)morphinan, 17-allyl-4,5α-epoxy-3,14β-dihydroxy-6α-(N-ethyl-11-phenylundecanoamido)morphinan, 17-allyl-4,5α-epoxy-3,14β-dihydroxy-6α-(N-isopropyl-11-phenylundecanoamido)morphinan, 17-allyl-4,5α-epoxy-3,14β-dihydroxy-6α-(N-butyl-11-phenylundecanoamido)morphinan, 17-allyl-4,5α-epoxy-3,14β-dihydroxy-6α-(N-isobutyl-11-phenylundecanoamido)morphinan, 17-allyl-4,5α-epoxy-3,14β-dihydroxy-6α-(N-pentyl-11-phenyl-undecanoamido)morphinan, 17-allyl-4,5α-epoxy-3-methoxy-14β-hydroxy-6α-(N-methyl-11-phenylundecanoamido)-morphinan, 17-allyl-4,5α-epoxy-3-methoxy-14β-hydroxy-6α-(N-ethyl-11-phenylundecanoamido)morphinan, 17-allyl-4,5α-epoxy-3-methoxy-14β-hydroxy-6α-(N-isopropyl-11-phenyl-undecanoamido)morphinan, 17-allyl-4,5α-epoxy-3-methoxy-14β-hydroxy-6α-(N-butyl-11-phenylundecanoamido)morphinan, 17-allyl-4,5α-epoxy-3-methoxy-14β-hydroxy-6α-(N-isobutyl-11-phenylundecanoamido)morphinan, 17-allyl-4,5α-epoxy-3-methoxy-14β-hydroxy-6α-(N-pentyl-11-phenylundecanoamido)-morphinan, 17-allyl-4,5α-epoxy-3-acetoxy-14β-hydroxy-6α-(N-methyl-11-phenylundecanoamido)morphinan, 17-allyl-4,5α-epoxy-3-acetoxy-14β-hydroxy-6α-(N-ethyl-11-phenyl-undecanoamido)morphinan, 17-allyl-4,5α-epoxy-3-acetoxy-14β-hydroxy-6α-(N-isopropyl-11-phenylundecanoamido)-morphinan, 17-allyl-4,5α-epoxy-3-acetoxy-14β-hydroxy-6α-(N-butyl-11-phenylundecanoamido)morphinan, 17-allyl-4,5α-epoxy-3- acetoxy-14β-hydroxy-6α-(N-isobutyl-11-phenyl-undecanoamido)morphinan, 17-allyl-4,5α-epoxy-3-acetoxy-14β-hydroxy-6α-(N-pentyl-11-phenylundecanoamido)-morphinan, 17-allyl-4,5α-epoxy-3,14β-dihydroxy-6α-(N-methyl-5-cyclohexylpentanoamido)morphinan, 17-allyl-4,5α-epoxy-3,14β-dihydroxy-6α-(N-ethyl-5-cyclohexylpentanoamido)morphinan, 17-allyl-4,5α-epoxy-3,14β-dihydroxy-6α-(N-isopropyl-5-cyclohexylpentanoamido)-morphinan, 17-allyl-4,5α-epoxy-3,14β-dihydroxy-6α-(N-butyl-5-cyclohexylpentanoamido)morphinan, 17-allyl-4,5α-epoxy-3,14β-dihydroxy-6α-(N-isobutyl-5-cyclohexylpentanoamido)morphinan, 17-allyl-4,5α-epoxy-3,14β-dihydroxy-6α-(N-pentyl-5-cyclohexylpentanoamido)morphinan, 17-allyl-4,5α-epoxy-3-methoxy-14β-hydroxy-6α-(N-methyl-5-cyclohexylpentanoamido)morphinan, 17-allyl-4,5α-epoxy-3-methoxy-14β-hydroxy-6α-(N-ethyl-5-cyclohexylpentanoamido)morphinan, 17-allyl-4,5α-epoxy-3-methoxy-14β-hydroxy-6α-(N-isopropyl-5-cyclohexylpentanoamido)morphinan, 17-allyl-4,5α-epoxy-3-methoxy-14β-hydroxy-6α-(N-butyl-5-cyclohexylpentanoamido)-morphinan, 17-allyl-4,5α-epoxy-3-methoxy-14β-hydroxy-6α-(N-isobutyl-5-cyclohexylpentanoamido)morphinan, 17-allyl-4,5α-epoxy-3-methoxy-14β-hydroxy-6α-(N-pentyl-5-cyclohexylpentanoamido)morphinan, 17-allyl-4,5α-epoxy-3-acetoxy-14β-hydroxy-6α-(N-methyl-5-cyclohexylpentanoamido)morphinan, 17-allyl-4,5α-epoxy-3-acetoxy-14β-hydroxy-6α-(N-ethyl-5-cyclohexylpentanoamido)morphinan, 17-allyl-4,5α-epoxy-3-acetoxy-14β-hydroxy-6α-(N-isopropyl-5-cyclohexylpentanoamido)morphinan, 17-allyl-4,5α-epoxy-3-acetoxy-14β-hydroxy-6α-(N-butyl-5-cyclohexylpentanoamido)morphinan, 17-allyl-4,5α-epoxy-3-acetoxy-14β-hydroxy-6α-(N-isobutyl-5-cyclohexylpentanoamido)morphinan, 17-allyl-4,5α-epoxy-3-acetoxy-14β-hydroxy-6α-(N-pentyl-5-cyclohexylpentanoamido)morphinan, 17-allyl-4,5α-epoxy-3,14β-dihydroxy-6α-(N-methyl-5-benzoylpentanoamido)morphinan, 17-allyl-4,5α-epoxy-3,14β-dihydroxy-6α-(N-ethyl-5-benzoylpentanoamido)morphinan, 17-allyl-4,5α-epoxy-3,14β-dihydroxy-6α-(N-isopropyl-5-benzoylpentanoamido)-morphinan, 17-allyl-4,5α-epoxy-3,14β-dihydroxy-6α-(N-butyl-5-benzoylpentanoamido)morphinan, 17-allyl-4,5α-epoxy-3,14β-dihydroxy-6α-(N-isobutyl-5-benzoylpentanoamido)morphinan, 17-allyl-4,5α-epoxy-3,14β-dihydroxy-6α-(N-pentyl-5-benzoylpentanoamido)morphinan, 17-allyl-4,5α-epoxy-3-methoxy-14β-hydroxy-6α-(N-methyl-5-benzoylpentanoamido)morphinan, 17-allyl-4,5α-epoxy-3-methoxy-14β-hydroxy-6α-(N-ethyl-5-benzoylpentanoamido)morphinan, 17-allyl-4,5α-epoxy-3-methoxy-14β-hydroxy-6α-(N-isopropyl-5-benzoylpentanoamido)morphinan, 17-allyl-4,5α-epoxy-3-methoxy-14β-hydroxy-6α-(N-butyl-5-benzoylpentanoamido)morphinan, 17-allyl-4,5α-epoxy-3-methoxy-14β-hydroxy-6α-(N-isobutyl-5-benzoylpentanoamido)morphinan, 17-allyl-4,5α-epoxy-3-methoxy-14β-hydroxy-6α-(N-pentyl-5-benzoylpentanoamido)morphinan, 17-allyl-4,5α-epoxy-3-acetoxy-14β-hydroxy-6α-(N-methyl-5-benzoylpentanoamido)-morphinan, 17-allyl-4,5α-epoxy-3-acetoxy-14β-hydroxy-6α-(N-ethyl-5-benzoylpentanoamido)morphinan, 17-allyl-4,5α-epoxy-3-acetoxy-14β-hydroxy-6α-(N-isopropyl-5-benzoylpentanoamido)morphinan, 17-allyl-4,5α-epoxy-3-acetoxy-14β-hydroxy-6α-(N-butyl-5-benzoylpentanoamido)morphinan, 17-allyl-4,5α-epoxy-3-acetoxy-14β-hydroxy-6α-(N-isobutyl-5-benzoylpentanoamido)morphinan, 17-allyl-4,5α-epoxy-3-acetoxy-14β-hydroxy-6α-(N-pentyl-5-benzoylpentanoamido)-morphinan, 17-allyl-4,5α-epoxy-3,14β-dihydroxy-6α-(N-methyl-6-phenylhexylamino)morphinan, 17-allyl-4,5α-epoxy-3,14β-dihydroxy-6α-(N-ethyl-6-phenylhexylamino)morphinan, 17-allyl-4,5α-epoxy-3,14β-dihydroxy-6α-(N-isopropyl-6-phenylhexylamino)morphinan, 17-allyl-4,5α-epoxy-3,14β-dihydroxy-6α-(N-butyl-6-phenylhexylamino)morphinan, 17-allyl-4,5α-epoxy-3,14β-dihydroxy-6α-(N-isobutyl-6-phenylhexylamino)morphinan, 17-allyl-4,5α-epoxy-3,14β-dihydroxy-6α-(N-pentyl-6-phenylhexylamino)morphinan, 17-allyl-4,5α-epoxy-3-methoxy-14β-hydroxy-6α-(N-methyl-6-phenylhexylamino)morphinan, 17-allyl-4,5α-epoxy-3-methoxy-14β-hydroxy-6α-(N-ethyl-6-phenylhexylamino)-morphinan, 17-allyl-4,5α-epoxy-3-methoxy-14β-hydroxy-6α-(N-isopropyl-6-phenylhexylamino)morphinan, 17-allyl-4,5α-epoxy-3-methoxy-14β-hydroxy-6α-(N-butyl-6-phenylhexyl-amino)morphinan, 17-allyl-4,5α-epoxy-3-methoxy-14β-hydroxy-6α-(N-isobutyl-6-phenylhexylamino)morphinan, 17-allyl-4,5α-epoxy-3-methoxy-14β-hydroxy-6α-(N-pentyl-6-phenylhexylamino)morphinan, 17-allyl-4,5α-epoxy-3-acetoxy-14β-hydroxy-6α-(N-methyl-6-phenylhexylamino)-morphinan, 17-allyl-4,5α-epoxy-3-acetoxy-14β-hydroxy-6α-(N-ethyl-6-phenylhexylamino)morphinan, 17-allyl-4,5α-epoxy-3-acetoxy-14β-hydroxy-6α-(N-isopropyl-6-phenylhexylamino)morphinan, 17-allyl-4,5α-epoxy-3-acetoxy-14β-hydroxy-6α-(N-butyl-6-phenylhexylamino)morphinan, 17-allyl-4,5α-epoxy-3-acetoxy-14β-hydroxy-6α-(N-isobutyl-6-phenylhexylamino)morphinan, 17-allyl-4,5α-epoxy-3-acetoxy-14β-hydroxy-6α-(N-pentyl-6-phenylhexylamino)-morphinan, 17-cyclopropylmethyl-4,5α-epoxy-3,14β-dihydroxy-6β-(N-ethyl-3-trifluoromethylcinnamamido)-morphinan, 17-cyclopropylmethyl-4,5α-epoxy-3,14β-dihydroxy-6β-(N-isopropyl-3-trifluoromethylcinnamamido)-morphinan, 17-cyclopropylmethyl-4,5α-epoxy-3,14β-dihydroxy-6β-(N-butyl-3-trifluoromethylcinnamamido)-morphinan, 17-cyclopropylmethyl-4,5α-epoxy-3,14β-dihydroxy-6β-(N-pentyl-3-trifluoromethylcinnamamido)morphinan, 17-cyclopropylmethyl-4,5α-epoxy-3-methoxy-14β-hydroxy-6β-(N-ethyl-3-trifluoromethylcinnamamido)morphinan, 17-cyclopropylmethyl-4,5α-epoxy-3-methoxy-14β-hydroxy-6β-(N-isopropyl-3-trifluoromethylcinnamamido)morphinan, 17-cyclopropylmethyl-4,5α-epoxy-3-methoxy-14β-hydroxy-6β-(N-butyl-3-trifluoromethylcinnamamido)morphinan, 17-cyclopropylmethyl-4,5α-epoxy-3-methoxy-14β-hydroxy-6β-(N-pentyl-3-trifluoromethylcinnamamido)morphinan, 17-cyclopropylmethyl-4,5α-epoxy-3-acetoxy-14β-hydroxy-6β-(N-ethyl-3-trifluoromethylcinnamamido)morphinan, 17-cyclopropylmethyl-4,5α-epoxy-3-acetoxy-14β-hydroxy-6β-(N-isopropyl-3-trifluoromethylcinnamamido)morphinan, 17-cyclopropylmethyl-4,5α-epoxy-3-acetoxy-14β-hydroxy-6β-(N-butyl-3-trifluoromethylcinnamamido)morphinan, 17-cyclopropylmethyl-4,5α-epoxy-3-acetoxy-14β-hydroxy-6β-(N-pentyl-3-trifluoromethylcinnamamido)morphinan, 17-cyclopropylmethyl-4,5α-epoxy-3,14β-dihydroxy-6β-(N-ethyl-6-phenylhexanoamido)morphinan, 17-cyclopropylmethyl-4,5α-epoxy-3,14β-dihydroxy-6β-(N-isopropyl-6-phenylhexanoamido)-morphinan, 17-cyclopropylmethyl-4,5α-epoxy-3,14β-dihydroxy-6β-(N-butyl-6-phenylhexanoamido)morphinan, 17-cyclopropylmethyl-4,5α-epoxy-3,14β-dihydroxy-6β-(N-isobutyl-6-phenylhexanoamido)morphinan, 17-cyclopropyl-ethyl-4,5α-epoxy-3,14β-dihydroxy-6β-(N-pentyl-6-phenylhexanoamido)morphinan, 17-cyclopropylmethyl-4,5α-epoxy-3-methoxy-14β-hydroxy-6β-(N-ethyl-6-phenylhexanoamido)-morphinan, 17-cyclopropylmethyl-4,5α-epoxy-3-methoxy-14β-hydroxy-6β-(N-isopropyl-6-phenylhexanoamido)morphinan, 17-cyclopropylmethyl-4,5α-epoxy-3-methoxy-14β-hydroxy-6β-(N-butyl-6-phenylhexanoamido)morphinan, 17-cyclopropylmethyl-4,5α-epoxy-3-methoxy-14β-hydroxy-6β-(N-isobutyl-6-phenylhexanoamido)morphinan, 17-cyclopropylmethyl-4,5α-epoxy-3-methoxy-14β-hydroxy-6β-(N-pentyl-6-phenylhexanoamido)morphinan, 17-cyclopropylmethyl-4,5α-epoxy-3-acetoxy-14β-hydroxy-6β-(N-ethyl-6-phenylhexanoamido)-morphinan, 17-cyclopropylmethyl-4,5α-epoxy-3-acetoxy-14β-hydroxy-6β-(N-isopropyl-6-phenylhexanoamido)morphinan, 17-cyclopropylmethyl-4,5α-epoxy-3-acetoxy-14β-hydroxy-6β-(N-butyl-6-phenylhexanoamido)morphinan, 17-cyclopropylmethyl-4,5α-epoxy-3-acetoxy-14β-hydroxy-6β-(N-isobutyl-6-phenylhexanoamido)morphinan, 17-cyclopropylmethyl-4,5α-epoxy-3-acetoxy-14β-hydroxy-6β-(N-pentyl-6-phenylhexanoamido)morphinan, 17-cyclopropylmethyl-4,5α-epoxy-3,14β-dihydroxy-6β-(N-methyl-8-phenyloctanoamido)morphinan, 17-cyclopropylmethyl-4,5α-epoxy-3,14β-dihydroxy-6β-(N-ethyl-8-phenyloctanoamido)morphinan, 17-cyclopropylmethyl-4,5α-epoxy-3,14β-dihydroxy-6β-(N-isopropyl-8-phenyloctanoamido)morphinan, 17-cyclopropylmethyl-4,5α-epoxy-3,14β-dihydroxy-6β-(N-butyl-8-phenyloctanoamido)-morphinan, 17-cyclopropylmethyl-4,5α-epoxy-3,14β-dihydroxy-6β-(N-isobutyl-8-phenyloctanoamido)morphinan, 17-cyclopropylmethyl-4,5α-epoxy-3,14β-dihydroxy-6β-(N-pentyl-8-phenyloctanoamido)morphinan, 17-cyclopropylmethyl-4,5α-epoxy-3-methoxy-14β-hydroxy-6β-(N-methyl-8-phenyloctanoamido)morphinan, 17-cyclopropylmethyl-4,5α-epoxy-3-methoxy-14β-hydroxy-6β-(N-ethyl-8-phenyloctanoamido)morphinan, 17-cyclopropylmethyl-4,5α-epoxy-3-methoxy-14β-hydroxy-6β-(N-isopropyl-8-phenyloctanoamido)morphinan, 17-cyclopropylmethyl-4,5α-epoxy-3-methoxy-14β-hydroxy-6β-(N-butyl-8-phenyloctanoamido)morphinan, 17-cyclopropylmethyl-4,5α-epoxy-3-methoxy-14β-hydroxy-6β-(N-isobutyl-8-phenyloctanoamido)morphinan, 17-cyclopropylmethyl-4,5α-epoxy-3-methoxy-14β-hydroxy-6β-(N-pentyl-8-phenyloctanoamido)morphinan, 17-cyclopropylmethyl-4,5α-epoxy-3-acetoxy-14β-hydroxy-6β-(N-methyl-8-phenyloctanoamido)morphinan, 17-cyclopropylmethyl-4,5α-epoxy-3-acetoxy-14β-hydroxy-6β-(N-ethyl-8-phenyloctanoamido)morphinan, 17-cyclopropylmethyl-4,5α-epoxy-3-acetoxy-14β-hydroxy-6β-(N-isopropyl-8-phenyloctanoamido)-morphinan, 17-cyclopropylmethyl-4,5α-epoxy-3-acetoxy-14β-hydroxy-6β-(N-butyl-8-phenyloctanoamido)morphinan, 17-cyclopropylmethyl-4,5α-epoxy-3-acetoxy-14β-hydroxy-6β-(N-isobutyl-8-phenyloctanoamido)morphinan, 17-cyclopropylmethyl-4,5α-epoxy-3-acetoxy-14β-hydroxy-6β-(N-pentyl-8-phenyloctanoamido)morphinan, 17-cyclopropylmethyl-4,5α-epoxy-3,14β-dihydroxy-6β-(N-methyl-11-phenylundecanoamido)morphinan, 17-cyclopropylmethyl-4,5α-epoxy-3,14β-dihydroxy-6β-(N-ethyl-11-phenylundecanoamido)morphinan, 17-cyclopropylmethyl-4,5α-epoxy-3,14β-dihydroxy-6β-(N-isopropyl-11-phenylundecanoamido)morphinan, 17-cyclopropylmethyl-4,5α-epoxy-3,14β-dihydroxy-6β-(N-butyl-11-phenylundecanoamido)morphinan, 17-cyclopropylmethyl-4,5α-epoxy-3,14β-dihydroxy-6β-(N-isobutyl-11-phenylundecanoamido)morphinan, 17-cyclopropylmethyl-4,5α-epoxy-3,14β-dihydroxy-6β-(N-pentyl-11-phenylundecanoamido)morphinan, 17-cyclopropylmethyl-4,5α-epoxy-3-methoxy-14β-hydroxy-6β-(N-methyl-11-phenylundecanoamido)morphinan, 17-cyclopropylmethyl-4,5α-epoxy-3-methoxy-14β-hydroxy-6β-(N-ethyl-11-phenylundecanoamido)morphinan, 17-cyclopropylmethyl-4,5α-epoxy-3-methoxy-14β-hydroxy-6β-(N-isopropyl-11-phenylundecanoamido)morphinan, 17-cyclopropylmethyl-4,5α-epoxy-3-methoxy-14β-hydroxy-6β-(N-butyl-11-phenylundecanoamido)morphinan, 17-cyclopropylmethyl-4,5α-epoxy-3-methoxy-14β-hydroxy-6β-(N-isobutyl-11 -phenyl-undecanoamido)morphinan, 17-cyclopropylmethyl-4,5α-epoxy-3-methoxy-14β-hydroxy-6β-(N-pentyl-11-phenylundecanoamido)morphinan, 17-cyclopropylmethyl-4,5α-epoxy-3-acetoxy-14β-hydroxy-6β-(N-methyl-11-phenylundecanoamido)morphinan, 17-cyclopropylmethyl-4,5α-epoxy-3-acetoxy-14β-hydroxy-6β-(N-ethyl-11-phenylundecanoamido)morphinan, 17-cyclopropylmethyl-4,5α-epoxy-3-acetoxy-14β-hydroxy-6β-(N-isopropyl-11-phenylundecanoamido)morphinan, 17-cyclopropylmethyl-4,5α-epoxy-3-acetoxy-14β-hydroxy-6β-(N-butyl-11-phenylundecanoamido)-morphinan, 17-cyclopropylmethyl-4,5α-epoxy-3-acetoxy-14β-hydroxy-6β-(N-isobutyl-11-phenylundecanoamido)morphinan, 17-cyclopropylmethyl-4,5α-epoxy-3-acetoxy-14β-hydroxy-6β-(N-pentyl-11-phenylundecanoamido)morphinan, 17-cyclopropylmethyl-4,5α-epoxy-3,14β-dihydroxy-6β-(N-methyl-5-cyclohexylpentanoamido)morphinan, 17-cyclopropylmethyl-4,5α-epoxy-3,14β-dihydroxy-6β-(N-ethyl-5-cyclohexylpentanoamido)morphinan, 17-cyclopropylmethyl-4,5α-epoxy-3,14β-dihydroxy-6β-(N-isopropyl-5-cyclohexylpentanoamido)morphinan, 17-cyclopropylmethyl-4,5α-epoxy-3,14β-dihydroxy-6β-(N-butyl-5-cyclohexylpentanoamido)morphinan, 17-cyclopropylmethyl-4,5α-epoxy-3,14β-dihydroxy-6β-(N-isobutyl-5-cyclohexylpentanoamido)morphinan, 17-cyclopropylmethyl-4,5α-epoxy-3,14β-dihydroxy-6β-(N-pentyl-5-cyclohexylpentanoamido)morphinan, 17-cyclopropylmethyl-4,5α-epoxy-3-methoxy-14β-hydroxy-6β-(N-methyl-5-cyclohexylpentanoamido)morphinan, 17-cyclopropylmethyl-4,5α-epoxy-3-methoxy-14β-hydroxy-6β-(N-ethyl-5-cyclohexylpentanoamido)morphinan, 17-cyclopropylmethyl-4,5α-epoxy-3-methoxy-14β-hydroxy-6β-(N-isopropyl-5-cyclohexylpentanoamido)morphinan, 17-cyclopropylmethyl-4,5α-epoxy-3-methoxy-14β-hydroxy-6β-(N-butyl-5-cyclohexylpentanoamido)morphinan, 17-cyclopropylmethyl-4,5α-epoxy-3-methoxy-14β-hydroxy-6β-(N-isobutyl-5-cyclohexylpentanoamido)morphinan, 17-cyclopropylmethyl-4,5α-epoxy-3-methoxy-14β-hydroxy-6β-(N-pentyl-5-cyclohexylpentanoamido)morphinan, 17-cyclopropylmethyl-4,5α-epoxy-3-acetoxy-14β-hydroxy-6β-(N-methyl-5-cyclohexylpentanoamido)morphinan, 17-cyclopropylmethyl-4,5α-epoxy-3-acetoxy-14β-hydroxy-6β-(N-ethyl-5-cyclohexylpentanoamido)morphinan, 17-cyclopropylmethyl-4,5α-epoxy-3-acetoxy-14β-hydroxy-6β-(N-isopropyl-5-cyclohexylpentanoamido)morphinan, 17-cyclopropylmethyl-4,5α-epoxy-3-acetoxy-14β-hydroxy-6β-(N-butyl-5-cyclohexylpentanoamido)morphinan, 17-cyclopropylmethyl-4,5α-epoxy-3-acetoxy-14β-hydroxy-6β-(N-isobutyl-5-cyclohexylpentanoamido)morphinan, 17-cyclopropylmethyl-4,5α-epoxy-3-acetoxy-14β-hydroxy-6β-(N-pentyl-5-cyclohexylpentanoamido)morphinan, 17-cyclopropylmethyl-4,5α-epoxy-3,14β-dihydroxy-6β-(N-methyl-5-benzoylpentanoamido)- morphinan, 17-cyclopropylmethyl-4,5α-epoxy-3,14β-dihydroxy-6β-(N-ethyl-5-benzoylpentanoamido) morphinan, 17-cyclopropylmethyl-4,5α-epoxy-3,14β-dihydroxy-6β-(N-isopropyl-5-benzoylpentanoamido) morphinan, 17-cyclopropylmethyl-4,5α-epoxy-3,14β-dihydroxy-6β-(N-butyl-5-benzoylpentanoamido) morphinan, 17-cyclopropylmethyl-4,5α-epoxy-3,14β-dihydroxy-6β-(N-isobutyl-5-benzoylpentanoamido) morphinan, 17-cyclopropylmethyl-4,5α-epoxy-3,14β-dihydroxy-6β-(N-pentyl-5-benzoylpentanoamido) morphinan, 17-cyclopropylmethyl-4,5α-epoxy-3-methoxy-14β-hydroxy-6β-(N-methyl-5-benzoylpentanoamido) morphinan, 17-cyclopropylmethyl-4,5α-epoxy-3-methoxy-14β-hydroxy-6β-(N-ethyl-5-benzoylpentanoamido) morphinan, 17-cyclopropylmethyl-4,5α-epoxy-3-methoxy-14β-hydroxy-6β-(N-isopropyl-5-benzoylpentanoamido) morphinan, 17-cyclopropylmethyl-4,5α-epoxy-3-methoxy-14β-hydroxy-6β-(N-butyl-5-benzoylpentanoamido)-morphinan, 17-cyclopropylmethyl-4,5α-epoxy-3-methoxy-14β-hydroxy-6β-(N-isobutyl-5-benzoylpentanoamido) morphinan, 17-cyclopropylmethyl-4,5α-epoxy-3-methoxy-14β-hydroxy-6β-(N-pentyl-5-benzoylpentanoamido) morphinan, 17-cyclopropylmethyl-4,5α-epoxy-3-acetoxy-14β-hydroxy-6β-(N-methyl-5-benzoylpentanoamido) morphinan, 17-cyclopropylmethyl-4,5α-epoxy-3-acetoxy-14β-hydroxy-6β-(N-ethyl-5-benzoylpentanoamido) morphinan, 17-cyclopropylmethyl-4,5α-epoxy-3-acetoxy-14β-hydroxy-6β-(N-isopropyl-5-benzoylpentanoamido) morphinan, 17-cyclopropylmethyl-4,5α-epoxy-3-acetoxy-14β-hydroxy-6β-(N-butyl-5-benzoylpentanoamido) morphinan, 17-cyclopropylmethyl-4,5α-epoxy-3-acetoxy-14β-hydroxy-6β-(N-isobutyl-5-benzoylpentanoamido) morphinan, 17-cyclopropylmethyl-4,5α-epoxy-3-acetoxy-14β-hydroxy-6β-(N-pentyl-5-benzoylpentanoamido) morphinan, 17-cyclopropylmethyl-4,5α-epoxy-3,14β-dihydroxy-6β-(N-methyl-6-phenylhexylamino)-morphinan, 17-cyclopropylmethyl-4,5α-epoxy-3,14β-dihydroxy-6β-(N-ethyl-6-phenylhexylamino)morphinan, 17-cyclopropylmethyl-4,5α-epoxy-3,14β-dihydroxy-6β-(N-isopropyl-6-phenylhexylamino)morphinan, 17-cyclopropylmethyl-4,5α-epoxy-3,14β-dihydroxy-6β-(N-butyl-6-phenylhexylamino)morphinan, 17-cyclopropylmethyl-4,5α-epoxy-3,14β-dihydroxy-6β-(N-isobutyl-6-phenylhexylamino)morphinan, 17-cyclopropylmethyl-4,5α-epoxy-3,14β-dihydroxy-6β-(N-pentyl-6-phenylhexylamino)morphinan, 17-cyclopropylmethyl-4,5α-epoxy-3-methoxy-14β-hydroxy-6β-(N-methyl-6-phenylhexylamino)morphinan, 17-cyclopropylmethyl-4,5α-epoxy-3-methoxy-14β-hydroxy-6β-(N-ethyl-6-phenylhexylamino)morphinan, 17-cyclopropylmethyl-4,5α-epoxy-3-methoxy-14β-hydroxy-6β-(N-isopropyl-6-phenylhexylamino)morphinan, 17-cyclopropylmethyl-4,5α-epoxy-3-methoxy-14β-hydroxy-6β-(N-butyl-6-phenylhexylamino)morphinan, 17-cyclopropylmethyl-4,5α-epoxy-3-methoxy-14β-hydroxy-6β-(N-isobutyl-6-phenylhexylamino)morphinan, 17-cyclopropylmethyl-4,5α-epoxy-3-methoxy-14β-hydroxy-6β-(N-pentyl-6-phenylhexylamino)-morphinan, 17-cyclopropylmethyl-4,5α-epoxy-3-acetoxy-14β-hydroxy-6β-(N-methyl-6-phenylhexylamino)morphinan, 17-cyclopropylmethyl-4,5α-epoxy-3-acetoxy-14β-hydroxy-6β-(N-ethyl-6-phenylhexylamino)morphinan, 17-cyclopropylmethyl-4,5α-epoxy-3-acetoxy-14β-hydroxy-6β-(N-isopropyl-6-phenylhexylamino)morphinan, 17-cyclopropylmethyl-4,5α-epoxy-3-acetoxy-14β-hydroxy-6β-(N-butyl-6 -phenylhexyl-amino)morphinan, 17-cyclopropylmethyl-4,5α-epoxy-3-acetoxy-14β-hydroxy-6β-(N-isobutyl-6-phenylhexylamino)-morphinan, 17-cyclopropylmethyl-4,5α-epoxy-3-acetoxy-14β-hydroxy-6β-(N-pentyl-6-phenylhexylamino)morphinan, 17-allyl-4,5α-epoxy-3,14β-dihydroxy-6β-(N-ethyl-3-trifluoromethylcinnamamido)morphinan, 17-allyl-4,5α-epoxy-3,14β-dihydroxy-6β-(N-isopropyl-3-trifluoromethylcinnamamido)morphinan, 17-allyl-4,5α-epoxy-3,14β-dihydroxy-6β-(N-butyl-3-trifluoromethylcinnamamido)-morphinan, 17-allyl-4,5α-epoxy-3,14β-dihydroxy-6β-(N-pentyl-3-trifluoromethylcinnamamido)morphinan, 17-allyl-4,5α-epoxy-3-methoxy-14β-hydroxy-6β-(N-ethyl-3-trifluoromethylcinnamamido)morphinan, 17-allyl-4,5α-epoxy-3-methoxy-14β-hydroxy-6β-(N-isopropyl-3-trifluoromethylcinnamamido)morphinan, 17-allyl-4,5α-epoxy-3-methoxy-14β-hydroxy-6β-(N-butyl-3-trifluoromethylcinnamamido)morphinan, 17-allyl-4,5α-epoxy-3-methoxy-14β-hydroxy-6β-(N-pentyl-3-trifluoromethylcinnamamido)morphinan, 17-allyl-4,5α-epoxy-3-acetoxy-14β-hydroxy-6β-(N-ethyl-3-trifluoromethylcinnamamido)morphinan, 17-allyl-4,5α-epoxy-3-acetoxy-14β-hydroxy-6β-(N-isopropyl-3-trifluoromethylcinnamamido)-morphinan, 17-allyl-4,5α-epoxy-3-acetoxy-14β-hydroxy-6β-(N-butyl-3-trifluoromethylcinnamamido)morphinan, 17-allyl-4,5α-epoxy-3-acetoxy-14β-hydroxy-6β-(N-pentyl-3-trifluoromethylcinnamamido)morphinan, 17-allyl-4,5α-epoxy-3,14β-dihydroxy-6β-(N-ethyl-6-phenylhexanoamido)-morphinan, 17-allyl-4,5α-epoxy-3,14β-dihydroxy-6β-(N-isopropyl-6-phenylhexanoamido)morphinan, 17-allyl-4,5α-epoxy-3,14β-dihydroxy-6β-(N-butyl-6-phenylhexanoamido)-morphinan, 17-allyl-4,5α-epoxy-3,14β-dihydroxy-6β-(N-isobutyl-6-phenylhexanoamido)morphinan, 17-allyl-4,5α-epoxy-3,14β-dihydroxy-6β-(N-pentyl-6-phenylhexanoamido)-morphinan, 17-allyl-4,5α-epoxy-3-methoxy-14β-hydroxy-6β-(N-ethyl-6-phenylhexanoamido)morphinan, 17-allyl-4,5α-epoxy-3-methoxy-14β-hydroxy-6β-(N-isopropyl-6-phenylhexanoamido)morphinan, 17-allyl-4,5α-epoxy-3-methoxy-14β-hydroxy-6β-(N-butyl-6-phenylhexanoamido)morphinan, 17-allyl-4,5α-epoxy-3-methoxy-14β-hydroxy-6β-(N-isobutyl-6-phenylhexanoamido)morphinan, 17-allyl-4,5α-epoxy-3-methoxy-14β-hydroxy-6β-(N-pentyl-6-phenylhexanoamido)-morphinan, 17-allyl-4,5α-epoxy-3-acetoxy-14β-hydroxy-6β-(N-ethyl-6-phenylhexanoamido) morphinan, 17-allyl-4,5α-epoxy-3-acetoxy-14β-hydroxy-6β-(N-isopropyl-6-phenylhexanoamido)morphinan, 17-allyl-4,5α-epoxy-3-acetoxy-14β-hydroxy-6β-(N-butyl-6-phenylhexanoamido)morphinan, 17-allyl-4,5α-epoxy-3-acetoxy-14β-hydroxy-6β-(N-isobutyl-6-phenylhexanoamido) morphinan, 17-allyl-4,5α-epoxy-3-acetoxy-14β-hydroxy-6β-(N-pentyl-6-phenylhexanoamido)-morphinan, 17-allyl-4,5α-epoxy-3,14β-dihydroxy-6β-(N-methyl-8-phenyloctanoamido) morphinan, 17-allyl-4,5α-epoxy-3,14β-dihydroxy-6β-(N-ethyl-8-phenyloctanoamido)-morphinan, 17-allyl-4,5α-epoxy-3,14β-dihydroxy-6β-(N-isopropyl-8-phenyloctanoamido)morphinan, 17-allyl-4,5α-epoxy-3,14β-dihydroxy-6β-(N-butyl-8-phenyloctanoamido)-morphinan, 17-allyl-4,5α-epoxy-3,14β-dihydroxy-6β-(N-isobutyl-8-phenyloctanoamido)morphinan, 17-allyl-4,5α-epoxy-3,14β-dihydroxy-6β-(N-pentyl-8-phenyloctanoamido)-morphinan, 17-allyl-4,5α-epoxy-3-methoxy-14β-hydroxy-6β-(N-methyl-8-phenyloctanoamido)morphinan, 17-allyl-4,5α-epoxy-3-methoxy-14β-hydroxy-6β-(N-ethyl-8-phenyloctanoamido) morphinan, 17-allyl-4,5α-epoxy-3-methoxy-14β-hydroxy- 6β-(N-isopropyl-8-phenyloctanoamido)morphinan, 17-allyl-4,5α-epoxy-3-methoxy-14β-hydroxy-6β-(N-butyl-8-phenyloctanoamido)morphinan, 17-allyl-4,5α-epoxy-3-methoxy-14β-hydroxy-6β-(N-isobutyl-8-phenyloctanoamido)-morphinan, 17-allyl-4,5α-epoxy-3-methoxy-14β-hydroxy-6β-(N-pentyl-8-phenyloctanoamido)morphinan, 17-allyl-4,5α-epoxy-3-acetoxy-14β-hydroxy-6β-(N-methyl-8-phenyloctanoamido)morphinan, 17-allyl-4,5α-epoxy-3-acetoxy-14β-hydroxy-6β-(N-ethyl-8-phenyloctanoamido)morphinan, 17-allyl-4,5α-epoxy-3-acetoxy-14β-hydroxy-6β-(N-isopropyl-8-phenyloctanoamido)morphinan, 17-allyl-4,5α-epoxy-3-acetoxy-14β-hydroxy-6β-(N-butyl-8 -phenyloctanoamido)-morphinan, 17-allyl-4,5α-epoxy-3-acetoxy-14β-hydroxy-6β-(N-isobutyl-8-phenyloctanoamido)morphinan, 17-allyl-4,5α-epoxy-3-acetoxy-14β-hydroxy-6β-(N-pentyl-8-phenyloctanoamido)morphinan, 17-allyl-4,5α-epoxy-3,14β-dihydroxy-6β-(N-methyl-11-phenylundecanoamido)morphinan, 17-allyl-4,5α-epoxy-3,14β-dihydroxy-6β-(N-ethyl-11-phenylundecanoamido)morphinan, 17-allyl-4,5α-epoxy-3,14β-dihydroxy-6β-(N-isopropyl-11-phenylundecanoamido)morphinan, 17-allyl-4,5α-epoxy-3,14β-dihydroxy-6β-(N-butyl-11-phenylundecanoamido)morphinan, 17-allyl-4,5α-epoxy-3,14β-dihydroxy-6β-(N-isobutyl-11-phenylundecanoamido)morphinan, 17-allyl-4,5α-epoxy-3,14β-dihydroxy-6β-(N-pentyl-11-phenylundecanoamido)morphinan, 17-allyl-4,5α-epoxy-3-methoxy-14β-hydroxy-6β-(N-methyl-11-phenylundecanoamido)-morphinan, 17-allyl-4,5α-epoxy-3-methoxy-14β-hydroxy-6β-(N-ethyl-11-phenylundecanoamido)morphinan, 17-allyl-4,5α-epoxy-3-methoxy-14β-hydroxy-6β-(N-isopropyl-11-phenyl-undecanoamido)morphinan, 17-allyl-4,5α-epoxy-3-methoxy-14β-hydroxy-6β-(N-butyl-11-phenylundecanoamido)morphinan, 17-allyl-4,5α-epoxy-3-methoxy-14β-hydroxy-6β-(N-isobutyl-11-phenylundecanoamido)morphinan, 17-allyl-4,5α-epoxy-3-methoxy-14β-hydroxy-6β-(N-pentyl-11-phenylundecanoamido)-morphinan, 17-allyl-4,5α-epoxy-3-acetoxy-14β-hydroxy-6β-(N-methyl-11-phenylundecanoamido)morphinan, 17-allyl-4,5α-epoxy-3-acetoxy-14β-hydroxy-6β-(N-ethyl-11-phenylundecanoamido)morphinan, 17-allyl-4,5α-epoxy-3-acetoxy-14β-hydroxy-6β-(N-isopropyl-11-phenylundecanoamido)-morphinan, 17-allyl-4,5α-epoxy-3-acetoxy-14β-hydroxy-6β-(N-butyl-11-phenylundecanoamido)morphinan, 17-allyl-4,5α-epoxy-3-acetoxy-14β-hydroxy-6β-(N-isobutyl-11-phenylundecanoamido)morphinan, 17-allyl-4,5α-epoxy-3-acetoxy-14β-hydroxy-6β-(N-pentyl-11-phenylundecanoamido)-morphinan, 17-allyl-4,5α-epoxy-3,14β-dihydroxy-6β-(N-methyl-5-cyclohexylpentanoamido)morphinan, 17-allyl-4,5α-epoxy-3,14β-dihydroxy-6β-(N-ethyl-5-cyclohexylpentanoamido)morphinan, 17-allyl-4,5α-epoxy-3,14β-dihydroxy-6β-(N-isopropyl-5-cyclohexylpentanoamido)-morphinan, 17-allyl-4,5α-epoxy-3,14β-dihydroxy-6β-(N-butyl-5-cyclohexylpentanoamido)morphinan, 17-allyl-4,5α-epoxy-3,14β-dihydroxy-6β-(N-isobutyl-5-cyclohexylpentanoamido)morphinan, 17-allyl-4,5α-epoxy-3,14β-dihydroxy-6β-(N-pentyl-5-cyclohexylpentanoamido)morphinan, 17-allyl-4,5α-epoxy-3-methoxy-14β-hydroxy-6β-(N-methyl-5-cyclohexylpentanoamido)morphinan, 17-allyl-4,5α-epoxy-3-methoxy-14β-hydroxy-6β-(N-ethyl-5-cyclohexylpentanoamido)morphinan, 17-allyl-4,5α-epoxy-3-methoxy-14β-hydroxy-6β-(N-isopropyl-5-cyclohexylpentanoamido)morphinan, 17-allyl-4,5α-epoxy-3-methoxy-14β-hydroxy-6β-(N-butyl-5-cyclohexylpentanoamido)-morphinan, 17-allyl-4,5α-epoxy-3-methoxy-14β-hydroxy-6β-(N-isobutyl-5-cyclohexylpentanoamido)morphinan, 17-allyl-4,5α-epoxy-3-methoxy-14β-hydroxy-6β-(N-pentyl-5-cyclohexylpentanoamido)morphinan, 17-allyl-4,5α-epoxy-3-acetoxy-14β-hydroxy-6β-(N-methyl-5-cyclohexylpentanoamido)morphinan, 17-allyl-4,5α-epoxy-3-acetoxy-14β-hydroxy-6β-(N-ethyl-5-cyclohexylpentanoamido)morphinan, 17-allyl-4,5α-epoxy-3-acetoxy-14β-hydroxy-6β-(N-isopropyl-5-cyclohexylpentanoamido)morphinan, 17-allyl-4,5α-epoxy-3-acetoxy-14β-hydroxy-6β-(N-butyl-5-cyclohexylpentanoamido)morphinan, 17-allyl-4,5α-epoxy-3-acetoxy-14β-hydroxy-6β-(N-isobutyl-5-cyclohexylpentanoamido)morphinan, 17-allyl-4,5α-epoxy-3-acetoxy-14β-hydroxy-6β-(N-pentyl-5-cyclohexylpentanoamido)morphinan, 17-allyl-4,5α-epoxy-3,14β-dihydroxy-6β-(N-methyl-5-benzoylpentanoamido)morphinan, 17-allyl-4,5α-epoxy-3,14β-dihydroxy-6β-(N-ethyl-5-benzoylpentanoamido)morphinan, 17-allyl-4,5α-epoxy-3,14β-dihydroxy-6β-(N-isopropyl-5-benzoylpentanoamido)-morphinan, 17-allyl-4,5α-epoxy-3,14β-dihydroxy-6β-(N-butyl-5-benzoylpentanoamido)morphinan, 17-allyl-4,5α-epoxy-3,14β-dihydroxy-6β-(N-isobutyl-5-benzoylpentanoamido)morphinan, 17-allyl-4,5α-epoxy-3,14β-dihydroxy-6β-(N-pentyl-5-benzoylpentanoamido)morphinan, 17-allyl-4,5α-epoxy-3-methoxy-14β-hydroxy-6β-(N-methyl-5-benzoylpentanoamido)morphinan, 17-allyl-4,5α-epoxy-3-methoxy-14β-hydroxy-6β-(N-ethyl-5-benzoylpentanoamido)morphinan, 17-allyl-4,5α-epoxy-3-methoxy-14β-hydroxy-6β-(N-isopropyl-5-benzoylpentanoamido)morphinan, 17-allyl-4,5α-epoxy-3-methoxy-14β-hydroxy-6β-(N-butyl-5-benzoylpentanoamido)morphinan, 17-allyl-4,5α-epoxy-3-methoxy-14β-hydroxy-6β-(N-isobutyl-5-benzoylpentanoamido)morphinan, 17-allyl-4,5α-epoxy-3-methoxy-14β-hydroxy-6β-(N-pentyl-5-benzoylpentanoamido)morphinan, 17-allyl-4,5α-epoxy-3-acetoxy-14β-hydroxy-6β-(N-methyl-5-benzoylpentanoamido)-morphinan, 17-allyl-4,5α-epoxy-3-acetoxy-14β-hydroxy-6β-(N-ethyl-5-benzoylpentanoamido)morphinan, 17-allyl-4,5α-epoxy-3-acetoxy-14β-hydroxy-6β-(N-isopropyl-5-benzoylpentanoamido)morphinan, 17-allyl-4,5α-epoxy-3-acetoxy-14β-hydroxy-6β-(N-butyl-5-benzoylpentanoamido)morphinan, 17-allyl-4,5α-epoxy-3-acetoxy-14β-hydroxy-6β-(N-isobutyl-5-benzoylpentanoamido)morphinan, 17-allyl-4,5α-epoxy-3-acetoxy-14β-hydroxy-6β-(N-pentyl-5-benzoylpentanoamido)-morphinan, 17-allyl-4,5α-epoxy-3,14β-dihydroxy-6β-(N-methyl-6-phenylhexylamino)morphinan, 17-allyl-4,5α-epoxy-3,14β-dihydroxy-6β-(N-ethyl-6-phenylhexylamino)morphinan, 17-allyl-4,5α-epoxy-3,14β-dihydroxy-6β-(N-isopropyl-6-phenylhexylamino)morphinan, 17-allyl-4,5α-epoxy-3,14β-dihydroxy-6β-(N-butyl-6-phenylhexylamino)morphinan, 17-allyl-4,5α-epoxy-3,14β-dihydroxy-6β-(N-isobutyl-6-phenylhexylamino)morphinan, 17-allyl-4,5α-epoxy-3,14β-dihydroxy-6β-(N-pentyl-6-phenylhexylamino)morphinan, 17-allyl-4,5α-epoxy-3-methoxy-14β-hydroxy-6β-(N-methyl-6-phenylhexylamino)morphinan, 17-allyl-4,5α-epoxy-3-methoxy-14β-hydroxy-6β-(N-ethyl-6-phenylhexylamino)-morphinan, 17-allyl-4,5α-epoxy-3-methoxy-14β-hydroxy-6β-(N-isopropyl-6-phenylhexylamino)morphinan, 17-allyl-4,5α-epoxy-3- methoxy-14β-hydroxy-6β-(N-butyl-6-phenylhexylamino) morphinan, 17-allyl-4,5α-epoxy-3-methoxy-14β-hydroxy-6β-(N-isobutyl-6-phenylhexylamino)morphinan, 17-allyl-4,5α-epoxy-3-methoxy-14β-hydroxy-6β-(N-pentyl-6-phenylhexylamino)morphinan, 17-allyl-4,5α-epoxy-3-acetoxy-14β-hydroxy-6β-(N-methyl-6-phenylhexylamino)-morphinan, 17-allyl-4,5α-epoxy-3-acetoxy-14β-hydroxy-6β-(N-ethyl-6-phenylhexylamino) morphinan, 17-allyl-4,5α-epoxy-3-acetoxy-14β-hydroxy-6β-(N-isopropyl-6-phenylhexylamino)morphinan, 17-allyl-4,5α-epoxy-3-acetoxy-14β-hydroxy-6β-(N-butyl-6-phenylhexylamino)morphinan, 17-allyl-4,5α-epoxy-3-acetoxy-14β-hydroxy-6β-(N-isobutyl-6-phenylhexylamino) morphinan, 17-allyl-4,5α-epoxy-3-acetoxy-14β-hydroxy-6β-(N-pentyl-6-phenylhexylamino)-morphinan, 17-cyclopropylmethyl-4,5α-epoxy-3,14β-dihydroxy-6β-(N-methyl-3-trifluoromethoxycinnamamido)morphinan, 17-cyclopropylmethyl-4,5α-epoxy-3,14β-dihydroxy-6α-(N-methyl-3-trifluoromethoxycinnamamido)morphinan, 17-allyl-4,5α-epoxy-3,14β-dihydroxy-6β-(N-methyl-3-trifluoromethoxycinnamamido)morphinan, and 17-allyl-4,5α-epoxy-3,14β-dihydroxy-6α-(N-methyl-3-trifluoromethoxycinnamamido)morphinan, but the present invention is not limited to these compounds. The compound of the present invention includes (+) form, (−) form and (±) form of these.

In addition, the novel compounds represented with general formula (I') are included in the brain cell protective agent of the present invention. Namely, the present invention relates to a morphinan derivative represented with general formula (I') or pharmacologically acceptable acid addition salt thereof:

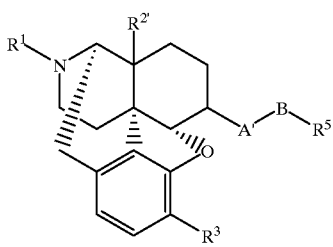

(I')

[wherein, $R^1$, $R^3$, B and $R^5$ are the same as previously defined; $R^{2'}$ represents a hydrogen atom, a hydroxy group, an alkanoyloxy group having 1–5 carbon atoms or an alkoxy group having 1–5 carbon atoms; A' represents —$NR^{4'}$C (=O)— or —$NR^{4'}$— (where, $R^{4'}$ represents a straight chain or branched chain alkyl group having 6–14 carbon atoms (which may be substituted with at least one type of substituent group selected from the group consisting of an alkoxy group having 1–5 carbon atoms, an alkanoyloxy group having 1–5 carbon atoms, fluorine, chlorine, bromine, iodine, a nitro group and a cyano group), a straight chain or branched chain alkyl group having 1–5 carbon atoms (which must be substituted with at least one type of substituent group selected from the group consisting of an alkoxy group having 1–5 carbon atoms, an alkanoyloxy group having 1–5 carbon atoms, fluorine, chlorine, bromine, iodine, a nitro group and a cyano group), a cycloalkylalkyl group having 4 to 15 carbon atoms (which may be substituted with at least one type of substituent group selected from the group consisting of an alkyl group having 1–5 carbon atoms, an aryl group having 6–12,carbon atoms, an alkoxy group having 1–5 carbon atoms, an alkanoyloxy group having 1–5 carbon atoms, fluorine, chlorine, bromine, iodine, a nitro group, a cyano group and a trifluoromethyl group), an aralkyl group having 7–15 carbon atoms (which may be substituted with at least one type of substituent group selected from the group consisting an alkyl group having 1–5 carbon atoms, an aryl group having 6–12 carbon atoms, an alkoxy group having 1–5 carbon atoms, an alkanoyloxy group having 1–5 carbon atoms, fluorine, chlorine, bromine, iodine, a nitro group, a cyano group and a trifluoromethyl group), or an aryl group having 6–12 carbon atoms (which is substituted with at least one substituent group selected from the group consisting of an alkyl group having 1–5 carbon atoms, an aryl group having 6–12 carbon atoms, an alkoxy group having 1–5 carbon atoms, an alkanoyloxy group having 1–5 carbon atoms, fluorine, chlorine, bromine, iodine, a nitro group, a cyano group and a trifluoromethyl group), and wherein $R^{4'}$ may be identical or different); and, general formula (I') includes the (+) form, (−) form and (±) form].

Here, preferable examples of R' include an alkyl group having 1–5 carbon atoms, a cycloalkylmethyl group having 4–7 carbon atoms, a cycloalkenylmethyl group having 5–7 carbon atoms, a phenylalkyl group having 7–13 carbon atoms, an alkenyl group having 4–7 carbon atoms, an allyl group, a furan-2-yl-alkyl group having 1–5 carbon atoms, and a thiophen-2-yl-alkyl group having 1–5 carbon atoms, while particularly preferable examples include methyl, ethyl, propyl, butyl, cyclopropylmethyl, cyclobutylmethyl, cyclopentylmethyl, cyclopentenylmethyl, cyclohexenylmethyl, benzyl, phenethyl, trans-2-butenyl, 2-methyl-2-butenyl, allyl, furan-2-yl-methyl and thiophen-2-yl-methyl groups.

Preferable examples of $R^{2'}$ include a hydrogen atom, hydroxy, acetoxy and methoxy groups.

Preferable examples of $R^3$ include a hydrogen atom, hydroxy, acetoxy and methoxy groups.

Preferable examples of A' include —$NR^{4'}$C(=O)— and —$NR^{4'}$—, and preferable examples of $R^4$ include a straight chain or branched chain alkyl group having 6–14 carbon atoms, a cycloalkylalkyl group having 4–15 carbon atoms and an aralkyl group having 7–15 carbon atoms, while there are also cases in which it is better for these groups to be substituted with a substituent group such as a methyl group, an ethyl group, a propyl group, a butyl group, a pentyl group, a phenyl group, a methoxy group, an ethoxy group, an acetoxy group, fluorine, chlorine, bromine, iodine, a nitro group, a cyano group or a trifluoromethyl group. Particularly preferable examples of these include a cyclohexylmethyl group, a benzyl group, a phenethyl group, a phenylpropyl group, a phenylbutyl group and a diphenylethyl group.

Preferable examples of B include —$(CH_2)$n— (n=0–14), —$(CH_2)$n—C(=O)— (n=1–14), —CH=CH—$(CH_2)$n— (n=0–10), —C≡C—$(CH_2)$n— (n=0–10), —$CH_2$—O—, —$CH_2$—S—, —$CH_2$—O—$(CH_2)_2$—O—$(CH_2)_2$—, —$CH_2$—O—$CH_2$—NH—$CH_2$—O—$CH_2$—, and —$CH_2$—O—$CH_2$—S—$CH_2$—O—$CH_2$—, while particularly preferable examples include —$(CH_2)$n— (n=0–14), —CH=CH—$(CH_2)$n— (n=0–10), —C≡C—$(CH_2)$n— (n=0–10), —$CH_2$— O— and —$CH_2$—S—.

Preferable examples of $R^5$ include a hydrogen atom or an organic group having the basic skeleton shown below:

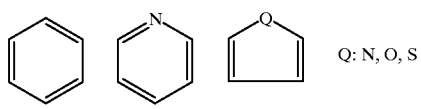

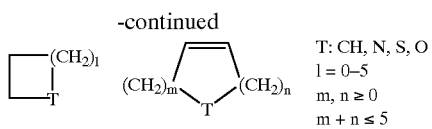

T: CH, N, S, O
l = 0–5
m, n ≥ 0
m + n ≤ 5

(which may be substituted with at least one type of substituent group selected from the group consisting of an alkyl group having 1–5 carbon atoms, an alkoxy group having 1–5 carbon atoms, an alkanoyloxy group having 1–5 carbon atoms, a hydroxy group, fluorine, chlorine, bromine, an amino group, a nitro group, a cyano group, an isothiocyanato group, a trifluoromethyl group and a trifluoromethoxy group), while particularly preferable examples include a hydrogen atom, phenyl, 3,4-dichlorophenyl, 4-chlorophenyl, 3-chlorophenyl, 2-chlorophenyl, 3,4-difluorophenyl, 4-fluorpheyl, 3-fluorophenyl, 2-fluorophenyl, 4-bromophenyl, 3-bromophenyl, 2-bromophenyl, 4-nitrophenyl, 3-nitrophenyl, 2-nitrophenyl, 4-trifluoromethylphenyl, 3-trifluoromethylphenyl, 2-trifluoromethylphenyl, 4-methylphenyl, 3-methylphenyl, 2-methylphenyl, 4-methoxyphenyl, 3-methoxyphenyl, 2-methoxyphenyl, 3-furanyl, 2-furanyl, 3-thienyl, 2-thienyl, cyclopentyl and cyclohexyl groups, although naturally not limited to these groups.

Examples of pharmacologically acceptable acid addition salts include inorganic acid salts such as hydrochloride, sulfate, nitrate, hydrobromide, hydroiodide and phosphate; organic carboxylates such as acetate, lactate, citrate, oxalate, glutarate, malate, tartrate, fumarate, mandelate, maleate, benzoate and phthalate; and, organic sulfonates such as methanesulfonate, ethanesulfonate, benzenesulfonate, p-toluenesulfonate and camphorsulfonate. Although hydrochloride, hydrobromide, phosphate, tartrate, and methanesulfonate and so forth are particularly preferable, pharmacologically acceptable acid addition salts are naturally not limited to these.

According to the above-described nomenclature, specific examples of the novel compound of the present invention include 17-cyclopropylmethyl-4,5α-epoxy-3,14β-dihydroxy-6α-[N-(2-phenethyl)-3-trifluoromethylcinnamamido]morphinan, 17-cyclopropylmethyl-4,5α-epoxy-3,14β-dihydroxy-6α-(N-cyclohexylmethyl-3-trifluoromethylcinnamamido)morphinan, 17-cyclopropylmethyl-4,5α-epoxy-3,14β-dihydroxy-6α-[N-(3-phenylpropyl)-3-trifluoromethylcinnamamido)morphinan, 17-cyclopropylmethyl-4,5α-epoxy-3,14β-dihydroxy-6α-[N-(4-phenylbutyl)-3-trifluoromethylcinnamamido]morphinan, 17-cyclopropylmethyl-4,5α-epoxy-3,14β-dihydroxy-6α-[N-(2,2-diphenylethyl)-3-trifluoromethylcinnamamido]morphinan, 17-cyclopropylmethyl-4,5α-epoxy-3-methoxy-14β-hydroxy-6α-[N-(2-phenethyl)-3-trifluoromethylcinnamamido]morphinan, 17-cyclopropylmethyl-4,5α-epoxy-3-methoxy-14β-hydroxy-6α-(N-cyclohexylmethyl-3-trifluoromethylcinnamamido)morphinan, 17-cyclopropylmethyl-4,5α-epoxy-3-methoxy-14β-hydroxy-6α-(N-(3-phenylpropyl)-3-trifluoromethylcinnamamido]-morphinan, 17-cyclopropylmethyl-4,5α-epoxy-3-methoxy-14β-hydroxy-6α-[N-(4-phenylbutyl)-3-trifluoromethylcinnamamido]morphinan, 17-cyclopropylmethyl-4,5α-epoxy-3-methoxy-14β-hydroxy-6α-[N-(2,2-diphenylethyl)-3-trifluoromethylcinnamamido]morphinan, 17-cyclopropylmethyl-4,5α-epoxy-3-acetoxy-14β-hydroxy-6α-[N-(2-phenethyl)-3-trifluoromethylcinnamamido]morphinan, 17-cyclopropylmethyl-4,5α-epoxy-3-acetoxy-14β-hydroxy-6α-(N-cyclohexylmethyl-3-trifluoromethylcinnamamido)morphinan, 17-cyclopropylmethyl-4,5α-epoxy-3-acetoxy-14β-hydroxy-6α-[N-(3-phenylpropyl)-3-trifluoromethylcinnamamido]-morphinan, 17-cyclopropylmethyl-4,5α-epoxy-3-acetoxy-14β-hydroxy-6α-[N-(4-phenylbutyl)-3-trifluoromethylcinnamamido]morphinan, 17-cyclopropylmethyl-4,5α-epoxy-3-acetoxy-14β-hydroxy-6α-[N-(2,2-diphenylethyl)-3-trifluoromethylcinnamamido]morphinan, 17-cyclopropylmethyl-4,5α-epoxy-3,14β-dihydroxy-6α-[N-(2-phenethyl)-6-phenylhexanoamido]morphinan, 17-cyclopropylmethyl-4,5α-epoxy-3,14β-dihydroxy-6α-(N-cyclohexylmethyl-6-phenylhexanoamido)morphinan, 17-cyclopropylmethyl-4,5α-epoxy-3,14β-dihydroxy-6α-[N-(3-phenylpropyl)-6-phenylhexanoamido]morphinan, 17-cyclopropylmethyl-4,5α-epoxy-3,14β-dihydroxy6α-[N-(4-phenylbutyl)-6-phenylhexanoamido]morphinan, 17-cyclopropylmethyl-4,5α-epoxy-3,14β-dihydroxy-6α-[N-(2,2-diphenylethyl)-6-phenylhexanoamido]morphinan, 17-cyclopropylmethyl-4,5α-epoxy-3-methoxy-14β-hydroxy-6α-[N-(2-phenethyl)-6-phenylhexanoamido]morphinan, 17-cyclopropylmethyl-4,5α-epoxy-3-methoxy-14β-hydroxy-6α-(N-cyclohexylmethyl-6-phenylhexanoamido)morphinan, 17-cyclopropylmethyl-4,5α-epoxy-3-methoxy-14β-hydroxy-6α-N-(3-phenylpropyl)-6-phenylhexanoamido]morphinan, 17-cyclopropylmethyl-4,5α-epoxy-3-methoxy-14β-hydroxy-6α-[N-(4-phenylbutyl)-6-phenylhexanoamido]morphinan, 17-cyclopropylmethyl-4,5α-epoxy-3-methoxy-14β-hydroxy-6α-[N-(2,2-diphenylethyl)-6-phenylhexanoamido]morphinan, 17-cyclopropylmethyl-4,5α-epoxy-3-acetoxy-14β-hydroxy-6α-[N-(2-phenethyl)-6-phenylhexanoamido]morphinan, 17-cyclopropylmethyl-4,5α-epoxy-3-acetoxy-14β-hydroxy-6α-(N-cyclohexylmethyl-6-phenylhexanoamido)morphinan, 17-cyclopropylmethyl-4,5α-epoxy-3-acetoxy-14β-hydroxy-6α-[N-(3 -phenylpropyl)-6-phenylhexanoamido]morphinan, 17-cyclopropylmethyl-4,5α-epoxy-3-acetoxy-14β-hydroxy-6α-[N-(4-phenylbutyl)-6-phenylhexanoamido]morphinan, 17-cyclopropylmethyl-4,5α-epoxy-3-acetoxy-14β-hydroxy-6α-[N-(2,2-diphenylethyl)-6-phenylhexanoamido]morphinan, 17-cyclopropylmethyl-4,5α-epoxy-3,14β-dihydroxy-6α-[N-(2-phenethyl)-8-phenyloctanoamido]morphinan, 17-cyclopropylmethyl-4,5α-epoxy-3,14β-dihydroxy-6α-(N-cyclohexylmethyl-8-phenyloctanoamido)morphinan, 17-cyclopropylmethyl-4,5α-epoxy-3,14β-dihydroxy-6α-[N-(3-phenylpropyl)-8-phenyloctanoamido]morphinan, 17-cyclopropylmethyl-4,5α-epoxy-3,14β-dihydroxy-6α-[N-(4-phenylbutyl)-8-phenyloctanoamido]morphinan, 17-cyclopropylmethyl-4,5α-epoxy-3,14β-dihydroxy-6α-[N-(2,2-diphenylethyl)-8-phenyloctanoamido]morphinan, 17-cyclopropylmethyl-4,5α-epoxy-3-methoxy-14β-hydroxy-6α-[N-(2-phenethyl)-8-phenyloctanoamido]morphinan, 17-cyclopropylmethyl-4,5α-epoxy-3-methoxy-14β-hydroxy-6α-(N-cyclohexylmethyl-8-phenyloctanoamido)morphinan, 17-cyclopropylmethyl-4,5α-epoxy-3-methoxy-14β-hydroxy-6α-[N-(3-phenylpropyl)-8-phenyloctanoamido]morphinan, 17-cyclopropylmethyl-4,5α-epoxy-3-methoxy-14β- hydroxy-6α-[N-(4-phenylbutyl)-8-phenyloctanoamido]morphinan, 17-cyclopropylmethyl-4,5α-epoxy-3-methoxy-14β-hydroxy-6α-[N-(2,2-diphenylethyl)-8-phenyloctanoamido]morphinan, 17-cyclopropylmethyl-4,5α-epoxy-3-acetoxy-14β-hydroxy-6α-[N-(2-phenethyl)-8-phenyloctanoamido]morphinan, 17-cyclopropylmethyl-4,5α-epoxy-3-acetoxy-14β-hydroxy-6α-(N-cyclohexylmethyl-8-phenyloctanoamido)morphinan, 17-cyclopropylmethyl-4,5α-epoxy-3-acetoxy-14β-hydroxy-6α-[N-(3-phenylpropyl)-8-phenyloctanoamido]morphinan, 17-cyclopropylmethyl-4,5α-epoxy-3-acetoxy-14β-hydroxy-6α-[N-(4-phenylbutyl)-8-phenyloctanoamido]morphinan, 17-cyclopropylmethyl-4,5α-epoxy-3-acetoxy-14β-hydroxy-6α-[N-(2,2-diphenylethyl)-8-phenyloctanoamido]morphinan, 17-cyclopropylmethyl-4,5α-epoxy-3,14β-dihydroxy-6α-[N-(2-phenethyl)-11-phenylundecanoamido]morphinan, 17-cyclopropylmethyl-4,5α-epoxy-3,14β-dihydroxy-6α-(N-cyclohexylmethyl-11-phenylundecanoamido)morphinan, 17-cyclopropylmethyl-4,5α-epoxy-3,14β-dihydroxy-6α-[N-(3-phenylpropyl)-11-phenylundecanoamido]morphinan, 17-cyclopropylmethyl-4,5α-epoxy-3,14β-dihydroxy-6α-[N-(4-phenylbutyl)-11-phenylundecanoamido morphinan, 17-cyclopropylmethyl-4,5α-epoxy-3,14β-dihydroxy-6α-[N-(2,2-diphenylethyl)-11-phenylundecanoamido]morphinan, 17-cyclopropylmethyl-4,5α-epoxy-3-methoxy-14β-hydroxy-6α-[N-(2-phenethyl)-11-phenylundecanoamido]morphinan, 17-cyclopropylmethyl-4,5α-epoxy-3-methoxy-14β-hydroxy-6α-(N-cyclohexylmethyl-11-phenylundecanoamido)morphinan, 17-cyclopropylmethyl-4,5α-epoxy-3-methoxy-14β-hydroxy-6α-[N-(3-phenylpropyl)-11-phenylundecanoamido]morphinan, 17-cyclopropylmethyl-4,5α-epoxy-3-methoxy-14β-hydroxy-6α-[N-(4-phenylbutyl)-11-phenylundecanoamido]morphinan, 17-cyclopropylmethyl-4,5α-epoxy-3-methoxy-14β-hydroxy-6α-[N-(2,2-diphenylethyl)-11-phenylundecanoamido]morphinan, 17-cyclopropylmethyl-4,5α-epoxy-3-acetoxy-14β-hydroxy-6α-[N-(2-phenethyl)-11-phenylundecanoamido]morphinan, 17-cyclopropylmethyl-4,5α-epoxy-3-acetoxy-14β-hydroxy-6α-(N-cyclohexylmethyl-11-phenylundecanoamido)morphinan, 17-cyclopropylmethyl-4,5α-epoxy-3-acetoxy-14β-hydroxy-6α-[N-(3-phenylpropyl)-11-phenylundecanoamido]morphinan, 17-cyclopropylmethyl-4,5α-epoxy-3-acetoxy-14β-hydroxy-6α-[N-(4-phenylbutyl)-11-phenylundecanoamido]morphinan, 17-cyclopropylmethyl-4,5α-epoxy-3-acetoxy-14β-hydroxy-6α-[N-(2,2-diphenylethyl)-11-phenylundecanoamido]morphinan, 17-cyclopropylmethyl-4,5α-epoxy-3,14β-dihydroxy-6α-[N-(2-phenethyl)-5-cyclohexylpentanoamido]morphinan, 17-cyclopropylmethyl-4,5α-epoxy-3,14β-dihydroxy-6α-(N-cyclohexylmethyl-5-cyclohexylpentanoamido)morphinan, 17-cyclopropylmethyl-4,5α-epoxy-3,14β-dihydroxy-6α-[N-(3-phenylpropyl)-5-cyclohexylpentanoamido]morphinan, 17-cyclopropylmethyl-4,5α-epoxy-3,14β-dihydroxy-6α-[N-(4-phenylbutyl)-5-cyclohexylpentanoamido]morphinan, 17-cyclopropylmethyl-4,5α-epoxy-3,14β-dihydroxy-6α-[N-(2,2-diphenylethyl)-5-cyclohexylpentanoamido]morphinan, 17-cyclopropylmethyl-4,5α-epoxy-3-methoxy-14β-hydroxy-6α-[N-(2-phenethyl)-5-cyclohexylpentanoamido]morphinan, 17-cyclopropylmethyl-4,5α-epoxy-3-methoxy-14β-hydroxy-6α-(N-cyclohexylmethyl-5-cyclohexylpentanoamido)morphinan, 17-cyclopropylmethyl-4,5α-epoxy-3-methoxy-14β-hydroxy-6α-[N-(3-phenylpropyl)-5-cyclohexylpentanoamido]morphinan, 17-cyclopropylmethyl-4,5α-epoxy-3-methoxy-14β-hydroxy-6α-[N-(4-phenylbutyl)-5-cyclohexylpentanoamido]morphinan, 17-cyclopropylmethyl-4,5α-epoxy-3-methoxy-14β-hydroxy-6α-[N-(2,2-diphenylethyl)-5-cyclohexylpentanoamido]morphinan, 17-cyclopropylmethyl-4,5α-epoxy-3-acetoxy-14β-hydroxy-6α-[N-(2-phenethyl)-5-cyclohexylpentanoamido]morphinan, 17-cyclopropylmethyl-4,5α-epoxy-3-acetoxy-14β-hydroxy-6α-(N-cyclohexylmethyl-5-cyclohexylpentanoamido)morphinan, 17-cyclopropylmethyl-4,5α-epoxy-3-acetoxy-14β-hydroxy-6α-[N-(3-phenylpropyl)-5-cyclohexylpentanoamido]morphinan, 17-cyclopropylmethyl-4,5α-epoxy-3-acetoxy-14β-hydroxy-6α-[N-(4-phenylbutyl)-5-cyclohexylpentanoamido]morphinan, 17-cyclopropylmethyl-4,5α-epoxy-3-acetoxy-14β-hydroxy-6α-[N-(2,2-diphenylethyl)-5-cyclohexylpentanoamido]morphinan, 17-cyclopropylmethyl-4,5α-epoxy-3,14β-dihydroxy-6α-[N-(2-phenethyl)-5-benzoylpentanoamido]morphinan, 17-cyclopropylmethyl-4,5α-epoxy-3,14β-dihydroxy-6α-(N-benzoylmethyl-5-benzoylpentanoamido)morphinan, 17-cyclopropylmethyl-4,5α-epoxy-3,14β-dihydroxy-6α-[N-(3-phenylpropyl)-5-benzoylpentanoamido]morphinan, 17-cyclopropylmethyl-4,5α-epoxy-3,14β-dihydroxy-6α-[N-(4-phenylbutyl)-5-benzoylpentanoamido]morphinan, 17-cyclopropylmethyl-4,5α-epoxy-3,14β-dihydroxy-6α-[N-(2,2-diphenylethyl)-5-benzoylpentanoamido]morphinan, 17-cyclopropylmethyl-4,5α-epoxy-3-methoxy-14β-hydroxy-6α-[N-(2-phenethyl)-5-benzoylpentanoamido]morphinan, 17-cyclopropylmethyl-4,5α-epoxy-3-methoxy-14β-hydroxy-6α-(N-benzoylmethyl-5-benzoylpentanoamido)morphinan, 17-cyclopropylmethyl-4,5α-epoxy-3-methoxy-14β-hydroxy-6α-[N-(3-phenylpropyl)-5-benzoylpentanoamido]morphinan, 17-cyclopropylmethyl-4,5α-epoxy-3-methoxy-14β-hydroxy-6α-[N-(4-phenylbutyl)-5-benzoylpentanoamido]morphinan, 17-cyclopropylmethyl-4,5α-epoxy-3-methoxy-14β-hydroxy-6α-[N-(2,2-diphenylethyl)-5-benzoylpentanoamido]morphinan, 17-cyclopropylmethyl-4,5α-epoxy-3-acetoxy-14β-hydroxy-6α-[N-(2-phenethyl)-5-benzoylpentanoamido]morphinan, 17-cyclopropylmethyl-4,5α-epoxy-3-acetoxy-14β-hydroxy-6α-(N-benzoylmethyl-5-benzoylpentanoamido)morphinan, 17-cyclopropylmethyl-4,5α-epoxy-3-acetoxy-14β-hydroxy-6α-[N-(3-phenylpropyl)-5-benzoylpentanoamido]morphinan, 17-cyclopropylmethyl-4,5α-epoxy-3-acetoxy-14β-hydroxy-6α-[N-(4-phenylbutyl)-5-benzoylpentanoamido]morphinan, 17-cyclopropylmethyl-4,5α-epoxy-3-acetoxy-14β-hydroxy-6α-[N-(2,2-diphenylethyl)-5-benzoylpentanoamido]morphinan, 17-cyclopropylmethyl-4,5α-epoxy-3,14β-dihydroxy-6α-[N-(2-phenethyl)-6-phenylhexylamino]morphinan, 17-cyclopropylmethyl-4,5α-epoxy-3,14β-dihydroxy-6α-(N-benzoylmethyl-6-phenylhexylamino)morphinan, 17-cyclopropylmethyl-4,5α-epoxy-3,14β-dihydroxy-6α-[N-(3-phenylpropyl)-6-phenylhexylamino]morphinan, 17-cyclopropylmethyl-4,5α-epoxy-3,14β-dihydroxy-6α-[N-(4-phenylbutyl)-6-phenylhexylamino]morphinan, 17-cyclopropylmethyl-4,5α-epoxy-3,14β-dihydroxy-6α-[N-(2,2-diphenylethyl)-6-phenylhexylamino]-morphinan, 17-cyclopropylmethyl-4,5α-epoxy-3-methoxy-14β-hydroxy-6α-[N-(2-phenethyl)-6- phenylhexylamino]morphinan, 17-cyclopropylmethyl-4,5α-epoxy-3-methoxy-14β-hydroxy-6α-(N-benzoylmethyl-6-phenylhexylamino)morphinan, 17-cyclopropylmethyl-4,5α-epoxy-3-methoxy-14β-hydroxy-6α-[N-(3-phenylpropyl)-6-phenylhexylamino]morphinan, 17-cyclopropylmethyl-4,5α-epoxy-3-methoxy-14β-hydroxy-6α-[N-(4-phenylbutyl)-6-phenylhexylamino]morphinan, 17-cyclopropylmethyl-4,5α-epoxy-3-methoxy-14β-hydroxy-6α-[N-(2,2-diphenylethyl)-6-phenylhexylamino]morphinan, 17-cyclopropylmethyl-4,5α-epoxy-3-acetoxy-14β-hydroxy-6α-[N-(2-phenethyl)-6-phenylhexylamino]morphinan, 17-cyclopropylmethyl-4,5α-epoxy-3-acetoxy-14β-hydroxy-6α-(N-benzoylmethyl-6-phenylhexylamino)morphinan, 17-cyclopropylmethyl-4,5α-epoxy-3-acetoxy-14β-hydroxy-6α-[N-(3-phenylpropyl)-6-phenylhexylamino]morphinan, 17-cyclopropylmethyl-4,5α-epoxy-3-acetoxy-14β-hydroxy-6α-[N-(4-phenylbutyl)-6-phenylhexylamino]morphinan, 17-cyclopropylmethyl-4,5α-epoxy-3-acetoxy-14β-hydroxy-6α-[N-(2,2-diphenylethyl)-6-phenylhexylamino]morphinan, 17-allyl-4,5α-epoxy-3,14β-dihydroxy-6α-[N-(2-phenethyl)-3-trifluoromethylcinnamamido]morphinan, 17-allyl-4,5α-epoxy-3,14β-dihydroxy-6α-(N-cyclohexylmethyl-3-trifluoromethylcinnamamido)morphinan, 17-allyl-4,5α-epoxy-3,14β-dihydroxy-6α-[N-(3-phenylpropyl)-3-trifluoromethylcinnamamido]morphinan, 17-allyl-4,5α-epoxy-3,14β-dihydroxy-6α-[N-(4-phenylbutyl)-3-trifluoromethylcinnamamido]morphinan, 17-allyl-4,5α-epoxy-3,14β-dihydroxy-6α-[N-(2,2-diphenylethyl)-3-trifluoromethylcinnamamido]morphinan, 17-allyl-4,5α-epoxy-3-methoxy-14β-hydroxy-6α-[N-(2-phenethyl)-3-trifluoromethylcinnamamido]morphinan, 17-allyl-4,5α-epoxy-3-methoxy-14β-hydroxy-6α-(N-cyclohexylmethyl-3-trifluoromethylcinnamamido)morphinan, 17-allyl-4,5α-epoxy-3-methoxy-14β-hydroxy-6α-[N-(3-phenylpropyl)-3-trifluoromethylcinnamamido]morphinan, 17-allyl-4,5α-epoxy-3-methoxy-14β-hydroxy-6α-[N-(4-phenylbutyl)-3-trifluoromethylcinnamamido]morphinan, acetoxy-14β-hydroxy-6α-[N-(3-phenylpropyl)-11-phenylundecanoamido]morphinan, 17-allyl-4,5α-epoxy-3-acetoxy-14β-hydroxy-6α-[N-(4-phenylbutyl)-11-phenylundecanoamido]morphinan, 17-allyl-4,5α-epoxy-3-acetoxy-14β-hydroxy-6α-[N-(2,2-diphenylethyl)-11-phenylundecanoamido]morphinan, 17-allyl-4,5α-epoxy-3,14β-dihydroxy-6α-[N-(2-phenethyl)-5-cyclohexylpentanoamido]-morphinan, 17-allyl-4,5α-epoxy-3,14β-dihydroxy-6α-(N-cyclohexylmethyl-5-cyclohexylpentanoamido)morphinan, 17-allyl-4,5α-epoxy-3,14β-dihydroxy-6α-[N-(3-phenylpropyl)-5-cyclohexylpentanoamido]morphinan, 17-allyl-4,5α-epoxy-3,14β-dihydroxy-6α-[N-(4-phenylbutyl)-5-cyclohexylpentanoamido]morphinan, 17-allyl-4,5α-epoxy-3,14β-dihydroxy-6α-[N-(2,2-diphenylethyl)-5-cyclohexylpentanoamido]morphinan, 17-allyl-4,5α-epoxy-3-methoxy-14β-hydroxy-6α-[N-(2-phenethyl)-5-cyclohexylpentanoamido]morphinan, 17-allyl-4,5α-epoxy-3-methoxy-14β-hydroxy-6α-(N-cyclohexylmethyl-5-cyclohexylpentanoamido)morphinan, 17-allyl-4,5α-epoxy-3-methoxy-14β-hydroxy-6α-[N-(3-phenylpropyl)-5-cyclohexylpentanoamido]morphinan, 17-allyl-4,5α-epoxy-3-methoxy-14β-hydroxy-6α-[N-(4-phenylbutyl)-5-cyclohexylpentanoamido]morphinan, 17-allyl-4,5α-epoxy-3-methoxy-14β-hydroxy-6α-[N-(2,2-diphenylethyl)-5-cyclohexylpentanoamido]morphinan, 17-allyl-4,5α-epoxy-3-acetoxy-14β-hydroxy-6α-[N-(2-phenethyl)-5-cyclohexylpentanoamido]morphinan, 17-allyl-4,5α-epoxy-3-acetoxy-14β-hydroxy-6α-(N-cyclohexylmethyl-5-cyclohexylpentanoamido)morphinan, 17-allyl-4,5α-epoxy-3-acetoxy-14β-hydroxy-6α-[N-(3-phenylpropyl)-5-cyclohexylpentanoamido]morphinan, 17-allyl-4,5α-epoxy-3-acetoxy-14β-hydroxy-6α-[N-(4-phenylbutyl)-5-cyclohexylpentanoamido]morphinan, 17-allyl-4,5α-epoxy-3-acetoxy-14β-hydroxy-6α-[N-(2,2-diphenylethyl)-5-cyclohexylpentanoamido]morphinan, 17-allyl-4,5α-epoxy-3,14β-dihydroxy-6α-[N-(2-phenethyl)-5-benzoylpentanoamido]morphinan, 17-allyl-4,5α-epoxy-3,14β-dihydroxy-6α-(N-benzoylmethyl-5-benzoylpentanoamido)morphinan, 17-allyl-4,5α-epoxy-3,14β-dihydroxy-6α-[N-(3-phenylpropyl)-5-benzoylpentanoamido]morphinan, 17-allyl-4,5α-epoxy-3,14β-dihydroxy-6α-[N-(4-phenylbutyl)-5-benzoylpentanoamido]morphinan, 17-allyl-4,5α-epoxy-3,14β-dihydroxy-6α-[N-(2,2-diphenylethyl)-5-benzoylpentanoamido]morphinan, 17-allyl-4,5α-epoxy-3-methoxy-14β-hydroxy-6-α-[N-(2-phenethyl)-5-benzoylpentanoamido]-morphinan, 17-allyl-4,5α-epoxy-3-methoxy-14β-hydroxy-6α-(N-benzoylmethyl-5-benzoylpentanoamido)morphinan, 17-allyl-4,5α-epoxy-3-methoxy-14β-hydroxy-6α-[N-(3-phenylpropyl)-5-benzoylpentanoamido]morphinan, 17-allyl-4,5α-epoxy-3-methoxy-14β-hydroxy-6α-[N-(4-phenylbutyl)-5-benzoylpentanoamido]morphinan, 17-allyl-4,5α-epoxy-3-methoxy-14β-hydroxy-6α-[N-(2,2-diphenylethyl)-5-benzoylpentanoamido]morphinan, 17-allyl-4,5α-epoxy-3-acetoxy-14β-hydroxy-6α-[N-(2-phenethyl)-5-benzoylpentanoamido]morphinan, 17-allyl-4,5α-epoxy-3-acetoxy-14β-hydroxy-6α-(N-benzoylmethyl-5-benzoylpentanoamido)-morphinan, 17-allyl-4,5α-epoxy-3-acetoxy-14β-hydroxy-6α-[N-(3-phenylpropyl)-5-benzoylpentanoamido]morphinan, 17-allyl-4,5α-epoxy-3-acetoxy-14β-hydroxy-6α-[N-(4-phenylbutyl)-5-benzoylpentanoamido]morphinan, 17-allyl-4,5α-epoxy-3-acetoxy-14β-hydroxy-6α-[N-(2,2-diphenylethyl)-5-benzoylpentanoamido]morphinan, 17-allyl-4,5α-epoxy-3,14β-dihydroxy-6α-[N-(2-phenethyl)-6-phenylhexylamino]morphinan, 17-allyl-4,5α-epoxy-3,14β-dihydroxy-6α-(N-benzoylmethyl-6-phenylhexylamino)-morphinan, 17-allyl-4,5α-epoxy-3,14β-dihydroxy-6α-[N-(3-phenylpropyl)-6-phenylhexylamino]morphinan, 17-allyl-4,5α-epoxy-3,14β-dihydroxy-6α-[N-(4-phenylbutyl)-6-phenylhexylamino]morphinan, 17-allyl-4,5α-epoxy-3,14β-dihydroxy-6α-[N-(2,2-diphenylethyl)-6-phenylhexylamino]-morphinan, 17-allyl-4,5α-epoxy-3-methoxy-14β-hydroxy-6α-[N-(2-phenethyl)-6-phenylhexylamino]morphinan, 17-allyl-4,5α-epoxy-3-methoxy-14β-hydroxy-6α-(N-benzoylmethyl-6-phenylhexylamino)morphinan, 17-allyl-4,5α-epoxy-3-methoxy-14β-hydroxy-6α-[N-(3-phenylpropyl)-6-phenylhexylamino]morphinan, 17-allyl-4,5α-epoxy-3-methoxy-14β-hydroxy-6α-[N-(4-phenylbutyl)-6-phenylhexylamino]-morphinan, 17-allyl-4,5α-epoxy-3-methoxy-14β-hydroxy-6α-[N-(2,2-diphenylethyl)-6-phenylhexylamino]morphinan, 17-allyl-4,5α-epoxy-3-acetoxy-14β-hydroxy-6α-(N-(2-phenethyl)-6-phenylhexylamino]morphinan, 17-allyl-4,5α-epoxy-3-acetoxy-14β-hydroxy-6α-(N-benzoylmethyl-6-phenylhexylamino)morphinan, 17-allyl-4,5α-epoxy-3-acetoxy-14β-hydroxy-6α-[N-(3-phenylpropyl)-6-phenylhexylamino]morphinan, 17-allyl-4,5α-epoxy-3-acetoxy-14β-hydroxy-6α-[N-(4-phenylbutyl)-6-phenylhexylamino]morphinan, 17-allyl-4,5α-epoxy-3-acetoxy-14β-hydroxy-6α-[N-(2,2-diphenylethyl)-6-phenylhexylamino]morphinan, 17-cyclopropylmethyl-4,5α-epoxy-3,14β-dihydroxy-6β-[N-(2-phenethyl)-3-trifluoromethylcinnamamido]morphinan, 17-cyclopropylmethyl-4,5α-epoxy-3,14β-dihydroxy-6β-(N-cyclohexylmethyl-3-trifluoromethylcinnamamido)morphinan, 17-cyclopropylmethyl-4,5α-epoxy-3,14β-dihydroxy-6β-[N-(3-phenylpropyl)-3-trifluoromethylcinnamamido]morphinan, 17-cyclopropylmethyl-4,5α-epoxy-3,14β-dihydroxy-6β-[N-(4-phenylbutyl)-3-trifluoromethylcinnamamido]morphinan, 17-cyclopropylmethyl-4,5α-epoxy-3,14β-dihydroxy-6β-[N-(2,2-diphenylethyl)-3-trifluoromethylcinnamamido]morphinan, 17-cyclopropylmethyl-4,5α-epoxy-3-methoxy-14β-hydroxy-6β-[N-(2-phenethyl)-3-trifluoromethylcinnamamido]morphinan, 17-cyclopropylmethyl-4,5α-epoxy-3-methoxy-14β-hydroxy-6β-(N-cyclohexylmethyl-3-trifluoromethylcinnamamido)-morphinan, 17-cyclopropylmethyl-4,5α-epoxy-3-methoxy-14β-hydroxy-6β-[N-(3-phenylpropyl)-3-trifluoromethylcinnamamido]morphinan, 17-cyclopropylmethyl-4,5α-epoxy-3-methoxy-14β-hydroxy-6β-[N-(4-phenylbutyl)-3-trifluoromethylcinnamamido]morphinan, 17-cyclopropylmethyl-4,5α-epoxy-3-methoxy-14β-hydroxy-6β-[N-(2,2-diphenylethyl)-3-trifluoromethylcinnamamido]morphinan, 17-cyclopropylmethyl-4,5α-epoxy-3-acetoxy-14β-hydroxy-6β-[N-(2-phenethyl)-3-trifluoromethylcinnamamido]morphinan, 17-cyclopropylmethyl-4,5α-epoxy-3-acetoxy-14β-hydroxy-6β-(N-cyclohexylmethyl-3-trifluoromethylcinnamamido)-morphinan, 17-cyclopropylmethyl-4,5α-epoxy-3-acetoxy-14β-hydroxy-6β-[N-(3-phenylpropyl)-3-trifluoromethylcinnamamido]morphinan, 17-cyclopropylmethyl-4,5α-epoxy-3-acetoxy-14β-hydroxy-6β-[N-(4-phenylbutyl)-3-trifluoromethylcinnamamido]morphinan, 17-cyclopropylmethyl-4,5α-epoxy-3-acetoxy-14β- hydroxy-6β-[N-(2,2-diphenylethyl)-3-trifluoromethylcinnamamido]morphinan, 17-cyclopropylmethyl-4,5α-epoxy-3,14β-dihydroxy-6β-[N-(2-phenethyl)-6-phenylhexanoamido]morphinan, 17-cyclopropylmethyl-4,5α-epoxy-3,14β-dihydroxy-6β-(N-cyclohexylmethyl-6-phenylhexanoamido)morphinan, 17-cyclopropylmethyl-4,5α-epoxy-3,14β-dihydroxy-6β-[N-(3-phenylpropyl)-6-phenylhexanoamido]morphinan, 17-cyclopropylmethyl-4,5α-epoxy-3,14β-dihydroxy-6β-[N-(4-phenylbutyl)-6-phenylhexanoamido]morphinan, 17-cyclopropylmethyl-4,5α-epoxy-3,14β-dihydroxy-6β-[N-(2,2-diphenylethyl)-6-phenylhexanoamido]morphinan, 17-cyclopropylmethyl-4,5α-epoxy-3-methoxy-14β-hydroxy-6β-[N-(2-phenethyl)-6-phenylhexanoamido]morphinan, 17-cyclopropylmethyl-4,5α-epoxy-3-methoxy-14β-hydroxy-6β-(N-cyclohexylmethyl-6-phenylhexanoamido)morphinan, 17-cyclopropylmethyl-4,5α-epoxy-3-methoxy-14β-hydroxy-6β-[N-(3-phenylpropyl)-6-phenylhexanoamido]morphinan, 17-cyclopropylmethyl-4,5α-epoxy-3-methoxy-14β-hydroxy-6β-[N-(4-phenylbutyl)-6-phenylhexanoamido]morphinan, 17-cyclopropylmethyl-4,5α-epoxy-3-methoxy-14β-hydroxy-6β-[N-(2,2-diphenylethyl)-6-phenylhexanoamido]morphinan, 17-cyclopropylmethyl-4,5α-epoxy-3-acetoxy-14β-hydroxy-6β-[N-(2-phenethyl)-6-phenylhexanoamido]morphinan, 17-cyclopropylmethyl-4,5α-epoxy-3-acetoxy-14β-hydroxy-6β-(N-cyclohexylmethyl-6-phenylhexanoamido)morphinan, 17-cyclopropylmethyl-4,5α-epoxy-3-acetoxy-14β-hydroxy-6β-[N-(3-phenylpropyl)-6-phenylhexanoamido]morphinan, 17-cyclopropylmethyl-4,5α-epoxy-3-acetoxy-14β-hydroxy-6β-[N-(4-phenylbutyl)-6-phenylhexanoamido]morphinan, 17-cyclopropylmethyl-4,5α-epoxy-3-acetoxy-14β-hydroxy-6β-[N-(2,2-diphenylethyl)-6-phenylhexanoamido]morphinan, 17-cyclopropylmethyl-4,5α-epoxy-3,14β-dihydroxy-6β-[N-(2-phenethyl)-8-phenyloctanoamido]morphinan, 17-cyclopropylmethyl-4,5α-epoxy-3,14β-dihydroxy-6β-(N-cyclohexylmethyl-8-phenyloctanoamido)morphinan, 17-cyclopropylmethyl-4,5α-epoxy-3,14β-dihydroxy-6β-[N-(3-phenylpropyl)-8-phenyloctanoamido]morphinan, 17-cyclopropylmethyl-4,5α-epoxy-3,14β-dihydroxy-6β-[N-(4-phenylbutyl)-8-phenyloctanoamido]morphinan, 17-cyclopropylmethyl-4,5α-epoxy-3,14β-dihydroxy-6β-[N-(2,2-diphenylethyl)-8-phenyloctanoamido]morphinan, 17-cyclopropylmethyl-4,5α-epoxy-3-methoxy-14β-hydroxy-6β-[N-(2-phenethyl)-8-phenyloctanoamido]morphinan, 17-cyclopropylmethyl-4,5α-epoxy-3-methoxy-14β-hydroxy-6β-(N-cyclohexylmethyl-8-phenyloctanoamido)morphinan, 17-cyclopropylmethyl-4,5α-epoxy-3-methoxy-14β-hydroxy-6β-[N-(3-phenylpropyl)-8-phenyloctanoamido]morphinan, 17-cyclopropylmethyl-4,5α-epoxy-3-methoxy-14β-hydroxy-6β-[N-(4-phenylbutyl)-8-phenyloctanoamido]morphinan, 17-cyclopropylmethyl-4,5α-epoxy-3-methoxy-14β-hydroxy-6β-[N-(2,2-diphenylethyl)-8-phenyloctanoamido]morphinan, 17-cyclopropylmethyl-4,5α-epoxy-3-acetoxy-14β-hydroxy-6β-[N-(2-phenethyl)-8-phenyloctanoamido]morphinan, 17-cyclopropylmethyl-4,5α-epoxy-3-acetoxy-14β-hydroxy-6β-(N-cyclohexylmethyl-8-phenyloctanoamido)morphinan, 17-cyclopropylmethyl-4,5α-epoxy-3-acetoxy-14β-hydroxy-6β-[N-(3-phenylpropyl)-8-phenyloctanoamido]morphinan, 17-cyclopropylmethyl-4,5α-epoxy-3-acetoxy-14β-hydroxy-6β-[N-(4-phenylbutyl)-8-phenyloctanoamido]morphinan, 17-cyclopropylmethyl-4,5α-epoxy-3-acetoxy-14β-hydroxy-6β-[N-(2,2-diphenylethyl)-8-phenyloctanoamido]morphinan, 17-cyclopropylmethyl-4,5α-epoxy-3,14β-dihydroxy-6β-[N-(2-phenethyl)-11-phenylundecanoamido]morphinan, 17-cyclopropylmethyl-4,5α-epoxy-3,14β-dihydroxy-6β-(N-cyclohexylmethyl-11-phenylundecanoamido)morphinan, 17-cyclopropylmethyl-4,5α-epoxy-3,14β-dihydroxy-6β-[N-(3-phenylpropyl)-11-phenylundecanoamido]-morphinan, 17-cyclopropylmethyl-4,5α-epoxy-3,14β-dihydroxy-6β-[N-(4-phenylbutyl)-11-phenylundecanoamido]-morphinan, 17-cyclopropylmethyl-4,5α-epoxy-3,14β-dihydroxy-6β-[N-(2,2-diphenylethyl)-11-phenylundecanoamido]morphinan, 17-cyclopropylmethyl-4,5α-epoxy-3-methoxy-14β-hydroxy-6β-[N-(2-phenethyl)-11-phenylundecanoamido]morphinan, 17-cyclopropylmethyl-4,5α-epoxy-3-methoxy-14β-hydroxy-6β-(N-cyclohexylmethyl-11-phenylundecanoamido)morphinan, 17-cyclopropylmethyl-4,5α-epoxy-3-methoxy-14β-hydroxy-6β-[N-(3-phenylpropyl)-11-phenylundecanoamido]morphinan, 17-cyclopropylmethyl-4,5α-epoxy-3-methoxy-14β-hydroxy-6β-[N-(4-phenylbutyl)-11-phenylundecanoamido]morphinan, 17-cyclopropylmethyl-4,5α-epoxy-3-methoxy-14β-hydroxy-6β-[N-(2,2-diphenylethyl)-11-phenylundecanoamido]morphinan, 17-cyclopropylmethyl-4,5α-epoxy-3-acetoxy-14β-hydroxy-6β-[N-(2-phenethyl)-11-phenylundecanoamido]morphinan, 17-cyclopropylmethyl-4,5α-epoxy-3-acetoxy-14β-hydroxy-6β-(N-cyclohexylmethyl-11-phenylundecanoamido)morphinan, 17-cyclopropylmethyl-4,5α-epoxy-3-acetoxy-14β-hydroxy-6β-[N-(3-phenylpropyl)-11-phenylundecanoamido]morphinan, 17-cyclopropylmethyl-4,5α-epoxy-3-acetoxy-14β-hydroxy-6β-[N-(4-phenylbutyl)-11-phenylundecanoamido]morphinan, 17-cyclopropylmethyl-4,5α-epoxy-3-acetoxy-14β-hydroxy-6β-[N-(2,2-diphenylethyl)-11-phenylundecanoamido]morphinan, 17-cyclopropylmethyl-4,5α-epoxy-3,14β-dihydroxy-6β-[N-(2-phenethyl)-5-cyclohexylpentanoamido]morphinan, 17-cyclopropylmethyl-4,5α-epoxy-3,14β-dihydroxy-6β-(N-cyclohexylmethyl-5-cyclohexylpentanoamido)morphinan, 17-cyclopropylmethyl-4,5α-epoxy-3,14β-dihydroxy-6β-[N-(3-phenylpropyl)-5-cyclohexylpentanoamido]morphinan, 17-cyclopropylmethyl-4,5α-epoxy-3,14β-dihydroxy-6β-[N-(4-phenylbutyl)-5-cyclohexylpentanoamido]morphinan, 17-cyclopropylmethyl-4,5α-epoxy-3,14β-dihydroxy-6β-[N-(2,2-diphenylethyl)-5-cyclohexylpentanoamido]morphinan, 17-cyclopropylmethyl-4,5α-epoxy-3-methoxy-14β-hydroxy-6β-[N-(2-phenethyl)-5-cyclohexylpentanoamido]morphinan, 17-cyclopropylmethyl-4,5α-epoxy-3-methoxy-14β-hydroxy-6β-(N-cyclohexylmethyl-5-cyclohexylpentanoamido)morphinan, 17-cyclopropylmethyl-4,5α-epoxy-3-methoxy-14β-hydroxy-6β-[N-(3-phenylpropyl)-5-cyclohexylpentanoamido]morphinan, 17-cyclopropylmethyl-4,5α-epoxy-3-methoxy-14β-hydroxy-6β-[N-(4-phenylbutyl)-5-cyclohexylpentanoamido]morphinan, 17-cyclopropylmethyl-4,5α-epoxy-3-methoxy-14β-hydroxy-6β-[N-(2,2-diphenylethyl)-5-cyclohexylpentanoamido]morphinan, 17-cyclopropylmethyl-4,5α-epoxy-3-acetoxy-14β-hydroxy-6β-[N-(2-phenethyl)-5-cyclohexylpentanoamido]morphinan, 17-cyclopropylmethyl-4,5α-epoxy-3-acetoxy-14β-hydroxy-6β-(N-cyclohexylmethyl-5-cyclohexylpentanoamido)morphinan, 17-cyclopropylmethyl-4,5α-epoxy-3-acetoxy-14β- hydroxy-6β-[N-(3-phenylpropyl)-5-cyclohexylpentanoamido]morphinan, 17-cyclopropylmethyl-4,5α-epoxy-3-acetoxy-14β-hydroxy-6β-[N-(4-phenylbutyl)-5-cyclohexylpentanoamido]morphinan, 17-cyclopropylmethyl-4,5α-epoxy-3-acetoxy-14β-hydroxy-6β-[N-(2,2-diphenylethyl)-5-cyclohexylpentanoamido]morphinan, 17-cyclopropylmethyl-4,5α-epoxy-3,14β-dihydroxy-6β-[N-(2-phenethyl)-5-benzoylpentanoamido]morphinan, 17-cyclopropylmethyl-4,5α-epoxy-3,14β-dihydroxy-6β-(N-benzoylmethyl-5-benzoylpentanoamido)morphinan, 17-cyclopropylmethyl-4,5α-epoxy-3,14β-dihydroxy-6β-[N-(3-phenylpropyl)-5-benzoylpentanoamido]morphinan, 17-cyclopropylmethyl-4,5α-epoxy-3,14β-dihydroxy-6β-[N-(4-phenylbutyl)-5-benzoylpentanoamido]morphinan, 17-cyclopropylmethyl-4,5α-epoxy-3,14β-dihydroxy-6β-[N-(2,2-diphenylethyl)-5-benzoylpentanoamido]morphinan, 17-cyclopropylmethyl-4,5α-epoxy-3-methoxy-14β-hydroxy-6β-[N-(2-phenethyl)-5-benzoylpentanoamido]morphinan, 17-cyclopropylmethyl-4,5α-epoxy-3-methoxy-14β-hydroxy-6β-(N-benzoylmethyl-5-benzoylpentanoamido)morphinan, 17-cyclopropylmethyl-4,5α-epoxy-3-methoxy-14β-hydroxy-6β-[N-(3-phenylpropyl)-5-benzoylpentanoamido]morphinan, 17-cyclopropylmethyl-4,5α-epoxy-3-methoxy-14β-hydroxy-6β-[N-(4-phenylbutyl)-5 -benzoylpentanoamido]morphinan, 17-cyclopropylmethyl-4,5α-epoxy-3-methoxy-14β-hydroxy-6β-[N-(2,2-diphenylethyl)-5-benzoylpentanoamido]morphinan, 17-cyclopropylmethyl-4,5α-epoxy-3-acetoxy-14β-hydroxy-6β-[N-(2-phenethyl)-5-benzoylpentanoamido]morphinan, 17-cyclopropylmethyl-4,5α-epoxy-3-acetoxy-14β-hydroxy-6β-(N-benzoylmethyl-5-benzoylpentanoamido)morphinan, 17-cyclopropylmethyl-4,5α-epoxy-3-acetoxy-14β-hydroxy-6β-[N-(3-phenylpropyl)-5-benzoylpentanoamido]morphinan, 17-cyclopropylmethyl-4,5α-epoxy-3-acetoxy-14β-hydroxy-6β-[N-(4-phenylbutyl)-5-benzoylpentanoamido]morphinan, 17-cyclopropylmethyl-4,5α-epoxy-3-acetoxy-14β-hydroxy-6β-[N-(2,2-diphenylethyl)-5-benzoylpentanoamido]morphinan, 17-cyclopropylmethyl-4,5α-epoxy-3,14β-dihydroxy-6β-[N-(2-phenethyl)-6-phenylhexylamino]morphinan, 17-cyclopropylmethyl-4,5α-epoxy-3,14β-dihydroxy-6β-(N-benzoylmethyl-6-phenylhexylamino)morphinan, 17-cyclopropylmethyl-4,5α-epoxy-3,14β-dihydroxy-6β-[N-(3-phenylpropyl)-6-phenylhexylamino]morphinan, 17-cyclopropylmethyl-4,5α-epoxy-3,14β-dihydroxy-6β-[N-(4-phenylbutyl)-6-phenylhexylamino]morphinan, 17-cyclopropylmethyl-4,5α-epoxy-3,14β-dihydroxy-6β-[N-(2,2-diphenylethyl)-6-phenylhexylamino]morphinan, 17-cyclopropylmethyl-4,5α-epoxy-3-methoxy-14β-hydroxy-6β-[N-(2-phenethyl)-6-phenylhexylamino]morphinan, 17-cyclopropylmethyl-4,5α-epoxy-3-methoxy-14β-hydroxy-6β-(N-benzoylmethyl-6-phenylhexylamino)morphinan, 17-cyclopropylmethyl-4,5α-epoxy-3-methoxy-14β-hydroxy-6β-[N-(3-phenylpropyl)-6-phenylhexylamino]morphinan, 17-cyclopropylmethyl-4,5α-epoxy-3-methoxy-14β-hydroxy-6β-[N-(4-phenylbutyl)-6-phenylhexylamino]morphinan, 17-cyclopropylmethyl-4,5α-epoxy-3-methoxy-14β-hydroxy-6β-[N-(2,2-diphenylethyl)-6-phenylhexylamino]morphinan, 17-cyclopropylmethyl-4,5α-epoxy-3-acetoxy-14β-hydroxy-6β-[N-(2-phenethyl)-6-phenylhexylamino]morphinan, 17-cyclopropylmethyl-4,5α-epoxy-3-acetoxy-14β-hydroxy-6β-(N-benzoylmethyl-6-phenylhexylamino)morphinan, 17-cyclopropylmethyl-4,5α-epoxy-3-acetoxy-14β-hydroxy-6β-[N-(3-phenylpropyl)-6-phenylhexylamino]morphinan, 17-cyclopropylmethyl-4,5α-epoxy-3-acetoxy-14β-hydroxy-6β-[N-(4-phenylbutyl)-6-phenylhexylamino]morphinan, 17-cyclopropylmethyl-4,5α-epoxy-3-acetoxy-14β-hydroxy-6β-[N-(2,2-diphenylethyl)-6-phenylhexylamino]morphinan, 17-allyl-4,5α-epoxy-3,14β-dihydroxy-6β-[N-(2-phenethyl)-3-trifluoromethylcinnamamido]morphinan, 17-allyl-4,5α-epoxy-3,14β-dihydroxy-6β-(N-cyclohexylmethyl-3-trifluoromethylcinnamamido)-morphinan, 17-allyl-4,5α-epoxy-3,14β-dihydroxy-6β-[N-(3-phenylpropyl)-3-trifluoromethylcinnamamido]morphinan, 17-allyl-4,5α-epoxy-3,14β-dihydroxy-6β-[N-(4-phenylbutyl)-3-trifluoromethylcinnamamido]morphinan, 17-allyl-4,5α-epoxy-3,14β-dihydroxy-6β-[N-(2,2-diphenylethyl)-3-trifluoromethylcinnamamido]morphinan, 17-allyl-4,5α-epoxy-3-methoxy-14β-hydroxy-6β-[N-(2-phenethyl)-3-trifluoromethylcinnamamido]morphinan, 17-allyl-4,5α-epoxy-3-methoxy-14β-hydroxy-6β-(N-cyclohexylmethyl-3-trifluoromethylcinnamamido)morphinan, 17-allyl-4,5α-epoxy-3-methoxy-14β-hydroxy-6β-[N-(3-phenylpropyl)-3-trifluoromethylcinnamamido]morphinan, 17-allyl-4,5α-epoxy-3-methoxy-14β-hydroxy-6β-[N-(4-phenylbutyl)-3-trifluoromethylcinnamamido]morphinan, 17-allyl-4,5α-epoxy-3-methoxy-14β-hydroxy-6β-[N-(2,2-diphenylethyl)-3-trifluoromethylcinnamamido]morphinan, 17-allyl-4,5α-epoxy-3-acetoxy-14β-hydroxy-6β-[N-(2-phenethyl)-3-trifluoromethylcinnamamido]morphinan, 17-allyl-4,5α-epoxy-3-acetoxy-14β-hydroxy-6β-(N-cyclohexylmethyl-3-trifluoromethylcinnamamido)morphinan, 17-allyl-4,5α-epoxy-3-acetoxy-14β-hydroxy-6β-[N-(3-phenylpropyl)-3-trifluoromethylcinnamamido]morphinan, 17-allyl-4,5α-epoxy-3-acetoxy-14β-hydroxy-6β-[N-(4-phenylbutyl)-3-trifluoromethylcinnamamido]morphinan, 17-allyl-4,5α-epoxy-3-acetoxy-14β-hydroxy-6-[N-(2,2-diphenylethyl)-3-trifluoromethylcinnamamido]morphinan, 17-allyl-4,5α-epoxy-3,14β-dihydroxy-6β-[N-(2-phenethyl)-6-phenylhexanoamido]morphinan, 17-allyl-4,5α-epoxy-3,14β-dihydroxy-6β-(N-cyclohexylmethyl-6-phenylhexanoamido)-morphinan, 17-allyl-4,5α-epoxy-3,14β-dihydroxy-6β-[N-(3-phenylpropyl)-6-phenylhexanoamido]morphinan, 17-allyl-4,5α-epoxy-3,14β-dihydroxy-6β-[N-(4-phenylbutyl)-6-phenylhexanoamido]morphinan, 17-allyl-4,5α-epoxy-3,14β-dihydroxy-6β-[N-(2,2-diphenylethyl)-6-phenylhexanoamido]-morphinan, 17-allyl-4,5α-epoxy-3-methoxy-14β-hydroxy-6β-[N-(2-phenethyl)-6-phenylhexanoamido]morphinan, 17-allyl-4,5α-epoxy-3-methoxy-14β-hydroxy-6β-(N-cyclohexylmethyl-6-phenylhexanoamido)morphinan, 17-allyl-4,5α-epoxy-3-methoxy-14β-hydroxy-6β-[N-(3-phenylpropyl)-6-phenylhexanoamido]morphinan, 17-allyl-4,5α-epoxy-3-methoxy-14β-hydroxy-6β-[N-(4-phenylbutyl)-6-phenylhexanoamido]morphinan, 17-allyl-4,5α-epoxy-3-methoxy-14β-hydroxy-6β-[N-(2,2-diphenylethyl)-6-phenylhexanoamido]morphinan, 17-allyl-4,5α-epoxy-3-acetoxy-14β-hydroxy-6β-[N-(2-phenethyl)-6-phenylhexanoamido]morphinan, 17-allyl-4,5α-epoxy-3-acetoxy-14β-hydroxy-6β-(N-cyclohexylmethyl-6-phenylhexanoamido)-morphinan, 17-allyl-4,5α-epoxy-3-acetoxy-14β-hydroxy-6β-[N-(3-phenylpropyl)-6-phenylhexanoamido]morphinan, 17-allyl-4,5α-epoxy-3-acetoxy-14β-hydroxy-6β-[N-(4-phenylbutyl)-6-phenylhexanoamido]morphinan, 17-allyl-4,5α-epoxy-3-acetoxy-14β-hydroxy-6β-[N-(2,2-diphenylethyl)-6-phenylhexanoamido]morphinan, 17-allyl-4,5α-epoxy-3,14β-dihydroxy-6β-[N-(2-phenethyl)-8-phenyloctanoamido]morphinan, 17-allyl-4,5α-epoxy-3,14β-dihydroxy-6β-(N-cyclohexylmethyl-8-phenyloctanoamido)-morphinan, 17-allyl-4,5α-epoxy-3,14β-dihydroxy-6β-[N-(3-phenylpropyl)-8-phenyloctanoamido]morphinan, 17-allyl-4,5α-epoxy-3,14β-dihydroxy-6β-[N-(4-phenylbutyl)-8-phenyloctanoamido]morphinan, 17-allyl-4,5α-epoxy-3,14β-dihydroxy-6β-[N-(2,2-diphenylethyl)-8-phenyloctanoamido]-morphinan, 17-allyl-4,5α-epoxy-3-methoxy-14β-hydroxy-6β-[N-(2-phenethyl)-8-phenyloctanoamido]morphinan, 17-allyl-4,5α-epoxy-3-methoxy-14β-hydroxy-6β-(N-cyclohexylmethyl-8-phenyloctanoamido)morphinan, 17-allyl-4,5α-epoxy-3-methoxy-14β-hydroxy-6β-[N-(3-phenylpropyl)-8-phenyloctanoamido]morphinan, 17-allyl-4,5α-epoxy-3-methoxy-14β-hydroxy-6β-[N-(4-phenylbutyl)-8-phenyloctanoamido]morphinan, 17-allyl-4,5α-epoxy-3-methoxy-14β-hydroxy-6β-[N-(2,2-diphenylethyl)-8-phenyloctanoamido]morphinan, 17-allyl-4,5α-epoxy-3-acetoxy-14β-hydroxy-6β-[N-(2-phenethyl)-8-phenyloctanoamido]morphinan, 17-allyl-4,5α-epoxy-3-acetoxy-14β-hydroxy-6β-(N-cyclohexylmethyl-8-phenyloctanoamido)-morphinan, 17-allyl-4,5α-epoxy-3-acetoxy-14β-hydroxy-6β-[N-(3-phenylpropyl)-8-phenyloctanoamido]morphinan, 17-allyl-4,5α-epoxy-3-acetoxy-14β-hydroxy-6β-[N-(4-phenylbutyl)-8-phenyloctanoamido]morphinan, 17-allyl-4,5α-epoxy-3-acetoxy-14β-hydroxy-6β-[N-(2,2-diphenylethyl)-8-phenyloctanoamido]morphinan, 17-allyl-4,5α-epoxy-3,14β-dihydroxy-6β-[N-(2-phenethyl)-11-phenylundecanoamido]morphinan, 17-allyl-4,5α-epoxy-3,14β-dihydroxy-6β-(N-cyclohexylmethyl-11-phenylundecanoamido)-morphinan, 17-allyl-4,5α-epoxy-3,14β-dihydroxy-6β-[N-(3-phenylpropyl)-11-phenylundecanoamido]morphinan, 17-allyl-4,5α-epoxy-3,14β-dihydroxy-6β-[N-(4-phenylbutyl)-11-phenylundecanoamido]morphinan, 17-allyl-4,5α-epoxy-3,14β-dihydroxy-6β-[N-(2,2-diphenylethyl)-11-phenylundecanoamido]morphinan, 17-allyl-4,5α-epoxy-3-methoxy-14β-hydroxy-6β-[N-(2-phenethyl)-11-phenylundecanoamido]-morphinan, 17-allyl-4,5α-epoxy-3-methoxy-14β-hydroxy-6β-(N-cyclohexylmethyl-11-phenylundecanoamido)morphinan, 17-allyl-4,5α-epoxy-3-methoxy-14β-hydroxy-6β-[N-(3-phenylpropyl)-11-phenylundecanoamido]morphinan, 17-allyl-4,5α-epoxy-3-methoxy-14β-hydroxy-6β-[N-(4-phenylbutyl)-11-phenylundecanoamido]morphinan, 17-allyl-4,5α-epoxy-3-methoxy-14β-hydroxy-6β-[N-(2,2-diphenylethyl)-11-phenylundecanoamido]morphinan, 17-allyl-4,5α-epoxy-3-acetoxy-14β-hydroxy-6β-[N-(2-phenethyl)-11-phenylundecanoamido]morphinan, 17-allyl-4,5α-epoxy-3-acetoxy-14β-hydroxy-6β-(N-cyclohexylmethyl-11-phenylundecanoamido)morphinan, 17-allyl-4,5α-epoxy-3-acetoxy-14β-hydroxy-6β-[N-(3-phenylpropyl)-11-phenylundecanoamido]morphinan, 17-allyl-4,5α-epoxy-3-acetoxy-14β-hydroxy-6β-[N-(4-phenylbutyl)-11-phenylundecanoamido]morphinan, 17-allyl-4,5α-epoxy-3-acetoxy-14β-hydroxy-6β-[N-(2,2-diphenylethyl)-11-phenylundecanoamido]morphinan, 17-allyl-4,5α-epoxy-3,14β-dihydroxy-6β-[N-(2-phenethyl)-5-cyclohexylpentanoamido]-morphinan, 17-allyl-4,5α-epoxy-3,14β-dihydroxy-6β-(N-cyclohexylmethyl-5-cyclohexylpentanoamido)morphinan, 17-allyl-4,5α-epoxy-3,14β-dihydroxy-6β-[N-(3-phenylpropyl)-5-cyclohexylpentanoamido]morphinan, 17-allyl-4,5α-epoxy-3,14β-dihydroxy-6β-[N-(4-phenylbutyl)-5-cyclohexylpentanoamido]morphinan, 17-allyl-4,5α-epoxy-3,14β-dihydroxy-6β-[N-(2,2-diphenylethyl)-5-cyclohexylpentanoamido]morphinan, 17-allyl-4,5α-epoxy-3-methoxy-14β-hydroxy-6β-[N-(2-phenethyl)-5-cyclohexylpentanoamido]morphinan, 17-allyl-4,5α-epoxy-3-methoxy-14β-hydroxy-6β-(N-cyclohexylmethyl-5-cyclohexylpentanoamido)morphinan, 17-allyl-4,5α-epoxy-3-methoxy-14β-hydroxy-6β-[N-(3-phenylpropyl)-5-cyclohexylpentanoamido]morphinan, 17-allyl-4,5α-epoxy-3-methoxy-14β-hydroxy-6β-[N-(4-phenylbutyl)-5-cyclohexylpentanoamido]morphinan, 17-allyl-4,5α-epoxy-3-methoxy-14β-hydroxy-6β-[N-(2,2-diphenylethyl)-5-cyclohexylpentanoamido]morphinan, 17-allyl-4,5α-epoxy-3-acetoxy-14β-hydroxy-6β-[N-(2-phenethyl)-5-cyclohexylpentanoamido]morphinan, 17-allyl-4,5α-epoxy-3-acetoxy-14β-hydroxy-6β-(N-cyclohexylmethyl-5-cyclohexylpentanoamido)morphinan, 17-allyl-4,5α-epoxy-3-acetoxy-14β-hydroxy-6β-[N-(3-phenylpropyl)-5-cyclohexylpentanoamido]morphinan, 17-allyl-4,5α-epoxy-3-acetoxy-14β-hydroxy-6β-[N-(4-phenylbutyl)-5-cyclohexylpentanoamido]morphinan, 17-allyl-4,5α-epoxy-3-acetoxy-14β-hydroxy-6β-[N-(2,2-diphenylethyl)-5-cyclohexylpentanoamido]morphinan, 17-allyl-4,5α-epoxy-3,14β-dihydroxy-6β-[N-(2-phenethyl),-5-benzoylpentanoamido]morphinan, 17-allyl-4,5α-epoxy-3,14β-dihydroxy-6β-(N-benzoylmethyl-5-benzoylpentanoamido)-morphinan, 17-allyl-4,5α-epoxy-3,14β-dihydroxy-6β-[N-(3-phenylpropyl)-5-benzoylpentanoamido]morphinan, 17-allyl-4,5α-epoxy-3,14β-dihydroxy-6β-[N-(4-phenylbutyl)-5-benzoylpentanoamido]morphinan, 17-allyl-4,5α-epoxy-3,14β-dihydroxy-6β-[N-(2,2-diphenylethyl)-5-benzoylpentanoamido]morphinan, 17-allyl-4,5α-epoxy-3-methoxy-14β-hydroxy-6β-[N-(2-phenethyl)-5-benzoylpentanoamido]-morphinan, 17-allyl-4,5α-epoxy-3-methoxy-14β-hydroxy-6β-(N-benzoylmethyl-5-benzoylpentanoamido)morphinan, 17-allyl-4,5α-epoxy-3-methoxy-14β-hydroxy-6β-[N-(3-phenylpropyl)-5-benzoylpentanoamido]morphinan, 17-allyl-4,5α-epoxy-3-methoxy-14β-hydroxy-6β-[N-(4-phenylbutyl)-5-benzoylpentanoamido]morphinan, 17-allyl-4,5α-epoxy-3-methoxy-14β-hydroxy-6β-[N-(2,2-diphenylethyl)-5-benzoylpentanoamido]morphinan, 17-allyl-4,5α-epoxy-3-acetoxy-14β-hydroxy-6β-[N-(2-phenethyl)-5-benzoylpentanoamido]morphinan, 17-allyl-4,5α-epoxy-3-acetoxy-14β-hydroxy-6β-(N-benzoylmethyl-5-benzoylpentanoamido)-morphinan, 17-allyl-4,5α-epoxy-3-acetoxy-14β-hydroxy-6β-[N-(3-phenylpropyl)-5-benzoylpentanoamido]morphinan, 17-allyl-4,5α-epoxy-3-acetoxy-14β-hydroxy-6β-[N-(4-phenylbutyl)-5-benzoylpentanoamido]morphinan, 17-allyl-4,5α-epoxy-3-acetoxy-14β-hydroxy-6β-[N-(2,2-diphenylethyl)-5-benzoylpentanoamido]morphinan, 17-allyl-4,5α-epoxy-3,14β-dihydroxy-6β-[N-(2-phenethyl)-6-phenylhexylamino]morphinan, 17-allyl-4,5α-epoxy-3,14β-dihydroxy-6β-(N-benzoylmethyl-6-phenylhexylamino)-morphinan, 17-allyl-4,5α-epoxy-3,14β-dihydroxy-6β-[N-(3-phenylpropyl)-6-phenylhexylamino]morphinan, 17-allyl-4,5α-epoxy-3,14β-dihydroxy-6β-[N-(4-phenylbutyl)-6-phenylhexylamino]morphinan, 17-allyl-4,5α-epoxy-3,14β-dihydroxy-6β-[N-(2,2-diphenylethyl)-6-phenylhexylamino]-morphinan, 17-allyl-4,5α-epoxy-3-methoxy-14β-hydroxy-6β-[N-(2-phenethyl)-6-phenylhexylamino]morphinan, 17-allyl-4,5α-epoxy-3-methoxy-14β-hydroxy-6β-(N-benzoylmethyl-6-phenylhexylamino)morphinan, 17-allyl-4,5α-epoxy-3-methoxy-14β-hydroxy-6β-[N-(3-phenylpropyl)-6-phenylhexylamino]morphinan, 17-allyl-4,5α-epoxy-3-methoxy-14β-hydroxy-6β-[N-(4-phenylbutyl)-6-phenylhexylamino]-morphinan, 17-allyl-4,5α-epoxy-3-methoxy-14β-hydroxy-6β-[N-(2,2-diphenylethyl)-6-phenylhexylamino]morphinan, 17-allyl-4,5α-epoxy-3- acetoxy-14β-hydroxy-6β-[N-(2-phenethyl)-6-phenylhexylamino]morphinan, 17-allyl-4,5α-epoxy-3-acetoxy-14β-hydroxy-6β-(N-benzoylmethyl-6-phenylhexylamino)morphinan, 17-allyl-4,5α-epoxy-3-acetoxy-14β-hydroxy-6β-[N-(3-phenylpropyl)-6-phenylhexylamino]morphinan, 17-allyl-4,5α-epoxy-3-acetoxy-14β-hydroxy-6β-[N-(4-phenylbutyl)-6-phenylhexylamino]morphinan, 17-allyl-4,5α-epoxy-3-acetoxy-14β-hydroxy-6β-[N-(2,2-diphenylethyl)-6-phenylhexylamino]morphinan, however, the present invention is by no means limited to these examples. The novel compound of the present invention includes (+) form, (−) form and (±) form of these.

The compounds of general formula (I) of the present invention can be obtained, specifically, according to the methods described below.

Among the compounds represented by the general formula (I) of the present invention, those wherein A is —XC(=Y)—, —XC(=Y)Z— or —XSO$_2$— (wherein X represents NR$^4$ or O, Y represents O or S, Z represents O, NH or S, and R$^4$ is the same as previously defined) can be obtained, specifically, according to the methods described below.

In general, as shown in Chart 1, said compounds can be obtained by condensing a carboxylic acid derivative represented by the general formula (III) (wherein B and R$^5$ are the same as previously defined), a formic acid derivative represented by the general formula (IV) (wherein Z, B and R$^5$ are the same as previously defined), an isocyanate or isothiocyanate derivative represented by the general formula (V) (wherein B and R are the same as previously defined) or a sulfonic acid derivative represented by the general formula (VI) (wherein B and R$^5$ are the same as previously defined), with a 6-amino or 6-hydroxy compounds represented by the general formula (II) (wherein R$^1$, R$^2$, R$^3$, R$^6$, R$^7$ and R$^8$ are the same as previously defined, and E represents NHR$^4$ (wherein R$^4$ is the same as previously defined) or OH).

Chart 1

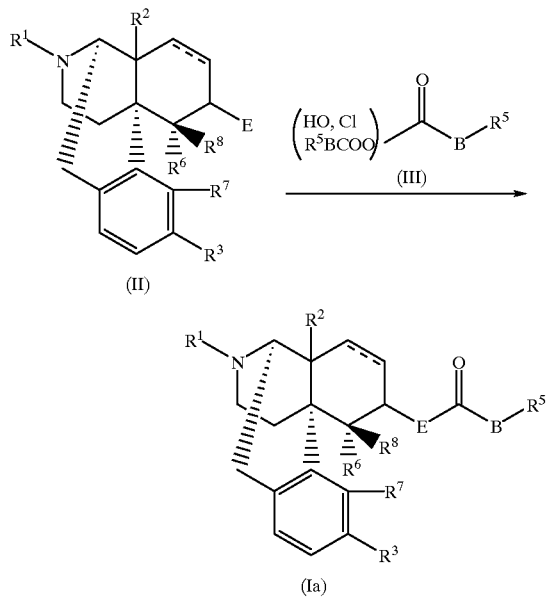

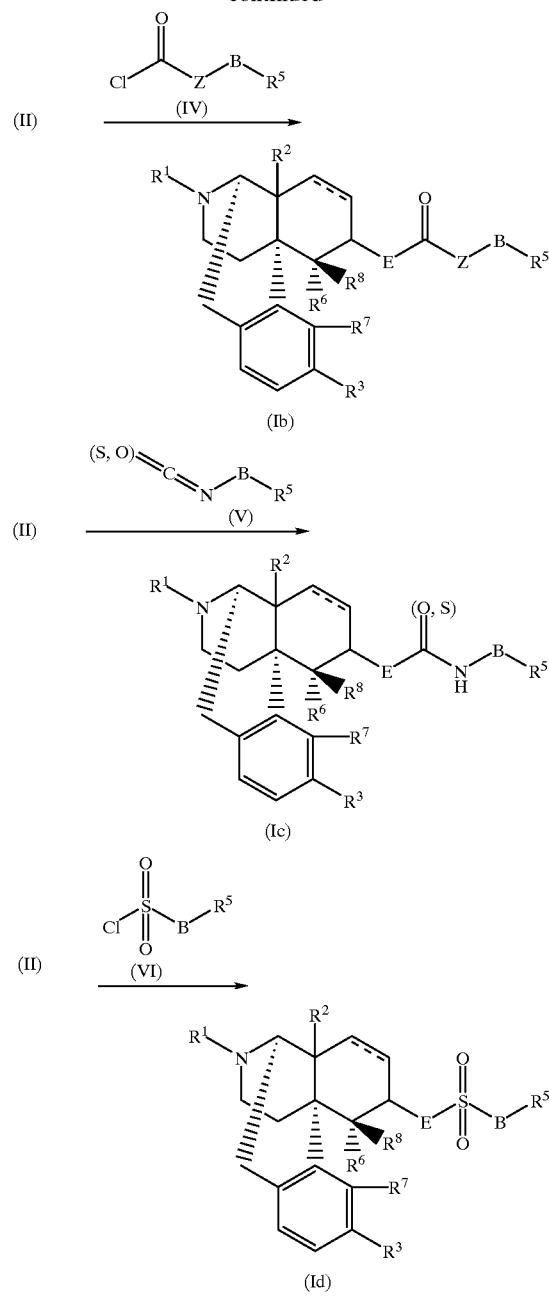

The 6-amino and 6-hydroxy compound used in this condensation can be obtained, specifically, by the processes described below.

As shown in Chart 2, a 6α-amino compound represented by the general formula (IIaα1) (wherein R$^1$, R$^2$, R$^3$, R$^6$, R$^7$ and R$^8$ are the same as previously described, and R$^4$ represents a straight-chain or branched alkyl group having 1–5 carbon atoms or an aryl group having 6–12 carbon atoms) is obtained by mixing a 6-keto compound represented the general formula (VIIa) (wherein R$^1$, R$^2$, R$^3$, R$^6$, R$^7$ and R$^8$ are the same as previously defined) and a primary amine represented by the general formula (VIII) (wherein R$^4$ is the same as previously defined) in a solvent and hydrogenating in the presence of suitable amounts of acid and metal catalyst, or reducing with a metal hydride reducing agent in the presence of acid. The hydrogenation reaction is more preferable in order to obtain the α-amino isomer with high selectivity. However, although the ratio varies according to the substrate, in the case of reduction using a metal hydride reducing agent, both the α form and β isomer are obtained simultaneously. Thus, this method is preferable in that it makes it possible to obtain a compound having the desired stereochemistry by using ordinary separation and purification techniques. In addition, the method in which the amine is obtained is also useful in the case of substrates having functional groups, such as olefins and so on, that react under hydrogenation conditions.

In the case of reduction using a hydrogenation reaction, 1–30 equivalents, and preferably 1–10 equivalents, of amine are used. Although any solvent including alcohols such as methanol and ethanol, ethers such as THF, ether, DME and dioxane, or aromatic hydrocarbons such as benzene and toluene, can be used as a reaction solvent as long as it is inert under hydrogenation conditions, alcohols are preferably used, with methanol used particularly preferably. Although any acid including inorganic acids such as hydrochloric acid, hydrobromic acid, sulfuric acid and phosphoric acid, or organic acids such as sulfonic acids including methanesulfonic acid and p-toluenesulfonic acid, benzoic acid, acetic acid or oxalic acid, can be used as long as it forms a salt with an amine, hydrochloric acid, sulfuric acid and methanesulfonic acid are preferably used. Normally, the use of hydrochloric acid in an amount of 1 equivalent less than the total amount of base yields satisfactory results. These acids can also be added to a reaction system after converting the substrate and reaction agents into salts in advance. Although all catalysts, including platinum catalysts such as platinum oxide and platinum hydroxide, palladium catalysts such as palladium hydroxide and palladium-carbon, and nickel catalysts such as Raney nickel, that are normally used in hydrogenation reactions can be used as a metal catalyst, platinum catalysts, and particularly platinum oxide, are used preferably. The reaction temperature is –30° C. to 80° C., and preferably –10° C. to 50° C., and the hydrogen pressure is 1–100 atmospheres and preferably 1–30 atmospheres. However, carrying out the reaction at room temperature and atmospheric pressure normally yields preferable results.

When reducing with a metal hydride, 1–30 equivalents, and preferably 1–15 equivalents, of amine are used. Although alcohols solvents such as methanol and ethanol, ethers such as THF, ether, DME and dioxane, or aromatic hydrocarbons such as benzene and toluene, can be used for as a solvent, alcohols are used preferably, with methanol used particularly preferably. Although any acid, including inorganic acids such as hydrochloric acid, hydrobromic acid, sulfuric acid and phosphoric acid, and organic acids such as sulfonic acids including methanesulfonic acid, p-toluenesulfonic acid, benzoic acid, acetic acid and oxalic acid, may be used in the reaction provided that it normally forms a salt with amines, hydrochloric acid, sulfuric acid and methanesulfonic acid are preferably used. In addition, these acids may also be added to the reaction system after converting the substrate and reaction agents into salts in advance. The metal hydride reducing agent used is that which allows the reaction to be carried out relatively stably in the presence of acid, examples of which include sodium borohydride, sodium cyanoborohydride, zinc borohydride, sodium triacetoxyborohydride, tetramethylammonium triacetoxyborohydride and borane-pyridine, with sodium cyanoborohydride used particularly preferably. Although the reaction can be carried out at a reaction temperature of –30° C. to 100° C. and preferably –10° C. to 50° C., satisfactory results can normally be obtained at room temperature.

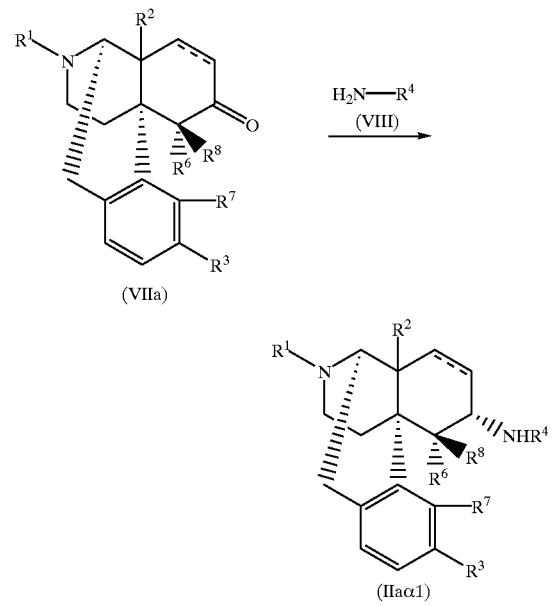

As shown in Chart 3, a 6β-amino compound represented by the general formula (IIaβ2) (wherein $R^1$, $R^2$, $R^3$, $R^6$, $R^7$ and $R^8$ are the same as previously defined, and $R^4$ represents a straight-chain or branched alkyl group having 1–5 carbon atoms or an aryl group having 6–12 carbon atoms) can be obtained from a 6-keto compound represented by the general formula (VIIb) (wherein $R^1$, $R^2$, $R^3$, $R^6$, $R^7$ and $R^8$ are the same as previously defined) with the 3 steps described below.

Step 1 involves the obtaining of an iminium intermediate represented by the general formula (X) (wherein $R^1$, $R^2$, $R^3$, $R^4$, $R^6$, $R^7$ and $R^8$ are the same as previously defined) by reaction of a keto compound with a secondary amine compound having at least one benzyl substituent group represented by the general formula (IX) (wherein $R^4$ is the same as defined above) in the presence of acid. It is desirable that the reaction be carried out while removing water produced either by azeotropic distillation or in the presence of a dehydrating agent. 1–30 equivalents, and preferably 1–10 equivalents, of secondary amine are used. Although any acid, including inorganic acids such as hydrochloric acid, hydrobromic acid, sulfuric acid and phosphoric acid, or organic acids such as sulfonic acids including methanesulfonic acid and p-toluenesulfonic acid, benzoic acid, acetic acid and oxalic acid, can be used in the reaction as long as it forms a salt with amine, hydrochloric acid, sulfuric acid, methanesulfonic acid and benzoic acid are used preferably, with hydrochloric acid and benzoic acid used particularly preferably. A method wherein these acids are added to the system after converting the substrate and reaction agents into salts in advance is also preferably carried out.

Moreover, in the case of carrying out the reaction in the presence of a weak acid, there are cases wherein preferable results are obtained if a strong acid such as inorganic acids such as hydrochloric acid, hydrobromic acid, sulfuric acid and phosphoric acid, or sulfonic acids such as methanesulfonic acid, p-toluenesulfonic acid and camphorsulfonic acid especially a strong acid such as p-toluenesulfonic acid is added as an acid catalyst. Examples of reaction solvents that can be used include ethers such as THF, ether, DME and dioxane, halocarbons such as dichloromethane and chloroform, aromatic hydrocarbons such as benzene, toluene and xylene, esters such as ethyl acetate and methyl acetate, or mixtures thereof. When using a conventional Dean-Stark water separator for the purpose of removing water, solvents are used preferably that have excellent azeotropic efficiency and water separation efficiency, such as aromatic hydrocarbons such as benzene and toluene. In this case, the mixing of a solvent such as ethyl acetate, THF or the like, for the purpose of lowering the azeotropic temperature, in amounts that do not lower water separation efficiency may provide preferable results. Although a temperature of 40–200° C., and preferably 50–150° C., can be considered as a reaction temperature, satisfactory results can be obtained at a reaction temperature of 50–130° C. In addition, it has also been found that a new method is effective wherein a dehydrating agent is packed into a Soxhlet type extractor followed by continuous removal of water. Although any of the solvents mentioned above can be used as a solvent in this case, ethers, esters and aromatic hydrocarbons, and particularly THF, DME, ethyl acetate, benzene and toluene, are preferably used. Although examples of dehydrating agents include molecular sieves and inorganic dehydrating agents such as anhydrous calcium sulfate, anhydrous copper sulfate, anhydrous sodium sulfate, anhydrous magnesium sulfate and calcium chloride, molecular sieves are used particularly preferably. The amount used is 1–100 times, and preferably 1–30 times as calculated from their water retentivity and the amount of moisture theoretically produced. Although a temperature of 40–200° C., and preferably 50–150° C., can be considered as a reaction temperature, satisfactory results are obtained at a reaction temperature of 50–120° C. In addition, a method can also be carried out wherein the reaction is allowed to proceed by directly adding dehydrating agent to the reaction system. Examples of dehydrating agents include molecular sieves, inorganic dehydrating agents such as anhydrous calcium sulfate, anhydrous copper sulfate, anhydrous sodium sulfate, anhydrous magnesium sulfate and calcium chloride, or titanium compounds having dehydration ability such as titanium tetraisopropoxide and titanium tetrachloride. In this case also, an amount used is 1–100 times, and preferably 1–30 times as calculated from the water retentivity and the amount of moisture theoretically produced. Although a temperature of −80–100° C. can be considered as a reaction temperature, satisfactory results are obtained at a reaction temperature of −30–50 C.

Step 2 is a step involving conversion to a 6-N-alkyl-N-benzylamino compound represented by the general formula (XI) (wherein $R^1$, $R^2$, $R^3$, $R^4$, $R^6$, $R^7$ and $R^8$ are the same as previously defined) by reducing with metal hydride reducing agent without isolating iminium salt. Although the same solvent used in step 1 may be used as is for the reaction solvent of this step, preferable results are obtained by reacting after mixing an alcohols such as methanol or ethanol, and particularly methanol. Naturally, the reaction may also be carried out with only alcohols such as methanol or ethanol after distilling off the reaction solvent of step 1 under reduced pressure. The reaction can be carried out with metal hydride reducing agent that is relatively stable under conditions in the presence of acid, such as sodium borohydride, sodium cyanoborohydride, zinc borohydride, sodium triacetoxyborohydride, tetramethylammonium triacetoxyborohydride and borane-pyridine, particularly preferably sodium cyanoborohydride. The reaction is carried out a reaction temperature of −20–150° C., and preferably 0–120° C. The resulting 6-N-alkyl-N-benzylamino compound represented by the general formula (XI) (wherein $R^1$, $R^2$, $R^3$, $R^4$, $R^6$, $R^7$ and $R^8$ are the same as previously defined) can also be obtained using a secondary amine by performing reductive amination using the metal hydride reducing agents of Chart 2. Moreover, if this step is performed using a corresponding secondary amine, the compound of general formula (I) can be obtained wherein A is —$NR^4$—.

Step 3 involves removing a benzyl group under hydrogenolysis conditions to form a 6β-amino form (IIaβ2). In this step, reacting the substrate either after converting into a salt in advance using an inorganic acid such as hydrochloric acid, hydrobromic acid, sulfuric acid or phosphoric acid, or an organic acid such as sulfonic acids including methanesulfonic acid, p-toluenesulfonic acid or camphor-sulfonic acid, benzoic acid, acetic acid, oxalic acid or phthalic acid, and preferably hydrochloric acid or phthalic acid, or adding suitable amount of these acids prior to the reaction, yields favorable results. Since there are cases in which a resulting secondary amine salt can be purified as a crystal depending on the acid, selection of acid is important. For example, when phthalic acid is used with a compound wherein $R^1$ is a cyclopropylmethyl group, $R^2$ and $R^3$ are hydroxy groups, $R^4$ is a methyl group, $R^6$ and $R^7$ are together —O— and $R^8$ is a hydrogen atom, a crystalline salt is obtained that is easily purified. Although any solvent such as alcohol-based solvents such as methanol and ethanol, ethers such as THF, ether, DME and dioxane, and organic hydrocarbons such as benzene and toluene, can be used as a reaction solvent provided it is inert under hydrogenation conditions, alcohols are used preferably, with methanol used particularly preferably. Although any catalyst that is used in normal hydrogenation reactions, such as, platinum catalysts such as platinum oxide and platinum hydroxide, palladium catalysts such as palladium hydroxide and palladium-carbon, and nickel catalysts such as Raney nickel, can be used as a metal catalyst, palladium catalysts, and particularly palladium-carbon, are particularly preferably used. The reaction temperature is −30 to 80° C., and preferably −10 to 50° C. while hydrogen pressure is 1 to 100 atmospheres, and preferably 1 to 30 atmospheres. However, carrying out the reaction at room temperature and atmospheric pressure normally yields favorable results.

Chart 3

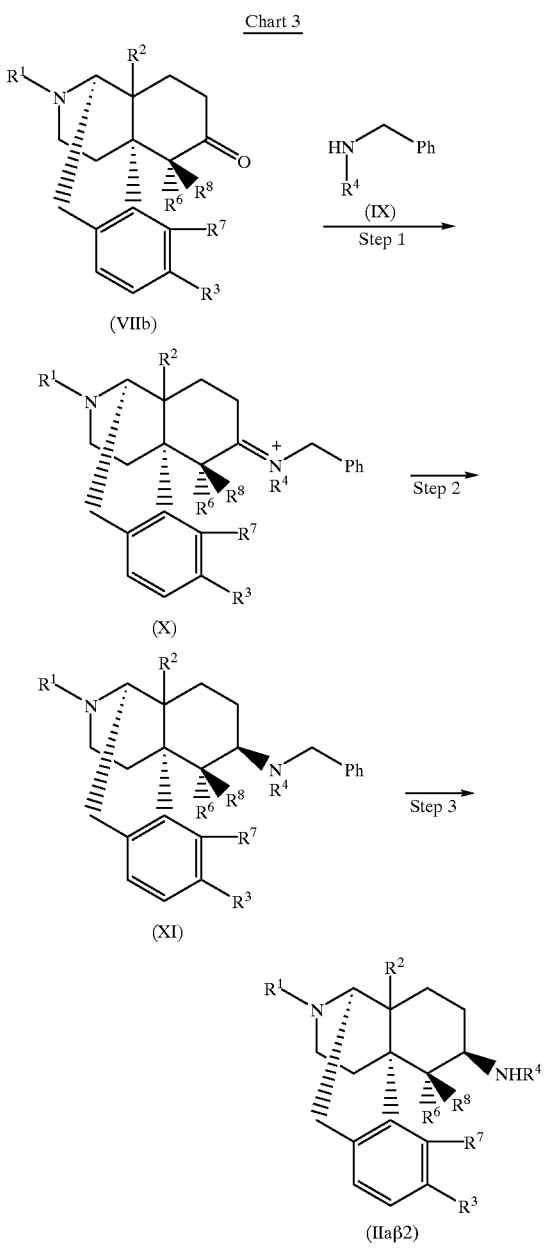

In addition, when ammonium acetate is used in place of primary amine in the reductive amination reaction shown in Chart 2, when dibenzylamine is used in the method shown in Chart 3, or after converting ketone into oxime using the method described in the literature (J. Med. Chem., 27, 1727 (1984)), a primary amine can be obtained by reducing with borane or under hydrogenation conditions. This primary amine can be converted into a secondary amine by effecting two steps of the acylation and reduction. This is also useful as an alternative route for obtaining the secondary amine.

As shown in Chart 3, a 6-α-alcohol represented by the general formula (IIbα) (wherein $R^1$, $R^2$, $R^3$, $R^6$, $R^7$ and $R^8$ are the same as previously defined) is obtained either by reducing a 6-keto compound represented by the general formula (VIIa) (wherein $R^1$, $R^2$, $R^3$, $R^6$, $R^7$ and $R^8$ are the same as previously defined) with metal hydride reducing agent or hydrogenation in the presence of acid and metal catalyst. Although metal hydride reducing agents including sodium borohydride, sodium cyanoborohydride, zinc borohydride, sodium triacetoxyborohydride, L-selectride and lithium aluminum hydride can be used, sufficiently satisfactory results are obtained with sodium borohydride. Although solvents including alcohols such as methanol and ethanol, and ethers such as THF, ether, DME and dioxane are used, alcohols, and particularly methanol, are preferably used. In the case of hydrogenation, examples of solvents that are used include alcohols such as methanol and ethanol, and ethers such as THF, ether and dioxane, with alcohols being used preferably, and methanol being used particularly preferably.

Although acids such as inorganic acids such as hydrochloric acid, hydrobromic acid, sulfuric acid or phosphoric acid, and organic acids such as sulfonic acids including methanesulfonic acid and p-toluenesulfonic acid, benzoic acid are used, acetic acid or oxalic acid, hydrochloric acid is preferably used. Although all catalysts that are used in normal hydrogenation reactions such as platinum catalysts such as platinum oxide or platinum hydroxide, palladium catalysts such as palladium hydroxide or palladium-carbon, and nickel catalysts such as Raney nickel can be used as a metal catalyst, platinum catalysts, and particularly platinum oxide are preferably used. Although the reaction can be carried out at a reaction temperature of −30–80° C., and preferably −10 −50° C., and under a hydrogen pressure of 1–100 atmospheres, and preferably 1–30 atmospheres, favorable results are normally obtained at room temperature and under atmospheric pressure.

Chart 4

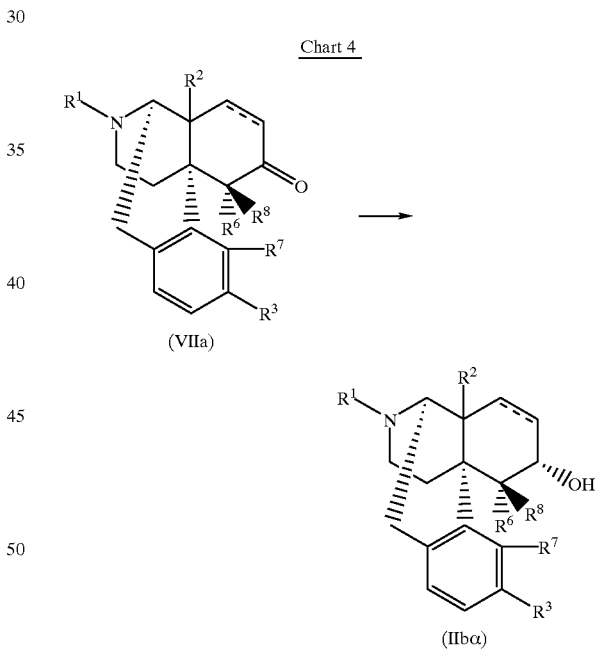

As shown in Chart 5, a 6β-hydroxy form represented by the general formula (IIbβ) (wherein $R^1$, $R^2$, $R^3$, $R^6$, $R^7$ and $R^8$ are the same as previously defined) can be obtained by reacting a 6-keto form represented by the general formula (VIIa) (wherein $R^1$, $R^2$, $R^3$, $R^6$, $R^7$ and $R^8$ are the same as previously defined) with formamidine sulfinic acid in the presence of a base. Preferable examples of a base used include inorganic bases such as sodium hydroxide, potassium hydroxide, potassium carbonate and sodium bicarbonate, with sodium hydroxide being used particularly preferably. Although examples of reaction solvents used include water, alcohols such as methanol and ethanol, and dipolar, aprotic solvents such as DMF and DMSO, the use of water normally yields satisfactory results. Although a temperature of 0–150° C. is considered as a reaction temperature, a temperature of 60–100° C. is preferable.

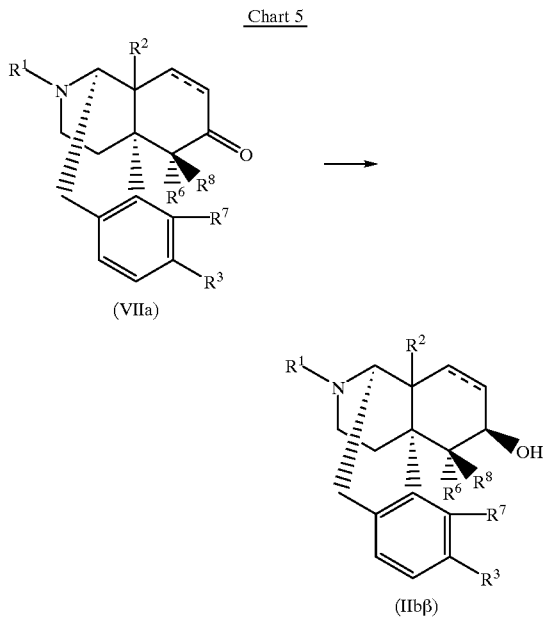

Chart 5

(VIIa)

(IIbβ)

Among the 6-amino or 6-hydroxy-compound synthesized in the above method, particularly a compound wherein $R^3$ is a hydrogen atom, is obtained by methods similar to those shown in Charts 2, 3, 4 and 5, using as a starting material a 3-dehydroxy-6-keto compound represented by the general formula (VIIe) (wherein $R^1$, $R^2$, $R^6$, $R^7$ and $R^8$ are the same as previously defined, provided that $R^7$ is not a hydroxy group), obtained by using as a substrate a 3-hydroxy-6-keto compound represented by the general formula (VIIc) (wherein $R^1$, $R^2$, $R^6$, $R^7$ and $R^8$ are the same as previously defined, provided that $R^7$ is not a hydroxy group) according to the scheme shown in Chart 6. In addition, an intermediate, wherein $R^3$ is a siloxy group, can be obtained by methods similar to those shown in Charts 2, 3, 4 and 5, by using for as a starting material: a 3-siloxy-6-keto form represented by the general formula (VIIf) (wherein $R^1$, $R^2$, $R^6$, $R^7$ and $R^8$ are the same as previously defined, provided that $R^7$ is not a hydroxy group and G represents an alkylsilyl group), obtained from a 3-hydroxy-6-keto compound (VIIc) by the scheme shown in Chart 7.

Namely, as shown in Chart 6, the first step for obtaining a 3-dehydroxy-6-keto compound represented by the general formula (VIIe) (wherein $R^1$, $R^2$, $R^6$, $R^7$ and $R^8$ are the same as previously defined, provided that $R^7$ is not a hydroxy group) is a step wherein trifluoromethane sulfonic anhydride is caused to act on a phenolic hydroxyl group in the presence of a base to form a trifate form represented by the general formula (VIId) (wherein $R^1$, $R^2$, $R^6$, $R^7$ and $R^8$ are the same as previously defined, provided that $R^7$ is not a hydroxy group). Although solvents such as halocarbons such as dichloromethane and chloroform, ethers such as THF, ether, DME and dioxane, and amines having large steric hindrances that can be used as solvents such as 2,6-lutidine and diisopropylethylamine, can be considered for use as a reaction solvent, halocarbons, and particularly dichloromethane, are preferably used.

Although tertiary amines such as triethylamine, diisopropylethylamine and proton sponge, as well as pyridine, 2,6-lutidine and imidazole are used as a coexisting base, 2,6-lutidine is preferably used. Although the reaction can be carried out at −30–50° C., satisfactory results can be normally attained at a temperature of 0° C. to room temperature normally yields. Step 2 is a step wherein a trifate form is reduced with formic acid in the presence of phosphorous ligand and a base using a palladium catalyst. Although amines usable as solvents such as triethylamine and diisopropylethylamine, ethers such as THF, ether, DME and dioxane, aromatic hydrocarbons such as benzene and toluene, alcohols such as methanol and ethanol and aprotic dipolar solvents such as DMF and DMSO are used for the reaction solvent, DMF is particularly preferably used. Although zero-valent complexes such as tetrakistriphenylphosphine palladium and bisbenzylideneacetone palladium, and bivalent complexes such as palladium acetate and palladium chloride are frequently used for the palladium catalyst, palladium acetate is used normally.

Although monodentate phosphines such as trimethylphosphine, triethylphosphine, triphenylphosphine and tris-o-toluphosphine, and bidentate phosphines such as bis-(diphenylphosphino)methane, 1,2-bis-(diphenylphosphino) ethane, 1,3-bis-(diphenylphosphino) propane and 1,1'-bis-diphenylphosphinoferrocene, are used as a phosphorous ligand, 1,1'-bis-diphenylphosphinoferrocene is particularly preferably used. Although amines such as triethylamine and diisopropylethylamine, and inorganic salts such as silver carbonate, sodium acetate and potassium acetate, are used as a base used in the reaction, triethylamine is preferably used. The reaction is carried out at a reaction temperature of 0–150° C., and satisfactory results are normally obtained at a room temperature to 80° C.

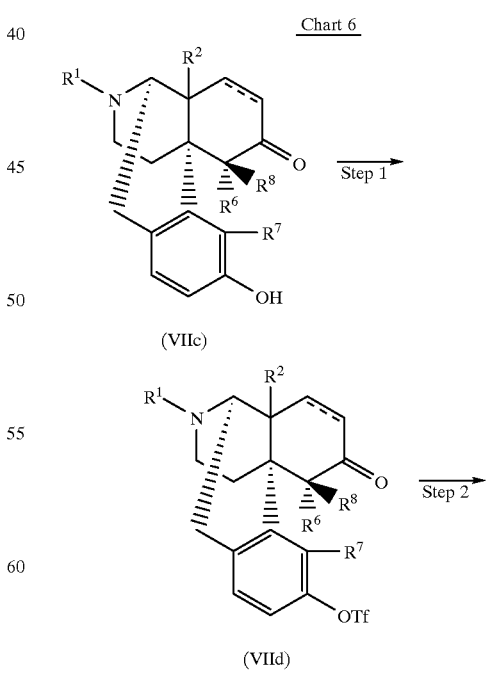

Chart 6

(VIIc)

(VIId)

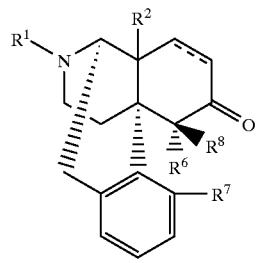

(VIIe)

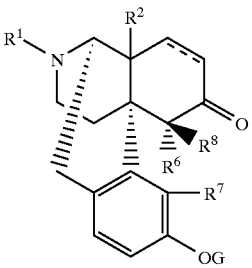

(VIIf)

As shown in Chart 7, a 3-hydroxy-6-keto form represented by the general formula (VIIc) (wherein $R^1$, $R^2$, $R^6$, $R^7$ and $R^8$ are the same as previously defined) may be reacted with silyl chloride in the presence of a base to obtain a 3-siloxy-6-keto form represented by the general formula (VIIf) (wherein $R^1$, $R^2$, $R^6$, $R^7$ and $R^8$ are the same as previously defined, provided that $R^7$ is not a hydroxy group and G represents an alkyl silyl group). Although trimethylsilyl chloride, triphenylsilyl chloride, t-butyldimethylsilyl chloride and diphenylmethylsilyl chloride are mentioned as silyl chlorides, t-butyldimethylsilyl chloride is preferably used. Although tertiary amines such as triethylamine, diisopropylethylamine and proton sponges, as well as pyridine, dimethylaminopyridine and imidazole are used as a base, imidazole is preferably used. Although halocarbons such as dichloromethane, chloroform, carbon tetrachloride and 1,2-dichloroethane, ethers, such as ether, THF, DME and dioxane, and pyridine are used as a solvent, dichloromethane is preferably used. The reaction can be carried out within a range of −80–100° C., and preferable results are obtained particularly in the vicinity of 0° C. to room temperature. Although the reaction can be carried out in 5–300 minutes, since there are cases in which 6th position ketone groups are also enolsilylated when reaction time is lengthened particularly with respect to compounds wherein ..... is a single bond and R6 and R7 together are —O—, a reaction time of 5–60 minutes is preferable.

Chart 7

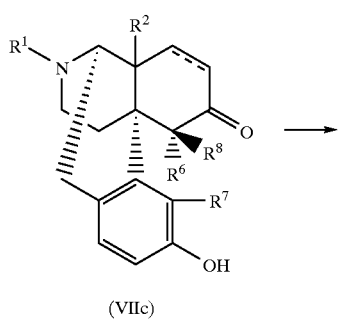

(VIIc)

As shown in Chart 8, compounds wherein X is $NR^4$ can be obtained by condensing a 6-amino form represented by the general formula (IIa) (wherein $R^1$, $R^2$, $R^3$, $R^4$, $R^6$, $R^7$ and $R^8$ are the same as previously defined,), obtained by the methods shown in Charts 2 and 3, with a carboxylic acid and carboxylic acid derivative represented by the general formula (III) (wherein B and $R^5$ are the same as previously defined), or with a formic acid derivative represented by the general formula (IV) (wherein Z, B and $R^5$ are the same as previously defined), or with a isocyanate or isothiocyanate derivative represented by the general formula (V) (wherein B and $R^5$ are the same as previously defined), or with a sulfonic acid derivative represented by the general formula (VI) (wherein B and $R^5$ are the same as previously defined), etc.

Condensation with a carboxylic acid derivative can be performed by reacting a 6-amino form with an acid chloride or acid anhydride that reacts in the presence of a base, or by reacting with carboxylic acid itself using, for example, N,N'-dicyclohexylcarbodiimide (abbreviated as DCC), 1,1'-carbonyldiimidazole, or bis-(2-oxo-3-oxazolidinyl) phosphinate chloride (abbreviated as BOPC1⁻), etc. Acid chloride or acid anhydride is used in an amount of 1–20 equivalents, and preferably 1–5 equivalents. Although halocarbons such as dichloromethane, chloroform, carbon tetrachloride and 1,2-dichloroethane, ethers such as ether, THF, DME and dioxane, pyridine, water or a mixture of these are used as reaction solvents, when using acid chloride, chloroform or a mixed solvent of THF and water is used preferably. In the case of using acid anhydride, pyridine is preferably used both as base and solvent. Although organic bases such as tertiary amines including triethylamine, diisopropylethylamine and proton sponges, pyridine, dimethylaminopyridine and imidazole, and inorganic bases such as potassium carbonate, sodium carbonate, sodium bicarbonate, sodium hydroxide and potassium hydroxide are used as bases, when using chloroform as the solvent, trimethylamine is normally used in an amount of 1–20 equivalents, and preferably 1–5 equivalents. In the case of using a mixed solvent of THF and water, the use of potassium carbonate, sodium carbonate or sodium bicarbonate in an amount of 1–20 equivalents, and preferably 1–5 equivalents, provides satisfactory results. The reaction can be carried out within a range of −80–100° C., and preferable results are obtained particularly at a temperature of from 0° C. to room temperature. In the case of using DCC as a condensing agent, an amount of 1–20 equivalents preferably 1–5 equivalents is used. Although halocarbons such as dichloromethane, chloroform, carbon tetrachloride and 1,2-dichloroethane, and ethers such as ether, THF, DME and dioxane are used as reaction solvents, dichloromethane and chloroform are particularly preferably used. Although organic bases such as tertiary amines including triethylamine, diisopropylethylamine and proton sponges, as well as pyridine, dimethylaminopyridine and imidazole are used as coexisting bases, dimethylaminopyridine in an amount of 0.01–2 equivalents is used particularly preferably. The reaction can be carried out within a range of –80–100° C., and preferable results are obtained in the vicinity of 0° C. to room temperature in particular.

In the case of using 1,1'-carbonyldiimidazole as a condensing agent, an amount of 1–20 equivalents, and preferably 1–5 equivalents is used. Although ethers such as ether, THF, DME and dioxane, and halocarbons such as dichloromethane, chloroform, carbon tetrachloride and 1,2-dichloroethane are used as reaction solvents, THF is particularly preferably used. The reaction can be carried out within a range of –20–120° C., and a temperature in the vicinity of room temperature to 100° C. is particularly preferable. In the case of using BOPCl as a condensing agent, it is used in an amount of 1–20 equivalents, and preferably 1–5 equivalents. Examples of solvents used for the reaction include halocarbons such as dichloromethane, chloroform, carbon tetrachloride and 1,2-dichloroethane, and ethers such as ether, THF, DME and dioxane, though dichloromethane and chloroform are particularly preferably used. Although organic bases such as tertiary amines including triethylamine, diisopropylethylamine, proton sponge and N-ethylpiperidine, as well as pyridine, dimethylaminopyridine and imidazole are used as coexisting bases, N-ethylpiperidine in an amount of 1–20 equivalents, and preferably 1–5 equivalents, is particularly preferably used. The reaction can be carried out within a range of –80–100° C., and preferable results are obtained at 0–50° C. in particular.

Condensation with a formic acid derivative can be performed by reacting a 6-amino form with 1–20 equivalents and preferably 1–5 equivalents of an acid chloride that reacts in the presence of base. Although halocarbons such as dichloromethane, chloroform, carbon tetrachloride and 1,2-dichloroethane, ethers such as ether, THF, DME and dioxane, pyridine, water or mixtures of these solvents are used as reaction solvents, chloroform and a mixed solvent of THF and water are particularly preferably used. Although organic bases such as tertiary amines including triethylamine, diisopropylethylamine and proton sponge, pyridine, dimethylaminopyridine and imidazole, and inorganic bases such as potassium carbonate, sodium carbonate and sodium bicarbonate are used as bases, triethylamine in an amount of 1–20 equivalents, and preferably 1–5 equivalents provides satisfactory results when chloroform is used as a solvent, while potassium carbonate, sodium carbonate and sodium bicarbonate used in an amount of 1–20 equivalents, and preferably 1–5 equivalents, normally provides favorable results when a mixed solvent of THF and water is used as a solvent. The reaction can be carried out within a range of –80–100° C., and preferable results are obtained from 0° C. to the vicinity of room temperature.

Condensation with an isocyanate or isothiocyanate derivative can be performed by reacting 1–20 equivalents, and preferably 1–5 equivalents, of a corresponding isocyanate ester with a 6-amino derivative. Although halocarbons such as dichloromethane, chloroform, carbon tetrachloride and 1,2-dichloroethane, and ethers such as ether, THF, DME and dioxane are used as reaction solvents, chloroform is particularly preferably used. The reaction can be carried out within a range of –80–100° C., and preferable results are obtained from 0° C. to the vicinity of room temperature.

Condensation with a sulfonic acid derivative can be performed by reacting 1–20 equivalents, and preferably 1–5 equivalents, of the corresponding sulfonyl chloride with a 6-amino form in the presence of base. Examples of bases that are used include tertiary amines such as triethylamine, diisopropylethylamine and proton sponges, as well as pyridine, dimethylaminopyridine and imidazole. Although halocarbons such as dichloromethane, chloroform, carbon tetrachloride and 1,2-dichloroethane, ethers such as ether, THF, DME and dioxane, and pyridine are used as reaction solvents, pyridine is particularly preferably used as both base and solvent. The reaction can be carried out within a range of –80–100° C., and preferable results are obtained from 0° C. to the vicinity of room temperature in particular.

Chart 8

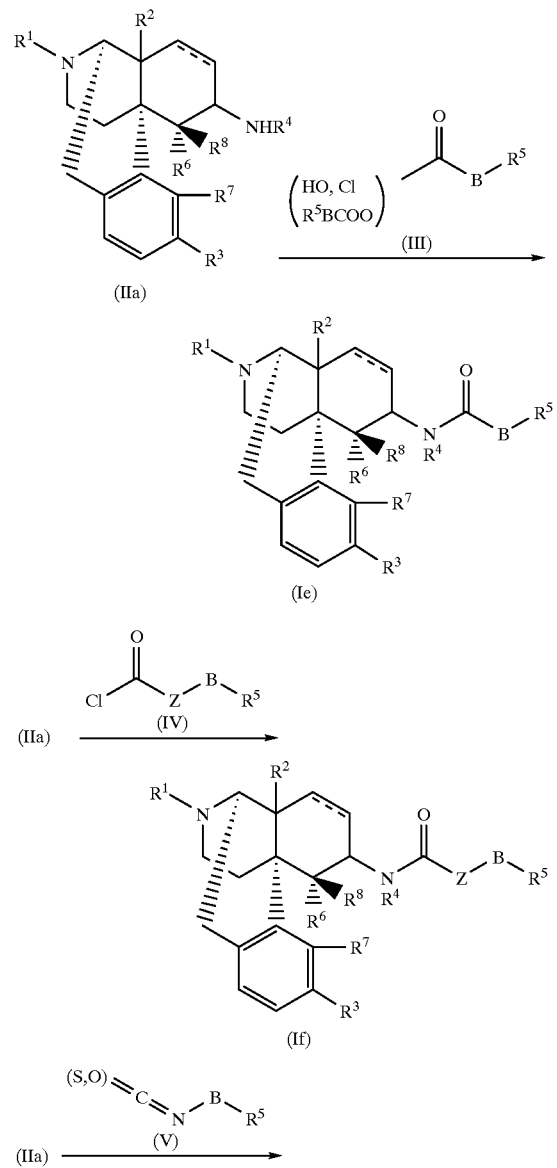

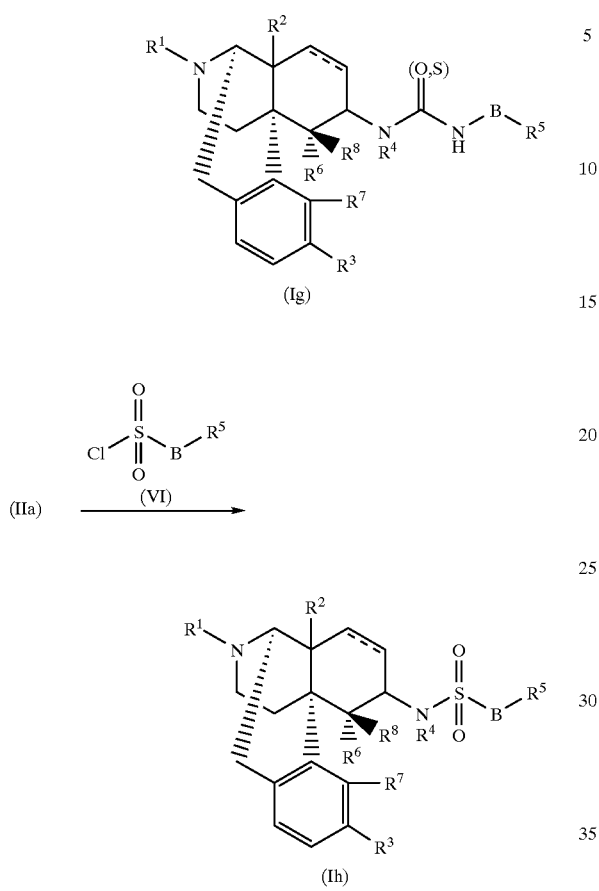

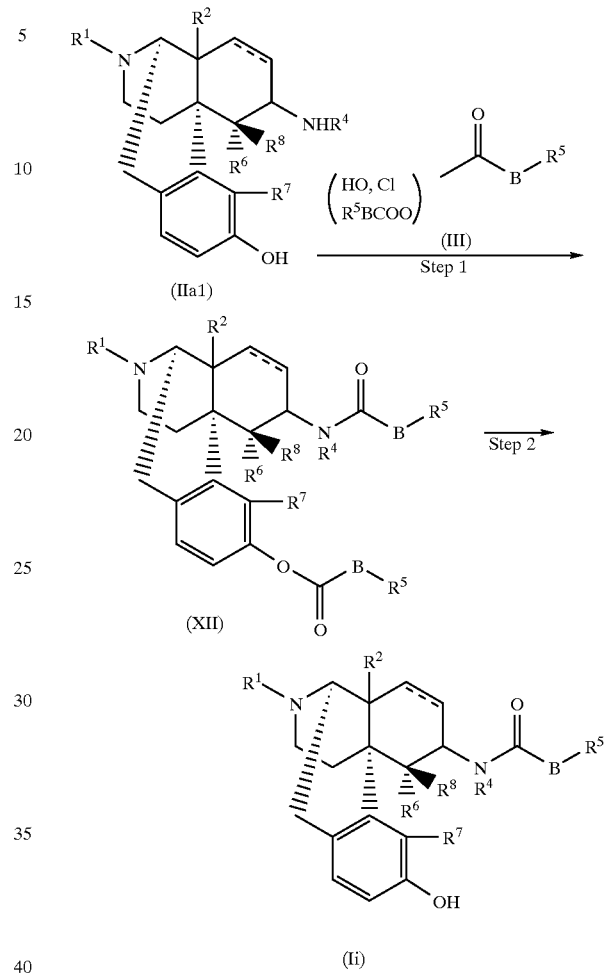

In the case of compounds wherein $R^3$ is a hydroxy group in particular, since there are cases in which phenolic hydroxyl groups may react simultaneously, after carrying out step 1 in the same manner as shown in Chart 8, as shown in Charts 9–11 with carboxylic acid derivative, formic acid derivative and isocyanate or isothiocyanate derivative, the target compound can be obtained by performing alkaline treatment for step 2. Examples of solvents used for a reaction solvent of step 2 include water, alcohols such as methanol and ethanol, ethers such as ether, THF, DME and dioxane, or mixed solvents of those solvents. When solubility is inadequate, halocarbons such as dichloromethane and chloroform can be suitably added. Examples of bases used include inorganic bases such as potassium carbonate, sodium carbonate, sodium bicarbonate, sodium hydroxide and potassium hydroxide. Normally, 1–20 equivalents, and preferably 1–10 equivalents, of potassium carbonate, sodium hydroxide and so forth are used preferably. The reaction can be carried out within a range of –80–100° C., and favorable results are obtained from 0–50° C. in particular.

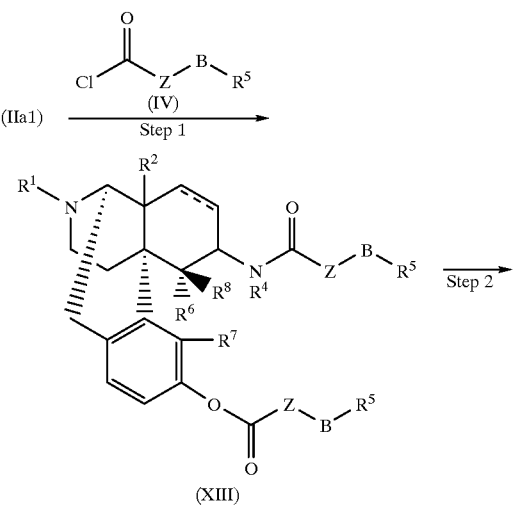

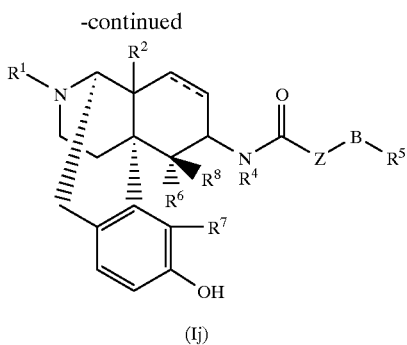

(Ij)

Chart 11

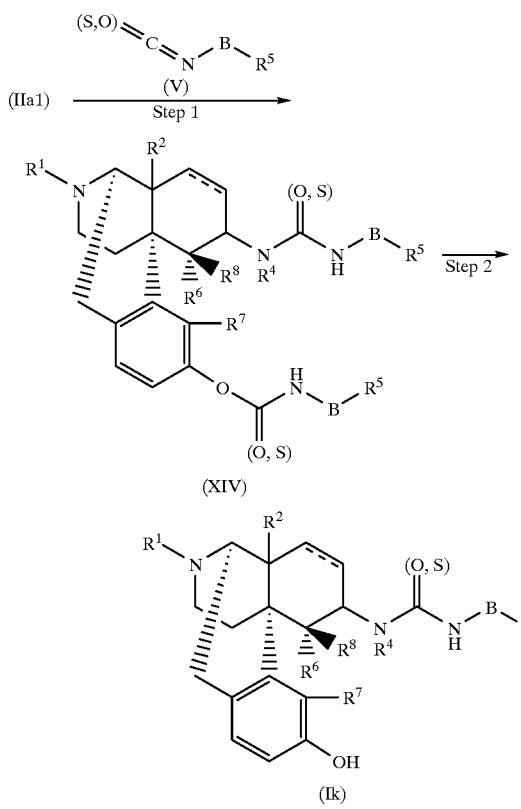

When condensing compounds wherein R³ is a hydroxy group with sulfonic acid derivative, as shown in Chart 12, preferable results are obtained by using a 3-siloxy-6-amino form, wherein phenolic hydroxyl groups are protected in advance with silyl ether groups and so forth, represented by the general formula (IIc) (wherein R¹, R², R⁴, R⁶, R⁷, R⁸ and G are the same as previously defined). Naturally, the following method can also be applied to condensation with a carboxylic acid derivative, formic acid derivative and isocyanate or isothiocyanate derivative. Namely, this method involves removing silyl groups after carrying out step 1 in the same manner as shown in Chart 8. Although quaternary ammonium salts such as tetrabutylaxmonium fluoride, tetrabutylammonium chloride and pyridinium hydrofluoride, or acids such as acetic acid, hydrochloric acid, sulfuric acid and hydrofluoric acid, are used for removal of silyl groups in step 2, normally 1–20 equivalents, and preferably 1–5 equivalents, of tetrabutylammonium fluoride are used.

Although ethers such as THF, ether, DME and dioxane, halocarbons such as dichloromethane and chloroform, and acetonitrile are used as solvents, THF is particularly preferably used. Although the reaction can be carried out at −20–100° C., satisfactory results can normally be obtained at room temperature.

Chart 12

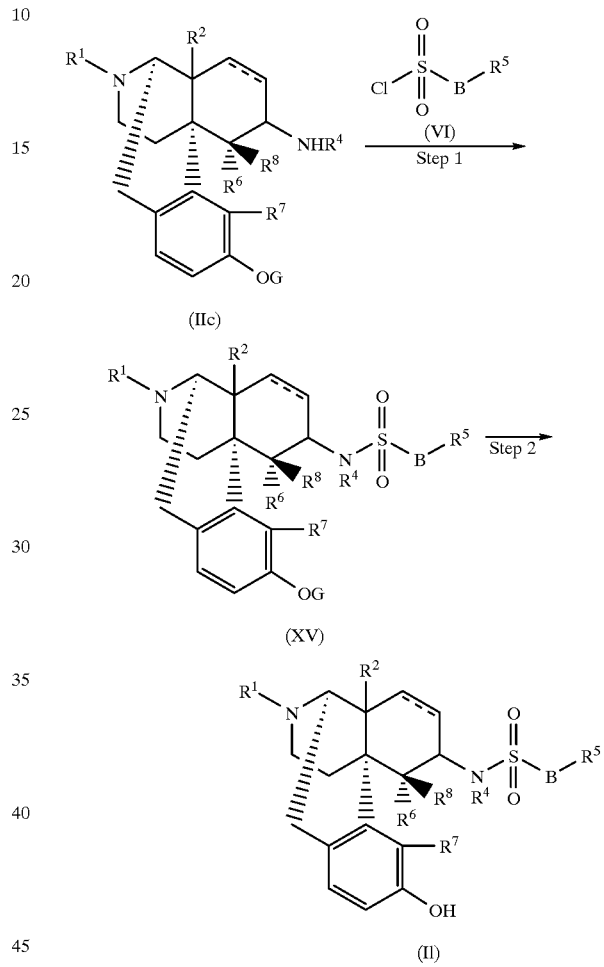

In addition, a 6-amino form represented by the general formula (Im) (wherein R¹, R², R³, R⁴, B, R⁵, R⁶, R⁷ and R⁸ are the same as previously defined), in which A is —NR⁴—, is obtained by reducing an amide form represented by the general formula (Ie') (wherein R¹, R², R³, R⁴, R⁵, R⁶, R⁷, R⁸ and B are the same as previously defined) using a metal hydride reducing agent. Examples of reducing agents used include metal hydride compounds having a strong reducing activity such as lithium aluminum hydride, diisobutylaluminum hydride, aluminum hydride, lithium borohydride and diborane, 1–20 equivalents, and preferably 1–5 equivalents of diborane are particularly preferably used. Ethers such as THF, DME, ether and dioxane are used preferably as a solvent when using lithium aluminum hydride, lithium borohydride or diborane, with THF being used particularly preferably. Aromatic hydrocarbons such as benzene and toluene are used preferably as a solvent when diisobutylaluminum hydride or aluminum hydride are used. The reaction can be carried out within a range of −40 to 100° C., and a temperature from 0° C. to the vicinity of room temperature is preferable.

Chart 13

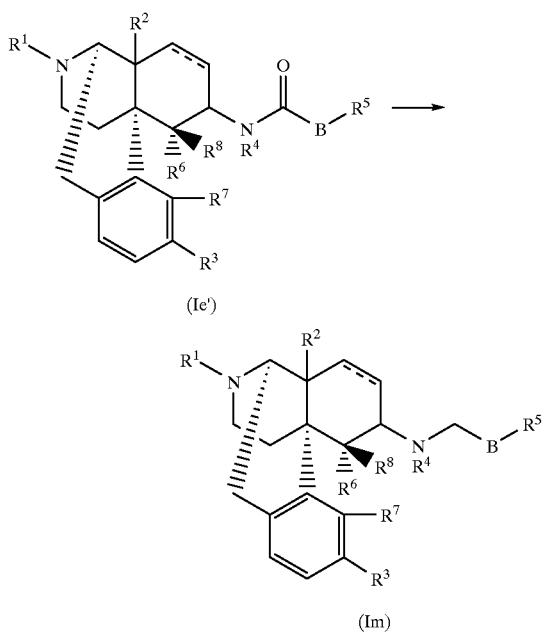

As shown in Chart 14, compounds wherein X is O can be obtained by condensing a 6-hydroxy form represented by the general formula (IIb) (wherein $R^1$, $R^2$, $R^3$, $R^6$, $R^7$ and $R^8$ are the same as previously defined) obtained in Charts 4 and 5, with a carboxylic acid derivative (III), a formic acid derivative (IV), an isocyanate or isothiocyanate derivative (V), or sulfonic acid derivative (VI) and so forth.

Condensation with a carboxylic acid derivative can be performed by treatment of a 6-hydroxy compound with 1–20 equivalents, and preferably 1–5 equivalents of an acid chloride or acid anhydride in the presence of base. Although halocarbons such as dichloromethane, chloroform, carbon tetrachloride and 1,2-dichloroethane, ethers such as ether, THF, DME and dioxane, and pyridine are used as a reaction solvents, chloroform is used preferably when using acid chloride, while pyridine is used preferably in the case of using acid anhydride. Although tertiary amines such as triethylamine, diisopropylethylamine and proton sponge, as well as pyridine, dimethylaminopyridine and imidazole are used as bases, the use of both diisopropylethylamine and dimethylaminopyridine in an amount of 1–20 equivalents, and preferably 1–5 equivalents, normally provides satisfactory results. The reaction can be carried out at –80 to 100° C., and preferable results are obtained at a temperature of from the vicinity of room temperature to 80° C. in particular.

Condensation with a formic acid derivative can be performed by reacting a 6-hydroxy compound with 1–20 equivalents, and preferably 1–5 equivalents, of the corresponding acid chloride in the presence of a base. Although halocarbons such as dichloromethane, chloroform, carbon tetrachloride and 1,2-dichloroethane, and ethers such as ether, THF, DME and dioxane are used as reaction solvents, chloroform and carbon tetrachloride are used particularly preferably. Although tertiary amines such as triethylamine, diisopropylethylamine and proton sponges, as well as pyridine, dimethylaminopyridine and imidazole are used as bases, the use of both diisopropylethylamine and dimethylaminopyridine in an amount of 1–20 equivalents, and preferably 1–5 equivalents, normally provides satisfactory results. The reaction can be carried out within a range of –80 to 100° C., and preferable results are obtained from the vicinity of room temperature to 80° C. in particular.

Condensation with an isocyanate or isothiocyanate derivative can be performed by reacting 1–20 equivalents, and preferably 1–5 equivalents, of the corresponding isocyanate ester with a 6-hydroxy form. Although halocarbons such as dichloromethane, chloroform, carbon tetrachloride and 1,2-dichloroethane, and ethers such as ether, THF, DME and dioxane are used as reaction solvent, chloroform is used particularly preferably. The reaction can be carried out within a range of –80 to 100° C., and preferable results are obtained at a temperature of from the vicinity of room temperature to 80° C. in particular.

Condensation with a sulfonic acid derivative can be carried out by treatment of 1–20 equivalents, and preferably 1–5 equivalents, of a corresponding sulfonyl chloride with a 6-hydroxy form in the presence of a base. Examples of a base used include tertiary amines such as triethylamine, diisopropylethylamine and proton sponges, as well as pyridine, dimethylaminopyridine and imidazole. Although halocarbons such as dichloromethane, chloroform, carbon tetrachloride and 1,2-dichloroethane, ethers such as ether, THF, DME and dioxane, and pyridine are used as reaction solvent, pyridine is used particularly preferably, both as base and solvent. The reaction can be carried out within a range of –80 to 100° C., and preferable results are obtained at a temperature of the vicinity of room temperature to 80° C. in particular.

Chart 14

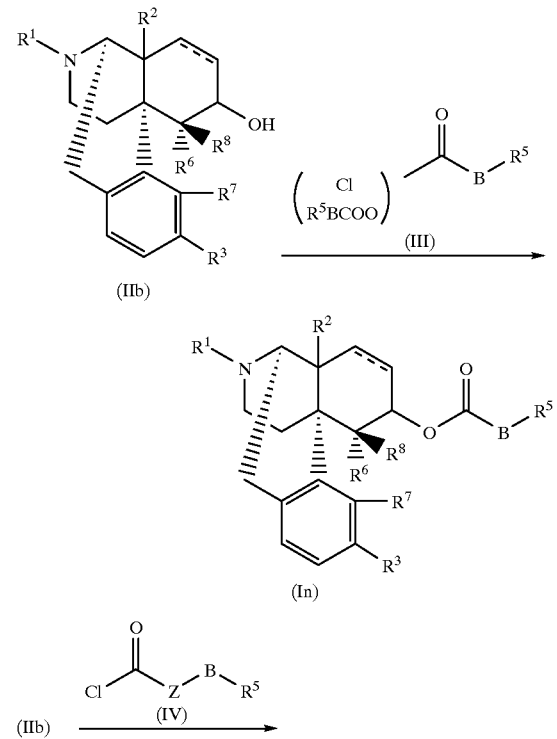

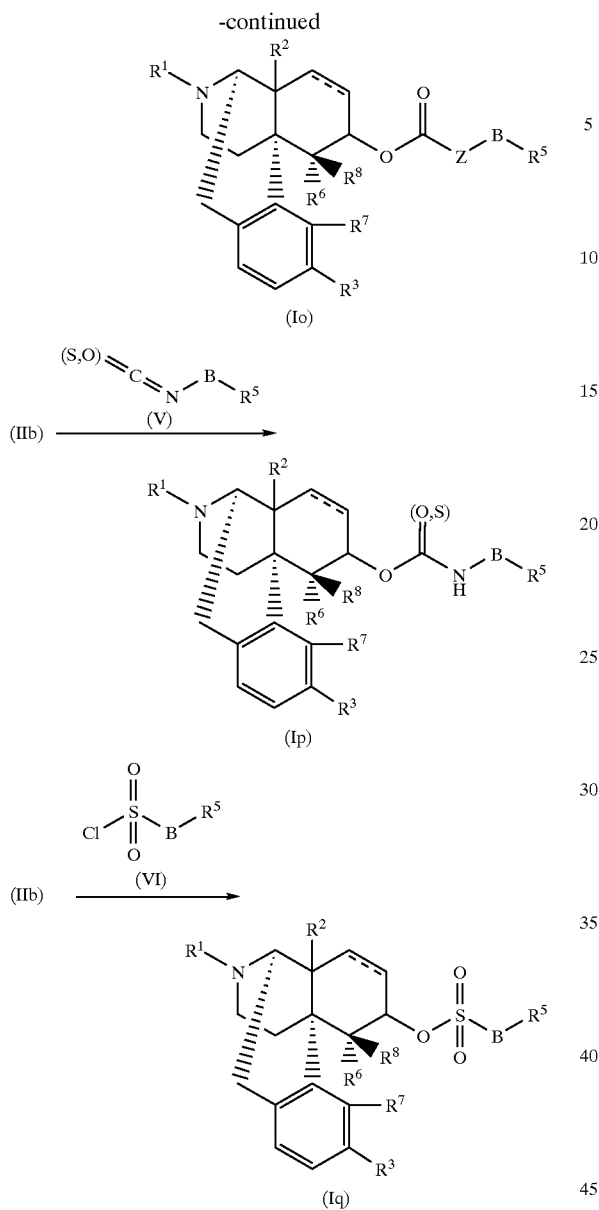

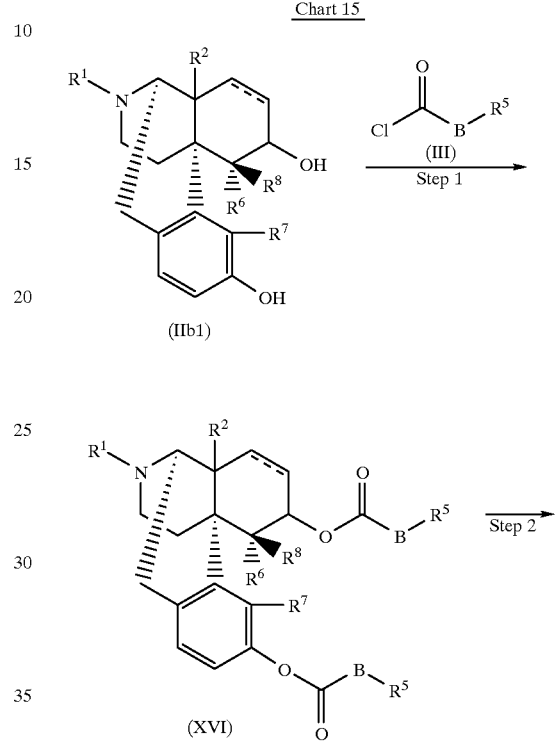

solvolysis of functional group at the 6 position may also proceed, in such cases, this problem is solved by either lowering the reaction temperature or shortening the reaction time.

In the case of compounds wherein $R^3$ is a hydroxy group in particular, since phenolic hydroxyl group also reacts simultaneously, in the case of carboxylic acid derivative, formic acid derivative, and isocyanate or isothiocyanate derivative, after performing a condensation reaction in the same manner as shown in Chart 14 as step 1, the target compound can be obtained by performing alkaline treatment for step 2 as shown in Charts 15–17. Examples of solvents used as reaction solvent of step 2 include water, alcohols such as methanol and ethanol, and when solubility is not adequate, halocarbons such as dichloromethane, and chloroform can be suitably added. Examples of a base used include inorganic bases such as potassium carbonate, sodium carbonate, sodium bicarbonate, sodium hydroxide and potassium hydroxide, with potassium carbonate normally being used preferably. The reaction can be carried out within a range of −80 to 100° C., and preferable results are obtained at −20 to 50° C. in particular. However, since

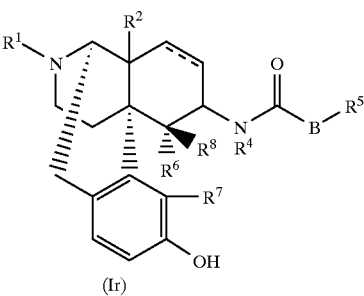

111
-continued

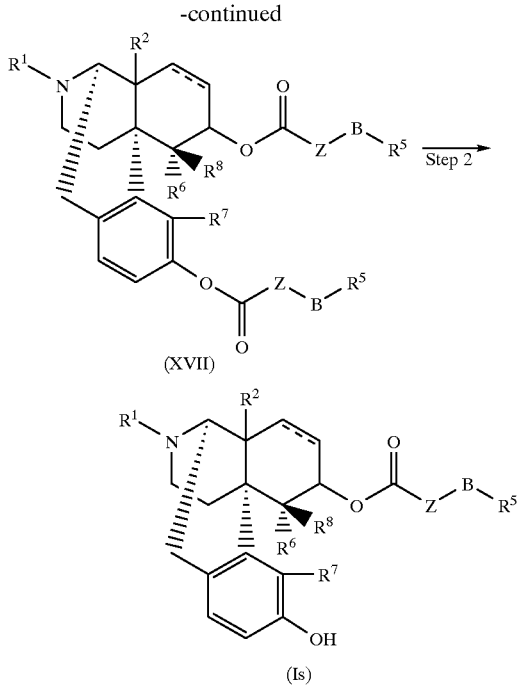

Chart 17

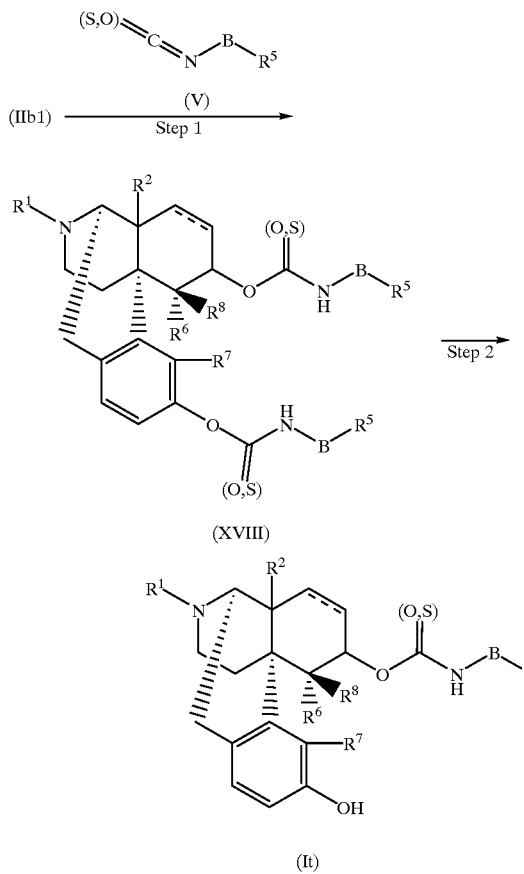

The use of a 3-siloxy-6-hydroxy form represented by the general formula (IId) (wherein $R^1$, $R^2$, $R^6$, $R^7$, $R^8$ and G are the same as previously defined), in which phenolic hydroxyl groups are protected in advance with silyl ether group and so forth, for condensation with a sulfonic acid derivative yields preferable results as shown in chart 18. Naturally, this method can be carried out for condensation with a carboxylic acid derivative, a formic acid derivative, an isocyanate or isothiocyanate derivative. After performing condensation in the same manner as shown in Chart 14 as step 1, silyl group is removed in step 2. Although quaternary ammonium salts such as tetrabutylammonium fluoride, tetrabutylammonium chloride and pyridinium hydrofluoride, or acids such as acetic acid, hydrochloric acid, sulfuric acid and hydrofluoric acid, may be used for removal of silyl groups, normally 1–20 equivalents, and preferably 1–5 equivalents, of tetrabutylammonium fluoride are used. Examples of solvents used include ethers such as THF, DME and dioxane, acetonitrile and halocarbons such as dichloromethane and chloroform, though THF is used particularly preferably. Although the reaction can be carried out at −20–100° C., satisfactory results are normally obtained at room temperature.

Chart 18

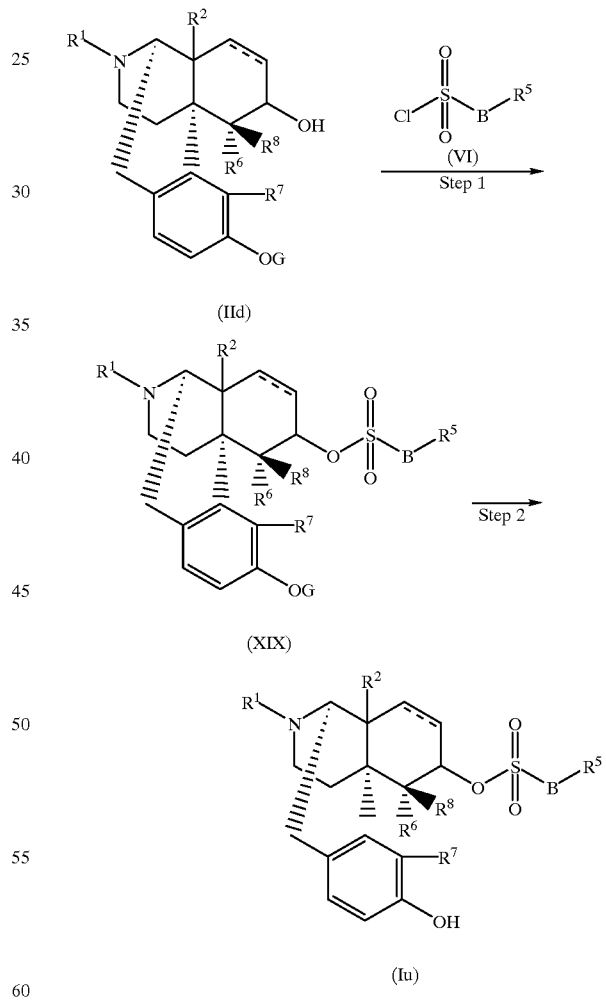

The free base obtained in the above steps can be converted into the salts with pharmacologically acceptable acids specifically by the methods shown below. Namely, a resulting free base is dissolved or suspended in a solvent followed by addition of acid and filtering of the precipitated solid or crystal, or in the case of not precipitating, a solvent of lower polarity is added, or the solvent is substituted with a solvent of lower polarity and filtering after precipitation. Alternatively, concentration and drying are performed after forming a salt. However, in the case organic solvent remains in these methods, drying under reduced pressure may be performed after freeze-drying in an aqueous solution. Examples of solvents used to dissolve or suspend the above free base include water, alcohols such as methanol, ethanol and isopropyl alcohol, halocarbons such as dichloromethane and chloroform, ethers such as ether, THF, DME and dioxane, esters such as ethyl acetate and methyl acetate, or their mixed solvents, while preferable examples include methanol, ethanol, isopropyl alcohol, ethyl acetate, chloroform, chloroform-methanol, water-methanol, and water-ethanol. Preferable examples of solvents used for precipitating solid include ether and ethyl acetate. Although it is desirable that an equivalent amount of acid be added, when it is possible to remove excess acid after washing the resulting salt, 1–10 equivalents may be used. In addition, acid may be added as is or suitably dissolved in the above-mentioned solvents and then added. For example, hydrochloric acid can be added in the form of concentrated hydrochloric acid, 1 N aqueous solution, a saturated methanol solution or a saturated ethyl acetate solution, while tartaric acid can be added in the form of a solid, an aqueous solution or a methanol solution. At the time of salt formation, since the temperature of the system may rise due to the heat of neutralization, there are cases in which favorable results are obtained if a water bath or ice bath is used.

As a result of both in vitro and in vivo pharmacological evaluation, the compounds of the present invention represented with general formula (I) were found to demonstrate excellent defensive effects against necrosis of brain nerve cells. Said compounds can therefore be used as brain cell protective agents for prevention and treatment of ischemic brain disorders, brain nerve cell disorders and dementia caused by impairment of brain nerve cells. More specifically, the compounds of the present invention are useful in pharmaceutical fields as inhibition and therapeutic agents of cerebrovascular diseases such as stroke, cerebral infarction, cerebral embolism, cerebral thrombosis, cerebral hemorrhage, subarachnoid hemorrhage and transitory ischemic attack (TIA); as preventive and therapeutic agents for sequelae based on these brain nerve cell disorders (consciousness disorders, motor paralysis, language disorders, sensory disorders, mental disorders and memory disorders); as preventive and therapeutic agents for neural diseases such as hypoxia, hypoglycemia, cerebral palsy, cerebral ischemic attack and Huntington's chorea; as preventive and therapeutic agents for cerebroneuronal function diseases such as senile dementia, Alzheimer's dementia, amnesia and cerebroneuronal disorders; suppression of activated oxygen disorders; and as preventive and therapeutic agents for degenerative nerve diseases such as epilepsy, depression and Parkinson's disease.

In addition, as a result of having the above-mentioned effects, the compounds of the present invention can be used as preventive or therapeutic drugs for ischemic heart diseases and circulatory organ diseases such as arteriosclerosis, myocardial infarction, arrhythmia and angina pectoris.

When the brain cell protective agent of the present invention is used clinically, it may be in the form of a free base or its salt. In addition, it may also be suitably mixed with stabilizers, buffers, diluents, isotonics, antiseptics and other vehicles. Examples of administrative forms include oral preparations such as tablets, capsules, granules, powders and syrups; injection preparations, parenteral preparations such as injection preparations, suppositories and liquids; or, local administration forms such as ointments, creams and compresses. It is desirable that the brain cell protective agent of the present invention contain from 1% to 90% by weight, and preferably from 30% to 70% by weight, of the above-mentioned active ingredients. Although the dose should be suitably selected according to symptoms, age, body weight and administration method, the normal adult dose is from 0.001 mg to 1 g per day as the amount of active ingredient in the case of injection preparations, and from 0.01 mg to 10 g in the case of oral preparations, each administered in a single dosing or divided among several dosings.

[EXAMPLES]

Although the following provides a detailed explanation of the present invention through its examples, the present invention is not limited to these examples.

[Reference Example 1]

17-Cyclopropylmethyl-3,14β-dihydroxy-4,5α-epoxy-6α-methylaminomorphinan 2

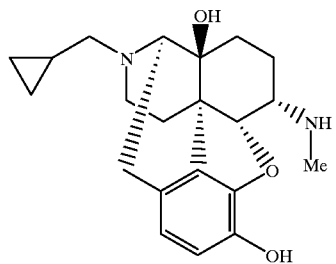

Naltrexone (1.0 g) and methylamine hydrochloride (0.99 g, 5 equivalents) were dissolved in methanol (15 ml) followed by stirring for 20 minutes at room temperature. This reaction solution was added to platinum oxide (0.05 g, 5 w %) in methanol (10 ml) activated in advance in a hydrogen atmosphere followed by hydrogenation for 4 hours at room temperature and atmospheric pressure. The catalyst was removed by Celite filtration and the solvent was distilled off. After adding saturated aqueous sodium bicarbonate (20 ml) and extracting with chloroform (20 ml×2), the extract was washed with saturated brine and dried with anhydrous sodium sulfate, and the solvent was distilled off. The resulting dark reddish-violet oily substance was dissolved in chloroform (2 ml) followed by addition of ethyl acetate (4 ml) to obtain the target compound (0.83 g, yield: 79%) by crystallization. A portion of this compound was removed and various spectra were measured in the form of a hydrochloride.

mp 270° C. (decomposition)

NMR (500 MHz, DMSO-$d_6$)

δ 0.40 (1H, m), 0.48 (1H, m), 0.61 (1H, m), 0.69 (1H, m), 0.95 (1H, m), 1.08 (1H, m), 1.47 (1H, m), 1.70 (1H, d, J=13.2 Hz), 1.81 (1H, m), 1.92 (1H, m), 2.49 (1H, m), 2.68 (3H, s), 2.72 (1H, m), 3.00 (1H, m), 3.08 (2H, m), 3.26 (2H, m), 3.57 (1H, m), 4.01 (3H, m), 4.97 (1H, brs), 6.50 (1H, s), 6.65 (1H, d, J=8.3 Hz), 6.78 (1H, d, J=8.3 Hz), 9.20 (2H, m).

1R (KBr)

υ 3200, 1510, 1464, 1238, 1116, 982, 859 $cm^{-1}$.

Mass (EI)

m/z 356 (M+) (measured in the free form)

Elementary Analysis: As $C_{21}H_{28}N_2O_3 \cdot 2HCl \cdot 0.2H_2O$

Calculated values: C 58.25; H 7.08; N 6.47; Cl 16.38

Measured values: C 58.35; H 7.20; N 6.44; Cl 16.14

[Reference Example 2]

17-Cyclopropylmethyl-3,14β-dihydroxy-4,5α-epoxy-6α-isobutylaminomorphinan 3 was obtained by following the procedure of Reference Example 1 but using isobutylamine instead of methylamine.

3

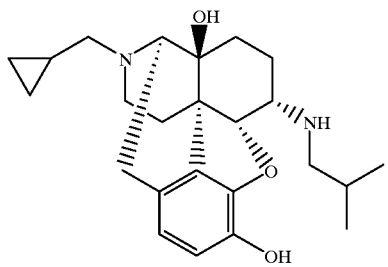

NMR (500 MHz, CDCl$_3$)

δ 0.22 (2H, m), 0.53 (2H, m), 0.84 (1H, m), 0.92 (1H, m), 0.94 (3H, d, J=6.7 Hz), 0.95 (3H, d, J=6.1 Hz), 1.40 (1H, dd, J=14.7, 10.4 Hz), 1.57 (1H, m), 1.68 (2H, m), 1.83 (1H, m), 2.30 (4H, m), 2.55 (2H, m), 2.63 (2H, m), 3.00 (1H, d, J=18.3 Hz), 3.06 (1H, d, J=6.7 Hz), 3.18 (1H, dt, J=13.4, 3.7 Hz), 4.3–5.2 (3H, br), 4.66 (1H, d, J=3.7 Hz), 6.46 (1H, d, J=7.9 Hz), 6.64 (1H, d, J=7.9 Hz).

IR (neat)

υ 3350, 1609, 1460, 1249, 1118, 913 cm$^{-1}$.

Mass (EI)

m/z 398 (M+).

[Reference Example 3]

17-cyclopropylmethyl-3,14β-dihydroxy-4,5α-epoxy-6β-N-methylbenzylamino)morphinan 4

4

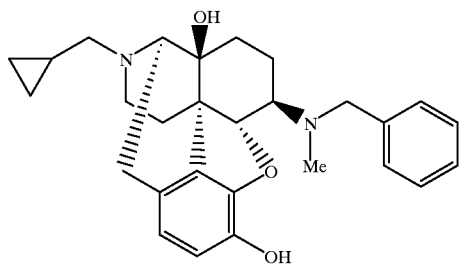

10.1 g of Naltrexone hydrochloride was separated with 150 ml of a 4:1 solution of chloroform and methanol and 150 ml of saturated aqueous sodium bicarbonate. The aqueous layer was extracted twice with 100 ml of a 4:1 solution of chloroform and methanol. The resulting organic layer was dried with anhydrous sodium sulfate followed by the addition of 3.26 g of benzoic acid and concentration after completely dissolving. After adequately drying the residue with a vacuum pump, the residue was suspended in 400 ml of benzene. After adding 5.2 ml of benzylmethylamine, 4.9 g of benzoic acid and 0.23 g of p-toluenesulfonic acid, the resulting mixture was stirred for 18 hours in a 110° C. oil bath while boiling off the water. After distilling off 330 ml of benzene at atmospheric pressure, 330 ml of ethanol and 4 g of molecular sieves 4A were added to the reaction mixture followed by cooling to 0° C. Next, 2.52 g of sodium cyanoborohydride was added followed by stirring for 2 hours at room temperature. After adding 200 ml of methanol to the reaction system, the molecular sieves was filtered out and the filtrate was concentrated. 200 ml of chloroform and 150 ml of saturated aqueous sodium bicarbonate were added to the resulting residue and the resulting precipitate was filtered followed by separation. The aqueous layer was extracted twice with 100 ml of chloroform, and the organic layer was concentrated after drying with anhydrous sodium sulfate. The resulting crude product was purified with silica gel column chromatography (480 g ammonia saturated ammonium chloroform/chloroform=2/1) to obtain 10.87 g of the oily target compound (yield: 91%). This was then recrystallized from methanol.

mp 71–80° C. (decomposition)

NMR (400 MHz, CDCl$_3$)

δ 0.09–0.13 (2H, m), 0.49–0.55 (2H, m), 0.79–0.88 (1H, m), 1.25–1.35 (1H, m), 1.43–1.49 (1H, m), 1.59–1.66 (2H, m), 1.87–2.00 (1H, m), 2.11 (1H, dt, J=3.4, 11.7 Hz), 2.19–2.27 (1H, m), 2.34 (3H, s), 2.35 (2H, d, J=6.8 Hz), 2.50–2.59 (1H, m), 2.56 (1H, dd, J=5.4, 18.1 Hz), 2.62 (1H, dd, J=4.4, 11.7 Hz), 2.99 (1H, d, J=18.1 Hz), 3.04 (1H, d, J=5.4 Hz), 3.53 (1H, d, J=13.2 Hz), 3.82 (1H, d, J=13.7 Hz), 4.68 (1H, d, J=8.3 Hz), 6.51 (1H, d, J=8.3 Hz), 6.65 (1H, d, J=8.3 Hz), 7.20–7.35 (5H, m).

IR (KBr)

υ 3428, 3220, 1638, 1615,1502, 1458, 1375, 1330, 1238, 1147, 1116, 1033, 990, 917, 857, 735 cm$^{-1}$.

Mass (EI)

m/z 446 (M+), 355, 286, 160.

Elementary Analysis: As $C_{28}H_{34}N_2O_3 \cdot 0.5H_2O$

Calculated values: C, 73.82; H, 7.74; N, 6.15.

Measured values: C, 73.94; H. 7.79; N, 6.08.

[Reference Example 4]

17-cyclopropylmethyl-3,14β-dihydroxy-4,5α-epoxy-6β-(N-ethylbenzylamino)morphinan 5·2 hydrochloride

5

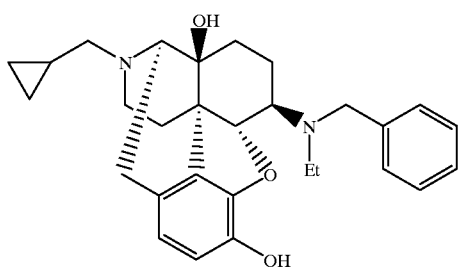

After suspending 7.24 g of naltrexone benzoate in 140 ml of benzene followed by the addition of 3.48 ml of benzylethylamine, the suspension was heated and refluxed for 17 hours while removing water by azeotropic distillation in a 110° C. oil bath. After allowing to cool by standing at room temperature, a solution containing 1.47 g of sodium cyanoborohydride dissolved in 140 ml of methanol was added and stirred for 1 hour at room temperature. After concentrating the reaction solution, 200 ml of 1% aqueous sodium bicarbonate was added followed by extracting three times with 150 ml of ethyl acetate. After combining the organic layers and washing with 50 ml of saturated brine, the product was dried with anhydrous sodium sulfate and concentrated. After suspending the resulting raw crystals in methanol, the suspension was filtered to obtain 4.744 g of the salt-free base of the target compound. After dissolving in hydrogen chloride/methanol followed by concentration, the product was reprecipitated from methanol-ethyl acetate to obtain 5.64 g of the target compound (yield: 68%).

mp>205° C. (decomposition)

NMR (400 MHz, DMSO-$d_6$)

δ 0.40 (1H, m), 0.52 (1H, m), 0.60 (1H, m), 0.68 (1H, m), 1.06 (1H, m), 1.57 (1.2H, t, J=7.8 Hz), 1.25 (1.8H, t, J=7.8 Hz), 1.29 (1H, m), 1.49 (1H, m), 1.82 (1H, m), 2.12 (1H, m), 2.26 (1H, m), 2.45 (1H, m), 2.61 (1H, m), 2.88 (1H, m), 2.97–3.18 (3H, m), 3.20–3.50 (4H, m), 3.92 (1H, m), 4.33 (0.4H, m), 4.47 (0.6H, m), 4.62 (0.4H, m), 4.68 (0.6H, m), 5.37 (0.4H, d, J=7.3 Hz), 5.42 (0.6H, d, J=7.8 Hz), 6.65 (0.6H, d, J=8.3 Hz), 6.67 (0.4H, s, OH), 6.69 (0.4H, d, J=8.3 Hz), 6.79 (0.6H, d, J=8.3 Hz), 6.81 (0.6H, s, OH), 6.83 (0.4H, d, J=8.3 Hz), 7.38–7.47 (3H, m), 7.62–7.75 (2H, m), 8.95 (1H, br s, NH+), 9.63 (0.6H, s, OH), 9.70 (0.4H, s, OH), 10.45 (0.6H, br s, NH+), 10.55 (0.4H, br s, NH+).

IR (KBr)

υ 3320, 1649, 1729, 1638, 1626, 1506, 1462, 1377, 1328, 1272, 1245, 1178, 1125, 1035, 922, 748, 702 cm$^{-1}$.

Mass (FAB)

m/z 461 ((M+H)$^+$).

Elementary analysis: As $C_{29}H_{36}N_2O_3 \cdot 2HCl \cdot 0.5H_2O \cdot 0.25EtOAc$ Calculated values: C 63.82; H 7.32; Cl 12.56; N 4.96
Measured values: C 63.97; H 7.41; Cl 12.32; N 4.98

[Reference Examples 5–8]

17-cyclopropylmethyl-3,14β-dihydroxy-4,5α-epoxy-6β-(N-isopropylbenzylamino)morphinan 6·2 hydrochloride (yield: 27%), 17-cyclopropylmethyl-3,14β-dihydroxy-4,5α-epoxy-6β-(N-isobutylbenzylamino)morphinan 7·2 hydrochloride (yield: 60%), 17-cyclopropylmethyl-3,14β-dihydroxy-4,5α-epoxy-6β-(N-butylbenzylamino)morphinan 8·2 hydrochloride (yield: 62%) and 17-cyclopropylmethyl-3,14β-dihydroxy-4,5α-epoxy-6β-(N-pentylbenzylamino)morphinan 9·2 hydrochloride (yield: 92%) were obtained by following the procedure of Reference Example 4 and using benzylisopropylamine, benzylisobutylamine, benzylbutylamine and benzylpentylamine instead of benzylethylamine.

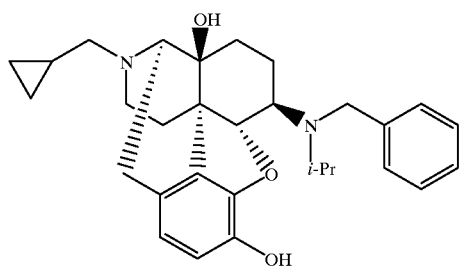

6

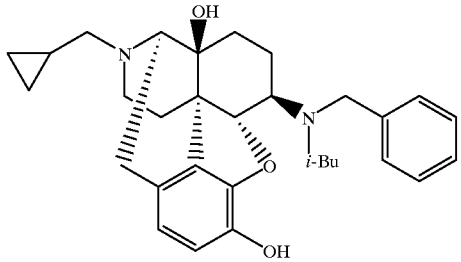

7

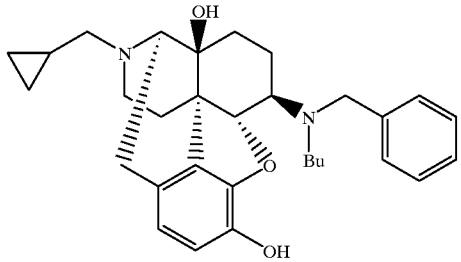

8

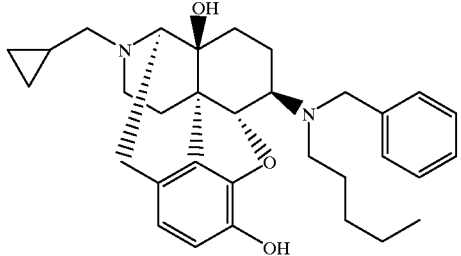

9

Compound 6·2 hydrochloride mp>165° C. (decomposition)

NMR (400 MHz, DMSO-$d_6$)

δ 0.41 (1H, m), 0.52 (1H, m), 0.59 (1H, m), 0.68 (1H, m), 1.07 (1H, m), 1.25 (2.1H, d, J=6.3 Hz), 1.34 (0.9H, d, J=6.3 Hz), 1.40 (3H, d, J=6.3 Hz), 1.40–1.52 (2H, m), 1.74 (1H, m), 1.88 (1H, m), 2.18 (1H, m), 2.45 (1H, m), 2.60 (1H, m), 2.86 (1H, m), 2.96–3.08 (2H, m), 3.25–3.48 (3H, m), 3.73 (1H, m), 3.92 (1H, m), 4.47 (0.7H, m), 4.61 (0.3H, m), 4.85 (0.7H, m), 4.91 (0.3H, m), 5.36 (1H, d, J=7.8 Hz), 6.68 (0.3H, d, J=8.3 Hz), 6.70 (0.7H, d, J=8.3 Hz), 6.81 (0.3H, d, J=8.3 Hz), 6.82 (1H, s, OH)., 6.85 (0.7H, d, J=8.3 Hz), 7.40–7.48 (3H, m), 7.63–7.74 (2H, m), 8.92 (1H, br s, NH+), 9.63 (0.7H, br s, NH+), 9.63 (0.3H, br s, OH), 9.67 (0.7H, s, OH), 9.90 (0.3H, br S, NH+).

IR (KBr)

υ 3388, 1729, 1638, 1620, 1506, 1460, 1379, 1325, 1247, 1178, 1123, 1035, 922, 748, 700 cm$^{-1}$.

Mass (FAB)

m/z 475 ((M+H)$^+$).

Elementary analysis: As $C_{30}H_{38}N_2O_3 \cdot 2HCl \cdot 0.6H_2O \cdot 0.3EtOAc$ Calculated values: C 64.08; H 7.51; Cl 12.12; N 4.79
Measured values: C 64.36; H 7.77; Cl 11.82; N 4.85

Compound 7·2 hydrochloride mp>190° C. (decomposition)

NMR (400 MHz, DMSO-$d_6$)

δ 0.42 (1H, m), 0.53 (2.1H, d, J=6.3 Hz), 0.55 (1H, m), 0.59 (1H, m), 0.68 (1H, m), 0.73 (0.9H, d, J=6.3 Hz), 0.88 (2.1H, d, J=6.5 Hz), 0.94 (0.9H, , J=6.5 Hz), 1.08 (1H, m), 1.20–1.58 (2H, m), 1.80 (1H, m), 2.06–2.50 (3H, m), 2.66 (1H, m), 2.82–3.14 (4H, m), 3.30–3.60 (5H, m), 3.92 (1H, m), 4.45–4.75 (2H, m), 5.39 (0.7H, d, J=7.3 Hz), 5.48 (0.3H, d, J=7.3 Hz), 6.55–7.30 (1H, m, OH), 6.66 (0.3H, d, J=8.1 Hz), 6.72 (0.7H, d, J=8.1 Hz), 6.78 (0.3H, d, J=8.1 Hz), 6.81 (0.7H, d, J=8.1 Hz), 7.38–7.48 (3H, m), 7.72–7.92 (2H, m), 8.78 (0.3H, br s, NH+), 8.95 (0.7H, br s, NH+), 9.27 (0.3H, br s, OH), 9.55 (0.7H, br s, OH), 9.58 (0.3H, s, NH+), 9.93 (0.7H, br s, NH+).

IR (KBr)
υ 3378, 1721, 1638, 1626, 1504, 1462, 1377, 1325, 1274, 1176, 1125, 1035, 922 cm$^{-1}$.

Mass (FAB)
m/z 489 ((M+H)$^+$).

Elementary analysis: As $C_{31}H_{40}N_2O_3 \cdot 2HCl \cdot 0.35EtOAc$
Calculated values: C 65.69; H 7.62; Cl 11.97; N 4.73
Measured values: C 65.96; H 7.60; Cl 11.72; N 4.87

Compound 8·2 hydrochloride
mp>180° C. (decomposition)
NMR (400 MHz, DMSO-d$_6$)
δ 0.41 (1H, m), 0.52 (1H, m), 0.60 (1H, m), 0.68 (1H, m), 0.78 (1.8H, t, J=7.3 Hz), 0.85 (1.2H, t, J=7.3 Hz), 1.07 (1H, m), 1.11–1.37 (3H, m), 1.60–1.77 (3H, m), 1.81 (1H, m), 2.14 (1H, m), 2.26 (1H, m), 2.45 (1H, m), 2.61 (1H, m), 2.88 (1H, m), 2.94–3.18 (3H, m), 3.20–3.45 (4H, m), 3.91 (1H, m), 4.36 (0.4H, m), 4.46 (0.6H, m), 4.57 (0.4H, m), 4.69 (0.6H, m), 5.38 (0.4H, d, J=7.3 Hz), 5.43 (0.6H, d, J=7.8 Hz), 6.66 (0.6H, d, J=8.1 Hz), 6.69 (0.4H, d, J=8.1 Hz), 6.72 (0.4H, s, OH), 6.79 (0.6H, d, J=8.1 Hz), 6.82 (0.6H, s, OH), 6.83 (0.4H, d, J=8.1 Hz), 7.38–7.47 (3H, m), 7.62–7.80 (2H, m), 8.95 (1H, br s, NH+), 9.62 (0.6H, s, OH), 9.66 (0.4H, s, OH), 10.48 (0.6H, br s, NH+), 10.54 (0.4H, br s, NH+).

IR (KBr)
υ 3330, 1729, 1642, 1626, 1506, 1462, 1383, 1325, 1249, 1176, 1125, 1035, 996, 922, 861, 812, 748, 702 cm$^{-1}$.

Mass (EI)
m/z 488 (M$^+$).

Elementary analysis: As $C_{31}H_{40}N_2O_3 \cdot 2HCl \cdot 0.2H_2O \cdot 0.2EtOAc$
Calculated values: C 65.52; H 7.61; Cl 12.17; N 4.81
Measured values: C 65.52; H 7.81; Cl 12.11; N 4.81

Compound 9·2 hydrochloride
mp>185° C. (decomposition)
NMR (400 MHz, DMSO-d$_6$)
δ 0.41 (1H, m), 0.52 (1H, m), 0.59 (1H, m), 0.67 (1H, m), 0.78 (1.2H, t, J=7.1 Hz), 0.83 (1.8H, t, J=7.1 Hz), 1.05–1.85 (10H, m), 2.14 (1H, m), 2.26 (1H, m), 2.45 (1H, m), 2.60 (1H, m), 2.82–3.46 (8H, m), 3.91 (1H, m), 4.37 (0.4H, m), 4.47 (0.6H, m), 4.58 (0.4H, m), 4.68 (0.6H, m), 5.37 (0.4H, d, J=7.3 Hz), 5.43 (0.6H, d, J=7.8 Hz), 6.66 (0.6H, d, J=8.3 Hz), 6.69 (0.4H, d, J=8.3 Hz), 6.72, 6.74 (1H, br s, OH), 6.78 (0.6H, d, J=8.3 Hz), 6.82 (0.4H, d, J=8.3 Hz), 7.38–7.48 (3H, m), 7.60–7.82 (2H, m), 8.95 (1H, br s, NH+), 9.60 (0.6H, s, OH), 9.65 (0.4H, s, OH), 10.46 (0.6H, br s, NH+), 10.54 (0.4H, br s, NH+).

IR (KBr)
υ 3350, 1649, 1638, 1626, 1508, 1460, 1365, 1323, 1270, 1251, 1125, 1033, 924, 748, 700 cm$^{-1}$.

Mass (FAB)
m/z 503 ((M+H)$^+$).

Elementary analysis: As $C_{32}H_{42}N_2O_3 \cdot 2HCl$
Calculated values: C 66.77; H 7.70; Cl 12.32; N 4.87
Measured values: C 66.91; H 7.60; Cl 12.17; N 5.09

[EXAMPLES 1–5]

17-cyclopropylmethyl-3,14β-dihydroxy-4,5α-epoxy-6β-(N-2-phenethylbenzylamino)morphinan 10·2 hydrochloride (yield: 92%), 17-cyclopropylmethyl-3,14β-dihydroxy-4,5α-epoxy-6β-[N-(cyclohexylmethyl)benzylamino]morphinan 11·2 tartrate (yield: 50%), 17-cyclopropylmethyl-3,14β-dihydroxy-4,5α-epoxy-6β-(N-3-phenylpropylbenzylamino) morphinan 12·1 tartrate (yield: 65%), 17-cyclopropylmethyl- 3,14β-dihydroxy-4,5α-epoxy-6β-(N-4-phenylbutylbenzylamino) morphinan 13·2 tartrate (yield: 68%) and 17-cyclopropylmethyl-3,14β-dihydroxy-4, 5α-epoxy-6β-[N-(2,2-diphenylethyl)benzylamino) morphinan 14·2 tartrate (yield: 62%) were obtained by following the procedure of Reference Example 4 and using N-2-phenethylbenzylamine, N-(cyclohexylmethyl) benzylamine, N-3-phenylpropylbenzylamine, N-4-phenylbutylbenzylamine and N-(2,2-diphenylethyl) benzylamine instead of benzylethylamine.

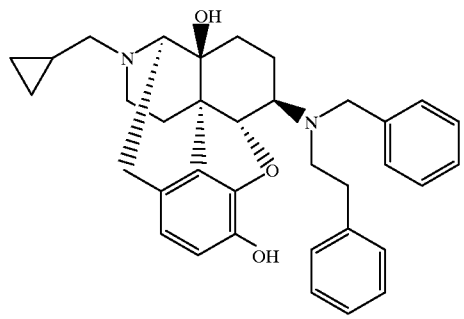

10

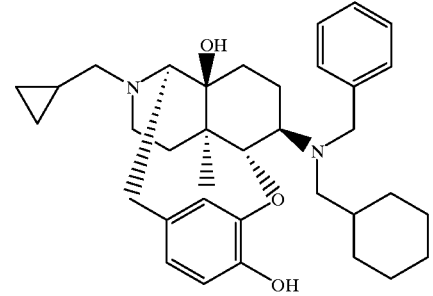

11

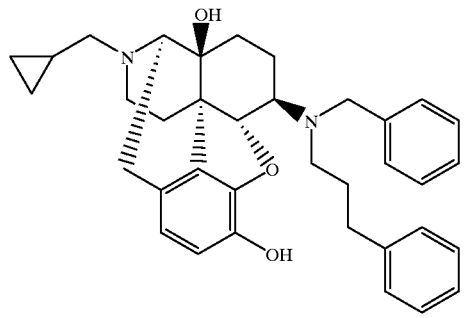

12

13

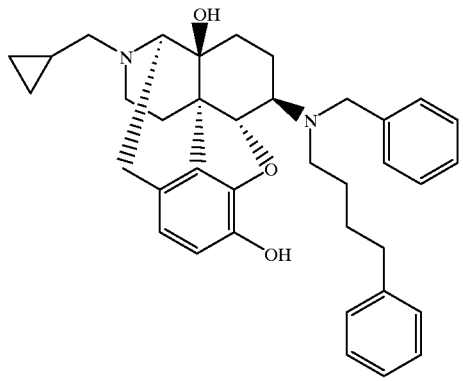

14

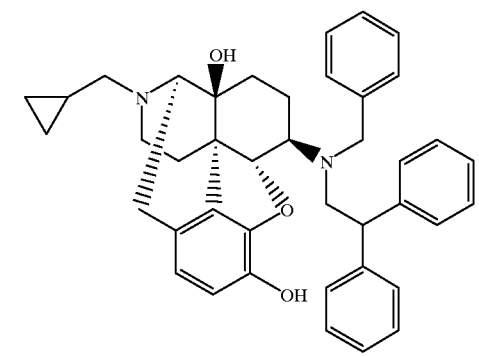

Compound 10·2 hydrochloride
mp>178° C. (decomposition)
NMR (400 MHz, DMSO-d₆)
δ 0.41 (1H, m), 0.52 (1H, m), 0.60 (1H, m), 0.69 (1H, m), 1.08 (1H, m), 1.29 (1H, m), 1.52 (1H, br d, J=11.2 Hz), 1.83 (1H, m), 2.22 (1H, m), 2.31 (1H, m), 2.47 (1H, m), 2.62 (1H, m), 2.77–3.18 (8H, m), 3.30–3.42 (2H, m), 3.93 (1H, m), 4.46 (0.4H, m), 4.58 (0.6H, m), 4.72 (0.4H, m), 4.78 (0.6H, m), 5.43 (0.4H, d, J=7.8 Hz), 5.51 (0.6H, d, J=7.8 Hz), 6.68 (0.6H, d, J=8.1 Hz), 6.71 (0.4H, d, J=8.1 Hz), 6.78 (1H, m, OH), 6.81 (0.6H, d, J=8.1 Hz), 6.86 (0.4H, d, J=8.1 Hz), 7.05–7.54 (7H, m), 7.58–7.90 (3H, m), 8.97 (1H, br s, NH+), 9.60 (1H, s, NH+), 9.74 (1H, s, OH).
IR (KBr)
υ 3500, 1638, 1622, 1502, 1460, 1323, 1241, 1127, 1035, 920, 754, 745 cm⁻¹.
Mass (FAB)
m/z 537 ((M+H)⁺).
Elementary analysis: As $C_{35}H_{40}N_2O_3 \cdot 2HCl$
Calculated values: C 68.96; H 6.94; Cl 11.63; N 4.60
Measured values: C 69.03; H 6.93; Cl 11.85; N 4.83
Compound 11·2 tartrate
mp>120° C. (decomposition)
NMR (400 MHz, DMSO-d₆)
δ 0.20–0.31 (2H, m), 0.47–0.60 (2H, m), 0.87–0.98 (1H, m), 1.12–1.22 (1H, m), 1.33 (1H, d, J=10.7 Hz), 1.41–1.71 (4H, m), 1.72–1.85 (1H, m), 2.12–2.30 (2H, m), 2.43–2.87 (9H, m), 3.09 (1H, d, J=19.0 Hz), 3.33 (1H, br s), 3.60 (1H, d, J=15.1 Hz), 3.87 (1H, d, J=14.7 Hz) 4.06 (2H, s), 4.58 (1H, d, J=7.8 Hz), 6.50 (1H, d, J=8.3 Hz), 6.61 (1H, d, J=7.8 Hz), 7.05–9.31 (8H, m), 7.43 (2H, d, J=7.3 Hz).

IR (KBr)
υ 3316, 1731, 1603, 1460, 1398, 1338, 1309, 1267, 1125, 1069 cm⁻¹.
Mass (FAB)
m/z 529 ((M+H)⁺).
Elementary analysis: As $C_{34}H_{44}N_2O_3 \cdot 2C_4H_6O_6$
Calculated values: C 60.86; H 6.81; N 3.38
Measured values: C 60.87; H 6.86; N 3.48
Compound 12·1 tartrate
mp>120° C. (decomposition)
NMR (400 MHz, DMSO-d₆)
δ 0.20–0.31 (2H, m), 0.47–0.60 (2H, m), 0.87–0.98 (1H, m), 1.12–1.22 (1H, m), 1.33 (1H, d, J=10.7 Hz), 1.41–1.71 (4H, m), 1.72–1.85 (1H, m), 2.12–2.30 (2H, m), 2.43–2.87 (9H, m), 3.09 (1H, d, J=19.0 Hz), 3.33 (1H, br s), 3.60 (1H, d, J=15.1 Hz), 3.87 (1H, d, J=14.7 Hz), 4.06 (2H, s), 4.22 (9H, br s, OH), 4.58 (1H, d, J=7.8 Hz), 6.50 (1H, d, J=8.3 Hz), 6.61 (1H, d, J=7.8 Hz), 7.05–7.31 (8H, m), 7.43 (2H, d, J=7.3 Hz), 9.20 (1H, br s, OH).
IR (KBr)
υ 3420, 1603, 1460, 1311, 1129, 1069, 1033 cm⁻¹.
Mass (FAB)
m/z 551 ((M+H)⁺).
Elementary analysis: As $C_{36}H_{42}N_2O_3 \cdot C_4H_6O_6 \cdot 0.5H_2O$
Calculated values: C 67.68; H 6.96; N 3.95
Measured values: C 67.63; H 6.77; N 4.09
Compound 13·2 tartrate
mp>110° C. (decomposition)
NMR (400 MHz, DMSO-d₆)
δ 0.22–0.38 (2H, m), 0.47–0.65 (2H, m), 0.89–1.02 (1H, m), 1.12–1.22 (1H, m), 1.27–1.67 (7H, m), 1.72–1.87 (1H, ), 2.05–4.40 (9H, br), 2.19–2.36 (2H, m), 2.40–2.54 (4H, m), 2.57–2.69 (2H, m), 2.72–3.00 (3H, m), 3.14 (1H, d, J=19.0 Hz), 3.44 (1H, m), 3.57 (1H, d, J=14.7 Hz), 3.84 (1H, d, J=14.7 Hz), 4.14 (4H, s), 4.61 (1H, d, J=7.8.Hz), 6.51 (1H, d, J=8.3 Hz), 6.62 (1H, d, J=7.8 Hz), 7.05–7.48 (10H, m), 9.17 (1H, br).
IR (KBr)
υ 3400, 1603, 1458, 1309, 1267, 1216, 1131, 1069, 1035 cm⁻¹.
Mass (FAB)
m/z 565 ((M+H)⁺).
Elementary analysis: As $C_{37}H_{44}N_2O_3 \cdot 2C_4H_6O_6$
Calculated values: C 62.49; H 6.53; N 3.24
Measured values: C 62.32; H 6.43; N 3.45
Compound 14·2 tartrate
mp>120° C. (decomposition)
NMR (400 MHz, DMSO-d₆)
δ 0.21–0.38 (2H, m), 0.47–0.64 (2H, m), 0.88–1.11 (3H, m), 1.28–1.48 (2H, m), 1.78 (1H, m), 2.00–4.80 (5H, br s, OH), 2.20–2.34 (2H, m), 2.44 (1H, m), 2.58–3.20 (4H, m), 3.07–3.22 (2H, m), 3.24–3.33 (1H, m), 3.36–3.49 (1H, m), 3.73 (1H, d, J=14.5 Hz), 3.87 (1H, d, J=14.5 Hz), 4.10 (1H, t, J=7.3 Hz), 4.15 (4H, s), 4.66 (1H, d, J=7.8 Hz), 6.53 (1H, d, J=8.1 Hz), 6.69 (1H, d, J=8.1 Hz), 6.80–10.00 (4H, br s, OH), 7.05–7.40 (15H, m), 9.35 (1H, br s, OH).
IR (KBr)
υ 3480, 1603, 1458, 1129, 1069, 1035, 746, 702 cm⁻¹.
Mass (FAB)
m/z 613 ((M+H)+).
Elementary analysis: As $C_{41}H_{44}N_2O_3 \cdot 2C_4H_6O_6 \cdot 0.5H_2O$
Calculated values: C 63.83, H 6.23; N 3.04
Measured values: C 63.79; H 6.21; N 3.16

[Reference Example 5]

17-Cyclopropylmethyl-4,5α-epoxy-3,14β-dihydroxy-6β-methylaminomorphinan 15

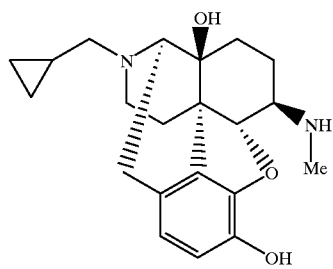

12.65 g of 17-cyclopropylmethyl-4,5α-epoxy-3,14β-dihydroxy-6β-N-methylbenzylaminomorphinan 4·2 hydrochloride synthesized in Reference Example 3 (converted to a hydrochloride by established methods) was dissolved in 250 ml of methanol followed by the addition of 2.53 g of 5% palladium-carbon and stirring for 4 hours in a hydrogen atmosphere. After removing the catalyst using Celite, the filtrate was concentrated. 100 ml of a 4:1 solution of chloroform and ethanol and 100 ml of saturated aqueous sodium bicarbonate were added to the resulting residue to separate, and the aqueous layer was then extracted twice with 100 ml of a 4:1 solution of chloroform and ethanol. After drying the organic layer with anhydrous sodium sulfate, the dried organic layer was concentrated to obtain 8.00 g of crude product. This was then recrystallized from methanol to obtain 5.84 g of the target compound (yield: 67%).

NMR (400 MHz, CDCl$_3$)

δ 0.10–0.14 (2H, m), 0.50–0.55 (2H, m), 0.79–0.86 (1H, m), 1.38 (1H, dt, J=2.9 Hz, 12.8 Hz), 1.41–1.48 (1H, m), 1.58–1.72 (2H, m), 1.78–1.91 (1H, m), 2.08–2.25 (2H, m), 2.36 (1H, d, J=6.6 Hz), 2.45 (3H, s), 2.49–2.65 (3H, m), 3.00 (1H, d, J=18.3 Hz), 3.05 (1H, d, J=5.9 Hz), 4.48 (1H, d, J=7.7 Hz), 6.54 (1H, d, J=8.1 Hz), 6.66 (1H, d, J=8.1 Hz).

IR (KBr)

υ 3380, 2926, 1638, 1607, 1462, 1255, 1180, 795 cm$^{-1}$.

Mass (EI)

m/e 356 (M+)

Elementary Analysis: C$_{21}$H$_{28}$O$_3$N$_2$

Calculated values: C, 70.76; H, 7.92; N, 7.86.

Measured values: C, 70.51; H, 7.94; N, 7.84.

[Reference Examples 10–14]

17-cyclopropylmethyl-3,14β-dihydroxy-4,5α-epoxy-6β-ethylaminomorphinan 16 (yield: 100%), 17-cyclopropylmethyl- 3,14β-dihydroxy-4,5α-epoxy-6β-isopropylaminomorphinan 17 (yield: 100%), 17-cyclopropylmethyl-3,14β-dihydroxy-4,5α-epoxy-6β-isobutylaminomorphinan 18 (yield: 100%), 17-cyclopropylmethyl-3,14β-dihydroxy-4,5α-epoxy-6β-butylaminomorphinan 19 (yield: 100%) and 17-cyclopropylmethyl-3,14β-dihydroxy-4,5α-epoxy-6β-pentylaminomorphinan 20 (yield: 100%) were obtained by following the procedure of Reference Example 9 and using 17-cyclopropylmethyl-3,14β-dihydroxy-4,5α-epoxy-6β-(N-ethylbenzylamino)morphinan 5·2 hydrochloride, 17-cyclopropylmethyl-3,14β-dihydroxy-4,5α-epoxy-6β-(N-isopropylbenzylamino)morphinan 6·2 hydrochloride, 17-cyclopropylmethyl-3,14β-dihydroxy-4,5α-epoxy-6β-(N-isobutylbenzylamino)morphinan 7·2 hydrochloride, 17-cyclopropylmethyl-3,14β-dihydroxy-4,5α-epoxy-6β-(N-butylbenzylamino)morphinan 8·2 hydrochloride and 17-cyclopropylmethyl-3,14β-dihydroxy-4,5α-epoxy-6β-(N-pentylbenzylamino)morphinan 9·2 hydrochloride instead of 17-cyclopropylmethyl-3,14β-dihydroxy-4,5α-epoxy-6β-N-methylbenzylaminomorphinan 4·2 hydrochloride for the starting material.

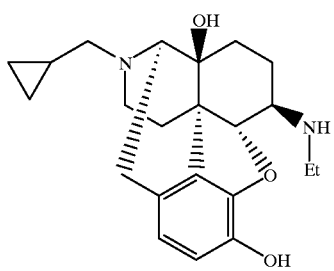

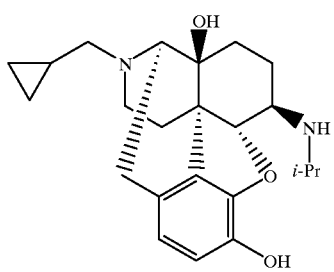

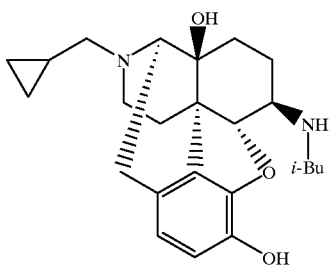

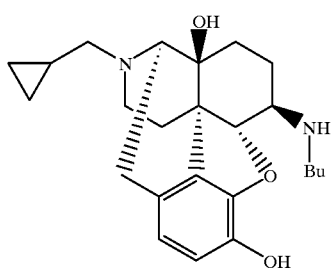

-continued

Compound 16
NMR (400 MHz, CDCl₃)
δ 0.08–0.17 (2H, m), 0.48–0.56 (2H, m), 0.83 (1H, m), 1.21 (3H, t, J=7.1 Hz), 1.34–1.45 (2H, m), 1.60 (1H, m), 1.67 (1H, m), 1.92 (1H, m), 2.13 (1H, ddd, J=12.2, 12.2, 3.4 Hz), 2.20 (1H, ddd, J=12.2, 12.2, 4.9 Hz), 2.37 (2H, d, J=6.3 Hz), 2.52–2.68 (3H, m), 2.71 (1H, m), 2.83 (1H, m), 2.99 (1H, d, J=18.0 Hz), 3.05 (1H, d, J=5.9 Hz), 4.51 (1H, d, J=7.3 Hz), 5.10 (3H, br s, 2×OH+NH), 6.54 (1H, d, J=8.1 Hz), 6.65 (1H, d, J=8.1 Hz).
IR (liquid film)
υ 3374, 1638, 1609, 1510, 1454, 1396, 1321, 1247, 1112, 1035, 984, 919, 853, 754 cm⁻¹.
Mass (EI)
m/z 370 (M⁺).

Compound 17
NMR (400 MHz, CDCl₃)
δ 0.12 (2H, m), 0.52 (2H, m), 0.83 (1H, m), 1.05 (3H, t, J=6.3 Hz), 1.13 (3H, d, J=6.3 Hz), 1.36 (1H, ddd, J=13.2, 13.2, 3.4 Hz), 1.43 (1H, br d, J=12.7 Hz), 1.59 (1H, ddd, J=13.2, 3.4, 3.0 Hz), 1.68 (1H, m), 1.78 (1H, m), 2.12 (1H, ddd, J=12.2 12.2, 3.5 Hz), 2.20 (1H, ddd, J=12.2, 12.2, 4.4 Hz), 2.36 (2H, d, J=6.8 H), 2.40 (2H, br s, OH, NH), 2.52–2.64 (3H, m), 3.00 (1H, d, J=18.1 Hz), 3.03–3.09 (2H, m), 4.41 (1H, d, J=7.3 Hz), 5.05 (1H, br s, OH), 6.55 (1H, d, J=8.1 Hz), 6.69 (1H, d, J=8.1 Hz).
IR (liquid film)
υ 3288, 1636, 1609, 1506, 1458, 1388, 1334, 1151, 1120, 1036, 984, 752 cm⁻¹.
Mass (EI)
m/z 384 (M⁺).

Compound 18
NMR (400 MHz, CDCl₃)
δ 0.12 (2H, m), 0.52 (2H, m), 0.83 (1H, m), 0.98 (3H, t, J=6.3 Hz), 1.01 (3H, d, J=6.3 Hz), 1.36–1.44 (2H, m), 1.57–1.70 (2H, m), 1.84 (1H, m), 1.94 (1H, m), 2.00 (2H, br s, OH, NH), 2.13 (1H, ddd, J=12.2, 12.2, 3.4 Hz), 2.21 (1H, ddd, J=12.2, 12.2., 4.4 Hz), 2.36 (2H, d, J=6.8 Hz), 2.47–2.68 (5H, m), 2.99 (1H, d, J=18.5 Hz), 3.05 (1H, d, J=5.9 Hz), 4.50 (1H, d, J=7.3 Hz), 5.15 (1H, br S, OH), 6.53 (1H, d, J=8.3 Hz), 6.63 (1H, d, J=8.3 Hz).
IR (liquid film)
υ 3318, 1607, 1456, 1394, 1334, 1257, 1149, 1120, 1036, 980, 915, 857, 750 cm⁻¹.
Mass (EI)
m/z 398 (M⁺).

Compound 19
NMR (400 MHz, CDCl₃)
δ 0.12 (2H, m), 0.52 (2H, m), 0.83 (1H, m), 0.94 (3H, t, J=7.3 Hz), 1.34–1.48 (4H, m), 1.53–1.69 (4H, m),1.94 (1H, m), 2.13 (1H, ddd, J=12.2, 12.2, 3.4 Hz), 2.21 (1H, ddd, J=12.2, 12.2, 4.9 Hz), 2.36 (2H, d, J=6.3 Hz), 2.40 (2H, br S, OH, NH), 2.53–2.77 (5H, m), 2.99 (1H, d, J=18.1 Hz), 3.04 (1H, d, J=5.6 Hz), 4.49 (1H, d, J=7.3 Hz), 5.12 (1H, br s, OH), 6.53 (1H, d, J=8.1 Hz), 6.63 (1H, d, J=8.1 Hz).
IR (liquid film)
υ 3302, 1636, 1609, 1506, 1458, 1396, 1334, 1257, 1218, 1149, 1114, 1036, 982, 915, 855, 803, 748 cm⁻¹.
Mass (EI)
m/z 398 (M⁺).

Compound 20
NMR (400 MHz, CDCl₃)
δ 0.12 (2H, m), 0.52 (2H, m), 0.83 (1H, m), 0.91 (3H, t, J=7.1 Hz), 1.28–1.45 (6H, m), 1.56–1.69 (4H, m), 1.94 (1H, m), 2.13 (1H, ddd, J=12.2, 12.2, 3.4 Hz), 2.21 (1H, ddd, J=12.2, 12.2, 4.4 Hz), 2.36 (2H, d, J=7.8 Hz), 2.52–2.73 (5H, m), 2.99 (1H, d, J=18.5 Hz), 3.04 (1H, d, J=5.4 Hz), 4.19 (1H, d, J=7.3 Hz), 5.12 (3H, br s, 2×OH+NH), 6.53 (1H, d, J=8.1 Hz), 6.63 (1H, d, J=8.1 Hz).
IR (liquid film)
υ 3386, 1638, 1607, 1504, 1460, 1398, 1334, 1255, 1149, 1116, 1036, 982, 915, 855, 801, 748 cm⁻¹.
Mass (EI)
m/z 412 (M⁺).

[EXAMPLES 6–10]

17-cyclopropylmethyl-3,14β-dihydroxy-4,5α-epoxy-6β-(2-phenethylamino)morphinan 21 (yield: 95%), 17-cyclopropylmethyl-3,14β-dihydroxy-4,5α-epoxy-6β-(cyclohexylmethyl)aminomorphinan 22 (yield: 98%), 17-cyclopropylmethyl-3,14β-dihydroxy-4,5α-epoxy-6β-(3-phenylpropylamino)morphinan 23 (yield: 99%), 17-cyclopropylmethyl-3,14β-dihydroxy-4,5α-epoxy-6β-(4-phenylbutylamino)morphinan 24 (yield: 100%) and 17-cyclopropylmethyl-3,14β-dihydroxy-4,5α-epoxy-6β-(2,2-diphenylethylamino)morphinan 25 (yield: 97%) were obtained by following the procedure of Reference Example 9 and using 17-cyclopropylmethyl-3,14β-dihydroxy-4,5α-epoxy-6β-(N-2-phenethylbenzylamino)morphinan 10·2 hydrochloride, 17-cyclopropylmethyl-3,14β-dihydroxy-4,5α-epoxy-6β-[N-(cyclohexylmethyl)benzylamino]morphinan 11·2 hydrochloride, 17-cyclopropylmethyl-3,14β-dihydroxy-4,5α-epoxy-6β-(N-3-phenylpropylbenzylamino)morphinan 12·2 hydrochloride, 17-cyclopropylmethyl-3,14β-dihydroxy-4,5α-epoxy-6β-(N-4-phenylbutylbenzylamino)morphinan 13·2 hydrochloride and 17-cyclopropylmethyl-3,14β-dihydroxy-4,5α-epoxy-6β-[N-(2,2-diphenylethyl)benzylamino)morphinan 14·2 hydrochloride instead of 17-cyclopropylmethyl-3,14β-dihydroxy-4,5α-epoxy-6β-N-methylbenzylaminomorphinan 4·2 hydrochloride for the starting material.

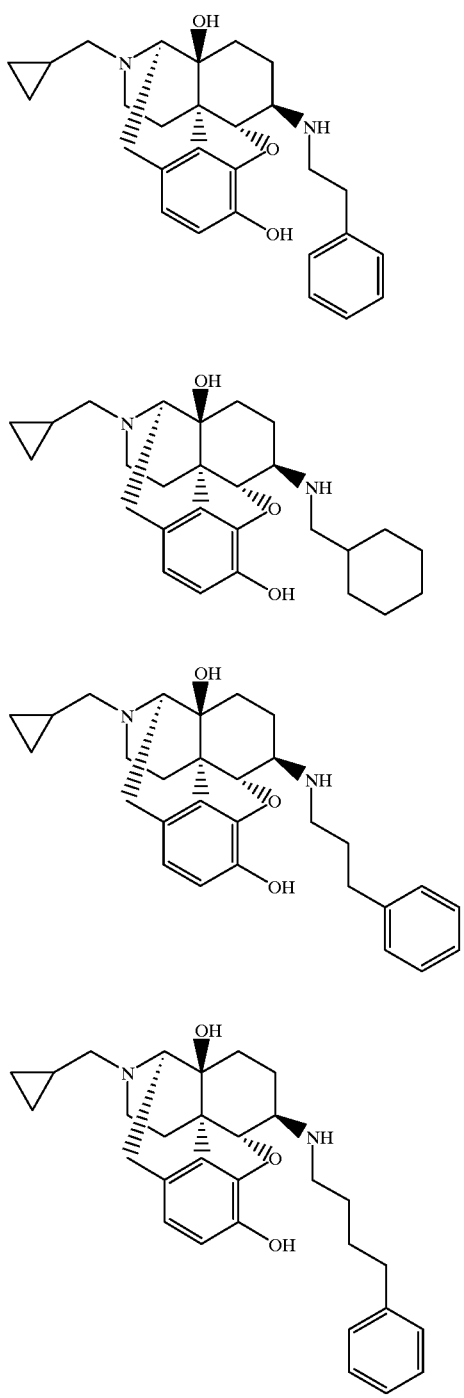

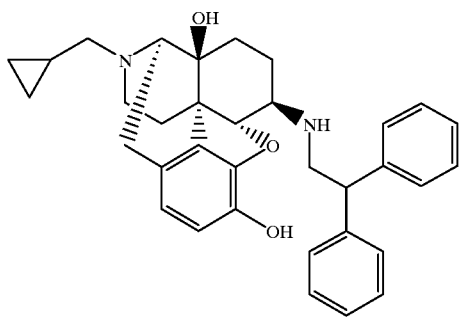

Compound 21
NMR (400 MHz, CDCl₃)

δ 0.12 (2H, m), 0.52 (2H, m), 0.83 (1H, m), 1.36 (1H, ddd, J=13.2, 13.2, 2.9 Hz), 1.42 (1H, m), 1.58 (1H, m), 1.65 (1H, m), 1.87 (1H, m), 2.12 (1H, ddd, J=12.2, 12.2, 3.4 Hz), 2.20 (1H, ddd, J=12.2, 12.2, 4.4 Hz), 2.30 (2H, br s, OH, NH), 2.35 (2H, d, J=6.8 Hz), 2.53–2.64 (3H, m), 2.73–3.05 (6H, m), 4.36 (1H, d, J=7.3 Hz), 4.95 (1H, br s, OH), 6.54 (1H, d, J=8.1 Hz), 6.65 (1H, d, J=8.1 Hz), 7.18–7.34 (5H, m).

IR (liquid film)

υ 3300, 1636, 1605, 1497, 1456, 1325, 1245, 1187, 1129, 1035, 982, 915, 857, 748 cm⁻¹.

Mass (FAB)

m/z 447 ((M+H⁺)).

Compound 22
NMR (400 MHz, CDCl₃)

δ 0.12 (2H, m), 0.51 (2H, m), 0.83 (1H, m), 0.92–1.07 (2H, m), 1.13–1.30 (3H, m), 1.35–1.47 (2H, m), 1.52–1.82 (7H, m), 1.85 (2H, br s, OH, NH), 1.88–2.02 (2H, m), 2.14 (1H, ddd, J=12.2, 12.2, 3.4 Hz), 2.21 (1H, ddd, J=12.2, 12.2, 4.9 Hz), 2.36 (2H, d, J=6.3 Hz), 2.47–2.72 (5H, m), 2.99 (1H, d, J=18.0 Hz), 3.03 (1H, d, J=5.4 Hz), 4.46 (1H, d, J=7.3 Hz), 5.15 (1H, br s, OH), 6.53 (1H, d, J=8.3 Hz), 6.61 (1H, d, J=8.3 Hz).

IR (liquid film)

υ 3322, 1638, 1605, 1460, 1398, 1336, 1257, 1218, 1151, 1036, 977, 915, 861, 803, 754 cm⁻¹.

Mass (EI)

m/z 438 (M⁺).

Compound 23
NMR (400 MHz, CDCl₃)

δ 0.12 (2H, m), 0.52 (2H, m), 0.83 (1H, m), 1.34–1.43 (2H, m), 1.50 (2H, br s, OH, NH), 1.58–1.68 (2H, m), 1.85–1.96 (3H, m), 2.07–2.22 (2H, m), 2.35 (2H, d, J=6.3 Hz), 2.52–2.81 (7H, m), 2.99 (1H, d, J=18.1 Hz), 3.04 (1H, d, J=5.4 Hz), 4.48 (1H, d, J=7.8 Hz), 5.10 (1H, br s, OH), 6.54 (1H, d, J=7.9 Hz), 6.64 (1H, d, J=7.9 Hz), 7.14–7.28 (5H, m).

IR (liquid film)

υ 3310, 1636, 1605, 1497, 1456, 1396, 1334, 1255, 1218, 1149, 1129, 1035, 980, 913 cm$^{-1}$.

Mass (EI)

m/z 460 (M$^+$).

Compound 24

NMR (400 MHz, CDCl$_3$)

δ 0.08–0.18 (2H, m), 0.47–0.57 (2H, m), 0.83 (1H, m), 1.20–3.13 (2H, br s), 1.33–1.44 (2H, m), 1.53–1.72 (6H, m), 1.86–1.99 (1H, m), 2.08–2.26 (2H, m), 2.36 (2H, d, J=6.4 Hz), 2.49–2.74 (7H, m), 2.99 (1H, d, J=18.7 Hz), 3.05 (1H, d, J=5.4 Hz), 4.47 (1H, d, J=7.3 Hz), 5.11 (1H, br s), 6.54 (1H, d, J=8.3 Hz), 6.63 (1H, d, J=8.3 Hz), 7.10–7.30 (5H, m).

IR (KBr)

υ 3370, 1605, 1497, 1456, 1334, 1255, 1035, 982, 915, 855, 746 cm$^{-1}$.

Mass (EI)

m/z 474 (M$^+$).

Compound 25

NMR (400 MHz, CDCl$_3$)

δ 0.07–0.16 (2H, m), 0.47–0.56 (2H, m), 0.82 (1H, m), 1.20–1.95 (2H, br s), 1.25–1.42 (2H, m), 1.52–1.85 (3H, m), 2.06–2.23 (2H, m), 2.35 (2H, d, J=6.3 Hz), 2.46–2.65 (3H, m), 2.99 (1H, d, J=18.1 Hz), 3.04 (1H, d, J=5.4 Hz), 3.21 (1H, dd, J=11.7, 7.3 Hz), 3.35 (1H, dd, J=11.7, 7.8 Hz), 4.18 (1H, m), 4.30 (1H, d, J=6.8 Hz), 5.11 (1H, br s), 6.54 (1H, d, J=8.1 Hz), 6.65 (1H, d, J=8.1 Hz), 7.14–7.39 (10H, m).

IR (KBr)

υ 3360, 1603, 1493, 1456, 1398, 1325, 1243, 1133, 1035, 980, 913, 853, 745 cm$^{-1}$.

Mass (EI)

m/z 522 (M$^+$).

[Reference Example 15]

17-cyclopropylmethyl-3,14β-dihydroxy-4,5α-epoxy-6α-(N-methyl-3,4-dichlorophenylacetoamido)morphinan 1·hydrochloride

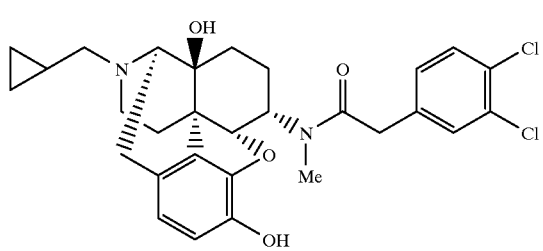

1

8.9 g of the 17-cyclopropylmethyl-3,14β-dihydroxy-4,5α-epoxy-6α-methylaminomorphinan 2 obtained in Reference Example 1 were dissolved in 180 ml of chloroform. After adding 10.4 ml of triethylamine, 10.4 ml of 3,4-dichlorophenylacetyl chloride (acid chloride obtained from commercially available carboxylic acid by standard methods) were dropped in at 0° C. Following completion of dropping, the solution was stirred for 1 hour at room temperature followed by addition of 150 ml of saturated aqueous sodium bicarbonate to the reaction system and liquid separation. The aqueous layer was then extracted twice with 100 ml of chloroform. The organic layer was concentrated after drying with anhydrous sodium sulfate.

The resulting residue was dissolved in a mixed solvent of 140 ml of methanol and 14 ml of chloroform followed by the addition of 1.7 g of potassium carbonate at room temperature and stirring for 30 minutes. Next, 100 ml of water and 350 ml of chloroform were added to the reaction system followed by liquid separation. The aqueous layer was extracted twice with 80 ml of chloroform. The resulting organic layer was concentrated after drying with anhydrous sodium sulfate. The resulting residue was recrystallized from ethyl acetate/methanol=2/1 to obtain 8.15 g of free base. This free base was dissolved to a mixture of chloroform and methanol followed by the addition of hydrogen chloride-methanol. After adjusting the pH to 3 and concentrating, the solution was reprecipitated with chloroform, methanol and ether to obtain 8.44 g of the target compound (yield: 58%).

mp 252–254° C.

NMR (400 MHz, DMSO-d$_6$)

δ 0.43 (2H, m), 0.65 (2H, m), 1.05 (1H, m), 1.16 (1.5H, m), 1.37 (1H, m), 1.58 (2H, m), 1.92 (1H, m), 2.43 (1H, m), 2.68 (1H, m), 2.81 (0.5H, s), 2.96 (2.5H, s), 3.05 (2.5H, m), 3.30 (2H, m), 3.85 (3H, m), 4.48 (0.2H, m), 4.62 (0.8H, d, J=3.9 Hz), 4.75 (0.2H, m), 4.96 (0.8H, m), 6.21 (0.8H, m), 6.46 (0.2H, m), 6.58 (1H, d, J=8.3 Hz), 6.72 (1H, d, J=8.3 Hz), 7.25 (1H, m), 7.55 (2H, m), 8.80 (1H, brs), 9.32 (1H, brs).

IR (KBr)

υ 3370, 1620, 1510, 1473, 1120, 1035 cm$^{-1}$.

Mass (FAB)

m/z 543 ((M+H)$^+$).

Elementary analysis: As $C_{29}H_{32}N_2O_4Cl_2 \cdot HCl \cdot 0.5H_2O$

Calculated values: C 59.14; H 5.82; N 4.75; Cl 18.06

Measured values: C 59.34; H 5.78; N 4.78; Cl 17.78

[Reference Examples 16–24]

17-cyclopropylmethyl-3,14β-dihydroxy-4,5α-epoxy-6α-(N-methylphenylacetoamido)morphinan 26·hydrochloride (yield: 70%), 17-cyclopropylmethyl-3,14β-dihydroxy-4,5α-epoxy-6α-(N-methylcinnamamido)morphinan 27·hydrochloride (yield: 74%), 17-cyclopropylmethyl-3,14β-dihydroxy-4,5α-epoxy-6α-(N-methylacetoamido) morphinan 28·hydrochloride (yield: 93%), 17-cyclopropylmethyl-3,14β-dihydroxy-4,5α-epoxy-6α-[(R)-N-methylmethoxyphenylacetoamido]morphinan 29·hydrochloride (yield: 98%), 17-cyclopropylmethyl-3,14β-dihydroxy-4,5α-epoxy-6α-[(S)-N-methyl-2-phenylpropioamido) morphinan 30·tartrate (yield: 85%), 17-cyclopropylmethyl-3,14β-dihydroxy-4,5α-epoxy-6α-(N-methylcyclohexylcarboxamido)morphinan 31·hydrochloride (yield: 58%), 17-cyclopropylmethyl-3,14β-dihydroxy-4,5α-epoxy-6α-(N-methylbenzamido) morphinan 32·hydrochloride (yield: 52%), 17-cyclopropylmethyl-3,14β-dihydroxy-4,5α-epoxy-6α-(N-methyl-4-phenylbutyroamido)morphinan 33·hydrochloride (yield: 80%) and 17-cyclopropylmethyl-3,14β-dihydroxy-4,5α-epoxy-6α-(N-methyl-6-phenylhexanoamido)morphinan 34·hydrochloride (yield: 63%) were obtained by following the procedure of Reference Example 15 and using phenylacetyl chloride, trans-cinnamoyl chloride, acetyl chloride, (R)-(−)-methoxyphenylacetyl chloride, S-(+)-2-phenylpropionyl chloride, cyclohexanecarbonyl chloride, benzoyl chloride, 4-phenylbutanoyl chloride and 6-phenylhexanoyl chloride instead of 3,4-dichlorophenylacetyl chloride.

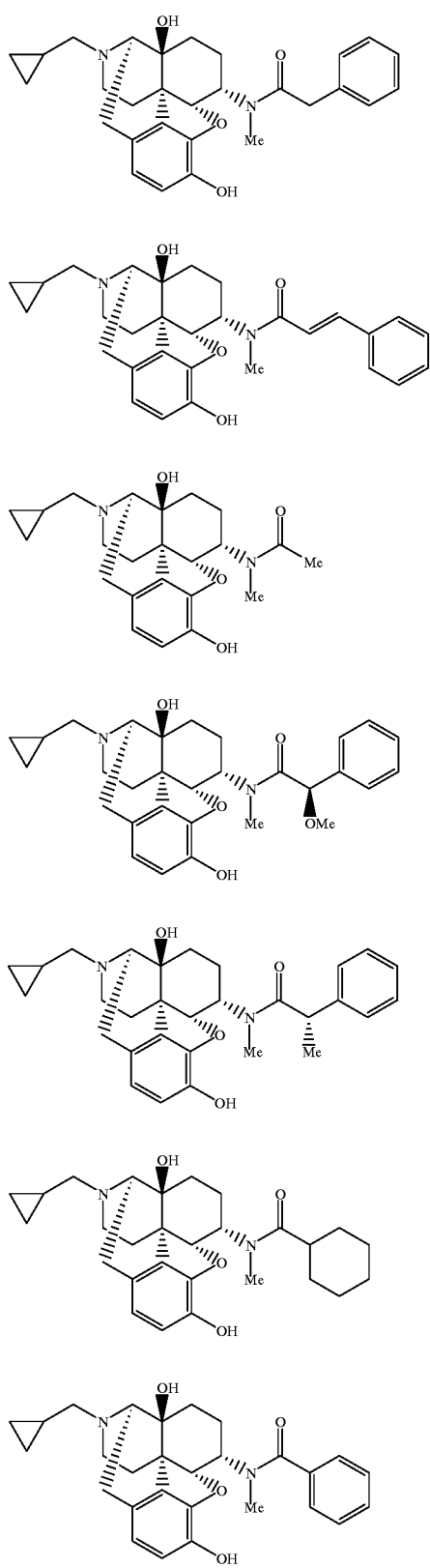

-continued

Compound 26·hydrochloride
mp 253.0–257.0° C. (decomposition, ether)
NMR (400 MHz, DMSO-$d_6$)
δ 0.40 (1H, m), 0.47 (1H, m), 0.60 (1H, m), 0.69 (1H, m), 1.05 (1H, m), 1.09 (1H, m), 1.34 (1H, m), 1.47 (1H, m), 1.56 (1H, dd, J=14.7, 9.3 Hz), 1.61 (1H, d, J=13.7 Hz), 1.91 (1H, m), 2.36~2.52 (2H, m), 2.69 (1H, m), 2.80 (0.8H, s), 2.93 (1H, m), 2.95 (2.2H, s), 3.15 (1H, d, J=12.2 Hz), 3.09 (1H, dd, J=19.8, 7.1 Hz), 3.76 (2H, s), 3.89 (1H, br s), 4.27 (0.27H, s), 4.51 (0.27H, m), 4.63 (0.73H, d, J=3.4 Hz), 5.00 (0.73H, dt, J=13.7, 3.4 Hz), 6.20 (0.73H, brs), 6.40 (0.27H, m), 6.58 (1H, d, J=8.3 Hz), 6.72 (1H, dd, J=8.3, 2.0 Hz), 7.22~7.29 (2H, m), 7.30~7.38 (3H, m), 8.80 (1H, br s), 9.29 (1H, d, J=5.9 Hz).
IR (KBr)
υ 3400, 3100, 2952, 1620, 1508, 1475, 1319, 1120, 1036, 806 cm$^{-1}$.
Mass (FAB)
m/z 475 (M+H)+.
Elementary Analysis: As $C_{29}H_{35}N_2O_4Cl·0.3H_2O$
Calcd.: C, 67.44; H, 6.95; N, 5.43; Cl, 6.86.
Found.: C, 67.45; H, 7.15; N. 5.40; Cl, 6.99.
Compound 27·hydrochloride
mp 254–257° C.
NMR (400 MHz, DMSO-$d_6$)
δ 0.21 (2H, m), 0.52 (2H, m), 0.91 (1H, m), 1.20 (1.5H, m), 1.48 (3H, m), 1.78 (1H, m), 2.26 (2.5H, m), 2.58 (1H, m), 2.73 (2H, m), 2.91 (0.5H, s), 3.06 (1H, m), 3.09 (2.5H, m), 3.20– 3.90 (4H, br), 4.03 (1H, s), 4.5–5.1 (2H, m), 6.52 (1H, d, J=7.9 Hz), 6.62 (1H, d, J=7.9 Hz), 7.09 (0.2H, d, J=15.9 Hz), 7.23 (0.8H, d, J=15.9 Hz), 7.40–7.60 (4H, m), 7.60–7.80 (2H, m), 8.80–9.20 (1H, br).
IR (KBr)
υ 3400, 1644, 1593, 1317, 1118, 1038, 768 cm$^{-1}$.
Mass (FAB)
m/z 487 ((M+H)$^+$).
Elementary Analysis: As $C_{32}H_{37}N_2O_7·0.8H_2O$
Calcd.: C, 66.72; H, 6.75; N, 4.86
Found.: C, 66.56; H, 6.74; N, 5.08
Compound 28·hydrochloride
mp>300.0° C. (decomposition, ether)

NMR (400 MHz, DMSO-d$_6$)

δ 0.40 (1H, m), 0.48 (1H, m), 0.61 (1H, m), 0.69 (1H, m), 1.05 (1H, m), 1.13 (1H, m), 1.33 (1H, m), 1.55 (1H, dd, J=15.3, 9.8 Hz), 1.59 (1H, d, J=14.0 Hz),1.92 (1H, dt, J=15.3, 9.5 Hz), 2.05 (2.5H, S), 2.13 (0.5H, S), 2.43 (1H, dt, J=13.4, 4.9 Hz), 2.69 (1H, m), 2.77 (0.5H, s), 2.89 (2.5H, s), 2.94 (1H, dd, J=13.1, 7.0 Hz), 3.03 (1H, br d, J=10.3 Hz), 3.09 (1H, dd, J=20.1, 7.3 Hz), 3.24~3.38 (2H, m), 3.91 (1H, d, J=6.7 Hz), 4.37 (0.17H, br d, J=12.2 Hz), 4.61 (0.83H, d, J=4.3 Hz), 4.81 (0.17H, d, J=4.3 Hz), 4.94 (0.83H, dt, J=14.0, 3.7 Hz), 6.26 (0,83H, s), 6.46 (0.17H, S), 6.58 (1H, d, J=8.2 Hz), 6.73 (1H, dd, J=8.2, 1.8 Hz), 8.82 (1H, br s), 9.31 (1H, s).

IR (KBr)

υ 3400, 3100, 2866, 1618, 1500, 1301, 1172, 1120, 1038, 920 cm$^{-1}$.

Mass (FAB)

m/z 399 (M+H)+.

Elementary Analysis: As $C_{23}H_{30}N_2O_4 \cdot 1.12HCl \cdot 0.5H_2O$

Calcd.: C, 61.61; H, 7.22; N, 6.25; Cl, 8.86.

Found.: C, 61.43; H, 7.21; N, 6.33; Cl, 9.00.

Compound 29·hydrochloride mp 207.0–211.0° C. (decomposition, ether)

NMR (400 MHz, DMSO-d$_6$)

δ 0.39 (1H, m), 0.47 (1H, m), 0.61 (1H m), 0.68 (1H, m), 1.07 (1H, m), 1.22 (1H, m), 1.39 (1H, m), 1.50 (1H, dd, J=15.1, 9.3 Hz), 1.63 (1H, d, J=11.2 Hz), 1.90 (1H, m), 2.30 (0.15H, dt, J=13.2, 4.9 Hz), 2.47 (0.85H, dt, J=13.2, 4.9 Hz), 2.64 (1H, m), 2.81 (0.45H, s), 2.88 (2.55H, s), 2.95~3.10 (3H, m), 3.20~3.35 (2H, m), 3.30 (0.45H, s), 3.40 (2.55H, s), 3.78 (0.15H, br s), 3.92 (0.85H, br d, J=6.8 Hz), 4.64 (0.15H, br d, J=12.7 Hz), 4.69 (1H, d, J=3.4 Hz), 4.95 (0.85H, br d, J=13.7 Hz), 5.26 (0.85H, s), 5.35 (0.15H, s), 6.28 (0.85H, s), 6.54 (0.15H, d, J=8.3 Hz), 6.57 (0.85H, d, J=8.3 Hz), 6.63 (0.15H, s), 6.69 (0.15H, d, J=8.3 Hz), 6.72 (0.85H, d, J=8.3 Hz), 7.31~7.46 (5H, m), 8.86 (0.85H, br s), 8.92 (0.15H, br s), 9,27 (0.15H, s), 9.34 (0.85H, s).

IR (KBr)

υ 3400, 1638, 1460, 1321, 1120, 1035, 600, 418 cm$^{-1}$.

Mass (FAB)

m/z 505 ((M+H)$^+$).

Elementary Analysis: As $C_{30}H_{37}N_2O_5Cl \cdot 0.4H_2O$

Calcd.: C, 65.72; H, 6.95; N, 5.11; Cl, 6.47.

Found.: C, 65.77; H, 7.14; N, 5.23; Cl, 6.41.

Compound 30 mp 162–165° C.

NMR (400 MHz, DMSO-d$_6$)

δ 0.21 (2H, m), 0.53 (2H, m), 0.91 (1H, m), 1.09 (1H, m), 1.28 (3H, d, J=6.4 Hz), 1.3–1.5 (3.3H, m), 1.75 (0.7H, m), 2.2–2.3 (2H, m), 2.4–2.8 (4H, m), 2.78 (1H, s), 2.84 (2H, s), 3.0–3.3 (2H, m), 4.04 (1H, s), 4.0–4.1 (1H, m), 4.4–5.1 (2H, m), 6.47 (1H, m), 6.59 (1H, m), 7.2–7.4 (5H, m).

IR (KBr)

υ 3400, 1620, 1462, 1120, 1067, 704 cm$^{-1}$.

Mass (FAB)

m/z 489 ( (M+H)$^+$).

Elementary Analysis: As $C_{32}H_{39}N_2O_7 \cdot 0.4H_2O$

Calcd.: C, 67.33; H, 7.03; N, 4.91

Found.: C, 67.28; H, 7.26; N, 4.90

Compound 31·hydrochloride mp>260° C. (decomposition, methanol-ether)

NMR (400 MHz, CD$_3$OD; data only for major amide form (approximately 90%))

δ 0.49 (2H, m), 0.73 (1H, m), 0.83 (1H, m), 1.08 (1H, m), 1.22–1.57 (7H, m), 1.62–1.98 (8H, m), 2.57–2.74 (2H, m), 2.83–3.02 (2H, m), 3.04–3.20 (2H, m), 3.06 (3H, s), 3.22–3.39 (2H, m), 3.97 (1H, m), 4.74 (1H, m), 5.08 (1H, ddd, J=14.7, 3.9, 3.9 Hz), 6.67 (1H, d, J=8.3 Hz), 6.75 (1H, d, J=8.3 Hz).

IR (KBr)

υ 3366, 1607, 1510, 1473, 1319, 1197, 1118, 1038, 907, 804 cm$^{-1}$.

Mass (FAB)

m/z 467 ((M+H)$^+$).

Elementary Analysis: As $C_{28}H_{38}N_2O_4 \cdot HCl$

Calcd.: C, 66.85; H, 7.81; N 5.57; Cl, 7.05.

Found.: C, 66.87; H, 7.90; N, 5.53; Cl, 7.03.

Compound 32·hydrochloride mp 235° C. (decomposition)

NMR (500 MHz, DMSO-d$_6$)

δ 0.35–0.76 (4H, m), 0.96–1.14 (1H, m), 1.16–1.42 (2H, m), 1.43–1.82 (3H, m), 1.96–2.20 (1H, m), 2.58–2.77 (1H, m), 2.78–3.07 (6H, m), 3.20–3.35 (2H, m), 3.79 (0.2H, m), 3.96 (0.8H, m), 4.35 (0.2H, m), 4.58 (0.2H, m), 4.87 (0.8H, m), 5.01 (0.8H, m), 5.95 (0.2H, br s), 6.38 (0.8H, br s), 6.59 (1H, d, J=7.3 Hz), 6.73 (1H, d, J=7.3 Hz), 7.40–7.50 (5H, m), 8.63 (0.2H, br s), 8.88 (0.8H, br s), 9.31 (0.8H, br s), 9.38 (0.2H, br s).

IR (KBr)

υ 3270, 3072, 1613, 1506, 1475, 1321, 1120, 1069, 905, 806, 710 cm$^{-1}$.

Mass (FAB)

m/z 461 ((M+H)$^+$).

Elementary Analysis: As $C_{28}H_{32}N_2O_4 \cdot HCl \cdot 0.7H_2O$

Calcd.: C, 65.99; H, 6.80; N, 5.49; Cl, 6.96.

Found.: C, 65.97; H, 6.86; N, 5.55; Cl, 6.94.

Compound 33·hydrochloride mp 235° C. (decomposition)

NMR (400 MHz, DMSO-d$_6$)

δ 0.40 (1H, m), 0.47 (1H, m), 0.61 (1H, m), 0.68 (1H, m), 1.01–1.09 (2H, m), 1.36 (1H, m), 1.50–1.64 (2H, m), 1.80–1.98 (3H, m), 2.34–2.46 (3H, m), 2.60–2.75 (3H, m), 2.80 (0.6H, s), 2.85 (2.4H, s), 2.88–3.14 (3H, m), 3.22–3.35 (2H, m), 3.90 (1H, m), 4.41 (0.2H, m), 4.61 (0.8H, d, J=3.9 Hz), 4.68 (0.2H, m), 4.97 (0.8H, m), 6.24 (0.8H, br s), 6.46 (0.2H, br s), 6.58 (1H, d, J=8.1 Hz), 6.75 (1H, m), 7.16–7.26 (3H, m), 7.30 (2H, m), 8.82 (1H, br s), 9.30 (0.8H, s), 9.33 (0.2H, s).

IR (KBr)

υ 3068, 1618, 1508, 1475, 1369, 1317, 1118, 1036, 919, 806, 750, 704 cm$^{-1}$.

Mass (FAB)

m/z 503 ((M+H)$^+$)+.

Elementary Analysis: As $C_{31}H_{38}N_2O_4 \cdot HCl$

Calcd.: C, 69.06; H, 7.29; N, 5.19; Cl, 6.58.

Found.: C, 69.05; H, 7.43; N, 5.27; Cl, 6.43.

Compound 34·hydrochloride mp 225° C. (decomposition)

NMR (400 MHz, DMSO-d$_6$)

δ 0.40 (1H, m), 0.47 (1H, m), 0.61 (1H, m), 0.68 (1H, m), 1.01–1.20 (2H, m), 1.25–1.37 (3H, m), 1.50–1.64 (6H, m), 1.91 (1H, m), 2.33 (2H, t, J=7.1 Hz), 2.42 (1H, m), 2.58 (2H, t, J=7.5 Hz), 2.68 (1H, m), 2.78 (0.6H, s), 2.87 (2.4H, s), 2.93 (1H, m), 2.99–3.14 (2H, m), 3.24–3.35 (2H, m), 3.89 (1H, m), 4.42 (0.2H, m), 4.59

(0.8H, d, J=3.4 Hz), 4.76 (0.2H, m), 4.96 (0.8H, m), 6.22 (0.8H, s), 6.44 (0.2H, s), 6.58 (1H, d, J=7.8 Hz), 6.72 (1H, d, J=7.8 Hz), 7.16–7.23 (3H, m), 7.24–7.30 (2H, m), 8.81 (1H, br S), 9.29 (0.8H, s), 9.31 (0.2H, s).
IR (KBr)
υ 3086, 1618, 1508, 1460, 1315, 1174, 1120, 1038, 748, 700 cm$^{-1}$.
Mass (FAB)
m/z 531 ((M+H)+).
Elementary Analysis: As $C_{33}H_{42}N_2O_4 \cdot HCl$
Calcd.: C, 69.88; H, 7.64; N, 4.94; Cl, 6.25.
Found.: C, 69.70; H, 7.64; N, 4.98; Cl, 6.25.

[Reference Examples 25–26]

17-cyclopropylmethyl-3,14β-dihydroxy-4,5α-epoxy-6α-(N-isobutyl-3,4-dichlorophenylacetoamido)morphinan 35 hydrochloride (yield: 78%), and 17-cyclopropylmethyl-3,14β-dihydroxy-4,5α-epoxy-6α-(3,4-dichlorophenylacetoamido) morphinan 36·hydrochloride (yield: 92%) were obtained by following the procedure of Reference Example 15 but using 17-cyclopropylmethyl-3,14β-dihydroxy-4,5α-epoxy-6α-isobutylaminomorphinan 3, and 17-cyclopropylmethyl-3,14β-dihydroxy-4,5α-epoxy-6α-aminomorphinan (J. B. Jiang, R. N. Hanson, P. S. Portoghese, and A. E. Takemori, J. Med. Chem., 20, 1100 (1977).) instead of the starting material 17-cyclopropylmethyl-3,14β-dihydroxy-4,5α-epoxy-6α-methylaminomorphinan 2.

Compound 35·hydrochloride

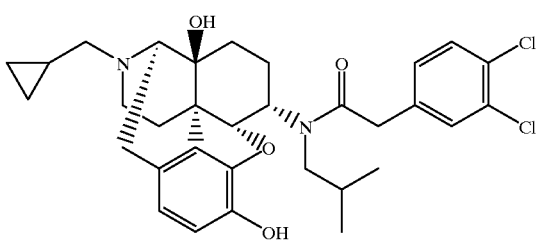

35

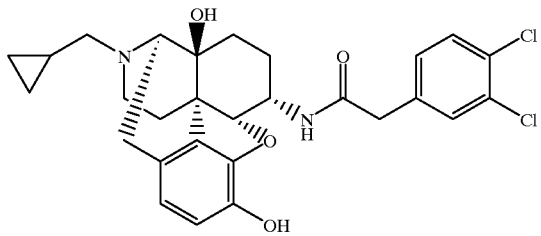

36 mp 185–188° C.
NMR (400 MHz, DMSO-d$_6$)
δ 0.40 (1H, m), 0.48 (1H, m), 0.61 (1H, m), 0.72 (4H, m), 0.88 (4H, m), 1.06 (2H, m), 1.57 (3H, m), 1.90 (2H, m), 2.42 (1H, m), 2.68 (1H, m), 3.00 (3H, m), 3.36 (2H, m), 3.45 (1H, m), 3.86 (3H, m), 4.4–5.1 (2H, m), 6.19 (0.7H, S), 6.50 (0.3H, s), 6.58 (1H, m), 6.73 (1H, d, J=7.8 Hz), 7.27 (1H, m), 7.52 (1H, d, J=4.4 Hz), 7.59 (1H, t, J=8.3 Hz), 8.82 (1H, brs), 9.26 (0.7H, s), 9.30 (0.3H, s).
IR (KBr)
υ 3370, 1620, 1510, 1468, 1120, 1035 cm$^{-1}$.
Mass (FAB)
m/z 585 ((M+H)$^+$).
Elementary Analysis: As $C_{32}H_{38}N_2O_4Cl_2 \cdot HCl \cdot 0.2H_2O$
Calcd.: C, 61.43; H, 6.35; N, 4.48; Cl, 17.00.
Found.: C, 61.44; H, 6.42; N, 4.45; Cl, 16.82.
Compound 36·hydrochloride
mp 212.0–215.0° C. (decomposition, ether)
NMR (400 MHz, DMSO-d$_6$)
δ 0.39 (1H, m), 0.47 (1H, m), 0.60 (1H, m), 0.68 (1H, m), 0.97 (1H, m), 1.05 (1H, m), 1.40 (2H, dd, J=14.7, 9.8 Hz), 1.60 (1H, d, J=10.7 Hz), 1.84 (1H, dt, J=15.1, 9.3 Hz), 2.44 (1H, dt, J=13.2, 4.9 Hz), 2.70 (1H, br q, J=12.7 Hz), 2.94 (1H, m), 3.04 (2H, dd, J=19.5, 6.8 Hz), 3.25~3.35 (2H, m), 3.55 (2H, s), 3.89 (1H, d, J=6.8 Hz), 4.38 (1H, m), 4.59 (1H, d, J=3.4 Hz), 6.25 (1H, s), 6.56 (1H, d, J=8.3 Hz), 6.73 (1H, d, J=8.3 Hz), 7.29 (1H, dd, J=8.3, 2.0 Hz), 7.56 (1H, d, J=2.0 Hz), 7.57 (1H, d, J=8.3 Hz), 8.14 (1H, d, J=8.3 Hz), 8.83 (1H, br s), 9.28 (1H, s).
IR (KBr)
υ 3400, 2942, 1651, 1510, 1460, 1236, 1120, 1035, 903, 787 cm$^{-1}$.
Mass (FAB)
m/z 529 ((M+H)$^+$).
Elementary Analysis: As $C_{28}H_{31}N_2O_4Cl_3 \cdot 0.3H_2O$
Calcd.: C, 58.86; H, 5.58; N, 4.90; Cl, 18.62.
Found.: C, 58.99; H, 5.79; N, 4.93; Cl, 18.61.

[Reference Example 27]

17-cyclopropylmethyl-3,14β-dihydroxy-4,5α-epoxy-6α-(N-isobutyl-6-phenylhexanoamido)morphinan 37·methane-sulfonate (yield: 37%) was obtained by following the procedure of Reference Example 15 and using 17-cyclopropylmethyl-3,14β-dihydroxy-4,5α-epoxy-6α-isobutylaminomorphinan 3 instead of 17-cyclopropylmethyl-3,14β-dihydroxy-4,5α-epoxy-6α-methylaminomorphinan 2 for the starting material, and using 6-phenylhexanoyl chloride instead of 3.4-dichlorophenylacetylchloride.

37

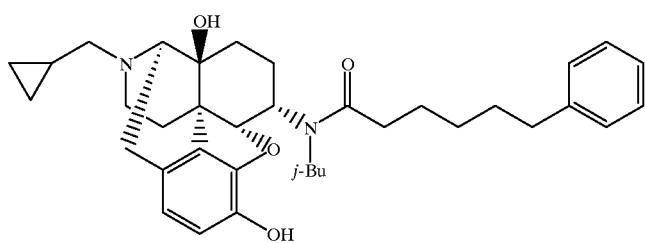

mp>120° C. (decomposition)

NMR (400 MHz, DMSO-$d_6$)

δ 0.43 (2H, m), 0.65 (2H, m), 0.73 (2H, dd, J=17.1, 6.8 Hz), 0.81 (4H, t, J=5.9 Hz), 0.98–1.25 (2H, m), 1.27–1.37 (2H, m), 1.45–1.66 (7H, m), 1.73–1.97 (2H, m), 2.3 (3H, s), 2.27–2.50 (3H, m), 2.54–2.62 (2H, m), 2.63–2.77 (1H, m), 2.85–3.48 (7H, m), 3.83–3.90 (1H, m), 4.47 (0.4H, m), 4.67–4.73 (1H, m), 5.01 (0.6H, m), 6.11 (0.6H, s), 6.29 (0.4H, s), 6.54–6.60 (1H, m), 6.69–6.74 (1H, m), 7.14–7.22 (3H, m), 7.24–7.31 (2H, m), 8.75 (1H, br s), 9.21 (0.6H, s), 9.26 (0.4H, s).

IR (KBr)

υ 3420, 1620, 1508, 1460, 1323, 1207, 1120, 1044 cm$^{-1}$.

Mass (FAB)

m/z 573 ((M+H)$^+$).

Elementary analysis: As $C_{36}H_{48}N_2O_4 \cdot CH_3SO_3H \cdot 0.4H_2O$

Calculated values: C 65.73; H 7.87; N 4.14; S 4.74

Measured values: C 65.65; H 7.73; N 4.23; S 4.81

[Reference Examples 28–29]

17-cyclopropylmethyl-3,14β-dihydroxy-4,5α-epoxy-6β-(N-methyl-3,4-dichlorophenylacetoamido)morphinan 38·hydrochloride (yield: 51%) and 17-cyclopropylmethyl-3,14β-dihydroxy-4,5α-epoxy-6β-(N-isobutyl-3,4-dichlorophenylacetoamido)morphinan 39·0.8 tartrate (yield: 48%) were obtained by following the procedure of Reference Example 15 and using 17-cyclopropylmethyl-3,14β-dihydroxy-4,5α-epoxy-6β-methylaminomorphinan 15 and 17-cyclopropylmethyl-3,14β-dihydroxy-4,5α-epoxy-6β-isobutylaminomorphinan 18 instead of 17-cyclopropylmethyl-3,14β-dihydroxy-4,5α-epoxy-6α-methylaminomorphinan 2 for the starting material.

38

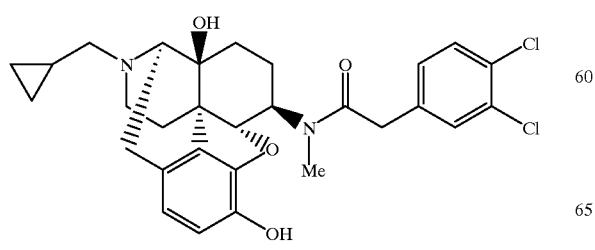

39

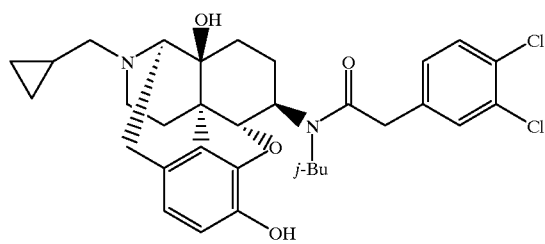

Compound 38·hydrochloride mp 194–196° C. (decomposition)

NMR (400 MHz, CDCl$_3$+D20; Data for free base)

δ 0.09–0.17 (2H, m), 0.49–0.57 (2H, m), 0.78–0.89 (2H, m), 1.05 (0.7 H, dt, J=13.2, 3.4 Hz), 1.42–1.51 (0.3H, m), 1.49 (2H, br d, J=13.2 Hz), 1.97–2.29 (3H, m), 2.36 (2H, d, J=6.4 Hz), 2.56–2.69 (2H, m), 2.92 (2.1H, s), 2.99 (0.9H, s), 3.00–3.08 (2H, m). 3.48 (0.7H, d, J=15.6 Hz), 3.49–3.56 (1H, m), 3.66 (0.7H, d, J=15.6 Hz), 3.70 (0.6H, s), 4.55 (0.3H, d, J=8.3 Hz), 4.58 (0.7H, d, J=8.3 Hz), 6.57 (0.3H, d, J=8.3 Hz), 6.73 (0.3H, d, J=8.3 Hz), 6.78–6.82 (1.4H, m), 6.83 (0.7H, d, J=8.3 Hz), 7.11 (0.3H, dd, J=8.3, 2.5 Hz), 7.23 (0.7H, d, J=8.3 Hz), 7.36 (0.3H, d, J=2.0 Hz), 7.39 (0.3H, d, J=8.3 Hz).

IR (KBr)

υ 3420, 1620, 1321, 1127, 1035 cm$^{-1}$.

Mass (FAB)

m/z 543 ((M+H)$^+$).

Elementary analysis: As $C_{29}H_{32}N_2O_4Cl_2 \cdot HCl \cdot 0.7H_2O$

Calculated values: C 58.78; H 5.85; N 4.73; Cl 17.95

Measured values: C 58.72; H 5.86; N 4.71; Cl 18.03

Compound 39 mp>238° C. (decomposition)

NMR (400 MHz, DMSO-$_6$)

δ 0.22 (2H, m), 0.52 (2H, m), 0.82–0.94 (7H, m), 1.12–1.38 (3H, m), 1.53 (1H, m), 1.73–2.34 (4H, m), 2.54 (1H, m), 2.61–2.82 (4H, m), 3.05–3.20 (2H, m), 3.22–3.35 (2H, m), 3.50–3.77 (2H, m), 3.55 (4.2H, s, OH), 4.08 (1.6H, s), 4.56 (0.6H, d J=8.0 Hz), 5.16 (0.4H, d, J=7.7 Hz), 6.56 (0.4H, d, J=8.1 Hz), 6.64 (0.4H, d, J=8.1 Hz), 6.66 (0.6H, d, J=8.1 Hz), 6.73 (0.6H, d, J=8.1 Hz), 6.95 (0.6H, br d, J=8.4 Hz), 7.00 (0.6H, br s), 7.23 (0.4H, dd, J=8.4, 1.8 Hz), 7.51 (0.6H, d, J=8.1 Hz), 7.52 (0.4H, br s,), 7.58 (0.4H, d, J=8.1 Hz), 9.46 (1H, m, NH+).

IR (KBr)

υ 3322, 1636, 1510, 1473, 1460, 1388, 1309, 1241, 1135, 1033 cm$^{-1}$.

Mass (FAB)

m/z 585 ((M+H)⁺).
Elementary analysis: As C₃₂H₃₈Cl₂N₂O₄·0.8C₄H₆O₆·0.5H₂O
Calculated values: C 59.16; H 6.18; Cl 9.92; N 3.92
Measured values: C 69.15; H 6.18; Cl 9.88; N 3.89

[Reference Examples 30–46]

17-cyclopropylmethyl-3,14β-dihydroxy-4,5α-epoxy-6β-(N-methyl-3-phenylpropioamido)morphinan 40·hydrochloride (yield: 84%), 17-cyclopropylmethyl-3,14β-dihydroxy-4,5α-epoxy-6β-(N-methylphenoxyacetoamido)morphinan 41·0.5 tartrate (yield: 75%), 17-cyclopropylmethyl-3,14β-dihydroxy-4,5α-epoxy-6β-(N-methyl-3-trifluoromethylcinnamamido)morphinan 42·0.5 tartrate (yield: 84%), 17-cyclopropylmethyl-3,14β-dihydroxy-4,5α-epoxy-6β-[N-methyl-trans-3-(3-furyl)acrylamido]morphinan 43·0.5 tartrate (yield: 91%), 17-cyclopropylmethyl-3,14β-dihydroxy-4,5α-epoxy-6β-(N-methyl-3-cyclohexylacrylamido) morphinan 44·tartrate (yield: 77%), 17-cyclopropylmethyl-3,14β-dihydroxy-4,5α-epoxy-6β-(N-methylbenzamido)morphinan 45·hydrochloride (yield: 86%), 17-cyclopropylmethyl-3,14β-dihydroxy-4,5α-epoxy-6β-(N-methyl-3-methylcinnamamido) morphinan 46·hydrochloride (yield: 87%), 17-cyclopropylmethyl-3,14β-dihydroxy-4,5α-epoxy-6β-(N-methylphenylacetoamido)morphinan 47·hydrochloride (yield: 57%), 17-cyclopropylmethyl-3,14β-dihydroxy-4,5α-epoxy-6β-(N-methylbutyroxycarbamido)morphinan 48·0.5 tartrate (yield: 81%), 17-cyclopropylmethyl-3,14β-dihydroxy-4,5α-epoxy-6β-(N-methylhexanoamido)morphinan 49·1 tartrate (yield: 43%), 17-cyclopropylmethyl-3,14β-dihydroxy-4,5α-epoxy-6β-(N-methyl-3-methoxycinnamamido)morphinan 50·0.5 tartrate (yield: 88%), 17-cyclopropylmethyl-3,14β-dihydroxy-4,5α-epoxy-6β-(N-methyl-3-cyclopentylpropioamido) morphinan 51·1 tartrate (yield: 39%), 17-cyclopropylmethyl-3,14β-dihydroxy-4,5α-epoxy-6β-(N-methyl-2-naphthamido)morphinan 52·hydrochloride (yield: 95%), 17-cyclopropylmethyl-3,14β-dihydroxy-4,5α-epoxy-6β-[N-methyl-trans-3-(2-furyl)acrylamido]morphinan 53·hydrochloride (yield: 80%), 17-cyclopropylmethyl-3,14β-dihydroxy-4,5α-epoxy-6β-[N-methyl-trans-3-(3-thienyl)acrylamido]morphinan 54·methanesulfonate (yield: 88%), 17-cyclopropylmethyl-3,14β-dihydroxy-4,5α-epoxy-6β-(N-methyl-2-trifluoromethylcinnamamido)morphinan 55·hydrochloride (yield: 93%) and 17-cyclopropylmethyl-3,14β-dihydroxy-4,5α-epoxy-6β-(N-methyl-4-trifluoromethylcinnamamido) morphinan 56·0.5 tartrate (yield: 84%) were obtained by following the procedure of Reference Example 15, using 17-cyclopropylmethyl-3,14β-dihydroxy-4,5α-epoxy-6β-methylaminomorphinan 15 instead of 17-cyclopropylmethyl-3,14β-dihydroxy-4,5α-epoxy-6α-methylaminomorphinan 2 for the starting material, and using 3-phenylpropionyl chloride, phenoxyacetyl chloride, 3-trifluoromethylcinnamoyl chloride, trans-3-(3-furyl)acryloyl chloride, trans-3-cyclohexylacryloyl chloride, benzoyl chloride, 3-methylcinnamoyl chloride, phenylacetyl chloride, butylchloroformate, hexanoyl chloride, 3-methoxycinnamoyl chloride, 3-cyclopentylpropionyl chloride, 2-naphthoyl chloride, trans-3-(2-furyl)acryloyl chloride, trans-3-(3-thienyl)acryloyl chloride, 2-trifluoromethylcinnamoyl chloride and 4-trifluoromethylcinnamoyl chloride instead of 3,4-dichlorophenylacetyl chloride.

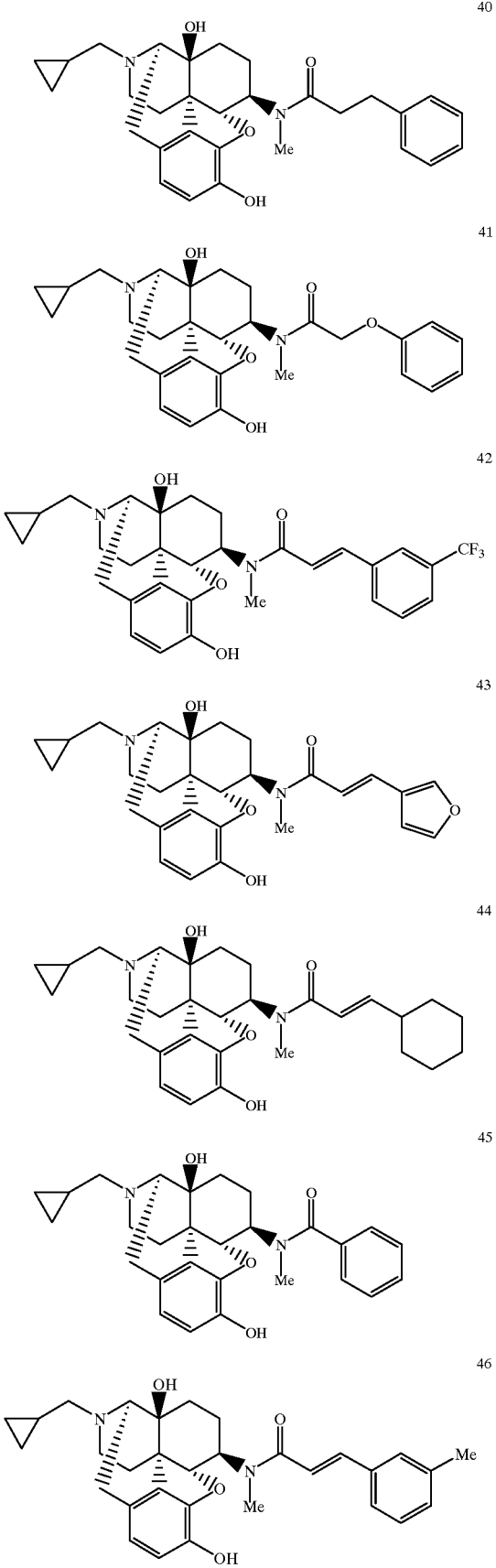

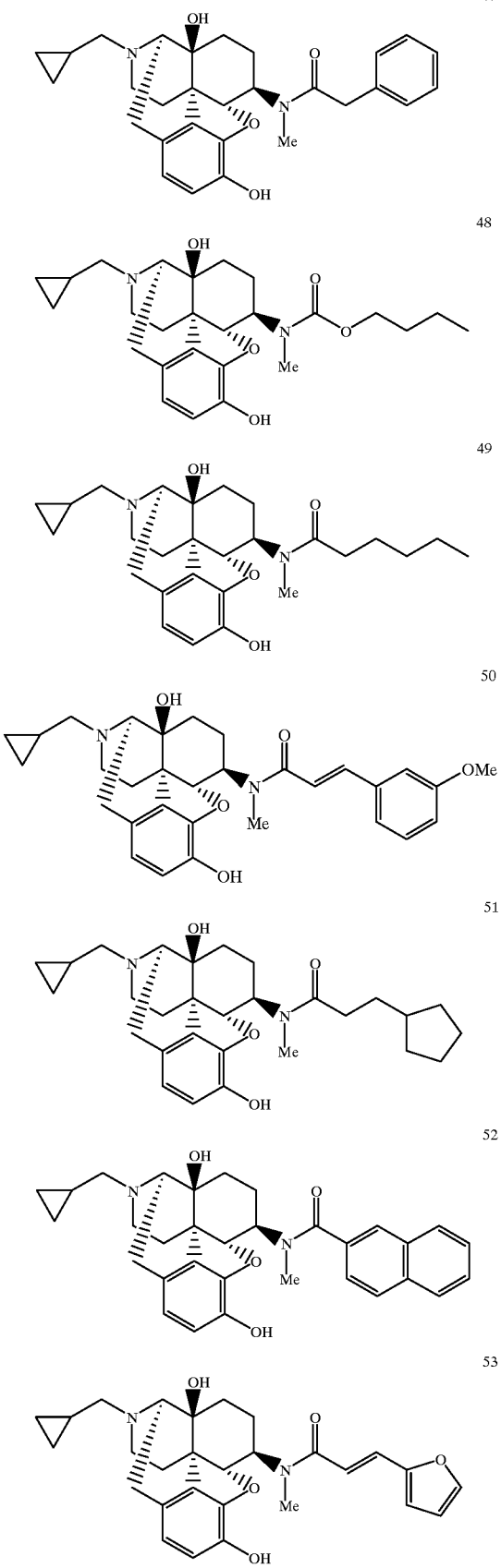

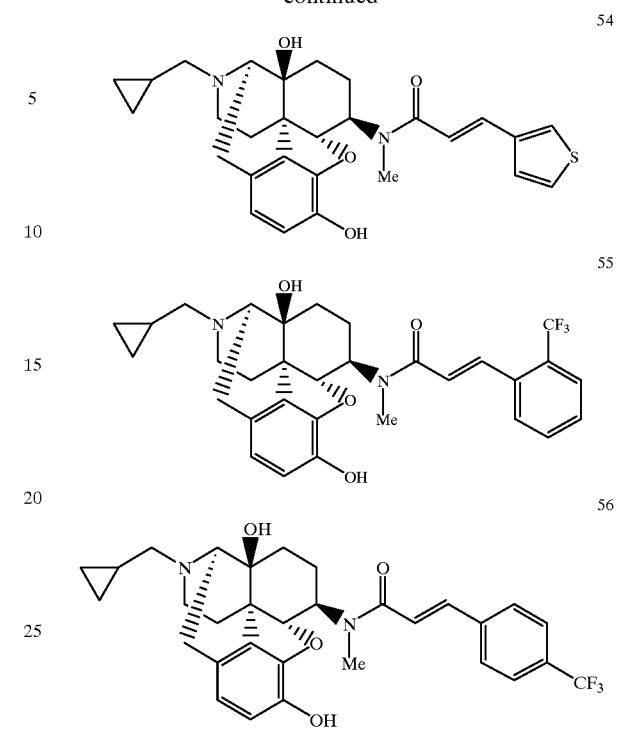

Compound 40·hydrochloride
mp 207.0° C. (decomposition)
NMR (400 MHz, DMSO-$_6$)
δ 0.31–0.47 (1H, m), 0,47–0.55 (1H, m), 0.55–0.63 (1H, m), 0.63–0.75 (1H, m), 0.99–1.13 (1H, m), 1.13–1.50 (3H, m), 1.60–1.78 (1H, m), 1.98–2.16 (1H, m), 2.28–2.52 (3H, m), 2.52–2.95 (4H, m), 2.83 (2.4H, s), 2.96 (0.6H, s), 2.95–3,16 (2H, m), 3.22–3.35 (2H, m), 3.36–3.53 (1H, m), 3.83 (1H, m), 4.79 (0.8H, d, J=7.8 Hz), 4.85 (0.2H, d, J=8.3 Hz), 6.38 (0.2H, m), 6.46 (0.8H, m), 6.60–6.80 (2H, m), 7.02–7.32 (5H, m), 8.82 (1H, br s), 9.29 (0.2H, s), 9.56 (0.8H, s).
IR (KBr)
υ 3416, 1622, 1502, 1454,–1410, 1383, 1321, 1125 cm$^{-1}$.
Mass (FAB)
m/z 489 (M+).
Elementary Analysis: As $C_{30}H_{37}N_2O_4Cl_1·0.2H_2O$
Calcd.: C, 67.92; H, 7.11; N, 5.28; Cl, 6.68
Found.: C, 67.96; H, 7.06; N, 5.27; Cl, 6.85
Compound 41·0.5 tartarate
mp 150–200° C. (decomposition)
NMR (500 MHz, DMSO-$_6$)
δ 0.21 (2H, m), 0.46–0.58 (2H, m), 0.90 (1H, m), 1.15–1.46 (3H, m), 1.57 (1H, m), 2.03–2.17 (2H, m), 2.28 (1H, m), 2.58–2.78 (3H, m), 2.82 (2.4H, s), 3.00 (0.6H, s), 3.08 (1H, d, J=18.9 Hz), 3.24 (1H, m), 3.45 (1H, m), 3.50 (3H, br s, 3×OH), 4.00–4.05 (1H, m), 4.04 (1H, s), 4.63–4.82 (3H, m), 6.54–6.67 (2H, m), 6.78–6.95 (3H, m), 7.18–7.29 (2H, m), 9.34 (1H, br s, NH+).
IR (KBr)
υ 3390, 1638, 1601, 1497, 1323, 1241, 1118, 1064, 1035, 922, 859 cm$^{-1}$.
Mass (FAB)
m/z 491 ( (M+H)+).

Elementary Analysis: As $C_{29}H_{34}N_2O_5 \cdot 0.5C_4H_6O_6 \cdot 1.1H_2O$

Calcd.: C, 63.60; H, 6.75; N, 4.78.

Found.: C, 63.69; H, 6.63; N, 4.72.

Compound 42·0.5 tartarate mp 156–159° C.

NMR (400 MHz, DMSO-$_6$)

δ 0.21 (2H, m), 0.52 (2H, m), 0.91 (1H, m), 1.2–1.5 (3H, m), 1.57 (1H, d, J=13.2 Hz), 2.12 (2H, m), 2.29 (1H, m), 2.49 (1H, m), 2.6–2.8 (3H, m), 2.90 (2H, s), 3.08 (1H, d, J=18.6 Hz), 3.17 (1H, s), 3.26 (1H, m), 3.67 (0.7H, m), 4.02 (1H, s), 4.21 (0.3H, m), 4.68 (0.7H, d, J=7.8 Hz), 4.79 (0.3H, d, J=8.3 Hz), 6.6–6.8 (2.6H, m), 7.37 (1H, dd, J=7.3, 16.1 Hz), 7.5–7.8 (3.8H, m), 8.02 (0.3H, d, J=7.8 Hz), 8.14 (0.3H, s).

IR (KBr)

υ 3350, 1649, 1601, 1336, 1168, 1127 cm$^{-1}$.

Mass (FAB)

m/z 555 ((M+H)$^+$).

Elementary Analysis: As $C_{31}H_{33}N_2O_4F_3 \cdot 0.5(C_4H_6O_6) \cdot 0.3H_2O$ Calcd.: C, 62.41; H, 5.81; N, 4.41; F, 8.98

Found.: C, 62.32; H, 5.99; N, 4.48; F, 8.88

Compound 43·0.5 tartarate mp 168–172° C.

NMR (400 MHz, DMSO-$_6$)

δ 0.20 (2H, brs), 0.52 (2H, m), 0.90 (1H, m), 1.2–1.4 (3H, m), 1.56 (1H, d, J=13.2 Hz), 2.12 (2H, m), 2.24 (1H, m), 2.47 (1H, m), 2.5–2.8 (3H, m), 2.86 (2H, s), 3.08 (1H, d, J=19.6 Hz), 3.10 (1H, s), 3.22 (1H, m), 3.60 (0.7H, m), 4.00 (1H, s), 4.19 (0.3H, m), 4.66 (0.7H, d, J=8.3 Hz), 4.76 (0.3H, d, J=8.3 Hz), 6.39 (0.7H, d, J=15.6 Hz), 6.5–6.7 (2H, m), 6.74 (0.7H, d, J=8.3 Hz), 6.89 (0.3H, d, J=15.1 Hz), 7.00 (0.3H, s), 7.21 (0.7H, d, J=15.6 Hz), 7.36 (0.3H, d, J=15.1 Hz), 7.66 (0.7H, s), 7.72 (0.3H, s), 7.92 (0.7H, s), 8.03 (0.3H, s).

IR (KBr)

υ 3370, 1651, 1599, 1323, 1158, 1114 cm$^{-1}$.

Mass (FAB)

m/z 477 ((M+H)$^+$).

Elementary Analysis: As $C_{28}H_{32}N_2O_5 \cdot 0.5(C_4H_6O_6) \cdot 0.2H_2O$

Calcd.: C, 64.90; H, 6.43; N, 5.04.

Found.: C, 64.79; H, 6.59; N, 5.01.

Compound 44 tartarate mp 154.0° C. (decomposition)

NMR (500 MHz, DMSO-$_6$)

δ 0.16–0.32 (2H, m), 0.42–0.62 (2H, m), 0.82–1.02 (2H, m), 1.02–1.42 (7H, m), 1.42–1.80 (6H, m), 1.88–2.33 (4H, m), 2.42–2.58 (1H, m), 2.58–2.87 (3H, m), 2.60–5.10 (3H, br s), 2.81 (2.1H, s), 3.01 (0.9H, s), 3.09 (1H, br d, J=18.3 Hz), 3.28 (1H, br s), 3.60 (0.7H, m), 4.05 (1H, s), 4.11 (0.3H, m), 4.61 (0.7H, d, J=7.9 Hz), 4.73 (0.3H, d, J=8.5 Hz), 5.93 (0.7H, d, J=15.3 Hz), 6.33 (0.7H, d, J=15.3 Hz), 6.34 (0.3H, d, J=15.3 Hz), 6.52–6.62 (1.6H, m), 6.66 (0.7H, d, J=8.5 Hz), 8.60–9.60 (1H, br s).

IR (KBr)

υ 3322, 1651, 1601, 1504, 1450, 1410, 1311, 1267, 1216, 1129, 681 cm$^{-1}$.

Mass (FAB)

m/z 493 ((M+H)+).

Elementary Analysis: As $C_{32.8}H_{44.2}N_2O_{8.2} \cdot 0.8H_2O$

Calcd.: C, 64.36; H, 7.54; N, 4.58

Found.: C, 64.37; H, 7.67; N, 4.58

Compound 45·hydrochloride mp>195° C. (decomposition)

NMR (400 MHz, DMSO-$_6$)

δ 0.37 (1H, m), 0.48 (1H, m), 0.56 (1H, m), 0.64 (1H, m), 0.92 (1H, m), 1.02 (1H, m), 1.21 (1H, m), 1.36–1.64 (2H, m), 2.13 (1H, m), 2.37 (1H, m), 2.78–3.08 (3H, m), 3.03 (3H, s), 3.21 (1H, br d, J=19.1 Hz), 3.25–40 (3H, m), 3.74 (1H, br d, J=3.9 Hz), 4.96 (1H, d, J=7.8 Hz), 6.44 (1H, s, OH), 6.52 (1H, d, J=8.1 Hz), 6.66 (1H, d, J=8.1 Hz), 7.21–7.48 (5H, m), 8.78 (1H, m, NH+), 9.60 (1H, br s, OH).

IR (KBr)

υ 3386, 1620, 1576, 1506, 1437, 1319, 1253, 1122, 1033, 922 cm$^{-1}$.

Mass (FAB)

m/z 461 ((M+H)$^+$).

Elementaly analysis: As $C_{28}H_{32}N_2O_4 \cdot HCl \cdot 0.6H_2O$

Calculated values: C 66.22; H 6.79; N 5.52; Cl 6.98

Measured values: C 66.35; H 6.98; N 5.42; Cl 6.90

Compound 46·hydrochloride mp 245° C. (decomposition)

NMR (400 MHz, DMSO-$_6$)

δ 0.42 (1H, m), 0.50 (1H, m), 0.59 (1H, m), 0.69 (1H, m), 1.07 (1H, m), 1.2–1.5 (3H, m), 1.72 (1H, d, J=13.7), 2.12 (1H, m), 2.34 (3H, s), 2.4–2.6 (2H, m), 2.88 (1H, m), 2.92 (2H, s), 3.0–3.1 (2H, m), 3.18 (1H, s), 3.3–3.4 (2H, m), 3.66 (0.7H, m), 3.83 (1H, m), 4.20 (0.3H, m), 4.83 (0.7H, d, J=7.8 Hz), 4.90 (0.3H, d, J=8.3 Hz), 6.6–6.8 (2H, m), 6.85 (0.7H, d, J=8.3 Hz), 7.1–7.3 (4.4H, m), 7.41 (0.3H, d, J=15.1 HZ), 7.48 (0.3H, d, J=7.3 Hz), 7.54 (0.3H, brs).

IR (KBr)

υ 3390, 1647, 1605, 1323, 1127, 1035 cm$^{-1}$.

Mass (FAB)

m/z 501 ((M+H)$^+$).

Elementary Analysis: As $C_{31}H_{36}N_2O_4 \cdot HCl \cdot 0.8H_2O$

Calcd.: C, 67.51; H, 7.06; N, 5.08; Cl, 6.43.

Found.: C, 67.35; H, 7.05; N, 5.17; Cl, 6.53.

Compound 47·hydrochloride mp 205–207° C.

NMR (500 MHz, DMSO-d$_6$)

δ 0.40 (1H, m), 0.50 (1H, m), 0.57 (1H, m), 0.67 (1H, m), 0.81 (1H, m), 1.00–1.08 (2H, m), 1.37–1.56 (2H, m), 1.97 (1H, m), 2.42–2.53 (2H, m), 2.83 (3H, s), 2.85 (1H, m), 2.45–3.07 (3H, m), 3.25–3,37 (2H, m), 3.46–3.57 (2H, m), 3.81 (0.8H, m), 4.04 (0.2H, m), 4.81 (0.8H, m), 4.88 (0.2H, m), 6.31 (0.2H, br s), 6.42 (0.8H, br s), 6.63 (0.2H, d, J=8.1 Hz), 6.70 (0.2H, d, J=8.1 Hz), 6.75 (0.8H, d, J=8.1 Hz), 6.77–6.80 (1.4H, m), 6.84 (0.8H, d, J=8.1 Hz), 7.12–7.33 (3.6H, m), 8.80 (1H, br s), 9.27 (0.2H, s), 9.65 (0.8H, s).

IR (KBr)

υ 3400, 1620, 1502, 1460, 1321, 1125, 1033, 920, 859, 748, 719 cm$^{-1}$.

Mass (FAB)

m/z 475 ((M+H)$^+$).

Elementary Analysis: As $C_{29}H_{34}N_2O_4 \cdot HCl \cdot 0.5H_2O$

Calcd.: C, 66.98; H. 6.98; N, 5.40; Cl, 6.82.

Found.: C, 67.25; H, 7.05; N, 5.40; Cl, 6.43.

Compound 48·0.5 tartarate mp 110–150° C. (decomposition)

NMR (400 MHz, DMSO-$_6$)

d 0.20 (2H, m), 0.45–0.56 (2H, m), 0.76–0.96 (4H, m), 1.14–1.40 (5H, m), 1.40–1.60 (3H, m), 2.01–2.15 (2H, m), 2.25 (1H, m), 2.55–2.77 (3H, m), 2.82 (3H, s), 3.06 (1H, d, J=18.6 Hz), 3.23 (1H, m), 3.53 (3H, br s, 3×OH), 3.53–3.68 (2H, m), 3.84–3.98 (2H, m), 4.01 (1H, s), 4.67 (1H, m), 6.55 (1H, d, J=8.1 Hz), 6.61 (1H, d, J=8.1 Hz), 9.10 (1H, br s, NH+).

IR (KBr)

υ 3420, 1678, 1607, 1460, 1408, 1359, 1315, 1164, 1122, 1067, 1035, 922, 861 cm$^{-1}$.

Mass (FAB)

m/z 457 ((M+H)+).

Elementary Analysis: As $C_{26}H_{36}N_2O_5 \cdot 0.5C_4H_6O_6 \cdot 0.5H_2O$

Calcd.: C, 62.21; H, 7.46; N, 5.18.

Found.: C, 62.21; H, 7.59; N, 5.33.

Compound 49·1 tartarate mp 150–158° C. (decomposition)

NMR (400 MHz, DMSO-$_6$)

δ 0.23 (2H, m), 0.48–0.59 (2H, m), 0.79 (2.1H, br t, J=6.8 Hz), 0.88 (0.9H, br t, J=6.8 Hz), 0.92 (1H, m), 1.11–1.22 (3H, m), 1.23–1.51 (6H, m), 1.58 (1H, m), 1.98–2.33 (5H, m), 2.52 (1H, m), 2.67–2.82 (3H, m), 2.77 (2.1H, s), 2.93 (0.9H, s), 3.11 (1H, br d, J=19.1 Hz), 3.33 (1H, m), 3.48 (1H, m), 3.50 (5H, br s, 5×OH), 4.08 (2H, s), 4.60 (0.7H, d, J=8.3 Hz), 4.72 (0.3H, d, J=8.3 Hz), 6.56 (0.3H, d, J=7.8 Hz), 6.60 (0.7H, d, J=7.8 Hz), 6.62 (0.3H, d, J=7.8 Hz), 6.67 (0.7H, d, J=7.8 Hz), 9.26 (1H, br s, NH+).

IR (KBr)

υ 3314, 1719, 1618, 1460, 1412, 1311, 1267, 1120, 1069, 1035, 922, 859 cm$^{-1}$.

Mass (FAB)

m/z 455 ((M+H)+).

Elementary Analysis: As $C_{27}H_{38}N_2O_4 \cdot C_4H_6O_6 \cdot 1.0H_2O$

Calcd.: C, 59.79; H, 7.45; N, 4.50.

Found.: C, 59.59; H, 7.46; N, 4.67.

Compound 50·0.5 tartarate mp 160° C. (decomposition)

NMR (400 MHz, DMSO-$_6$)

δ 0.15–0.35 (2H, m), 0.45–0.65 (2H, m), 0.85–1.05 (1H, m), 1.20–1.50 (3H, m), 1.52–1.70 (1H, m), 2.00–2.25 (2H, m), 2.25–2.42 (1H, m), 2.63–2.77 (3H, m), 2.90 (1.8H, s), 2.90–4.20 (3H, br s), 3.05–3.22 (1H, m), 3.15 (1.2H, s), 3.22–3.42 (1H, m), 3.50–3.74 (1.6H, m), 3.77 (1.8H, s), 3.80 (1.2H, s), 4.00 (1H, s), 4.20 (0.4H, br S), 4.71 (0.6H, d, J=7.8 Hz), 4.80 (0.4H, d, J=8.3 Hz), 6.55–6.71 (2.6H, m), 6.92 (0.6H, dd, J=8.3, 2.5 Hz), 6.95–7.03 (1H, m), 7.10 (0.6H, d, J=7.3 Hz), 7.17 (0.4H, d, J=15.1 Hz), 7.23–7.35 (2.4H, m), 7.42 (0.4H, d, J=15.6 Hz), 9.07 (0.4H, br s), 9.37 (0.6H, br s).

IR (KBr)

υ 3390, 1642, 1599, 1460, 1408, 1313, 1272, 1127, 1035, 787, 683 cm$^{-1}$.

Mass (FAB)

m/z 517 ((M+H)+).

Elementary Analysis: As $C_{33}H_{39}N_2O_8 \cdot 0.7H_2O$

Calcd.: C, 65.59; H, 6.74; N, 4.64

Found.: C, 65.46; H, 6.78; N, 4.70

Compound 51·1 tartarate mp 145–160° C. (decomposition)

NMR (400 MHz, DMSO-$_6$)

δ 0.23 (2H, m), 0.48–0.59 (2H, m), 0.82–1.12 (3H, m), 1.14–1.78 (13H, m), 2.00–2.33 (5H, m), 2.52 (1H, m), 2.66–2.81 (3H, m), 2.76 (2.4H, s), 2.93 (0.6H, s), 3.11 (1H, br d, J=18.6 Hz), 3.31 (1H, m), 3.46 (1H, m), 3.50 (5H, br s, 5×OH), 4.07 (2H, s), 4.61 (0.8H, d, J=7.8 Hz), 4.71 (0.2H, d, J=7.8 Hz), 6.56 (0.2H, d, J=8.0 Hz), 6.59 (0.8H, d, J=8.0 Hz), 6.61 (0.2H, d, J=8.0 Hz), 6.66 (0.8H, d, J=8.0 Hz), 9.25 (1H, br S, NH+).

IR (KBr)

υ 3398, 1721, 1620, 1456, 1408, 1325, 1243, 1125, 1071, 1035, 922, 859 cm$^{-1}$.

Mass (FAB)

m/z 481 ((M+H)+).

Elementary Analysis: As $C_{29}H_{40}N_2O_4 \cdot C_4H_6O_6 \cdot 0.3H_2O$

Calcd.: C, 62.31; H. 7.38; N, 4.40.

Found.: C, 62.18; H, 7.65; N. 4.57.

Compound 52·hydrochloride mp 220° C. (decomposition)

NMR (400 MHz, DMSO-$_6$)

δ 0.34 (1H, m), 0.47 (1H, m), 0.54 (1H, m), 0.62 (1H, m), 0.87 (1H, m), 0.99 (1H, m), 1.28 (1H, m), 1.4–1.6 (2H, m), 2.17 (1H, m), 2.34 (1H, m), 2.52 (1H, m), 2.7–2.9 (2H, m), 3.01 (1H, m), 3.10 (2H, s), 3.2–3.4 (3.7H, m), 3.70 (0.7H, m), 3.87 (0.3H, m), 4.15 (0.3H, m), 5.00 (0.7H, d, J=7.8 Hz), 5.06 (0.3H, m), 6.37 (0.3H, m), 6.39 (0.7H, d, J=7.8 Hz), 6.58 (0.7H, d, J=8.3 Hz), 6.71 (0.3H, m), 7.6–8.0 (7H, m).

IR (KBr)

υ 3400, 1620, 1319, 1176, 1120, 1035 cm$^{-1}$.

Mass (FAB)

m/z 511 (M+H).

Elementary Analysis: As $C_{32}H_{34}N_2O_4 \cdot HCl \cdot 0.4H_2O$

Calcd.: C, 69.34; H, 6.51; N, 5.05; Cl, 6.40

Found.: C, 69.13; H, 6.86; N, 4.96; Cl, 6.73

Compound 53·hydrochloride mp 200° C. (decomposition)

NMR (400 MHz, DMSO-d$_6$)

δ 0.42 (1H, m), 0.53 (1H, m), 0.61 (1H, m), 0.69 (1H, m), 1.08 (1H, m), 1.28 (0.5H, m), 1.3–1.5 (2.5H, m), 1.74 (1H, m), 2.15 (1H, m), 2.4–2.6 (2.5H, m), 2.8–2.9 (1.5H, m), 2.93 (1.5H, s), 3.0–3.1 (2H, m), 3.16 (1.5H, s), 3.3–3.4 (2H, m), 3.61 (0.5H, m), 3.85 (1H, brs), 4.20 (0.5H, m), 4.85 (0.5H, d, J=7.3 Hz), 4.91 (0.5H, d, J=7.8 Hz), 6.4–6.7 (3.5H, m), 6.8–6.9 (1.5H, m), 7.14 (0.5H, d, J=15.1 Hz), 7.28 (0.5H, d, J=15.6 Hz), 7.68 (0.5H, s), 7.80 (0.5H, s).

IR (KBr)

υ 3390, 1647, 1597, 1321, 1127, 1017 cm$^{-1}$.

Mass (FAB)

m/z 477 (M+H).

Elementary Analysis: As $C_{28}H_{32}N_2O_5 \cdot HCl \cdot 0.6H_2O$

Calcd.: C, 64.20; H, 6.58; N, 5.35; Cl, 6.77.

Found.: C, 64.21; H, 6.84; N, 5.38; Cl, 6.69.

Compound 54·methanesulfonate mp 235° C. (decomposition)

NMR (400 MHz, DMSO-$_6$)

δ 0.42 (1H, m), 0.51 (1H, m), 0.60 (1H, m), 0.68 (1H, m), 1.08 (1H, m), 1.2–1.5 (3H, m), 1.72 (1H, d, J=12.2 Hz), 2.12 (1H, m), 2.34 (3H, s), 2.4–2.5 (2H, m), 2.86 (1H, m), 2.91 (2H, s), 3.0–3.1 (2H, m), 3.15 (1H, s), 3.3–3.5 (2H, m), 3.61 (0.7H, m), 3.82 (1H, brs), 4.19 (0.3H, m), 4.81 (0.7H, d, J=7.8 Hz), 4.89 (0.3H, d, J=8.3 Hz), 6.46 (0.7H, d, J=15.6 Hz), 6.6–6.7 (1.3H, m), 6.85 (0.7H, d, J=7.8 Hz), 7.00 (0.3H, d, J=15.1 Hz), 7.26 (0.7H, d, J=4.9 Hz), 7.31 (0.7H, d, J=15.6 Hz), 7.46 (0.3H, d, J=15.1 Hz), 7–5–7.7 (2H, m), 7.87 (0.3H, s).

IR (KBr)

υ 3410, 1642, 1595, 1323, 1127, 1035, 859 cm$^{-1}$.

Mass (FAB)

m/z 493 (M+H).

Elementary Analysis: As $C_{28}H_{32}N_2O_4S \cdot CH_3SO_3H \cdot 0.2H_2O$

Calcd.: C, 58.80; H, 6.19; N, 4.73; S, 10.83

Found.: C, 58.60; H. 6.42; N, 4.72; S, 10.82

Compound 55·hydrochloride mp 196–199° C.

NMR (400 MHz, DMSO-$_6$)

δ 0.41 (1H, m), 0,53 (1H, m), 0.59 (1H, m), 0.67 (1H, m), 1.09 (1H, m), 1.3–1.5 (3H, m), 1.73 (1H, d, J=13.2 Hz), 2.20 (1H, m), 2.4–2.6 (2H, m), 2.88 (1H, m), 2.97 (2H, s), 3.0–3.1 (2H, m), 3.23 (1H, s), 3.3–3.4 (2H, m), 3.68 (0.7H, m), 3.87 (1H, brs), 4.18 (0.3H, m), 4.88 (0.7H, d, J=7.8 Hz), 4.97 (0.3H, d, J=8.3 Hz), 6.6–6.9 (2.7H, m), 7.28 (0.3H, d, J=15.1 Hz), 7.5–7.7 (1.7H, m), 7.7–7.9 (3H, m), 8.14 (0.3H, d, J=7.8 Hz).

IR (KBr)

υ 3400, 1649, 1605, 1460, 1317, 1125, 1036 cm$^{-1}$.

Mass (FAB)

m/z 555 (M+H).

Elementary Analysis: As $C_{31}H_{33}N_2O_4F_3 \cdot 1.1HCl \cdot 0.4H_2O$

Calcd.: C, 61.86; H, 5.84; N, 4.65; F, 9.47; Cl, 6.48

Found.: C, 61.88; H, 5.94; N, 4.67; F, 9.47; Cl, 6.44

Compound 56·0.5 tartarate mp 167–170° C.

NMR (400 MHz, DMSO-$_6$)

δ 0.21 (2H, m), 0.52 (2H, m),0.91 (1H, m), 1.2–1.4 (3H, m), 1.58 (1H, m), 2.1–2.2 (2H, m), 2.30 (1H, m), 2.49 (1H, m), 2.6–2.8 (3H, m), 2.90 (2H, s), 3.18 (1H, d, J=18.6 Hz), 3.16 (1H, s), 3.24 (1H, m), 3.65 (0.7H, m), 4.03 (1H, s), 4.20 (0.3H, m), 4.68 (0.7H, d, J=8.3 Hz), 4.79 (0.3H, d, J=7.8 Hz), 6.5–6.7 (1.3H, m), 6.8–6.9 (1.4H, m), 7.34 (1H, d, J=15.6 Hz), 7.51 (0.3H, d, J=15.6 Hz), 7.7–7.8 (3.7H, m), 7.94 (0.3H, d, J=8.3 Hz).

IR (KBr)

υ 3400, 1649, 1601, 1325, 1168, 1114 cm$^{-1}$.

Mass (FAB)

m/z 555 (M+H).

Elementary Analysis: As $C_{31}H_{33}N_2O_4F_3 \cdot 0.5(C_4H_6O_6) \cdot 0.3H_2O$ Calcd.: C, 62.41; H, 5.81; N, 4.41; F, 8.98

Found.: C, 62.36; H, 5.80; N, 4.41; F, 8.98

[Reference Examples 47–52]

17-cyclopropylmethyl-3,14β-dihydroxy-4,5α-epoxy-6β-(N-isobutyl-3-methylcinnamamido)morphinan 57·1 tartrate (yield: 91%), 17-cyclopropylmethyl-3,14β-dihydroxy-4,5α-epoxy-6β-(N-isobutyl-6-phenylhexanoamido)morphinan 58·1 tartrate (yield: 85%), 17-cyclopropylmethyl-3,14β-dihydroxy-4,5α-epoxy-6β-(N-isobutyl-8-phenyloctanoamido) morphinan 59·1 tartrate (yield: 82%), 17-cyclopropylmethyl-3,14β-dihydroxy-4,5α-epoxy-6β-(N-isobutyl-11-phenylundecanoamido)morphinan 60·1 tartrate (yield: 74%), 17-cyclopropylmethyl-3,14β-dihydroxy-4,5α-epoxy-6β-(N-isobutyl-5-benzoylpentanoamido)morphinan 61·methanesulfonate (yield: 71%) and 17-cyclopropylmethyl-3,14β-dihydroxy-4,5α-epoxy-6β-(N-isobutyl-5-cyclohexylpentanoamido)morphinan 62·phosphate (yield: 82%) were obtained by following the procedure of Reference Example 15, using 17-cyclopropylmethyl-3,14β-dihydroxy-4,5α-epoxy-6β-isobutylaminomorphinan 18 instead of 17-cyclopropylmethyl-3,14β-dihydroxy-4,5α-epoxy-6α-methylaminomorphinan 2 for the starting material, and using 3-methylcinnamoyl chloride; 6-phenylhexanoyl chloride, 8-phenyloctanoyl chloride, 11-phenylundecanoyl chloride, 5-benzoylpentanoyl chloride and 5-cyclohexylpentanoyl chloride instead of 3,4-dichlorophenylacetyl chloride.

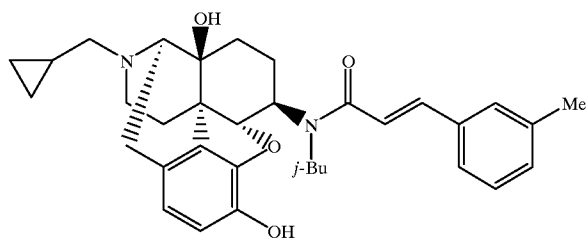

57

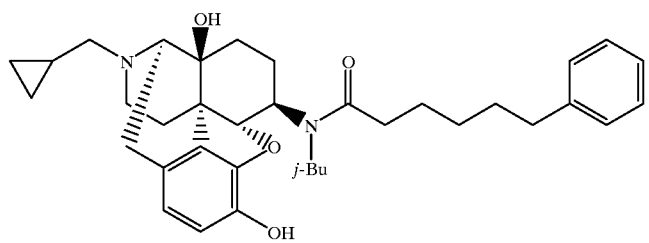

58

59

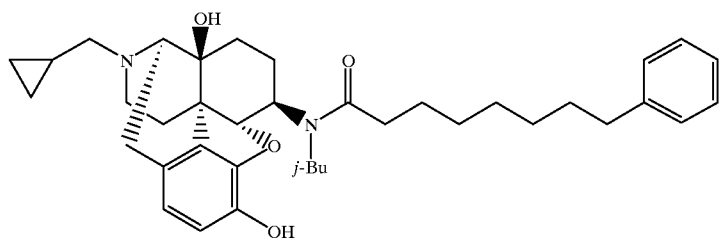

60

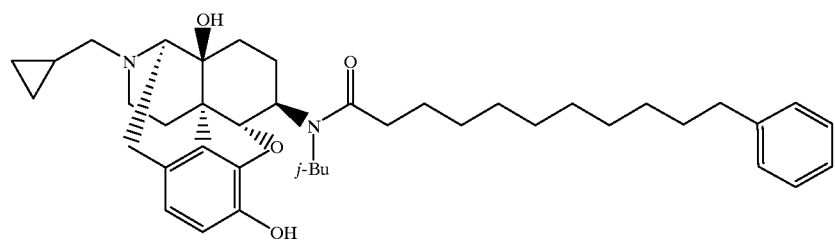

61

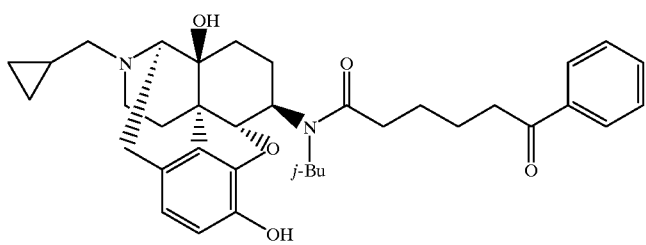

62

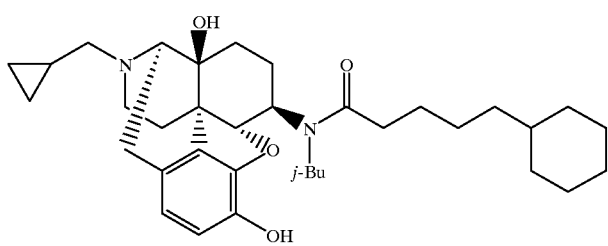

Compound 57·1 tartrate
mp>103° C. (decomposition)
NMR (400 MHz, DMSO-$d_6$)
δ 0.26 (2H, m), 0.53 (2H, m), 0.83–0.98 (7H, m), 1.26–1.86 (4H, m), 2.13–2.34 (3H, m), 2.33 (3H, s), 2.50–2.85 (4H, m), 3.07–3.40 (5H, m), 3.60 (5H, br s, 5×OH), 3.67 (1H, m), 4.09 (2H, s), 4.58 (0.5H, m), 5.24 (0.5H, m), 6.57–6.67 (2H, m). 6.75 (0.5H, m), 7.08–7.33 (4H, m), 7.43–7.53 (1.5H, m), 9.15 (0.5H, m, NH+), 9.40 (0.5H, m, NH+).
IR (KBr)
υ 3318, 1736, 1638, 1593, 1460, 1377, 1315, 1245, 1125, 1069, 1033, 984, 922, 787 cm$^{-1}$.
Mass (FAB)
m/z 543 ((M+H)$^+$).
Elementary analysis: As $C_{34}H_{42}N_2O_4 \cdot C_4H_6O_6 \cdot 0.4H_2O$
Calculated values: C 65.20; H 7.03; N 4.00
Measured values: C 65.13; H 7.09; N 3.96
Compound 58·1 tartrate
mp>110° C. (decomposition)
NMR (400 MHz, DMSO-$d_6$)
δ 0.24 (2H, m), 0.54 (2H, m), 0.78–0.88 (6H, m), 0.92 (1H, m), 1.14–1.76 (11H, m), 1.91–2.32 (5H, m), 2.46–2.83 (6H, m), 2.96–3.16 (2H, m), 3.26–3.38 (2H, m), 3.48 (1H, m), 3.60 (5H, br s, 5×OH), 4.09 (2H, s), 4.55 (0.5H, br d, J=7.8 Hz), 5.17 (0.5H, br d, J=7.3 Hz), 6.55 (0.5H, d, J=8.1 Hz), 6.56 (0.5H, d, J=8.1 Hz), 6.64 (0.5H, d, J=8.1 Hz), 6.65 (0.5H, d, J=8.1 Hz), 7.12–7.22 (3H, m), 7.22–7.29 (2H, m), 9.25 (1H, m, NH+).
IR (KBr)
υ 3300, 1738, 1622, 1504, 1460, 1421, 1388, 1365, 1319, 1270, 1123, 1071, 1033, 922, 748 cm$^{-1}$.
Mass (FAB)
m/z 573 ((M+H)$^+$).
Elementary analysis: As $C_{36}H_{48}N_2O_4 \cdot C_4H_6O_6 \cdot 0.2H_2O$
Calculated values: C 66.13; H 7.55; N 3.86
Measured values: C 66.10; H 7.52; N 3.90
Compound 59·1 tartrate
mp>110° C. (decomposition)
NMR (400 MHz, DMSO-$d_6$)
δ 0.24 (2H, m), 0.54 (2H, m). 0.79–0.88 (6H, m), 0.92 (1H, m), 1.10–1.78 (15H, m), 1.91–2.32 (5H, m), 2.48–2.83 (6H, m), 2.96–3.16 (2H, m), 3.26–3.38 (2H, m), 3.47 (1H, m), 3.65 (5H, br s, 5×OH), 4.09 (2H, s), 4.50 (0.5H, br d, J=7.8 Hz), 5.17 (0.5H, br d, J=7.3 Hz), 6.56 (0.5H, d, J=8.1 Hz), 6.56 (0.5H, d, J=8.1 Hz), 6.64 (0.5H, d, J=8.1 Hz), 6.65 (0.5H, d, J=8.1 Hz), 7.13–7.21 (3H, m), 7.23–7.29 (2H, m), 9.25 (1H, m, NH+).
IR (KBr)
υ 3323, 1731, 1611, 1508, 1460, 1421, 1388, 1365, 1321, 1276, 1123, 1069, 1033, 922, 748 cm$^{-1}$.
Mass (FAB)
m/z 601 ( (M+H)$^+$)
Elementary analysis: As $C_{38}H_{52}N_2O_4 \cdot C_4H_6O_6 \cdot 0.4H_2O$
Calculated values: C 66.54; H 7.82; N 3.70
Measured values: C 66.45; H 7.77; N 3.81
Compound 60·tartrate
mp>105° C. (decomposition)
NMR (400 MHz, DMSO-$_6$)
δ 0.24(2H, m), 0.53 (2H, m), 0.76–0.88 (6H, m), 0.92 (1H, m), 0.96–1.78 (21H, m), 1.91–2.32 (5H, m), 2.48–2.83 (6H, m), 2.97–3.17 (2H, m), 3.26–3.38 (2H, m), 3.40 (5H, br s, 5×OH), 3.47 (1H, m), 4.10 (2H, s), 4.53 (0.5H, br d, J=7.3 Hz), 5.16 (0.5H, m), 6.55 (0.5H, d, J=7.8 Hz), 6.57 (0.5H, d, J=7.8 Hz), 6.64 (0.5H, d, J=7.8 Hz), 6.65 (0.5H, d, J=7.8 Hz), 7.10–7.22 (3H, m), 7.25–7.32 (2H, m), 9.20 (1H, m, NH+).
IR (KBr)
υ 3314, 1731, 1611, 1508, 1462, 1421, 1365, 1321, 1272, 1243, 1123, 1071, 1033, 922, 702 cm$^{-1}$.
Mass (FAB)
m/z 643 ((M+H)$^+$).
Elementary analysis: As $C_{41}H_{58}N_2O_4 \cdot C_4H_6O_6 \cdot 0.5H_2O$
Calculated values: C 67.39; H 8.17; N 3.65
Measured values: C 67.33; H 8.08; N 3.65
Compound 61·methanesulfonate
mp>125° C. (decomposition)
NMR (400 MHz, DMSO-$_6$)
δ 0.42 (1H, m), 0.48 (1H, m), 0.59 (1H, m), 0.68 (1H, m), 0.82 (1.5H, d, J=6.3 Hz), 0.84 (1.5H, d, J=6.3 Hz), 0.86 (1.5H, d, J=6.3 Hz), 0.87 (1.5H, d, J=6.3 Hz), 1.15 (1H, m), 1.31 (1H, m), 1.38–1.77 (7H, m), 1.91–2.69 (6H, m), 2.30 (3H, s), 2.82–3.12 (6H, m), 3.27–3.38 (2H, m), 3.42–3.54 (2H, m), 3.80 (1H, br dd, J=8.6, 5.4 Hz), 4.62 (0.5H, d, J=7.3 Hz), 5.23 (0.5H, d, J=7.3 Hz), 5.89 (0.5H, s, OH), 6.21 (0.5H, s, OH), 6.63 (0.5H, d, J=7.8 Hz), 6.64 (0.5H, d, J=7.8 Hz), 6.71 (0.5H, d, J=7.8 Hz), 6.73 (0.5H, d, J=7.8 Hz), 7.51–7.56 (2H, m), 7.64 (1H, ddd, J=7.3, 7.3, 2.0 Hz), 7.92 (1H, br d, J=7.3 Hz), 7.98 (1H, br d, J=7.3 Hz), 8.67 (0.5H, br s, NH+), 8.76 (0.5H, br s, NH+), 9.25 (0.5H, br s, OH), 9.47 (0.5H, br s, OH).
IR (KBr)
υ 3250, 1682, 1630, 1508, 1473, 1423, 1377, 1321, 1225, 1125, 1044, 924, 857, 810, 779, 649 cm$^{-1}$.
Mass (FAB)
m/z 587 ((M+H)$^+$).
Elementary analysis: As $C_{36}H_{46}N_2O_4 \cdot CH_3SO_3H \cdot 0.5H_2O$
Calculated values: C 64.23; H 7.43; N 4.05; S 4.63
Measured values: C 64.12; H 7.16; N 4.15; S 4.89
Compound 62·phosphate
mp>147° C. (decomposition)
NMR (400 MHz, DMSO-d$_6$)
δ 0.22 (2H, m), 0.52 (2H, m), 0.73–0.95 (9H, m), 0.98–1.76 (20H, m), 1.93–2.33 (5H, m), 2.50–2.80 (5H, m), 2.94–3.52 (4H, m), 4.48 (0.6H, d, J=7.8 Hz), 5.16 (0.4H, d, J=6.8 Hz), 6.50 (5H, br s, 4×OH, NH+), 6.54 (0.4H, d, J=8.3 Hz), 6.58 (0.6H, d, J=8.3 Hz), 6.63 (0.4H, d, J=8.3 Hz), 6.66 (0.6H, d, J=8.3 Hz).
IR (KBr)
υ 3220, 1638, 1622, 1508, 1460, 1388, 1321, 1236, 1125, 1033, 926, 857 cm$^{-1}$.
Mass (FAB)
m/z 565 ((M+H)$^+$).
Elementary analysis: As $C_{35}H_{52}N_2O_4 \cdot 0.95H_3PO_4 \cdot 0.9H_2O$
Calculated values: C 62.36; H 8.47; N 4.16; P 4.36
Measured values: C 62.63; H 8.22; N 4.26; P 4.02

[Reference Examples 53–56]

17-cyclopropylmethyl-3,14β-dihydroxy-4,5α-epoxy-6β-(N-ethyl-3-trifluoromethylcinnamarido)morphinan 63·0.5 tartrate (yield: 87%), 17-cyclopropylmethyl-3,14β-dihydroxy-4,5α-epoxy-6β-(N-isopropyl-3-trifluoromethylcinnamamido)morphinan 64·hydrochloride (yield: 21%), 17-cyclopropylmethyl-3,14β-dihydroxy-4,5α-epoxy-6β-(N-isobutyl-3-trifluoromethylcinnamamido) morphinan 65·0.5 tartrate (yield: 81%) and 17-cyclopropylmethyl-3,14β-dihydroxy-4,5α-epoxy-6β-(N-butyl-3-trifluoromethylcinnamamido)morphinan 66·1 tartrate (yield: 78%) were obtained by following the procedure of Reference Example 15, using 17-cyclopropylmethyl-3,14β-dihydroxy-4,5α-epoxy-6β-ethylaminomorphinan 16, 17-cyclopropylmethyl-3,14β-dihydroxy-4,5α-epoxy-6β-isopropylaminomorphinan 17, 17-cyclopropylmethyl-3,14β-dihydroxy-4,5α-epoxy-6β-isobutylaminomorphinan 18 and 17-cyclopropylmethyl-3,14β-dihydroxy-4,5α-epoxy-6β-butylaminomorphinan 19 instead of 17-cyclopropylmethyl-3,14β-dihydroxy-4,5α-epoxy-6α-methylaminomorphinan 2 for the starting material, and using 3-trifluoromethylcinnamoyl chloride instead of 3,4-dichlorophenylacetyl chloride.

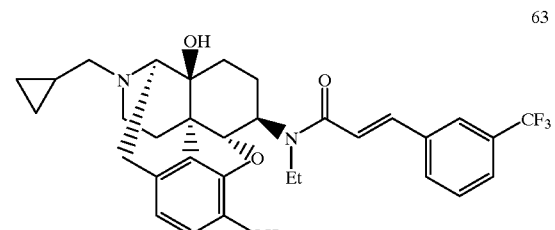

63

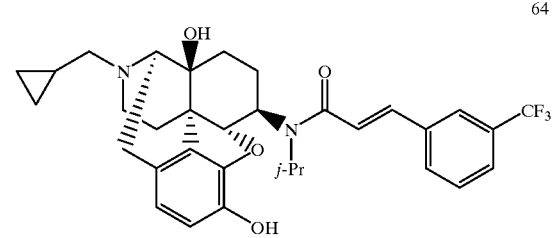

64

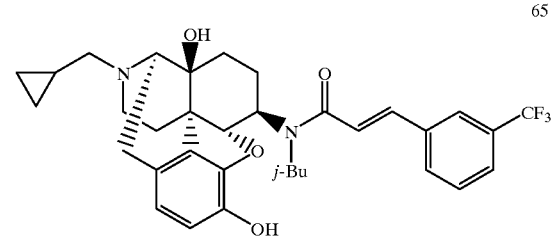

65

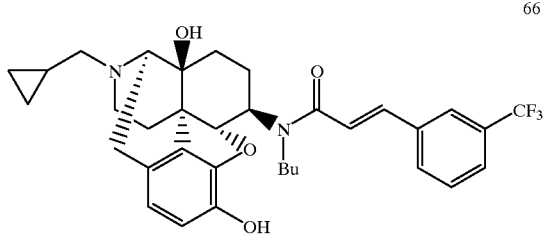

66

Compound 63·0.5 tartrate
m>200° C. (decomposition)
NMR (400 MHz, DMSO-₆)

δ 0.22 (2H, m), 0.53 (2H, m), 0.91 (1H, m), 1.19 (1.5H, t, J=6.8 Hz), 1.21 (1.5H, t, J=6.8 Hz), 1.27–1.62 (4H, m), 2.04–2.38 (3H, m), 2.48 (1H, m), 2.55–2.80 (3H, m), 3.09 (1H, m), 3.14–3.34 (2H, m), 3.50–3.75 (2H, m), 3.55 (3H, br s, 3×OH), 4.03 (1H, S), 4.60 (0.5H, br d, J=6.3 Hz), 4.99 (0.5 H, m), 6.57 (0.5H, d, J=8.1 Hz), 6.61 (0.5H, d, J=8.1 Hz), 6.63 (0.5H, d, J=8.1 Hz), 6.70 (0.5H, J=8.1 Hz), 6.75 (0.5H, br d, J=15.6 Hz), 7.26 (0.5H, d, J=15.6 Hz), 7.37 (0.5H, br d, J=15.6 Hz), 7.57 (0.5H, d, J=15.6 Hz), 7.58–7.83 (3H, m), 8.03 (0.5H, d, J=7.8 Hz), 8.12 (0.5H, br s), 9.33 (1H, m, NH+).

IR (KBr)
υ 3386, 1649, 1595, 1506, 1433, 1328, 1243, 1168, 1118, 1073, 982, 920, 859, 804 cm⁻¹.

Mass (FAB)
m/z 569 ( (M+H)⁺)
Elementary analysis: As $C_{32}H_{35}F_3N_2O_4 \cdot 0.5C_4H_6O_6 \cdot 0.3H_2O$
Calculated values: C 62.92; H 5.99; F 8.78; N 4.32
Measured values: C 62.89; H 6.05; F 8.84; N 4.29

Compound 64·hydrochloride
mp>200° C. (decomposition)
NMR (400 MHz, DMSO-₆)

δ 0.42 (1H, m), 0.52 (1H, m), 0.61 (1H, m), 0.68 (1H, m), 1.02 (1.5H, br d, J=5.8 Hz), 1.04–1.13 (2H, m), 1.17 (1.5H, br d, J=5.8 Hz), 1.36–1.48 (2H, m), 1.43 (1.5H, d, J=6.8 Hz), 1.51 (1.5H, d, J=6.8 Hz), 1.73 (1H, m), 2.10–2.60 (3H, m), 2.82–2.95 (2H, m), 2.98–3.12 (2H, m), 3.25–3.42 (2H, m), 3.55 (0.5H, m), 3.85 (1H, d, J=4.9 Hz), 4.48 (0.5H, m), 4.80 (0.5H, d, J=8.3 Hz), 5.34 (0.5H, m), 6.01 (0.5H, s, OH), 6.51 (0.5H, s, OH), 6.64 (0.5H, d, J=15.6 Hz), 6.66 (0.5H, d, J=8.3 Hz), 6.68 (0.5H, d, J=8.3 Hz), 6.75 (0.5H, d, J=8.3 Hz), 6.82 (0.5H, d, J=8.3 Hz), 7.28 (0.5H, d, J=15.6 Hz), 7.42–7.78 (4H, m), 8.02 (0.5H, d, J=7.8 Hz), 8.14 (1H, br s), 8.84 (1H, m, NH+), 9.29 (0.5, s, OH), 9.65 (0.5H, s).

IR (KBr)
υ 3362, 1651, 1605, 1510, 1462, 1439, 1334, 1201, 1168, 1125, 1033, 980, 917, 857, 806 cm⁻¹.

Mass (FAB)
m/z 583 ((M+H)⁺).
Elementary analysis: As $C_{33}H_{37}F_3N_2O_4 \cdot HCl \cdot 0.7H_2O$
Calculated values: C 62.74; H 6.29; Cl 5.61; F 9.02; N 4.43
Measured values: C 62.76; H 6.29; Cl 5.50; F 9.28; N 4.45

Compound 65·0.5 tartrate
mp>140° C. (decomposition)
NMR (400 MHz, DMSO-₆)

δ 0.31 (2H, m), 0.53 (2H, m), 0.81–0.98 (7H, m), 1.27–1.61 (4H, m), 1.78–2.34 (3H, m), 2.42–2.80 (4H, m), 3.00–3.15 (2H, m), 3.20–3.44 (3H, m), 3.50 (3H, br s, OH), 3.70 (1H, m), 4.03 (1H, s), 4.55 (0.5H, m), 5.22 (0.5H, m), 6.57 (0.5H, d, J=7.8 Hz), 6.58 (0.5H, d, J=7.8 Hz), 6.64 (0.5H, d, J=7.8 Hz), 6.65 (0.5H, d, J=7.8 Hz), 6.78 (0.5H, m), 7.31 (0.5H, m), 7.31 (0.5H, d, J=15.1 Hz), 7.55–7.82 (3H, m), 7.57 (0.5H, d, J=15.1 Hz), 8.05 (0.5H, d, J=8.3 Hz), 8.06 (0.5H, br s), 9.25 (1H, m, NH+).

IR (KBr)
υ 3358, 1649, 1603, 1504, 1460, 1334, 1232, 1168, 1125, 1071, 1035, 984, 924, 859, 801 cm⁻¹.

Mass (FAB)
m/z 597 ((M+H)⁺).
Elementary analysis: As $C_{34}H_{39}F_3N_2O_4 \cdot 0.5C_4H_6O_6$
Calculated values: C 64.37; H 6.30; F 8.48; N 4.17
Measured values: C 64.21; H 6.40; F 8.47; N 4.21

Compound 66 ·1 tartrate
mp>130° C. (decomposition)
NMR (400 MHz, DMSO-₆)

δ 0.27 (2H, m), 0.53 (2H, m), 0.92 (1.5H, t, J=7.8 Hz), 0.93 (1H, m), 0.94 (1.5H, t, J=7.8 Hz), 1.28–1.63 (7H, m), 2.03–2.38 (2H, m), 2.54 (1H, m), 2.67–2.85 (3H, m), 3.07–3.18 (2H, m), 3.30–3.53 (4H, m), 3.50 (5H, br s, OH), 3.68 (1H, m), 4.10 (2H, s), 4.61 (0.5H, m), 5.05 (0.5H, m), 6.58 (0.5H, d, J=8.3 Hz), 6.62 (0.5H, d, J=8.3 Hz), 6.65 (0.5H, d, J=8.3 Hz), 6.70 (0.5H, d, J=8.3 Hz), 6.75 (0.5H, br d, J=15.6 Hz), 7.24 (0.5H, d, J=15.6 Hz), 7.35 (0.5H, br d, J=15.6 Hz), 7.57 (0.5H, d, J=15.6 Hz), 7.58–7.82 (3H, m), 8.03 (0.5H, d, J=7.8 Hz), 8.07 (0.5H, br s), 9.32 (1H, m, NH+).

IR (KBr)
υ 3316, 1731, 1649, 1593, 1506, 1459, 1334, 1251, 1199, 1170, 1122, 1075, 1035, 980, 922, 859, 803 cm⁻¹.

Mass (FAB)
m/z 597 ((M+H)⁺).
Elementary analysis: As $C_{34}H_{39}F_3N_2O_4 \cdot C_4H_6O_6$
Calculated values: C 61.12; H 6.07; F 7.63; N 3.75
Measured values: C 60.88; H 6.20; F 7.73; N 3.74

[EXAMPLES 11–13]

17-cyclopropylmethyl-3,14β-dihydroxy-4,5α-epoxy-6β-[N-(2-phenethyl)-3-trifluoromethylcinnamamido]morphinan 67·1 tartrate (yield: 60%), 17-cyclopropylmethyl-3,14β-dihydroxy-4,5α-epoxy-6β-(N-cyclohexylmethyl-3-trifluoromethylcinnamamido)morphinan 68·1 tartrate (yield: 92%) and 17-cyclopropylmethyl-3,14β-dihydroxy-4,5α-epoxy-6β-[N-(3-phenylpropyl)-3-trifluoromethylcinnamamido]-morphinan 69·1 tartrate (yield: 93%) were obtained by following the procedure of Reference Example 15, using 17-cyclopropylmethyl-3,14β-dihydroxy-4,5α-epoxy-6β-(2-phenethylamino)morphinan 21, 17-cyclopropylmethyl-3,14β-dihydroxy-4,5α-epoxy-6β-(cyclohexylmethyl)aminomorphinan 22 and 17-cyclopropylmethyl-3,14β-dihydroxy-4,5α-epoxy-6β-(3-phenylpropylamino)morphinan 23 instead of 17-cyclopropylmethyl-3,14β-dihydroxy-4,5(α-epoxy-6α-methylaminomorphinan 2 for the starting material, and using 3-trifluoromethylcinnamoyl chloride instead of 3,4-dichlorophenylacetyl chloride.

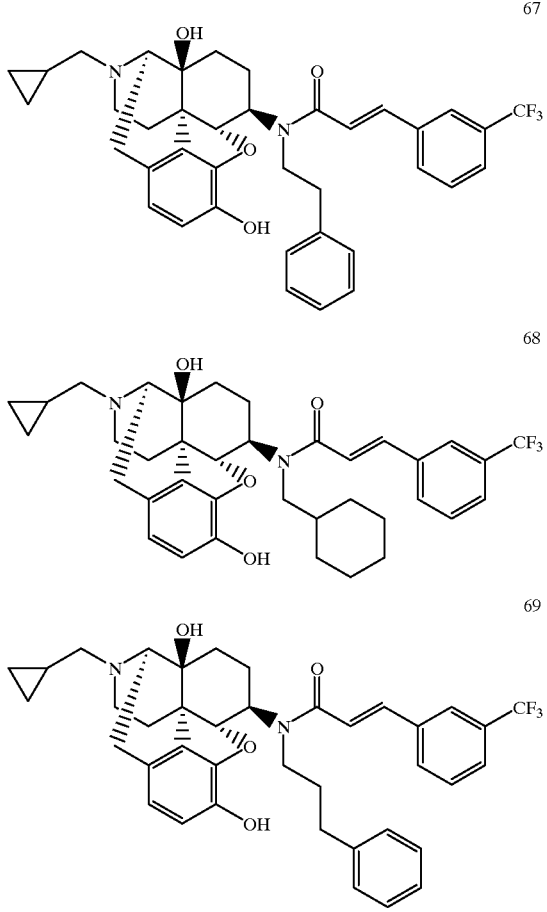

Compound 67·1 tartrate
mp>125° C. (decomposition)
NMR (400 MHz, DMSO-$_6$)

δ 0.27 (2H, m), 0.54 (2H, m), 0.93 (1H, m), 1.28–1.64 (4H, m), 2.06–2.38 (3H, m), 2.57 (1H, m), 2.70–2.94 (4H, m), 3.02–3.42 (3H, m), 3.50 (5H, br s, 5×OH), 3..57–3.85 (2H, m), 4.13 (2H, s), 4.60 (0.5H, m), 5.18 (0.5H, m), 6.61 (0.5H, d, J=8.1 Hz), 6.63 (0.5H, d, J=8.1 Hz), 6.70 (0.5H, d, J=8.1 Hz), 6.72 (0.5H, d, J=8.1 Hz), 6.83 (1H, m), 7.13–7.48 (6H, m), 7.58–7.92 (4H, m), 9.32 (1H, m, NH+).

IR (KBr)

υ 3316, 1736, 1649, 1599, 1456, 1433, 1334, 1168, 1122, 1073, 919, 859, 801, 692 cm$^{-1}$.

Mass (FAB)

m/z 645 ( (M+H)$^+$).

Elementary analysis: As $C_{38}H_{39}F_3N_2O_4 \cdot C_4H_6O_6 \cdot 0.6H_2O$
Calculated values: C 62.62; H 5.78; F 7.07; N 3.48
Measured values: C 62.54; H 5.88; F 7.07; N 3.47

Compound 68·1 tartrate
mp>125° C. (decomposition)
NMR (400 MHz, DMSO-$_6$)

δ 0.25 (2H, m), 0.53 (2H, m), 0.87–1.04 (3H, m), 1.17–1.48 (6H, m), 1.50–1.90 (7H, m), 2.01–2.37 (2H, m), 2.57 (1H, m), 2.63–2.89 (4H, m), 3.02–3.44 (4H, m), 3.50 (5H, br s, 5×OH), 3.68 (1H, m), 4.11 (2H, s), 4.55 (0.5H, m), 5.28 (0.5H, m), 6.58 (0.5H, d, J=8.1 Hz), 6.59 (0.5H, d, J=8.1 Hz), 6.67 (1H, d, J=8.1 Hz), 6.75 (0.5H, m), 7.29 (1H, d, J=15.6 Hz), 7.57 (1H, d, J=15.6 Hz), 7.58–7.80 (2.5H, m), 8.04 (1H, m), 9.26 (1H, m, NH+).

IR (KBr)

υ 3324, 1736, 1651, 1603, 1508, 1450, 1336, 1249, 1201, 1168, 1122, 1073, 1033, 984, 808, 694 cm$^{-1}$.

Mass (FAB)

m/z 637 ( (M+H)$^+$).

Elementary analysis: As $C_{37}H_{43}F_3N_2O_4 \cdot C_4H_6O_6$
Calculated values: C 62.59; H 6.28; F 7.24; N 3.58
Measured values: C 62.43; H 6.44; F 7.24; N 3.78

Compound 69·1 tartrate
mp>125° C. (decomposition)
NMR (400 MHz, DMSO-$_6$)

δ 0.26 (2H, m), 0.54 (2H, m), 0.93 (1H, m), 1.29–1.52 (3H, m), 1.58 (1H, m), 1.78–2.35 (4H, m), 2.52–2.85 (6H, m), 3.07–3.27 (2H, m), 3.35 (1H, m), 3.41–3.55 (2H, m), 3.50 (5H, br s, 5×OH), 3.68 (1H, m), 4.10 (2H, s), 4.58 (0.5H, m), 4.95 (0.5H, m), 6.59 (0.5H, d, J=8.1 Hz), 6.62 (0.5H, d, J=8.1 Hz), 6.67 (0.5H, d, J=8.1 HJz), 6.70 (0.5H, d, J=8.1 Hz), 6.74 (0.5H, m), 7.05 (0.5H, d, J=15.6 Hz), 7.16–7.41 (5.5H, m), 7.55 (0.5H, d, J=15.6 Hz), 7.55–7.80 (3H, m), 7.87 (0.5H, m), 8.00 (0.5H, m), 9.32 (1H, m, NH+).

IR (KBr)

υ 3370, 1736, 1649, 1603, 1499, 1458, 1367, 1336, 1245, 1199, 1166, 1123, 1073, 1033, 980, 922, 803, 748, 694 cm$^{-1}$.

Mass (FAB)

m/z 659 ((M+H)$^+$).

Elementary analysis: As $C_{39}H_{41}F_3N_2O_4 \cdot C_4H_6O_6$
Calculated values: C 63.85; H 5.86; F 7.05; N 3.46
Measured values: C 63.64; H 5.91; F 7.11; N 3.57

[Reference Example 57]

17-cyclopropylmethyl-3,14β-dihydroxy-4,5α-epoxy-6β-(N-pentyl-6-phenylhexanoamido)morphinan 70·methanesulfonate (yield: 90%) was obtained by following the procedure of Reference Example 15, using 17-cyclopropylmethyl-3,14β-dihydroxy-4,5α-epoxy-6β-pentylaminomorphinan 20 instead of 17-cyclopropylmethyl-3,14β-dihydroxy-4,5α-epoxy-6α-methylaminomorphinan 2 for the starting material, and using 6-phenylhexanoyl chloride instead of 3,4-dichlorophenylacetyl chloride.

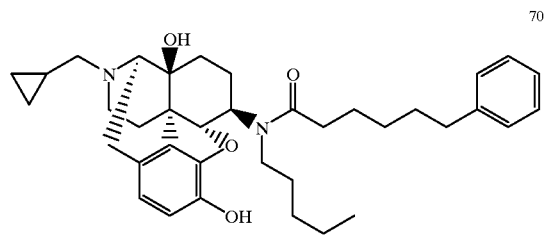

mp 104–115° C. (decomposition)
NMR (400 MHz, DMSO-d$_6$)

δ 0.42 (1H, m), 0.48 (1H, m), 0.59 (1H, m), 0.69 (1H, m), 0.85 (1.2H, t, J=7.3 Hz), 0.89 (1.8H, t, J=7.3 Hz), 1.15 (1H, m), 1.12–1.74 (17H, m), 1.94–2.28 (3H, m), 2.31 (3H, s), 2.41–2.60 (3H, m), 2.86 (1H, m), 2.96–3.23 (4H, m), 3.28–3.55 (3H, m), 3.77 (0.4H, br d, J=5.4 Hz), 3.81 (0.6H, br d, J=5.9 Hz), 4.62 (0.6H, d, J=7.8 Hz), 5.08 (0.4H, m), 5.94 (0.4H, br s, OH), 6.20 (0.6H, br s, OH), 6.62 (0.4H, d, J=8.1 Hz), 6.64 (0.6H, d, J=8.1

Hz), 6.71 (0.4H, d, J=8.1 Hz), 6.73 (0.6H, d, J=8.1 Hz), 7.13–7.21 (3H, m), 7.23–7.39 (2H, m), 8.68 (0.6H, br s, NH+), 8.74 (0.4H, br s, NH+), 9.28 (0.4H, br s, OH), 9.43 (0.6H, br s, OH).
IR (KBr) ν 3232, 1638, 1508, 1460, 1433, 1377, 1325, 1220, 1168, 1123, 1042, 922, 859, 772, 748, 700 cm$^{-1}$.
Mass (FAB) m/z 587 ((M+H)$^+$).
Elementary analysis: As $C_{37}H_{50}N_2O_4 \cdot 1.1CH_3SO_3H \cdot 0.2H_2O$
Calculated values: C 65.74; H 7.93; N 4.02; S 5.07
Measured values: C 65.81; H 7.93; N 4.11; S 5.06

Examples 14–17

17-cyclopropylmethyl-3,14β-dihydroxy-4,5α-epoxy-6β-(N-cyclohexylmethyl-6-phenylhexanoamido)morphinan 71.methanesulfonate (yield: 83%), 17-cyclopropylmethyl-3,14β-dihydroxy-4,5α-epoxy-6β-[N-(3-phenylpropyl)-6-phenylhexanoamido)morphinan 72.methanesulfonate (yield: 78%), 17-cyclopropylmethyl-3,14β-dihydroxy-4,5α-epoxy-6β-[N-(4-phenylbutyl)-6-phenylhexanoamido) morphinan 73·methanesulfonate (yield: 81%) and 17-cyclopropylmethyl-3,14β-dihydroxy-4,5α-epoxy-6β-[N-(2,2-diphenylethyl)-6-phenylhexanoamido)morphinan 74.methanesulfonate (yield: 82%) were obtained by following the procedure of Reference Example 15, using 17-cyclopropylmethyl-3,14β-dihydroxy-4,5α-epoxy-6β-(cyclohexylmethyl)aminomorphinan 22, 17-cyclopropylmethyl-3,14β-dihydroxy-4,5α-epoxy-6β-(3-phenylpropylamino)morphinan 23, 17-cyclopropylmethyl-3,14β-dihydroxy-4,5α-epoxy-6β-(4-phenylbutylamino) morphinan 24 and 17-cyclopropylmethyl-3,14β-dihydroxy-4,5α-epoxy-6β-(2,2-diphenylethylamino)morphinan 25 instead of 17-cyclopropylmethyl-3,14β-dihydroxy-4,5α-epoxy-6α-methylaminomorphinan 2, and using 6-phenylhexanoyl chloride instead of 3,4-dichlorophenylacetyl chloride,

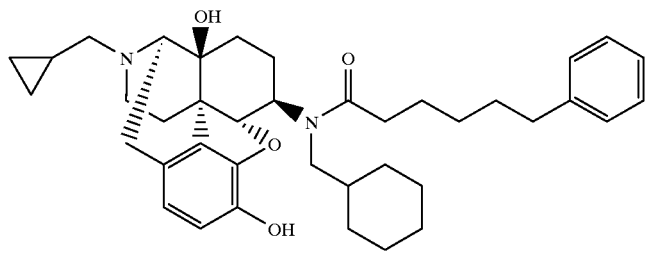

71

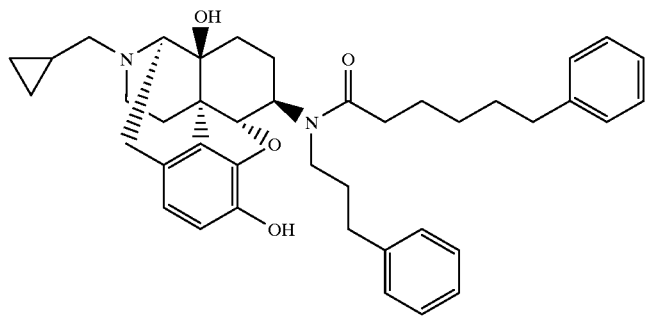

72

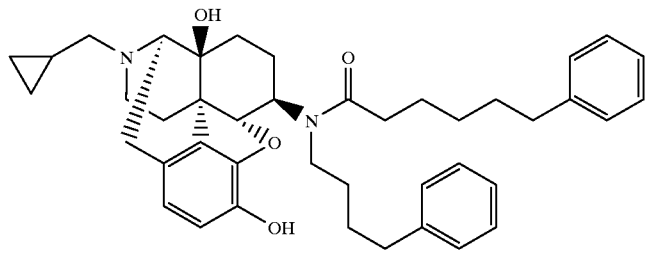

73

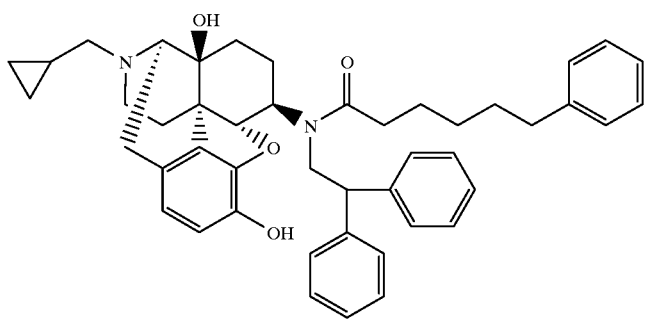

74

Compound 71·methanesulfonate
mp >120° C. (decomposition)
NMR (400 MHz, DMSO-d$_6$)
δ 0.42 (1H, m), 0.48 (1H, m), 0.60 (1H, m), 0.68 (1H, m), 0.78–0.96 (2H, m), 1.02–1.77 (20H, m, 1.90–2.30 (3H, m), 2.31 (3H, s), 2.37–2.72 (3H, m), 2.81–3.10 (5H, m), 3.27–3.52 (4H, m), 3.77 (0.5H, br d, J=5.4 Hz), 3.81 (0.5H, br d, J=5.4 Hz), 4.59 (0.5H, d, J=7.8 Hz), 5.24 (0.5H, m), 5.87 (0.5H, br s, OH), 6.20 (0.5H, br s, OH), 6.62 (0.5H, d, J=8.1 Hz), 6.64 (0.5H, d, J=8.1 Hz), 6.72 (0.5H, d, J=8.1 Hz), 6.73 (0.5H, d, J=8.1 Hz), 7.13–7.22 (3H, m), 7.23–7.39 (2H, m), 8.68 (0.5H, br s, NH+), 8.76 (0.5H, br s, NH+), 9.30 (0.5H, br s, OH), 9.43 (0.5H, br s, OH).
IR (KBr) ν 3214, 1638, 1626, 1508, 1460, 1321, 1199, 1180, 1125, 1044, 919, 857, 777, 748, 708 cm$^{-1}$.
Mass (FAB) m/z 613 ((M+H)$^+$).
Elementary analysis: As C$_{39}$H$_{52}$N$_2$O$_4$·CH$_3$SO$_3$H·0.2H$_2$O
Calculated values: C 67.42; H 7.98; N 3.93; S 4.50
Measured values: C 67.36; H 7.89; N 4.06; S 4.64
Compound 72·methanesulfonate
mp >117° C. (decomposition)
NMR (400 MHz, DMSO-d$_6$)
δ 0.43 (1H, m), 0.48 (1H, m), 0.59 (1H, m), 0.69 (1H, m), 1.16 (1H, m), 1.13–1.57 (9H, m), 1.64–2.20 (6H, m), 2.31 (3H, s), 2.37–2.64 (6H, m), 2.86 (1H, m), 2.98–3.48 (7H, m), 3.77 (0.4H, br d, J=5.4 Hz), 3.81 (0.6H, br d, J=5.4 Hz), 4.59 (0.6H, d, J=8.3 Hz), 5.04 (0.4H, m), 5.94 (0.4H, br s, OH), 6.17 (0.6H, br s, OH), 6.64 (0.4H, d, J=8.3 Hz), 6.64 (0.6H, d, J=8.3 Hz), 6.72 (0.4H, d, J=8.3 Hz), 6.73 (0.6H, d, J=8.3 Hz), 7.12–7.32 (10H, m), 8.68 (0.6H, br s, NH+), 8.73 (0.4H, br s, NH+), 9.30 (0.4H, br s, OH), 9.43 (0.6H, br s, OH).
IR (KBr) ν 3382, 1638, 1630, 1508, 1458, 1431, 1377, 1325, 1170, 1125, 1044, 922, 859, 775, 748, 700 cm$^{-1}$.
Mass (FAB) m/z 635 ((M+H)$^+$).
Elementary analysis: As C$_{41}$H$_{50}$N$_2$O$_4$·CH$_3$SO$_3$H·0.2H$_2$O
Calculated values: C 68.67; H 7.46; N 3.81; S 4.37
Measured values: C 68.61; H 7.26; N 3.92; S 4.40
Compound 73·methanesulfonate
mp >100° C. (decomposition)
NMR (400 MHz, DMSO-d$_6$)
δ 0.37–0.75 (4H, m), 0.99–1.75 (15H, m), 1.91–2.27 (3H, m), 2.30 (3H, s), 2.36–2.69 (6H, m), 2.70–3.55 (8H, m), 3.74–3.86 (1H, m), 4.61 (0.6H, d, J=7.8 Hz), 5.08 (0.4H, br s), 5.93 (0.4H, br s, OH), 6.20 (0.6H, br s, OH), 6.64 (1H, d, J=8.1 Hz), 6.73 (1H, d, J=8.1 Hz), 7.09–7.33 (10H, m), 8.63–8.78 (1H, m, OH), 9.32 (0.4H, br s, OH), 9.42 (0.6H, br s, OH).
IR (KBr) ν 3220, 1620, 1497, 1454, 1375, 1315, 1190, 1044, 700 cm$^{-1}$.
Mass (FAB) m/z 649 ((M+H)$^+$).
Elementary analysis: As C$_{42}$H$_{52}$N$_2$O$_4$·CH$_4$O$_3$S·0.3H$_2$O
Calculated values: C, 68.83; H, 7.60; N, 3.73; S, 4.27.
Measured values: C, 68.58; H, 7.63; N, 3.99; S, 4.37.
Compound 74·methanesulfonate
mp >130° C. (decomposition)
NMR (400 MHz, DMSO-d$_6$)
δ 0.35–0.72 (4H, m), 0.95–1.64 (11H, m), 1.87–2.70 (8H, m), 2.31 (3H, s), 2.78–3.08 (3H, m), 3.21–3.39 (2H, m), 3.55–4.55 (4H, m), 5.21–5.33 (1H, m), 5.81 (0.7H, br s), 6.08 (0.3H, br s), 6.59 (0.3H, d, J=8.1 Hz), 6.66 (0.7H, d, J=8.3 Hz), 6.69 (0.3H, d, J=8.1 Hz), 6.81 (0.7H, d, J=8.3 Hz), 7.04–7.48 (15H, m), 8.58 (0.3H, br s), 8.73 (0.7H, br s), 9.41 (0.3H, br s), 9.60 (0.7H, br s).
IR (KBr) ν 3250, 1638, 1497, 1454, 1365, 1325, 1210, 1044, 704 cm$^{-1}$.
Mass (FAB) m/z 697 ((M+H)$^+$)
Elementary analysis: As C$_{46}$H$_{52}$N$_2$O$_4$·CH$_4$O$_3$S·0.5H$_2$O
Calculated values: C 70.38; H 7.16; N 3.49; S 4.00
Measured values: C 69.99; H 7.24; N 3.81; S 4.34

Reference Example 58

17-cyclopropylmethyl-3,14β-dihydroxy-4,5α-epoxy-6β-(N-methyl-trans-2-hexenoamido)morphinan 75.tartrate

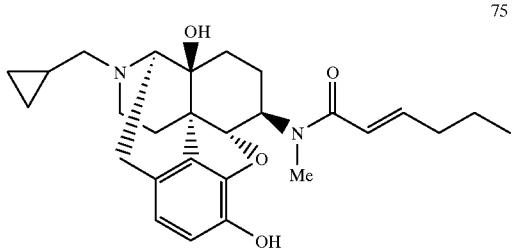

75

266.5 mg (0.748 mmol) of 17-cyclopropylmethyl-3,14β-dihydroxy-4,5α-epoxy-6β-methylaminomorphinan 15 and 170.2 mg (1.49 mmol) of trans-2-hexenic acid were dissolved in 8 ml of chloroform followed by the addition of 308.4 mg (1.49 mmol) of dicyclohexylcarbodiimide and 4.5 mg (0.037 mmol) of 4-(N,N-dimethylamino)pyridine to this solution and stirring for 1 hour at room temperature. After filtering out the solid that formed in the reaction solution, the residue was washed with chloroform and the filtrate and washing were combined and concentrated. The resulting solid was dissolved in 7 ml of methanol followed by the addition of 230 mg (1.66 mmol) of potassium carbonate and stirring for 1 hour at room temperature. 10 ml of water were then added to the reaction solution followed by extraction with chloroform (3×10 ml). The organic layers were then combined and concentrated to obtain 577 mg of a solid. This solid was then purified with column chromatography [silica gel 70 g: chloroform-methanol (50:1→30:1)] to obtain 320.5 mg of the free base of the target compound (yield: 95%). This crystal was then dissolved in methanol followed by the addition of a methanol solution containing 53.1 mg of tartaric acid and concentration. Ethyl acetate was added and the precipitated solid was filtered to obtain 224.3 mg of the target compound (yield: 52%).

mp >145° C. (decomposition)

NMR (400 MHz, DMSO-d$_6$)

δ 0.25 (2H, m), 0.48–0.59 (2H, m), 0.79 (2.1H, t, J=7.3 Hz), 0.90 (0.9H, t, J=7.3 Hz), 0.92 (1H, m), 1.20–1.48 (5H, m), 1.58 (1H, m), 1.91–2.20 (4H, m), 2.29 (1H, m), 2.53 (1H, m), 2.67–2.85 (3H, m), 2.81 (2.1H, s), 3.01 (0.9H, s), 3.11 (1H, br d, J=18.6 Hz), 3.31 (1H, m), 3.45 (4.2H, br s, 3.6×OH+0.6×COOH), 3.57 (1H, m), 4.06 (1.6H, s), 4.62 (0.7H, d, J=7.8 Hz)., 4.74 (0.3H, d, J=7.8 Hz), 6.05 (0.7H, d, J=15.1 Hz), 6.35–6.44 (1.0H, m), 6.54–6.71 (2.3H, m), 9.26 (1H, br s, NH+).

IR (KBr) ν 3396, 1736, 1655, 1601, 1460, 1410, 1319, 1123, 1067, 1035, 922, 859 cm$^{-1}$.

Mass (FAB) m/z 453 ((M+H)$^+$).

Elementary analysis: As C$_{27}$H$_{36}$N$_2$O$_4$·0.8C$_4$H$_6$O$_6$·1.1H$_2$O

Calculated values: C 61.22; H 7.32; N 4.73

Measured values: C 61.13; H 7.23; N 4.82

Reference Examples 59–63

17-cyclopropylmethyl-3,14β-dihydroxy-4,5α-epoxy-6β-(N-methylcinnamamido)morphinan 76·hydrochloride (yield: 46%), 17-cyclopropylmethyl-3,14β-dihydroxy-4,5α-epoxy-6β-(N-methylphenylpropiolamido)morphinan 77·hydrochloride (yield: 49%), 17-cyclopropylmethyl-3,14β-dihydroxy-4,5α-epoxy-6β-(N-methyl-3-nitrocinnamamido)morphinan 78·0.5 tartrate (yield: 47%), 17-cyclopropylmethyl-3,14β-dihydroxy-4,5α-epoxy-6β-(N-methyl-3-fluorocinnamamido)morphinan 79·1 tartrate (yield: 81%) and 17-cyclopropylmethyl-3,14β-dihydroxy-4,5α-epoxy-6β-(N-methylbenzoylacetoamido) morphinan 80·0.5 tartrate (yield: 52%) were obtained by following the procedure of Reference Example 58 and using cinnamic acid, phenylpropolic acid, 3-nitrocinnamic acid, 3-fluorocinnamic acid and benzoylacetic acid instead of trans-2-hexenoic acid.

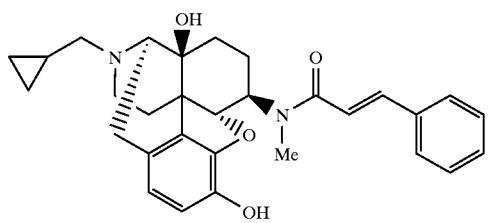

76

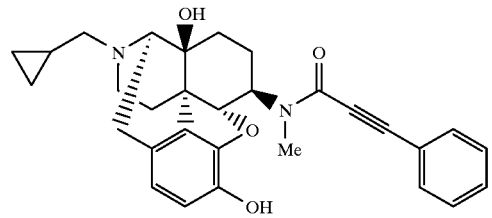

77

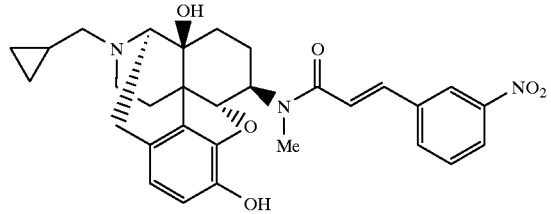

78

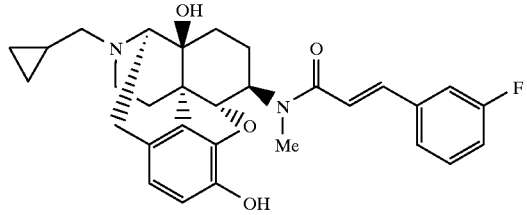

79

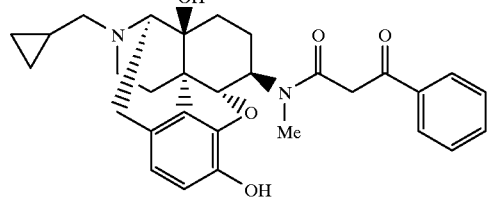

80

Compound 76·hydrochloride mp 225° C. (decomposition)

NMR (400 MHz, DMSO-d$_6$)

δ 0.42 (1H, m), 0.50 (1H, m), 0.59 (1H, m), 0.68 (1H, m), 1.07 (1H, m), 1.20–1.50 (3.5H, m), 1.72 (1H, m), 2.13 (1H, m), 2.40–2.60 (2.5H, m), 2.87 (1H, m), 2.92 (2H, s), 3.06 (2H, m), 3.19 (1H, s), 3.32 (2H, m), 3.6–4.3 (2H, m), 4.85 (0.7H, m), 4.92 (0.3H, m), 6.30 (1H, m), 6.68 (2H, m), 6.88 (0.5H, d, J=8.3 Hz), 7.30–7.50 (5H, m), 7.71 (0.5H, d, J=6.4 Hz), 8.79 (1H, m), 9.29 (0.3H, s), 9.70 (0.7H, s)

IR (KBr) ν 3380, 1642, 1599, 1499, 1321, 1127, 768 cm$^{-1}$.

Mass (FAB) m/z 487 (M+H)

Elementary Analysis: As C$_{30}$H$_{34}$N$_2$O$_4$·HCl·0.3H$_2$O Calcd.: C, 68.18; H, 6.79; N, 5.30; Cl, 6.71 Found.: C, 68.06; H, 7.11; N, 5.46; Cl, 6.37

Compound 77·hydrochloride mp 208.0–225.0° C. (decomposition, ether)

NMR (400 MHz, DMSO-d$_6$) (data for 0.5 tartrate)

δ 0.25 (2H, br s), 0.54 (2H, m), 0.93 (1H, m), 1.27–1.47 (3H, m), 1.66 (1H, m), 1.88–5.20 (3H, br OH×2), 2.08–2.19 (2H, m), 2.30 (1H, m), 2.44–2.53 (2H, m), 2.58–2.80 (3H, m), 2.93 (2.1H, s), 3.12 (1H, m), 3.17 (0.9H, s), 3.27 (1H, br s), 4.00 (1H, s), 4.06 (0.3H, m), 4.20 (0.7H, m), 4.73 (0.7H, d, J=8.3 Hz), 4.82 (0.3H, d, J=8.3 Hz), 6.55–6.67 (2H, m), 7.19 (1.55H, d, J=7.3

Hz), 7.37 (1.55H, t, J=7.3 Hz), 7.45–7.56 (1.40H, m), 7.60 (0.5H, d, J=6.8 Hz), 9.15 (1H, br s).
IR (KBr) (Data for free base) ν 3218, 2218, 1618, 1458 cm$^{-1}$.
Mass (FAB) m/z 485 (M+H)+.
Elementary Analysis: As $C_{30}H_{33}N_2O_4Cl \cdot 0.7H_2O$ Calcd.: C, 67.52; H, 6.50; N, 5.25; Cl, 6.64. Found.: C, 67.43; H, 6.65; N, 5.25; Cl, 6.67.
Compound 78·0.5 tartarate
mp 161–164° C.
NMR (400 MHz, DMSO-d$_6$)
δ 0.18–0.30 (2H, m), 0.46–0.60 (2H, m), 0.85–0.97 (1H, m), 1.22–1.50 (3H, m), 1.53–1.62 (1H, m), 2.03–2.21 (2H, m), 2.23–2.35 (1H, m), 2.50–2.90 (4H, m), 2.91 (2.1H, s), 3.18 (0.9H, s), 3.10–4.20 (3H, m), 4.05 (1H, s), 4.67 (0.7H, d, J=8.3 Hz), 4.81 (0.3H, d, J=8.3 Hz), 6.58 (0.3H, d, J=7.8 Hz), 6.63 (1H, d, J=7.8 Hz), 6.73 (0.7H, d, J=7.8 Hz), 6.84 (0.7H, d, J=15.6 Hz), 7.42 (0.3H, d, J=15.9 Hz), 7.45 (0.7H, d, J=15.6 Hz), 7.57 (0.3H, d, J=15.6 Hz), 7.66 (0.7H, dd, J=8.3, 7.8 Hz), 7.71 (0.3H, dd, 8.3, 7.8 Hz), 7.93 (0.7H, d, J=7.8 Hz), 8.15–8.27 (2H, m), 8.60 (0.3H, s), 9.12 (0.3H, br s), 9.28 (0.7H, br s).
IR (KBr) ν 3380, 1649, 1601, 1531, 1352, 1127, 1035, 922, 859, 810, 743 cm$^{-1}$.
Mass (FAB) m/z 532 ((M+H)+).
Elementary Analysis: As $C_{30}H_{33}N_3O_6 \cdot 0.5C_4H_6O_6 \cdot 2.2H_2O$ Calcd.: C, 59.47; H, 6.30; N, 6.50. Found.: C, 59.42; H, 5.96; N, 6.25.
Compound 79·1 tartarate
mp 145–153° C.
NMR (400 MHz, DMSO-d$_6$)
δ 0.20–0.32 (2H, m), 0.46–0.62 (2H, m), 0.88–1.00 (1H, m), 1.20–1.50 (3H, m), 1.55–1.65 (1H, m), 2.00–2.40 (3H, m), 2.42–2.60 (2H, m), 2.70–2.88 (3H, m), 2.90 (2.1H, s), 3.15 (0.9H, m), 3.05–4.00 (7H, m), 4.11 (2H, s), 4.71 (0.7H, d, J=8.1 Hz), 4.81 (0.3H, d, J=8.1 Hz), 6.58–6.68 (3H, m), 7.14–7.68 (5H, m), 9.15 (0.3H, br s), 9.45 (0.7H, br s).
IR (KBr) ν 3320, 1731, 1647, 1586, 1412, 1311, 1270, 1127, 1077, 1033, 980, 859, 789, 677 cm$^{-1}$
Mass (FAB) m/z 505 ((M+H)+).
Elementary Analysis: As $C_{30}H_{33}N_2O_4F \cdot C_4H_6O_6 \cdot H_2O$ Calcd.: C, 60.71; H, 6.14; N, 4.16; F, 2.82. Found.: C, 60.63; H, 6.22; N, 4.07; F, 2.81.
Compound 80·0.5 tartarate
mp >161° C. (decomposition)
NMR (400 MHz, DMSO-d$_6$)
δ 0.17–0.27 (2H, m), 0.45–0.58 (2H, m), 0.89(1H, m), 1.16–1.44 (3H, m), 1.50–1.61 (1H, m), 2.02–2.18 (2H, m), 2.28 (1H, m), 2.43 (1H, m), 2.53–2.78 (3H, m), 2.81 (1.68H, s), 2.93 (0.18H, s), 2.98 (0.72H, s), 3.04 (1H, br d, J=19.1 Hz), 3.10 (0.42H, s), 3.17–3.28 (1H, m), 3.35 (1H, m), 3.50 (3H, br s, 3×OH), 3.98–4.37 (1.4H, m), 4.04 (1H, s), 4.67 (0.8H, d, J=7.8 Hz), 4.76 (0.14H, d, J=8.3 Hz), 4.77 (0.06H, d, J=8.3 Hz), 5.62 (0.06H, s), 6.12 (0.24H, s), 6.52 (0.56H, d, J=8.3 Hz), 6.52–6.78 (0.88H, m), 6.61 (0.56H, d, J=8.3 Hz), 7.41–7.96 (5H, m), 9.02–9.60 (1H, m, NH+), 15.50 (0.06H, s), 15.76 (0.24H, s).
IR (KBr) ν 3390, 1686, 1626, 1452, 1323, 1278, 1125, 1035, 926, 859 cm$^{-1}$.
Mass (FAB) m/z 503 ((M+H)+).
Elementary Analysis: As $C_{30}H_{34}N_2O_5 \cdot 0.5C_4H_6O_6 \cdot 1.2H_2O$ Calcd.: C, 64.14; H, 6.63; N, 4.67. Found.: C, 64.20; H, 6.57; N, 4.61.

Reference Example 64

17-cyclopropylmethyl-3,14β-dihydroxy-4,5α-epoxy-6α-(N-methylphenylpropiolamido)morphinan 81·hydrochloride (yield: 16%) was obtained by following the procedure of Reference Example 58, using 17-cyclopropylmethyl-4,5α-epoxy-3,14β-dihydroxy-6α-methylaminomorphinan 2 instead of 17-cyclopropylmethyl-4,5α-epoxy-3,14β-dihydroxy-6β-methylaminomorphinan 15 for the starting material, and using phenylpropiolic acid instead of trans-2-hexenoic acid.

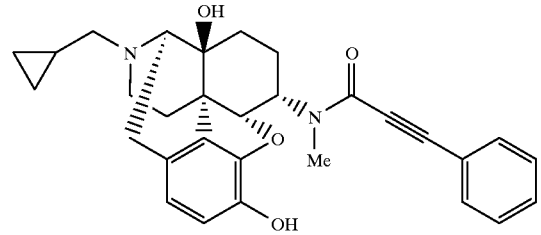

81 mp 206.0–209.0° C. (decomposition, ether)
NMR (400 MHz, DMSO-d$_6$)
δ 0.41 (1H, m), 0.49 (1H, m), 0.62 (1H, m), 0.69 (1H, m), 1.08 (1H, m), 1.19 (0.5H, m), 1.27 (0.5H, m), 1.45–1.72 (3H, m), 1.95 (0.5H, m), 2.02 (0.5H, m), 2.48 (1H, m), 2.71 (1H, m), 2.92 (1.5H, s), 2.94–3.06 (2H, m), 3.12 (1H, dd, J=19.5, 6.7 Hz), 3.24 (1.,5H, s), 3.27–3.28 (2H, m), 3.95 (1H, dd, J=15.6, 6.7 Hz), 4.71 (0.5H, d, J=3.7 Hz), 4.81 (0.5H, d, J=3.7 Hz), 4.92 (0.5H, br d, J=13.4 Hz), 5.09 (0.5H, br d, J=13.4 Hz), 6.32 (0.5H, s), 6.42 (0.5H, s), 6.61 (0.5H, d, J=7.9 Hz), 6.62 (0.5H, d, J=7.9 Hz), 6.74 (0.5H, d, J=7.9 Hz), 6.75 (0.5H, d, J=7.9 Hz), 7.49 (1H, t, J=7.3 Hz), 7.52–7.57 (2H, m), 7.66 (1H, d, J=8.5 Hz), 7.72 (1H, d, J=7.3 Hz), 8.85 (0.5H, br s), 8.93 (0.5H, br s), 9.37 (1H, s).
IR (KBr) ν 3400, 2952, 2216, 1613, 1493, 1377, 1321, 1120, 1036, 692 cm$^{-1}$.
Mass (FAB) m/z 485 ((M+H)+).
Elementary analysis: As $C_{30}H_{32}N_2O_4 \cdot 1.15HCl \cdot 0.8H_2O$
Calculated values: C 66.61; H 6.48; N 5.18; Cl 7.54
Measured values: C 66.42; H 6.55; N 5.19; Cl 7.72

Reference Example 65

17-cyclopropylmethyl-3,14β-dihydroxy-4,5α-epoxy-6α-(N-methyl-3-trifluoromethylphenylacetoamido)morphinan 82·hydrochloride

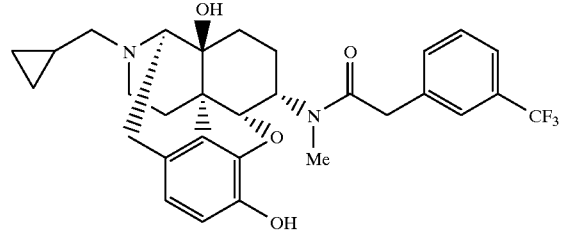

82

154 mg of 3-trifluoromethylphenylacetic acid and 131 mg of carbonyldiimidazole were dissolved in 2.5 ml of anhydrous tetrahydrofuran. After refluxing while heating for 30 minutes, the solution was cooled to room temperature. Next, a solution resulting from dissolving 200 mg of 17-cyclopropylmethyl-3,14β-dihydroxy-4,5α-epoxy-6α-methylaminomorphinan 2 in 17.5 ml of anhydrous tetrahydrofuran was added to the reaction solution followed by refluxing while heating for 2 hours. After cooling to room temperature and concentrating, the resulting residue was dissolved in 16 ml of methanol followed by the addition of 1 ml of 1 N sodium hydroxide and stirring for 1 hour. Next, the reaction solution was concentrated followed by the addition of 40 ml of ethyl acetate to the residue. After sequentially washing with 25 ml of water and 25 ml of saturated brine, the organic layer was concentrated after drying with anhydrous sodium sulfate to obtain 373 mg of the crude product. This was then recrystallized from ethyl acetate to obtain 83 mg of the free base of the target compound. The mother liquor was purified with silica gel chromatography (25 g chloroform/methanol=19/1) to obtain 188 mg of the free base of the target compound. This resulting free base was dissolved in methanol and concentrated after adjusting to pH 4 by addition of a solution of hydrogen chloride in methanol. The residue was then reprecipitated with ethyl acetate and filtered to obtain 251 mg of the target compound (yield: 78%).

mp 192.0–200.0° C. (decomposition, ethyl acetate)

NMR (400 MHz, DMSO-$d_6$)

δ 0.31–0.42 (1H, m), 0.42–0.53 (1H, m), 0.53–0.62 (1H, m), 0.62–0.77 (1H, m), 0.96–1.12 (1H, m), 1.12–1.31 (1H, m), 1.31–1.47 (1H, m), 1.47–1.69 (2H, m), 1.82–2.04 (1H, m), 2.30–2.49 (1H, m), 2.59–2.78 (1H, m), 2.81 (0.4H, s), 2.86–3.18 (3H, m), 2.99 (2.6H, s), 3.18–3.40 (2H, m), 3.90 (2H, s), 3.90–4.1 (1H, m), 4.53 (0.2H, m), 4.62 (0.8H, d, J=3.9 Hz), 4.77 (0.2H, br s), 4.98 (0.8H, dt, J=13.7, 3.9 Hz), 6.24 (1H, br s), 6.58 (1H, d, J=7.8 Hz), 6.74 (1H, d, J=8.3 Hz), 7.49–7.68 (4H, m), 8.82 (1H, br s), 9.33 (1H, s).

IR (KBr) ν 1620, 1508, 1460, 1334, 1166, 1120, 1077, 1036, 801, 702 $cm^{-1}$.

Mass (FAB) m/z 543 ((M+H)$^+$).

Elementary analysis: As $C_{30}H_{34}N_2O_4ClF_3 \cdot 0.5H_2O$

Calculated values: C 61.27; H 6.00; N 4.76; Cl 6.02; F 9.69

Measured values: C 61.37; H 6.08; N 4.75; Cl 5.89; F 9.92

Reference Examples 66–72

17-cyclopropylmethyl-3,14β-dihydroxy-4,5α-epoxy-6β-(N-methyl-2-naphthylacetoamido)morphinan 83·hydrochloride (yield: 63%), 17-cyclopropylmethyl-3,14β-dihydroxy-4,5α-epoxy-6β-(N-methyl-3-trifluoromethylphenylacetoamido)morphinan 84.hydrochloride (yield: 57%), 17-cyclopropylmethyl-3,14β-dihydroxy-4,5α-epoxy-6β-(N-methyl-3-chlorophenylacetoamido) morphinan 85·hydrochloride (yield; 84%), 17-cyclopropylmethyl-3,14β-dihydroxy-4,5α-epoxy-6β-(N-methyl-1-naphthylacetoamido)morphinan 86.hydrochloride (yield: 61%), 17-cyclopropylmethyl-3,14β-dihydroxy-4,5α-epoxy-6β-(N-methyl-3-benzo[b]thienylacetoamrido)morphinan 87·hydrochloride (yield: 55%), 17-cyclopropylmethyl-3,14β-dihydroxy-4,5α-epoxy-6β-(N-methyl-9-fluorenylamido) morphinan 88·hydrochloride (yield: 65%) and 17-cyclopropylmethyl-3,14β-dihydroxy-4,5α-epoxy-6β-(N-methyl-2,3,4,5,6-pentafluorophenylacetoamido)morphinan 89·hydrochloride (yield: 68%) were obtained by following the procedure of Reference Example 65, using 17-cyclopropylmethyl-3,14β-dihydroxy-4,5α-epoxy-6β-methylaminomorphinan 15 instead of 17-cyclopropylmethyl-3,14β-dihydroxy-4,5α-epoxy-6α-methylaminomorphinan 2 for the starting material, and using 2-naphthylacetic acid, 3-trifluoromethylphenylacetic acid, 3-chlorophenylacetic acid, 1-naphthylacetic acid, 3-benzo[b]thienylacetic acid, 9-fluorencarboxylic acid and 2,3,4,5,6-pentafluorophenylacetic acid instead of 3-trifluoromethylphenylacetic acid.

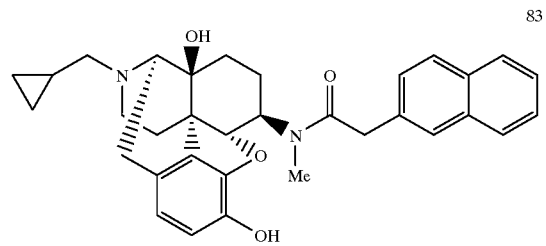

83

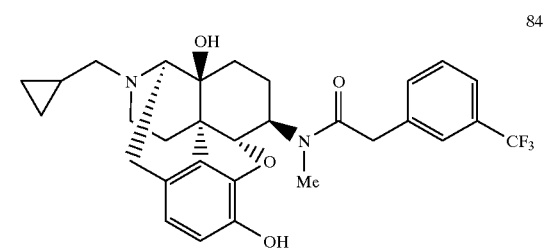

84

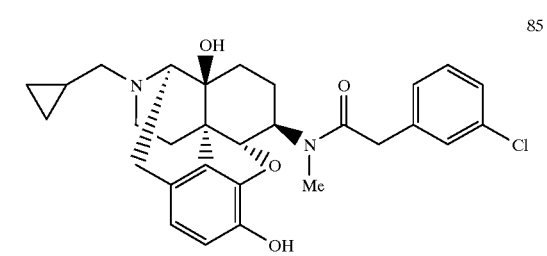

85

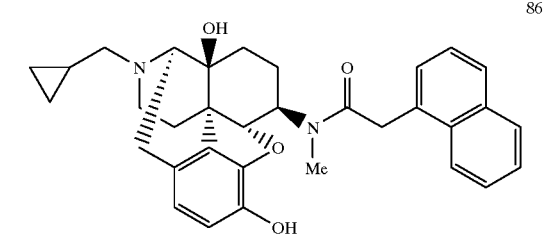

86

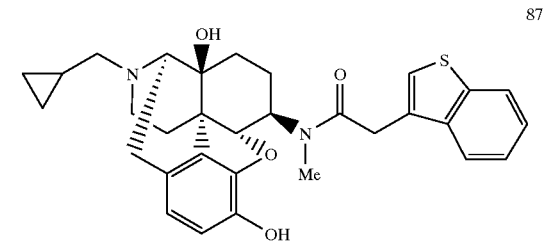

87

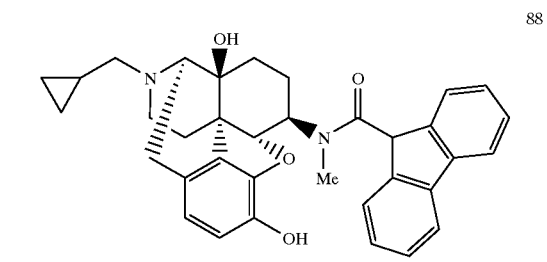

88

-continued

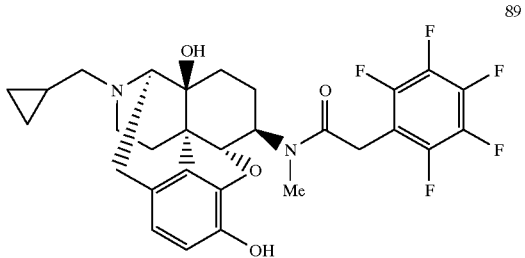

Compound 83·hydrochlorate
mp 207.0–214.0° C. (decomposition, diethylether)
NMR (400 MHz, CD₃OD)
δ 0.35–0.58 (3H, m), 0.61–0.91 (3H, m), 0.91–1.18 (1H, m), 1.23 (1H, brd, J=14.2 Hz), 1.39–1.81 (2H, m), 1.89 (1H, dq, J=13.2, 2.9 Hz), 2.42–2.76 (2H, m), 2.76–3.02 (2H, m), 2.92 (2.6H, s), 3.10 (0.4H, s), 3.02–3.20 (2H, m), 3.60–3.82 (2H, m), 3.86 (1H, d, J=21.5 Hz), 3.95 (1H, d, J=18.1 Hz), 4.75 (1H, d, J=8.3 Hz), 6.87–7.00 (2H, m), 7.00–7.13 (2H, m), 7.35–7.49 (2H, m), 7.49–7.58 (1H, m), 7.70 (1H, d, J=8.3 Hz), 7.73–7.80 (1H, m)
IR (KBr) ν 1620, 1504, 1460, 1408, 1321, 1125, 1035, 859, 803, 748 cm⁻¹.
Mass (FAB) m/z 525 ((M+H)+).
Elementary Analysis: As $C_{33}H_{37}N_2O_4Cl$ Calcd.: C, 70.64; H, 6.65; N, 4.99; Cl, 6.32 Found.: C, 70.39; H, 6.75; N, 5.05; Cl, 6.00

Compound 84·hydrochloride
mp 195.0–203.0° C. (decomposition, methanol)
NMR (400 MHz, DMSO-d₆)
δ 0.31–0.45 (1H, m), 0.45–0.53 (1H, m), 0.53–0.63 (1H, m), 0.63–0.77 (1H, m), 0.96–1.12 (2H, m), 1.12–1.30 (1H, m), 1.30–1.80 (3H, m), 2.06 (1H, br q, J=13.2 Hz), 2.39–2.59 (2H, m), 2.85 (2.4H, s), 3.05 (0.6H, s), 2.71–2.92 (1H, m), 2.92–3.12 (2H, m), 3.41–3.58 (1H, m), 3.68 (1H, d, J=3.4 Hz), 3.58–3.77 (1H, m), 3.77–4.10 (2H, m), 4.84 (0.8H, br d, J=5.4 Hz), 4.88 (0.2H, br d, J=5.4 Hz), 6.30 (0.2H, br s), 6.42 (0.8H, br s), 6.62 (0.2H, d, J=8.3 Hz), 6.69 (0.2H, d, J=8.3 Hz), 6.72 (0.8H, d, J=8.3 Hz), 6.81 (0.8H, d, J=8.3 Hz), 7.13 (0.8H, s), 7.17 (0.2H, d, J=6.8 Hz), 7.22–7.28 (0.2H, m), 7.30 (0.8H, d, J=7.8 Hz), 7.48 (1H, t, J=7.8 Hz), 7.52–7.63 (1H, m), 8.80 (1H, br s), 9.25 (0.2H, s), 9.64 (0.8H, s)
IR (KBr) ν 1628, 1508, 1460, 1334, 1166, 1127, 1077, 1035, 922, 704 cm⁻¹.
Mass (FAB) m/z 543 ((M+H)+).
Elementary Analysis: As $C_{30}H_{34}N_2O_4ClF_3$ Calcd.: C, 62.23; H, 5.92; N, 4.84; Cl, 6.12; F, 9.84 Found.: C, 62.19; H, 6.04; N, 4.82; Cl, 5.76; F, 9.87

Compound 85·hydrochloride
mp 200.0–209.0° C. (decomposition, methanol)
NMR (400 MHz, CD₃OD)
δ 0.31–0.58 (2H, m), 0.61–0.75 (1H, m), 0.75–0.89 (2H, m), 0.96–1.24 (2H, m), 1.34–1.82 (3H, m), 2.03 (1H, dq, J=13.2, 2.9 Hz), 2.42–2.73 (2H, m), 2.73–2.88 (1H, m), 2.91 (2.5H, s), 3.09 (0.5H, s), 2.97–3.20 (3H, m), 3.54–3.65 (1H, m), 3.68 (2H, s), 3.73–4.97 (1H, m), 4.75 (1H, d, J=8.3 Hz), 6.62–7.39 (6H, m)
IR (KBr) ν 1620, 1502, 1460, 1321, 1125, 1035, 924, 808 cm⁻¹.
Mass (FAB) m/z 509 ((M+H)+).
Elementary Analysis: As $C_{29}H_{34}N_2O_4Cl_3·0.3H_2O$ Calcd.: C, 63.22; H, 6.33; N, 5.08; Cl, 12.87 Found.: C, 63.20; H, 6.50; N, 5.03; Cl, 12.69

Compound 86·hydrochloride
mp 210.0–215.0° C. (decomposition, diethylether)
NMR (400 MHz, CD₃OD)
δ 0.31–0.60 (3H, m), 0.61–0.91 (3H, m), 0.91–1.18 (1H, m), 1.31 (1H, brd, J=14.2 Hz), 1.43–1.81 (2H, m), 1.89 (1H, dq, J=13.2, 2.9 Hz), 2.42–2.73 (2H, m), 2.73–3.00 (2H, m), 2.92 (2.6H, s), 3.15 (0.4H, s), 3.00–3.19 (2H, m), 3.54–3.85 (2H, m), 3.99 (1H, d, J=16.1 Hz), 4.23 (1H, d, J=16.1 Hz), 4.75 (1H, d, J=8.3 Hz), 6.80 (1H, d, J=8.30 Hz), 6.90 (1H, d, J=7.82 Hz), 7.00 (1H, d, J=6.84 Hz), 7.27 (1H, t, J=7.6 Hz), 7.31–7.59 (2H, m), 7.70 (2H, t, J=8.30 Hz), 7.80 (1H, d, J=8.3 Hz)
IR (KBr) ν 1620, 1510, 1502, 1460, 1402, 1321, 1125, 1035, 924, 797 cm⁻¹.
Mass (FAB) m/z 525 ((M+H)+).
Elementary Analysis: As $C_{33}H_{37}N_2O_4Cl·0.3H_2O$ Calcd.: C, 69.96; H, 6.69; N, 4.94; Cl, 6.26 Found.: C, 70.04; H, 6.68; N, 5.03; Cl, 6.20

Compound 87·hydrochloride
mp 215.0–225.0° C. (decomposition, ethyl acetate, diethylether)
NMR (400 MHz, DMSO-d₆)
δ 0.31–0.45 (1H, m), 0.45–0.53 (1H, m), 0.53–0.62 (1H, m), 0.62–0.73 (1H, m), 0.79–0.89 (1H, m), 0.89–1.12 (2H, m), 1.34–1.60 (2H, m), 1.98–2.07 (1H, m), 2.39–2.55 (2H, m), 2.73–2.98 (1H, m), 2.85 (2.4H, s), 3.07 (0.6H, s), 2.98–3.13 (2H, m), 3.17–3.39 (2H, m), 3.50–3.61 (1H, m), 3.68 (1H, d, J=16.1 Hz), 3.78 (1H, br d, J=3.9 Hz), 3.88 (1H, d, J=16.1 Hz), 4.83 (0.8H, d, J=8.3 Hz), 4.90 (0.2H, d, J=8.3 Hz), 6.29 (0.2H, s), 6.35 (0.8H, s), 6.03 (0.2H, d, J=8.3 Hz), 6.70 (0.2H, d, J=8.3 Hz), 6.74 (0.8H, d, J=8.3 Hz), 6.82 (0.8H, d, J=8.3 Hz), 7.08 (0.8H, s), 7.21–7.42 (2.8H, m), 7.48 (0.2H, s), 7.77–7.82 (0.2H, m), 7.92 (0.8H, d, J=7.8 Hz), 7.97–8.02 (0.2H, m), 8.78 (1H, br s), 9.28 (0.2H, s), 9.68 (0.8H, s)
IR (KBr) ν 1626, 1502, 1460, 1319, 1125, 1035 cm⁻¹.
Mass (FAB) m/z 531 ((M+H)+).
Elementary Analysis: As $C_{31}H_{35}N_2O_4ClS·0.4H_2O$ Calcd.: C, 64.83; H, 6.28; N, 4.88; Cl, 6.17; S, 5.58 Found.: C, 64.85; H, 6.42; N, 4.89; Cl, 6.15; S, 5.53

Compound 88·hydrochloride
mp 215.0–224.0° C. (decomposition, ethyl acetate)
NMR (400 MHz, DMSO-d₆)
δ 0.31–0.47 (1H, m), 0.47–0.57 (1H, m), 0.57–0.64 (1H, m), 0.64–0.77 (1H, m), 0.98–1.13 (1H, m), 1.20–1.60 (2H, m), 1.60–1.92 (2H, m), 2.31–2.70 (2H, m), 2.79–2.91 (1H, m), 2.97 (2.1H, s), 2.99–3.15 (2H, m), 3.36 (0.9H, s), 3.37–3.60 (2H, m), 3.81 (0.3H, br d, J=5.2 Hz), 3.89 (0.7H, br d, J=5.2 Hz), 3.72–3.93 (0.3H, m), 4.12–4.29 (0.7H, m), 4.90–5.02 (0.3H, m), 5.04 (0.7H, d, J=7.3 Hz), 5.09 (0.7H, s), 5.38 (0.3H, m), 6.17 (0.3H, br s), 6.46 (0.7H, br s), 6.61 (1H, s), 6.55–6.78 (1H, m), 7.08–7.52 (6H, m), 7.64 (1H, d, J=7.3 Hz), 7.84 (1H, dd, J=7.8, 4.4 Hz), 7.91 (1H, d, J=7.3 Hz), 8.77 (0.3H, br s), 8.83 (0.7H, br s), 9.24 (0.3H, s), 9.26 (0.7H, s)
IR (KBr) ν 1620, 1510, 1460, 748 cm⁻¹.
Mass (FAB) m/z 549 ((M+H)+).
Elementary Analysis: As $C_{35}H_{37}N_2O_4Cl·0.6H_2O$ Calcd.: C, 70.54; H, 6.46; N, 4.70; Cl, 5.95 Found.: C, 70.77; H, 6.54; N, 4.71; Cl, 5.58

Compound 89·hydrochloride
mp 208.0–214.0° C. (decomposition, methanol)
NMR (400 MHz, DMSO-d₆)
δ 0.31–0.47 (1H, m), 0.47–0.56 (1H, m), 0.56–0.63 (1H, m), 0.63–0.77 (1H, m), 1.00–1.13 (1H, m), 1.20–1.65

(3H, m), 1.74 (1H, br t, J=13.4 Hz), 2.16 (1H, br q, J=12.7 Hz), 2.39–2.62 (2H, m), 2.89 (2.4H, s), 2.76–2.96 (1H, m), 2.96–3.12 (2H, m), 3.17 (0.6H, s), 3.20–3.45 (2H, m), 3.62–3.75 (1H, m), 3.75–3.98 (3H, m), 4.85 (0.8H, d, J=7.8 Hz), 4.94 (0.2H, d, J=7.8 Hz), 6.38 (0.2H, br s), 6.52 (0.8H, brs), 6.62 (0.2H, d, J=8.3 Hz), 6.68 (1H, d, J=8.3 Hz), 6.74 (0.8H, d, J=7.8 Hz), 8.85 (1H, br s), 9.41 (0.2H, s), 9.27 (0.8H, s)

IR (KBr) ν 1638, 1510, 1315, 1127, 1009, 919, 859 cm$^{-1}$.

Mass (FAB) m/z 565 ((M+H)+).

Elementary Analysis: As $C_{29}H_{30}N_2O_4ClF_5 \cdot 0.2H_2O$ Calcd.: C, 57.61; H, 5.07; N, 4.63; Cl, 5.86; F, 15.71 Found.: C, 57.60; H, 5.36; N, 4.74; Cl, 5.94; F, 15.51

Reference Example 73

17-Cyclopropylmethyl-3,14β-dihydroxy-4,5α-epoxy-6β-[N-methyl-3-(3-trifluoromethylphenyl)propiolamido]morphinan 90·hydrochloride.

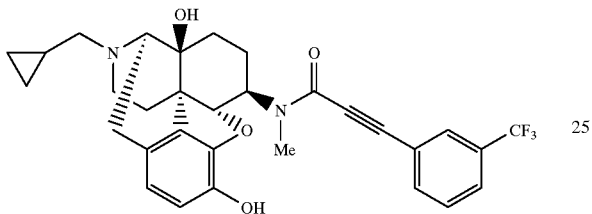

400 mg (1.12 mmol) of 17-cyclopropylmethyl-4,5α-epoxy-3,14β-dihydroxy-6β-methylaminomorphinan 15 and 360 mg (1.68 mmol) of 3-(3-trifluoromethylphenyl)propiolic acid were dissolved in 12 ml of chloroform followed by sequential addition of 0.40 ml (2.91 mmol) of N-ethylpiperidine and 428 mg (1.68 mmol) of bis-(2-oxo-3-oxazolidinyl)phosphinic chloride and stirring for 12 hours at room temperature. Then, 15 ml of 1 N aqueous sodium hydroxide were added to separate layers, and the organic layer was washed with 10 ml each of water and saturated brine, dried and concentrated. The residue was dissolved in 10 ml of methanol followed by the addition of 2 ml of 1 N aqueous sodium hydroxide and stirring for 3 hours. 30 ml of ethyl acetate were then added to separate layers, and the resulting organic layer was washed with 20 ml of saturated brine, dried and concentrated. The residue was purified with silica gel column chromatography (Merk 9385, 30 g, chloroform/methanol=30/1) to obtain 562.8 mg of the free base of the target compound. This was then re-precipitated from hexane and ethyl acetate, and the resulting solid was dissolved in ethyl acetate. An excess amount of ethyl acetate solution of hydrogen chloride was added followed by stirring and filtration of the resulting precipitate to obtain 274 mg of the target compound (yield: 42%).

mp >195° C. (decomposition)

NMR (400 MHz, DMSO-d$_6$)

δ 0.42 (1H, m), 0.52 (1H, m), 0.59 (1H, m), 0.67 (1H, m), 1.07 (1H, m), 1.29–1.51 (3H, m), 1.73–1.83 (1H, m), 2.09–2.26 (1H, m), 2.40–2.58 (2H, m), 2.86 (1H, m), 2.98 (2.4H, s), 3.02–3.11 (2H, m), 3.31 (0.6H, s), 3.30–3.38 (2H, m), 3.87 (1H, br d, J=5.9 Hz), 4.13 (1H, m), 4.89 (0.8H, d, J=8.3 Hz), 4.96 (0.2H, d, J=8.3 Hz), 6.40 (0.2H, s, OH), 6.46 (0.8H, d, J=7.3 Hz), 6.53 (0.8H, s, OH), 6.60 (0.8H, d, J=7.3 Hz), 6.66 (0.2H, d, J=7.3 Hz), 6.72 (0.2H, d, J=7.3 Hz), 7.47 (0.8H, br s), 7.57 (0.8H, d, J=7.8 Hz), 7.63 (0.8H, dd, J=7.8, 7.8 Hz), 7.73 (0.2H, dd, J=7.8, 7.8 Hz),7.83 (0.8H, d, J=7.8 Hz), 7.90 (0.2H, d, J=7.8 Hz), 7.97 (0.2H, d, J=7.8 Hz), 8.06 (0.2H, br s), 8.81 (1H, m, NH+), 9.30 (0.8H, s, OH), 9.31 (0.2H, s, OH).

IR (KBr) ν 3400, 2224, 1620, 1439, 1334, 1170, 1127, 1073, 1035, 924, 806 cm$^{-1}$.

Mass (FAB) m/z 553 ((M+H)+).

Elementary Analysis: As $C_{31}H_{31}F_3N_2O_4 \cdot HCl \cdot 0.5H_2O$ Calcd.: C, 62.26; H, 5.56; Cl, 5.93; F, 9.53; N, 4.68 Found.: C, 62.25; H, 5.64; Cl, 5.78; F, 9.49; N, 4.73

Reference Example 74

17-Allyl-3,14β-dihydroxy-4,5α-epoxy-6α-methylaminomorphinan 91

17-Allyl-3,14β-dihydroxy-4,5α-epoxy-6β-methylaminomorphinan 92

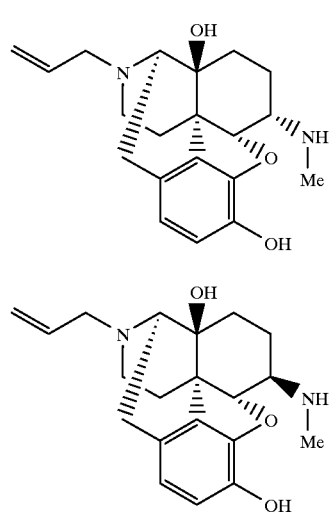

Naloxone hydrochloride (3.0 g), methylamine hydrochloride (5.57 g) and sodium cyanoborohydride (0.33 g) were suspended in anhydrous methanol (40 ml) and stirred for 17 hours at room temperature. After addition of concentrated hydrochloric acid (1.0 ml) and removal of solvent by distillation, distilled water (50 ml) was added followed by washing with chloroform (20 ml). Saturated aqueous sodium bicarbonate (10 ml) was added to make the solution basic followed by extraction with chloroform (30 ml×3). After drying with anhydrous magnesium sulfate, the solvent was distilled off. The resulting crude product was purified with silica gel column chromatography (Merck 7734 100 g; ethyl acetate/methanol/aqueous ammonia=90/10/1→80/20/2) to obtain the target compound in the form of a pure fraction (91 0.4 g, 12%; 92 0.8 g, 24%).

Compound 91

NMR (400 MHz, CDCl$_3$)

δ 0.87 (1H, m), 1.39 (1H, m), 1.66 (3H, m), 2,19 (1H, dt, J=12.2, 4.9 hz), 2.29(1H, dt, J=12.7, 3.4 Hz), 2.55 (3H, m), 2.59 (3H, s), 2.90 (1H, d, J=6.4 Hz), 3.09 (2H, m), 3.18 (1H, m), 4.76 (1H, d, J=3.4 Hz), 4.7–4.9 (1H, br), 5.17 (2H, m), 5.80 (1H, m), 6.50 (1H, d, J=7.8 Hz), 6.69 (1H, d, J=7.8 Hz)

IR (neat) ν 3400, 1618, 1450, 1386, 1160, 1067, 750 cm$^{-1}$.

Mass (EI) m/z 342 (M+)

Compound 92

NMR (500 MHz, CDCl$_3$)

δ 1.42 (2H, m), 1.61 (2H, m), 1.91 (1H, dq, J=12.8, 3.1 Hz), 2.16 (2H, m), 2.47 (3H, s), 2.56 (3H, m), 2.87 (1H, d, J=5.5 Hz), 3.03 (1H, d, J=18.3 Hz), 3.11 (2H, d, J=6.7 Hz), 4.51 (1H, d, J=7.9 Hz), 4.7–5.2 (3H, br), 5.18 (2H, m), 5.79 (1H, m), 6.55 (1H, d, J=7.9 Hz), 6.64 (1H, d, J=7.9 Hz)

IR (neat) ν 3400, 1560, 1543, 1458, 1255, 1036, 731 cm$^{-1}$.

Mass (EI) m/z 342 (M+)

Reference Example 75

17-allyl-3,14β-dihydroxy-4,5α-epoxy-6β-(N-methyl-3,4-dichlorophenylacetoamido)morphinan 93·hydrochloride (yield: 76%) was obtained by following the procedure of Reference Example 65, using 17-allyl-3,14β-dihydroxy-4,5α-epoxy-6β-methylaminomorphinan 92 instead of 17-cyclopropylmethyl-3,14β-dihydroxy-4,5α-epoxy-6α-methylaminomorphinan 2 for the starting material, and using 3,4-dichlorophenylacetic acid instead of 3-trifluoromethylphenylacetic acid.

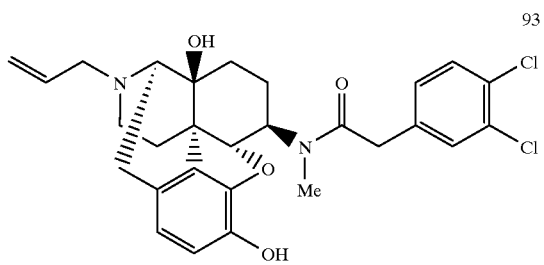

93 mp 185° C. (decomposition)

NMR (500 MHz, DMSO-d$_6$)

δ 1.15–1.39 (2H, m), 1.44 (0.2H, br d, J=9.2 Hz), 1.51 (0.8H, br d, J=9.8 Hz), 1.61–1.68 (1H, m), 2.00–2.11 (1H, m), 2.44–2.57 (2H, m), 2.83 (2.4H, s), 2.90–3.00 (1H, m), 3.02 (0.6H, s), 3.07–3.15 (1H, m), 3.35–3.39 (0.2H, m), 3.37 (0.8H, d, J=6.7 Hz), 3.43–3.55 (2H, m), 3.57 (1.6H, d, J=3.1 Hz), 3.70–3.79 (1.4H, m), 3.88–4.05 (1H, m), 4.80–4.88 (1H, m), 5.52 (1H, br d, J=11.0 Hz), 5.62 (1H, d, J=7.1 Hz), 5.83–5.96 (1H, m), 6.10–6.38 (1H, m), 6.64 (0.2H, d, J=8.2 Hz), 6.69 (0.2H, d, J=8.2 Hz), 6.73 (0.8H, d, J=8.2 Hz), 6.80 (0.8H, d, J=8.2 Hz), 6.99 (0.8H, dd, J=8.6, 1.8 Hz), 7.10 (0.8H, d, J=1.8 Hz), 7.19–7.23 (0.2H, m), 7.47–7.50 (0.2H, m), 7.50 (0.8H, d, J=8.5 Hz), 7.55 (0.2H, d, J=8.6 Hz), 9.18 (1H, br s), 9.25 (0.2H, s), 9.63 (0.8H, s).

IR (KBr) ν 3380, 1620, 1502, 1475, 1321, 1125, 1033 cm$^{-1}$.

Mass (FAB) m/z 528 (M+).
Elementary analysis: As C$_{28}$H$_{30}$N$_2$O$_4$Cl$_2$·HCl·H$_2$O
Calculated values: C 57.59; H 5.70; N 4.80; Cl 18.21
Measured values: C 57.93; H 5.80; N 4.82; Cl 17.85

Reference Example 76

17- cyclopropylmethyl-3,14β-dihydroxy-4,5α-epoxy-6α-(N-methyl-N-2-(3,4-dichlorophenyl)ethylamino]morphinan 94·1.8 hydrochloride

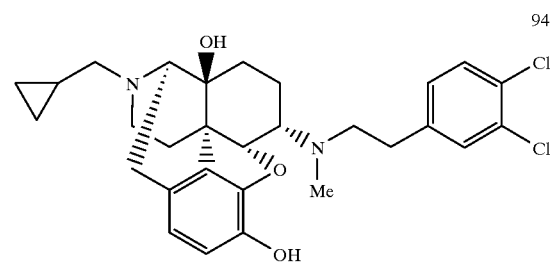

94

234.5 g (0.431 mmol) of the 17-cyclopropylmethyl-3,14β-dihydroxy-4,5α-epoxy-6α-(N-methyl- 3,4-dichlorophenylacetoamido)morphinan 1 obtained in Reference Example 15 were dissolved in 5.0 ml of anhydrous THF under argon followed by dropping in 1.1 ml (2.2 mmol) of 2.0 M anhydrous THF solution of borane-dimethylsulfide complex at 0° C. and refluxing for 1.5 hours. After cooling this reaction solution to 0° C., 2 ml of 6 N hydrochloric acid were added followed by refluxing again for 1 hour. After cooling the reaction solution to 0° C., 25 ml of saturated sodium bicarbonate solution were added to make the solution basic. After extracting with chloroform-methanol (4:1) (3×20 ml), the organic layers were combined and dried followed by concentration to obtain 281 mg of an oily substance. This oily substance was then purified with column chromatography [silica gel 25 g; chloroform-methanol (50:1→40:1)] to obtain 191.0 mg of the free base of the target compound. This free base was dissolved in methanol followed by the addition of a methanol solution of hydrogen chloride and concentration. The resulting hydrochloride was then purified with Cephadex gel column chromatography [methanol] to obtain 193.3 mg of the target compound (yield: 74%).

mp >205° C. (decomposition)

NMR (400 MHz, CDCl$_3$; data of free base)

δ 0.13 (2H, m), 0.53 (2H, m), 0.85 (1H, m), 1.00 (1H, m), 1.49 (1H, dd, J=15.1, 8.8 Hz), 1.53–1.62 (2H, m), 1.71 (1H, ddd, J=15.1, 9.5, 9.5 Hz), 2.0–3.1 (1H, br s, OH), 2.15–2.40 (4H, m), 2.51 (3H, s), 2.55–2.67 (2H, m), 2.72–2.85 (3H, m), 2.89 (1H, m), 2.98–3.10 (3H, m), 4.78 (1H, dd, J=3.0, 2.0 Hz), 4.98 (1H, br s, OH), 6.50 (1H, d, J=8.1 Hz), 6.68 (1H, d, J=8.1 Hz), 7.03 (1H, dd, J=8.3, 2.0 Hz), 7.28 (1H, d, J=2.0 Hz), 7.33 (1H, d, J=8.3 Hz).

IR (KBr) ν 3422, 1638, 1620, 1508, 1470, 1390, 1323, 1241, 1172, 1122, 1035, 982, 919, 886 cm$^{-1}$.

Mass (FAB) m/z 529 ((M+H)$^+$).
Elementary analysis: As C$_{29}$H$_{34}$Cl$_2$N$_2$O$_3$·1.8HCl·0.4H$_2$O
Calculated values: C 57.83; H 6.12; N 4.65; Cl 22.37
Measured values: C 57.73; H 6.31; N 4.60; Cl 22.38

Reference Examples 77–81

17-cyclopropylmethyl-3,14β-dihydroxy-4,5α-epoxy-6α-(N-methylbenzylamino)morphinan 95·2 hydrochloride (yield: 68%), 17-cyclopropylmethyl-3,14β-dihydroxy-4,5α-epoxy-6β-[N-methyl-N-2-(3,4-dichlorophenyl)ethylamino) morphinan 96·1.9 hydrochloride (yield: 65%), 17-cyclopropylmethyl-3,14β-dihydroxy-4,5α-epoxy-6β-(N-methylbenzylamino) morphinan 4·2 hydrochloride (yield: 70%), 17-cyclopropylmethyl-3,14β-dihydroxy-4,5α-epoxy-6α-(N-isobutyl-6-phenylhexylamino)morphinan 97·2 hydrochloride (yield: 90%) and 17-cyclopropylmethyl-3,14β-dihydroxy-4,5α-epoxy-6β-(N-isobutyl-6-phenylhexylamino)morphinan 98·2 hydrochloride (yield:

85%) were obtained by following the procedure of Reference Example 76 and using 17-cyclopropylmethyl-3,14β-dihydroxy-4,5α-epoxy-6α-(N-methylbenzamido) morphinan 32, 17-cyclopropylmethyl-3,14β-dihydroxy-4,5α-epoxy-6β-(N-methy-3,4-dichlorophenylacetoamido) morphinan 38, 17-cyclopropylmethyl-3,14β-dihydroxy-4,5α-epoxy-6β-(N-methylbenzamido)morphinan 45, 17-cyclopropylmethyl-3,14β-dihydroxy-4,5α-epoxy-6α-(N-isobutyl-6-phenylhexanoamido) morphinan 37 and 17-cyclopropylmethyl-3,14β-dihydroxy-4,5α-epoxy-6β-(N-isobutyl-6-phenylhexanoamido)morphinan 58 instead of 17-cyclopropylmethyl-3,14β-dihydroxy-4,5α-epoxy-6α-(N-methyl-3,4-dichlorophenylacetoamido)morphinan 1 for the starting material.

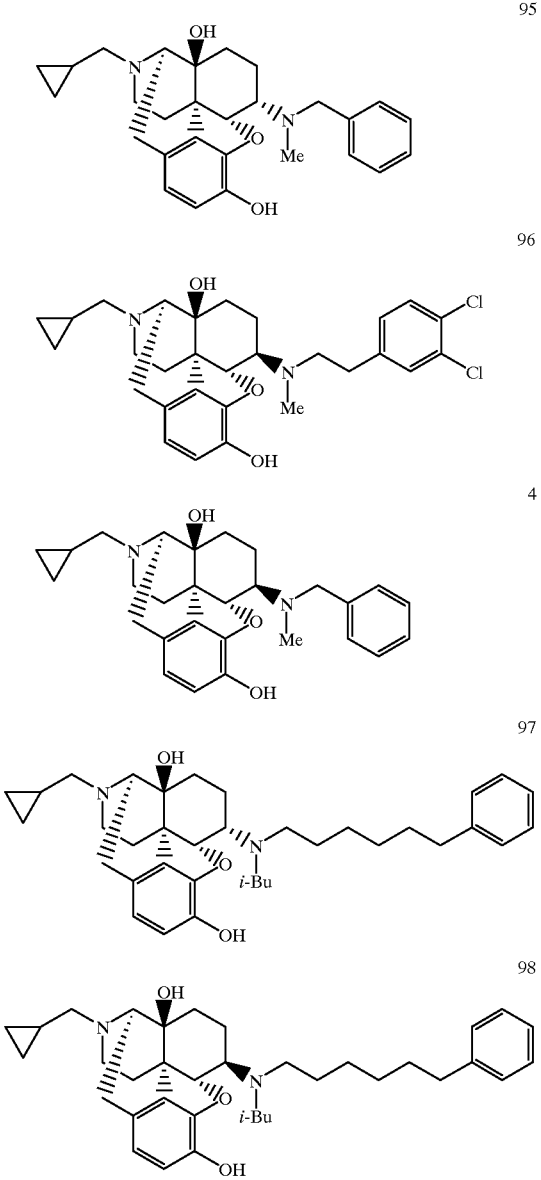

Compound 95·2 hydrochloride
mp >205° C. (decomposition)
NMR (400 MHz, DMSO-d$_6$)
δ 0.39 (1H, m), 0.47 (1H, m), 0.61 (1H, m), 0.68 (1H, m), 1.05 (1H, m), 1.16 (1H, m), 1.54 (1H, m), 1.68 (1H, m), 1.97 (1H, m), 2.08–2.55 (2H, m), 2.64–2.84 (3H, m), 2.93–3.15 (3H, m), 3.18–3.50 (3H, m), 3.82–4.03 (2H, m), 4.37 (1H, m), 4.52–4.61 (1H, m), 5.24 (1H, m), 6.55 (1H, br s, OH), 6.64 (1H, d, J=8.1 Hz), 6.80 (1H, d, J=8.1 Hz), 7.43–7.53 (3H, m), 7.65–7.75 (2H, m), 8.92 (1H, m, MH+), 9.41 and 9.47 (1H, br s, OH), 10.99 and 11.04 (1H, m, NH+).
IR (KBr) ν 3380, 1638, 1620, 1508, 1460, 1321, 1249, 1122, 1035, 919 cm$^{-1}$.
Mass (FAB) m/z 447 ((M+H)$^+$).
Elementary analysis: As C$_{28}$H$_{34}$N$_2$O$_3$·2HCl·0.35CH$_3$CO$_2$C$_2$H$_5$·0.15H$_2$O
Calculated values: C 63.85; H 7.13; N 5.07; Cl 12.82
Measured values: C 64.09; H 7.24; N 5.18; Cl 12.53
Compound 96·1.9 hydrochloride
mp >185° C. (decomposition)
NMR (400 MHz, CDCl$_3$; free base)
δ 0.12 (2H, m), 0.52 (2H, m), 0.83 (1H, m), 1.29 (1H, ddd, J=13.2, 13.2, 2.9 Hz), 1.44 (1H, m), 1.51 (1H, m), 1.61 (1H, ddd, J=13.2, 2.9, 2.9 Hz), 1.86 (1H, m), 2.0–3.8 (2H, br s, 2×OH), 2.11 (1H, ddd, 11.7, 11.7, 3.4 Hz), 2.21 (1H, ddd, J=12.2, 12.2, 4.9 Hz), 2.33–2.38 (2H, m), 2.41 (3H, s), 2.47–2.56 (2H, m), 2.57–2.75 (4H, m), 2.81 (1H, m), 2.97–3.06 (2H, m), 4.56 (1H, d, J=8.3 Hz), 6.56 (1H, d, J=8.1 Hz), 6.71 (1H, d, J=8.1 Hz), 7.01 (1H, dd, J=8.3, 2.0 Hz), 7.29 (1H, d, J=2.0 Hz), 7.30 (1H, d, J=8.3 Hz).
IR (KBr) ν 3250, 1638, 1618, 1473, 1398, 1330, 1241, 1218, 1116, 1035, 982, 919, 855, 756 cm$^{-1}$.
Mass (FAB) m/z 529 ((M+H)$^+$).
Elementary analysis: As C$_{29}$H$_{34}$Cl$_2$N$_2$O$_3$·1.9HCl·0.5H$_2$O
Calculated values: C 57.31; H 6.12; N 4.61; Cl 22.75
Measured values: C 57.40; H 6.22; N 4.55; Cl 22.54
Compound 4·2 hydrochloride
mp >205° C. (decomposition)
NMR (400 MHz, DMSO-d$_6$)
δ 0.40 (1H, m), 0.51 (1H, m), 0.59 (1H, m), 0.68 (1H, m), 1.07 (1H, m), 1.13–1.35 (1H, m), 1.48 (1H, m), 1.82 (1H, m), 1.97–2.27 (2H, m), 2.37–2.48 (1H, m), 2.63 (1H, m), 2.78–3.10 (7H, m), 3.24–3.38 (2H, m), 3.90 (1H, m), 4.38 (1H, m), 4.48–4.60 (1H, m), 5.37 (1H, m), 6.62 and 6.68 (1H, d, J=8.1 Hz), 6.73 and 6.83 (1H, br s, OH), 6.75 and 6.82 (1H, d, J=8.1 Hz), 7.36–7.47 (3H, m), 7.55 (1H, m), 7.73 (1H, m), 8.94 (1H, m, NH+), 9.61 and 9.65 (1H, br s, OH), 10.57 and 11.67 (1H, m, NH+).
IR (KBr) ν 3392, 1640, 1626, 1508, 1460, 1377, 1328, 1253, 1123, 1035, 922 cm$^{-1}$.
Mass (FAB) m/z 447 ((M+H$^+$).
Elementary analysis: As C$_{28}$H$_{34}$N$_2$O$_3$·2HCl·0.25CH$_3$CO$_2$C$_2$H$_5$·0.1H$_2$O
Calculated values: C 64.11; H 7.09; N 5.16; Cl 13.05
Measured values: C 64.38; H 7.16; N 5.27; Cl 12.83
Compound 97·2 hydrochloride
mp >172° C. (decomposition)
NMR (400 MHz, DMSO-d$_6$)
δ 0.40 (1H, m), 0.48 (1H, m), 0.61 (1H, m), 0.68 (1H, m), 0.98–1.04 (6H, m), 1.05–1.15 (2H, m), 1.28–1.42 (4H, m), 1.53–2.22 (9H, m), 2.40–2.75 (4H, m), 2.86–3.41 (9H, m), 3.90–4.02 (2H, m), 5.25 (0.6H, br s), 5.31 (0.4H, br s), 6.64 (1H, d, J=8.1 Hz), 6.75 (1H, m, OH), 6.64 (1H, d, J=8.1 Hz), 7.14–7.23 (3H, m), 7.24–7.31 (2H, m), 8.93 (1H, br s, NH+), 9.43 (0.6H, s, OH), 9.49 (0.4H, s, OH), 9.96 (0.6H, br s, NH+), 10.07 (0.4H, br s, NH+).
IR (KBr) ν 3358, 3180, 1638, 1618, 1508, 1460, 1373, 1321, 1241, 1174, 1122, 1073, 1036, 994, 928, 748, 700 cm$^{-1}$.

Mass (FAB) m/z 559 ((M+H)⁺).
Elementary analysis: As $C_{36}H_{50}N_2O_3 \cdot 2HCl \cdot 0.1H_2O$
Calculated values: C 68.25; H 8.31; Cl 11.19; N 4.42
Measured values: C 68.21; H 8.19; Cl 11.05; N 4.58
Compound 98·2 hydrochloride
mp >174° C. (decomposition)
NMR (400 MHz, DMSO-$d_6$)
δ 0.41 (1H, m), 0.52 (1H, m), 0.59 (1H, m), 0.68 (1H, m), 0.96–1.04 (6H, m), 1.08 (1H, m), 1.23–1.52 (6H, m), 1.53–1.83 (5H, m), 1.92–2.15 (3H, m), 2.38–2.68 (4H, m), 2.86–3.45 (10H, m), 3.92 (1H, m), 5.24 (0.7H, d, J=7.8 Hz), 5.29 (0.3H, d, J=7.3 Hz), 6.70 (0.3H, d, J=7.8 Hz), 6.70 (0.7H, d, J=7.8 Hz), 6.81 (0.3H, d, J=7.8 Hz), 6.83 (0.7H, d, J=7.8 Hz), 6.93 (1H, m, OH), 7.14–7.22 (3H, m), 7.25–7.31 (2H, m), 8.95 (1H, br s, NH+), 9.40 (0.3H, br s, NH+), 9.49 (0.7H, br s, NH+), 9.56 (0.3H, s, OH), 9.62 (0.7H, s, OH).
IR (KBr) ν 3378, 3180, 1638, 1620, 1508, 1460, 1377, 1325, 1238, 1178, 1125, 1035, 998, 922, 861, 748, 700 cm⁻¹.
Mass (FAB) m/z 559 ((M+H)⁺).
Elementary analysis: As $C_{36}H_{50}N_2O_3 \cdot 2HCl \cdot 0.2H_2O$
Calculated values: C 68.06; H 8.31; Cl 11.16; N 4.41
Measured values: C 68.19; H 8.15; Cl 10.82; N 4.56

Reference Examples 82–83

17-cyclopropylmethyl-3,14β-dihydroxy-4,5α-epoxy-6α-(N-methylbenzyloxycarbamido)morphinan 99·hydrochloride (yield: 61%) and 17-cyclopropylmethyl-3,14β-dihydroxy-4,5α-epoxy-6α-(N-methyl-2-methoxyethoxycarbamido)morphinan 100·0.5 tartrate (yield: 49%) were obtained by following the procedure of Reference Example 15 and using benzylchloroformate and 2-methoxyethylchloroformate instead of 3,4-dichlorophenylacetylchloride.

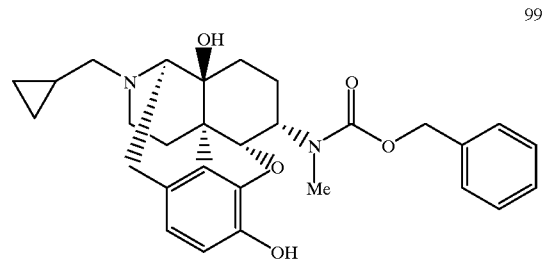

Compound 99·hydrochloride
mp 254.0–259.0° C. (decomposition, ether)
NMR (400 MHz, DMSO-$d_6$)
δ 0.40 (1H, m), 0.47 (1H, m), 0.60 (1H, m), 0.69 (1H, m), 1.06 (1H, m), 1.40–1.64 (3H, m), 1.90 (1H, m), 2.44 (1H, m), 2.69 (1H, m), 2.85 (3H, s), 2.92 (1H, m), 3.03 (1H, m), 3.09 (1H, dd, J=20.0, 6.4 Hz), 3.23–3.38 (3H, m), 3.89 (1H, br d, J=5.4 Hz), 4.59, 4.63, 4.67 (2H, each br s), 5.13–5.23 (2H, m), 6.23 (1H, s), 6.58 (1H, d, J=8.1 Hz), 6.71 (1H, d, J=8.1 Hz), 7.35 (1H, m), 7.39, 7.40 (4H, each s), 8.80 (1H, br s), 9.29 (1H, br s).
IR (KBr) ν 3500, 3100, 2850, 1663, 1470, 1350, 1317, 1156, 1120, 1035 cm⁻¹.
Mass (FAB) m/z 491 (M+H)⁺.
Elementary analysis: As $C_{29}H_{35}N_2O_5Cl \cdot 0.2H_2O$
Calculated values: C 65.64; H 6.72; N 5.28; Cl 6.68
Measured values: C 65.66; H 6.71; N 5.30; Cl 6.70
Compound 100·0.5 tartrate
mp >132° C. (decomposition)
NMR (400 MHz, DMSO-$d_6$)
δ 0.20 (2H, m), 0.48–0.58 (2H, m), 0.91 (1H, m), 1.10 (1H, m), 1.22–1.54 (3H, m), 1.73 (1H, m), 2.06–2.34 (2H, m), 2.45–2.62 (2H, m), 2.65–2.78 (2H, m), 2.81 (3H, s), 3.06 (1H, br d, J=18.6 Hz), 3.27 (1H, m), 3.29 (3H, br s), 3.50 (3.2H, br s, 3.1×OH+0.1×COOH), 3.52–3.59 (2H, m), 4.06 (1.1H, s), 4.07–4.30 (2H, m), 4.40–4.64 (2H, m), 6.51 (1H, d, J=8.0 Hz), 6.62 (1H, d, J=8.0 Hz), 9.06 (1H, br s, NH+).
IR (KBr) ν 3342, 1686, 1609, 1462, 1406, 1346, 1317, 1249, 1176, 1120, 1069, 1036, 924, 903, 806 cm⁻¹.
Mass (FAB) m/z 459 ((M+H)⁺).
Elementary analysis: As $C_{25}H_{34}N_2O_6 \cdot 0.55C_4H_6O_6 \cdot 0.9H_2O$
Calculated values: C 58.62; H 7.07; N 5.03
Measured values: C 58.67; H 7.06; N 4.91

Reference Examples 84–85

17-cyclopropylmethyl-3,14β-dihydroxy-4,5α-epoxy-6β-(N-methylbenzyloxycarbamido)morphinan 101·hydrochloride (yield: 57%) and 17-cyclopropylmethyl-3,14β-dihydroxy-4,5α-epoxy-6β-(N-methyl-2-methoxyethoxycarbamido)morphinan 102·tartrate (yield: 63%) were obtained by following the procedure of Reference Example 15, using 17-cyclopropylmethyl-3,14β-dihydroxy-4,5α-epoxy-6β-methylaminomorphinan 15 instead of 17-cyclopropylmethyl-3,14β-dihydroxy-4,5α-epoxy-6α-methylaminomorphinan 2 for the starting material, and using benzylchloroformate and 2-methoxyethylchloroformate instead of 3,4-dichlorophenylacetylchloride.

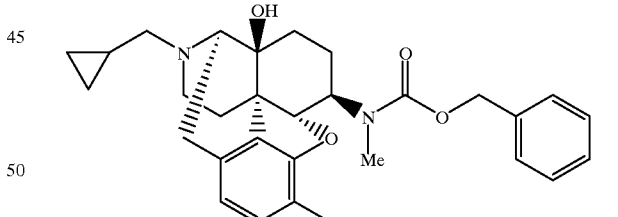

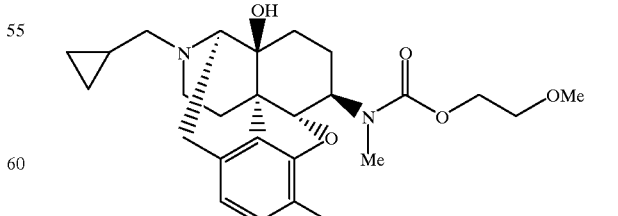

Compound 101·hydrochloride
mp 189.0–192.0° C. (decomposition, diethyl ether)
NMR (400 MHz, DMSO-$d_6$)

δ 0.31–0.47 (1H, m), 0.47–0.56 (1H, m), 0.56–0.63 (1H, m), 0.63–0.76 (1H, m), 1.00–1.14 (1H, m), 1.20–1.52 (3H, m), 1.63–1.82 (1H, m), 2.03–2.22 (1H, m), 2.34–2.59 (1H, m), 2.80–2.90 (1H, m), 2.90 (1.7H, s), 2.93 (1.3H, s), 2.98–3.17 (2H, m), 3.22–3.40 (2H, m), 3.60–3.72 (0.6H, m), 3.72–3.80 (0.4H, m), 3.84 (1H, d, J=4.9 Hz), 4.83 (1H, br t), 4.98 (0.4H, d, J=13.2 Hz), 5.04 (1H, d, J=12.7 Hz), 5.09 (0.6H, d, J=13.2 Hz), 6.42 (1H, br s), 6.72 (0.6H, d, J=8.3 Hz), 6.77 (0.4H, d, J=7.8 Hz), 7.37 (5H, s), 7.16–7.45 (2H, m), 8.83 (1H, br s), 9.32 (0.4H, s), 9.45 (0.6H, s).

IR (KBr) ν 1678, 1560, 1543, 1460, 1315, 1152, 1033 cm$^{-1}$.

Mass (FAB) m/z 491 ((M+H)$^+$).

Elementary analysis: As $C_{29}H_{35}N_2O_5Cl$
Calculated values: C 66.09; H 6.69; N 5.31; Cl 6.73
Measured values: C 66.10; H 6.64; N 5.18; Cl 6.56

Compound 102
mp >130° C. (decomposition)
NMR (400 MHz, DMSO-d$_6$)

δ 0.23 (2H, m), 0.48–0.58 (2H, m), 0.92 (1H, m), 1.23–1.38 (3H, m), 1.58 (1H, m), 2.02–2.18 (2H, m), 2.27 (1H, m), 2.52 (1H, m), 2.66–2.79 (3H, m), 2.81–2.87 (3H, m), 3.08 (1H, br d, J=18.6 Hz), 3.14 (1.5H, br s), 3.28 (1.5H, br s), 3.30 (1H, m), 3.42–3.57 (2H, m), 3.50 (4H, br s, 3.5×OH+0.5×COOH), 3.61 (1H, m), 4.02–4.13 (2H, m), 4.05 (1.5H, s), 4.69 (1H, m), 6.56 (1H, d, J=8.3 Hz), 6.63 (1H, m), 9.15 (1H, br s, NH+).

IR (KBr) ν 3424, 1686, 1609, 1460, 1410, 1313, 1251, 1123, 1066, 1033, 922, 905, 859 cm$^{-1}$.

Mass (FAB) m/z 459 ((M+H)$^+$).

Elementary analysis: As $C_{25}H_{34}N_2O_6 \cdot 0.75C_4H_6O_6 \cdot 0.8H_2O$
Calculated values: C 57.44; H 6.90; N 4.78
Measured values: C 57.41; H 6.89; N 4.71

Reference Example 86

17-Cyclopropylmethyl-3,14β-dihydroxy-4,5α-epoxy-6α-[N-methyl-N'-(3,4-dichlorophenyl)ureido]morphinan 103·hydrochloride.

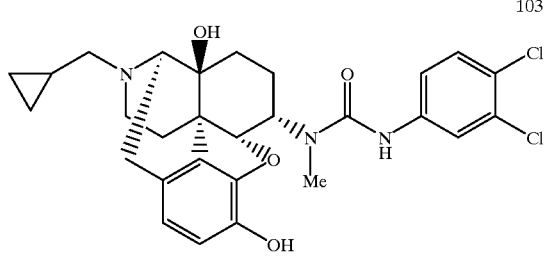

103

17-Cyclopropylmethyl-3,14β-dihydroxy-4,5α-epoxy-6α-methylaminomorphinan 4 (0.20 g) was dissolved in chloroform (5 ml) followed by the addition of 3,4-dichlorophenylisocyanate (0.26 g, 2.5 equivalents) and reacting for 5 minutes at room temperature. The precipitated solid was filtered out and dissolved in chloroform (8 ml) and methanol (10 ml) followed by the addition of 3 N aqueous sodium hydroxide to carry out hydrolysis for 5 minutes at room temperature. The solvent was distilled off followed by addition of saturated aqueous sodium bicarbonate (10 ml) and distilled water (4 ml), extraction with chloroform and methanol (12/2+10/2 ml), and drying with anhydrous sodium sulfate. After purifying with silica gel column chromatography (Merck 9385, 20 g; chloroform→3% methanol/chloroform), the residue was again dissolved in chloroform and methanol (5/0.5 ml) followed by addition of methanol solution of hydrogen chloride to obtain the target compound (0.23 g, 70%) in the form of its hydrochloride.

mp 210° C. (decomposition)
NMR (400 MHz, DMSO-d$_6$)

δ 0.41 (1H, m), 0.44 (1H, m), 0.62 (1H, m), 0.68 (1H, m), 1.0–1.2 (2H, m), 1.40 (1H, m), 1.60 (2H, m), 1.94 (1H, m), 2.4–2.5 (1H, m), 2.68 (1H, m), 2.92 (3H, s), 2.9–3.2 (3H, m), 3.3–3.4 (2H, m), 3.91 (1H, d, J=6.8 Hz), 4.74 (1H, d, J=3.9 Hz), 4.81 (1H, dt, J=13.7, 3.9 Hz), 6.34 (1H, s), 6.59 (1H, d, J=7.8 Hz), 6.73 (1H, d, J=7.8 Hz), 7.49 (1H, d, J=8.8 Hz), 7.55 (1H, dd, J=9.3, 2.4 Hz), 7.94 (1H, d, J=2.4 Hz), 8.73 (1H, s), 8.82 (1H, brs), 9.32 (1H, s)

IR (KBr) ν 3300, 1638, 1510, 1477, 1120, 1040 cm$^{-1}$.

Mass (FAB) m/z 544 (M+H)

Elementary Analysis: As $C_{28}H_{31}N_3O_4Cl_2 \cdot HCl \cdot 0.4H_2O$
Calcd.: C 57.18; H 5.62; N 7.14; Cl 18.08 Found.: C 57.32; H 5.83; N 7.04; Cl 17.85

Reference Examples 87–88

17-Cyclopropylmethyl-3,14β-dihydroxy-4,5α-epoxy-6α-(N-methyl-N'-benzylureido)morphinan 104·0.5 tartrate (yield: 65%) and 17-cyclopropylmethyl-3,14β-dihydroxy-4,5α-epoxy-6α-(N-methyl-N'-benzylthioureido)morphinan 105·0.5 tartrate (yield: 88%) were obtained by following the procedure of Reference Example 86 but using benzylisocyanate and benzylisothiocyanate instead of 3,4-dichlorophenylisocyanate.

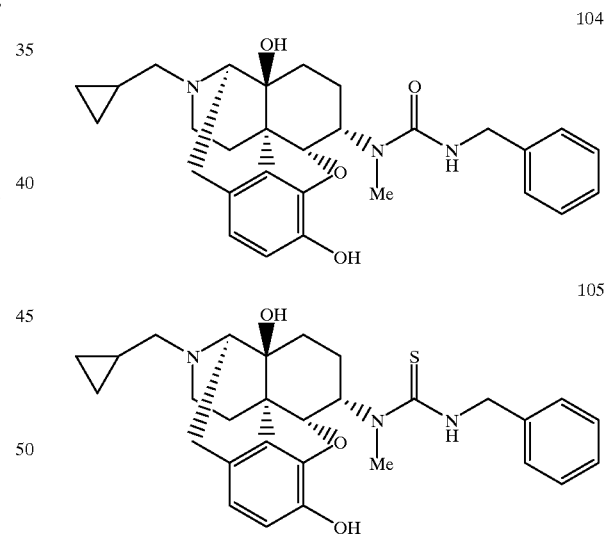

Compound 104·0.5 tartarate
mp 202–205° C. (decomposition, methanol-ethyl acetate)
NMR (400 MHz, DMSO-d$_6$)

δ 0.28 (2H, m). 0.52 (2H, m), 0.89 (1H, m), 1.10 (1H, m), 1.24 (1H, m), 1.38–1.53 (2H, m), 1.73 (1H, m), 2.15–2.30 (2H, m), 2.62–2.76 (2H, m), 2.78 (3H, s), 3.04 (1H, br d, J=18.6 Hz), 3.24 (1H, m), 3.39–3.52 (2H, m), 3.53 (3H, br s, 3×OH), 3.99 (1H, s), 4.28 (2H, d, J=5.9 Hz), 4.53 (1H, d, J=3.4 Hz), 4.70 (1H, m), 6.49 (1H, d, J=8.1 Hz), 6.61 (1H, d, J=8.1 Hz), 6.89 (1H, t, J=5.9 Hz, NH), 7.18–7.34 (5H, m), 9.03 (1H, br s, NH+).

IR (KBr) ν 3422, 3204, 1630, 1615, 1589, 1535, 1468, 1359, 1319, 1123, 903, 735 cm$^{-1}$.

Mass (FAB) m/z 490 ((M+H)+).

Elementary Analysis: As $C_{29}H_{35}N_3O_4 \cdot 0.5C_4H_6O_6$ Calcd.: C, 65.94; H, 6.78; N, 7.44 Found.: C, 65.95; H, 6.74; N, 7.47

Compound 105·0.5 tartarate mp 155–195° C. (decomposition)

NMR (500 MHz, DMSO-d$_6$)

δ 0.29 (2H, m), 0.52 (2H, m), 0.90 (1H, m), 1.18 (1H, m), 1.35 (1H, m), 1.43 (1H, br d, J=9.1 Hz), 1.50 (1H, dd, J=14.6, 9.1 Hz), 1.77 (1H, m), 2.18–2.28 (2H, m), 2.42–2.57 (2H, m), 2.66–2.78 (2H, m), 2.95 (3H, s), 3.04 (1H, br d, J=18.9 Hz), 3.23 (1H, m), 3.48 (3H, br s, 3×OH), 4.01 (1H, s), 4.80 (1H, d, J=3.6 Hz), 4.82 (1H, dd, J=15.3, 6.1 Hz), 4.89 (1H, dd, J=15.3, 6.1 Hz), 5.81 (1H, m), 6.51 (1H, d, J=7.9 Hz), 6.62 (1H, d, J=7.9 Hz), 7.23 (1H, m), 7.28–7.33 (4H, m), 8.01 (1H, dd, J=6.1, 6.1 Hz, NH), 9.03 (1H, br s, NH+).

IR (KBr) ν 3374, 1605, 1535, 1460, 1381, 1330, 1243, 1176, 1118, 1067, 1036, 907, 698 cm$^{-1}$.

Mass (FAB) m/z 506 ((M+H)+).

Elementary Analysis: As $C_{29}H_{35}N_3O_3S \cdot 0.5C_4H_6O_6 \cdot 0.3H_2O \cdot 0.15CH_3COOC_2H_5$ Calcd.: C, 63.33; H, 6.69; N, 7.01; S, 5.35 Found.: C, 63.44; H, 6.56; N, 6.90; S, 5.35

Reference Example 89

17-cyclopropylmethyl-3,14β-dihydroxy-4,5α-epoxy-6β-(N-methyl-N'-benzylthioureido)morphinan 106·tartrate (yield: 74%) was obtained by following the procedure of Reference Example 86, using 17-cyclopropylmethyl-3,14β-dihydroxy-4,5α-epoxy-6β-methylaminomorphinan 15 instead of 17-cyclopropylmethyl-3,14β-dihydroxy-4,5α-epoxy-6α-methylaminomorphinan 2 for the starting material, and using benzylisothiocyanate instead of 3,4-dichlorophenylisocyanate.

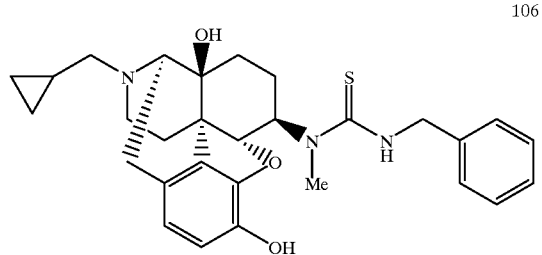

106 mp 160–180° C. (decomposition)

NMR (400 MHz, DMSO-d$_6$)

δ 0.22 (2H, m), 0.47–0.58 (2H, m), 0.91 (1H, m), 1.27–1.47 (3H, m), 1.55 (1H, m), 1.94 (1H, m), 2.12 (1H, m), 2.28 (1H, m), 2.43–2.78 (5H, m), 3.07 (1H, m), 3.08 (3H, s), 3.26 (1H, m), 3.50 (3.6H, br s, 3.3×OH+0.3×COOH), 4.01 (1.3H, s), 4.60 (1H, dd, J=15.3, 4.9 Hz), 4.74 (1H, d, J=8.3 Hz), 4.93 (1H, dd, J=15.3, 5.9 Hz), 6.55 (1H, d, J=8.3 Hz), 6.60 (1H, d, J=8.3 Hz), 7.19–7.34 (5H, m), 7.95 (1H, dd, J=5.9, 4.9 Hz, NH), 9.11 (1H, br s, NH+).

IR (KBr) ν 3352, 1721, 1605, 1531, 1456, 1330, 1238, 1125, 1067, 1033, 915, 859 cm$^{-1}$.

Mass (FAB) m/z 506 ((M+H)$^+$).

Elementary analysis: As $C_{29}H_{35}N_3O_3S \cdot 0.65C_4H_6O_6 \cdot 0.4H_2O$

Calculated values: C 62.18; H 6.56; N 6.88; S 5.25
Measured values: C 62.09; H 6.74; N 6.83; S 5.21

Reference Example 90

Naltrexone-3-tert-butyldimethylsilylether 107

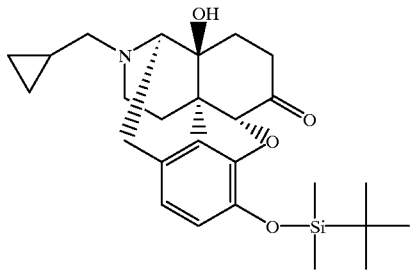

107

3.49 g of naltrexone hydrochloride was suspended in 10.5 ml of N,N-dimethylformamide. After adding 3.46 g of imidazole, 3.48 g of tert-butyldimethylchlorosilane was added followed by stirring for 35 minutes at room temperature. 30 ml of water and 50 ml of diethyl ether were added to the reaction system followed by separation. The aqueous layer was extracted twice with 30 ml of diethyl ether. The combined extracts were dried over anhydrous sodium sulfate and concentrated. The resulting residue was recrystallized from ethanol to obtain 3.2 g of the target compound (yield: 76%).

NMR (90 MHz, CDCl$_3$)

δ 0.0–1.2 (5H, m), 0.2 (3H, s), 0.3 (3H, s), 1.0 (9H, s), 1.3–2.0 (3H, m), 2.0–3.2 (8H, m), 2.4 (2H, d, J=4.4 Hz), 4.60 (1H, s), 6.5 (1H, d, J=6.4 Hz), 6.6 (1H, d, J=6.4 Hz).

Reference Example 91

17-cyclopropylmethyl-3-tert-butyldimethylsilyloxy-14β-hydroxy-4,5α-epoxy-6α-methylaminomorphinan 108 (yield: 50%) was obtained by following the procedure of Reference Example 1, using naltrexone-3-tert-butyldimethyl-silylether 107 instead of NaI.

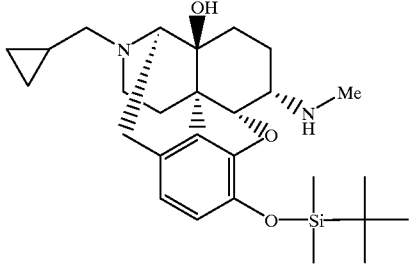

108

NMR (90 MHz, CDCl$_3$)

δ 0.0–1.2 (5H, m), 0.19 (3H, s), 0.2 (3H, s), 1.0 (9H, s), 1.3–1.9 (4H, m), 2.2–2.8 (7H, m), 2.56 (3H, s), 3.0 (1H, d, J=7.6 Hz), 3.0–3.3 (2H, m), 4.75 (1H, d, J=3.6 Hz), 6.5 (1H, d, J=7.2 Hz), 6.63 (1H, d, J=7.2 Hz)

Reference Example 92

17-cyclopropylmethyl-3-tert-butyldimethylsilyloxy-14β-hydroxy-4,5α-epoxy-6α-(N-methyl-3,4-dichlorophenylmethanesulfonamido)morphinan 109

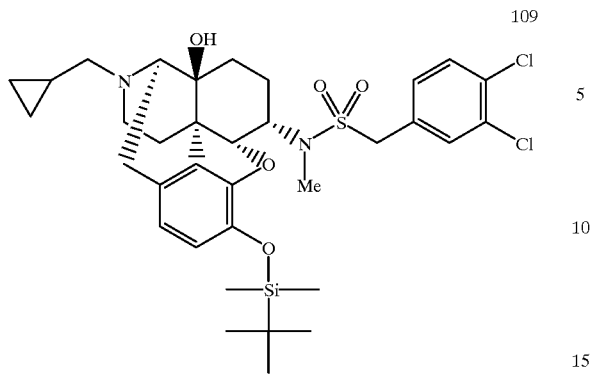

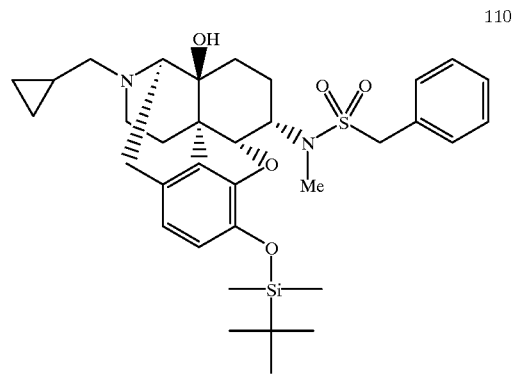

203.9 mg of 17-cyclopropylmethyl-3-tert-butyldimethylsilyloxy-14β-hydroxy-4,5α-epoxy-6α-methylaminomorphinan 108 obtained in reference example 91 was dissolved in 3 ml of pyridine followed by the addition of 124 mg of 3,4-dichorophenylmethanesufonylchloride and stirring for 30 minutes at room temperature. After concentrating the reaction system, 3 ml of saturated aqueous sodium bicarbonate and 3 ml of chloroform were added to separate layers, after which the aqueous layer was extracted twice with 3 ml of chloroform. After drying with anhydrous sodium sulfate, the organic layer was concentrated to obtain the oily crude product. This was then purified with silica gel column chromatography (30 g benzene/ethyl acetate=5/1) to obtain 235.4 mg of the target compound (yield: 78%).

NMR (500 MHz, CDCl$_3$)

δ 0.09–0.16 (2H, m), 0.15 (3H, s), 0.21 (3H, s), 0.51–0.57 (2H, m), 0.80–0.89 (1H, m), 0.97 (9H, s), 1.21–1.30 (2H, m), 1.42–1.49 (2H, m), 1.71 (1H, dt, J=14.7, 9.5 Hz), 2.15 (1H, dt, J=12.5, 5.1 Hz), 2.22 (1H, dt, J=12.5, 3.7 Hz), 2.30 (1H, dd, J=12.8, 6.6 Hz), 2.35 (1H, dd, J=12.8, 6.6 Hz), 2.56 (1H, dd, J=18.7, 7.0 Hz), 2.60–2.65 (1H, m), 2.89 (3H, B), 3.01 (1H, d, J=18.7 Hz), 3.05 (1H, d, J=7.0 Hz), 4.16 (1H, d, J=13.9 Hz), 4.19 (1H, d, J=13.9 Hz), 4.22–4.28 (1H, m), 4.41 (1H, d, J=3.3 Hz), 4.90 (1H, brs), 6.48 (1H, d, J=8.1 Hz), 6.62 (1H, d, J=8.1 Hz), 7.31 (1H, dd, J=8.1, 2.2 Hz), 7.46 (1H, d, J=8.1 Hz), 7.53 (1H, d, J=2.2 Hz).

Mass (EI) m/z 692 (M$^+$)

Reference Example 93

17-cyclopropylmethyl-3-tert-butyldimethylsilyloxy-14β-hydroxy-4,5α-epoxy-6α-(N-methylphenylmethanesulfonamido)morphinan 110 (yield: 50%) was obtained by following the procedure of Reference example 92 but using phenylmethanesulfonyl chloride instead of 3,4-dichlorophenylmethanesulfonyl chloride.

NMR (500 MHz, CDCl$_3$)

δ 0.08–0.13 (2H, m), 0.14 (3H, s), 0.20 (3H, s), 0.50–0.55 (2H, m), 0.79–0.87 (1H, m), 0.97 (9H, s), 1.10–1.22 (2H, m), 1.37–1.43 (2H, m), 1.64 (1H, dt, J=15.0, 9.5 Hz), 2.12 (1H, dt, J=12.5, 5.1 Hz), 2.20 (1H, dt, J=12.5, 3.3 Hz), 2.29 (1H, dd, J=12.5, 6.6 Hz), 2.33 (1H, dd, J=12.5, 6.6 Hz), 2.54 (1H, dd, J=18.7, 7.0 Hz), 2.59–2.63 (1H, m), 2.83 (3H, s), 2.99 (1H, d, J=18.7 Hz), 3.02 (1H, d, J=7.0 Hz), 4.19–4.24 (1H, m), 4.24 (1H, d, J=13.9 Hz), 4.28 (1H, d, J=13.9 Hz), 4.34 (1H, d, J=2.9 Hz), 4.88 (1H, brs), 6.46 (1H, d, J=8.1 Hz), 6.61 (1H, d, J=8.1 Hz), 7.32–7.40 (3H, m), 7.42–7.47 (2H, m).

Mass (EI) m/z 624 (M$^+$)

Reference Example 94

17-cyclopropylmethyl-3,14β-dihydroxy-4,5α-epoxy-6α-(N-methyl-3,4-dichlorophenylmethanesulfonamido) morphinan 111.tartrate

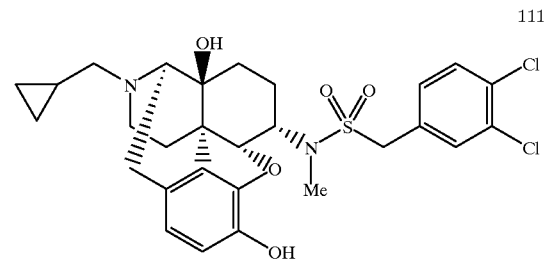

227 mg of 17-cyclopropylmethyl-3-tert-butyldimethylsilyloxy-14β-hydroxy-4,5α-epoxy-6α-(N-methyl-3,4-dichlorophenylmethanesulfonamido)morphinan 109 obtained in Reference example 92 was dissolved in 4.5 ml of tetrahydrofuran followed by the addition of 0.39 ml of tetrabutylammonium fluoride and stirring for 30 minutes. 15 ml of ethyl acetate and 10 ml of saturated aqueous ammonium chloride were added to separate layers, and the aqueous layer was extracted twice with 10 ml of ethyl acetate. The resulting organic layer was concentrated after drying with anhydrous sodium sulfate, and the residue was purified with silica gel column chromatography (25 g chloroform/methanol=20/1) to obtain the crude compound. This was then recrystallized from ethyl acetate and methanol to obtain 158 mg of the free base of the target compound. This was dissolved in a mixed solvent of chloroform and methanol, completely dissolved by addition of 20.4 mg of tartaric acid and concentrated. This residue was re-precipitated from methanol and ether followed by filtration to obtain 105 mg of the target compound (yield: 49%).

mp >149° C. (decomposition)

NMR (400 MHz, DMSO-$d_6$)

δ 0.13–0.22 (2H, m), 0.47–0.58 (2H, m), 0.82–0.92 (1H, m), 0.98–1.11 (1H, m), 1.18–1.27 (1H, m), 1.35–1.48 (2H, m), 1.55–1.67 (1H, m), 2.07–2.26 (2H, m), 2.48–2.60 (1H, m), 2.60–2.73 (2H, m), 2.83 (3H, s), 3.01 (1H, brd, J=8.6 Hz), 2.90–4.00 (5H, m, 3×OH), 3.98–4.07 (1H, m), 4.11 (1H, s), 4.35 (1H, d, J=3.4 Hz), 4.49 (1H, d, J=13.7 Hz), 4.53 (1H, d, J=13.7 Hz), 6.49 (1H, d, J=8.3 Hz), 6.61 (1H, d, J=8.3 Hz), 7.44 (1H, dd, J=2.0, 8.3 Hz), 7.67 (1H, d, J=8.3 Hz), 7.71 (1H, d, J=2.0 Hz), 9.08 (1H, brs).

IR (KBr) ν 3410, 1607, 1470, 1323, 1122, 1035, 959, 917 $cm^{-1}$.

Mass (FAB) m/z 579 (M+H)+.

Elementary Analysis: As $C_{28}H_{32}N_2O_5Cl_2S \cdot 0.65C_4H_6N_6 \cdot 0.4H_2O$ Calcd.: C, 53.71; H, 5.41; N, 4.09; Cl, 10.36; S, 4.69 Found.: C, 53.79; H, 5.50; N, 4.12; Cl, 10.09; S, 4.58

Reference Example 95

17-cyclopropylmethyl-3,14β-dihydroxy-4,5α-epoxy-6α-(N-methyl-phenylmethanesulfonamido)morphinan 112·0.5 tartrate (yield: 87%) was obtained by following the procedure of Reference Example 94 but using 17-cyclopropylmethyl-3-tert-butyldimethylsilyloxy-14β-hydroxy-4,5α-epoxy-6α-(N-methyl-phenylmethanesulfonamido)morphinan 110 instead of the starting material of 17-cyclopropylmethyl-3-tert-butyldimethylsilyloxy-14β-hydroxy- 4,5α-epoxy-6α-(N-methyl-3,4-dichlorophenylmethanesulfonamido)morphinan 109.

112

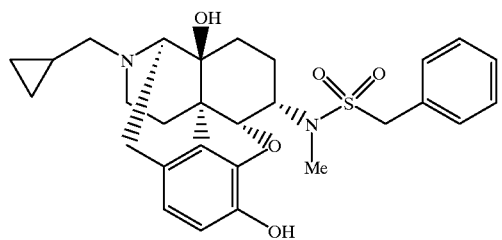

mp >147° C. (decomposition)

NMR (400 MHz, DMSO-$d_6$)

δ 0.13–0.22 (2H, m), 0.45–0.58 (2H, m), 0.82–1.07 (2H, m), 1.09–1.19 (1H, m), 1.33–1.42 (2H, m), 1.50–1.62 (1H, m), 2.07–2.27 (2H, m), 2.40–2.72 (3H, m), 2.79 (3H, s), 2.99 (1H, brd, J=9.0 Hz), 2.95–4.15 (5H, m, 3×OH), 3.98–4.07 (1H, m),. 4.10 (1H, s), 4.34 (1H, d, J=3.4 Hz), 4.40 (1H, d, J=13.9 Hz), 4.45 (1H, d, J=13.9 Hz), 6.47 (1H, d, J=8.0 Hz), 6.61 (1H, d, J=8.0 Hz), 7.31–7.46 (5H, m), 9.10 (1H, brs).

IR (KBr) ν 3420, 1603, 1460, 1321, 1122, 1069, 1036, 959, 917 $cm^{31\ 1}$.

Mass (FAB) m/z 511 (M+H)+.

Elementary Analysis: As $C_{28}H_{34}N_2O_5S \cdot 0.5C_4H_6N_6 \cdot H_2O$ Calcd.: C, 59.67; H, 6.51; N, 4.64; S, 5.31 Found.: C, 59.50; H, 6.47; N, 4.68; S, 5.21

Reference Example 96

17-cyclopropylmethyl-3,14β-dihydroxy-4,5α-epoxy-6α-(3-phenylpropionyloxy)morphinanan 113·tartrate

113

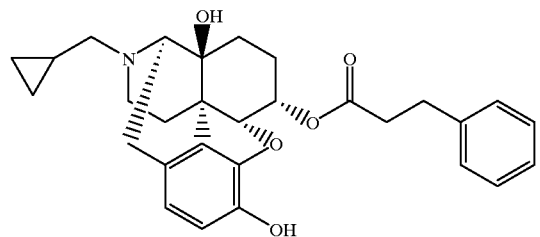

148 mg of 17-cyclopropylmethyl-3,6α,14β-trihydroxy-4,5α-epoxy-morphinan (N. Chatterjie, C. E. Inturrisi, H. B. Dayton, and H. Blumberg, *J. Med. Chem.*, 18, 490 (1975); H. C. Brown and S. Krishnamurthy, *J. Am. Chem. Soc.*, 94, 7159 (1972)) was dissolved in 0.9 ml of carbon tetrachloride and 0.3 ml of methylene chloride followed by the addition of 0.225 ml diisopropylethylamine and 26 mg of 4-dimethylaminopyridine, and the dropwise addition of 0.13 ml of 3-phenylpropionyl chloride at 0° C. After stirring for 20 hours at room temperature, 2 ml of saturated aqueous sodium bicarbonate was added to the reaction system to separate layers, and the aqueous layer was extracted twice with chloroform. The organic layer was concentrated after drying with anhydrous sodium sulfate. The resulting residue was dissolved in a mixed solvent of chloroform and methanol followed by the addition of 30 mg of potassium carbonate and stirring for 1 hour. Water was then added to the reaction mixture to separate layer, and the aqueous layer was extracted twice with chloroform. The resulting organic layer was concentrated after drying with anhydrous sodium sulfate, and the residue was purified with silica gel column chromatography (15 g chloroform/methanol=20/1) to obtain 95.3 mg of the free base of the target compound. This was then dissolved in methanol, completely dissolved by addition of 15 mg of tartaric acid and concentrated. The residue was re-precipitated from ether followed by filtration to obtain 103 mg of the target compound (yield: 43%).

mp >110° C. (decomposition)

NMR (500 MHz, DMSO-$d_6$)

δ 0.18–0.28 (2H, m), 0.47–0.60 (2H, m), 0.83–0.95 (1H, m), 1.19–1.28 (1H, m), 1.32–1.49 (3H, m), 1.74–1.82 (1H, m), 2.19–2.29 (2H, m), 2.40–2.47 (2H, m), 2.55–2.80 (6H, m), 3.08 (1H, brd, J=18.9 Hz), 3.28 (1H, brs), 3.36 (5H, m), 4.10 (2H, s), 4.64 (1H, d, J=4.9 Hz), 5.27–5.31 (1H, m), 6.51 (1H, d, J=8.2 Hz), 6.63 (1H, d, J=8.2 Hz), 7.13–7.19 (3H, m), 7.22–7.28 (2H, m), 9.10 (1H, brs).

IR (KBr) ν 3400, 1719, 1460, 1307, 1267, 1122, 1069, 1036 $cm^{-1}$.

Mass (FAB) m/z 476 (M+H)+.

Elementary Analysis: As $C_{29}H_{33}NO_5 \cdot 0.95C_4H_6O_6 \cdot 0.17C_4H_{10}O \cdot 0.17C_2H_6O \cdot 0.4H_2O$ Calcd.: C, 62.91; H, 6.59; N, 2.17 Found.: C, 62.92; H, 6.56; N, 2.32

Reference Example 97

17-cyclopropylmethyl-3-acetoxy-14β-hydroxy-4,5α-epoxy-6β-(N-methylcinnamamido)morphinan 114·tartrate 200 mg of 17-cyclopropylmethyl-3,14β-dihydroxy-4,5α-epoxy-6β-(N-methylcinnamamido)morphinan 76 obtained in Reference Example 59 were dissolved in 2 ml of pyridine followed by the addition of 0.058 ml of acetic anhydride and stirring for 1 hour at room temperature. The reaction system was then concentrated and the resulting residue was purified with silica gel column chromatography (chloroform-methanol; 50:1→25:1). After dissolving 153 mg of the resulting free base of the target compound in chloroform-methanol, 21.7 mg of tartaric acid were added followed by concentration and reprecipitation from methanol-ether to obtain 105 mg of the target compound (yield: 42%).

114

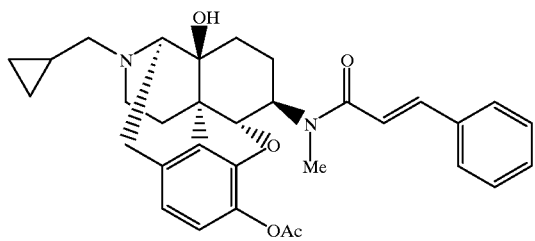

mp 142–146° C. (decomposition, ethyl acetate)

NMR (400 MHz, DMSO-$d_6$)

δ 0.23 (2H, br s), 0.54 (2H, m), 0.92 (1H, m), 1.30 (1H, m), 1.38–1.50 (2H, m), 1.60 (1H, m), 1.85 (1.73H, s), 2.09–2.26 (2H, m), 2.21 (1.27H, s), 2.33 (1H, m), 2.60–4.40 (5H, br OH×5), 2.69 (1H, m), 2.78 (2H, m), 2.90 (1.73H, s), 3.13 (1.27H, s), 3.30 (1H, m), 3.33 (1H, m), 3.72 (1H, m), 3.89 (1H, m), 4.13 (2H, s), 4.78 (0.67H, d, J=7.8 Hz), 5.00 (0.33H, d, J=8.3 Hz), 6.72–7.72 (9H, m).

IR (KBr) ν 3350, 1760, 1640, 1600, 1493, 1309, 1189 cm$^{-1}$.

Mass (FAB) m/z 529 ((M+H)$^+$).

Elementary analysis: As $C_{36}H_{42}N_2O_{11}$

Calculated values: C 63.71; H 6.24; N 4.13

Measured values: C 63.51; H 6.37; N 4.10

Reference Example 98

17-cyclopropylmethyl-3-hydroxy-14β-acetoxy-4,5α-epoxy-6β-(N-methylcinnamamido)morphinan 115·0.5 tartrate 0.27 g of the 17-cyclopropylmethyl-3,14β-dihydroxy-4,5α-epoxy-6β-(N-methylcinnamamido)morphinan 76 obtained in Reference Example 59 were dissolved in 10 ml of acetic anhydride followed by refluxing while heating for 1 hour. After concentrating the reaction system, 9 ml of water, 1 ml of sulfuric acid and 4 ml of methanol were added to the residue followed by stirring for 40 hours at room temperature. Next, 1.5 ml of 28% aqueous sodium hydroxide were added to the reaction system to make the system basic followed by extraction with 2×10 ml of chloroform. After drying the organic layer with anhydrous sodium sulfate and concentrating, the residue was purified with silica gel column chromatography (25 g, chloroform→2% chloroform/methanol). The resulting salt-free form of the target compound was derived to tartaric acid by normal methods to obtain 160 mg of the target compound (yield: 48%).

115

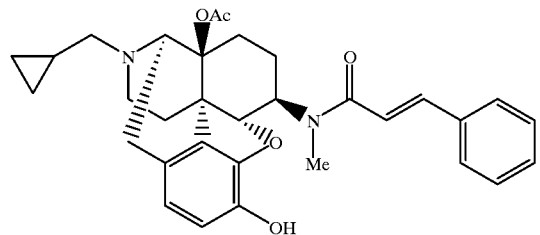

mp 154–157° C.

NMR (400 MHz, DMSO-$d_6$)

δ 0.06 (2H, m), 0.42 (2H, d, J=8.3 Hz), 0.72 (1H, m), 1.2–1.4 (3H, m), 1.93 (1H, m), 2.05 (1H, m), 2.11 (3H, s), 2.24 (1H, m), 2.37 (2H, m), 2.43 (1H, m), 2.62 (1H, m), 2.89 (2H, s), 3.03 (1H, d, J=18.1 Hz), 3.15 (1H, s), 3.2–3.4 (1H, m), 3.69 (0.7H, m), 4.15 (0.3H, m), 4.28 (1H, s), 4.70 (0.7H, d, J=7.8 Hz), 4.82 (0.3H, d, J=8.3 Hz), 6.5–6.8 (3H, m), 7.1–7.5 (5.3H, m), 7.71 (0.7H, d, J=6.3 Hz).

IR (KBr) ν 3390, 1738, 1647, 1590, 1408, 1122 cm$^{-1}$.

Mass (FAB) m/z 529 (M+H).

Elementary analysis: As $C_{32}H_{36}N_2O_5$·0.5($C_4H_6O_6$)·1.0$H_2O$

Calculated values: C 65.68; H 6.65; N 4.50

Measured values: C 65.85; H 6.66; N 4.43

Reference Example 99

17-cyclopropylmethyl-3,14β-dihydroxy-4,5α-epoxy-6β-(N-methyl-3-aminocinnamamido)morphinan 116.hydrochloride 360 mg of the 17-cyclopropylmethyl-3,14β-dihydroxy-4,5α-epoxy-6β-(N-methyl-3-nitrocinnamamido)morphinan 78 and 1.07 g of stannous chloride dihydrate were dissolved in 7.5 ml of ethanol followed by heating to 70° C. and stirring for 2 hours. After cooling the reaction mixture to room temperature, 2 N aqueous sodium hydroxide was added while cooling with ice to neutralize followed by extraction with dichloromethane. The organic layers were combined and washed with saturated brine followed by drying and concentration. Inorganic substances were removed by chromatographic filtration [silica gel; chloroform:methanol (9:1)]. The resulting unpurified target compound was converted to a 2 hydrochloride to obtain 310 mg.

116

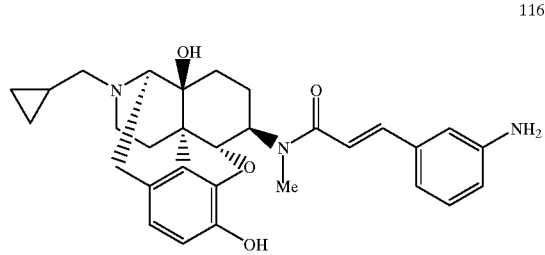

Mass (FAB) m/z 502 ((M+H)$^+$).

Reference Example 100

17-cyclopropylmethyl-3,14β-dihydroxy-4,5α-epoxy-6β-(N-methyl-3-isothiocyanatocinnamamido)morphinan 117·methanesulfonate 300 mg of the 17-cyclopropylmethyl-3,14β-dihydroxy-4,5α-epoxy-6β-(N-methyl-3-aminocinnamamido)morphinan 116·hydrochloride obtained in Reference Example 99 were dissolved in 9 ml of water and cooled with ice. A solution of 40 μl of thiophosgene dissolved in 2 ml of chloroform was dropped into this solution followed by warming to room temperature and stirring for 5 hours. While cooling with ice, saturated aqueous sodium bicarbonate was added to neutralize followed by extraction with chloroform. The organic layers were combined and washed with saturated brine followed by drying and concentration. The resulting residue was purified with column chromatography [silica gel; chloroform:methanol (97.5:2.5)] and the resulting target compound was converted to a methanesulfonate to obtain 208 mg (yield: 52% according to Reference Example 99).

117

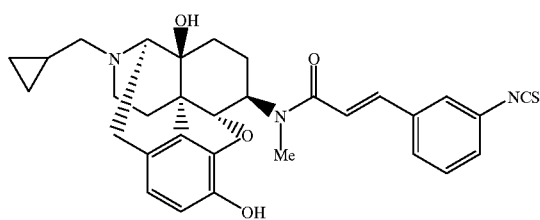

mp 170° C. (decomposition)

NMR (500 MHz, DMSO-$d_6$)

δ 0.42 (1H, m), 0.49 (1H, m), 0.60 (1H, m), 0.69 (1H, m), 1.07 (1H, m), 1.27–1.58 (3H, m), 1.72 (1H, m), 2.11 (1H, m), 2.31 (3H, s), 2.43–2.52 (2H, m), 2.86 (1H, m), 2.92 (2.1H, s), 3.02–3.14 (2H, m), 3.18 (0.9H, s), 3.30–3.38 (2H, m), 3.70 (0.7H, m), 3.83 (1H, m), 4.19 (0.3H, m), 4.80 (0.7H, d, J=8.3 Hz), 4.90 (0.3H, d, J=8.3 Hz), 6.14 (0.3H, br s), 6.22 (0.7H, br s), 6.65–6.84 (2.1H, m), 6.88 (0.7H, d, J=7.8 Hz), 7.29 (1H, d, J=15.6 Hz), 7.40–7.50 (3.6H, m), 7.69 (0.3H, d, J=7.8 Hz), 7.91 (0.3H, s), 8.74 (1H, br s), 9.30 (0.3H, br s), 9.54 (0.7H, br s).

IR (KBr) ν 3380, 3210, 2124, 1649, 1599, 1197, 1060, 785 cm$^{-1}$.

Mass (FAB) m/z 544 ((M+H)$^+$).

Elementary analysis: As $C_{31}H_{33}N_3O_4S·CH_3SO_3H·H_2O$

Calculated values: C 58.43; H 5.98; N 6.39; S 9.75

Measured values: C 58.67; H 6.15; N 6.11; S 9.78

Reference Example 101

17-cyclopropylmethyl-3-methoxy-14β-hydroxy-4,5α-epoxy-6β-[trans-3-(3-furyl)acryloylthio]morphinan 118 (yield: 59%) was obtained by following the procedure of Reference Example 15, using 17-cyclopropylmethyl-3-methoxy-14β-hydroxy-4,5α-epoxy-6β-mercaptomorphinan (K. Kanematsu, T. Toshiyasu, M. Yoshida., Chem. Pharm. Bull., 38, 1141 (1990)) instead of 17-cyclopropylmethyl-3,14β-dihydroxy-4,5α-epoxy-6α-(N-methylamino) morphinan 2, and using trans-3-(3-furyl)acryloyl chloride instead of 3,4-dichlorophenylacetyl chloride.

118

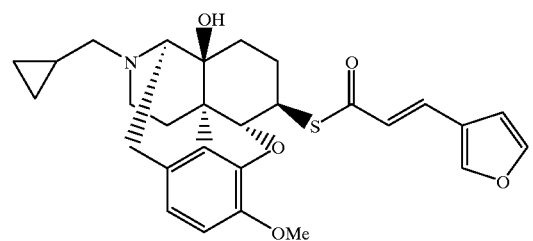

NMR (400 MHz, DMSO-$d_6$)

δ 0.08–0.18 (2H, m), 0.50–0.58 (2H, m), 0.78–0.90 (1H, m), 1.43–1.67 (4H, m), 1.78–1.86 (1H, m), 2.05–2.18 (2H, m), 2.24 (1H, dt, J=4.9, 12.2 Hz), 2.37 (2H, d, J=6.3 Hz), 2.60–2.70 (2H, m), 3.04 (1H, d, J=19.0 Hz), 3.08 (1H, d, J=6.4 Hz), 3.44–3.54 (1H, m), 3.84 (3H, s), 4.55 (1H, d, J=8.8 Hz), 5.10 (1H, br s), 6.42 (1H, d, J=15.6 Hz), 6.58 (1H, d, J=1.5 Hz), 6.64 (1H, d, J=8.3 Hz), 6.73 (1H, d, J=8.3 Hz), 7.43 (1H, br s), 7.46 (1H, d, J=15.6 Hz), 7.68 (1H, s).

Mass (EI) m/z 493 (M)$^+$.

Reference Example 102

17-cyclopropylmethyl-4,5α-epoxy-3,14β-dihydroxy-6β-[trans-3-(3-furyl)acryloylthio]morphinan 119·0.5 tartrate 4.1 ml of a 1 M boron tribromide/dichloromethane solution were added to 2.7 ml of chloroform followed by cooling to 0° C. A chloroform solution (6 ml) containing 257 mg of 17-cyclopropylmethyl-3-methoxy-14β-hydroxy-4,5α-epoxy-6β-[trans-3-(3-furyl)acryloylthio]morphinan 118 was added to this solution followed by stirring for 15 minutes at room temperature. The reaction solution was poured into ice water. After adding concentrated ammonia to make the solution basic, the solution was extracted twice with chloroform after which the organic layers were combined, dried and concentrated. The resulting crude product was purified with column chromatography (silica gel; chloroform-methanol 30:1). The resulting crystals were recrystallized by methanol-dichloromethane to obtain 68 mg of the salt-free form of the target compound. This form was then converted to tartrate by normal methods to obtain 70 mg of the target compound (yield: 21%).

119

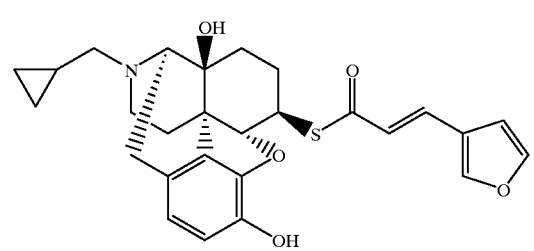

mp 225° C. (decomposition)

NMR (400 MHz, DMSO-$d_6$)

δ 0.15–0.24 (2H, m), 0.45–0.57 (2H, m), 0.84–0.93 (1H, m), 1.23–1.43 (2H, m), 1.52–1.67 (2H, m), 1.92–2.29 (3H, m), 2.40–2.52 (1H, m), 2.53–2.78 (3H, m), 3.08 (1H, d, J=19.1 Hz), 3.19–3.30 (1H, m), 4.01 (1H, s), 4.52 (1H, d, J=8.8 Hz), 6.60 (1H, d, J=7.8 Hz), 6.64

(1H, d, J=7.8 Hz), 6.74 (1H, d, J=15.6 Hz), 7.01 (1H, d, J=1.5 Hz), 7.50 (1H, d, J=15.6 Hz), 7.76 (1H, br s), 8.18 (1H, s), 9.18 (1H, br s).

IR (KBr) ν 3402, 3222, 1665, 1649, 1613, 1578, 1315, 1040, 859, 795, 673 cm$^{-1}$.

Mass (FAB) m/z 480 ((M+H)$^+$).

Elementary analysis: As $C_{27}H_{29}NO_5S \cdot 0.5C_4H_6O_6 \cdot 0.3H_2O$

Calculated values: C 62.19; H 5.87; N 2.50; S 5.73
Measured values: C 62.21; H 5.86; N 2.57; S 5.65

Reference Example 103

17-cyclopropylmethyl-3,14β-dihydroxy-4,5α-epoxy-6β-(N-methyl-3-trifluoromethoxycinnamamido)morphinan 120·tartrate (yield: 49%) was obtained by following the procedure of Reference Example 15 and using 3-trifluoromethoxycinnamoyl chloride instead of 3,4-trichlorophenylacetyl chloride.

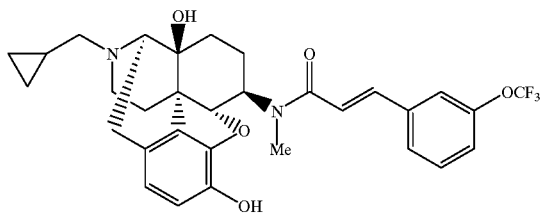

120 mp 152–155° C.

NMR (400 MHz, DMSO-d$_6$)

δ 0.23 (2H, m), 0.52 (2H, m), 0.91 (1H, m), 1.25–1.45 (3H, m), 1.59 (1H, m), 2.05–2.20 (2H, m), 2.31 (1H, m), 2.53 (1H, m), 2.65–2.80 (3H, m), 2.90 (2H, s), 3.11 (1H, d, J=18.6 Hz), 3.16 (1H, s), 3.41 (1H, m), 3.63 (0.7H, m), 4.06 (1H, s), 4.20 (0.3H, m), 4.70 (0.7H, d, J=8.3 Hz),.4.80 (0.3H, d, J=8.3 Hz), 6.55–6.75 (2.7H, m), 7.30–7.55 (4.7H, m), 7.74 (0.3H, d, J=7.8 Hz), 7.81 (0.3H, s).

IR (KBr) ν 3350, 1649, 1603, 1261, 1216, 1127 cm$^{-1}$.

Mass (FAB) m/z 571 (M+H).

Elementary analysis: As $C_{31}H_{33}N_2O_5F_3 \cdot 0.5C_4H_6O_6 \cdot 1.3H_2O$ Calculated values: C 59.24; H 5.82; N 4.19; F 8.52
Measured values: C 59.43; H 5.66; N 4.13; F 8.45

Example 18

Cultured Nerve Cell Protective Active Against Glutamate Acid Toxicity

When blood flow to the brain is temporarily interrupted due to transient cerebral ischemia, hypoglycemia, hypoxia or trauma, delayed neuronal death is known to be induced [T. Kirino, Brain Research, 239, 57 (1982)]. One of the possible causes of this nerve cell disorder is believed to be excitatory toxicity caused by excitatory neurotransmitters such as glutamate released in excess accompanying ischemia [S. M. Rotherman and J. W. Olney, Trends in Neuroscience, 10, 299 (1987)]. Compounds that protect nerve cells from this cytotoxicity caused by glutamate are considered to be promising for use as preventive and therapeutic agents for ischemic brain disorders, brain nerve cell disorders and dementia which are problems that the present invention is attempting to solve. The procedure described below was performed as a means of evaluating this protective action in vitro.

Fetuses were removed from the abdomens of female Wistar rats on days 18–19 of pregnancy under sterile conditions, and their brains were extracted after opening the skull. The brains were placed in ice-cooled L-15 medium and the cerebral cortex was isolated microscopically. After preparing thin sections of the cerebral cortex from the brains of roughly 30 fetuses, the thin sections were suspended in 10 ml of 0.25% trypsin and 0.2 ml of 0.01% DNase and cultured for 30 minutes at 37° C. Next, 2 ml of serum were added followed immediately by centrifuging for 2 minutes at 1200 rpm after which the sediment was isolated. 7 ml of DF medium (containing 20 nM of transferrin, 5 μg/ml of insulin, 20 nM of progesterone, 60 nM of selenite, 50 U/ml of penicillin and 50 U/ml of streptomycin added to a mixture of equal volumes of Dulbecco's modified Eagle medium and F-12 medium) was added to this sediment after which a cell suspension was obtained by repeating pipetting 20 times with a 10 ml plastic pipette. Moreover, isolated cells were removed by filtering with Nylon mesh (pore size: 43 μm). The resulting isolated cells were diluted with DF medium to a concentration of $6.0 \times 10^5$ cells/ml. 500 μl aliquots of these diluted cells were then placed in a 48-well culture plate precoated with poly-lysine followed by culturing for 1 day at 37° C. in the presence of 5% $CO_2$. The medium was replaced with fresh DF medium on the second day and 10 μl aliquots of 0.5 M glutamate solution dissolved in distilled water were added to each well (resulting in a final glutamate concentration of 10 mM). This was followed by additional culturing for 24 hours at 37° C. in the presence of 5% $CO_2$. The test compounds were dissolved in distilled water, 10% DMSO, 100% DMSO or 10% methanol, and 5 μl aliquots were added to each well immediately before addition of glutamate. The enzyme activity of lactate dehydrogenase (LDH) that leaks into the medium from cells that have been damaged was measured as the indicator of nerve cell damage. The amount of leaked LDH was measured according to the respective concentrations of each test compound, and the dose reaction curve was determined according to the modified Cochrane-Amitige method. The 50% effective doses ($ED_{50}$) were then determined for each test compound from this curve. Those results are shown in Table 1.

TABLE 1

Cultured Nerve Cell Protective Action Against Glutamate Toxicity

| Compound | $ED_{50}$ (μM) | Compound | $ED_{50}$ (μM) | Compound | $ED_{50}$ (μM) |
|---|---|---|---|---|---|
| 1 | 0.50 | 4 | 5.75 | 5 | 24.55 |
| 6 | 1.93 | 7 | 0.32 | 8 | 1.20 |
| 9 | 0.29 | 10 | 0.28 | 11 | 0.17 |
| 12 | 0.13 | 13 | 0.21 | 14 | 0.11 |
| 26 | 1.61 | 27 | 1.91 | 28 | 7.60 |
| 29 | 7.95 | 30 | 2.14 | 31 | 2.53 |
| 32 | 0.18 | 33 | 0.64 | 34 | 0.23 |
| 35 | 0.03 | 36 | 1.01 | 37 | 0.06 |
| 38 | 2.51 | 39 | 0.39 | 40 | 15.27 |
| 41 | 16.67 | 42 | 1.80 | 43 | 32.57 |
| 44 | 1.41 | 45 | 3.72 | 46 | 4.42 |
| 47 | 17.10 | 48 | 7.04 | 49 | 29.87 |
| 50 | 3.44 | 51 | 13.59 | 52 | 1.49 |
| 53 | 18.19 | 54 | 13.51 | 55 | 1.73 |
| 56 | 1.08 | 57 | 0.66 | 58 | 0.10 |
| 59 | 0.48 | 60 | 0.09 | 61 | 2.22 |
| 62 | 0.14 | 63 | 1.25 | 64 | 0.69 |
| 65 | 0.31 | 66 | 0.33 | 67 | 0.10 |
| 68 | 0.10 | 69 | 0.16 | 70 | 0.19 |
| 71 | 0.10 | 72 | 0.11 | 73 | 0.14 |
| 74 | 0.22 | 75 | 16.49 | 76 | 6.79 |

TABLE 1-continued

Cultured Nerve Cell Protective Action Against Glutamate Toxicity

| Compound | ED$_{50}$ ($\mu$M) | Compound | ED$_{50}$ ($\mu$M) | Compound | ED$_{50}$ ($\mu$M) |
|---|---|---|---|---|---|
| 77 | 12.18 | 78 | 5.45 | 79 | 12.22 |
| 80 | 7.39 | 81 | 2.70 | 82 | 0.25 |
| 83 | 4.69 | 84 | 2.37 | 85 | 4.22 |
| 86 | 7.36 | 87 | 2.15 | 88 | 4.64 |
| 89 | 6.28 | 90 | 4.37 | 93 | 1.50 |
| 94 | 0.29 | 95 | 0.56 | 96 | 0.64 |
| 97 | 0.16 | 98 | 0.16 | 99 | 0.40 |
| 100 | 38.80 | 101 | 5.23 | 103 | 0.54 |
| 104 | 0.58 | 105 | 20.65 | 106 | 10.90 |
| 111 | 0.54 | 112 | 1.45 | 113 | 0.53 |
| 114 | 60.29 | 115 | 5.41 | 117 | 9.57 |
| 119 | 1.47 | 120 | 1.06 | | |

As a result, compounds 1, 4-14, 26-90, 93-101, 103-106, 111-115, 117 and 119-120 of the present invention clearly possessed action that protects nerve cells from cytotoxicity caused by glutamate.

Example 19

Protective Action from Delayed Neuronal Death

Those compounds that provide protection from and suppress delayed neuronal death described in Example 18 are considered to be promising as preventive and therapeutic agents for ischemic brain disorders, brain nerve cell disorders and dementia, which are problems that the present invention is attempting to solve. The pharmacological activity of the compounds of the present invention was evaluated in the manner below using jerbils for the animal model.

A midline incision was made in mongolian having body weights of 50–70 g under ether anesthesia. Blood flow through the carotid arteries on both sides was interrupted to create an ischemic state by ligating the vessels for 5 minutes. The test compound was administered subcutaneously either 30 minutes or 1 hour prior to ligation ischemia, and the rectal temperature of the animals was controlled to 37±2° C. using a heating pad or heater starting 5 minutes before to 30 minutes after ligation ischemia. 1 week after ligation, 4% neutral buffered formalin was perfused from the heart throughout the body followed by extraction of the brain. After post-fixing the extracted brain in the same solution, the tissue was prepared into sections after embedding in paraffin. The sections were stained with hematoxylin and eosin, and the number of nerve cells in the CA1 region of the hippocampus over a width of 1 mm to the left and right was counted. The total number of nerve cells on the right and left sides was then used for evaluation. Those results are shown in Table 2.

TABLE 2

Protective Action from Delayed Neuronal Death

| Compound | Dose (mg/kg) | No. of Residual Nerve Cells |
|---|---|---|
| 34 | 0.03 (30 minutes before ischemia) | 38.8 ± 19.6 |
| | 0.3 (30 minutes before ischemia) | 85.5 ± 34.9 |
| | 3 (30 minutes before ischemia) | 68.0 ± 45.3 |
| 35 | 0.03 (30 minutes before ischemia) | 17.8 ± 6.9 |
| | 0.3 (30 minutes before ischemia) | 46.4 ± 15.1 |
| | 3 (30 minutes before ischemia) | 203.1 ± 40.1 |
| 42 | 0.3 (1 hour before ischemia) | 52.1 ± 14.8 |
| | 0.3 (1 hour before ischemia) | 148.3 ± 28.5 |
| | 3 (1 hour before ischemia) | 284.5 ± 7.1 |
| 46 | 0.03 (30 minutes before ischemia) | 12.4 ± 3.0 |
| | 0.3 (30 minutes before ischemia) | 43.3 ± 19.1 |
| | 3 (30 minutes before ischemia) | 178.3 ± 30.4 |
| 78 | 0.03 (30 minutes before ischemia) | 12.0 ± 3.0 |
| | 0.3 (30 minutes before ischemia) | 14.8 ± 1.2 |
| | (30 minutes before ischemia) | 106.2 ± 65.6 |
| Sham Group | Not dosed | 323.4 ± 6.8 |
| Control Group | 10% DMSO | 21.9 ± 8.5 |

As a result, compounds 34, 35, 42, 46 and 78 of the present invention significantly inhibited defluxion of brain nerve cells caused by ischemia, thus making it clear that said compounds have brain nerve cell protective action.

INDUSTRIAL APPLICABILITY

The compounds used in the present invention clearly demonstrated excellent defensive effects against brain nerve cell necrosis in both in vitro and in vivo pharmacological evaluations. Thus, the compounds of the present invention can clearly be expected to be useful in the field of pharmaceutics as preventive and therapeutic agents of ischemic brain disorders, brain nerve cell disorders and dementia, examples of which include preventive and therapeutic agents of sequelae based on cerebrovascular diseases and brain nerve cell disorders, preventive and therapeutic agents of neural diseases and cerebroneural function diseases, preventive and therapeutic agents of cardiac ischemic diseases and circulatory diseases, and preventive and therapeutic agents of neural degenerative diseases.

We claim:

1. A method of protecting brain nerve cells against cytotoxic damage caused by ischemic brain disorder, the method comprising administering to a patient in need thereof an effective brain cell protecting amount of a brain cell protective agent of formula (I) or pharmacologically acceptable acid addition salt thereof:

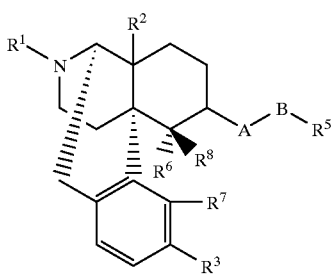

(I)

wherein, the dashed line "- - - -" represents an optional double bond;

$R^1$ represents an alkyl group having 1–5 carbon atoms, a cycloalkylalkyl group having 4–7 carbon atoms, a cycloalkenylalkyl group having 5–7 carbon atoms, an aryl group having 6–12 carbon atoms, an aralkyl group having 7–13 carbon atoms, an alkenyl group having 4–7 carbon atoms, or an allyl group;

$R^2$ represents a hydrogen atom, a hydroxy group, a nitro group, an alkanoyloxy group having 1–5 carbon atoms, an alkoxy group having 1–5 carbon atoms, a straight chain alkyl group having 1–5 carbon atoms or —$NR^9R^{10}$, wherein, $R^9$ represents a hydrogen atom or an alkyl group having 1–5 carbon atoms, and $R^{10}$ represents a hydrogen atom, an alkyl group having 1–5 carbon atoms or —C(=O)$R^{11}$ (wherein $R^{11}$ represents a hydrogen atom, phenyl group or alkyl group having 1–5 carbon atoms);

$R^3$ represents a hydrogen atom, a hydroxy group, an alkanoyloxy group having 1–5 carbon atoms or an alkoxy group having 1–5 carbon atoms;

A represents —XC(=Y)—, —XC(=Y)Z—, —X— or —$XSO_2$—, where, X represents $NR_4$, and Y and Z respectively and independently represent $NR^4$, S or O, $R^4$ represents a hydrogen atom, a straight chain alkyl group having 1–14 carbon atoms or a branched chain alkyl group having 3 to 14 carbon atoms (which may be substituted with at least one substituent selected from the group consisting of an alkoxy group having 1–5 carbon atoms, an alkanoyloxy group having 1–5 carbon atoms, fluorine, chlorine, bromine, iodine, a nitro group and a cyano group), a cycloalkylalkyl group having 4 to 15 carbon atoms (which may be substituted with at least one substituent selected from the group consisting of an alkyl group having 1–5 carbon atoms, an aryl group having 6–12 carbon atoms, an alkoxy group having 1–5 carbon atoms, an alkanoyloxy group having 1–5 carbon atoms, fluorine, chlorine, bromine, iodine, a nitro group, a cyano group and a trifluoromethyl group), an aralkyl group having 7–15 carbon atoms (which may be substituted with at least one substituent selected from the group consisting of an alkyl group having 1–5 carbon atoms, an aryl group having 6–12 carbon atoms, an alkoxy group having 1–5 carbon atoms, an alkanoyloxy group having 1–5 carbon atoms, fluorine, chlorine, bromine, iodine, a nitro group, a cyano group and a trifluoromethyl group), or an aryl group having 6–12 carbon atoms (which may be substituted with at least one substituent selected from the group consisting of an alkyl group having 1–5 carbon atoms, an aryl group having 6–12 carbon atoms, an alkoxy group having 1–5 carbon atoms, an alkanoyloxy group having 1–5 carbon atoms, fluorine, chlorine, bromine, iodine, a nitro group, a cyano group and a trifluoromethyl group), and wherein said $R^4$ groups may be identical or different;

B represents a valence bond, a straight chain alkylene group having 1–14 carbon atoms or a branched chain alkylene group having 3–14 carbon atoms (which may be substituted with at least one substituent selected from the group consisting of an alkoxy group having 1–5 carbon atoms, an alkanoyloxy group having 1–5 carbon atoms, a hydroxy group, fluorine, chlorine, bromine, iodine, an amino group, a nitro group, a cyano group, a trifluoromethyl group and a phenoxy group, and wherein from 1 to 3 methylene groups that are not adjacent may be replaced with carbonyl groups), a straight chain, acyclic, unsaturated hydrocarbon having 2–14 carbon atoms or a branched chain, acyclic, unsaturated hydrocarbon having 3 to 14 carbon atoms, and having from 1 to 3 double and/or triple bonds (which may be substituted with at least one substituent selected from the group consisting of an alkoxy group having 1–5 carbon atoms, an alkanoyloxy group having 1–5 carbon atoms, a hydroxy group, fluorine, chlorine, bromine, iodine, an amino group, a nitro group, a cyano group, a trifluoromethyl group and a phenoxy group, and wherein from 1 to 3 methylene groups that are not adjacent may be replaced with carbonyl groups), or a straight chain, saturated hydrocarbon having 1–14 carbon atoms, a straight chain unsaturated hydrocarbon having 2–14 carbon atoms, or a branched chain saturated or unsaturated hydrocarbon having 3 to 14 carbon atoms, having from 1 to 5 thioether, ether and/or amino bonds (wherein hetero atoms are not bonded directly to A);

R represents a hydrogen atom or an organic group having a structure as shown below:

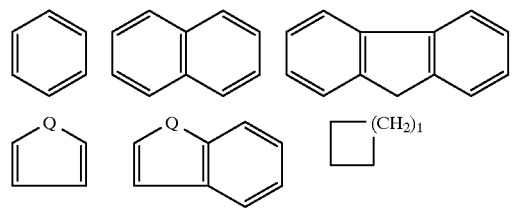

wherein Q is N, O or S, l is 2 or 3, m and n are greater than or equal to 0, and m+n is less than or equal to 5, and which organic group may be substituted with one or two same or different substituents selected from the group consisting of $C_{1-5}$ alkyl, $C_{1-5}$ alkoxy, $C_{1-5}$ alkanoyloxy, hydroxy, fluoro, chloro, bromo, iodo, amino, nitro, cyano, isothiocyanate, and trifluoromethyl;

$R^6$ and $R^7$ collectively represent —O—;

$R^8$ represents a hydrogen atom, a straight chain alkyl group having 1–5 carbon atoms or an alkanoyl group having 1–5 carbon atoms.

2. The method as recited in claim 1 wherein, in the formula (I), A is —$NR^4C(=O)$—, —$NR^4C(=O)O$—, —$NR^4C(=O)NR^4$—, —$NR^4C(=S)NR^4$—, —$NR^4$— or —$NR^4SO_2$— (wherein $R^4$ is the same as previously defined).

3. The method as recited in claim 1 wherein, in the formula (I), A is —$NR^4C(=O)$—, —$NR^4C(=O)O$—, —$NR^4C(=O)NR^4$—, —$NR^4C(=S)NR^4$— or —$NR^4$— (where $R^4$ is the same as previously defined).

4. The method as recited in claim 1 wherein, in the formula (I), A is —NR⁴C(=O)— or —NR⁴— (where R⁴ is the same as previously defined).

5. The method as recited in claim 2 wherein, in the formula (I), A is —NR⁴C(=O)—, =NR⁴C(=O)O—, —NR⁴C(=O)NR⁴—, —NR⁴C(=S)NR⁴— or —NR⁴— (where R⁴ is the same as previously defined).

6. The method as recited in claim 2 wherein, in the formula (I), A is —NR⁴C(O=)— or —NR⁴— (where R⁴ is the same as previously defined).

7. The method as recited in claim 3, wherein, in the formula (I), A is —NR⁴C(=O)— or —NR⁴— (where NR⁴ is the same as previously defined).

8. A method of protecting brain nerve cells against cytotoxic damage caused by ischemic brain disorder, the method comprising administering to a patient in need thereof an effective brain cell protecting amount of a brain cell protective agent of formula (I') or a pharmacologically acceptable acid addition salt thereof:

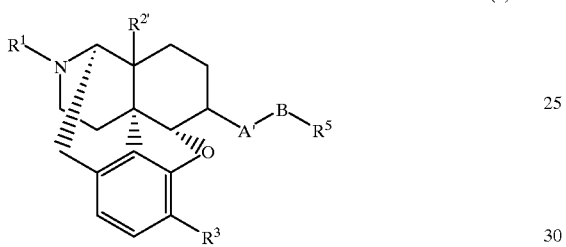

(I')

wherein,

R¹ represents an alkyl group having 1–5 carbon atoms, a cycloalkylalkyl group having 4–7 carbon atoms, a cycloalkenylalkyl group having 5–7 carbon atoms, an aryl group having 6–12 carbon atoms, an aralkyl group having 7–13 carbon atoms, an alkenyl group having 4–7 carbon atoms, or an allyl group;

R² represents a hydrogen atom, hydroxy group, alkanoyloxy group having 1–5 carbon atoms or alkoxy group having 1–5 carbon atoms;

R³ represents a hydrogen atom, a hydroxy group, an alkanoyloxy group having 1–5 carbon atoms or an alkoxy group having 1–5 carbon atoms;

A' represent —NR⁴'C(=O)— or —NR⁴'—, where R⁴' represents a straight chain or branched chain alkyl group having 6–14 carbon atoms (which may be substituted with at least one substituent selected from the group consisting of an alkoxy group having 1–5 carbon atoms, an alkanoyloxy group having 1–5 carbon atoms, fluorine, chlorine, bromine, iodine, a nitro group and a cyano group), a straight chain alkyl group having 1–5 carbon atoms or a branched chain alkyl group having 3–5 carbon atoms (which is substituted with at least one substituent selected from the group consisting of an alkoxy group having 1–5 carbon atoms, an alkanoyloxy group having 1–5 carbon atoms, fluorine, chlorine, bromine, iodine, a nitro group and a cyano group), a cycloalkylalkyl group having 4 to 15 carbon atoms (which may be substituted with at least one substituent selected from the group consisting of an alkyl group having 1–5 carbon atoms, an aryl group having 6–12 carbon atoms, an alkoxy group having 1–5 carbon atoms, an alkanoyloxy group having 1–5 carbon atoms, fluorine, chlorine, bromine, iodine, a nitro group, a cyano group and a trifluoromethyl group), an aralkyl group having 7–15 carbon atoms (which may be substituted with at least one substituent selected from the group consisting of an alkyl group having 1–5 carbon atoms, an aryl group having 6–12 carbon atoms, an alkoxy group having 1–5 carbon atoms, an alkanoyloxy group having 1–5 carbon atoms, fluorine, chlorine, bromine, iodine, a nitro group, a cyano group and a trifluoromethyl group), or an aryl group having 6–12 carbon atoms (which is substituted with at least one substituent group selected from the group consisting of an alkyl group having 1–5 carbon atoms, an aryl group having 6–12 carbon atoms, an alkoxy group having 1–5 carbon atoms, an alkanoyloxy group having 1–5 carbon atoms, fluorine, chlorine, bromine, iodine, a nitro group, a cyano group and a trifluoromethyl group;

B represents a valence bond, a straight chain alkylene group having 1–14 carbon atoms or a branched chain alkylene group having 3–14 carbon atoms (which may be substituted with at least one substituent selected from the group consisting of an alkoxy group having 1–5 carbon atoms, an alkanoyloxy group having 1–5 carbon atoms, a hydroxy group, fluorine, chlorine, bromine, iodine, an amino group, a nitro group, a cyano group, a trifluoromethyl group and a phenoxy group, and wherein from 1 to 3 methylene groups that are not adjacent may be replaced with carbonyl groups), a straight chain, acyclic, unsaturated hydrocarbon having 2–14 carbon atoms or a branched chain, acyclic, unsaturated hydrocarbon having 3 to 14 carbon atoms, and having from 1 to 3 double and/or triple bonds (which may be substituted with at least one substituent selected from the group consisting of an alkoxy group having 1–5 carbon atoms, an alkanoyloxy group having 1–5 carbon atoms, a hydroxy group, fluorine, chlorine, bromine, iodine, an amino group, a nitro group, a cyano group, a trifluoromethyl group and a phenoxy group, and wherein from 1 to 3 methylene groups that are not adjacent may be replaced with carbonyl groups), or a straight chain, saturated hydrocarbon having 1–14 carbon atoms, a straight chain unsaturated hydrocarbon having 2–14 carbon atoms, or a branched chain saturated or unsaturated hydrocarbon having 3 to 14 carbon atoms, having from 1 to 5 thioether, ether and/or amino bonds (wherein hetero atoms are not bonded directly to A);

R⁵ represents a hydrogen atom or an organic group having a structure as shown below:

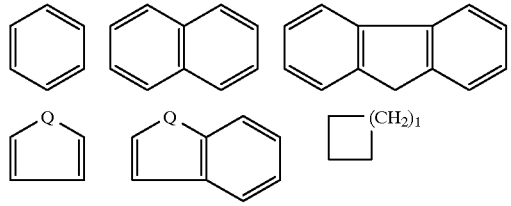

wherein Q is N, O, or S, l is 2 or 3, m and n are greater than or equal to 0, and m+n is less than or equal to 5, and which organic group may be substituted with one or two same or different substituents selected from the group consisting of $C_{1-5}$ alkyl, $C_{1-5}$ alkoxy, $C_{1-5}$ alkanoyloxy, hydroxy, fluoro, chloro, bromo, iodo, amino, nitro, cyano, isothiocyanate, and trifluoromethyl.

9. The method as recited in claim 1, wherein said formula (I) compound is 17-cyclopropylmethyl-3,14β-dihydroxy-4, 5α-epoxy-6β-(N-methyl-3-trifluoromethylcinnamamido) morphinan, or a pharmaceutically acceptable salt thereof.

10. A method of protecting brain nerve cells against cytotoxic damage caused by glutamate, the method comprising administering to a patient in need thereof an effective brain cell protecting amount of a brain cell protective agent of formula (I) or pharmacologically acceptable acid addition salt thereof:

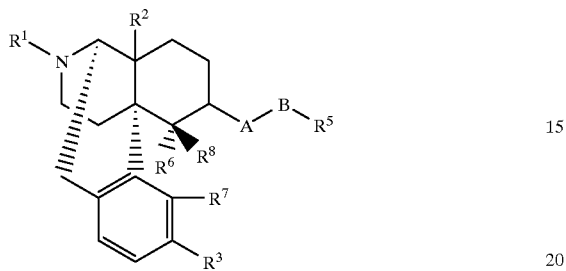

(I)

wherein, the dashed line "- - - -" represents an optional double bond;

$R^1$ represents an alkyl group having 1–5 carbon atoms, a cycloalkylalkyl group having 4–7 carbon atoms, a cycloalkenylalkyl group having 5–7 carbon atoms, an aryl group having 6–12 carbon atoms, an aralkyl group having 7–13 carbon atoms, an alkenyl group having 4–7 carbon atoms, or an allyl group;

$R^2$ represents a hydrogen atom, a hydroxy group, a nitro group, an alkanoyloxy group having 1–5 carbon atoms, an alkoxy group having 1–5 carbon atoms, a straight chain alkyl group having 1–5 carbon atoms or —$NR^9R^{10}$, wherein, $R^9$ represents a hydrogen atom or an alkyl group having 1–5 carbon atoms, and $R^{10}$ represents a hydrogen atom, an alkyl group having 1–5 carbon atoms or —C(=O)$R^{11}$ (wherein $R^{11}$ represents a hydrogen atom, phenyl group or alkyl group having 1–5 carbon atoms);

$R^3$ represents a hydrogen atom, a hydroxy group, an alkanoyloxy group having 1–5 carbon atoms or an alkoxy group having 1–5 carbon atoms;

A represents —XC(=Y)—, —XC(=Y)Z—, —X— or —$XSO_2$—, where, X represents $NR_4$, and Y and Z respectively and independently represent $NR^4$, S or O, $R^4$ represents a hydrogen atom, a straight chain alkyl group having 1–14 carbon atoms or a branched chain alkyl group having 3 to 14 carbon atoms (which may be substituted with at least one substituent selected from the group consisting of an alkoxy group having 1–5 carbon atoms, an alkanoyloxy group having 1–5 carbon atoms, fluorine, chlorine, bromine, iodine, a nitro group and a cyano group), a cycloalkylalkyl group having 4 to 15 carbon atoms (which may be substituted with at least one substituent selected from the group consisting of an alkyl group having 1–5 carbon atoms, an aryl group having 6–12 carbon atoms, an alkoxy group having 1–5 carbon atoms, an alkanoyloxy group having 1–5 carbon atoms, fluorine, chlorine, bromine, iodine, a nitro group, a cyano group and a trifluoromethyl group), an aralkyl group having 7–15 carbon atoms (which may be substituted with at least one substituent selected from the group consisting of an alkyl group having 1–5 carbon atoms, an aryl group having 6–12 carbon atoms, an alkoxy group having 1–5 carbon atoms, an alkanoyloxy group having 1–5 carbon atoms, fluorine, chlorine, bromine, iodine, a nitro group, a cyano group and a trifluoromethyl group), or an aryl group having 6–12 carbon atoms (which may be substituted with at least one substituent selected from the group consisting of an alkyl group having 1–5 carbon atoms, an aryl group having 6–12 carbon atoms, an alkoxy group having 1–5 carbon atoms, an alkanoyloxy group having 1–5 carbon atoms, fluorine, chlorine, bromine, iodine, a nitro group, a cyano group and a trifluoromethyl group), and wherein said $R^4$ groups may be identical or different;

B represents a valence bond, a straight chain alkylene group having 1–14 carbon atoms or a branched chain alkylene group having 3–14 carbon atoms (which may be substituted with at least one substituent selected from the group consisting of an alkoxy group having 1–5 carbon atoms, an alkanoyloxy group having 1–5 carbon atoms, a hydroxy group, fluorine, chlorine, bromine, iodine, an amino group, a nitro group, a cyano group, a trifluoromethyl group and a phenoxy group, and wherein from 1 to 3 methylene groups that are not adjacent may be replaced with carbonyl groups), a straight chain, acyclic, unsaturated hydrocarbon having 2–14 carbon atoms or a branched chain, acyclic, unsaturated hydrocarbon having 3 to 14 carbon atoms, and having from 1 to 3 double and/or triple bonds (which may be substituted with at least one substituent selected from the group consisting of an alkoxy group having 1–5 carbon atoms, an alkanoyloxy group having 1–5 carbon atoms, a hydroxy group, fluorine, chlorine, bromine, iodine, an amino group, a nitro group, a cyano group, a trifluoromethyl group and a phenoxy group, and wherein from 1 to 3 methylene groups that are not adjacent may be replaced with carbonyl groups), or a straight chain, saturated hydrocarbon having 1–14 carbon atoms, a straight chain unsaturated hydrocarbon having 2–14 carbon atoms, or a branched chain saturated or unsaturated hydrocarbon having 3 to 14 carbon atoms, having from 1 to 5 thioether, ether and/or amino bonds (wherein hetero atoms are not bonded directly to A);

$R^5$ represents a hydrogen atom or an organic group having a structure as shown below:

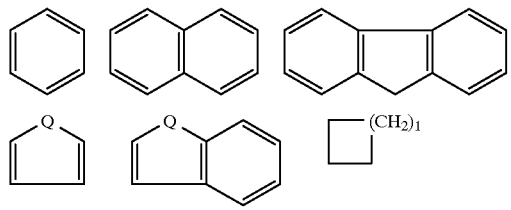

wherein Q is N, O or S, 1 is 2 or 3, m and n are greater than or equal to 0, and m+n is less than or equal to 5, and which organic group may be substituted with one or two same or different substituents selected from the group consisting of $C_{1-5}$ alkyl, $C_{1-5}$ alkoxy, $C_{1-5}$ alkanoyloxy, hydroxy, fluoro, chloro, bromo, iodo, amino, nitro, cyano, isothiocyanate, and trifluoromethyl;

$R^6$ and $R^7$ collectively represent —O—;

$R^8$ represents a hydrogen atom, a straight chain alkyl group having 1–5 carbon atoms or an alkanoyl group having 1–5 carbon atoms.

11. A method of protecting brain nerve cells against cytotoxic damage caused by glutamate, the method comprising administering to a patient in need thereof an effective brain cell protecting amount of a brain cell protective agent of formula (I') or a pharmacologically acceptable acid addition salt thereof:

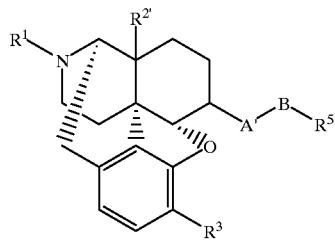
(I')

wherein,
$R^1$ represents an alkyl group having 1–5 carbon atoms, a cycloalkylalkyl group having 4–7 carbon atoms, a cycloalkenylalkyl group having 5–7 carbon atoms, an aryl group having 6–12 carbon atoms, an aralkyl group having 7–13 carbon atoms, an alkenyl group having 4–7 carbon atoms, or an allyl group;

$R^2$ represents a hydrogen atom, hydroxy group, alkanoyloxy group having 1–5 carbon atoms or alkoxy group having 1–5 carbon atoms;

$R^3$ represents a hydrogen atom, a hydroxy group, an alkanoyloxy group having 1–5 carbon atoms or an alkoxy group having 1–5 carbon atoms;

A' represent —$NR^{4'}C(=O)$— or —$NR^{4'}$—, where $R^{4'}$ represents a straight chain or branched chain alkyl group having 6–14 carbon atoms (which may be substituted with at least one substituent selected from the group consisting of an alkoxy group having 1–5 carbon atoms, an alkanoyloxy group having 1–5 carbon atoms, fluorine, chlorine, bromine, iodine, a nitro group and a cyano group), a straight chain alkyl group having 1–5 carbon atoms or a branched chain alkyl group having 3–5 carbon atoms (which is substituted with at least one substituent selected from the group consisting of an alkoxy group having 1–5 carbon atoms, an alkanoyloxy group having 1–5 carbon atoms, fluorine, chlorine, bromine, iodine, a nitro group and a cyano group), a cycloalkylalkyl group having 4 to 15 carbon atoms (which may be substituted with at least one substituent selected from the group consisting of an alkyl group having 1–5 carbon atoms, an aryl group having 6–12 carbon atoms, an alkoxy group having 1–5 carbon atoms, an alkanoyloxy group having 1–5 carbon atoms, fluorine, chlorine, bromine, iodine, a nitro group, a cyano group and a trifluoromethyl group), an aralkyl group having 7–15 carbon atoms (which may be substituted with at least one substituent selected from the group consisting of an alkyl group having 1–5 carbon atoms, an aryl group having 6–12 carbon atoms, an alkoxy group having 1–5 carbon atoms, an alkanoyloxy group having 1–5 carbon atoms, fluorine, chlorine, bromine, iodine, a nitro group, a cyano group and a trifluoromethyl group), or an aryl group having 6–12 carbon atoms (which is substituted with at least one substituent group selected from the group consisting of an alkyl group having 1–5 carbon atoms, an aryl group having 6–12 carbon atoms, an alkoxy group having 1–5 carbon atoms, an alkanoyloxy group having 1–5 carbon atoms, fluorine, chlorine, bromine, iodine, a nitro group, a cyano group and a trifluoromethyl group;

B represents a valence bond, a straight chain alkylene group having 1–14 carbon atoms or a branched chain alkylene group having 3–14 carbon atoms (which may be substituted with at least one substituent selected from the group consisting of an alkoxy group having 1–5 carbon atoms, an alkanoyloxy group having 1–5 carbon atoms, a hydroxy group, fluorine, chlorine, bromine, iodine, an amino group, a nitro group, a cyano group, a trifluoromethyl group and a phenoxy group, and wherein from 1 to 3 methylene groups that are not adjacent may be replaced with carbonyl groups), a straight chain, acyclic, unsaturated hydrocarbon having 2–14 carbon atoms or a branched chain, acyclic, unsaturated hydrocarbon having 3 to 14 carbon atoms, and having from 1 to 3 double and/or triple bonds (which may be substituted with at least one substituent selected from the group consisting of an alkoxy group having 1–5 carbon atoms, an alkanoyloxy group having 1–5 carbon atoms, a hydroxy group, fluorine, chlorine, bromine, iodine, an amino group, a nitro group, a cyano group, a trifluoromethyl group and a phenoxy group, and wherein from 1 to 3 methylene groups that are not adjacent may be replaced with carbonyl groups), or a straight chain, saturated hydrocarbon having 1–14 carbon atoms, a straight chain unsaturated hydrocarbon having 2–14 carbon atoms, or a branched chain saturated or unsaturated hydrocarbon having 3 to 14 carbon atoms, having from 1 to 5 thioether, ether and/or amino bonds (wherein hetero atoms are not bonded directly to A);

$R^5$ represents a hydrogen atom or an organic group having a structure as shown below:

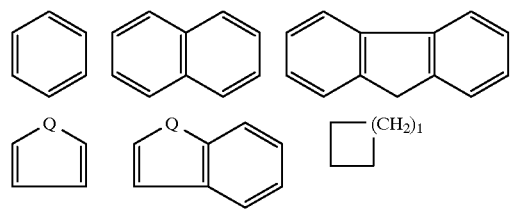

wherein Q is N, O, or S, l is 2 or 3, m and n are greater than or equal to 0, and m+n is less than or equal to 5, and which organic group may be substituted with one or two same or different substituents selected from the group consisting of $C_{1-5}$ alkyl, $C_{1-5}$ alkoxy, $C_{1-5}$ alkanoyloxy, hydroxy, fluoro, chloro, bromo, iodo, amino, nitro, cyano, isothiocyanate, and trifluoromethyl.

* * * * *